United States Patent
Meena et al.

(10) Patent No.: US 12,180,472 B2
(45) Date of Patent: Dec. 31, 2024

(54) CHIRAL DESIGN

(71) Applicant: WAVE LIFE SCIENCES LTD., Singapore (SG)

(72) Inventors: Meena Meena, Belmont, MA (US); David Butler, Medford, MA (US); Naoki Iwamoto, Boston, MA (US); Nenad Svrzikapa, Cambridge, MA (US); Gregory L. Verdine, Boston, MA (US); Ivan Zlatev, Cambridge, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 263 days.

(21) Appl. No.: 17/016,313

(22) Filed: Sep. 9, 2020

(65) Prior Publication Data

US 2021/0115444 A1    Apr. 22, 2021

Related U.S. Application Data

(62) Division of application No. 16/109,638, filed on Aug. 22, 2018, now Pat. No. 10,815,482, which is a division of application No. 15/112,146, filed as application No. PCT/IB2015/000395 on Jan. 16, 2015, now Pat. No. 10,160,969.

(60) Provisional application No. 62/063,359, filed on Oct. 13, 2014, provisional application No. 61/928,405, filed on Jan. 16, 2014.

(51) Int. Cl.
    *C12N 15/113*    (2010.01)

(52) U.S. Cl.
    CPC ........ *C12N 15/113* (2013.01); *C12N 2310/31* (2013.01); *C12N 2310/315* (2013.01); *C12N 2320/30* (2013.01)

(58) Field of Classification Search
    CPC .. C12N 15/113; C12N 15/87; C12N 2310/31; C12N 2310/315; C12N 2310/11; C12N 2310/14; C12N 2320/30
    USPC ..................... 435/6.1, 91.1, 91.31, 455, 458; 514/44 A; 536/23.1, 24.5
    See application file for complete search history.

(56) References Cited

U.S. PATENT DOCUMENTS

| | | | |
|---|---|---|---|
| 10,696,711 B2 | 6/2020 | Shimizu et al. |
| 10,724,035 B2 | 7/2020 | Vargeese et al. |
| 10,815,482 B2 | 10/2020 | Meena et al. |
| 11,013,757 B2 | 5/2021 | Zhang et al. |
| 11,136,346 B2 | 10/2021 | Shimizu et al. |
| 11,407,775 B2 | 8/2022 | Butler et al. |
| 11,596,646 B2 | 3/2023 | Zhang et al. |
| 11,597,927 B2 | 3/2023 | Vargeese et al. |
| 11,603,532 B2 | 3/2023 | Vargeese et al. |
| 11,608,355 B2 | 3/2023 | Bowman et al. |
| 11,634,710 B2 | 4/2023 | Frank-Kamenetsky et al. |
| 11,643,657 B2 | 5/2023 | Butler et al. |
| 11,718,638 B2 | 8/2023 | Butler et al. |
| 11,739,325 B2 | 8/2023 | Vargeese et al. |
| 11,873,316 B2 | 1/2024 | Butler et al. |
| 2020/0157545 A1 | 5/2020 | Vargeese et al. |
| 2020/0190515 A1 | 6/2020 | Vargeese et al. |
| 2020/0231620 A1 | 7/2020 | Bowman et al. |
| 2020/0299692 A1 | 9/2020 | Frank-Kamenetsky et al. |
| 2020/0362337 A1 | 11/2020 | Dodart et al. |
| 2020/0385420 A1 | 12/2020 | Shimizu et al. |
| 2021/0032620 A1 | 2/2021 | Vargeese et al. |
| 2021/0130821 A1 | 5/2021 | Butler et al. |
| 2021/0198305 A1 | 7/2021 | Vargeese et al. |
| 2021/0228615 A1 | 7/2021 | Zhang et al. |
| 2021/0254062 A1 | 8/2021 | Zhang et al. |
| 2022/0098585 A1 | 3/2022 | Brown et al. |
| 2022/0127301 A1 | 4/2022 | Shimizu et al. |
| 2022/0145300 A1 | 5/2022 | Liu et al. |
| 2022/0162598 A1 | 5/2022 | Vargeese et al. |
| 2022/0186217 A1 | 6/2022 | Zhang et al. |
| 2022/0195429 A1 | 6/2022 | Vargeese et al. |
| 2022/0306573 A1 | 9/2022 | Zhang et al. |
| 2022/0307019 A1 | 9/2022 | Yokota et al. |
| 2022/0356204 A1 | 11/2022 | Butler et al. |
| 2022/0401467 A1 | 12/2022 | Zhang et al. |
| 2023/0089442 A1 | 3/2023 | Kandasamy et al. |
| 2023/0136645 A1 | 5/2023 | Butler et al. |
| 2023/0145795 A1 | 5/2023 | Byrne et al. |

(Continued)

FOREIGN PATENT DOCUMENTS

| WO | WO-1996/039154 A1 | 12/1996 |
| WO | WO-2020/118246 A1 | 6/2020 |

(Continued)

OTHER PUBLICATIONS

U.S. Appl. No. 17/375,658.*

(Continued)

*Primary Examiner* — Jane J Zara

(74) *Attorney, Agent, or Firm* — Choate, Hall & Stewart LLP; Brenda Herschbach Jarrell; Xiaodong Li

(57) ABSTRACT

The present invention relates to chirally controlled oligonucleotides of select designs, chirally controlled oligonucleotide compositions, and methods of making and using the same. In some embodiments, a provided chirally controlled oligonucleotide composition provides different cleavage patterns of a nucleic acid polymer than a reference oligonucleotide composition. In some embodiments, a provided chirally controlled oligonucleotide composition provides single site cleavage within a complementary sequence of a nucleic acid polymer.

27 Claims, 52 Drawing Sheets

Specification includes a Sequence Listing.

(56) References Cited

U.S. PATENT DOCUMENTS

| | | |
|---|---|---|
| 2023/0203087 A1 | 6/2023 | Kandasamy et al. |
| 2023/0220384 A1 | 7/2023 | Monian et al. |
| 2023/0295617 A1 | 9/2023 | Vargeese et al. |
| 2023/0295619 A1 | 9/2023 | Maguire et al. |
| 2023/0329201 A1 | 10/2023 | Yang et al. |
| 2023/0348524 A1 | 11/2023 | Bowman et al. |
| 2023/0392137 A1 | 12/2023 | Monian et al. |
| 2024/0026358 A1 | 1/2024 | Monian et al. |
| 2024/0109931 A1 | 4/2024 | Vargeese et al. |
| 2024/0117347 A1 | 4/2024 | Butler et al. |
| 2024/0132894 A1 | 4/2024 | Vargeese et al. |
| 2024/0150756 A1 | 5/2024 | Frank-Kamenetsky et al. |
| 2024/0174710 A1 | 5/2024 | Butler et al. |
| 2024/0175016 A1 | 5/2024 | Liu et al. |
| 2024/0175018 A1 | 5/2024 | Vargeese et al. |

FOREIGN PATENT DOCUMENTS

| | | |
|---|---|---|
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/178237 A2 | 9/2021 |
| WO | WO-2021/234459 A2 | 11/2021 |
| WO | WO-2021/237223 A1 | 11/2021 |
| WO | WO-2022/046667 A1 | 3/2022 |
| WO | WO-2022/046723 A1 | 3/2022 |
| WO | WO-2022/099159 A1 | 5/2022 |
| WO | WO-2023/049475 A1 | 3/2023 |
| WO | WO-2023/049477 A2 | 3/2023 |
| WO | WO-2023/075766 A1 | 5/2023 |
| WO | WO-2023/076352 A2 | 5/2023 |
| WO | WO-2023/154528 A1 | 8/2023 |
| WO | WO-2023/168014 A2 | 9/2023 |
| WO | WO-2023/201095 A2 | 10/2023 |
| WO | WO-2023/220440 A1 | 11/2023 |
| WO | WO-2024/035946 A1 | 2/2024 |

OTHER PUBLICATIONS

U.S. Appl. No. 17/907,895, filed Aug. 29, 2022, Maguire et al.
U.S. Appl. No. 17/953,292, filed Sep. 26, 2022, Monian et al.
U.S. Appl. No. 17/956,741, filed Sep. 29, 2022, Vargeese et al.
U.S. Appl. No. 17/960,090, filed Oct. 4, 2022, Vargeese et al.
U.S. Appl. No. 18/022,509, filed Feb. 21, 2023, Yang et al.
U.S. Appl. No. 18/062,422, filed Dec. 6, 2022, Butler et al.
U.S. Appl. No. 18/072,296, filed Nov. 30, 2022, Vargeese et al.
U.S. Appl. No. 18/178,470, filed Mar. 3, 2023, Vargeese et al.
Buczko, W. et al., Modulation of plasminogen activator inhibitor type-1 biosynthesis in vitro and in vivo with oligo(nucleoside phosphorothioate)s and related constructs, Pharmacol. Ther., 76(1-3):161-175 (1997).
Ostergaard, M.E. et al., Differential effects on allele selective silencing of mutant huntingtin by two stereoisomers of a,β-constrained nucleic acid, ACS Chem. Biol., 9(9):1975-1979 (2014).
Stein, C.A. et al., Phosphorothioate oligodeoxynucleotides—antisense inhibitors of gene expression? Pharmacol. Ther., 52(3):365-384 (1991).
Wickstrom, E., Antisense DNA therapeutics: neutral analogs and their stereochemistry, Gene Regulation: Biology of Antisense RNA and DNA. New York, NY: Raven Press Publishers, 14 pages, (1992).
U.S. Appl. No. 18/185,901, filed Mar. 17, 2023, Bowman et al.
U.S. Appl. No. 18/204,895, filed Jun. 1, 2023, Vargeese et al.
U.S. Appl. No. 18/252,029, filed May 5, 2023, Monian et al.
U.S. Appl. No. 18/305,195, filed Apr. 21, 2023, Frank-Kamenetsky et al.
U.S. Appl. No. 18/316,932, filed May 12, 2023, Butler et al.
U.S. Appl. No. 18/522,146, filed Nov. 28, 2023, Butler et al.
U.S. Appl. No. 18/613,034, filed Mar. 21, 2024, Vargeese et al.
U.S. Appl. No. 18/695,346, filed Mar. 25, 2024, Monian et al.
U.S. Appl. No. 18/695,348, filed Mar. 25, 2024, Acker et al.
U.S. Appl. No. 18/704,629, filed Apr. 25, 2024, Byrne et al.

\* cited by examiner (PANEL A)

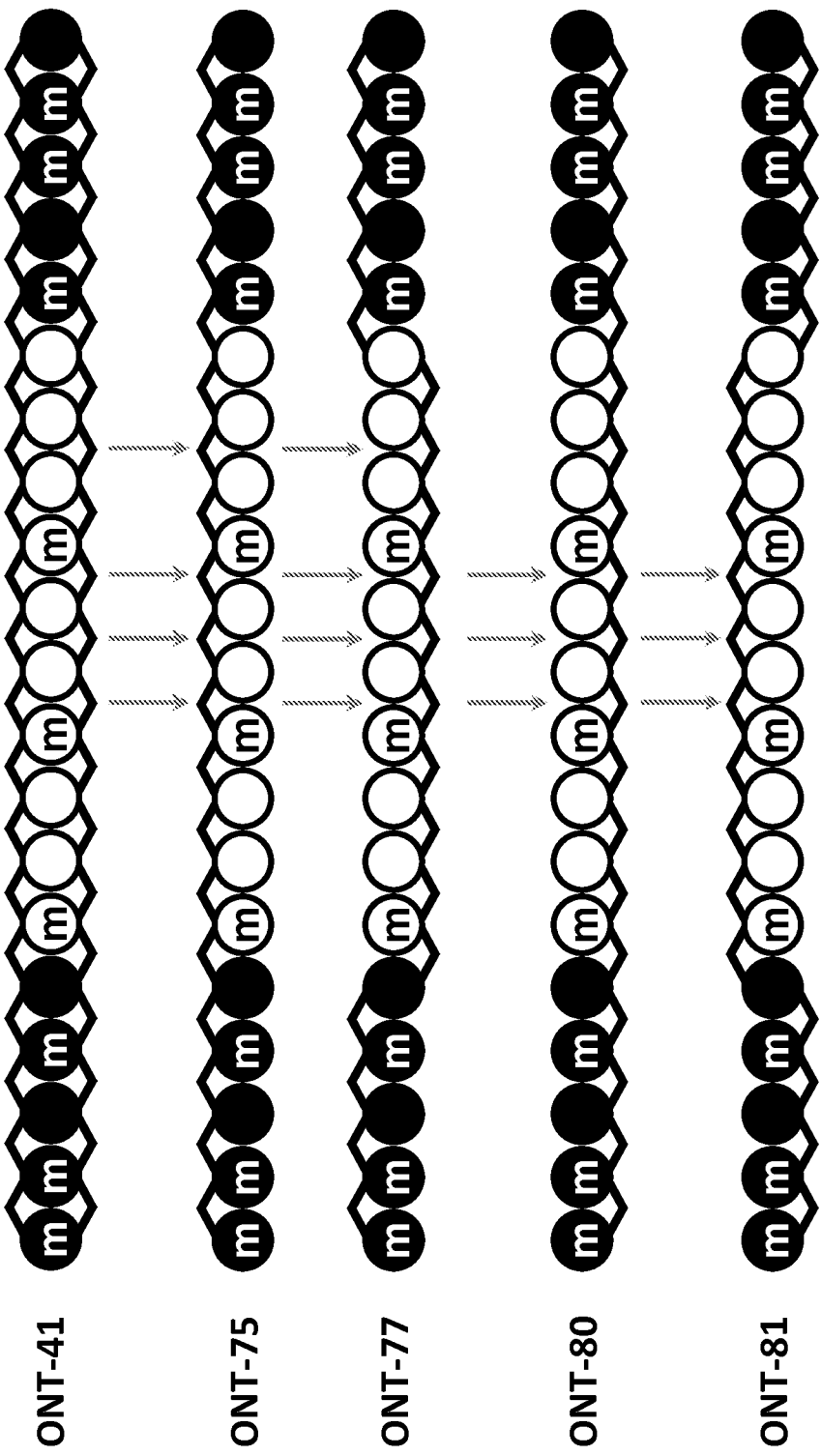
FIG. 9 (CONTINUED) (PANEL B)

(PANEL C)

(PANEL A)

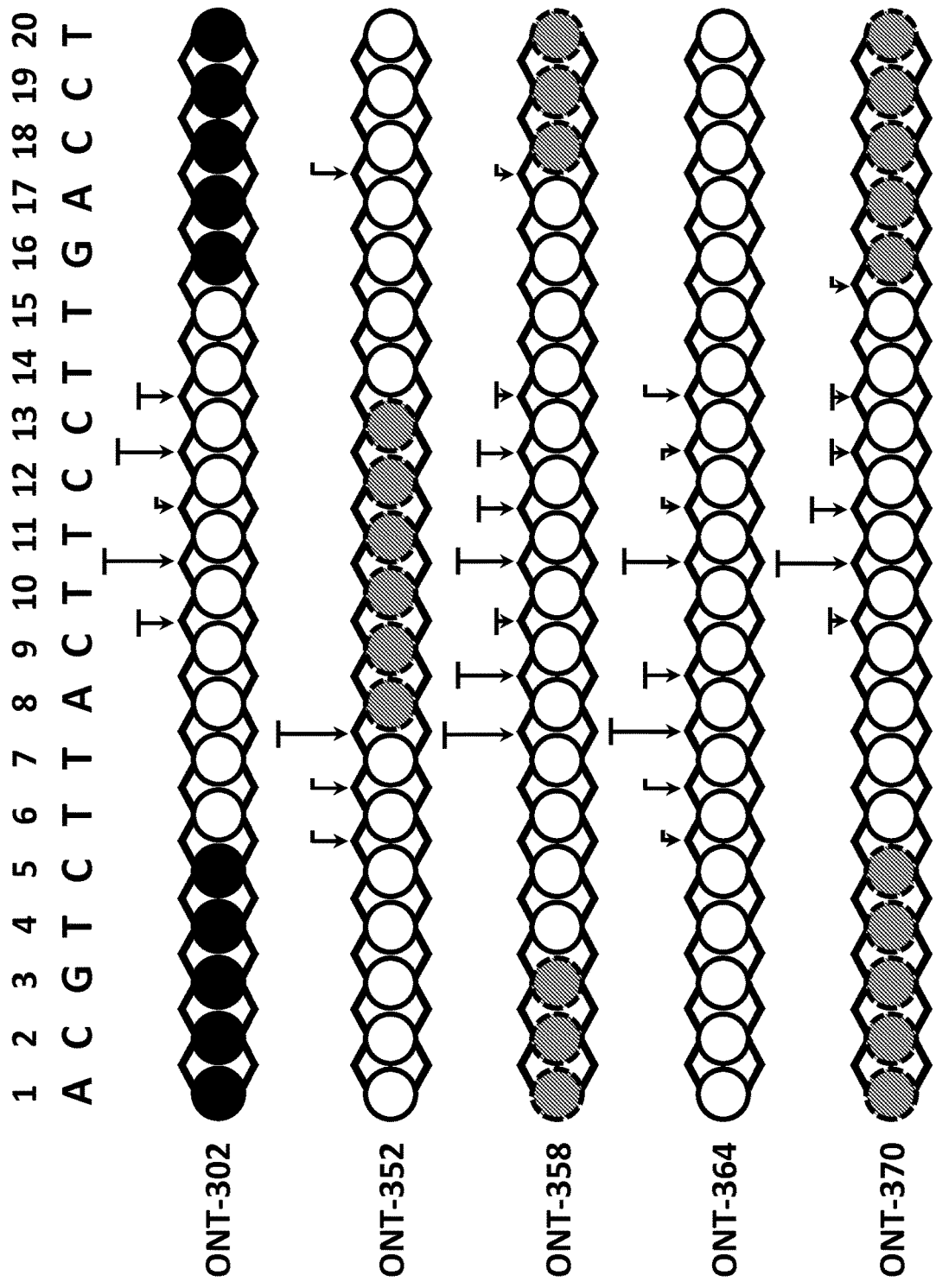
FIG. 10 (CONTINUED) (PANEL B)

(PANEL C)

(PANEL A)

(PANEL B)

(PANEL A)

(PANEL B)

(PANEL A)

(PANEL B)

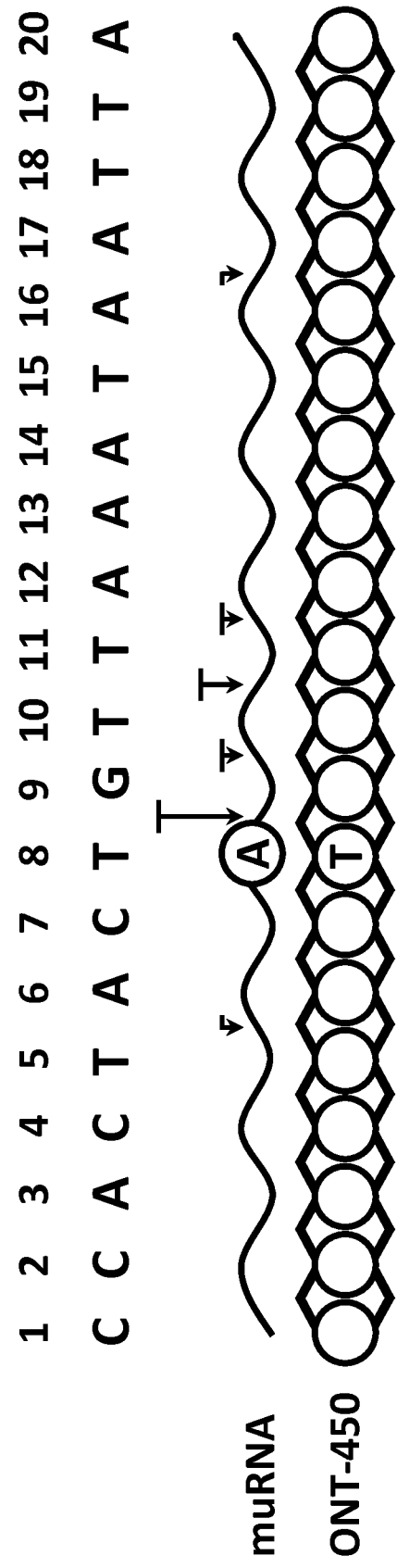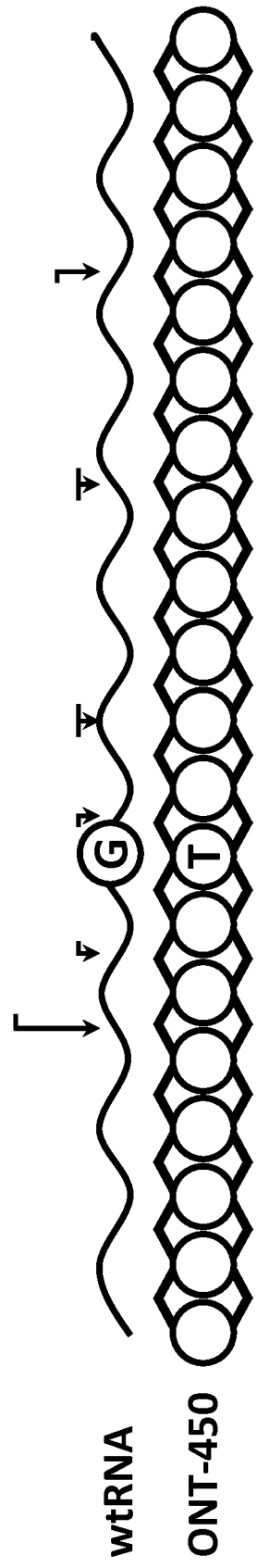
FIG. 22 (CONTINUED) (PANEL C)

(PANEL D)

(PANEL E)

(PANEL F)

(PANEL G)

(PANEL H)

(PANEL A)

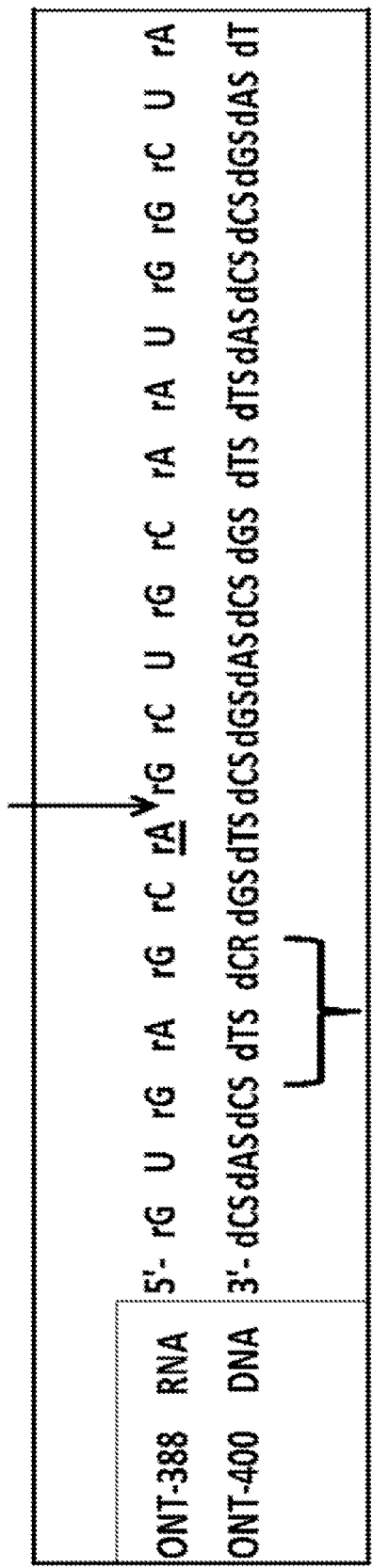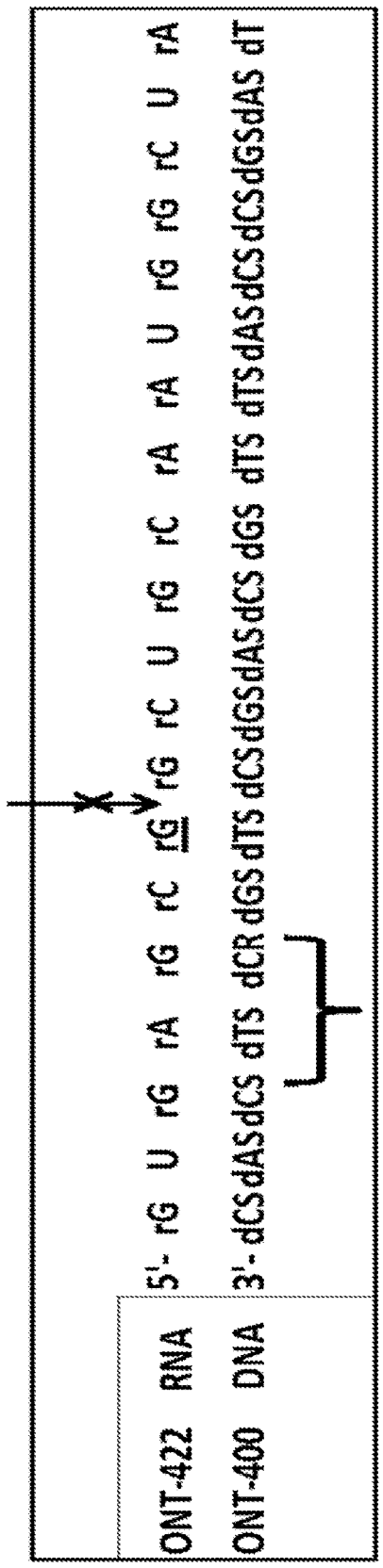
FIG. 23 (CONTINUED) (PANEL B)

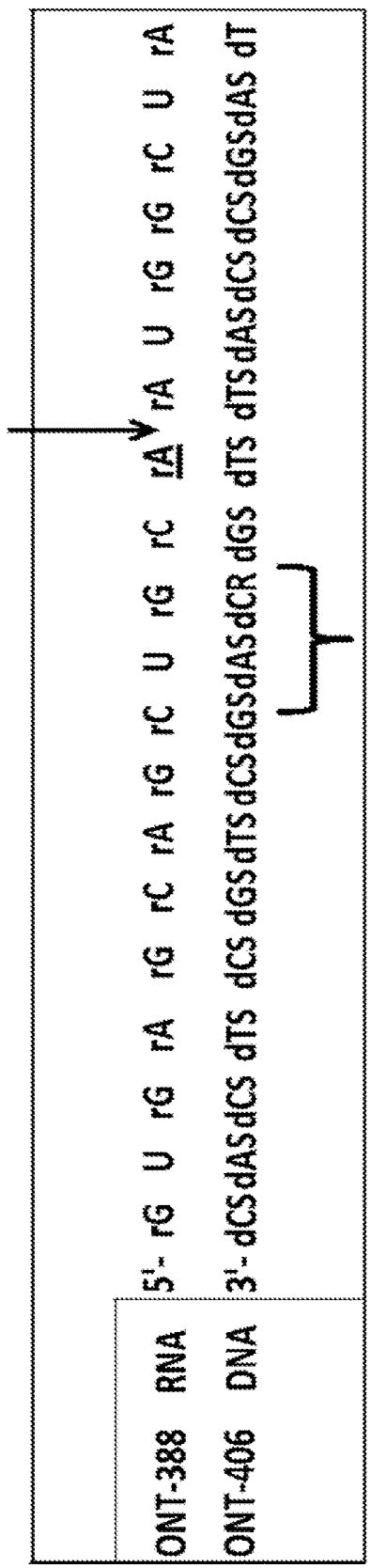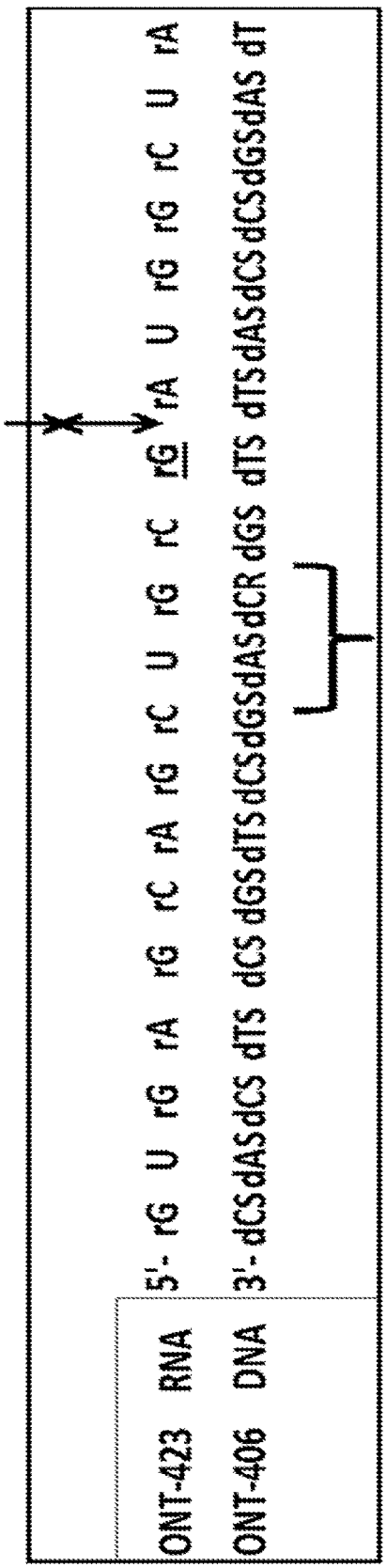
FIG. 23 (CONTINUED) (PANEL C)

(PANEL A)

(PANEL B)

(PANEL A)

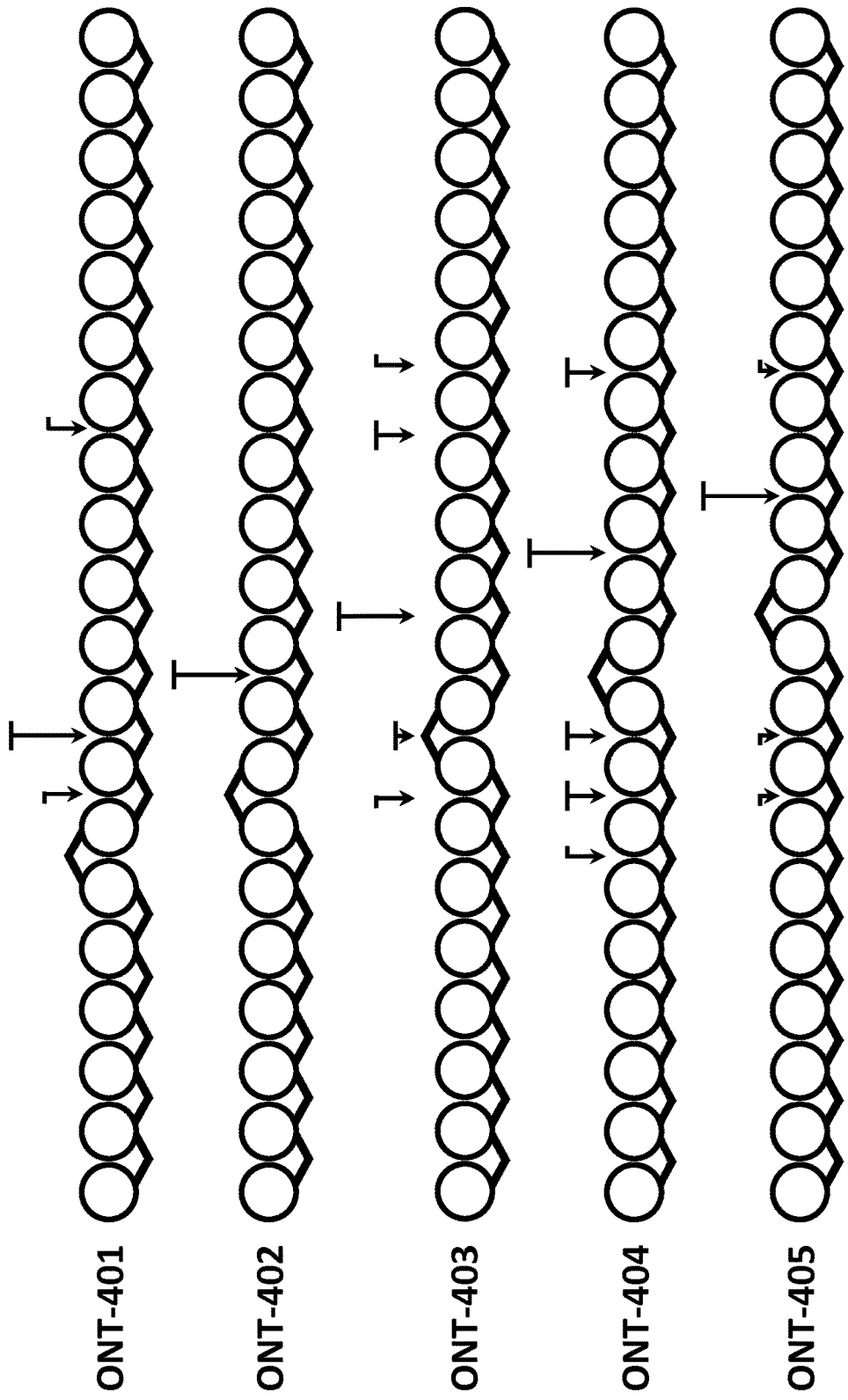
FIG. 26 (CONTINUED) (PANEL B)

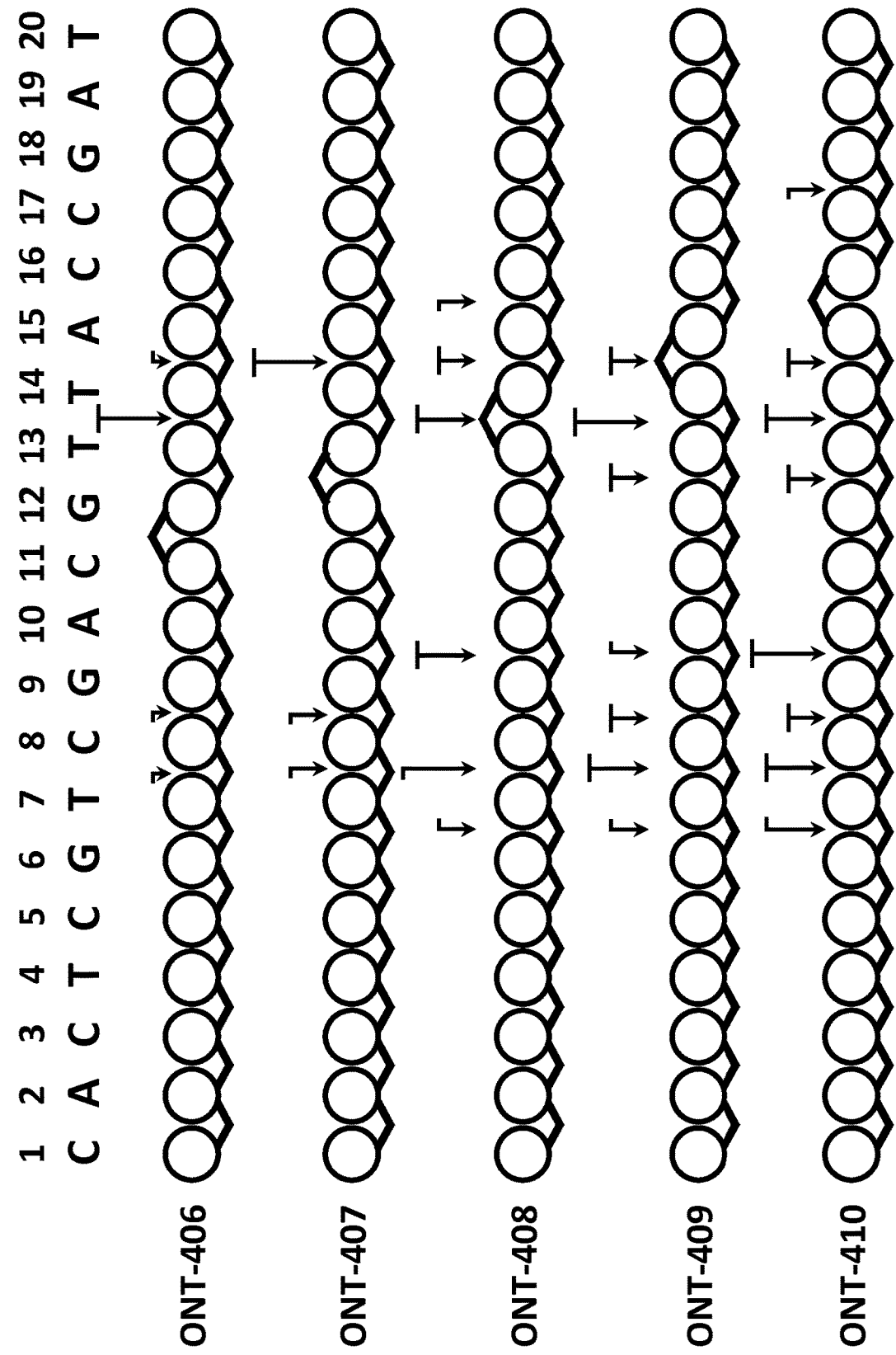
FIG. 26 (CONTINUED) (PANEL C)

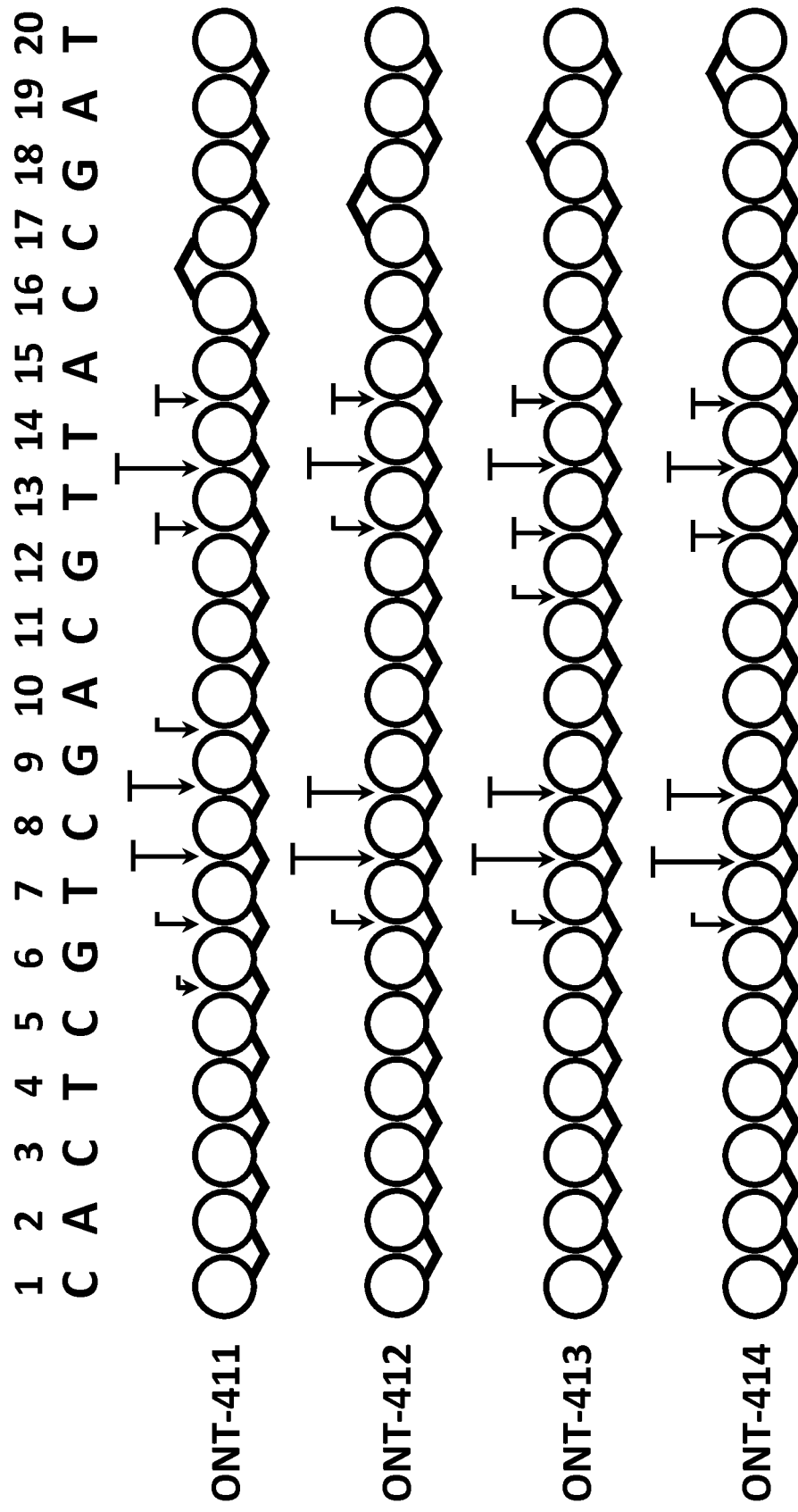
FIG. 26 (CONTINUED) (PANEL D)

(PANEL A)

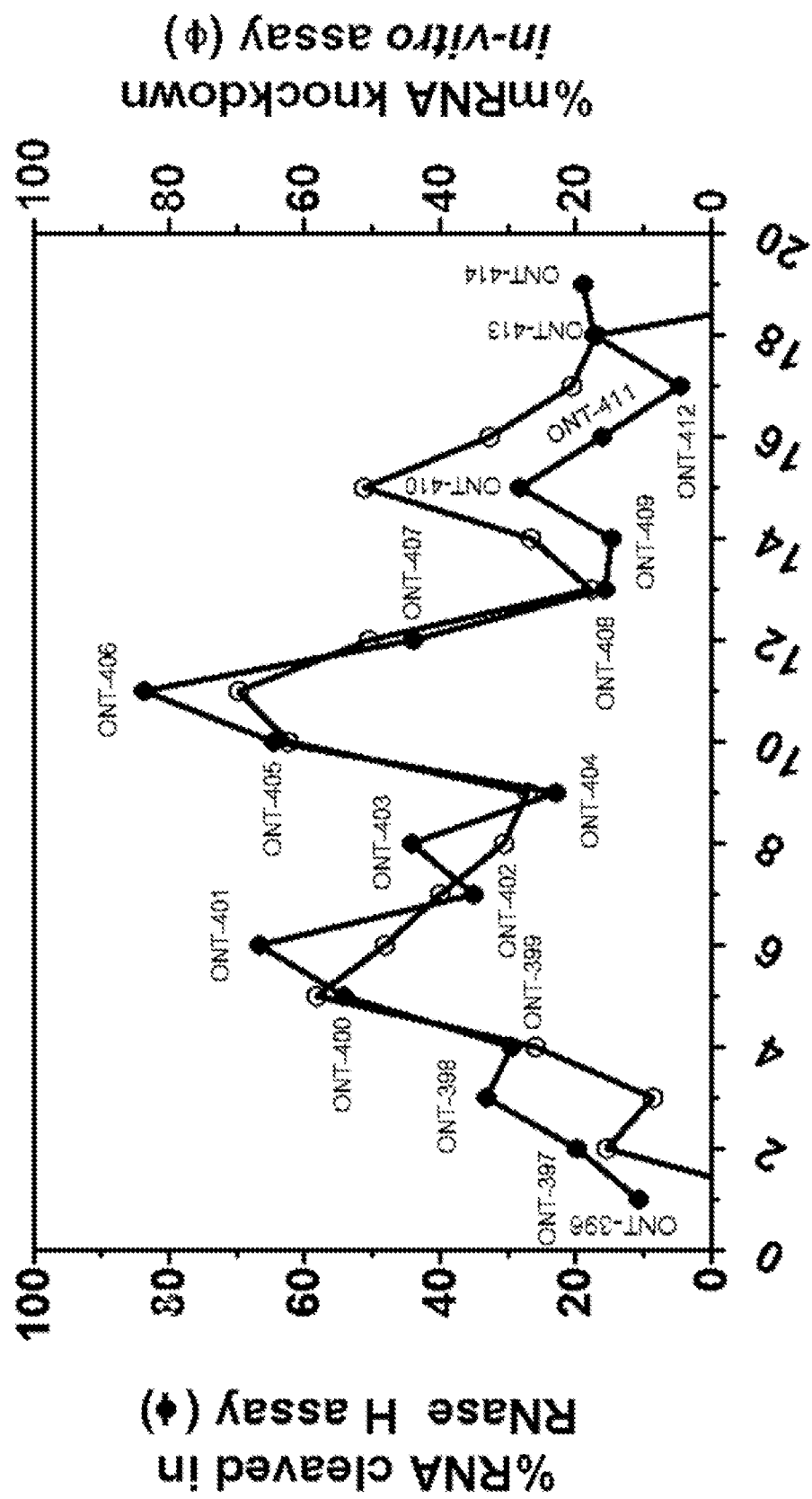
FIG. 27 (CONTINUED) (PANEL B)

(PANEL A)

(PANEL B)

(PANEL C)

CHIRAL DESIGN

CROSS-REFERENCE TO RELATED APPLICATIONS

This application is a divisional application of U.S. patent application Ser. No. 16/109,638, filed Aug. 22, 2018, issued as U.S. Pat. No. 10,815,482, which is a divisional application of U.S. patent application Ser. No. 15/112,146, filed Jul. 15, 2016, issued as U.S. Pat. No. 10,160,969, which is a National Stage Entry of PCT/IB2015/000395, filed Jan. 16, 2015, which claims priority to U.S. Provisional Application Ser. No. 61/928,405, filed Jan. 16, 2014, and 62/063,359, filed Oct. 13, 2014, the entirety of each of which is incorporated herein by reference.

SEQUENCE LISTING

The present application contains a Sequence Listing which has been submitted electronically in ASCII format and is hereby incorporated by reference in its entirety. Said ASCII copy, created on Dec. 28, 2020, is named SequenceListing.txt and is 189,477 bytes in size.

BACKGROUND OF THE INVENTION

Oligonucleotides are useful in therapeutic, diagnostic, research and nanomaterials applications. The use of naturally occurring nucleic acids (e.g., unmodified DNA or RNA) for therapeutics can be limited, for example, because of their instability against extra- and intracellular nucleases and/or their poor cell penetration and distribution. Additionally, in vitro studies have shown that properties of antisense oligonucleotides such as binding affinity, sequence specific binding to the complementary RNA (Cosstick and Eckstein, 1985; LaPlanche et al., 1986; Latimer et al., 1989; Hacia et al., 1994; Mesmaeker et al., 1995), and stability to nucleases can be affected by the absolute stereochemical configurations of the phosphorus atoms (Cook, et al. US005599797A). Therefore, there is a need for new and improved oligonucleotides and oligonucleotide compositions, such as, e.g., new antisense and siRNA oligonucleotides and oligonucleotide compositions.

SUMMARY OF THE INVENTION

Among other things, the present invention encompasses the recognition that stereorandom oligonucleotide preparations contain a plurality of distinct chemical entities that differ from one another in the stereochemical structure of individual backbone chiral centers within the oligonucleotide chain. Moreover, the present invention encompasses the insight that it is typically unlikely that a stereorandom oligonucleotide preparation will include every possible stereoisomer of the relevant oligonucleotide. Thus, among other things, the present invention provides new chemical entities that are particular stereoisomers of oligonucleotides of interest. That is, the present invention provides substantially pure preparations of single oligonucleotide compounds, where a particular oligonucleotide compound may be defined by its base sequence, its length, its pattern of backbone linkages, and its pattern of backbone chiral centers.

The present invention demonstrates, among other things, that individual stereoisomers of a particular oligonucleotide can show different stability and/or activity from each other. Moreover, the present disclosure demonstrates that stability improvements achieved through inclusion and/or location of particular chiral structures within an oligonucleotide can be comparable to, or even better than those achieved through use of certain modified backbone linkages, bases, and/or sugars (e.g., through use of certain types of modified phosphates, 2'-modifications, base modifications, etc.).

Among other things, the present invention recognizes that properties and activities of an oligonucleotide can be adjusted by optimizing its pattern of backbone chiral centers. In some embodiments, the present invention provides compositions of oligonucleotides, wherein the oligonucleotides have a common pattern of backbone chiral centers which, unexpectedly, greatly enhances the stability and/or biological activity of the oligonucleotides. In some embodiments, a pattern of backbone chiral centers provides increased stability. In some embodiments, a pattern of backbone chiral centers provides surprisingly increased activity. In some embodiments, a pattern of backbone chiral centers provides increased stability and activity. In some embodiments, when an oligonucleotide is utilized to cleave a nucleic acid polymer, a pattern of backbone chiral centers of the oligonucleotide, surprisingly by itself, changes the cleavage pattern of a target nucleic acid polymer. In some embodiments, a pattern of backbone chiral centers effectively prevents cleavage at secondary sites. In some embodiments, a pattern of backbone chiral centers creates new cleavage sites. In some embodiments, a pattern of backbone chiral centers minimizes the number of cleavage sites. In some embodiments, a pattern of backbone chiral centers minimizes the number of cleavage sites so that a target nucleic acid polymer is cleaved at only one site within the sequence of the target nucleic acid polymer that is complementary to the oligonucleotide. In some embodiments, a pattern of backbone chiral centers enhances cleavage efficiency at a cleavage site. In some embodiments, a pattern of backbone chiral centers of the oligonucleotide improves cleavage of a target nucleic acid polymer. In some embodiments, a pattern of backbone chiral centers increases selectivity. In some embodiments, a pattern of backbone chiral centers minimizes off-target effect. In some embodiments, a pattern of backbone chiral centers increase selectivity, e.g., cleavage selectivity between two target sequences differing only by a single nucleotide polymorphism (SNP).

All publications and patent documents cited in this application are incorporated herein by reference in their entirety.

Definitions

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In some embodiments, aliphatic groups contain 1-50 aliphatic carbon atoms. Unless otherwise specified, aliphatic groups contain 1-10 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms.

In some embodiments, "cycloaliphatic" (or "carbocycle" or "cycloalkyl") refers to a monocyclic or bicyclic $C_3$-$C_{10}$ hydrocarbon that is completely saturated or that contains one or more units of unsaturation, but which is not aromatic, that has a single point of attachment to the rest of the molecule. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkylene: The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

Alkenylene: The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl" used alone or as part of a larger moiety as in "aralkyl," "aralkoxy," or "aryloxyalkyl," refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Characteristic structural element: The term "characteristic structural element" refers to a distinctive structural element (e.g., core structure, collection of pendant moieties, sequence element, etc) that is found in all members of a family of polypeptides, small molecules, or nucleic acids, and therefore can be used by those of ordinary skill in the art to define members of the family.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Equivalent agents: Those of ordinary skill in the art, reading the present disclosure, will appreciate that the scope of useful agents in the context of the present invention is not limited to those specifically mentioned or exemplified herein. In particular, those skilled in the art will recognize that active agents typically have a structure that consists of a core and attached pendant moieties, and furthermore will appreciate that simple variations of such core and/or pendant moieties may not significantly alter activity of the agent. For example, in some embodiments, substitution of one or more pendant moieties with groups of comparable three-dimensional structure and/or chemical reactivity characteristics may generate a substituted compound or portion equivalent to a parent reference compound or portion. In some embodiments, addition or removal of one or more pendant moieties may generate a substituted compound equivalent to a parent reference compound. In some embodiments, alteration of core structure, for example by addition or removal of a small number of bonds (typically not more than 5, 4, 3, 2, or 1 bonds, and often only a single bond) may generate a substituted compound equivalent to a parent reference compound. In many embodiments, equivalent compounds may be prepared by methods illustrated in general reaction schemes as, for example, described below, or by modifications thereof, using readily available starting materials, reagents and conventional or provided synthesis procedures. In these reactions, it is also possible to make use of variants, which are in themselves known, but are not mentioned here.

Equivalent Dosage: The term "equivalent dosage" is used herein to compare dosages of different pharmaceutically active agents that effect the same biological result. Dosages of two different agents are considered to be "equivalent" to one another in accordance with the present invention if they achieve a comparable level or extent of the biological result. In some embodiments, equivalent dosages of different pharmaceutical agents for use in accordance with the present invention are determined using in vitro and/or in vivo assays as described herein. In some embodiments, one or more lysosomal activating agents for use in accordance with the present invention is utilized at a dose equivalent to a dose of a reference lysosomal activating agent; in some such embodiments, the reference lysosomal activating agent for such purpose is selected from the group consisting of small molecule allosteric activators (e.g., pyrazolopyrimidines), iminosugars (e.g., isofagomine), antioxidants (e.g., n-acetyl-cysteine), and regulators of cellular trafficking (e.g., Rab1a polypeptide).

Heteroaliphatic: The term "heteroaliphatic" refers to an aliphatic group wherein one or more units selected from C, CH, $CH_2$, or $CH_3$ are independently replaced by a heteroatom. In some embodiments, a heteroaliphatic group is heteroalkyl. In some embodiments, a heteroaliphatic group is heteroalkenyl.

Heteroaryl: The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" means one or more of oxygen, sulfur, nitrogen, phosphorus, boron, selenium, or silicon (including, any oxidized form of nitrogen, boron, selenium, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Heterocycle: As used herein, the terms "heterocycle," "heterocyclyl," "heterocyclic radical," and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Intraperitoneal: The phrases "intraperitoneal administration" and "administered intraperitonealy" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Lower alkyl: The term "lower alkyl" refers to a $C_{1-4}$ straight or branched alkyl group. Exemplary lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$, —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(P)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; —$SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —$O(C(R*_2))_{2-3}O$—, or —$S(C(R*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(haloR$^\bullet$), —OH, —$OR^\bullet$, —O(haloR$^\bullet$), —CN, —C(O)OH, —C(O)OR$^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(RT)S(O)_2R^\dagger$; wherein each $R^\dagger$ is independently hydrogen, $C_{1-6}$ aliphatic which may be substituted as defined below, unsubstituted —OPh, or an unsubstituted 5-6 membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12 membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(haloR$^\bullet$), —OH, —$OR^\bullet$, —O(haloR$^\bullet$), —CN, —C(O)OH, —C(O)OR$^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subscapular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prodrug: A general, a "prodrug," as that term is used herein and as is understood in the art, is an entity that, when administered to an organism, is metabolized in the body to deliver an active (e.g., therapeutic or diagnostic) agent of interest. Typically, such metabolism involves removal of at least one "prodrug moiety" so that the active agent is formed. Various forms of "prodrugs" are known in the art. For examples of such prodrug moieties, see:
   a) *Design of Prodrugs*, edited by H. Bundgaard, (Elsevier, 1985) and *Methods in Enzymology*, 42:309-396, edited by K. Widder, et al. (Academic Press, 1985);
   b) *Prodrugs and Targeted Delivery*, edited by J. Rautio (Wiley, 2011);
   c) *Prodrugs and Targeted Delivery*, edited by J. Rautio (Wiley, 2011);
   d) A Textbook of Drug Design and Development, edited by Krogsgaard-Larsen;
   e) Bundgaard, Chapter 5 "Design and Application of Prodrugs", by H. Bundgaard, p. 113-191 (1991);
   f) Bundgaard, *Advanced Drug Delivery Reviews*, 8:1-38 (1992);
   g) Bundgaard, et al., *Journal of Pharmaceutical Sciences*, 77:285 (1988); and
   h) Kakeya, et al., *Chem. Pharm. Bull.*, 32:692 (1984).

As with other compounds described herein, prodrugs may be provided in any of a variety of forms, e.g., crystal forms, salt forms etc. In some embodiments, prodrugs are provided as pharmaceutically acceptable salts thereof.

Protecting group: The term "protecting group," as used herein, is well known in the art and includes those described in detail in *Protecting Groups in Organic Synthesis*, T. W. Greene and P. G. M. Wuts, 3$^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. June 2012, the entirety of Chapter 2 is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4''-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4''-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group.

In some embodiments, a phosphorous protecting group is a group attached to the internucleotide phosphorous linkage throughout oligonucleotide synthesis. In some embodiments, the phosphorous protecting group is attached to the sulfur atom of the internucleotide phosphorothioate linkage. In some embodiments, the phosphorous protecting group is attached to the oxygen atom of the internucleotide phosphorothioate linkage. In some embodiments, the phosphorous protecting group is attached to the oxygen atom of the internucleotide phosphate linkage. In some embodiments the phosphorous protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl) aminoethyl, 4-[N-methyl-N-(2,2,2-trifluoroacetyl)amino] butyl.

Protein: As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain L-amino acids, D-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Sample: A "sample" as used herein is a specific organism or material obtained therefrom. In some embodiments, a sample is a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, a sample is an organism. In some embodiments, a sample is a plant. In some embodiments, a sample is an animal. In some embodiments, a sample is a human. In some embodiments, a sample is an organism other than a human.

Stereochemically isomeric forms: The phrase "stereochemically isomeric forms," as used herein, refers to different compounds made up of the same atoms bonded by the same sequence of bonds but having different three-dimensional structures which are not interchangeable. In some embodiments of the invention, provided chemical compositions may be or include pure preparations of individual stereochemically isomeric forms of a compound; in some embodiments, provided chemical compositions may be or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition may contain all diastereomers and/or enantiomers of the compound. In some embodiments, a chemical composition may contain less than all diastereomers and/or enantiomers of a compound. In some embodiments, if a particular enantiomer of a compound of the present invention is desired, it may be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization.

Subject: As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present invention. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the invention, chemical compositions may be provided that are or include pure preparations of a single tautomeric form of a compound. In some embodiments of the invention, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the invention, chemical compositions may contain all tautomeric forms of a compound. In some embodiments of the invention, chemical compositions may contain less than all tautomeric forms of a compound. In some embodiments of the invention, chemical compositions may contain one or more tautomeric forms of a compound in amounts that vary over time as a result of interconversion. In some embodiments of the invention, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present invention encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid" includes any nucleotides, analogs thereof, and polymers thereof. The term "polynucleotide" as used herein refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges (also referred to herein as "internucleotide linkages"). The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. The prefix poly-refers to a nucleic acid containing 2 to about 10,000 nucleotide monomer units and wherein the prefix oligo- refers to a nucleic acid containing 2 to about 200 nucleotide monomer units.

Nucleotide: The term "nucleotide" as used herein refers to a monomeric unit of a polynucleotide that consists of a heterocyclic base, a sugar, and one or more phosphate groups or phosphorus-containing internucleotidic linkages. The naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein.

Nucleoside: The term "nucleoside" refers to a moiety wherein a nucleobase or a modified nucleobase is covalently bound to a sugar or modified sugar.

Sugar: The term "sugar" refers to a monosaccharide in closed and/or open form. Sugars include, but are not limited to, ribose, deoxyribose, pentofuranose, pentopyranose, and hexopyranose moieties. As used herein, the term also encompasses structural analogs used in lieu of conventional sugar molecules, such as glycol, polymer of which forms the backbone of the nucleic acid analog, glycol nucleic acid ("GNA").

Modified sugar: The term "modified sugar" refers to a moiety that can replace a sugar. The modified sugar mimics the spatial arrangement, electronic properties, or some other physicochemical property of a sugar.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex.

Chiral ligand: The term "chiral ligand" or "chiral auxiliary" refers to a moiety that is chiral and can be incorporated into a reaction so that the reaction can be carried out with certain stereoselectivity.

Condensing reagent: In a condensation reaction, the term "condensing reagent" refers to a reagent that activates a less reactive site and renders it more susceptible to attack by another reagent. In some embodiments, such another reagent is a nucleophile.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule.

Solid support: The term "solid support" refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Linking moiety: The term "linking moiety" refers to any moiety optionally positioned between the terminal nucleoside and the solid support or between the terminal nucleoside and another nucleoside, nucleotide, or nucleic acid.

DNA molecule: A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

Coding sequence: A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence is, usually, be located 3' to the coding sequence. The term "non-coding sequence" or "non-coding region" refers to regions of a polynucleotide sequence that are not translated into amino acids (e.g. 5' and 3' un-translated regions).

Reading frame: The term "reading frame" refers to one of the six possible reading frames, three in each direction, of the double stranded DNA molecule. The reading frame that is used determines which codons are used to encode amino acids within the coding sequence of a DNA molecule.

Antisense: As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can associate via hydrogen bonds to a sense nucleic acid molecule.

Wobble position: As used herein, a "wobble position" refers to the third position of a codon. Mutations in a DNA molecule within the wobble position of a codon, in some embodiments, result in silent or conservative mutations at the amino acid level. For example, there are four codons that encode Glycine, i.e., GGU, GGC, GGA and GGG, thus mutation of any wobble position nucleotide, to any other nucleotide selected from A, U, C and G, does not result in a change at the amino acid level of the encoded protein and, therefore, is a silent substitution.

Silent substitution: a "silent substitution" or "silent mutation" is one in which a nucleotide within a codon is modified, but does not result in a change in the amino acid residue encoded by the codon. Examples include mutations in the third position of a codon, as well in the first position of certain codons such as in the codon "CGG" which, when mutated to AGG, still encodes Arg.

Gene: The terms "gene," "recombinant gene" and "gene construct" as used herein, refer to a DNA molecule, or portion of a DNA molecule, that encodes a protein or a portion thereof. The DNA molecule can contain an open reading frame encoding the protein (as exon sequences) and can further include intron sequences. The term "intron" as used herein, refers to a DNA sequence present in a given gene which is not translated into protein and is found in some, but not all cases, between exons. It can be desirable for the gene to be operably linked to, (or it can comprise), one or more promoters, enhancers, repressors and/or other regulatory sequences to modulate the activity or expression of the gene, as is well known in the art.

Complementary DNA: As used herein, a "complementary DNA" or "cDNA" includes recombinant polynucleotides synthesized by reverse transcription of mRNA and from which intervening sequences (introns) have been removed.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the invention. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

Heterologous: A "heterologous" region of a DNA sequence is an identifiable segment of DNA within a larger DNA sequence that is not found in association with the larger sequence in nature. Thus, when the heterologous region encodes a mammalian gene, the gene can usually be flanked by DNA that does not flank the mammalian genomic DNA in the genome of the source organism. Another example of a heterologous coding sequence is a sequence where the coding sequence itself is not found in nature (e.g., a cDNA where the genomic coding sequence contains introns or synthetic sequences having codons or motifs different than the unmodified gene). Allelic variations or naturally-occurring mutational events do not give rise to a heterologous region of DNA as defined herein.

Transition mutation: The term "transition mutations" refers to base changes in a DNA sequence in which a pyrimidine (cytidine (C) or thymidine (T)) is replaced by another pyrimidine, or a purine (adenosine (A) or guanosine (G)) is replaced by another purine.

Transversion mutation: The term "transversion mutations" refers to base changes in a DNA sequence in which a pyrimidine (cytidine (C) or thymidine (T)) is replaced by a purine (adenosine (A) or guanosine (G), or a purine is replaced by a pyrimidine.

Oligonucleotide: the term "oligonucleotide" refers to a polymer or oligomer of nucleotide monomers, containing any combination of nucleobases, modified nucleobases, sugars, modified sugars, phosphate bridges, or modified phosphorus atom bridges (also referred to herein as "internucleotidic linkage", defined further herein).

Oligonucleotides can be single-stranded or double-stranded. As used herein, the term "oligonucleotide strand" encompasses a single-stranded oligonucleotide. A single-stranded oligonucleotide can have double-stranded regions and a double-stranded oligonucleotide can have single-stranded regions. Exemplary oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, U1 adaptors, triplex-forming oligonucleotides, G-quadruplex oligonucleotides, RNA activators, immuno-stimulatory oligonucleotides, and decoy oligonucleotides.

Double-stranded and single-stranded oligonucleotides that are effective in inducing RNA interference are also referred to as siRNA, RNAi agent, or iRNA agent, herein. In some embodiments, these RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g., by Dicer, to produce smaller oligonucleotides that can enter the RISC machinery and participate in RISC mediated cleavage of a target sequence, e.g. a target mRNA.

Oligonucleotides of the present invention can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Internucleotidic linkage: As used herein, the phrase "internucleotidic linkage" refers generally to the phosphorus-containing linkage between nucleotide units of an oligonucleotide, and is interchangeable with "inter-sugar linkage" and "phosphorus atom bridge," as used above and herein. In some embodiments, an internucleotidic linkage is a phosphodiester linkage, as found in naturally occurring DNA and RNA molecules. In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described below. In some embodiments, an internucleotidic linkage is a phosphotriester linkage, phosphorothioate diester linkage

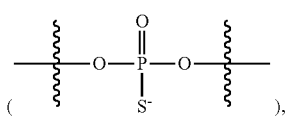 [SMILES: *OP(=O)([S-])O*]

or modified phosphorothioate triester linkage. It is understood by a person of ordinary skill in the art that the internucleotidic linkage may exist as an anion or cation at a given pH due to the existence of acid or base moieties in the linkage.

Unless otherwise specified, when used with an oligonucleotide sequence, each of s, s1, s2, s3, s4, s5, s6 and s7 independently represents the following modified internucleotidic linkage as illustrated in Table 1, below.

TABLE 1

Exemplary Modified Internucleotidic Linkage.

| Symbol | Modified Internucleotidic Linkage |
|---|---|
| s | phosphorothioate |
| s1 | |
| s2 | |
| s3 | |
| s4 | |
| s5 | |
| s6 | |
| s7 | |
| s8 | |
| s9 | |
| s10 | |

TABLE 1-continued

Exemplary Modified Internucleotidic Linkage.

| Symbol | Modified Internucleotidic Linkage |
|---|---|
| s11 | (structure) |
| s12 | (structure) |
| s13 | (structure) |
| s14 | (structure) |
| s15 | (structure) |
| s16 | (structure) |
| s17 | (structure) |
| s18 | (structure) |

For instance, (Rp, Sp)-ATsCs1GA has 1) a phosphorothioate internucleotidic linkage (structure)

between T and C; and 2) a phosphorothioate triester internucleotidic linkage having the structure of (structure)

between C and G. Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively. For instance, All-(Rp)-GsCsCsTsCsAsGsTsCsTsGsCsTsT-sCsGsCsAsCsC (SEQ ID NO: 1) indicates that all the chiral linkage phosphorus atoms in the oligonucleotide have Rp configuration; All-(Sp)-GsCsCsTsCsAsGsTsCsTsGsCsTsT-sCsGsCsAsCsC (SEQ ID NO: 2) indicates that all the chiral linkage phosphorus atoms in the oligonucleotide have Sp configuration.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR$^1$" groups in formula I). Oligonucleotides of a common designated "type" are structurally identical to one another.

One of skill in the art will appreciate that synthetic methods of the present invention provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. The present invention provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in predetermined relative amounts.

Chiral control: As used herein, "chiral control" refers to an ability to control the stereochemical designation of every chiral linkage phosphorus within an oligonucleotide strand. The phrase "chirally controlled oligonucleotide" refers to an oligonucleotide which exists in a single diastereomeric form with respect to the chiral linkage phosphorus.

Chirally controlled oligonucleotide composition: As used herein, the phrase "chirally controlled oligonucleotide composition" refers to an oligonucleotide composition that contains predetermined levels of individual oligonucleotide types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises a mixture of multiple oligonucleotide types. Exemplary chirally controlled oligonucleotide compositions are described further herein.

Chirally pure: as used herein, the phrase "chirally pure" is used to describe a chirally controlled oligonucleotide composition in which all of the oligonucleotides exist in a single diastereomeric form with respect to the linkage phosphorus.

Chirally uniform: as used herein, the phrase "chirally uniform" is used to describe an oligonucleotide molecule or type in which all nucleotide units have the same stereochemistry at the linkage phosphorus. For instance, an oligonucleotide whose nucleotide units all have Rp stereochemistry at the linkage phosphorus is chirally uniform. Likewise, an oligonucleotide whose nucleotide units all have Sp stereochemistry at the linkage phosphorus is chirally uniform.

Predetermined: By predetermined is meant deliberately selected, for example as opposed to randomly occurring or achieved. Those of ordinary skill in the art, reading the present specification, will appreciate that the present invention provides new and surprising technologies that permit selection of particular oligonucleotide types for preparation and/or inclusion in provided compositions, and further permits controlled preparation of precisely the selected particular types, optionally in selected particular relative amounts, so that provided compositions are prepared. Such provided compositions are "predetermined" as described herein. Compositions that may contain certain individual oligonucleotide types because they happen to have been generated through a process that cannot be controlled to intentionally generate the particular oligonucleotide types is not a "predetermined" composition. In some embodiments, a predetermined composition is one that can be intentionally reproduced (e.g., through repetition of a controlled process).

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is P* of formula I. In some embodiments, a linkage phosphorus atom is chiral. In some embodiments, a chiral linkage phosphorus atom is P* of formula I.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-R$^1$ wherein each of X, L and R$^1$ is independently as defined and described herein and below.

Blockmer: the term "blockmer," as used herein, refers to an oligonucleotide strand whose pattern of structural features characterizing each individual nucleotide unit is characterized by the presence of at least two consecutive nucleotide units sharing a common structural feature at the internucleotidic phosphorus linkage. By common structural feature is meant common stereochemistry at the linkage phosphorus or a common modification at the linkage phosphorus. In some embodiments, the at least two consecutive nucleotide units sharing a common structure feature at the internucleotidic phosphors linkage are referred to as a "block".

In some embodiments, a blockmer is a "stereoblockmer," e.g., at least two consecutive nucleotide units have the same stereochemistry at the linkage phosphorus. Such at lest two consecutive nucleotide units form a "stereoblock." For instance, (Sp, Sp)-ATsCs1GA is a stereoblockmer because at least two consecutive nucleotide units, the Ts and the Cs1, have the same stereochemistry at the linkage phosphorus (both Sp). In the same oligonucleotide (Sp, Sp)-ATsCs1GA, TsCs1 forms a block, and it is a stereoblock.

In some embodiments, a blockmer is a "P-modification blockmer," e.g., at least two consecutive nucleotide units have the same modification at the linkage phosphorus. Such at lest two consecutive nucleotide units form a "P-modification block". For instance, (Rp, Sp)-ATsCsGA is a P-modification blockmer because at least two consecutive nucleotide units, the Ts and the Cs, have the same P-modification (i.e., both are a phosphorothioate diester). In the same oligonucleotide of (Rp, Sp)-ATsCsGA, TsCs forms a block, and it is a P-modification block.

In some embodiments, a blockmer is a "linkage blockmer," e.g., at least two consecutive nucleotide units have identical stereochemistry and identical modifications at the linkage phosphorus. At least two consecutive nucleotide units form a "linkage block". For instance, (Rp, Rp)-ATsCsGA is a linkage blockmer because at least two consecutive nucleotide units, the Ts and the Cs, have the same stereochemistry (both Rp) and P-modification (both phosphorothioate). In the same oligonucleotide of (Rp, Rp)-ATsCsGA, TsCs forms a block, and it is a linkage block.

In some embodiments, a blockmer comprises one or more blocks independently selected from a stereoblock, a P-modification block and a linkage block. In some embodiments, a blockmer is a stereoblockmer with respect to one block, and/or a P-modification blockmer with respect to another block, and/or a linkage blockmer with respect to yet another block. For instance, (Rp, Rp, Rp, Rp, Rp, Sp, Sp, Sp)-AAsTsCsGsAs1Ts1Cs1Gs1ATCG (SEQ ID NO: 3) is a stereoblockmer with respect to the stereoblock AsTsCsGsAs1 (all Rp at linkage phosphorus) or Ts1Cs1Gs1 (all Sp at linkage phosphorus), a P-modification blockmer with respect to the P-modification block AsTsCsGs (all s linkage) or As1Ts1Cs1Gs1 (all s1 linkage), or a linkage blockmer with respect to the linkage block AsTsCsGs (all Rp at linkage phosphorus and all s linkage) or Ts1Cs1Gs1 (all Sp at linkage phosphorus and all s1 linkage).

Altmer: the term "altmer," as used herein, refers to an oligonucleotide strand whose pattern of structural features characterizing each individual nucleotide unit is characterized in that no two consecutive nucleotide units of the oligonucleotide strand share a particular structural feature at the internucleotidic phosphorus linkage. In some embodiments, an altmer is designed such that it comprises a repeating pattern. In some embodiments, an altmer is designed such that it does not comprise a repeating pattern.

In some embodiments, an altmer is a "stereoaltmer," e.g., no two consecutive nucleotide units have the same stereochemistry at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTsGsCsTsTsCsGsCsAsCsC (SEQ ID NO: 4).

In some embodiments, an altmer is a "P-modification altmer" e.g., no two consecutive nucleotide units have the same modification at the linkage phosphorus. For instance, All-(Sp)-CAs1GsT, in which each linkage phosphorus has a different P-modification than the others.

In some embodiments, an altmer is a "linkage altmer," e.g., no two consecutive nucleotide units have identical stereochemistry or identical modifications at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCs1CsTs1CsAs1GsTs1CsTs1GsCs1TsTs2CsGs3Cs As4CsC (SEQ ID NO: 5).

Unimer: the term "unimer," as used herein, refers to an oligonucleotide strand whose pattern of structural features characterizing each individual nucleotide unit is such that all nucleotide units within the strand share at least one common structural feature at the internucleotidic phosphorus linkage. By common structural feature is meant common stereochemistry at the linkage phosphorus or a common modification at the linkage phosphorus.

In some embodiments, a unimer is a "stereounimer," e.g., all nucleotide units have the same stereochemistry at the linkage phosphorus. For instance, All-(Sp)-CsAs1GsT, in which all the linkages have Sp phosphorus.

In some embodiments, a unimer is a "P-modification unimer", e.g., all nucleotide units have the same modification at the linkage phosphorus. For instance, (Rp, Sp, Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTsGsCsTsTsCsGsCsAsCsC (SEQ ID NO: 6), in which all the internucleotidic linkages are phosphorothioate diester.

In some embodiments, a unimer is a "linkage unimer," e.g., all nucleotide units have the same stereochemistry and the same modifications at the linkage phosphorus. For instance, All-(Sp)-GsCsCsTsCsAsGsTsCsTsGsCsTsTsCsGsCsAsCsC (SEQ ID NO: 7), in which all the internucleotidic linkages are phosphorothioate diester having Sp linkage phosphorus.

Gapmer: as used herein, the term "gapmer" refers to an oligonucleotide strand characterized in that at least one internucleotidic phosphorus linkage of the oligonucleotide strand is a phosphate diester linkage, for example such as those found in naturally occurring DNA or RNA. In some embodiments, more than one internucleotidic phosphorus linkage of the oligonucleotide strand is a phosphate diester linkage such as those found in naturally occurring DNA or RNA. For instance, All-(Sp)-CAs1GsT, in which the internucleotidic linkage between C and A is a phosphate diester linkage.

Skipmer: as used herein, the term "skipmer" refers to a type of gapmer in which every other internucleotidic phosphorus linkage of the oligonucleotide strand is a phosphate diester linkage, for example such as those found in naturally occurring DNA or RNA, and every other internucleotidic phosphorus linkage of the oligonucleotide strand is a modified internucleotidic linkage. For instance, All-(Sp)-AsTCs1GAs2TCs3G.

For purposes of this invention, the chemical elements are identified in accordance with the Periodic Table of the Elements, CAS version, *Handbook of Chemistry and Physics,* 67th Ed., 1986-87, inside cover.

The methods and structures described herein relating to compounds and compositions of the invention also apply to the pharmaceutically acceptable acid or base addition salts and all stereoisomeric forms of these compounds and compositions.

ONT-400 (SEQ ID NO: 575), ONT-402 (SEQ ID NO: 577), ONT-406 (SEQ ID NO: 581).

Figure 24:
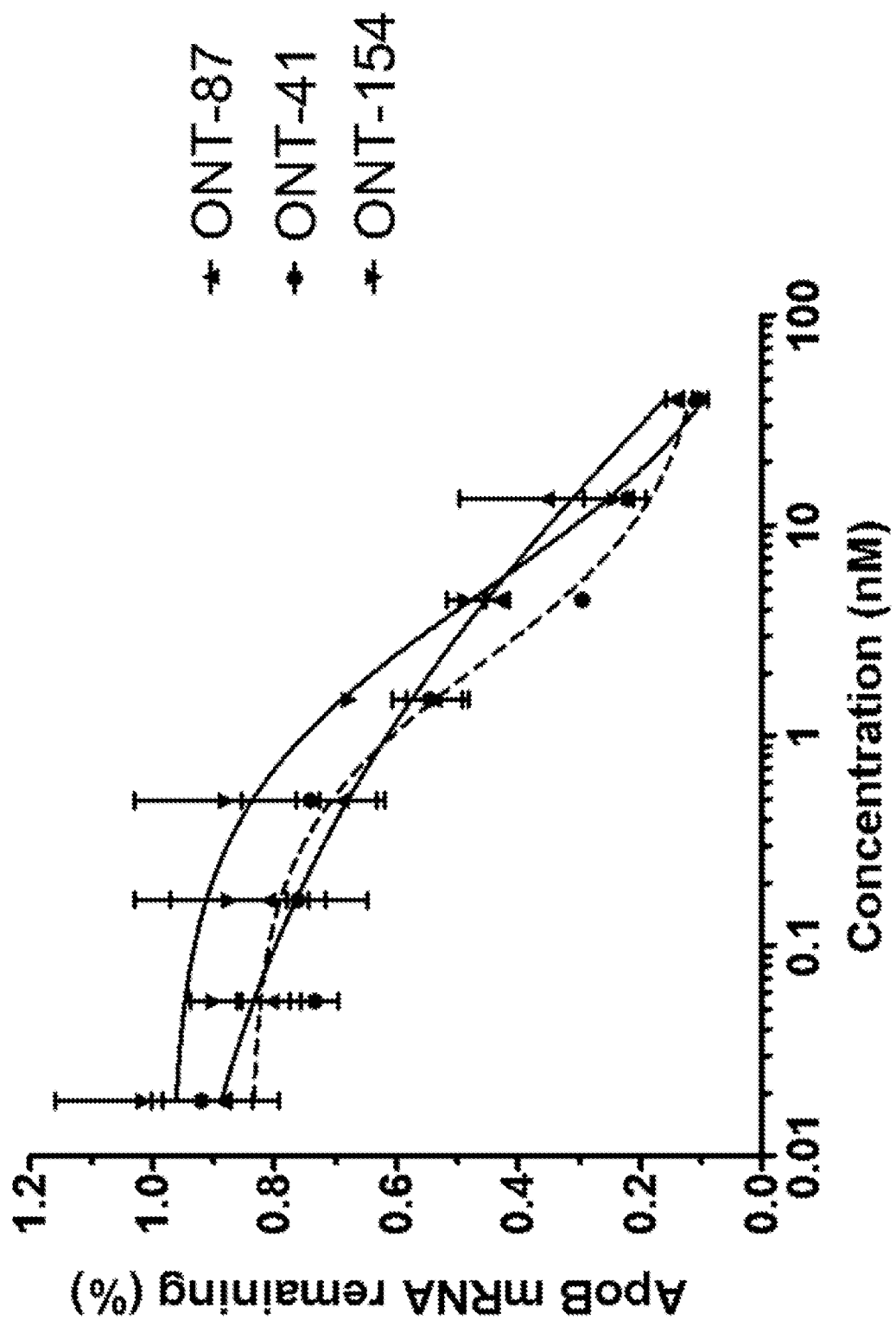

FIG. 24. In vitro dose response silencing of ApoB mRNA after treatment with ApoB oligonucleotides. Stereochemically pure diastereomers with and without 2'-MOE wings show similar efficacy as ONT-41 (Mipomersen).

Figure 25:
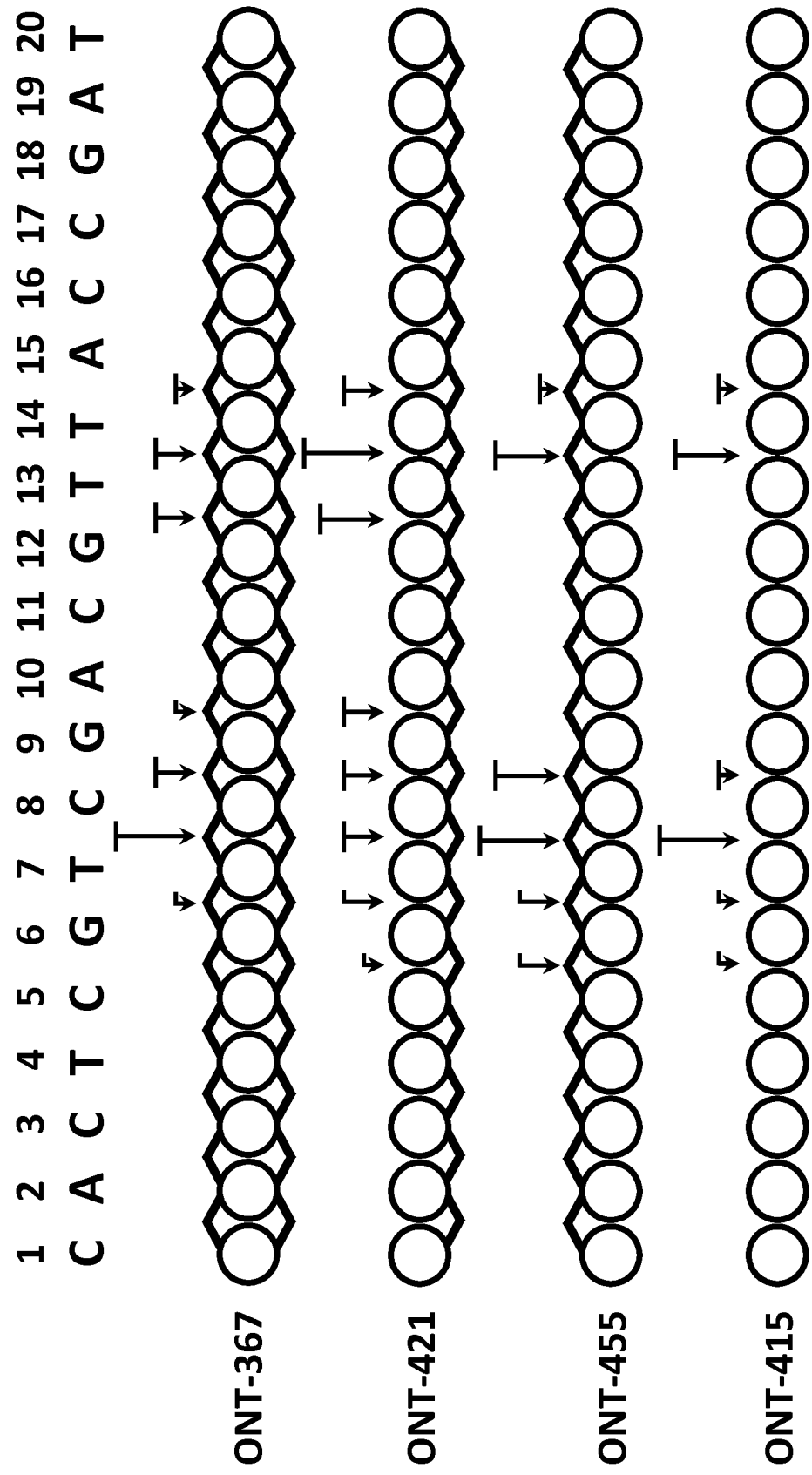
Figure 25:
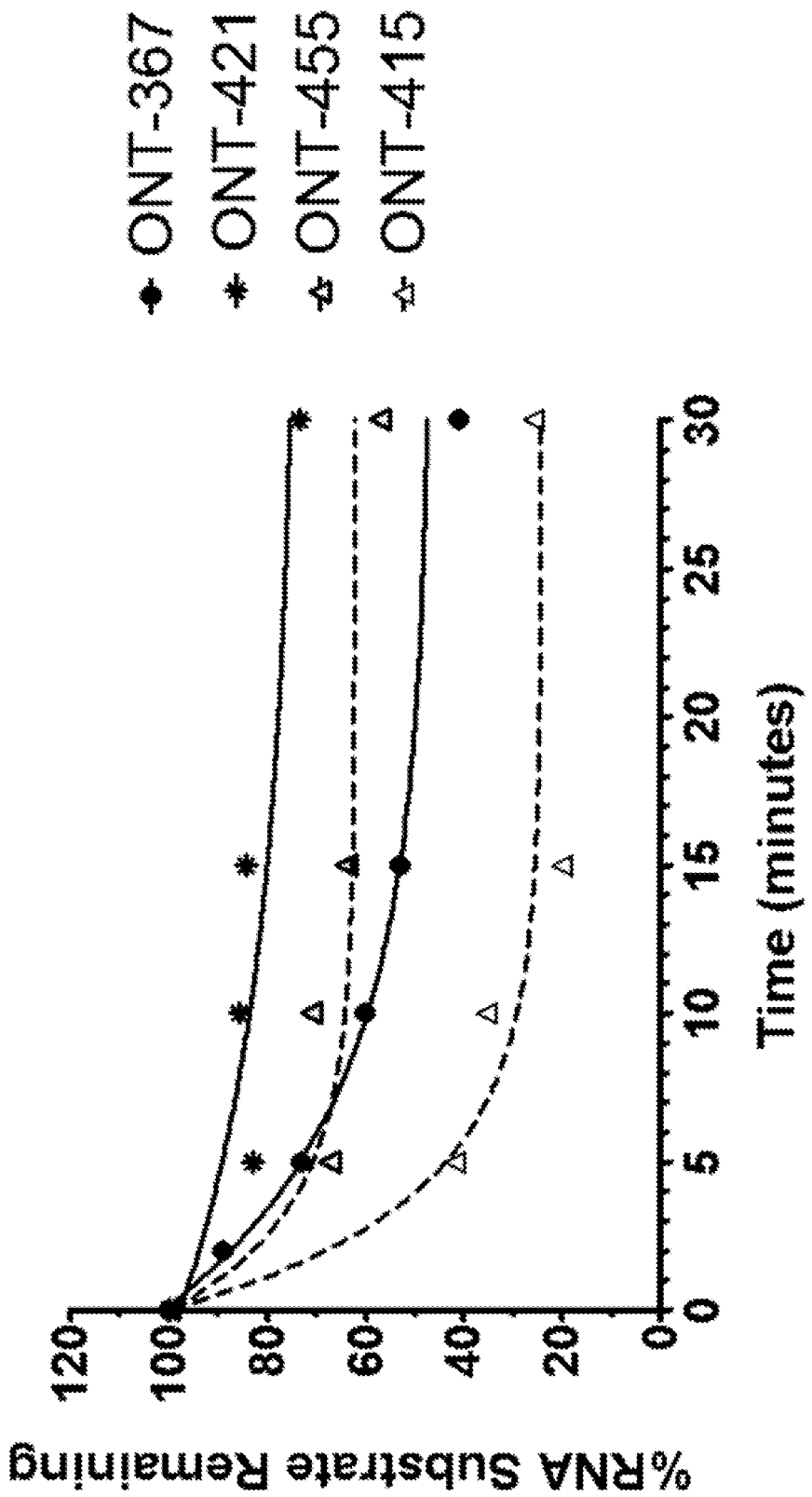

FIG. 25. Comparison of RNase H cleavage maps (A) and RNA cleavage rates (B) for stereorandom composition (ONT-367) and chirally controlled oligonucleotide compositions (ONT-421, all Sp and ONT-455, all Rp) and DNA (ONT-415). These sequences target the same region in FOXO1 mRNA. Cleavage maps were derived from the reaction mixtures obtained after 5 minutes of incubation of respective duplexes with RNase H1C in the presence of 1×PBS buffer at 37° C. Arrows indicate sites of cleavage. ( ⊤ ) indicates that both fragments, 5'-phosphate specie as well as 5'-OH 3'-OH specie were identified in reaction mixtures. ( ⌈ ) indicates that only 5'-phosphate specie was detected and ( ⌉ ) indicates that 5'-OH 3'-OH component was detected in mass spectrometry analysis. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate specie peak was used for quantification. Cleavage rates were determined by measuring amount of full length RNA remaining in the reaction mixtures by reverse phase HPLC. Reactions are quenched at fixed time points by 30 mM Na₂EDTA. ONT-367 (SEQ ID NO: 519), ONT-421 (SEQ ID NO: 590), ONT-455 (SEQ ID NO: 592), and ONT-415 (SEQ ID NO: 560).

Figure 26:
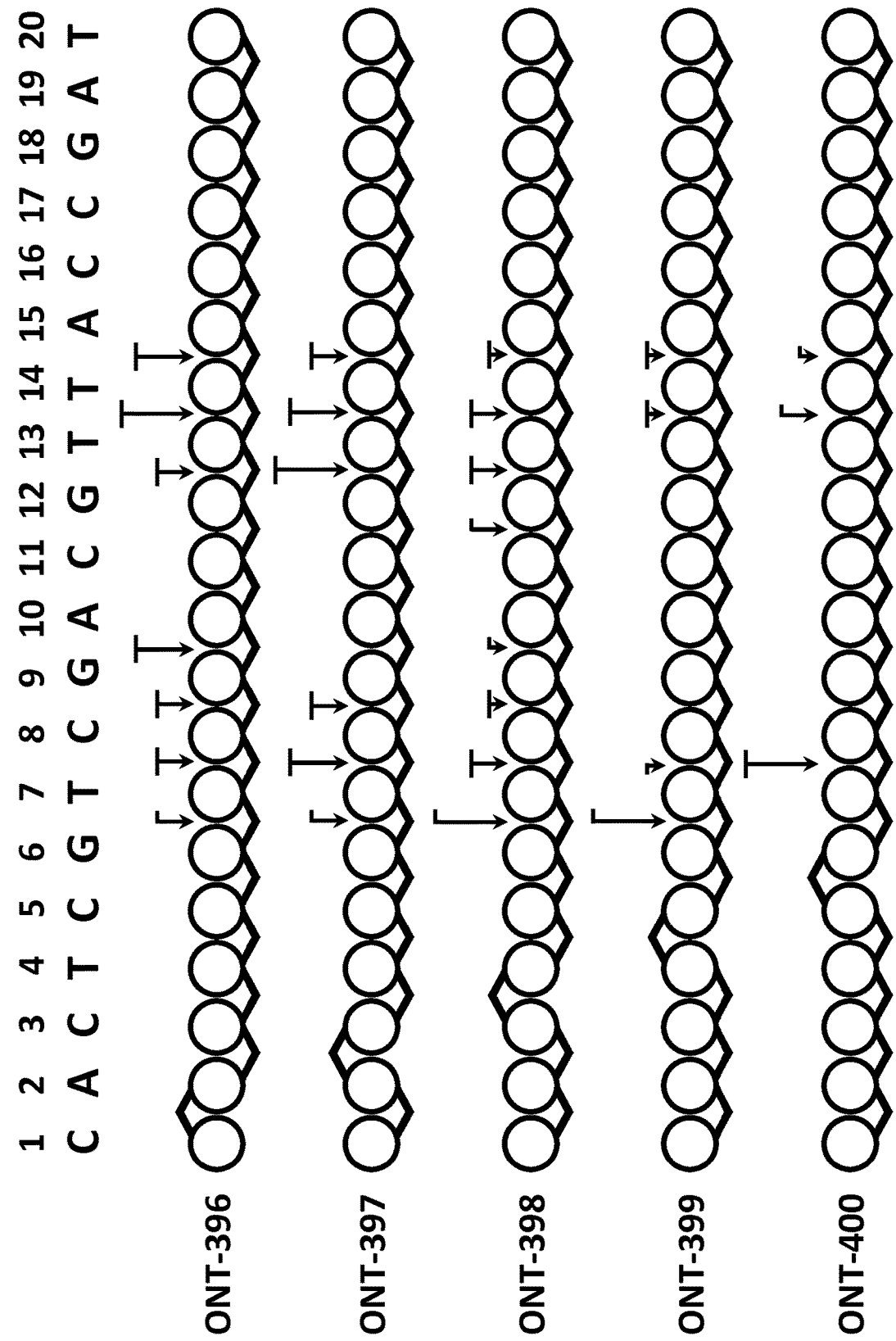

FIG. 26. Comparison of cleavage maps of sequences containing one Rp with change of position starting from 3'-end of DNA. These sequences target the same region in FOXO1 mRNA. Cleavage maps are derived from the reaction mixtures obtained after 5 minutes of incubation of respective duplexes with RNase H1C in the presence of 1×PBS buffer at 37° C. Arrows indicate sites of cleavage. ( ⊤ ) indicates that both fragments, 5'-phosphate specie as well as 5'-OH 3'-OH specie were identified in reaction mixtures. ( ⌈ ) indicates that only 5'-phosphate specie was detected and ( ⌉ ) indicates that 5'-OH 3'-OH component was detected in mass spectrometry analysis. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate specie peak was used for quantification. ONT-396 (SEQ ID NO: 571), ONT-397 (SEQ ID NO: 572), ONT-398 (SEQ ID NO: 573), ONT-399 (SEQ ID NO: 574), ONT-400 (SEQ ID NO: 575), ONT-401 (SEQ ID NO: 576), ONT-402 (SEQ ID NO: 577), ONT-403 (SEQ ID NO: 578), ONT-404 (SEQ ID NO: 579), ONT-405 (SEQ ID NO: 580), ONT-406 (SEQ ID NO: 581), ONT-407 (SEQ ID NO: 582), ONT-408 (SEQ ID NO: 583), ONT-409 (SEQ ID NO: 584), ONT-410 (SEQ ID NO: 585), ONT-411 (SEQ ID NO: 586), ONT-412 (SEQ ID NO: 587), ONT-413 (SEQ ID NO: 588), and ONT-414 (SEQ ID NO: 589).

Figure 27:
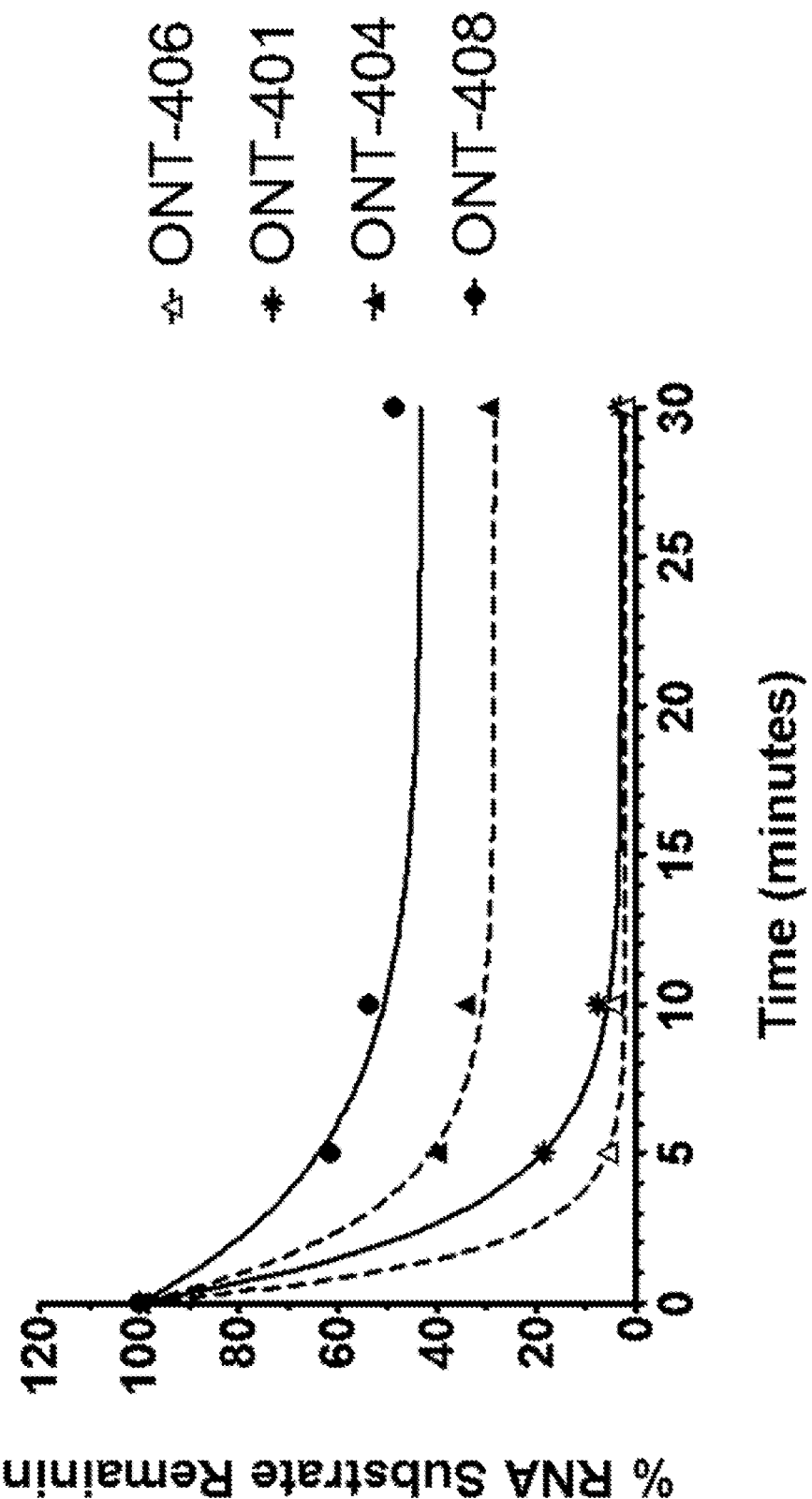

FIG. 27. (A) Comparison of RNase H cleavage rates for stereopure oligonucleotides (ONT-406), (ONT-401), (ONT-404) and (ONT-408). All four sequences are stereopure phosphorothioates with one Rp linkage. These sequences target the same region in FOXO1 mRNA. All duplexes were incubation with RNase H1C in the presence of 1×PBS buffer at 37° C. Reactions were quenched at fixed time points by 30 mM Na₂EDTA. Cleavage rates were determined by measuring amount of full length RNA remaining in the reaction mixtures by reverse phase HPLC. ONT-406 and ONT-401 were found to have superior cleavage rates. (B) Correlation between % RNA cleaved in RNase H assay (10 µM oligonucleotide) and % mRNA knockdown in in vitro assay (20 nM oligonucleotide). All sequences target the same region of mRNA in the FOXO1 target. The quantity of RNA remaining is determined by UV peak area for RNA when normalized to DNA in the same reaction mixture. All of the above maps are derived from the reaction mixture obtained after 5 minutes of incubation of respective duplexes with RNase H1C in the presence of 1×PBS buffer at 37° C. All sequences from ONT-396 to ONT-414 have one Rp phosphorothioate and they vary in the position of Rp. ONT-421 (All Sp) phosphorothioate was inactive in-vitro assay. It relates poor cleavage rate of RNA in RNase H assay when ONT-421 is duplexed with complementary RNA.

Figure 28:
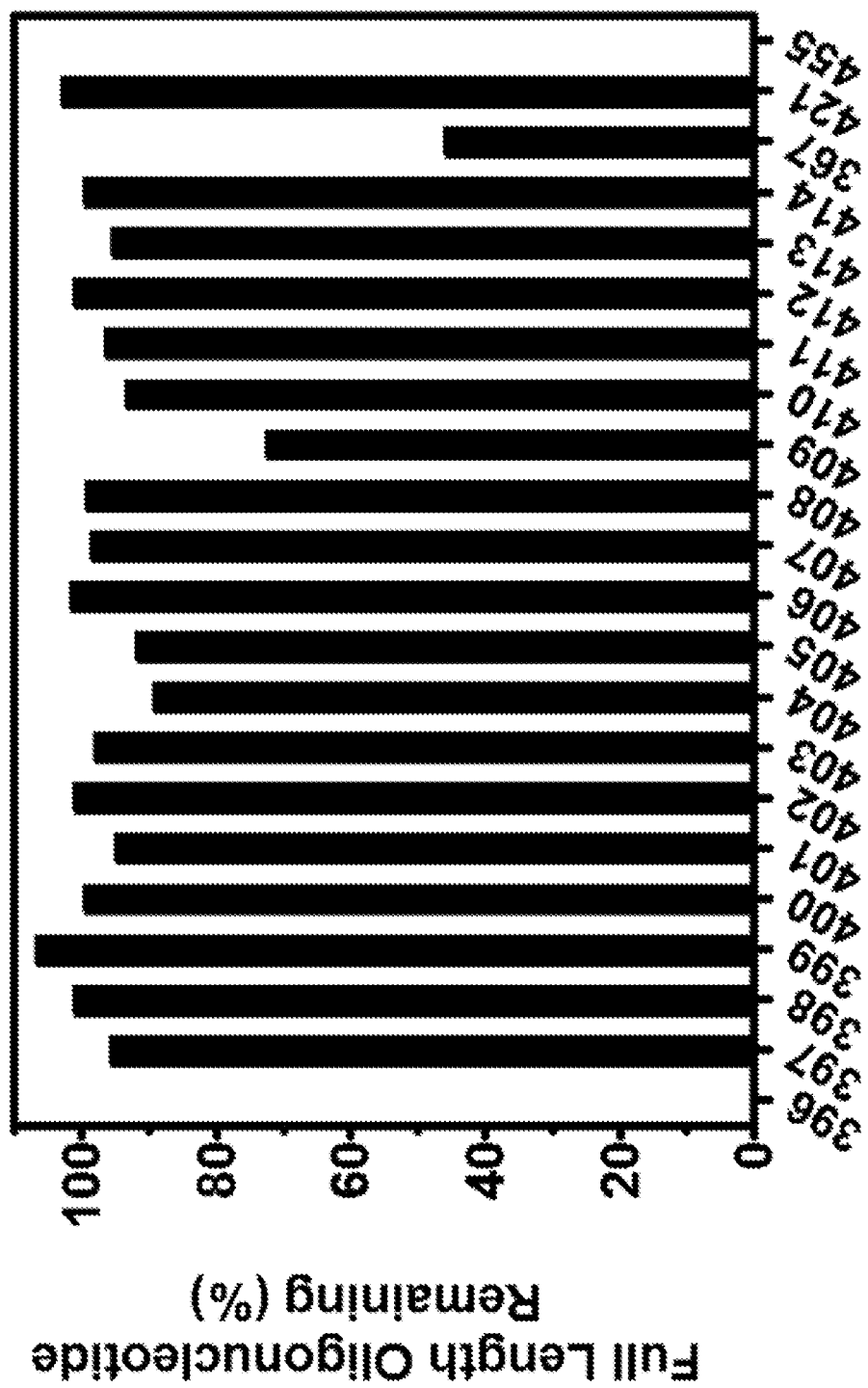

FIG. 28. Serum stability assay of single Rp walk PS DNA (ONT-396-ONT-414), stereorandom PS DNA (ONT-367), all-Sp PS DNA (ONT-421) and all-Rp PS DNA (ONT-455) in rat serum for 2 days. Note ONT-396 and ONT-455 decomposed at tested time point.

Figure 29:
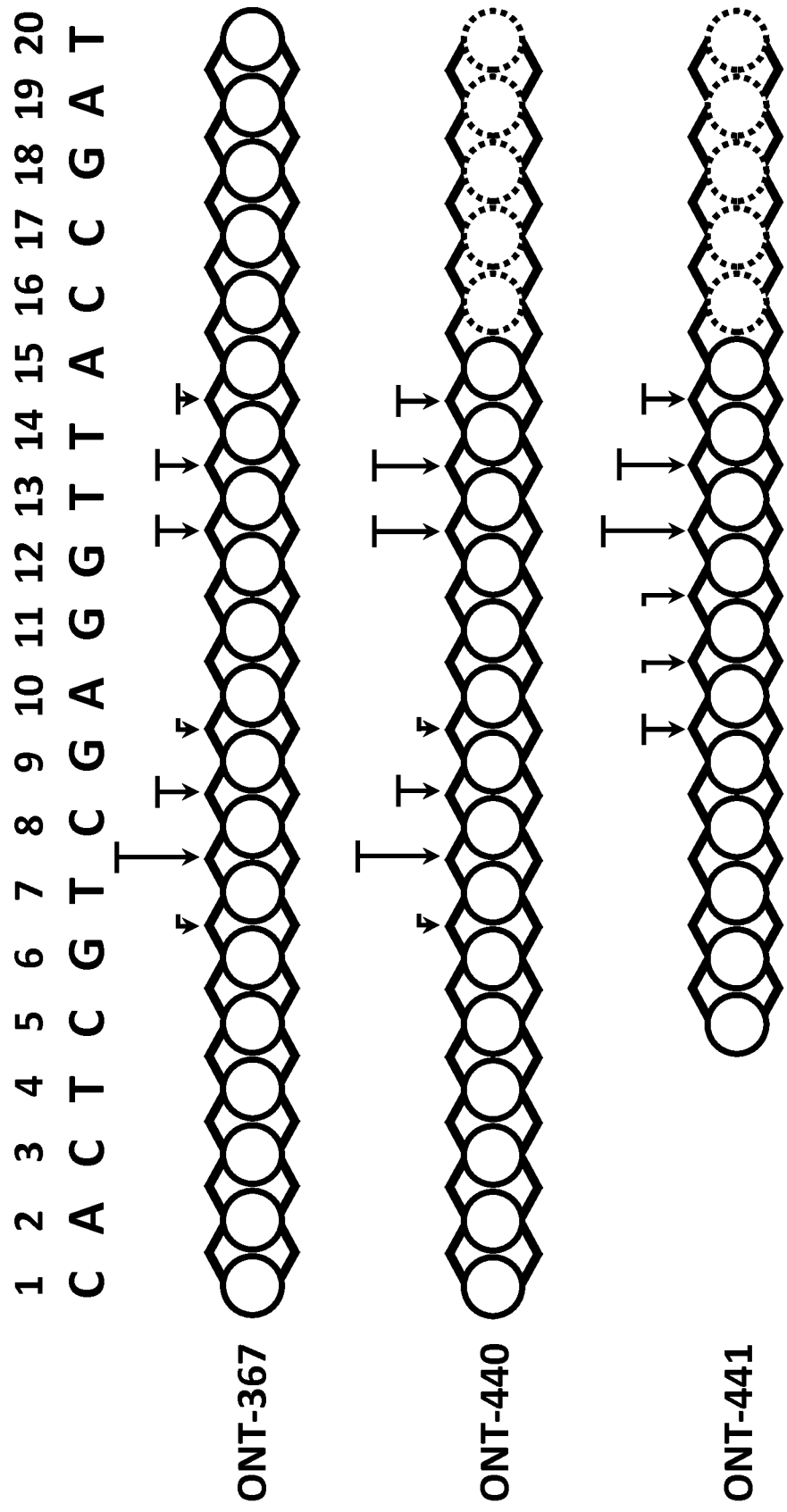
Figure 29:
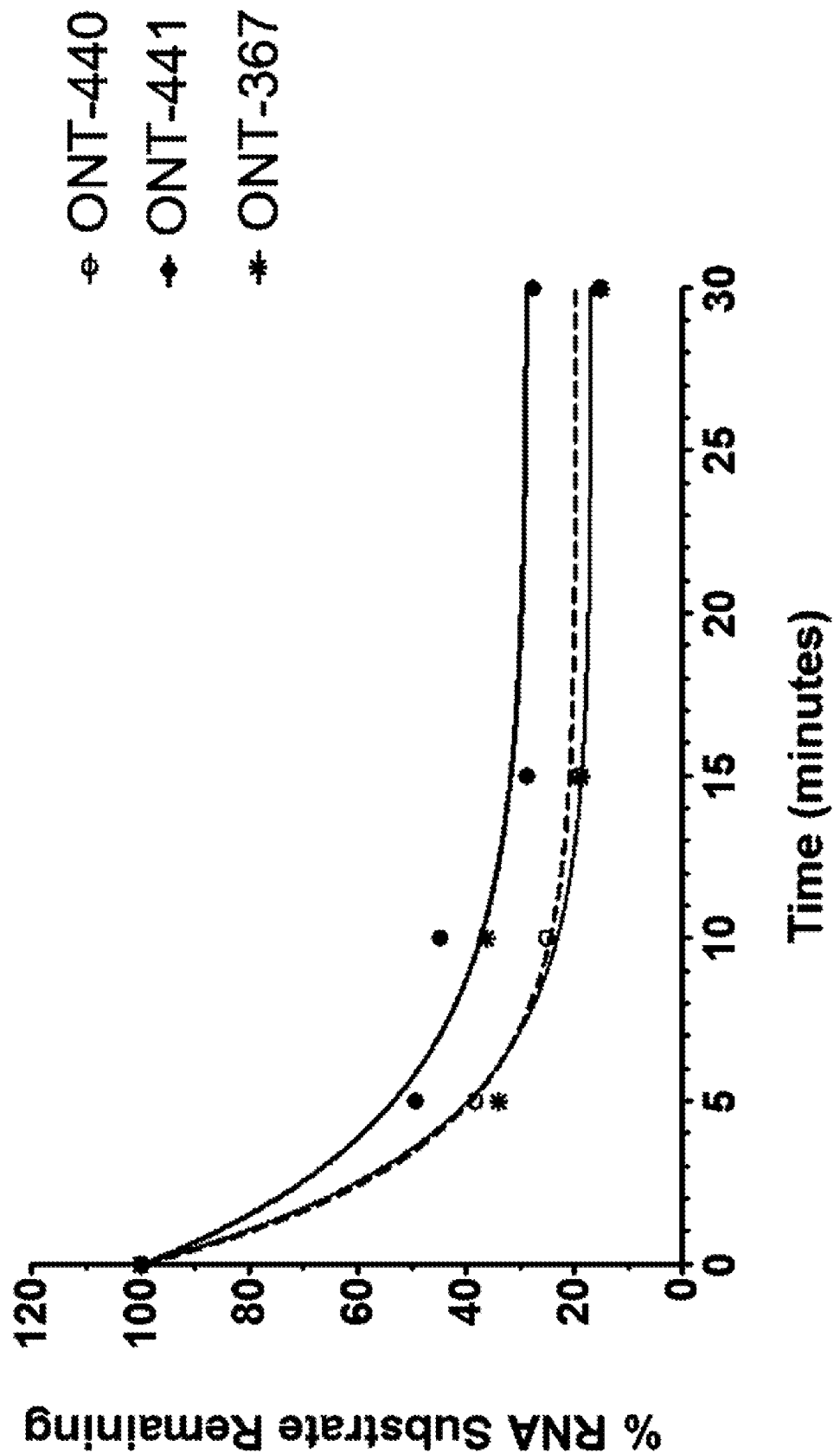
Figure 29:
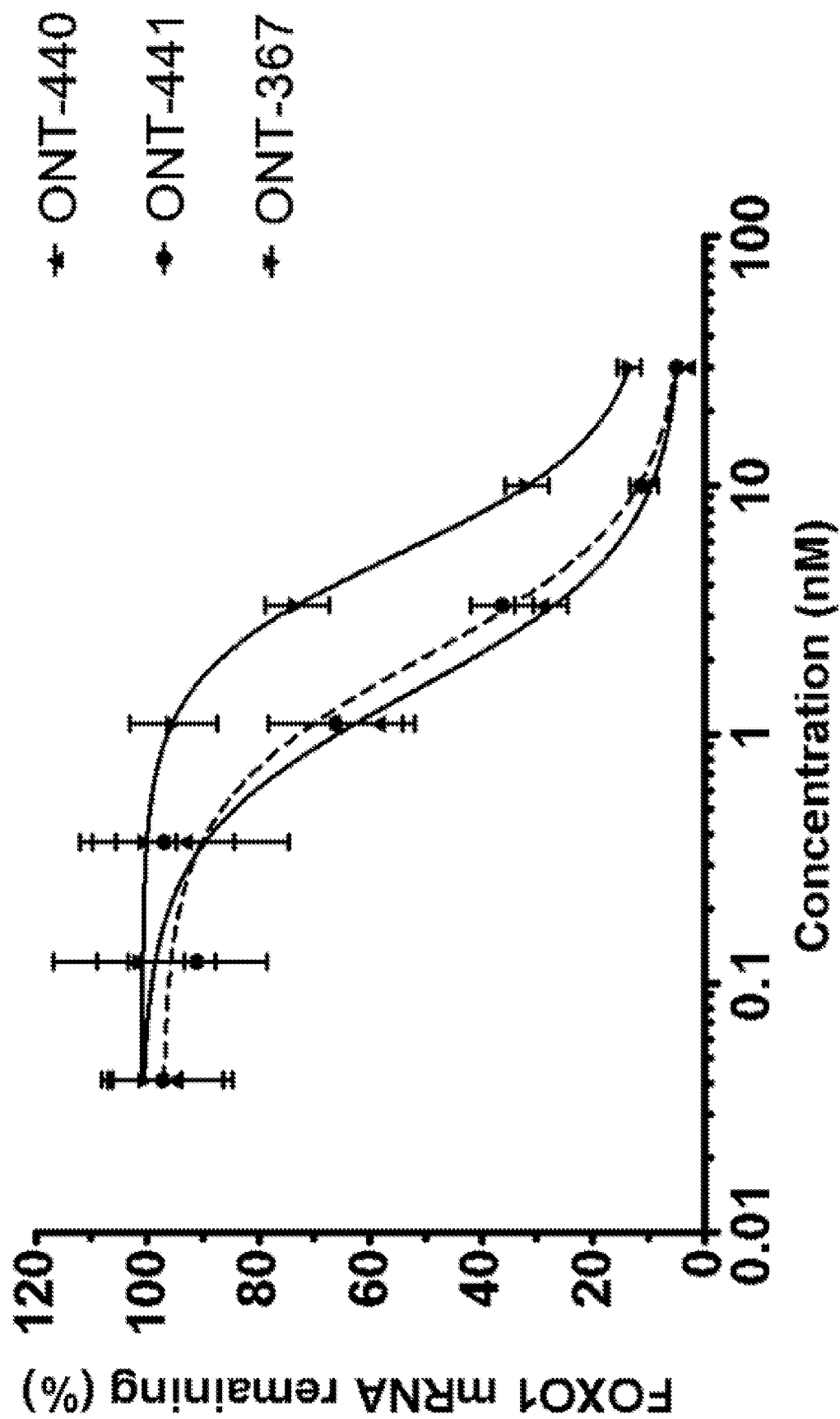

FIG. 29. Exemplary oligonucleotides including hemimers. (A): cleavage maps. (B): RNA cleavage assay. (C): FOXO1 mRNA knockdown. In some embodiments, introduction of 2'-modifications on 5'-end of the sequences increases stability for binding to target RNA while maintaining RNase H activity. ONT-367 (stereorandom phosphorothioate DNA) and ONT-440 (5-15, 2'-F-DNA) have similar cleavage maps and similar rate of RNA cleavage in RNase H assay (10 µM oligonucleotide). In some embodiments, ONT-440 (5-11, 2'-F-DNA) sequence can have better cell penetration properties. In some embodiments, asymmetric 2'-modifications provide Tm advantage while maintaining RNase H activity. Introduction of RSS motifs can further enhance RNase H efficiency in the hemimers. Cleavage maps are derived from the reaction mixtures obtained after 5 minutes of incubation of respective duplexes with RNase H1C in the presence of 1×PBS buffer at 37° C. Arrows indicate sites of cleavage. ( ⊤ ) indicates that both fragments, 5'-phosphate specie as well as 5'-OH 3'-OH specie were identified in reaction mixtures. ( ⌈ ) indicates that only 5'-phosphate specie was detected and ( ⌉ ) indicates that 5'-OH 3'-OH component was detected in mass spectrometry analysis. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate specie peak was used for quantification. ONT-367 (SEQ ID NO: 511), ONT-440 (SEQ ID NO: 611), ONT-441 (SEQ ID NO: 612).

Figure 30:
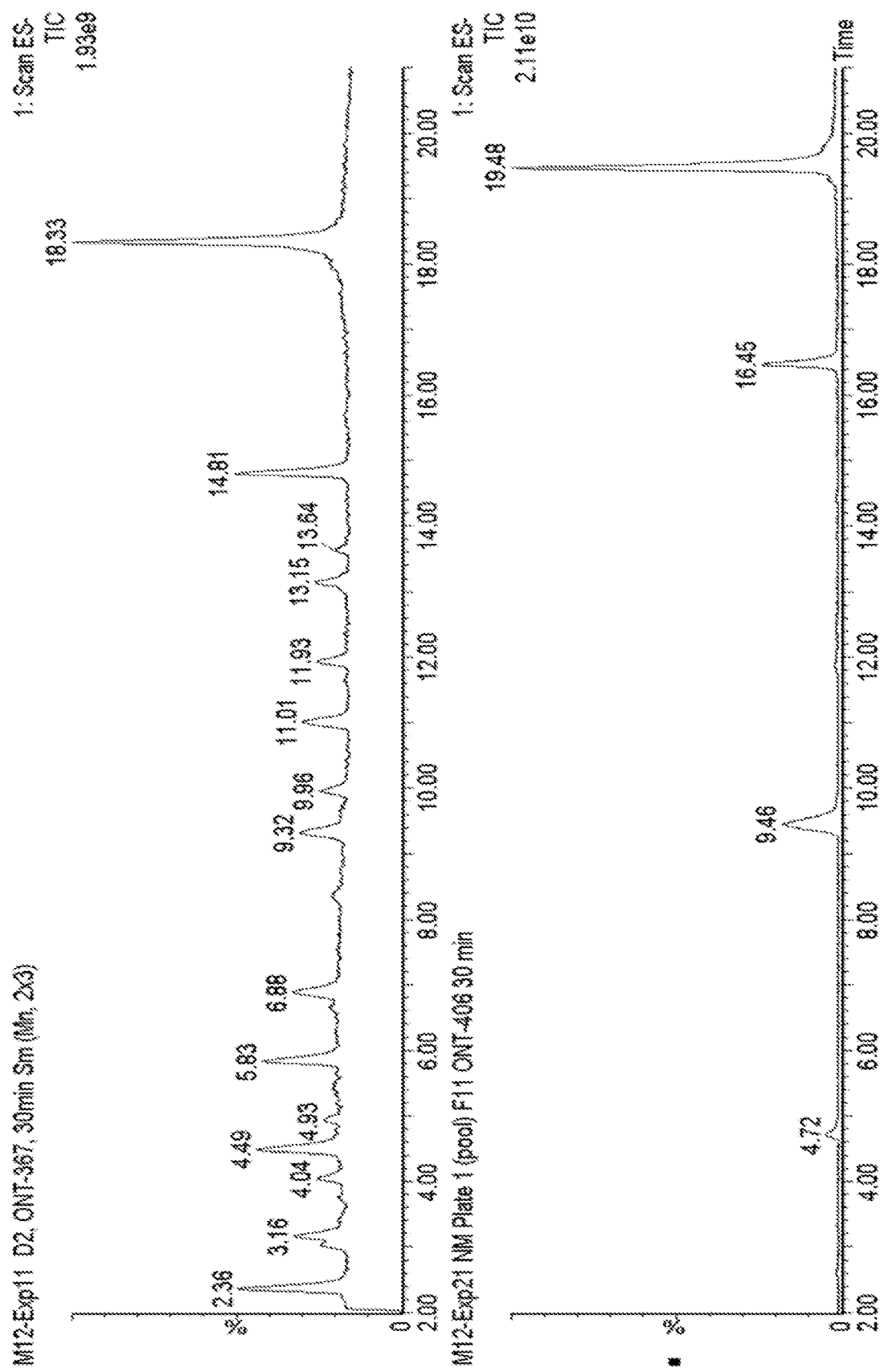

FIG. 30. Exemplary mass spectrometry data of cleavage assay. Top: data for ONT-367: 2.35 min: 7 mer; 3.16 min: 8 mer and P-6 mer; 4.58 min: P-7 mer; 5.91 min: P-8 mer; 7.19 min: 12 mer; 9.55 min: 13 mer; 10.13 min: P-11 mer; 11.14 min: P-12 mer and 14 mer; 12.11 min: P-13 mer; 13.29 min: P-14 mer; 14.80 min: full length RNA (ONT-388) and 18.33 min: stereorandom DNA (ONT-367). Bottom: data for ONT-406: 4.72 min: p-rArUrGrGrCrUrA, 5'-phosphorylated 7 mer RNA; 9.46 min: 5'-rGrUrGrArGrCrArGrCrUrGrCrA (SEQ ID NO: 8), 5'-OH 3'-OH 13 mer RNA; 16.45 min: full length RNA (ONT-388); 19.48 and 19.49 min: stereopure DNA (ONT-406).

DETAILED DESCRIPTION OF CERTAIN EMBODIMENTS

Synthetic oligonucleotides provide useful molecular tools in a wide variety of applications. For example, oligonucleotides are useful in therapeutic, diagnostic, research, and new nanomaterials applications. The use of naturally occurring nucleic acids (e.g., unmodified DNA or RNA) is limited, for example, by their susceptibility to endo- and exo-nucleases. As such, various synthetic counterparts have been developed to circumvent these shortcomings. These include synthetic oligonucleotides that contain backbone modifications, which render these molecules less susceptible to degradation. From a structural point of view, such modifications to internucleotide phosphate linkages introduce chirality. It has become clear that certain properties of oligonucleotides may be affected by the configurations of the phosphorus atoms that form the backbone of the oligonucleotides. For example, in vitro studies have shown that the properties of antisense nucleotides such as binding affinity, sequence specific binding to the complementary RNA, stability to nucleases are affected by, inter alia, chirality of the backbone (e.g., the configurations of the phosphorus atoms).

Among other things, the present invention encompasses the recognition that stereorandom oligonucleotide preparations contain a plurality of distinct chemical entities that differ from one another in the stereochemical structure of individual backbone chiral centers within the oligonucleotide chain. Moreover, the present invention encompasses the insight that it is typically unlikely that a stereorandom oligonucleotide preparation will include every possible stereoisomer of the relevant oligonucleotide. Thus, among other things, the present invention provides new chemical entities that are particular stereoisomers of oligonucleotides of interest. That is, the present invention provides substantially pure preparations of single oligonucleotide compounds, where a particular oligonucleotide compound may be defined by its base sequence, its length, its pattern of backbone linkages, and its pattern of backbone chiral centers.

The present invention demonstrates, among other things, that individual stereoisomers of a particular oligonucleotide can show different stability and/or activity from each other. Moreover, the present disclosure demonstrates that stability improvements achieved through inclusion and/or location of particular chiral structures within an oligonucleotide can be comparable to, or even better than those achieved through use of modified backbone linkages, bases, and/or sugars (e.g., through use of certain types of modified phosphates, 2'-modifications, base modifications, etc.). The present disclosure, in some embodiments, also demonstrates that activity improvements achieved through inclusion and/or location of particular chiral structures within an oligonucleotide can be comparable to, or even better than those achieved through use of modified backbone linkages, bases, and/or sugars (e.g., through use of certain types of modified phosphates, 2'-modifications, base modifications, etc.). In some embodiments, inclusion and/or location of particular chiral linkages within an oligonucleotide can surprisingly change the cleavage pattern of a nucleic acid polymer when such an oligonucleotide is utilized for cleaving said nucleic acid polymer. For example, in some embodiments, a pattern of backbone chiral centers provides unexpectedly high cleavage efficiency of a target nucleic acid polymer. In some embodiments, a pattern of backbone chiral centers provides new cleavage sites. In some embodiments, a pattern of backbone chiral centers provides fewer cleavage sites, for example, by blocking certain existing cleavage sites. Even more unexpectedly, in some embodiments, a pattern of backbone chiral centers provides cleavage at only one site of a target nucleic acid polymer within the sequence that is complementary to a oligonucleotide utilized for cleavage. In some embodiments, higher cleavage efficiency is achieved by selecting a pattern of backbone chiral centers to minimize the number of cleavage sites.

In some embodiments, the present invention provides chirally controlled (and/or stereochemically pure) oligonucleotide compositions comprising oligonucleotides defined by having:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers. A pattern of backbone chiral centers of an oligonucleotide can be designated by a combination of linkage phosphorus stereochemistry (Rp/Sp) from 5' to 3'. For example, as exemplified below ONT-154 has a pattern of 5S-(SSR)$_3$-5S, and ONT-80 has $S_{19}$.

In some embodiments, the present invention provides chirally controlled oligonucleotide composition of oligonucleotides in that the composition is enriched, relative to a substantially racemic preparation of the same oligonucleotides, for oligonucleotides of a single oligonucleotide type. In some embodiments, the present invention provides chirally controlled oligonucleotide composition of oligonucleotides in that the composition is enriched, relative to a substantially racemic preparation of the same oligonucleotides, for oligonucleotides of a single oligonucleotide type that share:
1) a common base sequence and length;
2) a common pattern of backbone linkages; and
3) a common pattern of backbone chiral centers.

In some embodiments, in a substantially racemic (or chirally uncontrolled) preparation of oligonucleotides, all or most coupling steps are not chirally controlled in that the coupling steps are not specifically conducted to provide enhanced stereoselectivity. An exemplary substantially racemic preparation of oligonucleotides is the preparation of phosphorothioate oligonucleotides through sulfurizing phosphite triesters with either tetraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions).

In some embodiments, the present invention provides a chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type. In some embodiments, a chirally controlled oligonucleotide composition is a substantially pure preparation of a oligonucleotide type in that oligonucleotides in the composition that are not of the oligonucleotide type are impurities form the preparation process of said oligonucleotide type, in some case, after certain purification procedures.

In some embodiments, at least about 20% of the oligonucleotides in the composition have a common base sequence and length, a common pattern of backbone linkages, and a common pattern of backbone chiral centers. In some embodiments, at least about 25% of the oligonucleotides in the composition have a common base sequence and length, a common pattern of backbone linkages, and a common pattern of backbone chiral centers. In some embodiments, at least about 30% of the oligonucleotides in the composition have a common base sequence and length, a common pattern of backbone linkages, and a common pattern of backbone chiral centers. In some embodiments, at least about 35% of the oligonucleotides in the composition have a common base sequence and length, a common pattern of backbone linkages, and a common pattern of backbone chiral centers. In some embodiments, at least about 40% of the oligonucleotides in the composition have a common base sequence and length, a common pattern of backbone linkages, and a common pattern of backbone chiral centers. In some embodiments, at least about 45% of the oligonucleotides in the composition have a common base sequence and length, a common pattern of backbone linkages, and a common pattern of backbone chiral centers. In some embodiments, at least about 50% of the oligonucleotides in the composition have a common base sequence and length, a common pattern of backbone linkages, and a common pattern of backbone chiral centers. In some embodiments, at least about 55% of the oligonucleotides in the composition have a common base sequence and length, a common pattern of backbone linkages, and a common pattern of backbone chiral centers. In some embodiments, at least about 60% of the oligonucleotides in the composition have a common base sequence and length, a common pattern of backbone linkages, and a common pattern of backbone chiral centers. In some embodiments, at least about 65% of the oligonucleotides in the composition have a common base sequence and length, a common pattern of backbone linkages, and a common pattern of backbone chiral centers. In some embodiments, at least about 70% of the oligonucleotides in the composition have a common base sequence and length, a common pattern of backbone linkages, and a common pattern of backbone chiral centers. In some embodiments, at least about 75% of the oligonucleotides in the composition have a common base sequence and length, a common pattern of backbone linkages, and a common pattern of backbone chiral centers. In some embodiments, at least about 80% of the oligonucleotides in the composition have a common base sequence and length, a common pattern of backbone linkages, and a common pattern of backbone chiral centers. In some embodiments, at least about 85% of the oligonucleotides in the composition have a common base sequence and length, a common pattern of backbone linkages, and a common pattern of backbone chiral centers. In some embodiments, at least about 90% of the oligonucleotides in the composition have a common base sequence and length, a common pattern of backbone linkages, and a common pattern of backbone chiral centers. In some embodiments, at least about 92% of the oligonucleotides in the composition have a common base sequence and length, a common pattern of backbone linkages, and a common pattern of backbone chiral centers. In some embodiments, at least about 94% of the oligonucleotides in the composition have a common base sequence and length, a common pattern of backbone linkages, and a common pattern of backbone chiral centers. In some embodiments, at least about 95% of the oligonucleotides in the composition have a common base sequence and length, a common pattern of backbone linkages, and a common pattern of backbone chiral centers. In some embodiments, at least about 91%, 92%, 93%, 94%, 95%, 96%, 97%, 98%, or 99% of the oligonucleotides in the composition have a common base sequence and length, a common pattern of backbone linkages, and a common pattern of backbone chiral centers. In some embodiments, greater than about 99% of the oligonucleotides in the composition have a common base sequence and length, a common pattern of backbone linkages, and a common pattern of backbone chiral centers. In some embodiments, purity of a chirally controlled oligonucleotide composition of an oligonucleotide can be expressed as the percentage of oligonucleotides in the composition that have a common base sequence and length, a common pattern of backbone linkages, and a common pattern of backbone chiral centers.

In some embodiments, purity of a chirally controlled oligonucleotide composition of an oligonucleotide type is expressed as the percentage of oligonucleotides in the composition that are of the oligonucleotide type. In some embodiments, at least about 10% of the oligonucleotides in a chirally controlled oligonucleotide composition are of the same oligonucleotide type. In some embodiments, at least about 20% of the oligonucleotides in a chirally controlled oligonucleotide composition are of the same oligonucleotide type. In some embodiments, at least about 30% of the oligonucleotides in a chirally controlled oligonucleotide composition are of the same oligonucleotide type. In some embodiments, at least about 40% of the oligonucleotides in a chirally controlled oligonucleotide composition are of the same oligonucleotide type. In some embodiments, at least about 50% of the oligonucleotides in a chirally controlled oligonucleotide composition are of the same oligonucleotide type. In some embodiments, at least about 60% of the oligonucleotides in a chirally controlled oligonucleotide composition are of the same oligonucleotide type. In some embodiments, at least about 70% of the oligonucleotides in a chirally controlled oligonucleotide composition are of the same oligonucleotide type. In some embodiments, at least about 80% of the oligonucleotides in a chirally controlled oligonucleotide composition are of the same oligonucleotide type. In some embodiments, at least about 90% of the oligonucleotides in a chirally controlled oligonucleotide composition are of the same oligonucleotide type. In some embodiments, at least about 92% of the oligonucleotides in a chirally controlled oligonucleotide composition are of the same oligonucleotide type. In some embodiments, at least about 94% of the oligonucleotides in a chirally controlled oligonucleotide composition are of the same oligonucleotide type. In some embodiments, at least about 95% of the oligonucleotides in a chirally controlled oligonucleotide composition are of the same oligonucleotide type. In some embodiments, at least about 96% of the oligonucleotides in a chirally controlled oligonucleotide composition are of the same oligonucleotide type. In some embodiments, at least about 97% of the oligonucleotides in a chirally controlled oligonucleotide composition are of the same oligonucleotide type. In some embodiments, at least about 98% of the oligonucleotides in a chirally controlled oligonucleotide composition are of the same oligonucleotide type. In some embodiments, at least about 99% of the oligonucleotides in a chirally controlled oligonucleotide composition are of the same oligonucleotide type.

In some embodiments, purity of a chirally controlled oligonucleotide composition can be controlled by stereoselectivity of each coupling step in its preparation process. In some embodiments, a coupling step has a stereoselectivity (e.g., diastereoselectivity) of 60% (60% of the new internucleotidic linkage formed from the coupling step has the intended stereochemistry). After such a coupling step, the new internucleotidic linkage formed may be referred to have a 60% purity. In some embodiments, each coupling step has a stereoselectivity of at least 60%. In some embodiments, each coupling step has a stereoselectivity of at least 70%. In some embodiments, each coupling step has a stereoselectivity of at least 80%. In some embodiments, each coupling step has a stereoselectivity of at least 85%. In some embodiments, each coupling step has a stereoselectivity of at least 90%. In some embodiments, each coupling step has a stereoselectivity of at least 91%. In some embodiments, each coupling step has a stereoselectivity of at least 92%. In some embodiments, each coupling step has a stereoselectivity of at least 93%. In some embodiments, each coupling step has a stereoselectivity of at least 94%. In some embodiments, each coupling step has a stereoselectivity of at least 95%. In some embodiments, each coupling step has a stereoselectivity of at least 96%. In some embodiments, each coupling step has a stereoselectivity of at least 97%. In some embodiments, each coupling step has a stereoselectivity of at least 98%. In some embodiments, each coupling step has a stereoselectivity of at least 99%. In some embodiments, each coupling step has a stereoselectivity of at least 99.5%. In some embodiments, each coupling step has a stereoselectivity of virtually 100%. In some embodiments, a coupling step has a stereoselectivity of virtually 100% in that all detectable product from the coupling step by an analytical method (e.g., NMR, HPLC, etc) has the intended stereoselectivity.

In some embodiments, provided chirally controlled (and/or stereochemically pure) preparations are antisense oligonucleotides (e.g., chiromersen). In some embodiments, provided chirally controlled (and/or stereochemically pure) preparations are siRNA oligonucleotides. In some embodiments, a provided chirally controlled oligonucleotide composition is of oligonucleotides that can be antisense oligonucleotide, antagomir, microRNA, pre-microRNs, antimir, supermir, ribozyme, U1 adaptor, RNA activator, RNAi agent, decoy oligonucleotide, triplex forming oligonucleotide, aptamer or adjuvant. In some embodiments, a chirally controlled oligonucleotide composition is of antisense oligonucleotides. In some embodiments, a chirally controlled oligonucleotide composition is of antagomir oligonucleotides. In some embodiments, a chirally controlled oligonucleotide composition is of microRNA oligonucleotides. In some embodiments, a chirally controlled oligonucleotide composition is of pre-microRNA oligonucleotides. In some embodiments, a chirally controlled oligonucleotide composition is of antimir oligonucleotides. In some embodiments, a chirally controlled oligonucleotide composition is of supermir oligonucleotides. In some embodiments, a chirally controlled oligonucleotide composition is of ribozyme oligonucleotides. In some embodiments, a chirally controlled oligonucleotide composition is of U1 adaptor oligonucleotides. In some embodiments, a chirally controlled oligonucleotide composition is of RNA activator oligonucleotides. In some embodiments, a chirally controlled oligonucleotide composition is of RNAi agent oligonucleotides. In some embodiments, a chirally controlled oligonucleotide composition is of decoy oligonucleotides. In some embodiments, a chirally controlled oligonucleotide composition is of triplex forming oligonucleotides. In some embodiments, a chirally controlled oligonucleotide composition is of aptamer oligonucleotides. In some embodiments, a chirally controlled oligonucleotide composition is of adjuvant oligonucleotides.

In some embodiments, provided chirally controlled (and/or stereochemically pure) preparations are of oligonucleotides that include one or more modified backbone linkages, bases, and/or sugars.

In some embodiments, a provided oligonucleotide comprises one or more chiral, modified phosphate linkages. In some embodiments, a provided oligonucleotide comprises two or more chiral, modified phosphate linkages. In some embodiments, a provided oligonucleotide comprises three or more chiral, modified phosphate linkages. In some embodiments, a provided oligonucleotide comprises four or more chiral, modified phosphate linkages. In some embodiments, a provided oligonucleotide comprises five or more chiral, modified phosphate linkages. In some embodiments, a provided oligonucleotide comprises 1, 2, 3, 4, 5, 6, 7, 8, 9, 10, 11, 12, 13, 14, 15, 16, 17, 18, 19, 20, 21, 22, 23, 24, or 25 chiral, modified phosphate linkages. In some embodiments, a provided oligonucleotide type comprises 5 or more chiral, modified phosphate linkages. In some embodiments, a provided oligonucleotide type comprises 6 or more chiral, modified phosphate linkages. In some embodiments, a provided oligonucleotide type comprises 7 or more chiral, modified phosphate linkages. In some embodiments, a provided oligonucleotide type comprises 8 or more chiral, modified phosphate linkages. In some embodiments, a provided oligonucleotide type comprises 9 or more chiral, modified phosphate linkages. In some embodiments, a provided oligonucleotide type comprises 10 or more chiral, modified phosphate linkages. In some embodiments, a provided oligonucleotide type comprises 11 or more chiral, modified phosphate linkages. In some embodiments, a provided oligonucleotide type comprises 12 or more chiral, modified phosphate linkages. In some embodiments, a provided oligonucleotide type comprises 13 or more chiral, modified phosphate linkages. In some embodiments, a provided oligonucleotide type comprises 14 or more chiral, modified phosphate linkages. In some embodiments, a provided oligonucleotide type comprises 15 or more chiral, modified phosphate linkages. In some embodiments, a provided oligonucleotide type comprises 16 or more chiral, modified phosphate linkages. In some embodiments, a provided oligonucleotide type comprises 17 or more chiral, modified phosphate linkages. In some embodiments, a provided oligonucleotide type comprises 18 or more chiral, modified phosphate linkages. In some embodiments, a provided oligonucleotide type comprises 19 or more chiral, modified phosphate linkages. In some embodiments, a provided oligonucleotide type comprises 20 or more chiral, modified phosphate linkages. In some embodiments, a provided oligonucleotide type comprises 21 or more chiral, modified phosphate linkages. In some embodiments, a provided oligonucleotide type comprises 22 or more chiral, modified phosphate linkages. In some embodiments, a provided oligonucleotide type comprises 23 or more chiral, modified phosphate linkages. In some embodiments, a provided oligonucleotide type comprises 24 or more chiral, modified phosphate linkages. In some embodiments, a provided oligonucleotide type comprises 25 or more chiral, modified phosphate linkages.

In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages. Exemplary such chiral, modified phosphate linkages are described above and herein. In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages in the Sp configuration.

In some embodiments, provided chirally controlled (and/or stereochemically pure) preparations are of a stereochemical purity of greater than about 80%. In some embodiments, provided chirally controlled (and/or stereochemically pure) preparations are of a stereochemical purity of greater than about 85%. In some embodiments, provided chirally controlled (and/or stereochemically pure) preparations are of a stereochemical purity of greater than about 90%. In some embodiments, provided chirally controlled (and/or stereochemically pure) preparations are of a stereochemical purity of greater than about 91%. In some embodiments, provided chirally controlled (and/or stereochemically pure) preparations are of a stereochemical purity of greater than about 92%. In some embodiments, provided chirally controlled (and/or stereochemically pure) preparations are of a stereochemical purity of greater than about 93%. In some embodiments, provided chirally controlled (and/or stereochemically pure) preparations are of a stereochemical purity of greater than about 94%. In some embodiments, provided chirally controlled (and/or stereochemically pure) preparations are of a stereochemical purity of greater than about 95%. In some embodiments, provided chirally controlled (and/or stereochemically pure) preparations are of a stereochemical purity of greater than about 96%. In some embodiments, provided chirally controlled (and/or stereochemically pure) preparations are of a stereochemical purity of greater than about 97%. In some embodiments, provided chirally controlled (and/or stereochemically pure) preparations are of a stereochemical purity of greater than about 98%. In some embodiments, provided chirally controlled (and/or stereochemically pure) preparations are of a stereochemical purity of greater than about 99%.

In some embodiments, a chiral, modified phosphate linkage is a chiral phosphorothioate linkage, i.e., phosphorothioate internucleotidic linkage. In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10, 20, 30, 40, 50, 60, 70, 80, or 90% chiral phosphorothioate internucleotidic linkages of a provided oligonucleotide are of the Sp conformation. In some embodiments, at least about 10% chiral phosphorothioate internucleotidic linkages of a provided oligonucleotide are of the Sp conformation. In some embodiments, at least about 20% chiral phosphorothioate internucleotidic linkages of a provided oligonucleotide are of the Sp conformation. In some embodiments, at least about 30% chiral phosphorothioate internucleotidic linkages of a provided oligonucleotide are of the Sp conformation. In some embodiments, at least about 40% chiral phosphorothioate internucleotidic linkages of a provided oligonucleotide are of the Sp conformation. In some embodiments, at least about 50% chiral phosphorothioate internucleotidic linkages of a provided oligonucleotide are of the Sp conformation. In some embodiments, at least about 60% chiral phosphorothioate internucleotidic linkages of a provided oligonucleotide are of the Sp conformation. In some embodiments, at least about 70% chiral phosphorothioate internucleotidic linkages of a provided oligonucleotide are of the Sp conformation. In some embodiments, at least about 80% chiral phosphorothioate internucleotidic linkages of a provided oligonucleotide are of the Sp conformation. In some embodiments, at least about 90% chiral phosphorothioate internucleotidic linkages of a provided oligonucleotide are of the Sp conformation. In some embodiments, at least about 95% chiral phosphorothioate internucleotidic linkages of a provided oligonucleotide are of the Sp conformation. In some embodiments, at least about 10, 20, 30, 40, 50, 60, 70, 80, or 90% chiral phosphorothioate internucleotidic linkages of a provided oligonucleotide are of the Rp conformation. In some embodiments, at least about 10% chiral phosphorothioate internucleotidic linkages of a provided oligonucleotide are of the Rp conformation. In some embodiments, at least about 20% chiral phosphorothioate internucleotidic linkages of a provided oligonucleotide are of the Rp conformation. In some embodiments, at least about 30% chiral phosphorothioate internucleotidic linkages of a provided oligonucleotide are of the Rp conformation. In some embodiments, at least about 40% chiral phosphorothioate internucleotidic linkages of a provided oligonucleotide are of the Rp conformation. In some embodiments, at least about 50% chiral phosphorothioate internucleotidic linkages of a provided oligonucleotide are of the Rp conformation. In some embodiments, at least about 60% chiral phosphorothioate internucleotidic linkages of a provided oligonucleotide are of the Rp conformation. In some embodiments, at least about 70% chiral phosphorothioate internucleotidic linkages of a provided oligonucleotide are of the Rp conformation. In some embodiments, at least about 80% chiral phosphorothioate internucleotidic linkages of a provided oligonucleotide are of the Rp conformation. In some embodiments, at least about 90% chiral phosphorothioate internucleotidic linkages of a provided oligonucleotide are of the Rp conformation. In some embodiments, at least about 95% chiral phosphorothioate internucleotidic linkages of a provided oligonucleotide are of the Rp conformation. In some embodiments, less than about 10, 20, 30, 40, 50, 60, 70, 80, or 90% chiral phosphorothioate internucleotidic linkages of a provided oligonucleotide are of the Rp conformation. In some embodiments, less than about 10% chiral phosphorothioate internucleotidic linkages of a provided oligonucleotide are of the Rp conformation. In some embodiments, less than about 20% chiral phosphorothioate internucleotidic linkages of a provided oligonucleotide are of the Rp conformation. In some embodiments, less than about 30% chiral phosphorothioate internucleotidic linkages of a provided oligonucleotide are of the Rp conformation. In some embodiments, less than about 40% chiral phosphorothioate internucleotidic linkages of a provided oligonucleotide are of the Rp conformation. In some embodiments, less than about 50% chiral phosphorothioate internucleotidic linkages of a provided oligonucleotide are of the Rp conformation. In some embodiments, less than about 60% chiral phosphorothioate internucleotidic linkages of a provided oligonucleotide are of the Rp conformation. In some embodiments, less than about 70% chiral phosphorothioate internucleotidic linkages of a provided oligonucleotide are of the Rp conformation. In some embodiments, less than about 80% chiral phosphorothioate internucleotidic linkages of a provided oligonucleotide are of the Rp conformation. In some embodiments, less than about 90% chiral phosphorothioate internucleotidic linkages of a provided oligonucleotide are of the Rp conformation. In some embodiments, less than about 95% chiral phosphorothioate internucleotidic linkages of a provided oligonucleotide are of the Rp conformation. In some embodiments, a provided oligonucleotide has only one Rp chiral phosphorothioate internucleotidic linkages. In some embodiments, a provided oligonucleotide has only one Rp chiral phosphorothioate internucleotidic linkages, wherein all internucleotide linkages are chiral phosphorothioate internucleotidic linkages.

In some embodiments, a chiral phosphorothioate internucleotidic linkage is a chiral phosphorothioate diester linkage. In some embodiments, each chiral phosphorothioate internucleotidic linkage is independently a chiral phosphorothioate diester linkage. In some embodiments, each internucleotidic linkage is independently a chiral phosphorothioate diester linkage. In some embodiments, each internucleotidic linkage is independently a chiral phosphorothioate diester linkage, and only one is Rp.

In some embodiments, provided chirally controlled (and/or stereochemically pure) preparations are of oligonucleotides that contain one or more modified bases. In some embodiments, provided chirally controlled (and/or stereochemically pure) preparations are of oligonucleotides that contain no modified bases. Exemplary such modified bases are described above and herein.

In some embodiments, provided chirally controlled (and/or stereochemically pure) preparations are of oligonucleotides having a common base sequence of at least 8 bases. In some embodiments, provided chirally controlled (and/or stereochemically pure) preparations are of oligonucleotides having a common base sequence of at least 9 bases. In some embodiments, provided chirally controlled (and/or stereochemically pure) preparations are of oligonucleotides having a common base sequence of at least 10 bases. In some embodiments, provided chirally controlled (and/or stereochemically pure) preparations are of oligonucleotides having a common base sequence of at least 11 bases. In some embodiments, provided chirally controlled (and/or stereochemically pure) preparations are of oligonucleotides having a common base sequence of at least 12 bases. In some embodiments, provided chirally controlled (and/or stereochemically pure) preparations are of oligonucleotides having a common base sequence of at least 13 bases. In some embodiments, provided chirally controlled (and/or stereochemically pure) preparations are of oligonucleotides having a common base sequence of at least 14 bases. In some embodiments, provided chirally controlled (and/or stereochemically pure) preparations are of oligonucleotides having a common base sequence of at least 15 bases. In some embodiments, provided chirally controlled (and/or stereochemically pure) preparations are of oligonucleotides having a common base sequence of at least 16 bases. In some embodiments, provided chirally controlled (and/or stereochemically pure) preparations are of oligonucleotides having a common base sequence of at least 17 bases. In some embodiments, provided chirally controlled (and/or stereochemically pure) preparations are of oligonucleotides having a common base sequence of at least 18 bases. In some embodiments, provided chirally controlled (and/or stereochemically pure) preparations are of oligonucleotides having a common base sequence of at least 19 bases. In some embodiments, provided chirally controlled (and/or stereochemically pure) preparations are of oligonucleotides having a common base sequence of at least 20 bases. In some embodiments, provided chirally controlled (and/or stereochemically pure) preparations are of oligonucleotides having a common base sequence of at least 21 bases. In some embodiments, provided chirally controlled (and/or stereochemically pure) preparations are of oligonucleotides having a common base sequence of at least 22 bases. In some embodiments, provided chirally controlled (and/or stereochemically pure) preparations are of oligonucleotides having a common base sequence of at least 23 bases. In some embodiments, provided chirally controlled (and/or stereochemically pure) preparations are of oligonucleotides having a common base sequence of at least 24 bases. In some embodiments, provided chirally controlled (and/or stereochemically pure) preparations are of oligonucleotides having a common base sequence of at least 25 bases. In some embodiments, provided chirally controlled (and/or stereochemically pure) preparations are of oligonucleotides having a common base sequence of at least 30, 35, 40, 45, 50, 55, 60, 65, 70, or 75 bases.

In some embodiments, provided chirally controlled (and/or stereochemically pure) preparations comprise oligonucleotides containing one or more residues which are modified at the sugar moiety. In some embodiments, provided chirally controlled (and/or stereochemically pure) preparations comprise oligonucleotides containing one or more residues which are modified at the 2' position of the sugar moiety (referred to herein as a "2'-modification"). Exemplary such modifications are described above and herein and include, but are not limited to, 2'-OMe, 2'-MOE, 2'-LNA, 2'-F, etc. In some embodiments, provided chirally controlled (and/or stereochemically pure) preparations comprise oligonucleotides containing one or more residues which are 2'-modified. For example, in some embodiments, provided oligonucleotides contain one or more residues which are 2'-O-methoxyethyl (2'-MOE)-modified residues. In some embodiments, provided chirally controlled (and/or stereochemically pure) preparations comprise oligonucleotides which do not contain any 2'-modifications. In some embodiments, provided chirally controlled (and/or stereochemically pure) preparations are oligonucleotides which do not contain any 2'-MOE residues. That is, in some embodiments, provided oligonucleotides are not MOE-modified.

In some embodiments, provided chirally controlled (and/or stereochemically pure) oligonucleotides are of a general motif of wing-core-wing (also represented herein generally as X-Y-X). In some embodiments, each wing contains one or more residues having a particular modification, which modification is absent from the core "Y" portion. In some embodiment, each wing contains one or more residues having a 2' modification that is not present in the core portion. For instance, in some embodiments, provided chirally controlled (and/or stereochemically pure) oligonucleotides have a wing-core-wing motif represented as X-Y-X, wherein the residues at each "X" portion are 2'-modified residues of a particular type and the residues in the core "Y" portion are not 2'-modified residues of the same particular type. For instance, in some embodiments, provided chirally controlled (and/or stereochemically pure) oligonucleotides have a wing-core-wing motif represented as X-Y-X, wherein the residues at each "X" portion are 2'-MOE-modified residues and the residues in the core "Y" portion are not 2'-MOE-modified residues. In some embodiments, provided chirally controlled (and/or stereochemically pure) oligonucleotides have a wing-core-wing motif represented as X-Y-X, wherein the residues at each "X" portion are 2'-MOE-modified residues and the residues in the core "Y" portion are 2'-deoxyribonucleotide. One of skill in the relevant arts will recognize that all such 2'-modifications described above and herein are contemplated in the context of such X-Y-X motifs.

In some embodiments, each wing region independently has a length of one or more bases. In some embodiments, each wing region independently has a length of two or more bases. In some embodiments, each wing region independently has a length of three or more bases. In some embodiments, each wing region independently has a length of four or more bases. In some embodiments, each wing region independently has a length of five or more bases. In some embodiments, each wing region independently has a length of six or more bases. In some embodiments, each wing region independently has a length of seven or more bases. In some embodiments, each wing region independently has a length of eight or more bases. In some embodiments, each wing region independently has a length of nine or more bases. In some embodiments, each wing region independently has a length of ten or more bases. In certain embodiments, each wing region has a length of one base. In certain embodiments, each wing region has a length of two bases. In certain embodiments, each wing region has a length of three bases. In certain embodiments, each wing region has a length of four bases. In certain embodiments, each wing region has a length of five bases.

In some embodiments, a core region has a length of one or more bases. In some embodiments, a core region has a length of one or more bases. In some embodiments, a core region has a length of two or more bases. In some embodiments, a core region has a length of three or more bases. In some embodiments, a core region has a length of four or more bases. In some embodiments, a core region has a length of five or more bases. In some embodiments, a core region has a length of six or more bases. In some embodiments, a core region has a length of seven or more bases. In some embodiments, a core region has a length of eight or more bases. In some embodiments, a core region has a length of nine or more bases. In some embodiments, a core region has a length of ten or more bases. In some embodiments, a core region has a length of 11, 12, 13, 14, 15, 16, 17, 18, 19, 20, 25, or more bases. In certain embodiments, a core region has a length of ten bases. In certain embodiments, a core region has a length of 3 bases. In certain embodiments, a core region has a length of 4 bases. In certain embodiments, a core region has a length of 5 bases. In certain embodiments, a core region has a length of 6 bases. In certain embodiments, a core region has a length of 7 bases. In certain embodiments, a core region has a length of 8 bases. In certain embodiments, a core region has a length of 9 bases. In certain embodiments, a core region has a length of 10 bases. In certain embodiments, a core region has a length of 11 bases. In certain embodiments, a core region has a length of 12 bases. In certain embodiments, a core region has a length of 13 bases. In certain embodiments, a core region has a length of 14 bases. In certain embodiments, a core region has a length of 15 bases. In certain embodiments, a core region has a length of 16 bases. In certain embodiments, a core region has a length of 17 bases. In certain embodiments, a core region has a length of 18 bases. In certain embodiments, a core region has a length of 19 bases. In certain embodiments, a core region has a length of 11 or more bases. In certain embodiments, a core region has a length of 12 or more bases. In certain embodiments, a core region has a length of 13 or more bases. In certain embodiments, a core region has a length of 14 or more bases. In certain embodiments, a core region has a length of 15 or more bases. In certain embodiments, a core region has a length of 16 or more bases. In certain embodiments, a core region has a length of 17 or more bases. In certain embodiments, a core region has a length of 18 or more bases. In certain embodiments, a core region has a length of 19 or more bases. In certain embodiments, a core region has a length of 20 or more bases. In certain embodiments, a core region has a length of more than 20 bases.

In some embodiments, a wing-core-wing (i.e., X-Y-X) motif of a provided oligonucleotide is represented numerically as, e.g., 5-10-5, meaning each wing region of the oligonucleotide is 5 bases in length and the core region of the oligonucleotide is 10 bases in length. In some embodiments, a wing-core-wing motif is any of, e.g. 2-16-2, 3-14-3, 4-12-4, 5-10-5, etc. In certain embodiments, a wing-core-wing motif is 5-10-5.

In some embodiments, the internucleosidic linkages of provided oligonucleotides of such wing-core-wing (i.e., X-Y-X) motifs are all chiral, modified phosphate linkages. In some embodiments, the internucleosidic linkages of provided oligonucleotides of such wing-core-wing (i.e., X-Y-X) motifs are all chiral phosphorothioate internucleotidic linkages. In some embodiments, chiral internucleotidic linkages of provided oligonucleotides of such wing-core-wing motifs are at least about 10, 20, 30, 40, 50, 50, 70, 80, or 90% chiral, modified phosphate internucleotidic linkages. In some embodiments, chiral internucleotidic linkages of provided oligonucleotides of such wing-core-wing motifs are at least about 10, 20, 30, 40, 50, 60, 70, 80, or 90% chiral phosphorothioate internucleotidic linkages. In some embodiments, chiral internucleotidic linkages of provided oligonucleotides of such wing-core-wing motifs are at least about 10, 20, 30, 40, 50, 50, 70, 80, or 90% chiral phosphorothioate internucleotidic linkages of the Sp conformation.

In some embodiments, each wing region of a wing-core-wing motif optionally contains chiral, modified phosphate internucleotidic linkages. In some embodiments, each wing region of a wing-core-wing motif optionally contains chiral phosphorothioate internucleotidic linkages. In some embodiments, each wing region of a wing-core-wing motif contains chiral phosphorothioate internucleotidic linkages. In some embodiments, the two wing regions of a wing-core-wing motif have the same internucleotidic linkage stereochemistry. In some embodiments, the two wing regions have different internucleotidic linkage stereochemistry. In some embodiments, each internucleotidic linkage in the wings is independently a chiral internucleotidic linkage.

In some embodiments, the core region of a wing-core-wing motif optionally contains chiral, modified phosphate internucleotidic linkages. In some embodiments, the core region of a wing-core-wing motif optionally contains chiral phosphorothioate internucleotidic linkages. In some embodiments, the core region of a wing-core-wing motif comprises a repeating pattern of internucleotidic linkage stereochemistry. In some embodiments, the core region of a wing-core-wing motif has a repeating pattern of internucleotidic linkage stereochemistry. In some embodiments, the core region of a wing-core-wing motif comprises repeating pattern of internucleotidic linkage stereochemistry, wherein the repeating pattern is (Sp)mRp or Rp(Sp)m, wherein m is 2, 3, 4, 5, 6, 7 or 8. In some embodiments, the core region of a wing-core-wing motif has repeating pattern of internucleotidic linkage stereochemistry, wherein the repeating pattern is (Sp)mRp or Rp(Sp)m, wherein m is 2, 3, 4, 5, 6, 7 or 8. In some embodiments, the core region of a wing-core-wing motif has repeating pattern of internucleotidic linkage stereochemistry, wherein the repeating pattern is (Sp)mRp, wherein m is 2, 3, 4, 5, 6, 7 or 8. In some embodiments, the core region of a wing-core-wing motif has repeating pattern of internucleotidic linkage stereochemistry, wherein the repeating pattern is Rp(Sp)m, wherein m is 2, 3, 4, 5, 6, 7 or 8. In some embodiments, the core region of a wing-core-wing motif has repeating pattern of internucleotidic linkage stereochemistry, wherein the repeating pattern is (Sp)mRp or Rp(Sp)m, wherein m is 2, 3, 4, 5, 6, 7 or 8. In some embodiments, the core region of a wing-core-wing motif has repeating pattern of internucleotidic linkage stereochemistry, wherein the repeating pattern is a motif comprising at least 33% of internucleotidic linkage in the S conformation. In some embodiments, the core region of a wing-core-wing motif has repeating pattern of internucleotidic linkage stereochemistry, wherein the repeating pattern is a motif comprising at least 50% of internucleotidic linkage in the S conformation. In some embodiments, the core region of a wing-core-wing motif has repeating pattern of internucleotidic linkage stereochemistry, wherein the repeating pattern is a motif comprising at least 66% of internucleotidic linkage in the S conformation. In some embodiments, the core region of a wing-core-wing motif has repeating pattern of internucleotidic linkage stereochemistry, wherein the repeating pattern is a repeating triplet motif selected from RpRpSp and SpSpRp. In some embodiments, the core region of a wing-core-wing motif has repeating pattern of internucleotidic linkage stereochemistry, wherein the repeating pattern is a repeating RpRpSp. In some embodiments, the core region of a wing-core-wing motif has repeating pattern of internucleotidic linkage stereochemistry, wherein the repeating pattern is a repeating, SpSpRp.

In some embodiments, the present invention provides a chirally controlled oligonucleotide composition of an oligonucleotide type whose pattern of backbone chiral centers in the core region comprises (Sp)mRp or Rp(Sp)m. In some embodiments, the present invention provides a chirally controlled oligonucleotide composition of an oligonucleotide type whose pattern of backbone chiral centers in the core region comprises Rp(Sp)m. In some embodiments, the present invention provides a chirally controlled oligonucleotide composition of an oligonucleotide type whose pattern of backbone chiral centers in the core region comprises (Sp)mRp. In some embodiments, m is 2. In some embodiments, the present invention provides a chirally controlled oligonucleotide composition of an oligonucleotide type whose pattern of backbone chiral centers in the core region comprises Rp(Sp)$_2$. In some embodiments, the present invention provides a chirally controlled oligonucleotide composition of an oligonucleotide type whose pattern of backbone chiral centers in the core region comprises (Sp)$_2$Rp(Sp)$_2$. In some embodiments, the present invention provides a chirally controlled oligonucleotide composition of an oligonucleotide type whose pattern of backbone chiral centers in the core region comprises (Rp)$_2$Rp(Sp)$_2$. In some embodiments, the present invention provides a chirally controlled oligonucleotide composition of an oligonucleotide type whose pattern of backbone chiral centers in the core region comprises RpSpRp(Sp)$_2$. In some embodiments, the present invention provides a chirally controlled oligonucleotide composition of an oligonucleotide type whose pattern of backbone chiral centers in the core region comprises SpRpRp(Sp)$_2$. In some embodiments, the present invention provides a chirally controlled oligonucleotide composition of an oligonucleotide type whose pattern of backbone chiral centers in the core region comprises (Sp)$_2$Rp.

In some embodiments, the present invention provides a chirally controlled oligonucleotide composition of an oligonucleotide type whose pattern of backbone chiral centers comprises (Sp)mRp or Rp(Sp)m. In some embodiments, the present invention provides a chirally controlled oligonucleotide composition of an oligonucleotide type whose pattern of backbone chiral centers comprises Rp(Sp)m. In some embodiments, the present invention provides a chirally controlled oligonucleotide composition of an oligonucleotide type whose pattern of backbone chiral centers comprises (Sp)mRp. In some embodiments, m is 2. In some embodiments, the present invention provides a chirally controlled oligonucleotide composition of an oligonucleotide type whose pattern of backbone chiral centers comprises Rp(Sp)$_2$. In some embodiments, the present invention provides a chirally controlled oligonucleotide composition of an oligonucleotide type whose pattern of backbone chiral centers comprises (Sp)$_2$Rp(Sp)$_2$. In some embodiments, the present invention provides a chirally controlled oligonucleotide composition of an oligonucleotide type whose pattern of backbone chiral centers comprises (Rp)$_2$Rp(Sp)$_2$. In some embodiments, the present invention provides a chirally controlled oligonucleotide composition of an oligonucleotide type whose pattern of backbone chiral centers comprises RpSpRp(Sp)$_2$. In some embodiments, the present invention provides a chirally controlled oligonucleotide composition of an oligonucleotide type whose pattern of backbone chiral centers comprises SpRpRp(Sp)$_2$. In some embodiments, the present invention provides a chirally controlled oligonucleotide composition of an oligonucleotide type whose pattern of backbone chiral centers comprises (Sp)$_2$Rp.

As defined herein, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 2. In some embodiments, m is 3. In some embodiments, m is 4. In some embodiments, in is 5. In some embodiments, m is 6. In some embodiments, m is 7. In some embodiments, m is 8.

In some embodiments, a repeating pattern is (Sp)m(Rp)n, wherein n is independently 1, 2, 3, 4, 5, 6, 7 or 8, and m is independently as defined above and described herein. In some embodiments, the present invention provides a chirally controlled oligonucleotide composition of an oligonucleotide type whose pattern of backbone chiral centers comprises (Sp)m(Rp)n. In some embodiments, the present invention provides a chirally controlled oligonucleotide composition of an oligonucleotide type whose pattern of backbone chiral centers in the core region comprises (Sp)m(Rp)n. In some embodiments, a repeating pattern is (Rp)n(Sp)m, wherein n is independently 1, 2, 3, 4, 5, 6, 7 or 8, and m is independently as defined above and described herein. In some embodiments, the present invention provides a chirally controlled oligonucleotide composition of an oligonucleotide type whose pattern of backbone chiral centers comprises (Rp)n(Sp)m. In some embodiments, the present invention provides a chirally controlled oligonucleotide composition of an oligonucleotide type whose pattern of backbone chiral centers in the core region comprises (Rp)n(Sp)m. In some embodiments, (Rp)n(Sp)m is (Rp)(Sp)$_2$. In some embodiments, (Sp)n(Rp)m is (Sp)$_2$(Rp).

In some embodiments, a repeating pattern is (Sp)m(Rp)n(Sp)t, wherein each of n and t is independently 1, 2, 3, 4, 5, 6, 7 or 8, and m is as defined above and described herein. In some embodiments, the present invention provides a chirally controlled oligonucleotide composition of an oligonucleotide type whose pattern of backbone chiral centers comprises (Sp)m(Rp)n(Sp)t. In some embodiments, the present invention provides a chirally controlled oligonucleotide composition of an oligonucleotide type whose pattern of backbone chiral centers in the core region comprises (Sp)m(Rp)n(Sp)t. In some embodiments, a repeating pattern is (Sp)t(Rp)n(Sp)m, wherein each of n and t is independently 1, 2, 3, 4, 5, 6, 7 or 8, and m is as defined above and described herein. In some embodiments, the present invention provides a chirally controlled oligonucleotide composition of an oligonucleotide type whose pattern of backbone chiral centers comprises (Sp)t(Rp)n(Sp)m. In some embodiments, the present invention provides a chirally controlled oligonucleotide composition of an oligonucleotide type whose pattern of backbone chiral centers in the core region comprises (Sp)t(Rp)n(Sp)m.

In some embodiments, a repeating pattern is (Np)t(Rp)n(Sp)m, wherein each of n and t is independently 1, 2, 3, 4, 5, 6, 7 or 8, Np is independently Rp or Sp, and m is as defined above and described herein. In some embodiments, the present invention provides a chirally controlled oligonucleotide composition of an oligonucleotide type whose pattern of backbone chiral centers comprises (Np)t(Rp)n(Sp)m. In some embodiments, the present invention provides a chirally controlled oligonucleotide composition of an oligonucleotide type whose pattern of backbone chiral centers in the core region comprises (Np)t(Rp)n(Sp)m. In some embodiments, a repeating pattern is (Np)m(Rp)n(Sp)t, wherein each of n and t is independently 1, 2, 3, 4, 5, 6, 7 or 8, Np is independently Rp or Sp, and m is as defined above and described herein. In some embodiments, the present invention provides a chirally controlled oligonucleotide composition of an oligonucleotide type whose pattern of backbone chiral centers comprises (Np)m(Rp)n(Sp)t. In some embodiments, the present invention provides a chirally controlled oligonucleotide composition of an oligonucleotide type whose pattern of backbone chiral centers in the core region comprises (Np)m(Rp)n(Sp)t. In some embodiments, Np is Rp. In some embodiments, Np is Sp. In some embodiments, all Np are the same. In some embodiments, all Np are Sp. In some embodiments, at least one Np is different from the other Np. In some embodiments, t is 2.

As defined herein, n is 1, 2, 3, 4, 5, 6, 7 or 8. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8.

As defined herein, t is 1, 2, 3, 4, 5, 6, 7 or 8. In some embodiments, t is 2, 3, 4, 5, 6, 7 or 8. In some embodiments, t is 3, 4, 5, 6, 7 or 8. In some embodiments, t is 4, 5, 6, 7 or 8. In some embodiments, t is 5, 6, 7 or 8. In some embodiments, t is 6, 7 or 8. In some embodiments, t is 7 or 8. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8.

In some embodiments, at least one of in and t is greater than 2. In some embodiments, at least one of m and t is greater than 3. In some embodiments, at least one of m and t is greater than 4. In some embodiments, at least one of m and t is greater than 5. In some embodiments, at least one of m and t is greater than 6. In some embodiments, at least one of m and t is greater than 7. In some embodiments, each one of m and t is greater than 2. In some embodiments, each one of m and t is greater than 3. In some embodiments, each one of m and t is greater than 4. In some embodiments, each one of m and t is greater than 5. In some embodiments, each one of n and t is greater than 6. In some embodiments, each one of m and t is greater than 7.

In some embodiments, n is 1, and at least one of m and t is greater than 1. In some embodiments, n is 1 and each of m and t is independent greater than 1. In some embodiments, m>n and t>n. In some embodiments, (Sp)m(Rp)n(Sp)t is $(Sp)_2(Rp)_2(Sp)_2$. In some embodiments, (Sp)t(Rp)n(Sp)m is $(Sp)_2Rp(Sp)_2$. In some embodiments, (Sp)t(Rp)n(Sp)m is $SpRp(Sp)_2$. In some embodiments, (Np)t(Rp)n(Sp)m is (Np)tRp(Sp)m. In some embodiments, (Np)t(Rp)n(Sp)m is $(Np)_2Rp(Sp)m$. In some embodiments, (Np)t(Rp)n(Sp)m is $(Rp)_2Rp(Sp)m$. In some embodiments, (Np)t(Rp)n(Sp)m is $(Sp)_2Rp(Sp)m$. In some embodiments, (Np)t(Rp)n(Sp)m is RpSpRp(Sp)m. In some embodiments, (Np)t(Rp)n(Sp)m is SpRpRp(Sp)m.

In some embodiments, (Sp)t(Rp)n(Sp)m is SpRpSpSp. In some embodiments, (Sp)t(Rp)n(Sp)m is $(Sp)_2Rp(Sp)_2$. In some embodiments, (Sp)t(Rp)n(Sp)m is $(Sp)_3Rp(Sp)_3$. In some embodiments, (Sp)t(Rp)n(Sp)m is $(Sp)_4Rp(Sp)_4$. In some embodiments, (Sp)t(Rp)n(Sp)m is $(Sp)tRp(Sp)_5$. In some embodiments, (Sp)t(Rp)n(Sp)m is $SpRp(Sp)_5$. In some embodiments, (Sp)t(Rp)n(Sp)m is $(Sp)_2Rp(Sp)_5$. In some embodiments, (Sp)t(Rp)n(Sp)m is $(Sp)_3Rp(Sp)$. In some embodiments, (Sp)t(Rp)n(Sp)m is $(Sp)_4Rp(Sp)_5$. In some embodiments, (Sp)t(Rp)n(Sp)m is $(Sp)_5Rp(Sp)_5$.

In some embodiments, (Sp)m(Rp)n(Sp)t is $(Sp)_2Rp(Sp)_2$. In some embodiments, (Sp)m(Rp)n(Sp)t is $(Sp)_3Rp(Sp)_3$. In some embodiments, (Sp)m(Rp)n(Sp)t is $(Sp)_4Rp(Sp)_4$. In some embodiments, (Sp)m(Rp)n(Sp)t is $(Sp)mRp(Sp)_5$. In some embodiments, (Sp)m(Rp)n(Sp)t is $(Sp)_2Rp(Sp)_5$. In some embodiments, (Sp)m(Rp)n(Sp)t is $(Sp)_3Rp(Sp)_5$. In some embodiments, (Sp)m(Rp)n(Sp)t is $(Sp)_4Rp(Sp)_5$. In some embodiments, (Sp)m(Rp)n(Sp)t is $(Sp)_5Rp(Sp)_5$.

In some embodiments, the core region of a wing-core-wing motif comprises at least one Rp internucleotidic linkage. In some embodiments, the core region of a wing-core-wing motif comprises at least one Rp phosphorothioate internucleotidic linkage. In some embodiments, the core region of a wing-core-wing motif comprises at least two Rp internucleotidic linkages. In some embodiments, the core region of a wing-core-wing motif comprises at least two Rp phosphorothioate internucleotidic linkages. In some embodiments, the core region of a wing-core-wing motif comprises at least three Rp internucleotidic linkages. In some embodiments, the core region of a wing-core-wing motif comprises at least three Rp phosphorothioate internucleotidic linkages. In some embodiments, the core region of a wing-core-wing motif comprises at least 4, 5, 6, 7, 8, 9, or 10 Rp internucleotidic linkages. In some embodiments, the core region of a wing-core-wing motif comprises at least 4, 5, 6, 7, 8, 9, or 10 Rp phosphorothioate internucleotidic linkages.

In certain embodiments, a wing-core-wing motif is a 5-10-5 motif wherein the residues at each "X" wing region are 2'-MOE-modified residues. In certain embodiments, a wing-core-wing motif is a 5-10-5 motif wherein the residues in the core "Y" region are 2'-deoxyribonucleotide residues. In certain embodiments, a wing-core-wing motif is a 5-10-5 motif, wherein all internucleosidic linkages are phosphorothioate internucleosidic linkages. In certain embodiments, a wing-core-wing motif is a 5-10-5 motif, wherein all internucleosidic linkages are chiral phosphorothioate internucleosidic linkages. In certain embodiments, a wing-core-wing motif is a 5-10-5 motif wherein the residues at each "X" wing region are 2'-MOE-modified residues, the residues in the core "Y" region are 2'-deoxyribonucleotide, and all internucleosidic linkages are chiral phosphorothioate internucleosidic linkages.

In certain embodiments, a wing-core-wing motif is a 5-10-5 motif wherein the residues at each "X" wing region are not 2'-MOE-modified residues. In certain embodiments, a wing-core-wing motif is a 5-10-5 motif wherein the residues in the core "Y" region are 2'-deoxyribonucleotide residues. In certain embodiments, a wing-core-wing motif is a 5-10-5 motif, wherein all internucleosidic linkages are phosphorothioate internucleosidic linkages. In certain embodiments, a wing-core-wing motif is a 5-10-5 motif, wherein all internucleosidic linkages are chiral phosphorothioate internucleosidic linkages. In certain embodiments, a wing-core-wing motif is a 5-10-5 motif wherein the residues at each "X" wing region are not 2'-MOE-modified residues, the residues in the core "Y" region are 2'-deoxyribonucleotide, and all internucleosidic linkages are chiral phosphorothioate internucleosidic linkages.

In certain embodiments, provided chirally controlled (and/or stereochemically pure) preparations comprise oligonucleotides of base sequence GCCTCAGTCTGCTTCGCACC (SEQ ID NO: 9).

In some embodiments, the present invention provides stereochemical design parameters for oligonucleotides. That is, among other things, the present disclosure demonstrates impact of stereochemical structure at different positions along an oligonucleotide chain, for example on stability and/or activity of the oligonucleotide, including on interaction of the oligonucleotide with a cognate ligand and/or with a processing enzyme. The present invention specifically provides oligonucleotides whose structure incorporates or reflects the design parameters. Such oligonucleotides are new chemical entities relative to stereorandom preparations having the same base sequence and length.

In some embodiments, the present invention provides stereochemical design parameters for antisense oligonucleotides. In some embodiments, the present invention specifically provides design parameter for oligonucleotides that may be bound and/or cleaved by RNaseH. In some embodiments, the present invention provides stereochemical design parameters for siRNA oligonucleotides. In some embodiments, the present invention specifically provides design parameters for oligonucleotides that may be bound and/or cleaved by, e.g., DICER, Argonaute proteins (e.g., Argonaute-1 and Argonaute-2), etc.

In some embodiments, a single oligonucleotide of a provided composition comprises a region in which at least one of the first, second, third, fifth, seventh, eighth, ninth, eighteenth, nineteenth and twentieth internucleotidic linkages is chiral. In some embodiments, at least two of the first, second, third, fifth, seventh, eighth, ninth, eighteenth, nineteenth and twentieth internucleotidic linkages are chiral. In some embodiments, at least three of the first, second, third, fifth, seventh, eighth, ninth, eighteenth, nineteenth and twentieth internucleotidic linkages are chiral. In some embodiments, at least four of the first, second, third, fifth, seventh, eighth, ninth, eighteenth, nineteenth and twentieth internucleotidic linkages are chiral. In some embodiments, at least five of the first, second, third, fifth, seventh, eighth, ninth, eighteenth, nineteenth and twentieth internucleotidic linkages are chiral. In some embodiments, at least six of the first, second, third, fifth, seventh, eighth, ninth, eighteenth, nineteenth and twentieth internucleotidic linkages are chiral. In some embodiments, at least seven of the first, second, third, fifth, seventh, eighth, ninth, eighteenth, nineteenth and twentieth internucleotidic linkages are chiral. In some embodiments, at least eight of the first, second, third, fifth, seventh, eighth, ninth, eighteenth, nineteenth and twentieth internucleotidic linkages are chiral. In some embodiments, at least nine of the first, second, third, fifth, seventh, eighth, ninth, eighteenth, nineteenth and twentieth internucleotidic linkages are chiral. In some embodiments, one of the first, second, third, fifth, seventh, eighth, ninth, eighteenth, nineteenth and twentieth internucleotidic linkages is chiral. In some embodiments, two of the first, second, third, fifth, seventh, eighth, ninth, eighteenth, nineteenth and twentieth internucleotidic linkages are chiral. In some embodiments, three of the first, second, third, fifth, seventh, eighth, ninth, eighteenth, nineteenth and twentieth internucleotidic linkages are chiral. In some embodiments, four of the first, second, third, fifth, seventh, eighth, ninth, eighteenth, nineteenth and twentieth internucleotidic linkages are chiral. In some embodiments, five of the first, second, third, fifth, seventh, eighth, ninth, eighteenth, nineteenth and twentieth internucleotidic linkages are chiral. In some embodiments, six of the first, second, third, fifth, seventh, eighth, ninth, eighteenth, nineteenth and twentieth internucleotidic linkages are chiral. In some embodiments, seven of the first, second, third, fifth, seventh, eighth, ninth, eighteenth, nineteenth and twentieth internucleotidic linkages are chiral. In some embodiments, eight of the first, second, third, fifth, seventh, eighth, ninth, eighteenth, nineteenth and twentieth internucleotidic linkages are chiral. In some embodiments, nine of the first, second, third, fifth, seventh, eighth, ninth, eighteenth, nineteenth and twentieth internucleotidic linkages are chiral. In some embodiments, ten of the first, second, third, fifth, seventh, eighth, ninth, eighteenth, nineteenth and twentieth internucleotidic linkages are chiral.

In some embodiments, a single oligonucleotide of a provided composition comprises a region in which at least one of the first, second, third, fifth, seventh, eighteenth, nineteenth and twentieth internucleotidic linkages is chiral. In some embodiments, at least two of the first, second, third, fifth, seventh, eighteenth, nineteenth and twentieth internucleotidic linkages are chiral. In some embodiments, at least three of the first, second, third, fifth, seventh, eighteenth, nineteenth and twentieth internucleotidic linkages are chiral. In some embodiments, at least four of the first, second, third, fifth, seventh, eighteenth, nineteenth and twentieth internucleotidic linkages are chiral. In some embodiments, at least five of the first, second, third, fifth, seventh, eighteenth, nineteenth and twentieth internucleotidic linkages are chiral. In some embodiments, at least six of the first, second, third, fifth, seventh, eighteenth, nineteenth and twentieth internucleotidic linkages are chiral. In some embodiments, at least seven of the first, second, third, fifth, seventh, eighteenth, nineteenth and twentieth internucleotidic linkages are chiral. In some embodiments, one of the first, second, third, fifth, seventh, eighteenth, nineteenth and twentieth internucleotidic linkages is chiral. In some embodiments, two of the first, second, third, fifth, seventh, eighteenth, nineteenth and twentieth internucleotidic linkages are chiral. In some embodiments, three of the first, second, third, fifth, seventh, eighteenth, nineteenth and twentieth internucleotidic linkages are chiral. In some embodiments, four of the first, second, third, fifth, seventh, eighteenth, nineteenth and twentieth internucleotidic linkages are chiral. In some embodiments, five of the first, second, third, fifth, seventh, eighteenth, nineteenth and twentieth internucleotidic linkages are chiral. In some embodiments, six of the first, second, third, fifth, seventh, eighteenth, nineteenth and twentieth internucleotidic linkages are chiral. In some embodiments, seven of the first, second, third, fifth, seventh, eighteenth, nineteenth and twentieth internucleotidic linkages are chiral. In some embodiments, eight of the first, second, third, fifth, seventh, eighteenth, nineteenth and twentieth internucleotidic linkages are chiral.

In some embodiments, a single oligonucleotide of a provided composition comprises a region in which at least one of the first, second, third, fifth, seventh, eighth, ninth, eighteenth, nineteenth and twentieth internucleotidic linkages is chiral, and at least one internucleotidic linkage is achiral. In some embodiments, a single oligonucleotide of a provided composition comprises a region in which at least one of the first, second, third, fifth, seventh, eighth, nineteenth and twentieth internucleotidic linkages is chiral, and at least one internucleotidic linkage is achiral. In some embodiments, at least two internucleotidic linkages are achiral. In some embodiments, at least three internucleotidic linkages are achiral. In some embodiments, at least four internucleotidic linkages are achiral. In some embodiments, at least five internucleotidic linkages are achiral. In some embodiments, at least six internucleotidic linkages are achiral. In some embodiments, at least seven internucleotidic linkages are achiral. In some embodiments, at least eight internucleotidic linkages are achiral. In some embodiments, at least nine internucleotidic linkages are achiral. In some embodiments, at least 10 internucleotidic linkages are achiral. In some embodiments, at least 11 internucleotidic linkages are achiral. In some embodiments, at least 12 internucleotidic linkages are achiral. In some embodiments, at least 13 internucleotidic linkages are achiral. In some embodiments, at least 14 internucleotidic linkages are achiral. In some embodiments, at least 15 internucleotidic linkages are achiral. In some embodiments, at least 16 internucleotidic linkages are achiral. In some embodiments, at least 17 internucleotidic linkages are achiral. In some embodiments, at least 18 internucleotidic linkages are achiral. In some embodiments, at least 19 internucleotidic linkages are achiral. In some embodiments, at least 20 internucleotidic linkages are achiral. In some embodiments, one internucleotidic linkage is achiral. In some embodiments, two internucleotidic linkages are achiral. In some embodiments, three internucleotidic linkages are achiral. In some embodiments, four internucleotidic linkages are achiral. In some embodiments, five internucleotidic linkages are achiral. In some embodiments, six internucleotidic linkages are achiral. In some embodiments, seven internucleotidic linkages are achiral. In some embodiments, eight internucleotidic linkages are achiral. In some embodiments, nine internucleotidic linkages are achiral. In some embodiments, 10 internucleotidic linkages are achiral. In some embodiments, 11 internucleotidic linkages are achiral. In some embodiments, 12 internucleotidic linkages are achiral. In some embodiments, 13 internucleotidic linkages are achiral. In some embodiments, 14 internucleotidic linkages are achiral. In some embodiments, 15 internucleotidic linkages are achiral. In some embodiments, 16 internucleotidic linkages are achiral. In some embodiments, 17 internucleotidic linkages are achiral. In some embodiments, 18 internucleotidic linkages are achiral. In some embodiments, 19 internucleotidic linkages are achiral. In some embodiments, 20 internucleotidic linkages are achiral. In some embodiments, a single oligonucleotide of a provided composition comprises a region in which all internucleotidic linkages, except the at least one of the first, second, third, fifth, seventh, eighth, ninth, eighteenth, nineteenth and twentieth internucleotidic linkages which is chiral, are achiral.

In some embodiments, a single oligonucleotide of a provided composition comprises a region in which at least one of the first, second, third, fifth, seventh, eighth, ninth, eighteenth, nineteenth and twentieth internucleotidic linkages is chiral, and at least one internucleotidic linkage is phosphate. In some embodiments, a single oligonucleotide of a provided composition comprises a region in which at least one of the first, second, third, fifth, seventh, eighteenth, nineteenth and twentieth internucleotidic linkages is chiral, and at least one internucleotidic linkage is phosphate. In some embodiments, at least two internucleotidic linkages are phosphate. In some embodiments, at least three internucleotidic linkages are phosphate. In some embodiments, at least four internucleotidic linkages are phosphate. In some embodiments, at least five internucleotidic linkages are phosphate. In some embodiments, at least six internucleotidic linkages are phosphate. In some embodiments, at least seven internucleotidic linkages are phosphate. In some embodiments, at least eight internucleotidic linkages are phosphate. In some embodiments, at least nine internucleotidic linkages are phosphate. In some embodiments, at least 10 internucleotidic linkages are phosphate. In some embodiments, at least 11 internucleotidic linkages are phosphate. In some embodiments, at least 12 internucleotidic linkages are phosphate. In some embodiments, at least 13 internucleotidic linkages are phosphate. In some embodiments, at least 14 internucleotidic linkages are phosphate. In some embodiments, at least 15 internucleotidic linkages are phosphate. In some embodiments, at least 16 internucleotidic linkages are phosphate. In some embodiments, at least 17 internucleotidic linkages are phosphate. In some embodiments, at least 18 internucleotidic linkages are phosphate. In some embodiments, at least 19 internucleotidic linkages are phosphate. In some embodiments, at least 20 internucleotidic linkages are phosphate. In some embodiments, one internucleotidic linkage is phosphate. In some embodiments, two internucleotidic linkages are phosphate. In some embodiments, three internucleotidic linkages are phosphate. In some embodiments, four internucleotidic linkages are phosphate. In some embodiments, five internucleotidic linkages are phosphate. In some embodiments, six internucleotidic linkages are phosphate. In some embodiments, seven internucleotidic linkages are phosphate. In some embodiments, eight internucleotidic linkages are phosphate. In some embodiments, nine internucleotidic linkages are phosphate. In some embodiments, 10 internucleotidic linkages are phosphate. In some embodiments, 11 internucleotidic linkages are phosphate. In some embodiments, 12 internucleotidic linkages are phosphate. In some embodiments, 13 internucleotidic linkages are phosphate. In some embodiments, 14 internucleotidic linkages are phosphate. In some embodiments, 15 internucleotidic linkages are phosphate. In some embodiments, 16 internucleotidic linkages are phosphate. In some embodiments, 17 internucleotidic linkages are phosphate. In some embodiments, 18 internucleotidic linkages are phosphate. In some embodiments, 19 internucleotidic linkages are phosphate. In some embodiments, 20 internucleotidic linkages are phosphate. In some embodiments, a single oligonucleotide of a provided composition comprises a region in which all internucleotidic linkages, except the at least one of the first, second, third, fifth, seventh, eighth, ninth, eighteenth, nineteenth and twentieth internucleotidic linkages which is chiral, are phosphate.

In some embodiments, a single oligonucleotide of a provided composition comprises a region in which at least one of the first, second, third, fifth, seventh, eighth, ninth, eighteenth, nineteenth and twentieth internucleotidic linkages are chiral, and at least 10% of all the internucleotidic linkages in the region is achiral. In some embodiments, a single oligonucleotide of a provided composition comprises a region in which at least one of the first, second, third, fifth, seventh, eighteenth, nineteenth and twentieth internucleotidic linkages is chiral, and at least 10% of all the internucleotidic linkages in the region are achiral. In some embodiments, at least 20% of all the internucleotidic linkages in the region are achiral. In some embodiments, at least 30% of all the internucleotidic linkages in the region are achiral. In some embodiments, at least 40% of all the internucleotidic linkages in the region are achiral. In some embodiments, at least 50% of all the internucleotidic linkages in the region are achiral. In some embodiments, at least 60% of all the internucleotidic linkages in the region are achiral. In some embodiments, at least 70% of all the internucleotidic linkages in the region are achiral. In some embodiments, at least 80% of all the internucleotidic linkages in the region are achiral. In some embodiments, at least 90% of all the internucleotidic linkages in the region are achiral. In some embodiments, at least 50% of all the internucleotidic linkages in the region are achiral. In some embodiments, an achiral internucleotidic linkage is a phosphate linkage. In some embodiments, each achiral internucleotidic linkage in a phosphate linkage.

In some embodiments, the first internucleotidic linkage of the region is an Sp modified internucleotidic linkage. In some embodiments, the first internucleotidic linkage of the region is an Rp modified internucleotidic linkage. In some embodiments, the second internucleotidic linkage of the region is an Sp modified internucleotidic linkage. In some embodiments, the second internucleotidic linkage of the region is an Rp modified internucleotidic linkage. In some embodiments, the third internucleotidic linkage of the region is an Sp modified internucleotidic linkage. In some embodiments, the third internucleotidic linkage of the region is an Rp modified internucleotidic linkage. In some embodiments, the fifth internucleotidic linkage of the region is an Sp modified internucleotidic linkage. In some embodiments, the fifth internucleotidic linkage of the region is an Rp modified internucleotidic linkage. In some embodiments, the seventh internucleotidic linkage of the region is an Sp modified internucleotidic linkage. In some embodiments, the seventh internucleotidic linkage of the region is an Rp modified internucleotidic linkage. In some embodiments, the eighth internucleotidic linkage of the region is an Sp modified internucleotidic linkage. In some embodiments, the eighth internucleotidic linkage of the region is an Rp modified internucleotidic linkage. In some embodiments, the ninth internucleotidic linkage of the region is an Sp modified internucleotidic linkage. In some embodiments, the ninth internucleotidic linkage of the region is an Rp modified internucleotidic linkage. In some embodiments, the eighteenth internucleotidic linkage of the region is an Sp modified internucleotidic linkage. In some embodiments, the eighteenth internucleotidic linkage of the region is an Rp modified internucleotidic linkage. In some embodiments, the nineteenth internucleotidic linkage of the region is an Sp modified internucleotidic linkage. In some embodiments, the nineteenth internucleotidic linkage of the region is an Rp modified internucleotidic linkage. In some embodiments, the twentieth internucleotidic linkage of the region is an Sp modified internucleotidic linkage. In some embodiments, the twentieth internucleotidic linkage of the region is an Rp modified internucleotidic linkage.

In some embodiments, the region has a length of at least 21 bases. In some embodiments, the region has a length of 21 bases. In some embodiments, a single oligonucleotide in a provided composition has a length of at least 21 bases. In some embodiments, a single oligonucleotide in a provided composition has a length of 21 bases.

In some embodiments, a chiral internucleotidic linkage has the structure of formula I. In some embodiments, a chiral internucleotidic linkage is phosphorothioate. In some embodiments, each chiral internucleotidic linkage in a single oligonucleotide of a provided composition independently has the structure of formula I. In some embodiments, each chiral internucleotidic linkage in a single oligonucleotide of a provided composition is a phosphorothioate.

As known by a person of ordinary skill in the art and described in the disclosure, various modifications can be introduced to the 2'-position of the sugar moiety. Commonly used 2'-modifications include but are not limited to 2'-OR$^1$, wherein R$^1$ is not hydrogen. In some embodiments, a modification is 2'-OR, wherein R is optionally substituted aliphatic. In some embodiments, a modification is 2'-OMe. In some embodiments, a modification is 2'-O-MOE. In some embodiments, the present invention demonstrates that inclusion and/or location of particular chirally pure internucleotidic linkages can provide stability improvements comparable to or better than those achieved through use of modified backbone linkages, bases, and/or sugars. In some embodiments, a provided single oligonucleotide of a provided composition has no modifications on the sugars. In some embodiments, a provided single oligonucleotide of a provided composition has no modifications on 2'-positions of the sugars (i.e., the two groups at the 2'-position are either —H/—H or —H/—OH). In some embodiments, a provided single oligonucleotide of a provided composition does not have any 2'-MOE modifications.

In some embodiments, a single oligonucleotide in a provided composition is a better substrate for Argonaute proteins (e.g., hAgo-1 and hAgo-2) compared to stereorandom oligonucleotide compositions. Selection and/or location of chirally pure linkages as described in the present closure are useful design parameters for oligonucleotides that interacting with such proteins, such as siRNA.

In some embodiments, a single oligonucleotide in a provided composition has at least about 25% of its internucleotidic linkages in Sp configuration. In some embodiments, a single oligonucleotide in a provided composition has at least about 30% of its internucleotidic linkages in Sp configuration. In some embodiments, a single oligonucleotide in a provided composition has at least about 35% of its internucleotidic linkages in Sp configuration. In some embodiments, a single oligonucleotide in a provided composition has at least about 40% of its internucleotidic linkages in Sp configuration. In some embodiments, a single oligonucleotide in a provided composition has at least about 45% of its internucleotidic linkages in Sp configuration. In some embodiments, a single oligonucleotide in a provided composition has at least about 50% of its internucleotidic linkages in Sp configuration. In some embodiments, a single oligonucleotide in a provided composition has at least about 55% of its internucleotidic linkages in Sp configuration. In some embodiments, a single oligonucleotide in a provided composition has at least about 60% of its internucleotidic linkages in Sp configuration. In some embodiments, a single oligonucleotide in a provided composition has at least about 65% of its internucleotidic linkages in Sp configuration. In some embodiments, a single oligonucleotide in a provided composition has at least about 70% of its internucleotidic linkages in Sp configuration. In some embodiments, a single oligonucleotide in a provided composition has at least about 75% of its internucleotidic linkages in Sp configuration. In some embodiments, a single oligonucleotide in a provided composition has at least about 80% of its internucleotidic linkages in Sp configuration. In some embodiments, a single oligonucleotide in a provided composition has at least about 85% of its internucleotidic linkages in Sp configuration. In some embodiments, a single oligonucleotide in a provided composition has at least about 90% of its internucleotidic linkages in Sp configuration.

In some embodiments, a single oligonucleotide in a provided composition is not an oligonucleotide selected from:

| 143 | (Sp, Sp, Rp, Sp, Sp, Rp, Sp, Sp, Rp, Sp, Sp)-d[5mCs1As1Gs1Ts15mCs1Ts1Gs15mCs1Ts1Ts15mCs1G] | (SSR)₃-SS | (SEQ ID NO: 10) |
|---|---|---|---|
| ONT-87 | (Rp, Rp, Rp, Rp, Rp, Sp, Sp, Rp, Sp, Sp, Rp, Sp, Sp, Rp, Rp, Rp, Rp, Rp, Rp)-Gs5mCs5mCTs5mCsAsGsTs5mCsTsGs5mCsTsTs5mCsGs5mCsAs5mCs5mC | (5R-(SSR)₃-5R) | (SEQ ID NO: 11) | underlined nucleotides are 2'-modified.

In some embodiments, a single oligonucleotide in a provided composition is not an oligonucleotide selected from:

| 143 | (Sp, Sp, Rp, Sp, Sp, Rp, Sp, Sp, Rp, Sp, Sp)-d[5mCs1As1Gs1Ts15mCs1Ts1Gs15mCs1Ts1Ts15mCs1G] | (SSR)₃-SS | (SEQ ID NO: 12) |
|---|---|---|---|
| ONT-87 | (Rp, Rp, Rp, Rp, Rp, Sp, Sp, Rp, Sp, Sp, Rp, Sp, Sp, Rp, Rp, Rp, Rp, Rp, Rp)-Gs5mCs5mCTs5mCsAsGsTs5mCsTsGs5mCsTsTs5mCsGs5mCsAs5mCs5mC | (5R-(SSR)₃-5R) | (SEQ ID NO: 13) | underlined nucleotides are 2'-O-MOE modified.

In some embodiments, a single oligonucleotide in a provided composition is not an oligonucleotide selected from:

| ONT-106 | (Rp)-uucuAGAccuGuuuuGcuudTsdT | PCSK9 sense | (SEQ ID NO: 14) |
|---|---|---|---|
| ONT-107 | (Sp)-uucuAGAccuGuuuuGcuudTsdT | PCSK9 sense | (SEQ ID NO: 15) |
| ONT-108 | (Rp)-AAGcAAAAcAGGUCuAGAAdTsdT | PCSK9 antisense | (SEQ ID NO: 16) |
| ONT-109 | (Sp)-AAGcAAAAcAGGUCuAGAAdTsdT | PCSK9 antisense | (SEQ ID NO: 17) |
| ONT-110 | (Rp, Rp)-asAGcAAAAcAGGUCuAGAAdTsdT | PCSK9 antisense | (SEQ ID NO: 18) |
| ONT-111 | (Sp, Rp)-asGcAAAAcAGGUCuAGAAdTsdT | PCSK9 antisense | (SEQ ID NO: 19) |
| ONT-112 | (Sp, Sp)-asGcAAAAcAGGUCuAGAAdTsdT | PCSK9 antisense | (SEQ ID NO: 20) |
| ONT-113 | (Rp, Sp)-asGcAAAAcAGGUCuAGAAdTsdT | PCSK9 antisense | (SEQ ID NO: 21) | wherein lower case letters represent 2'-OMe RNA residues; capital letters represent 2'-OH RNA residues; and bolded and "s" indicates a phosphorothioate moiety; and

| PCSK9 (1) | (All (Sp))-ususcsusAsGsAscscsusGsusususususGscsususdTsdT | (SEQ ID NO: 22) |
|---|---|---|
| PCSK9 (2) | (All (Rp))-ususcsusAsGsAscscsusGsusususususGscsususdTsdT | (SEQ ID NO: 23) |
| PCSK9 (3) | (All (Sp))-usucuAsGsAsccuGsuuuuGscuusdTsdT | (SEQ ID NO: 24) |
| PCSK9 (4) | (All (Rp))-usucuAsGsAsccuGsuuuuGscuusdTsdT | (SEQ ID NO: 25) |

| | | |
|---|---|---|
| PCSK9 (5) | (Rp, Sp, Rp, Sp, Rp, Sp, Rp, Sp, Rp, Sp, Rp, Sp, Rp, Sp, Rp, Sp, Rp, Sp, Rp, Sp)-ususcsusAsGsAscscsusGsususususGscsususdTsdT | (SEQ ID NO: 26) |
| PCSK9 (6) | (Sp, Rp, Sp, Rp, Sp, Rp, Sp, Rp, Sp, Rp, Sp, Rp, Sp, Rp, Sp, Rp, Sp, Rp, Sp, Rp)-ususcsusAsGsAscscsusGsususususGscsususdTsdT | (SEQ ID NO: 27) | wherein lower case letters represent 2'-OMe RNA residues; capital letters represent RNA residues; d=2'-deoxy residues; and "s" indicates a phosphorothioate moiety; and

| | | |
|---|---|---|
| PCSK9 (7) | (All (Rp))-AsAsGscsAsAsAsAscsAsGsGsUsCsusAsGsAsAsdTsdT | (SEQ ID NO: 28) |
| PCSK9 (8) | (All (Sp))-AsAsGscsAsAsAsAscsAsGsGsUsCsusAsGsAsAsdTsdT | (SEQ ID NO: 29) |
| PCSK9 (9) | (All (Rp))-AsAGcAAAAcsAsGsGsUsCsusAsGsAsAsdTsdT | (SEQ ID NO: 30) |
| PCSK9 (10) | (All (Sp))-AsAGcAAAAcsAsGsGsUsCsusAsGsAsAsdTsdT | (SEQ ID NO: 31) |
| PCSK9 (11) | (All (Rp))-AAsGscsAsAsAsAscAGGUCuAGAAdTsdT | (SEQ ID NO: 32) |
| PCSK9 (12) | (All (Sp))-AAsGscsAsAsAsAscAGGUCuAGAAdTsdT | (SEQ ID NO: 33) |
| PCSK9 (13) | (All (Rp))-AsAsGscAsAsAsAscAsGsGsUsCsuAsGsAsAsdTsdT | (SEQ ID NO: 34) |
| PCSK9 (14) | (All (Sp))-AsAsGscAsAsAsAscAsGsGsUsCsuAsGsAsAsdTsdT | (SEQ ID NO: 35) |
| PCSK9 (15) | (All (Rp))-AsAGcAAAsAscAsGsGsUsCsusAsGsAsAsdTsdT | (SEQ ID NO: 36) |
| PCSK9 (16) | (All (Sp))-AsAGcAAAsAscAsGsGsUsCsusAsGsAsAsdTsdT | (SEQ ID NO: 37) |
| PCSK9 (17) | (Rp, Sp, Rp, Sp, Rp, Sp, Rp, Sp, Rp, Sp, Rp, Sp, Rp, Sp)-AsAGcAAAsAscAsGsGsUsCsusAsGsAsAsdTsdT | (SEQ ID NO: 38) |
| PCSK9 (18) | (Sp, Rp, Sp, Rp, Sp, Rp, Sp, Rp, Sp, Rp, Sp, Rp, Sp, Rp)-AsAGcAAAsAscAsGsGsUsCsusAsGsAsAsdTsdT | (SEQ ID NO: 39) | wherein lower case letters represent 2'-OMe RNA residues; capital letters represent RNA residues; d=2'-deoxy residues; "s" indicates a phosphorothioate moiety; and wherein lower case letters represent 2'-OMe RNA residues; capital letters represent 2'-F RNA residues; d=2'-deoxy residues; and "s" indicates a phosphorothioate moiety; and

| | | |
|---|---|---|
| PCSK9 (19) | (All (Rp))-UfsusCfsusAfsgsAfscsCfsusGfsusUfsusUfsgsCfsusUfsdTsdT | (SEQ ID NO: 40) |
| PCSK9 (20) | (All (Sp))-UfsusCfsusAfsgsAfscsCfsusGfsusUfsusUfsgsCfsusUfsdTsdT | (SEQ ID NO: 41) |
| PCSK9 (21) | (All (Rp))-UfsuCfsuAfsgAfscCfsuGfsuUfsuUfsgCfsuUfsdTsdT | (SEQ ID NO: 42) |
| PCSK9 (22) | (All (Sp))-UfsuCfsuAfsgAfscCfsuGfsuUfsuUfsgCfsuUfsdTsdT | (SEQ ID NO: 43) |
| PCSK9 (23) | (Rp, Sp, Rp, Sp, Rp, Sp, Rp, Sp, Rp, Sp, Rp, Sp, Rp, Sp, Rp, Sp, Rp, Sp, Rp, Sp)-UfsusCfsusAfsgsAfscsCfsusGfsusUfsusUfsgsCfsusUfsdTsdT | (SEQ ID NO: 44) |
| PCSK9 (24) | (Sp, Rp, Sp, Rp, Sp, Rp, Sp, Rp, Sp, Rp, Sp, Rp, Sp, Rp, Sp, Rp, Sp, Rp, Sp, Rp)-UfsusCfsusAfsgsAfscsCfsusGfsusUfsusUfsgsCfsusUfsdTsdT | (SEQ ID NO: 45) |

| | | | |
|---|---|---|---|
| PCSK9 (25) | (All (Rp))- asAfsgsCfsasAfsasAfscsAfsgsGfsusCfsusAfsgsAfsasdTsdT | | (SEQ ID NO: 46) |
| PCSK9 (26) | (All (Sp))- asAfsgsCfsasAfsasAfscsAfsgsGfsusCfsusAfsgsAfsasdTsdT | | (SEQ ID NO: 47) |
| PCSK9 (27) | (All (Rp))-asAfgCfaAfaAfcsAfsgsGfsusCfsusAfsgsAfsasdTsdT | | (SEQ ID NO: 48) |
| PCSK9 (28) | (All (Sp))-asAfgCfaAfaAfcsAfsgsGfsusCfsusAfsgsAfsasdTsdT | | (SEQ ID NO: 49) |
| PCSK9 (29) | (All (Rp))-asAfsgCfsaAfsaAfscAfsgGfsuCfsuAfsgAfsadTsdT | | (SEQ ID NO: 50) |
| PCSK9 (30) | (All (Sp))-asAfsgCfsaAfsaAfscAfsgGfsuCfsuAfsgAfsadTsdT | | (SEQ ID NO: 51) |
| PCSK9 (31) | (Rp, Sp, Rp, Sp, Rp, Sp, Rp, Sp, Rp, Sp, Rp, Sp, Rp, Sp)- asAfgCfaAfasAfscAfsgsGfsusCfsusAfsgsAfsasdTsdT | | (SEQ ID NO: 52) |
| PCSK9 (32) | (Sp, Rp, Sp, Rp, Sp, Rp, Sp, Rp, Sp, Rp, Sp, Rp, Sp, Rp)- asAfgCfaAfasAfscAfsgsGfsusCfsusAfsgsAfsasdTsdT | | (SEQ ID NO: 53) | wherein lower case letters represent 2'-OMe RNA residues; capital letters represent 2'-F RNA residues; d=2'-deoxy residues; and "s" indicates a phosphorothioate moiety.

In some embodiments, a single oligonucleotide in a provided composition is not an oligonucleotide selected from: d[$A_R C_S A_R C_S A_R C_S A_R C_S A_R C$] (SEQ ID NO: 54), d[$C_S C_S C_S C_R C_R C_S C_S C_S C_S C$] (SEQ ID NO: 55), d[$C_S C_S C_S C_S C_S C_S C_R C_R C_S C$] (SEQ ID NO: 56) and d[$C_S C_S C_S C_S C_S C_R C_R C_S C_S C$] (SEQ ID NO: 57), wherein R is Rp phosphorothioate linkage, and S is Sp phosphorothioate linkage.

In some embodiments, a single oligonucleotide in a provided composition is not an oligonucleotide selected from: GGA$_R$T$_S$G$_R$T$_S$T$_R$$^m$C$_S$TCGA (SEQ ID NO: 58), GGA$_R$T$_R$G$_S$T$_S$T$_R$$^m$C$_R$TCGA (SEQ ID NO: 59), GGA$_S$T$_S$G$_R$-T$_R$T$_S$C$_S$$^m$TCGA (SEQ ID NO: 60), wherein R is Rp phosphorothioate linkage, S is Sp phosphorothioate linkage, all other linkages are PO, and each $^m$C is a 5-methyl cytosine modified nucleoside.

In some embodiments, a single oligonucleotide in a provided composition is not an oligonucleotide selected from: T$_k$T$_k$$^m$C$_k$AGT$^m$CATGA$^m$CT$_k$T$^m$C$_k$$^m$C$_k$ (SEQ ID NO: 61), wherein each nucleoside followed by a subscript 'k' indicates a (S)-cEt modification, R is Rp phosphorothioate linkage, S is Sp phosphorothioate linkage, each $^m$C is a 5-methyl cytosine modified nucleoside, and all internucleoside linkages are phosphorothioates (PS) with stereochemistry patterns selected from RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

In some embodiments, a single oligonucleotide in a provided composition is not an oligonucleotide selected from: T$_k$T$_k$$^m$C$_k$AGT$^m$CATGA$^m$CTT$_k$$^m$C$_k$$^m$C$_k$ (SEQ ID NO: 62), wherein each nucleoside followed by a subscript 'k' indicates a (S)-cEt modification, R is Rp phosphorothioate linkage, S is Sp phosphorothioate linkage, each $^m$C is a 5-methyl cytosine modified nucleoside and all internucleoside linkages are phosphorothioates (PS) with stereochemistry patterns selected from: RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

Modified Oligonucleotide Structures

As noted above, in light of the usefulness of oligonucleotide compositions in various applications and indications, those skilled in the art have endeavored to develop modifications of oligonucleotide structures that may have preferred or desirable characteristics or attributes as compared with naturally-occurring oligonucleotide molecules, for example as used in particular applications and indications. Exemplary such modifications are described below.

WO2010/141471 (herein "Traversa I") teaches the modification of different types of nucleic acid constructs modified to have a reduced net polyanionic charge. WO2010/039543 (herein "Traversa II") teaches compositions and methods for making neutral polynucleotides (NNs) with reduced polyanionic charge. WO2008/008476 (herein, "Traversa III") describes the synthesis of SATE (Imbach-type) phosphate prodrugs. Traversa I, II, and III do not teach chirally controlled oligonucleotides, compositions thereof, and methods of making and using the same, as described by the present invention.

WO2010/072831 (herein "Girindus et al.") also teaches the modification of oligonucleotides. In particular, Girindus et al. teaches the use of sulfurization reagents to generate phosphorothioate triesters as prodrugs. Girindus et al. does not teach chirally controlled oligonucleotides, compositions thereof, and methods of making and using the same, as described by the present invention.

Similarly, WO2004/085454 (herein "Avecia I") teaches the preparation of phosphorothioate oligonucleotides through, e.g., transient silylation of poly-H-phosphonate diesters. WO2001/027126 (herein "Avecia II") teaches processes for the solid phase synthesis of phosphotriester oligonucleotides by coupling H-phosphonate monomers to a solid supported 5'-hydroxyl oligonucleotide and further sulfurization of the resulting H-phosphonate diester into a phosphorothioate triester. The disclosure of WO2001/064702 (herein "Avecia III") is similar to Avecia II and further describes solid-phase synthesis on different solid supports. Avecia I, II, and III do not teach chirally controlled oligonucleotides, compositions thereof, and methods of making and using the same, as described by the present invention.

WO1997/006183 (herein "Chiron") teaches oligonucleotides with cationic internucleotide linkages comprising asymmetric phosphorus, such as stereopure amidates. Chiron teaches stereopure oligonucleotides obtained via crystallization of a mixture of diastereomers or via resolution using, e.g., column chromatography. Chiron does not teach chirally controlled oligonucleotides, compositions thereof, and methods of making and using the same, as described by the present invention.

WO2009/146123 (herein "Spring Bank I") teaches compositions and methods for treating viral infections using substituted phosphate oligonucleotides and phosphorothioate triesters. WO2007/070598 (herein "Spring Bank II") teaches phosphotriester prodrugs as antiviral nucleic acids and teaches the synthesis of phosphorothioate prodrugs. Spring Bank I and II do not teach chirally controlled oligonucleotides, compositions thereof, and methods of making and using the same, as described by the present invention.

EP0779893 (herein "Hybridon") teaches lipophilic prodrugs for the increased cellular uptake of antisense oligonucleotides and observes that Rp and Sp phosphorothioates and phosphorothioate triester dimers can have different enzymatic stability properties. Hybridon does not teach chirally controlled oligonucleotides, compositions thereof, and methods of making and using the same, as described by the present invention.

WO1997/047637 (herein "Imbach I") teaches generally the Imbach "SATE" (S-acyl thioethyl) prodrug oligonucleotide compositions and methods. Imbach I describes, for example, bioreversible phosphotriester prodrugs and the preparation of certain prodrug oligonucleotides using post-synthetic alkylation or prodrug-group-containing phosphoramidites. U.S. Pat. No. 6,124,445 (herein "Imbach II") teaches modified antisense and chimeric prodrug oligonucleotides. Imbach I and II do not teach chirally controlled oligonucleotides, compositions thereof, and methods of making and using the same, as described by the present invention.

WO2006/065751 (herein "Beaucage") teaches CpG oligonucleotide phosphorothioate prodrugs that comprise thermolabile substituents (which substituents are introduced via a phosphoramidite monomer), and applications thereof. Beaucage does not teach chirally controlled oligonucleotides, compositions thereof, and methods of making and using the same, as described by the present invention.

Takeshi Wada et al. developed novel methods for the stereo-controlled synthesis of P-chiral nucleic acids using amidite chiral auxiliaries (JP4348077, WO2005/014609, WO2005/092909, and WO2010/064146, cumulatively referred to herein as "Wada I"). In particular, WO2010/064146 (referred to herein as "Wada II") discloses methods for synthesizing phosphorus atom-modified nucleic acids wherein the stereochemical configuration at phosphorus is controlled. However, the methods of Wada II are limited in that they do not provide for individual P-modification of each chiral linkage phosphorus in a controlled and designed manner. That is, the methods for P-modified linkages of Wada II provide for the generation of a condensed intermediate poly H-phosphonate oligonucleotide strand that, once built to a desired length, is mass modified at the linkage phosphorus to provide, e.g., a desired phosphorothioate diester, phosphoramidate or boranophosphate or other such phosphorus atom-modified nucleic acids (referred to as Route B in the document—Scheme 6, page 36). Furthermore, the H-phosphonate oligonucleotide strands of Wada II are of shorter lengths (e.g., dimer trimer, or tetramer). Combined with the fact that there is no capping step in route B, which generally presents low crude purity as a result of the accumulation of "n−1"-type byproducts, the Wada II route contains limitations in regards of the synthesis of longer oligonucleotides. While Wada II contemplates generally that a particular oligonucleotide could be envisaged to contain different modifications at each linkage phosphorus, Wada II does not describe or suggest methods for controlled iterative installation of such modifications, as are described herein. To the extent that Wada II depicts a synthetic cycle that does not require an H-phosphonate intermediate oligonucleotide to be completely assembled prior to modification at the linkage phosphorus (therein referred to as Route A, page 35, Scheme 5, "Synthesis of a nucleic acid comprising a chiral X-phosphonate moiety of Formula 1 via Route A"), this general disclosure does not teach certain key steps that are required to install certain P-modifications, as provided by the present invention, and especially not with any degree of efficiency and versatility such that this cycle would be useful in the synthesis of chirally controlled P-modified oligonucleotides, and especially oligonucleotides of longer lengths.

At least one such inefficiency of Wada II is noted by Wada et al. in WO2012/039448 (herein "Wada III"). Wada III teaches novel chiral auxiliaries for use in Wada II methods to produce H-phosphonate oligonucleotides that, once built, can be subsequently modified to provide, inter alia, phosphorothioates and the like. Wada et al. observe in Wada III that the four types of chiral auxiliaries disclosed in Wada II formed strong bonds with phosphorus at the linkage phosphorus and thus did not allow for efficient removal. Wada III notes that removal of the Wada II chiral auxiliaries required harsh conditions, which conditions were prone to compromising the integrity of the product oligonucleotide. Wada III observes that this is especially problematic when synthesizing long chain oligonucleotides for at least the reason that as the degradation reaction(s) proceed, additional byproducts are generated that can further react with and degrade the product oligonucleotide. Wada III therefore provides chiral auxiliaries that can be more efficiently cleaved from the oligonucleotide under mild acidic conditions by way of an $S_N1$ mechanism releasing the H-phosphonate internucleotide linkage (route B), or under relatively mild basic conditions, by a β-elimation pathway.

One of skill in the chemical and synthetic arts will immediately appreciate the complexities associated with generating chirally controlled oligonucleotides such as those provided by the present invention. For instance, in order to synthesize and isolate a chirally controlled oligonucleotide, conditions for each monomer addition must be designed such that (1) the chemistry is compatible with every portion of the growing oligonucleotide; (2) the byproducts generated during each monomer addition do not compromise the structural and stereochemical integrity of the growing oligonucleotide; and (3) the crude final product composition is a composition which allows for isolation of the desired chirally controlled oligonucleotide product.

Oligonucleotide phosphorothioates have shown therapeutic potential (Stein et al., Science (1993), 261:1004-12; Agrawal et al., Antisense Res. and Dev. (1992), 2:261-66; Bayever et al., Antisense Res. and Dev. (1993), 3:383-390). Oligonucleotide phosphorothioates prepared without regard to the stereochemistry of the phosphorothioate exist as a mixture of $2^n$ diastereomers, where n is the number of internucleotide phosphorothioates linkages. The chemical and biological properties of these diastereomeric phosphorothioates can be distinct. For example, Wada et al (Nucleic Acids Symposium Series No. 51 p. 119-120; doi:10.1093/nass/nrm060) found that stereodefined-(Rp)-(Ups)9U/(Ap)9A duplex showed a higher Tm value than that of natural-(Up)9U/(Ap)9A and stereodefined-(Sp)-(Ups)9U did not form a duplex. In another example, in a study by Tang et al., (Nucleosides Nucleotides (1995), 14:985-990) stereopure Rp-oligodeoxyribonucleoside phosphorothioates were found to possess lower stability to nucleases endogenous to human serum that the parent oligodeoxyribonucleoside phosphorothioates with undefined phosphorus chirality.

Chirally Controlled Oligonucleotides and Chirally Controlled Oligonucleotide Compositions The present invention provides chirally controlled oligonucleotides, and chirally controlled oligonucleotide compositions which are of high crude purity and of high diastereomeric purity. In some embodiments, the present invention provides chirally controlled oligonucleotides, and chirally controlled oligonucleotide compositions which are of high crude purity. In some embodiments, the present invention provides chirally controlled oligonucleotides, and chirally controlled oligonucleotide compositions which are of high diastereomeric purity.

In some embodiments, the present invention provides a chirally controlled oligonucleotide composition comprising oligonucleotides defined by having:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

In some embodiments, the present invention provides chirally controlled oligonucleotide composition of oligonucleotides in that the composition is enriched, relative to a substantially racemic preparation of the same oligonucleotides, for oligonucleotides of a single oligonucleotide type. In some embodiments, the present invention provides chirally controlled oligonucleotide composition of oligonucleotides in that the composition is enriched, relative to a substantially racemic preparation of the same oligonucleotides, for oligonucleotides of a single oligonucleotide type that share:
1) a common base sequence and length;
2) a common pattern of backbone linkages; and
3) a common pattern of backbone chiral centers.

In some embodiments, the present invention provides a chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type.

In some embodiments, as understood by a person having ordinary skill in the art, in a substantially racemic (or chirally uncontrolled) preparation of oligonucleotides, all or most coupling steps are not chirally controlled in that the coupling steps are not specifically conducted to provide enhanced stereoselectivity. An exemplary substantially racemic preparation of oligonucleotides is the preparation of phosphorothioate oligonucleotides through sulfurizing phosphite triesters with either tetraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions).

In some embodiments, a chirally controlled oligonucleotide composition is a substantially pure preparation of a oligonucleotide type in that oligonucleotides in the composition that are not of the oligonucleotide type are impurities form the preparation process of said oligonucleotide type, in some case, after certain purification procedures.

In some embodiments, the present invention provides oligonucleotides comprising one or more diastereomerically pure internucleotidic linkages with respect to the chiral linkage phosphorus. In some embodiments, the present invention provides oligonucleotides comprising one or more diastereomerically pure internucleotidic linkages having the structure of formula I. In some embodiments, the present invention provides oligonucleotides comprising one or more diastereomerically pure internucleotidic linkages with respect to the chiral linkage phosphorus, and one or more phosphate diester linkages. In some embodiments, the present invention provides oligonucleotides comprising one or more diastereomerically pure internucleotidic linkages having the structure of formula I, and one or more phosphate diester linkages. In some embodiments, the present invention provides oligonucleotides comprising one or more diastereomerically pure internucleotidic linkages having the structure of formula I-c, and one or more phosphate diester linkages. In some embodiments, such oligonucleotides are prepared by using stereoselective oligonucleotide synthesis, as described in this application, to form pre-designed diastereomerically pure internucleotidic linkages with respect to the chiral linkage phosphorus. For instance, in one exemplary oligonucleotide of (Rp/Sp, Rp/Sp, Rp/Sp, Rp, Rp, Sp, Sp, Sp, Sp, Sp Sp, Sp, Sp, Sp, Rp, Rp, Rp, Rp, Rp)-d [GsCsCsTsCsAsGsTsCsTsGsCsTsTsCsGs1Cs1As1CsC] (SEQ ID NO: 63), the first three internucleotidic linkages are constructed using traditional oligonucleotide synthesis method, and the diastereomerically pure internucleotidic linkages are constructed with stereochemical control as described in this application. Exemplary internucleotidic linkages, including those having structures of formula I, are further described below.

In some embodiments, the present invention provides a chirally controlled oligonucleotide, wherein at least two of the individual internucleotidic linkages within the oligonucleotide have different stereochemistry and/or different P-modifications relative to one another. In certain embodiments, the present invention provides a chirally controlled oligonucleotide, wherein at least two individual internucleotidic linkages within the oligonucleotide have different P-modifications relative to one another. In certain embodiments, the present invention provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage. In certain embodiments, the present invention provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate diester internucleotidic linkage. In certain embodiments, the present invention provides a chirally controlled oligonucleotide, wherein at least two of the individual internucleotidic linkages within the oligonucleotide have different P-modifications relative to one another, and wherein the chirally controlled oligonucleotide comprises at least one phosphorothioate triester internucleotidic linkage. In certain embodiments, the present invention provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate triester internucleotidic linkage.

In certain embodiments, the present invention provides a chirally controlled oligonucleotide comprising one or more modified internucleotidic linkages independently having the structure of formula I:

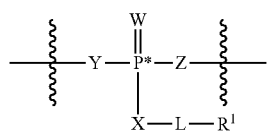

(I)

wherein each variable is as defined and described below. In some embodiments, the present invention provides a chirally controlled oligonucleotide comprising one or more modified internucleotidic linkages of formula I, and wherein individual internucleotidic linkages of formula I within the oligonucleotide have different P-modifications relative to one another. In some embodiments, the present invention provides a chirally controlled oligonucleotide comprising one or more modified internucleotidic linkages of formula I, and wherein individual internucleotidic linkages of formula I within the oligonucleotide have different —X-L-R$^1$ relative to one another. In some embodiments, the present invention provides a chirally controlled oligonucleotide comprising one or more modified internucleotidic linkages of formula I, and wherein individual internucleotidic linkages of formula I within the oligonucleotide have different X relative to one another. In some embodiments, the present invention provides a chirally controlled oligonucleotide comprising one or more modified internucleotidic linkages of formula I, and wherein individual internucleotidic linkages of formula I within the oligonucleotide have different -L-R$^1$ relative to one another.

In some embodiments, the present invention provides a chirally controlled oligonucleotide, wherein at least two of the individual internucleotidic linkages within the oligonucleotide have different stereochemistry and/or different P-modifications relative to one another. In some embodiments, the present invention provides a chirally controlled oligonucleotide, wherein at least two of the individual internucleotidic linkages within the oligonucleotide have different stereochemistry relative to one another, and wherein at least a portion of the structure of the chirally controlled oligonucleotide is characterized by a repeating pattern of alternating stereochemistry.

In some embodiments, the present invention provides a chirally controlled oligonucleotide, wherein at least two of the individual internucleotidic linkages within the oligonucleotide have different P-modifications relative to one another, in that they have different X atoms in their —XLR$^1$ moieties, and/or in that they have different L groups in their —XLR$^1$ moieties, and/or that they have different R$^1$ atoms in their —XLR$^1$ moieties.

In some embodiments, the present invention provides a chirally controlled oligonucleotide, wherein at least two of the individual internucleotidic linkages within the oligonucleotide have different stereochemistry and/or different P-modifications relative to one another and the oligonucleotide has a structure represented by the following formula:

$$[S^B n1 R^B n2 S^B n3 R^B n4 \ldots S^B nx R^B ny]$$

wherein:
each R$^B$ independently represents a block of nucleotide units having the R configuration at the linkage phosphorus;
each S$^B$ independently represents a block of nucleotide units having the S configuration at the linkage phosphorus;
each of n1-ny is zero or an integer, with the requirement that at least one odd n and at least one even n must be non-zero so that the oligonucleotide includes at least two individual internucleotidic linkages with different stereochemistry relative to one another; and
wherein the sum of n1-ny is between 2 and 200, and in some embodiments is between a lower limit selected from the group consisting of 2, 3, 4, 5, 6, 7, 8, 9, 10, 11, 12, 13, 14, 15, 16, 17, 18, 19, 20, 21, 22, 23, 24, 25 or more and an upper limit selected from the group consisting of 5, 10, 15, 20, 25, 30, 35, 40, 45, 50, 55, 60, 65, 70, 75, 80, 85, 90, 95, 100, 110, 120, 130, 140, 150, 160, 170, 180, 190, and 200, the upper limit being larger than the lower limit.

In some such embodiments, each n has the same value; in some embodiments, each even n has the same value as each other even n; in some embodiments, each odd n has the same value each other odd n; in some embodiments, at least two even ns have different values from one another; in some embodiments, at least two odd ns have different values from one another.

In some embodiments, at least two adjacent ns are equal to one another, so that a provided oligonucleotide includes adjacent blocks of S stereochemistry linkages and R stereochemistry linkages of equal lengths. In some embodiments, provided oligonucleotides include repeating blocks of S and R stereochemistry linkages of equal lengths. In some embodiments, provided oligonucleotides include repeating blocks of S and R stereochemistry linkages, where at least two such blocks are of different lengths from one another; in some such embodiments each S stereochemistry block is of the same length, and is of a different length from each R stereochemistry length, which may optionally be of the same length as one another.

In some embodiments, at least two skip-adjacent ns are equal to one another, so that a provided oligonucleotide includes at least two blocks of linkages of a first stereochemistry that are equal in length to one another and are separated by a block of linkages of the other stereochemistry, which separating block may be of the same length or a different length from the blocks of first stereochemistry.

In some embodiments, ns associated with linkage blocks at the ends of a provided oligonucleotide are of the same length. In some embodiments, provided oligonucleotides have terminal blocks of the same linkage stereochemistry. In some such embodiments, the terminal blocks are separated from one another by a middle block of the other linkage stereochemistry.

In some embodiments, a provided oligonucleotide of formula [$S^B$n1$R^B$n2$S^B$n3$R^B$n4 . . . $S^B$nx$R^B$ny] is a stereoblockmer. In some embodiments, a provided oligonucleotide of formula [$S^B$n1$R^B$n2$S^B$n3$R^B$n4 . . . $S^B$nx$R^B$ny] is a stereoskipmer. In some embodiments, a provided oligonucleotide of formula [$S^B$n1$R^B$n2$S^B$n3$R^B$n4 . . . $S^B$nx$R^B$ny] is a stereoaltmer. In some embodiments, a provided oligonucleotide of formula [$S^B$n1$R^B$n2$S^B$n3$R^B$n4 . . . $S^B$nx$R^B$ny] is a gapmer.

In some embodiments, a provided oligonucleotide of formula [$S^B$n1$R^B$n2$S^B$n3$R^B$n4 . . . $S^B$nx$R^B$ny] is of any of the above described patterns and further comprises patterns of P-modifications. For instance, in some embodiments, a provided oligonucleotide of formula [$S^B$n1$R^B$n2$S^B$n3$R^B$n4 . . . $S^B$nx$R^B$ny] and is a stereoskipmer and P-modification skipmer. In some embodiments, a provided oligonucleotide of formula [$S^B$n1$R^B$n2$S^B$n3$R^B$n4 . . . $S^B$nx$R^B$ny] and is a stereoblockmer and P-modification altmer. In some embodiments, a provided oligonucleotide of formula [$S^B$n1$R^B$n2$S^B$n3$R^B$n4 . . . $S^B$nx$R^B$ny] and is a stereoaltmer and P-modification blockmer.

In some embodiments, a provided oligonucleotide of formula [$S^B$n1$R^B$n2$S^B$n3$R^B$n4 . . . $S^B$nx$R^B$ny] is a chirally controlled oligonucleotide comprising one or more modified internucleotide linkages independently having the structure of formula I:

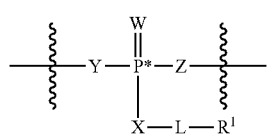

(I)

wherein:
P* is an asymmetric phosphorus atom and is either Rp or Sp;
W is O, S or Se;
each of X, Y and Z is independently —O—, —S—, —N(-L-$R^1$)—, or L;
L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
two R' on the same nitrogen are taken together with their intervening atoms to form an optionally substituted heterocyclic or heteroaryl ring, or
two R' on the same carbon are taken together with their intervening atoms to form an optionally substituted aryl, carbocyclic, heterocyclic, or heteroaryl ring;
-Cy- is an optionally substituted bivalent ring selected from phenylene, carbocyclylene, arylene, heteroarylene, or heterocyclylene;
each R is independently hydrogen, or an optionally substituted group selected from $C_1$-$C_6$ aliphatic, phenyl, carbocyclyl, aryl, heteroaryl, or heterocyclyl; and each ⸸ independently represents a connection to a nucleoside.

In some embodiments, a chirally controlled oligonucleotide comprises one or more modified internucleotidic phosphorus linkages. In some embodiments, a chirally controlled oligonucleotide comprises, e.g., a phosphorothioate or a phosphorothioate triester linkage. In some embodiments, a chirally controlled oligonucleotide comprises a phosphorothioate triester linkage. In some embodiments, a chirally controlled oligonucleotide comprises at least two phosphorothioate triester linkages. In some embodiments, a chirally controlled oligonucleotide comprises at least three phosphorothioate triester linkages. In some embodiments, a chirally controlled oligonucleotide comprises at least four phosphorothioate triester linkages. In some embodiments, a chirally controlled oligonucleotide comprises at least five phosphorothioate triester linkages. Exemplary such modified internucleotidic phosphorus linkages are described further herein.

In some embodiments, a chirally controlled oligonucleotide comprises different internucleotidic phosphorus linkages. In some embodiments, a chirally controlled oligonucleotide comprises at least one phosphate diester internucleotidic linkage and at least one modified internucleotidic linkage. In some embodiments, a chirally controlled oligonucleotide comprises at least one phosphate diester internucleotidic linkage and at least one phosphorothioate triester linkage. In some embodiments, a chirally controlled oligonucleotide comprises at least one phosphate diester internucleotidic linkage and at least two phosphorothioate triester linkages. In some embodiments, a chirally controlled oligonucleotide comprises at least one phosphate diester internucleotidic linkage and at least three phosphorothioate triester linkages. In some embodiments, a chirally controlled oligonucleotide comprises at least one phosphate diester internucleotidic linkage and at least four phosphorothioate triester linkages. In some embodiments, a chirally controlled oligonucleotide comprises at least one phosphate diester internucleotidic linkage and at least five phosphorothioate triester linkages. Exemplary such modified internucleotidic phosphorus linkages are described further herein.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled oligonucleotide is linked to a solid support. In some embodiments, a chirally controlled oligonucleotide is cleaved from a solid support.

In some embodiments, a chirally controlled oligonucleotide comprises at least one phosphate diester internucleotidic linkage and at least two consecutive modified internucleotidic linkages. In some embodiments, a chirally controlled oligonucleotide comprises at least one phosphate diester internucleotidic linkage and at least two consecutive phosphorothioate triester internucleotidic linkages.

In some embodiments, a chirally controlled oligonucleotide is a blockmer. In some embodiments, a chirally controlled oligonucleotide is a stereoblockmer. In some embodiments, a chirally controlled oligonucleotide is a P-modification blockmer. In some embodiments, a chirally controlled oligonucleotide is a linkage blockmer.

In some embodiments, a chirally controlled oligonucleotide is an altmer. In some embodiments, a chirally controlled oligonucleotide is a stereoaltmer. In some embodiments, a chirally controlled oligonucleotide is a P-modification altmer. In some embodiments, a chirally controlled oligonucleotide is a linkage altmer.

In some embodiments, a chirally controlled oligonucleotide is a unimer. In some embodiments, a chirally controlled oligonucleotide is a stereounimer. In some embodiments, a chirally controlled oligonucleotide is a P-modification unimer. In some embodiments, a chirally controlled oligonucleotide is a linkage unimer.

In some embodiments, a chirally controlled oligonucleotide is a gapmer.

In some embodiments, a chirally controlled oligonucleotide is a skipmer.

In some embodiments, the present invention provides a chirally controlled oligonucleotide comprising one or more modified internucleotidic linkages independently having the structure of formula I:

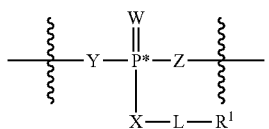

(I)

wherein:
P* is an asymmetric phosphorus atom and is either Rp or Sp;
W is O, S or Se;
each of X, Y and Z is independently —O—, —S—, —N(-L-$R^1$)—, or L;
L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
two R' on the same nitrogen are taken together with their intervening atoms to form an optionally substituted heterocyclic or heteroaryl ring, or
two R' on the same carbon are taken together with their intervening atoms to form an optionally substituted aryl, carbocyclic, heterocyclic, or heteroaryl ring;
-Cy- is an optionally substituted bivalent ring selected from phenylene, carbocyclylene, arylene, heteroarylene, or heterocyclylene;
each R is independently hydrogen, or an optionally substituted group selected from $C_1$-$C_6$ aliphatic, phenyl, carbocyclyl, aryl, heteroaryl, or heterocyclyl; and each $-\xi-$ independently represents a connection to a nucleoside.

As defined generally above and herein, P* is an asymmetric phosphorus atom and is either Rp or Sp. In some embodiments, P* is Rp. In other embodiments, P* is Sp. In some embodiments, an oligonucleotide comprises one or more internucleotidic linkages of formula I wherein each P* is independently Rp or Sp. In some embodiments, an oligonucleotide comprises one or more internucleotidic linkages of formula I wherein each P* is Rp. In some embodiments, an oligonucleotide comprises one or more internucleotidic linkages of formula I wherein each P* is Sp. In some embodiments, an oligonucleotide comprises at least one internucleotidic linkage of formula I wherein P* is Rp. In some embodiments, an oligonucleotide comprises at least one internucleotidic linkage of formula I wherein P* is Sp. In some embodiments, an oligonucleotide comprises at least one internucleotidic linkage of formula I wherein P* is Rp, and at least one internucleotidic linkage of formula I wherein P* is Sp.

As defined generally above and herein, W is O, S, or Se. In some embodiments, W is O. In some embodiments, W is S. In some embodiments, W is Se. In some embodiments, an oligonucleotide comprises at least one internucleotidic linkage of formula I wherein W is O. In some embodiments, an oligonucleotide comprises at least one internucleotidic linkage of formula I wherein W is S. In some embodiments, an oligonucleotide comprises at least one internucleotidic linkage of formula I wherein W is Se.

As defined generally above and herein, each R is independently hydrogen, or an optionally substituted group selected from $C_1$-$C_6$ aliphatic, phenyl, carbocyclyl, aryl, heteroaryl, or heterocyclyl.

In some embodiments, R is hydrogen. In some embodiments, R is an optionally substituted group selected from $C_1$-$C_6$ aliphatic, phenyl, carbocyclyl, aryl, heteroaryl, or heterocyclyl.

In some embodiments, R is an optionally substituted $C_1$-$C_6$ aliphatic. In some embodiments, R is an optionally substituted $C_1$-$C_6$ alkyl. In some embodiments, R is optionally substituted, linear or branched hexyl. In some embodiments, R is optionally substituted, linear or branched pentyl. In some embodiments, R is optionally substituted, linear or branched butyl. In some embodiments, R is optionally substituted, linear or branched propyl. In some embodiments, R is optionally substituted ethyl. In some embodiments, R is optionally substituted methyl.

In some embodiments, R is optionally substituted phenyl. In some embodiments, R is substituted phenyl. In some embodiments, R is phenyl.

In some embodiments, R is optionally substituted carbocyclyl. In some embodiments, R is optionally substituted $C_3$-$C_{10}$ carbocyclyl. In some embodiments, R is optionally substituted monocyclic carbocyclyl. In some embodiments, R is optionally substituted cycloheptyl. In some embodiments, R is optionally substituted cyclohexyl. In some embodiments, R is optionally substituted cyclopentyl. In some embodiments, R is optionally substituted cyclobutyl. In some embodiments, R is an optionally substituted cyclopropyl. In some embodiments, R is optionally substituted bicyclic carbocyclyl.

In some embodiments, R is an optionally substituted aryl. In some embodiments, R is an optionally substituted bicyclic aryl ring.

In some embodiments, R is an optionally substituted heteroaryl. In some embodiments, R is an optionally substituted 5-6 membered monocyclic heteroaryl ring having 1-3 heteroatoms independently selected from nitrogen, sulfur, or oxygen. In some embodiments, R is a substituted 5-6 membered monocyclic heteroaryl ring having 1-3 heteroatoms independently selected from nitrogen, oxygen, or sulfur. In some embodiments, R is an unsubstituted 5-6 membered monocyclic heteroaryl ring having 1-3 heteroatoms independently selected from nitrogen, sulfur, or oxygen.

In some embodiments, R is an optionally substituted 5 membered monocyclic heteroaryl ring having 1-3 heteroatoms independently selected from nitrogen, oxygen or sulfur. In some embodiments, R is an optionally substituted 6 membered monocyclic heteroaryl ring having 1-3 heteroatoms independently selected from nitrogen, oxygen, or sulfur.

In some embodiments, R is an optionally substituted 5-membered monocyclic heteroaryl ring having 1 heteroatom selected from nitrogen, oxygen, or sulfur. In some embodiments, R is selected from pyrrolyl, furanyl, or thienyl.

In some embodiments, R is an optionally substituted 5-membered heteroaryl ring having 2 heteroatoms independently selected from nitrogen, oxygen, or sulfur. In certain embodiments, R is an optionally substituted 5-membered heteroaryl ring having 1 nitrogen atom, and an additional heteroatom selected from sulfur or oxygen. Exemplary R groups include optionally substituted pyrazolyl, imidazolyl, thiazolyl, isothiazolyl, oxazolyl or isoxazolyl.

In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having 2 nitrogen atoms. In certain embodiments, R is an optionally substituted 6-membered heteroaryl ring having 1 nitrogen. Exemplary R groups include optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having 1 heteroatom independently selected from nitrogen, oxygen, or sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, or sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, or sulfur.

In certain embodiments, R is an optionally substituted 6,6-fused heteroaryl ring having 1-4 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having 1 heteroatom independently selected from nitrogen, oxygen, or sulfur. In some embodiments, R is an optionally substituted quinolinyl. In some embodiments, R is an optionally substituted isoquinolinyl. According to one aspect, R is an optionally substituted 6,6-fused heteroaryl ring having 2 heteroatoms independently selected from nitrogen, oxygen, or sulfur. In some embodiments, R is a quinazoline or a quinoxaline.

In some embodiments, R is an optionally substituted heterocyclyl. In some embodiments, R is an optionally substituted 3-7 membered saturated or partially unsaturated heterocyclic ring having 1-2 heteroatoms independently selected from nitrogen, oxygen, or sulfur. In some embodiments, R is a substituted 3-7 membered saturated or partially unsaturated heterocyclic ring having 1-2 heteroatoms independently selected from nitrogen, oxygen, or sulfur. In some embodiments, R is an unsubstituted 3-7 membered saturated or partially unsaturated heterocyclic ring having 1-2 heteroatoms independently selected from nitrogen, oxygen, or sulfur.

In some embodiments, R is an optionally substituted heterocyclyl. In some embodiments, R is an optionally substituted 6 membered saturated or partially unsaturated heterocyclic ring having 1-2 heteroatoms independently selected from nitrogen, oxygen, or sulfur. In some embodiments, R is an optionally substituted 6 membered partially unsaturated heterocyclic ring having 2 heteroatoms independently selected from nitrogen, oxygen, or sulfur. In some embodiments, R is an optionally substituted 6 membered partially unsaturated heterocyclic ring having 2 oxygen atom.

In certain embodiments, R is a 3-7 membered saturated or partially unsaturated heterocyclic ring having 1-2 heteroatoms independently selected from nitrogen, oxygen, or sulfur. In certain embodiments, R is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, R is an optionally substituted 5 membered saturated or partially unsaturated heterocyclic ring having 1-2 heteroatoms independently selected from nitrogen, oxygen, or sulfur.

In certain embodiments, R is an optionally substituted 5-6 membered partially unsaturated monocyclic ring having 1-2 heteroatoms independently selected from nitrogen, oxygen, or sulfur. In certain embodiments, R is an optionally substituted tetrahydropyridinyl, dihydrothiazolyl, dihydrooxazolyl, or oxazolinyl group.

In some embodiments, R is an optionally substituted 8-10 membered bicyclic saturated or partially unsaturated heterocyclic ring having 1-4 heteroatoms independently selected from nitrogen, oxygen, or sulfur. In some embodiments, R is an optionally substituted indolinyl. In some embodiments, R is an optionally substituted isoindolinyl. In some embodiments, R is an optionally substituted 1, 2, 3, 4-tetrahydroquinoline. In some embodiments, R is an optionally substituted 1, 2, 3, 4-tetrahydroisoquinoline.

As defined generally above and herein, each R' is independently —R, —C(O)R, —CO$_2$R, or —SO$_2$R, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring.

In some embodiments, R' is —R, —C(O)R, —CO$_2$R, or —SO$_2$R, wherein R is as defined above and described herein.

In some embodiments, R' is —R, wherein R is as defined and described above and herein. In some embodiments, R' is hydrogen.

In some embodiments, R' is —C(O)R, wherein R is as defined above and described herein. In some embodiments, R' is —CO$_2$R, wherein R is as defined above and described herein. In some embodiments, R' is —SO$_2$R, wherein R is as defined above and described herein.

In some embodiments, two R' on the same nitrogen are taken together with their intervening atoms to form an optionally substituted heterocyclic or heteroaryl ring. In some embodiments, two R' on the same carbon are taken together with their intervening atoms to form an optionally substituted aryl, carbocyclic, heterocyclic, or heteroaryl ring.

As defined generally above and herein, -Cy- is an optionally substituted bivalent ring selected from phenylene, carbocyclylene, arylene, heteroarylene, or heterocyclylene.

In some embodiments, -Cy- is optionally substituted phenylene. In some embodiments, -Cy- is optionally substituted carbocyclylene. In some embodiments, -Cy- is optionally substituted arylene. In some embodiments, -Cy- is optionally substituted heteroarylene. In some embodiments, -Cy- is optionally substituted heterocyclylene.

As defined generally above and herein, each of X, Y and Z is independently —O—, —S—, —N(-L-R$^1$)—, or L, wherein each of L and R$^1$ is independently as defined above and described below.

In some embodiments, X is —O—. In some embodiments, X is —S—. In some embodiments, X is —O— or —S—. In some embodiments, an oligonucleotide comprises at least one internucleotidic linkage of formula I wherein X is —O—. In some embodiments, an oligonucleotide comprises at least one internucleotidic linkage of formula I wherein X is —S—. In some embodiments, an oligonucleotide comprises at least one internucleotidic linkage of formula I wherein X is —O—, and at least one internucleotidic linkage of formula I wherein X is —S—. In some embodiments, an oligonucleotide comprises at least one internucleotidic linkage of formula I wherein X is —O—, and at least one internucleotidic linkage of formula I wherein X is —S—, and at least one internucleotidic linkage of formula I wherein L is an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, X is —N(-L-R$^1$)—. In some embodiments, X is —N(R$^1$)—. In some embodiments, X is —N(R')—. In some embodiments, X is —N(R)—. In some embodiments, X is —NH—.

In some embodiments, X is L. In some embodiments, X is a covalent bond. In some embodiments, X is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, X is an optionally substituted C$_1$-C$_{10}$ alkylene or C$_1$-C$_{10}$ alkenylene. In some embodiments, X is methylene.

In some embodiments, Y is —O—. In some embodiments, Y is —S—.

In some embodiments, Y is —N(-L-R$^1$)—. In some embodiments, Y is —N(R$^1$)—. In some embodiments, Y is —N(R')—. In some embodiments, Y is —N(R)—. In some embodiments, Y is —NH—.

In some embodiments, Y is L. In some embodiments, Y is a covalent bond. In some embodiments, Y is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Y is an optionally substituted C$_1$-C$_{10}$ alkylene or C$_1$-C$_{10}$ alkenylene. In some embodiments, Y is methylene.

In some embodiments, Z is —O—. In some embodiments, Z is —S—.

In some embodiments, Z is —N(-L-R$^1$)—. In some embodiments, Z is —N(R$^1$)—. In some embodiments, Z is —N(R')—. In some embodiments, Z is —N(R)—. In some embodiments, Z is —NH—.

In some embodiments, Z is L. In some embodiments, Z is a covalent bond. In some embodiments, Z is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Z is an optionally substituted C$_1$-C$_{10}$ alkylene or C$_1$-C$_{10}$ alkenylene. In some embodiments, Z is methylene.

As defined generally above and herein, L is a covalent bond or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L is a covalent bond. In some embodiments, L is an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L has the structure of -L$^1$-V—, wherein: L$^1$ is an optionally substituted group selected from

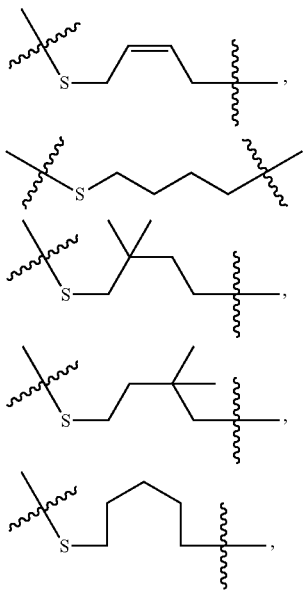

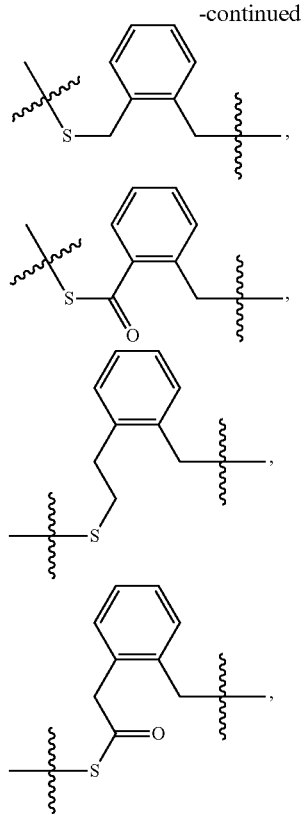

C$_1$-C$_6$ alkylene, C$_1$-C$_6$ alkenylene, carbocyclylene, arylene, C$_1$-C$_6$ heteroalkylene, heterocyclylene, and heteroarylene;
V is selected from —O—, —S—, —NR'—, C(R')$_2$, —S—S—, —B—S—S—C,

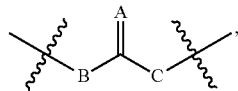

or an optionally substituted group selected from C$_1$-C$_6$ alkylene, arylene, C$_1$-C$_6$ heteroalkylene, heterocyclylene, and heteroarylene;
A is =O, =S, =NR', or =C(R')$_2$;
each of B and C is independently —O—, —S—, —NR'—, —C(R')$_2$—, or an optionally substituted group selected from C$_1$-C$_6$ alkylene, carbocyclylene, arylene, heterocyclylene, or heteroarylene; and
each R' is independently as defined above and described herein.

In some embodiments, L$^1$ is

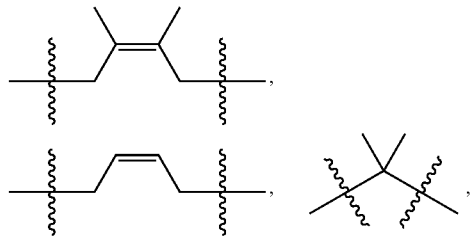

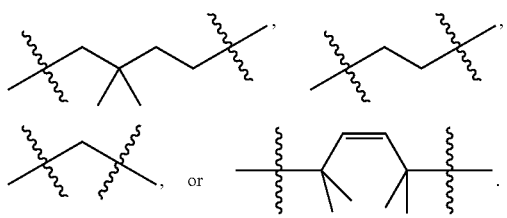

In some embodiments, L¹ is

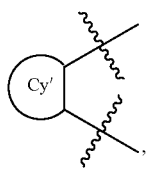

wherein Ring Cy' is an optionally substituted arylene, carbocyclylene, heteroarylene, or heterocyclylene. In some embodiments, L¹ is optionally substituted

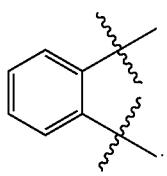 [SMILES: *c1ccccc1*]

In some embodiments, L¹ is

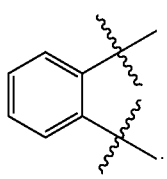 [SMILES: *c1ccccc1*]

In some embodiments, L¹ is connected to X. In some embodiments, L¹ is an optionally substituted group selected from

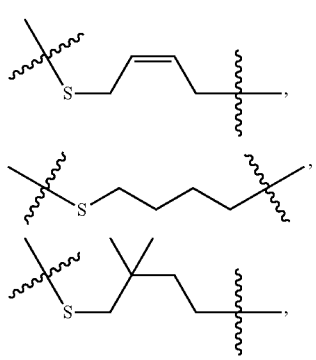

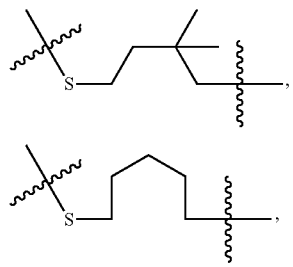

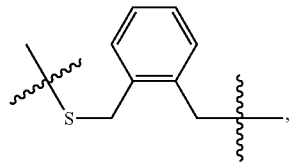

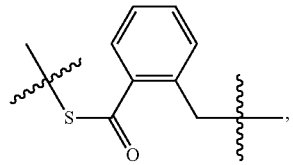

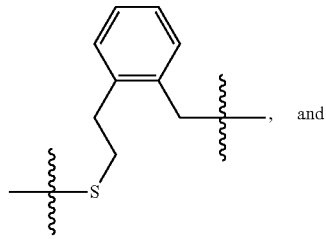

, and

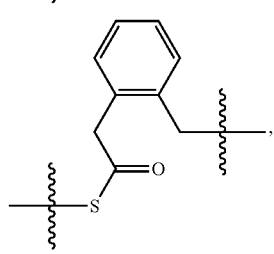

and the sulfur atom is connect to V. In some embodiments, L¹ is an optionally substituted group selected from

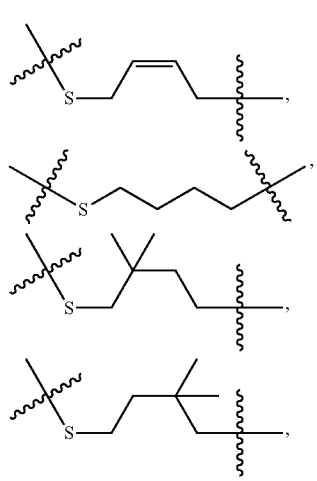

-continued

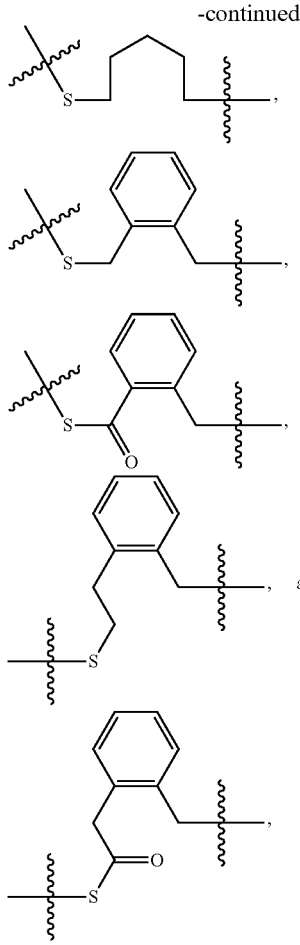

and the carbon atom is connect to X.

In some embodiments, L has the structure of:

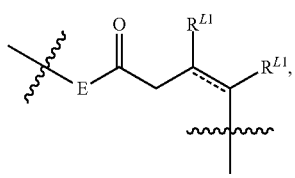

wherein:
E is —O—, —S—, —NR'— or —C(R')$_2$—;
==== is a single or double bond;
the two R$^{L1}$ are taken together with the two carbon atoms to which they are bound to form an optionally substituted aryl, carbocyclic, heteroaryl or heterocyclic ring; and each R' is independently as defined above and described herein.

In some embodiments, L has the structure of:

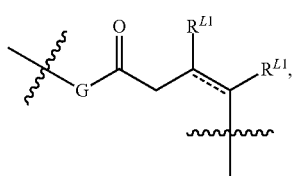

wherein:
G is —O—, —S—, or —NR';
==== is a single or double bond; and
the two R$^{L1}$ are taken together with the two carbon atoms to which they are bound to form an optionally substituted aryl, C$_3$-C$_{10}$ carbocyclic, heteroaryl or heterocyclic ring.

In some embodiments, L has the structure of:

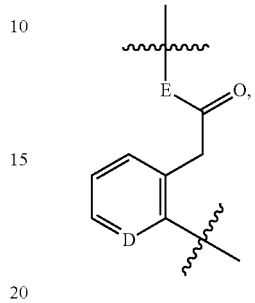

wherein:
E is —O—, —S—, —NR' or —C(R')$_2$—;
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

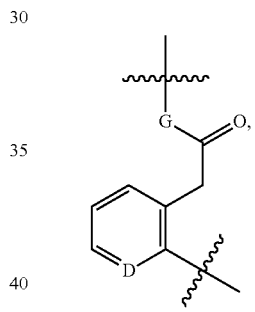

wherein:
G is —O—, —S—, or —NR';
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—.

In some embodiments, L has the structure of:

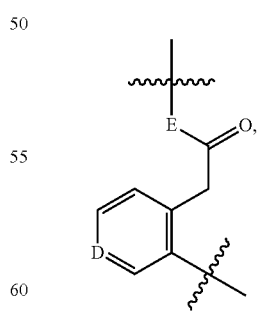

wherein:
E is —O—, —S—, —NR' or —C(R')$_2$—;
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

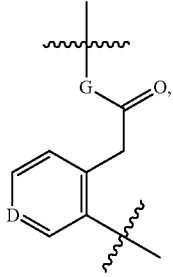

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—.

In some embodiments, L has the structure of:

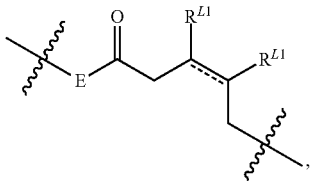

wherein:

E is —O—, —S—, —NR'— or —C(R')$_2$—;

==== is a single or double bond;

the two R$^{L1}$ are taken together with the two carbon atoms to which they are bound to form an optionally substituted aryl, C$_3$-C$_{10}$ carbocyclic, heteroaryl or heterocyclic ring;

and each R' is independently as defined above and described herein.

In some embodiments, L has the structure of:

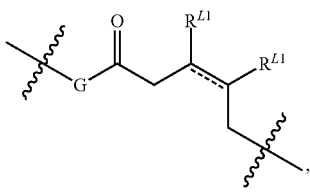

wherein:

G is —O—, —S—, or —NR';

==== is a single or double bond;

the two R$^{L1}$ are taken together with the two carbon atoms to which they are bound to form an optionally substituted aryl, C$_3$-C$_{10}$ carbocyclic, heteroaryl or heterocyclic ring; and each R' is independently as defined above and described herein.

In some embodiments, L has the structure of:

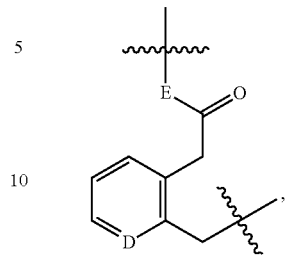

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

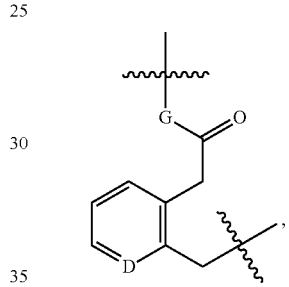

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

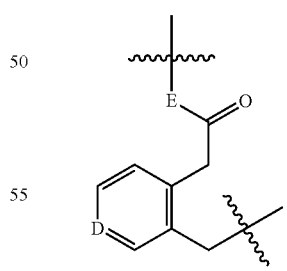

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

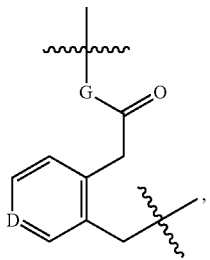

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

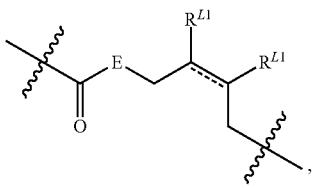

wherein:

E is —O—, —S—, —NR'— or —C(R')$_2$—;

⋯⋯ is a single or double bond;

the two R$^{L1}$ are taken together with the two carbon atoms to which they are bound to form an optionally substituted aryl, C$_3$-C$_{10}$ carbocyclic, heteroaryl or heterocyclic ring; and each R' is independently as defined above and described herein.

In some embodiments, L has the structure of:

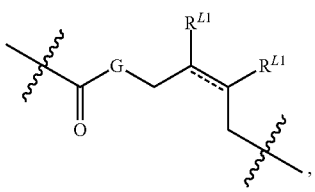

wherein:

G is —O—, —S—, or —NR';

⋯⋯ is a single or double bond;

the two R$^{L1}$ are taken together with the two carbon atoms to which they are bound to form an optionally substituted aryl, C$_3$-C$_{10}$ carbocyclic, heteroaryl or heterocyclic ring; and each R' is independently as defined above and described herein.

In some embodiments, L has the structure of:

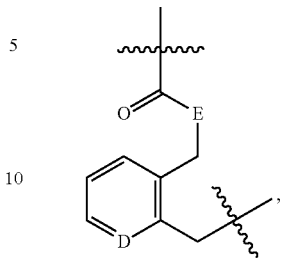

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

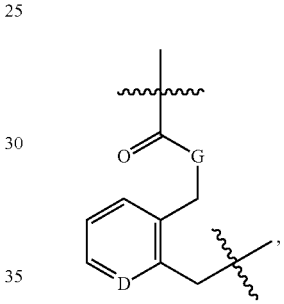

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and R' is as defined above and described herein.

In some embodiments, L has the structure of:

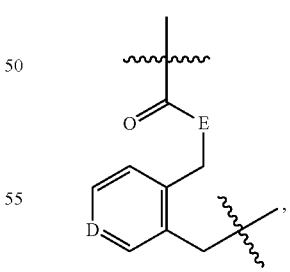

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

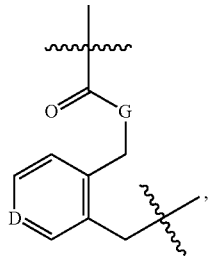

wherein:

G is —O—, —S—, or —NR';
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
R' is as defined above and described herein.

In some embodiments, L has the structure of:

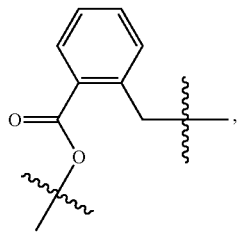 [SMILES: *Cc1ccccc1C(=O)O*]

wherein the phenyl ring is optionally substituted. In some embodiments, the phenyl ring is not substituted. In some embodiments, the phenyl ring is substituted.

In some embodiments, L has the structure of:

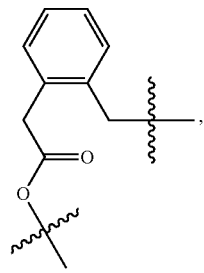 [SMILES: *Cc1ccccc1CC(=O)O*]

wherein the phenyl ring is optionally substituted. In some embodiments, the phenyl ring is not substituted. In some embodiments, the phenyl ring is substituted.

In some embodiments, L has the structure of:

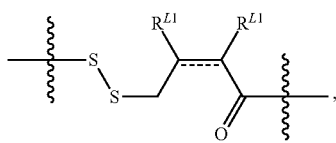

wherein:
---- is a single or double bond; and
the two R$^{L1}$ are taken together with the two carbon atoms to which they are bound to form an optionally substituted aryl, C$_3$-C$_{10}$ carbocyclic, heteroaryl or heterocyclic ring.

In some embodiments, L has the structure of:

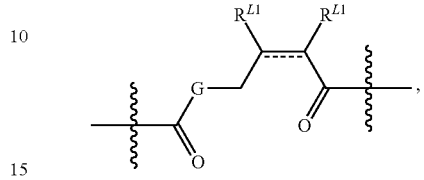

wherein:
G is —O—, —S—, or —NR';
---- is a single or double bond; and
the two R$^{L1}$ are taken together with the two carbon atoms to which they are bound to form an optionally substituted aryl, C$_3$-C$_{10}$ carbocyclic, heteroaryl or heterocyclic ring.

As defined generally above and herein, E is —O—, —S—, —NR'— or —C(R')$_2$—, wherein each R' independently as defined above and described herein. In some embodiments, E is —O—, —S—, or —NR'—. In some embodiments, E is —O—, —S—, or —NH—. In some embodiments, E is —O—. In some embodiments, E is —S—. In some embodiments, E is —NH—.

As defined generally above and herein, G is —O—, —S—, or —NR', wherein each R' independently as defined above and described herein. In some embodiments, G is —O—, —S—, or —NH—. In some embodiments, G is —O—. In some embodiments, G is —S—. In some embodiments, G is —NH—.

In some embodiments, L is -L$^3$-G-, wherein:
L$^3$ is an optionally substituted C$_1$-C$_5$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

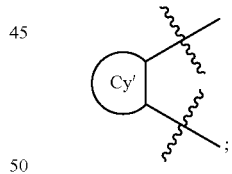

and
wherein each of G, R' and Ring Cy' is independently as defined above and described herein.

In some embodiments, L is -L$^3$-S—, wherein L$^3$ is as defined above and described herein. In some embodiments, L is -L$^3$-O—, wherein L$^3$ is as defined above and described herein. In some embodiments, L is -L$^3$-N(R')—, wherein each of L$^3$ and R' is independently as defined above and described herein. In some embodiments, L is -L$^3$-NH—, wherein each of L$^3$ and R' is independently as defined above and described herein.

In some embodiments, L$^3$ is an optionally substituted C$_5$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

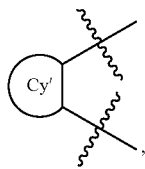 [SMILES: *CC*]

and each of R' and Ring Cy' is independently as defined above and described herein. In some embodiments, $L^3$ is an optionally substituted $C_5$ alkylene. In some embodiments, -$L^3$-G- is

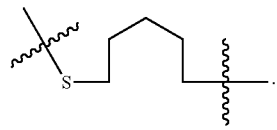 [SMILES: *CCCCCS*]

In some embodiments, $L^3$ is an optionally substituted $C_4$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

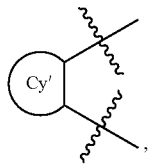 [SMILES: *CC*]

and each of R' and Cy' is independently as defined above and described herein.

In some embodiments, -$L^3$-G- is

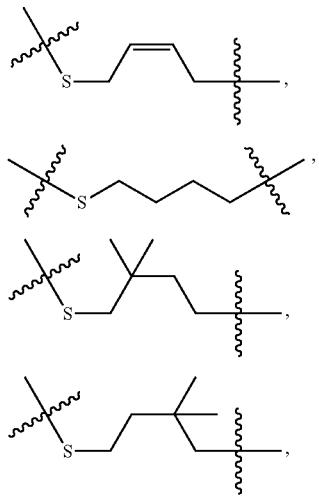

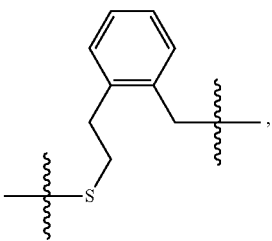

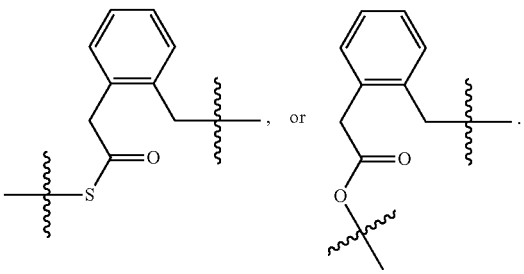

In some embodiments, $L^3$ is an optionally substituted $C_3$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

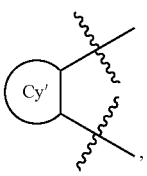 [SMILES: *CC*]

and each of R' and Cy' is independently as defined above and described herein.

In some embodiments, -$L^3$-G- is

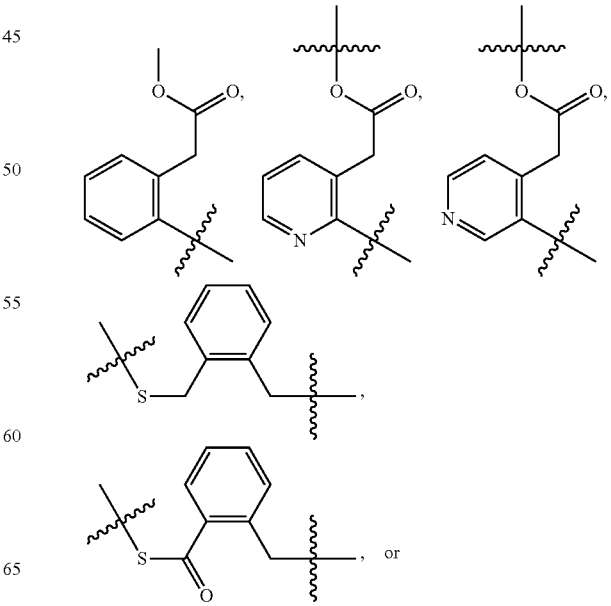

-continued

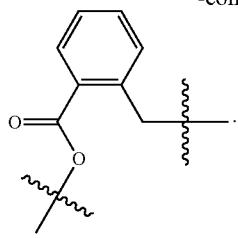

In some embodiments, L is

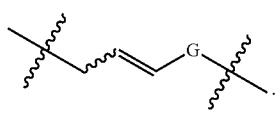

In some embodiments, L is

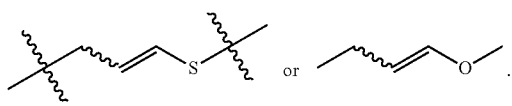

In some embodiments, L is

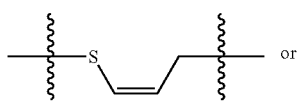

In some embodiments, $L^3$ is an optionally substituted $C_2$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

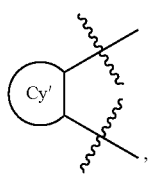 [SMILES: *CC*]

and each of R' and Cy' is independently as defined above and described herein.

In some embodiments, -$L^3$-G- is

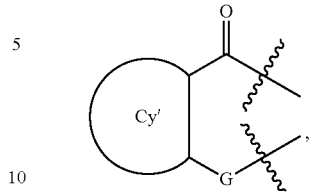

wherein each of G and Cy' is independently as defined above and described herein. In some embodiments, L is

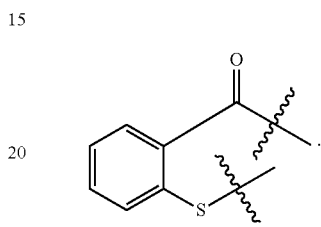

In some embodiments, L is -$L^4$-G-, wherein $L^4$ is an optionally substituted $C_1$-$C_2$ alkylene; and G is as defined above and described herein. In some embodiments, L is -$L^4$-G-, wherein $L^4$ is an optionally substituted $C_1$-$C_2$ alkylene; G is as defined above and described herein; and G is connected to $R^1$. In some embodiments, L is -$L^4$-G-, wherein $L^4$ is an optionally substituted methylene; G is as defined above and described herein; and G is connected to $R^1$. In some embodiments, L is -$L^4$-G-, wherein $L^4$ is methylene; G is as defined above and described herein; and G is connected to $R^1$. In some embodiments, L is -$L^4$-G-, wherein $L^4$ is an optionally substituted —(CH$_2$)$_2$—; G is as defined above and described herein; and G is connected to $R^1$. In some embodiments, L is -$L^4$-G-, wherein $L^4$ is —(CH$_2$)$_2$—; G is as defined above and described herein; and G is connected to $R^1$.

In some embodiments, L is

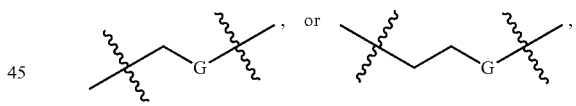

wherein G is as defined above and described herein, and G is connected to $R^1$. In some embodiments, L is

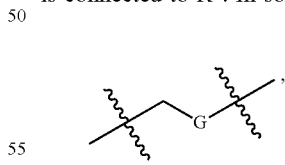

wherein G is as defined above and described herein, and G is connected to $R^1$. In some embodiments, L is

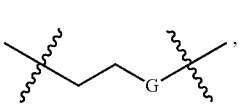

wherein G is as defined above and described herein, and G is connected to $R^1$. In some embodiments, L is

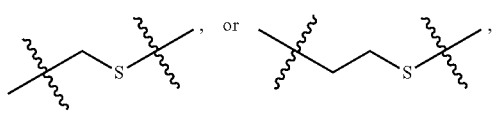

wherein the sulfur atom is connected to $R^1$. In some embodiments, L is

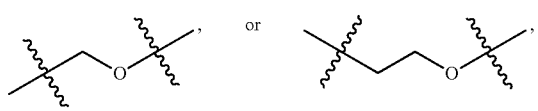

wherein the oxygen atom is connected to $R^1$.

In some embodiments, L is

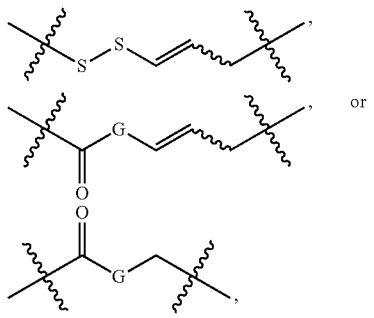

wherein G is as defined above and described herein.

In some embodiments, L is —S—$R^{L3}$— or —S—C(O)—$R^{L3}$—, wherein $R^{L3}$ is an optionally substituted, linear or branched, $C_1$-$C_9$ alkylene, wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each of R' and -Cy- is independently as defined above and described herein. In some embodiments, L is —S—$R^{L3}$ or —S—C(O)—$R^{L3}$—, wherein $R^{L3}$ is an optionally substituted $C_1$-$C_6$ alkylene. In some embodiments, L is —S—$R^{L3}$— or —S—C(O)—$R^{L3}$—, wherein $R^{L3}$ is an optionally substituted $C_1$-$C_6$ alkenylene. In some embodiments, L is —S—$R^{L3}$ or —S—C(O)—$R^{L3}$—, wherein $R^{L3}$ is an optionally substituted $C_1$-$C_6$ alkylene wherein one or more methylene units are optionally and independently replaced by an optionally substituted $C_1$-$C_6$ alkenylene, arylene, or heteroarylene. In some embodiments, $R^{L3}$ is an optionally substituted —S—($C_1$-$C_6$ alkenylene)-, —S—($C_1$-$C_6$ alkylene)-, —S—($C_1$-$C_6$ alkylene)-arylene-($C_1$-$C_6$ alkylene)-, —S—CO-arylene-($C_1$-$C_6$ alkylene)-, or —S—CO—($C_1$-$C_6$ alkylene)-arylene-($C_1$-$C_6$ alkylene)-.

In some embodiments, L is

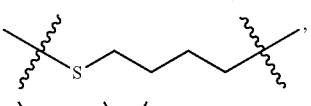

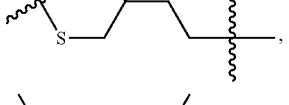

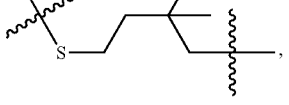

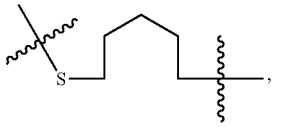

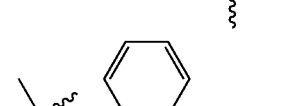

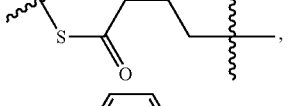

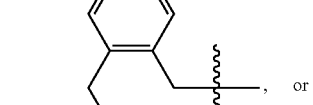

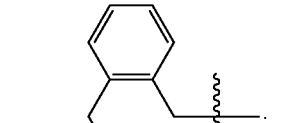

In some embodiments, L is

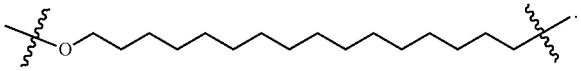 [SMILES: *CCCCCCCCCCCCCCCCO*]

In some embodiments, L is

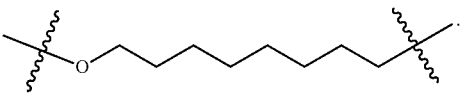 [SMILES: *CCCCCCCCO*]

In some embodiments,

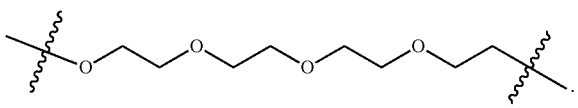 [SMILES: *CCOCCOCCOCCO*]

In some embodiments, the sulfur atom in the L embodiments described above and herein is connected to X. In some embodiments, the sulfur atom in the L embodiments described above and herein is connected to $R^1$.

As defined generally above and herein, $R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is halogen, R, or an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein.

In some embodiments, $R^1$ is hydrogen. In some embodiments, $R^1$ is halogen. In some embodiments, $R^1$ is —F. In some embodiments, $R^1$ is —Cl. In some embodiments, $R^1$ is —Br. In some embodiments, $R^1$ is —I.

In some embodiments, $R^1$ is R wherein R is as defined above and described herein.

In some embodiments, $R^1$ is hydrogen. In some embodiments, $R^1$ is an optionally substituted group selected from $C_1$-$C_{50}$ aliphatic, phenyl, carbocyclyl, aryl, heteroaryl, or heterocyclyl.

In some embodiments, $R^1$ is an optionally substituted $C_1$-$C_{50}$ aliphatic. In some embodiments, $R^1$ is an optionally substituted $C_1$-$C_{10}$ aliphatic. In some embodiments, $R^1$ is an optionally substituted $C_1$-$C_6$ aliphatic. In some embodiments, $R^1$ is an optionally substituted $C_1$-$C_6$ alkyl. In some embodiments, $R^1$ is optionally substituted, linear or branched hexyl. In some embodiments, $R^1$ is optionally substituted, linear or branched pentyl. In some embodiments, $R^1$ is optionally substituted, linear or branched butyl. In some embodiments, $R^1$ is optionally substituted, linear or branched propyl. In some embodiments, $R^1$ is optionally substituted ethyl. In some embodiments, $R^1$ is optionally substituted methyl.

In some embodiments, $R^1$ is optionally substituted phenyl. In some embodiments, $R^1$ is substituted phenyl. In some embodiments, $R^1$ is phenyl.

In some embodiments, $R^1$ is optionally substituted carbocyclyl. In some embodiments, $R^1$ is optionally substituted $C_3$-$C_{10}$ carbocyclyl. In some embodiments, $R^1$ is optionally substituted monocyclic carbocyclyl. In some embodiments, $R^1$ is optionally substituted cycloheptyl. In some embodiments, $R^1$ is optionally substituted cyclohexyl. In some embodiments, $R^1$ is optionally substituted cyclopentyl. In some embodiments, $R^1$ is optionally substituted cyclobutyl. In some embodiments, $R^1$ is an optionally substituted cyclopropyl. In some embodiments, $R^1$ is optionally substituted bicyclic carbocyclyl.

In some embodiments, $R^1$ is an optionally substituted $C_1$-$C_{50}$ polycyclic hydrocarbon. In some embodiments, $R^1$ is an optionally substituted $C_1$-$C_{50}$ polycyclic hydrocarbon wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is optionally substituted

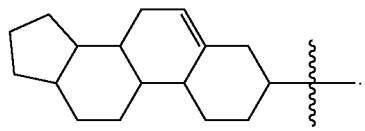 [SMILES: *C1CCC2C(=CCC3C4CCCC4CCC23)C1]

In some embodiments, $R^1$ is

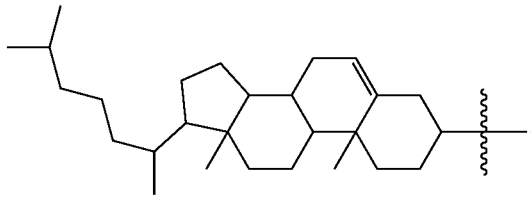

In some embodiments, $R^1$ is optionally substituted

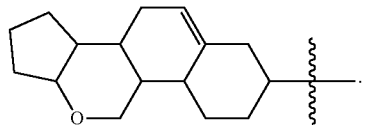 [SMILES: *C1CCC2C(=CCC3C4CCCC4OCC23)C1]

In some embodiments, $R^1$ is an optionally substituted $C_1$-$C_{50}$ aliphatic comprising one or more optionally substituted polycyclic hydrocarbon moieties. In some embodiments, $R^1$ is an optionally substituted $C_1$-$C_{50}$ aliphatic comprising one or more optionally substituted polycyclic hydrocarbon moieties, wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{50}$ aliphatic comprising one or more optionally substituted

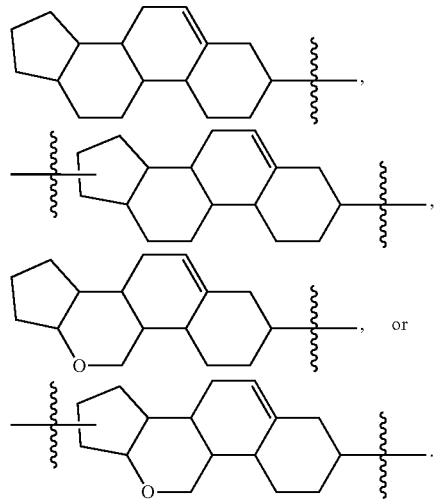

or

In some embodiments, $R^1$ is

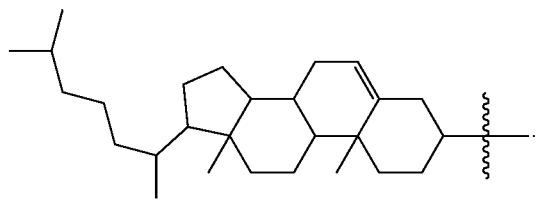 [SMILES: *C1CCC2(C)C(=CCC3C2CCC2(C)C(C(C)CCCC(C)C)CCC32)C1]

In some embodiments, $R^1$ is

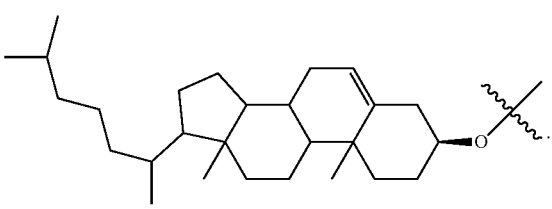 [SMILES: *O[C@H]1CCC2(C)C(=CCC3C2CCC2(C)C(C(C)CCCC(C)C)CCC32)C1]

In some embodiments, $R^1$ is

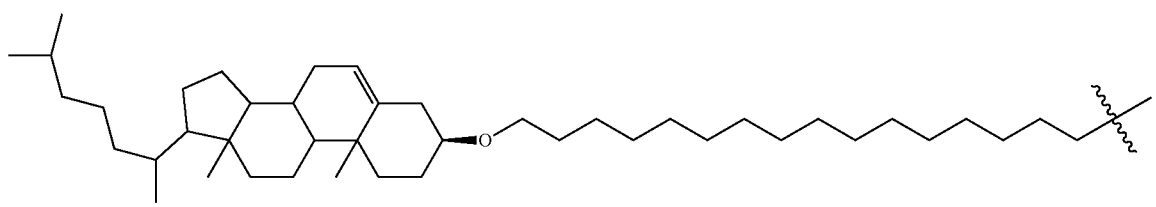 [SMILES: *CCCCCCCCCCCCCCCCO[C@H]1CCC2(C)C(=CCC3C2CCC2(C)C(C(C)CCCC(C)C)CCC32)C1]

In some embodiments, $R^1$ is

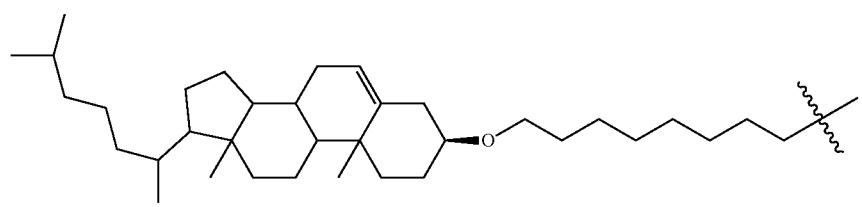 [SMILES: *CCCCCCCCO[C@H]1CCC2(C)C(=CCC3C2CCC2(C)C(C(C)CCCC(C)C)CCC32)C1]

In some embodiments, $R^1$ is

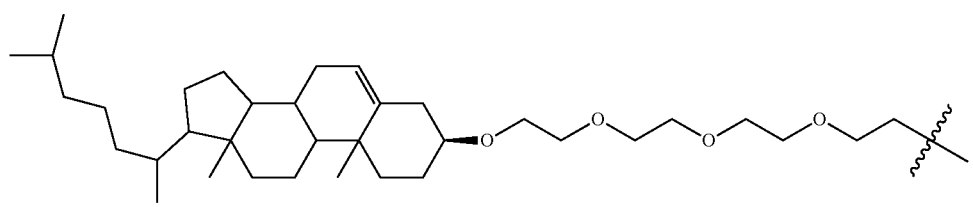 [SMILES: *CCOCCOCCOCCO[C@H]1CCC2(C)C(=CCC3C2CCC2(C)C(C(C)CCCC(C)C)CCC32)C1]

In some embodiments, $R^1$ is an optionally substituted aryl. In some embodiments, $R^1$ is an optionally substituted bicyclic aryl ring.

In some embodiments, $R^1$ is an optionally substituted heteroaryl. In some embodiments, $R^1$ is an optionally substituted 5-6 membered monocyclic heteroaryl ring having 1-3 heteroatoms independently selected from nitrogen, sulfur, or oxygen. In some embodiments, $R^1$ is a substituted 5-6 membered monocyclic heteroaryl ring having 1-3 heteroatoms independently selected from nitrogen, oxygen, or sulfur. In some embodiments, $R^1$ is an unsubstituted 5-6 membered monocyclic heteroaryl ring having 1-3 heteroatoms independently selected from nitrogen, sulfur, or oxygen.

In some embodiments, $R^1$ is an optionally substituted 5 membered monocyclic heteroaryl ring having 1-3 heteroatoms independently selected from nitrogen, oxygen or sulfur. In some embodiments, $R^1$ is an optionally substituted 6 membered monocyclic heteroaryl ring having 1-3 heteroatoms independently selected from nitrogen, oxygen, or sulfur.

In some embodiments, $R^1$ is an optionally substituted 5-membered monocyclic heteroaryl ring having 1 heteroatom selected from nitrogen, oxygen, or sulfur. In some embodiments, $R^1$ is selected from pyrrolyl, furanyl, or thienyl.

In some embodiments, $R^1$ is an optionally substituted 5-membered heteroaryl ring having 2 heteroatoms independently selected from nitrogen, oxygen, or sulfur. In certain embodiments, $R^1$ is an optionally substituted 5-membered heteroaryl ring having 1 nitrogen atom, and an additional heteroatom selected from sulfur or oxygen. Exemplary $R^1$ groups include optionally substituted pyrazolyl, imidazolyl, thiazolyl, isothiazolyl, oxazolyl or isoxazolyl.

In some embodiments, $R^1$ is a 6-membered heteroaryl ring having 1-3 nitrogen atoms. In other embodiments, $R^1$ is an optionally substituted 6-membered heteroaryl ring having 1-2 nitrogen atoms. In some embodiments, $R^1$ is an optionally substituted 6-membered heteroaryl ring having 2 nitrogen atoms. In certain embodiments, $R^1$ is an optionally substituted 6-membered heteroaryl ring having 1 nitrogen. Exemplary $R^1$ groups include optionally substituted pyridinyl, pyrimidinyl, pyrazinyl, pyridazinyl, triazinyl, or tetrazinyl.

In certain embodiments, $R^1$ is an optionally substituted 8-10 membered bicyclic heteroaryl ring having 1-4 heteroatoms independently selected from nitrogen, oxygen, or sulfur. In some embodiments, $R^1$ is an optionally substituted 5,6-fused heteroaryl ring having 1-4 heteroatoms independently selected from nitrogen, oxygen, or sulfur. In other embodiments, $R^1$ is an optionally substituted 5,6-fused heteroaryl ring having 1-2 heteroatoms independently selected from nitrogen, oxygen, or sulfur. In certain embodiments, $R^1$ is an optionally substituted 5,6-fused heteroaryl ring having 1 heteroatom independently selected from nitrogen, oxygen, or sulfur. In some embodiments, $R^1$ is an optionally substituted indolyl. In some embodiments, $R^1$ is an optionally substituted azabicyclo[3.2.1]octanyl. In certain embodiments, $R^1$ is an optionally substituted 5,6-fused heteroaryl ring having 2 heteroatoms independently selected from nitrogen, oxygen, or sulfur. In some embodiments, $R^1$ is an optionally substituted azaindolyl. In some embodiments, $R^1$ is an optionally substituted benzimidazolyl. In some embodiments, $R^1$ is an optionally substituted benzothiazolyl. In some embodiments, $R^1$ is an optionally substituted benzoxazolyl. In some embodiments, $R^1$ is an optionally substituted indazolyl. In certain embodiments, $R^1$ is an optionally substituted 5,6-fused heteroaryl ring having 3 heteroatoms independently selected from nitrogen, oxygen, or sulfur.

In certain embodiments, $R^1$ is an optionally substituted 6,6-fused heteroaryl ring having 1-4 heteroatoms independently selected from nitrogen, oxygen, or sulfur. In some embodiments, $R^1$ is an optionally substituted 6,6-fused heteroaryl ring having 1-2 heteroatoms independently selected from nitrogen, oxygen, or sulfur. In other embodiments, $R^1$ is an optionally substituted 6,6-fused heteroaryl ring having 1 heteroatom independently selected from nitrogen, oxygen, or sulfur. In some embodiments, $R^1$ is an optionally substituted quinolinyl. In some embodiments, $R^1$ is an optionally substituted isoquinolinyl. According to one aspect, $R^1$ is an optionally substituted 6,6-fused heteroaryl ring having 2 heteroatoms independently selected from nitrogen, oxygen, or sulfur. In some embodiments, $R^1$ is a quinazoline or a quinoxaline.

In some embodiments, $R^1$ is an optionally substituted heterocyclyl. In some embodiments, $R^1$ is an optionally substituted 3-7 membered saturated or partially unsaturated heterocyclic ring having 1-2 heteroatoms independently selected from nitrogen, oxygen, or sulfur. In some embodiments, $R^1$ is a substituted 3-7 membered saturated or partially unsaturated heterocyclic ring having 1-2 heteroatoms independently selected from nitrogen, oxygen, or sulfur. In some embodiments, $R^1$ is an unsubstituted 3-7 membered saturated or partially unsaturated heterocyclic ring having 1-2 heteroatoms independently selected from nitrogen, oxygen, or sulfur.

In some embodiments, $R^1$ is an optionally substituted heterocyclyl. In some embodiments, $R^1$ is an optionally substituted 6 membered saturated or partially unsaturated heterocyclic ring having 1-2 heteroatoms independently selected from nitrogen, oxygen, or sulfur. In some embodiments, $R^1$ is an optionally substituted 6 membered partially unsaturated heterocyclic ring having 2 heteroatoms independently selected from nitrogen, oxygen, or sulfur. In some embodiments, $R^1$ is an optionally substituted 6 membered partially unsaturated heterocyclic ring having 2 oxygen atoms.

In certain embodiments, $R^1$ is a 3-7 membered saturated or partially unsaturated heterocyclic ring having 1-2 heteroatoms independently selected from nitrogen, oxygen, or sulfur. In certain embodiments, $R^1$ is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, $R^1$ is an optionally substituted 5 membered saturated or partially unsaturated heterocyclic ring having 1-2 heteroatoms independently selected from nitrogen, oxygen, or sulfur.

In certain embodiments, $R^1$ is an optionally substituted 5-6 membered partially unsaturated monocyclic ring having 1-2 heteroatoms independently selected from nitrogen, oxygen, or sulfur. In certain embodiments, $R^1$ is an optionally substituted tetrahydropyridinyl, dihydrothiazolyl, dihydrooxazolyl, or oxazolinyl group.

In some embodiments, $R^1$ is an optionally substituted 8-10 membered bicyclic saturated or partially unsaturated heterocyclic ring having 1-4 heteroatoms independently selected from nitrogen, oxygen, or sulfur. In some embodiments, $R^1$ is an optionally substituted indolinyl. In some embodiments, $R^1$ is an optionally substituted isoindolinyl. In some embodiments, $R^1$ is an optionally substituted 1, 2, 3, 4-tetrahydroquinoline. In some embodiments, $R^1$ is an optionally substituted 1, 2, 3, 4-tetrahydroisoquinoline.

In some embodiments, $R^1$ is an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{10}$ aliphatic wherein one or more methylene units are optionally and independently replaced by an optionally -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—, wherein each R' is independently as defined above and described herein. In some embodiments, $R^1$ is an optionally substituted $C_1$-$C_{10}$ aliphatic wherein one or more methylene units are optionally and independently replaced by an optionally -Cy-, —O—, —S—, —S—S—, —N(R')—, —C(O)—, —OC(O)—, or —C(O)O—, wherein each R' is independently as defined above and described herein.

In some embodiments, $R^1$ is

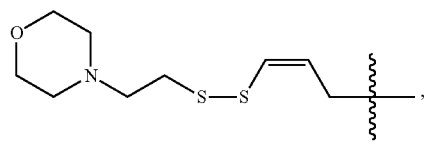

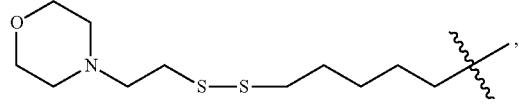

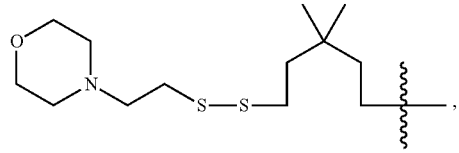

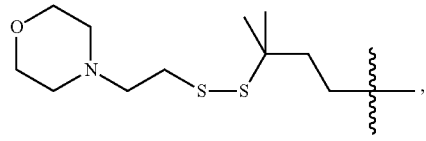

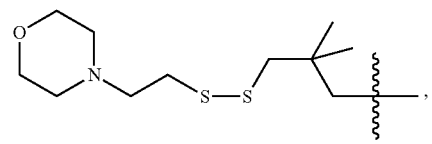

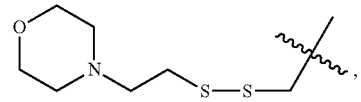

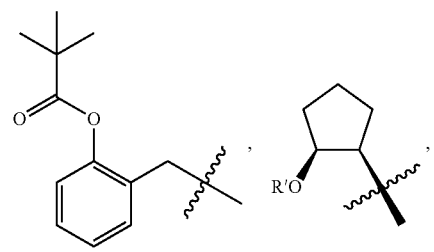

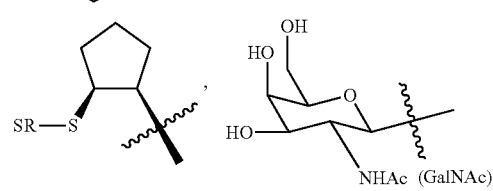

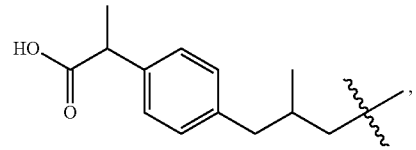

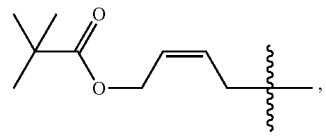

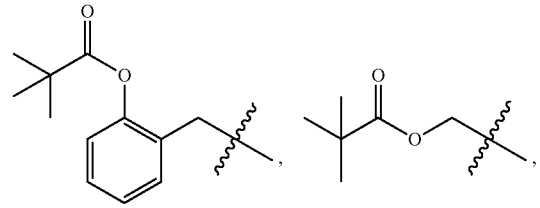

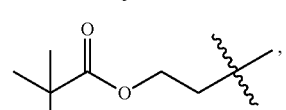

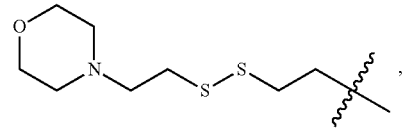

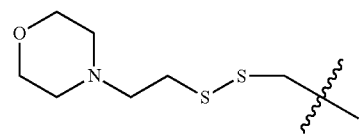

107
-continued
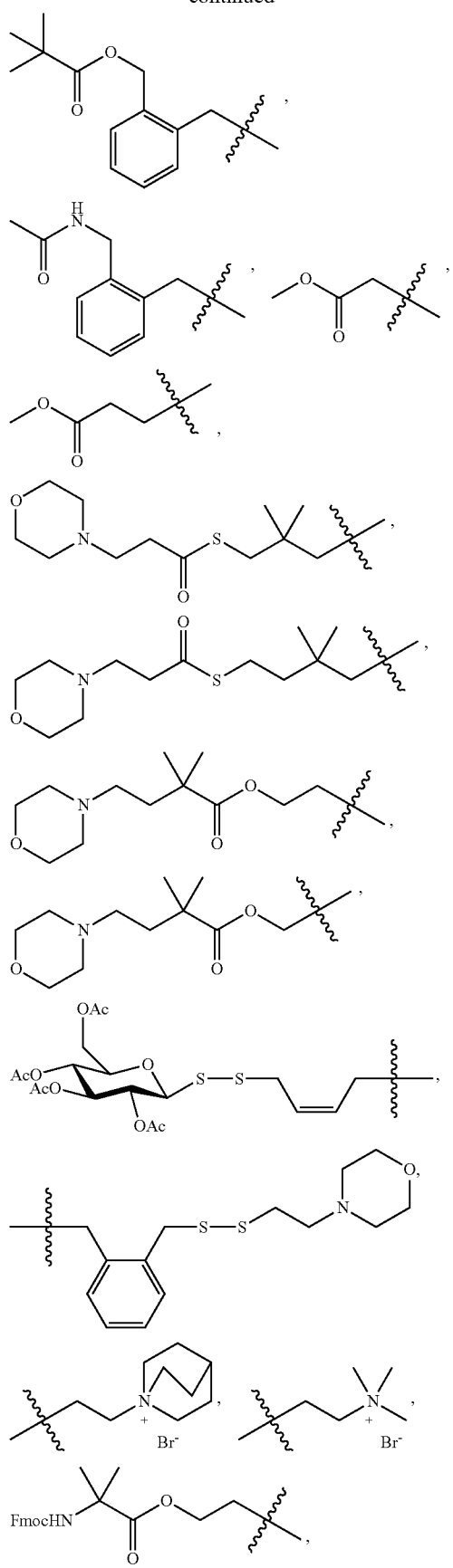
108
-continued
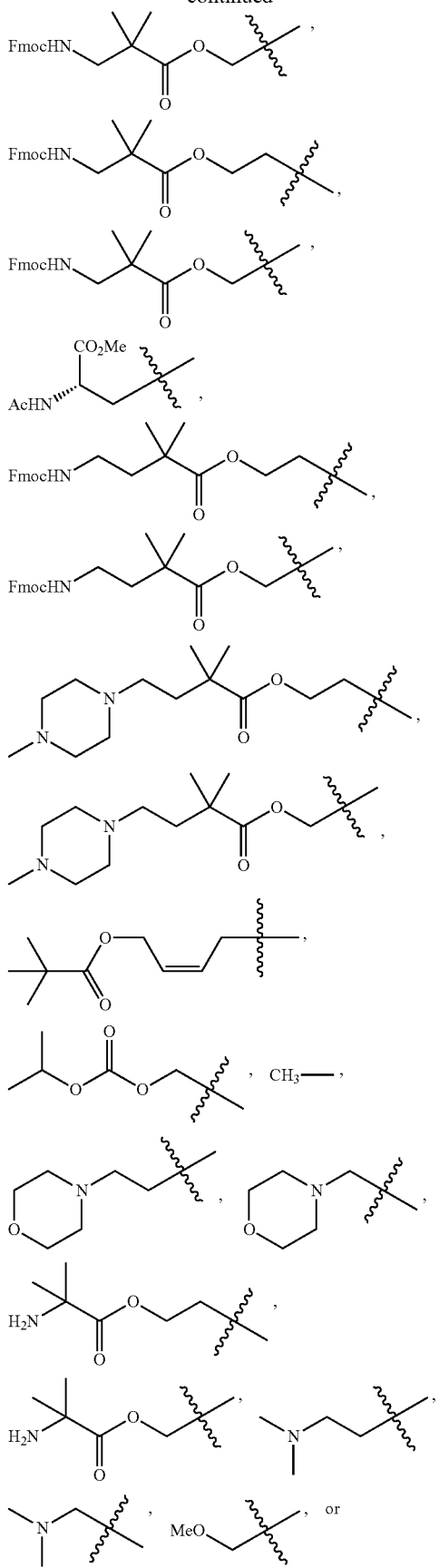

-continued

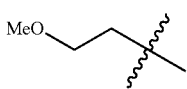

In some embodiments, R¹ is CH₃—,

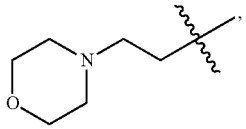

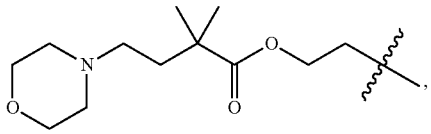

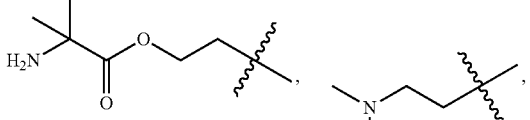

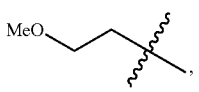, or

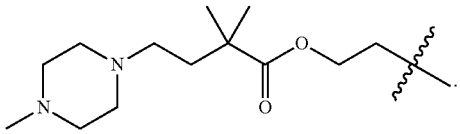

In some embodiments, R¹ comprises a terminal optionally substituted —(CH₂)₂— moiety which is connected to L. Exemplary such R¹ groups are depicted below:

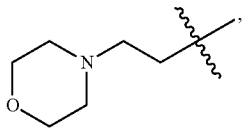

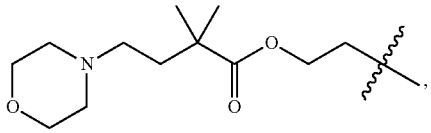

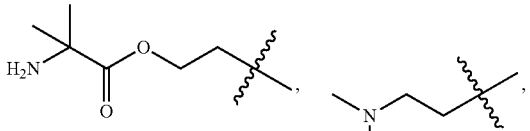

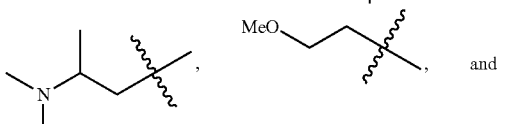, and

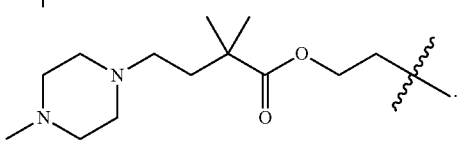

In some embodiments, R¹ comprises a terminal optionally substituted —(CH₂)— moiety which is connected to L. Exemplary such R¹ groups are depicted below:

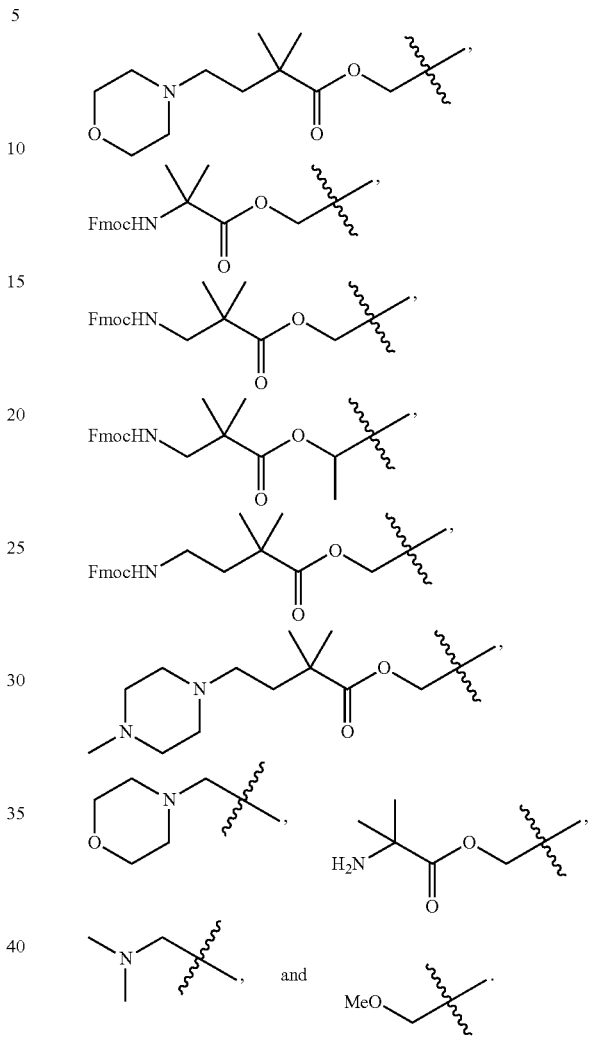

In some embodiments, R¹ is —S—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)₂—, —S(O)₂N(R')—, —N(R')S(O)₂—, —SC(O)—, —C(O)S—, —OC(O)—, or —C(O)O—, and each of R' and -Cy- is independently as defined above and described herein. In some embodiments, R¹ is —S—$R^{L2}$, wherein the sulfur atom is connected with the sulfur atom in L group.

In some embodiments, R¹ is —C(O)—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)₂—, —S(O)₂N(R')—, —N(R')S(O)₂—, —SC(O)—, —C(O)S—, —OC(O)—, or —C(O)O—, and each of R' and -Cy- is independently as defined above and described herein. In some embodiments, $R^1$ is —C(O)—$R^{L2}$, wherein the carbonyl group is connected with G in L group. In some embodiments, $R^1$ is —C(O)—$R^{L2}$, wherein the carbonyl group is connected with the sulfur atom in L group.

In some embodiments, $R^{L2}$ is optionally substituted $C_1$-$C_9$ aliphatic. In some embodiments, $R^{L2}$ is optionally substituted $C_1$-$C_9$ alkyl. In some embodiments, $R^{L2}$ is optionally substituted $C_1$-$C_9$ alkenyl. In some embodiments, $R^{L2}$ is optionally substituted $C_1$-$C_9$ alkynyl. In some embodiments, $R^{L2}$ is an optionally substituted $C_1$-$C_9$ aliphatic wherein one or more methylene units are optionally and independently replaced by -Cy- or —C(O)—. In some embodiments, $R^{L2}$ is an optionally substituted $C_1$-$C_9$ aliphatic wherein one or more methylene units are optionally and independently replaced by -Cy-. In some embodiments, $R^{L2}$ is an optionally substituted $C_1$-$C_9$ aliphatic wherein one or more methylene units are optionally and independently replaced by an optionally substituted heterocyclylene. In some embodiments, $R^{L2}$ is an optionally substituted $C_1$-$C_9$ aliphatic wherein one or more methylene units are optionally and independently replaced by an optionally substituted arylene. In some embodiments, $R^{L2}$ is an optionally substituted $C_1$-$C_9$ aliphatic wherein one or more methylene units are optionally and independently replaced by an optionally substituted heteroarylene. In some embodiments, $R^{L2}$ is an optionally substituted $C_1$-$C_9$ aliphatic wherein one or more methylene units are optionally and independently replaced by an optionally substituted $C_3$-$C_{10}$ carbocyclylene. In some embodiments, $R^{L2}$ is an optionally substituted $C_1$-$C_9$ aliphatic wherein two methylene units are optionally and independently replaced by -Cy- or —C(O)—. In some embodiments, $R^{L2}$ is an optionally substituted $C_1$-$C_9$ aliphatic wherein two methylene units are optionally and independently replaced by -Cy- or —C(O)—. Exemplary $R^{L2}$ groups are depicted below:

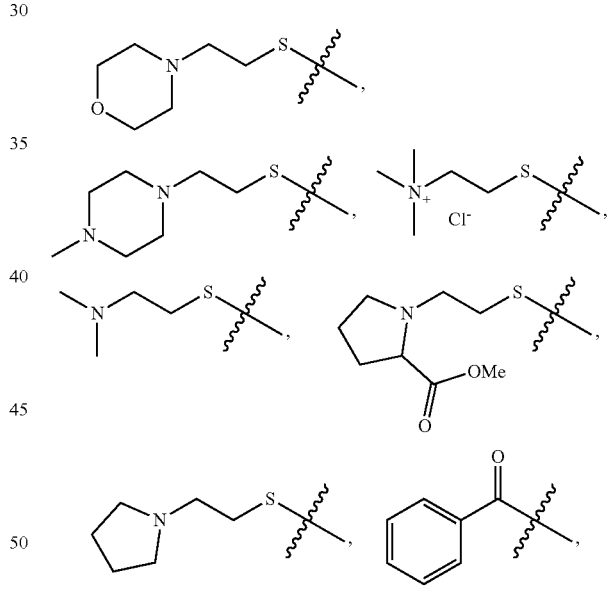

In some embodiments, $R^1$ is hydrogen, or an optionally substituted group selected from

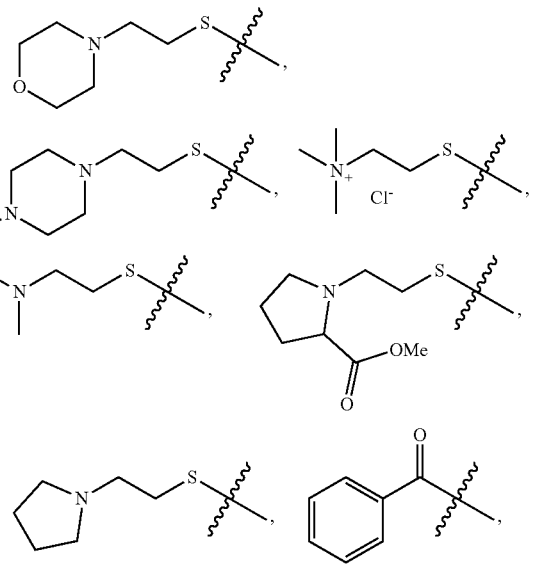

—S—($C_1$-$C_{10}$ aliphatic), $C_1$-$C_{10}$ aliphatic, aryl, $C_1$-$C_6$ heteroalkyl, heteroaryl and heterocyclyl. In some embodiments, $R^1$ is or —S—($C_1$-$C_{10}$ aliphatic). In some embodiments, $R^1$ is

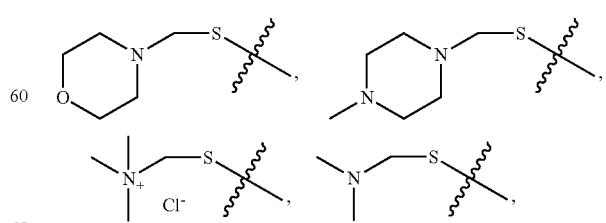

113

-continued

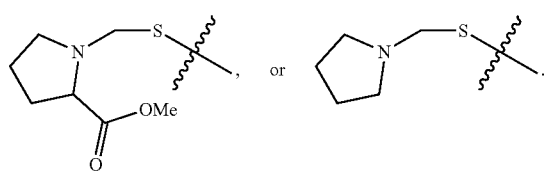

In some embodiments, $R^1$ is an optionally substituted group selected from —S—($C_1$-$C_6$ aliphatic), $C_1$-$C_{10}$ aliphatic, $C_1$-$C_6$ heteroaliphatic, aryl, heterocyclyl and heteroaryl.

In some embodiments, $R^1$ is

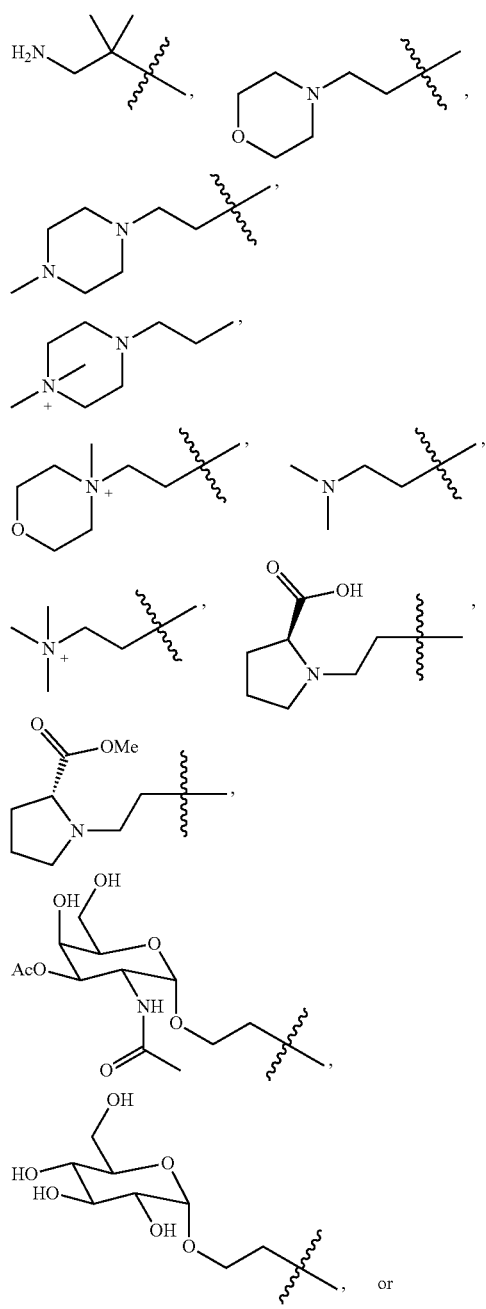

114

-continued

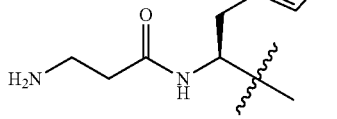

In some embodiments, the sulfur atom in the $R^1$ embodiments described above and herein is connected with the sulfur atom, G, E, or —C(O)— moiety in the L embodiments described above and herein. In some embodiments, the —C(O)— moiety in the $R^1$ embodiments described above and herein is connected with the sulfur atom, G, E, or —C(O)— moiety in the L embodiments described above and herein.

In some embodiments, -L-R' is any combination of the L embodiments and $R^1$ embodiments described above and herein.

In some embodiments, -L-$R^1$ is -$L^3$-G-$R^1$ wherein each variable is independently as defined above and described herein.

In some embodiments, -L-$R^1$ is -$L^4$-G-$R^1$ wherein each variable is independently as defined above and described herein.

In some embodiments, -L-$R^1$ is -$L^3$-G-S—$R^{L2}$, wherein each variable is independently as defined above and described herein.

In some embodiments, -L-$R^1$ is -$L^3$-G-C(O)—$R^{L2}$, wherein each variable is independently as defined above and described herein.

In some embodiments, -L-$R^1$ is

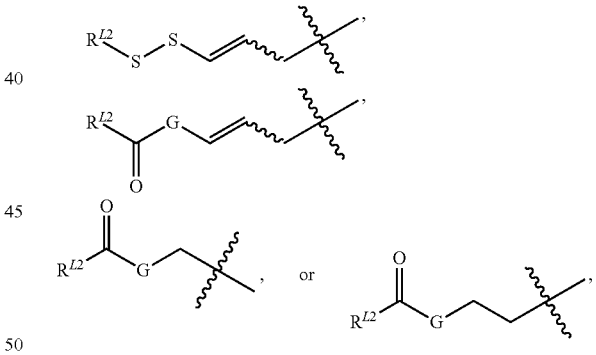

wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each G is independently as defined above and described herein.

In some embodiments, -L-$R^1$ is —$R^{L3}$—S—S—$R^{L2}$, wherein each variable is independently as defined above and described herein. In some embodiments, -L-$R^1$ is —$R^{L3}$—C(O)—S—S—$R^{L2}$, wherein each variable is independently as defined above and described herein.

In some embodiments, -L-R¹ has the structure of:

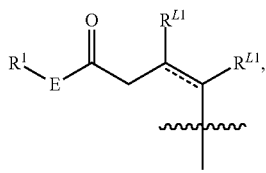

wherein each variable is independently as defined above and described herein.

In some embodiments, -L-R¹ has the structure of:

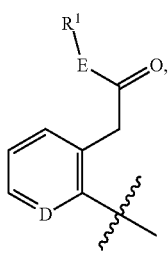

wherein each variable is independently as defined above and described herein.

In some embodiments, -L-R¹ has the structure of:

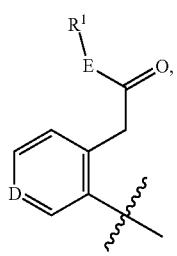

wherein each variable is independently as defined above and described herein.

In some embodiments -L-R¹ has the structure of:

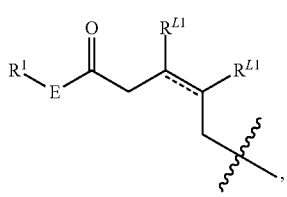

wherein each variable is independently as defined above and described herein.

In some embodiments, -L-R¹ has the structure of:

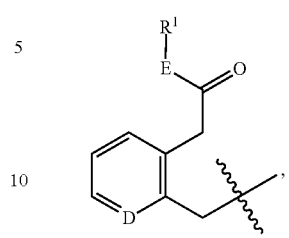

wherein each variable is independently as defined above and described herein.

In some embodiments, -L-R¹ has the structure of:

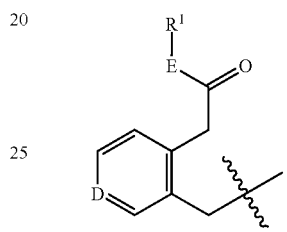

wherein each variable is independently as defined above and described herein.

In some embodiments, -L-R¹ has the structure of:

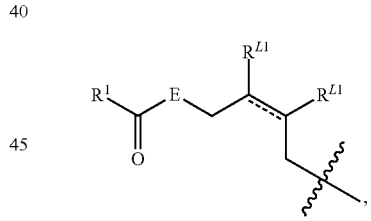

wherein each variable is independently as defined above and described herein.

In some embodiments, -L-R¹ has the structure of:

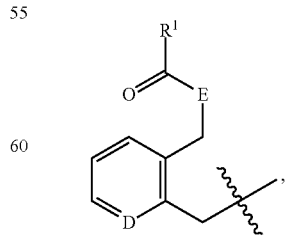

wherein each variable is independently as defined above and described herein.

In some embodiments, -L-R¹ has the structure of:

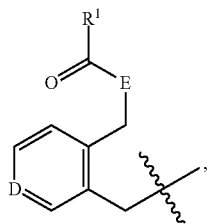

wherein each variable is independently as defined above and described herein.

In some embodiments, -L-R¹ has the structure of:

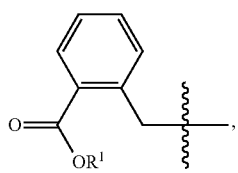

wherein each variable is independently as defined above and described herein.

In some embodiments, -L-R¹ has the structure of:

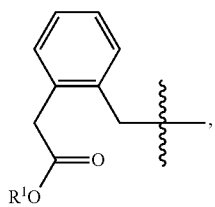

wherein each variable is independently as defined above and described herein.

In some embodiments, -L-R¹ has the structure of:

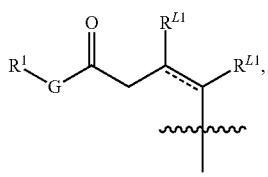

wherein each variable is independently as defined above and described herein.

In some embodiments, -L-R¹ has the structure of:

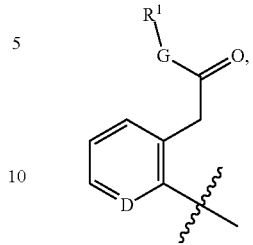

wherein each variable is independently as defined above and described herein.

In some embodiments, -L-R¹ has the structure of:

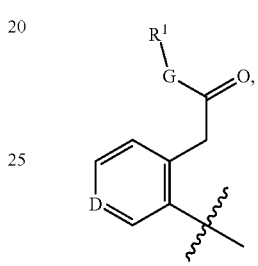

wherein each variable is independently as defined above and described herein.

In some embodiments, -L-R¹ has the structure of:

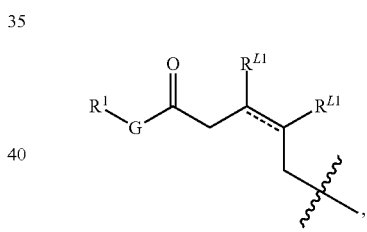

wherein each variable is independently as defined above and described herein.

In some embodiments, -L-R¹ has the structure of:

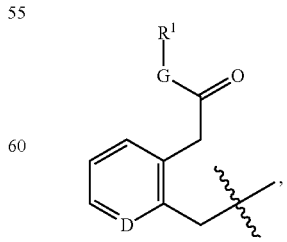

wherein each variable is independently as defined above and described herein.

In some embodiments, -L-R¹ has the structure of:

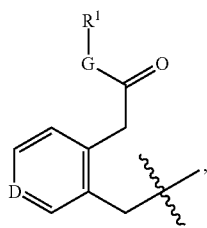

wherein each variable is independently as defined above and described herein.

In some embodiments, -L-R¹ has the structure of:

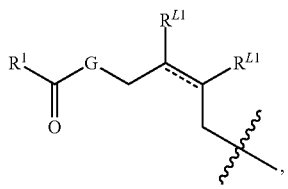

wherein each variable is independently as defined above and described herein.

In some embodiments, -L-R¹ has the structure of:

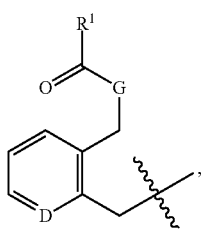

wherein each variable is independently as defined above and described herein.

In some embodiments, -L-R¹ has the structure of:

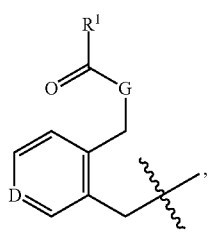

wherein each variable is independently as defined above and described herein.

In some embodiments, -L-R¹ has the structure of:

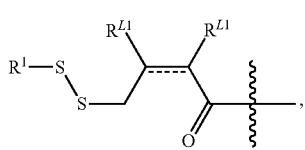

wherein each variable is independently as defined above and described herein.

In some embodiments, L has the structure of:

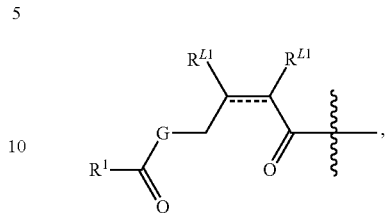

wherein each variable is independently as defined above and described herein.

In some embodiments, —X-L-R¹ has the structure of:

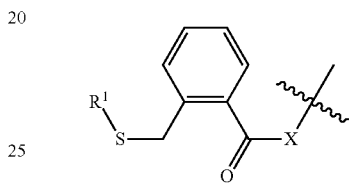

wherein:
the phenyl ring is optionally substituted, and
each of R¹ and X is independently as defined above and described herein.

In some embodiments, -L-R¹ is

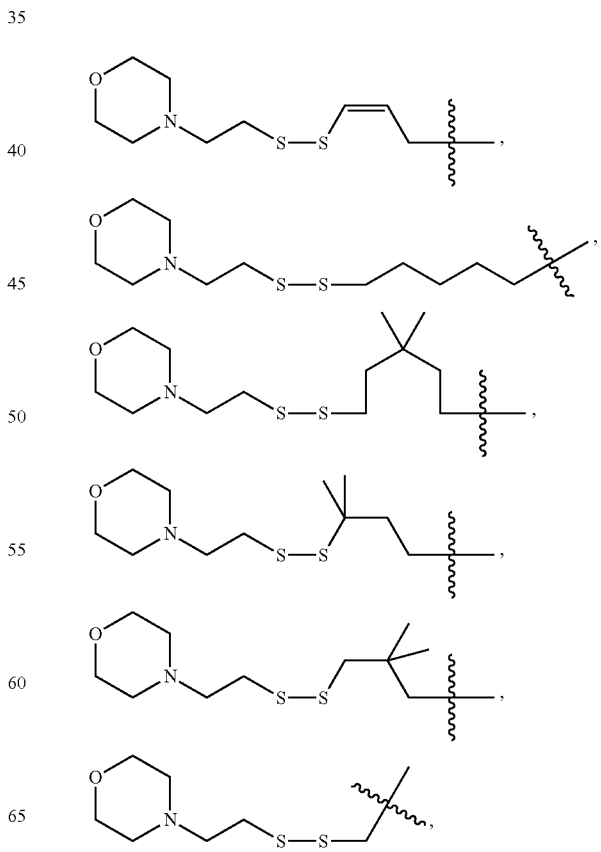

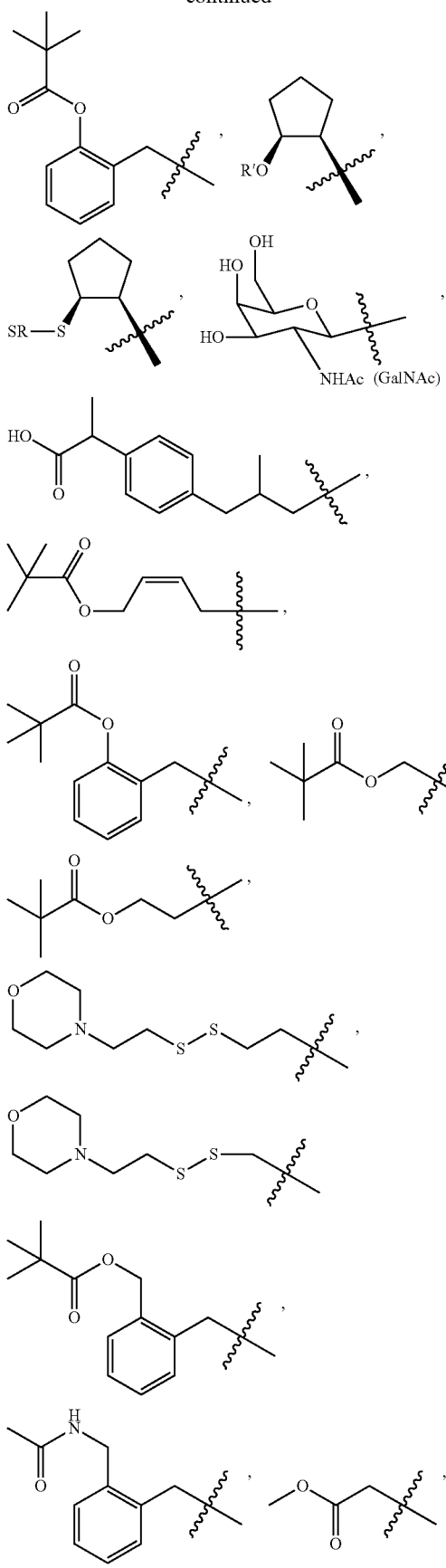
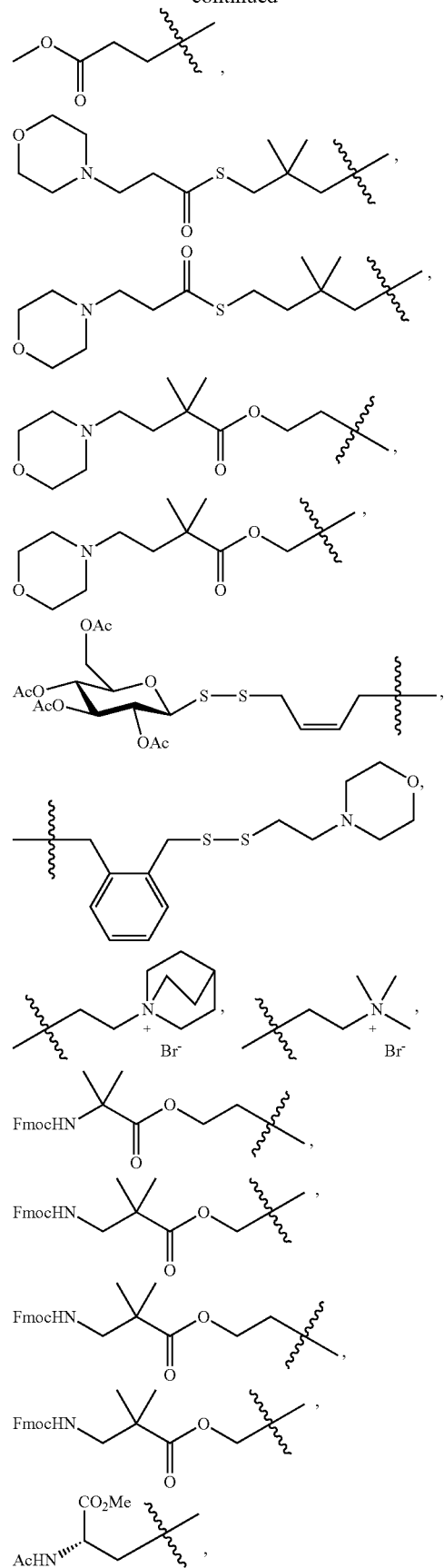

123
-continued
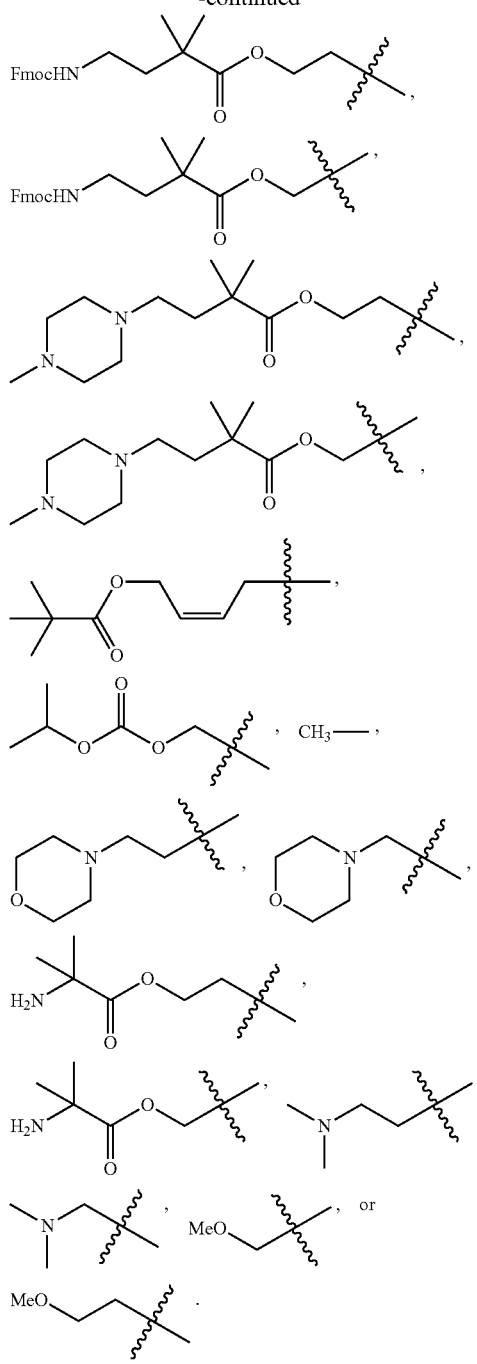
In some embodiments, -L-R$^1$ is:
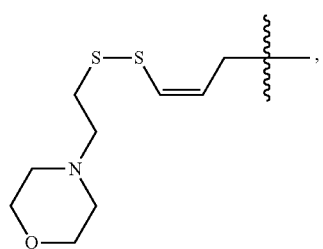
124
-continued
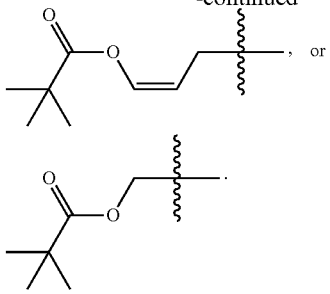
In some embodiments, -L-R$^1$ is CH$_3$—,
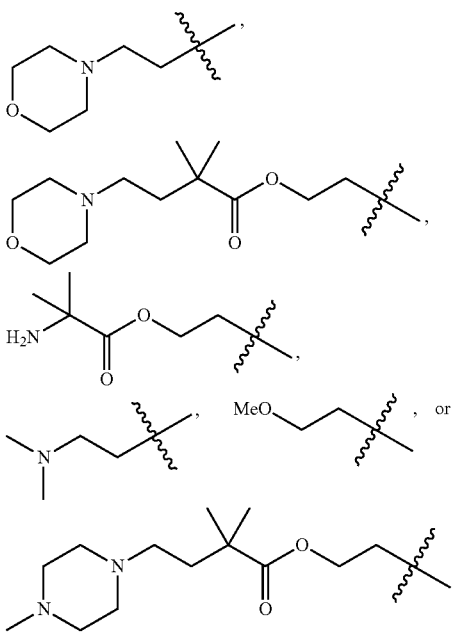
In some embodiments, -L-R$^1$ is
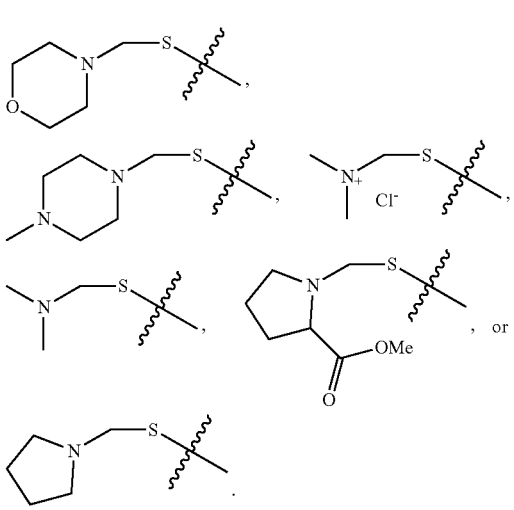
In some embodiments, -L-R$^1$ comprises a terminal optionally substituted —(CH$_2$)$_2$— moiety which is connected to X.

In some embodiments, -L-R$^1$ comprises a terminal —(CH$_2$)$_2$— moiety which is connected to X. Exemplary such -L-R$^1$ moieties are depicted below:

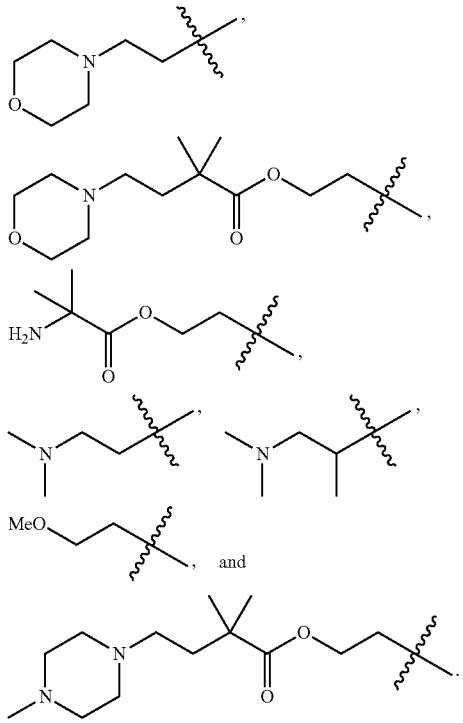

In some embodiments, -L-R$^1$ comprises a terminal optionally substituted —(CH$_2$)— moiety which is connected to X. In some embodiments, -L-R$^1$ comprises a terminal —(CH$_2$)— moiety which is connected to X. Exemplary such -L-R$^1$ moieties are depicted below:

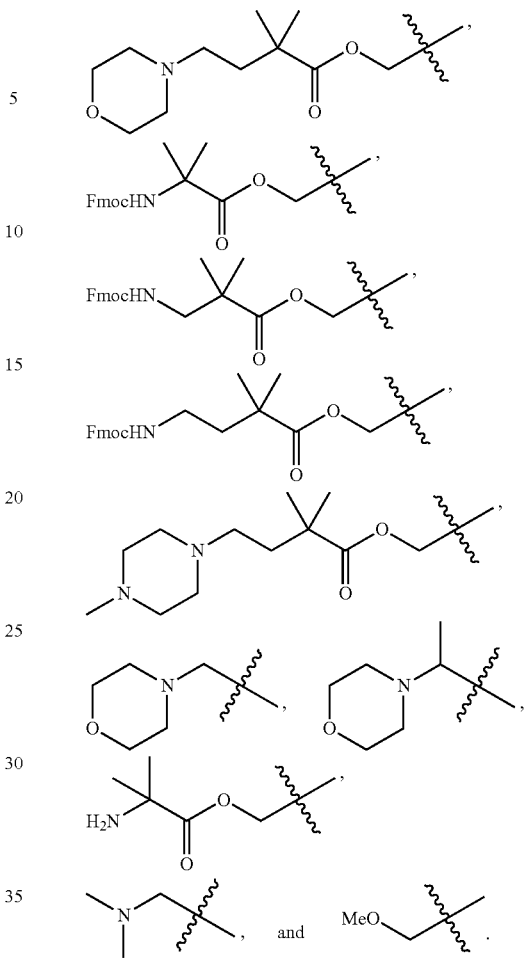

In some embodiments, -L-R$^1$ is

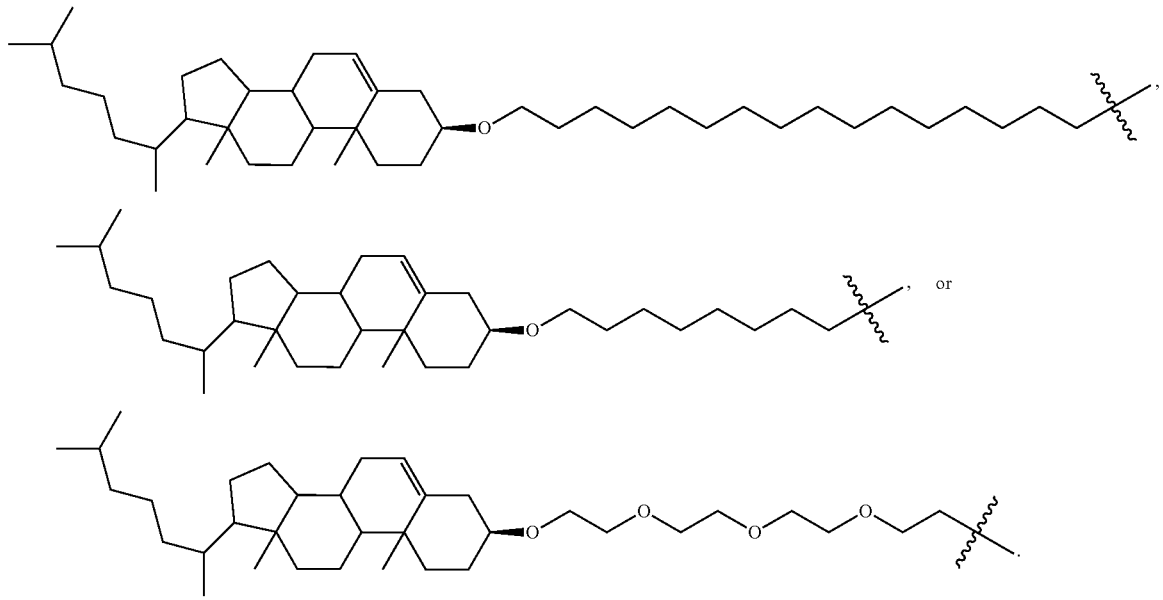

In some embodiments, -L-R¹ is CH₃—,
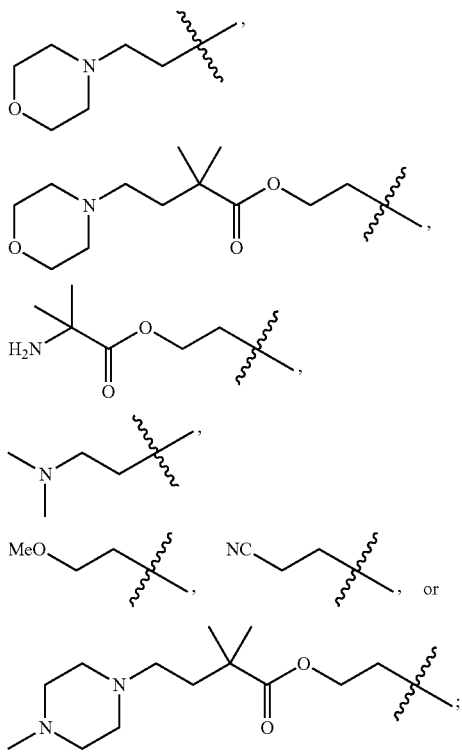
and X is —S—.
In some embodiments, -L-R¹ is CH₃—,
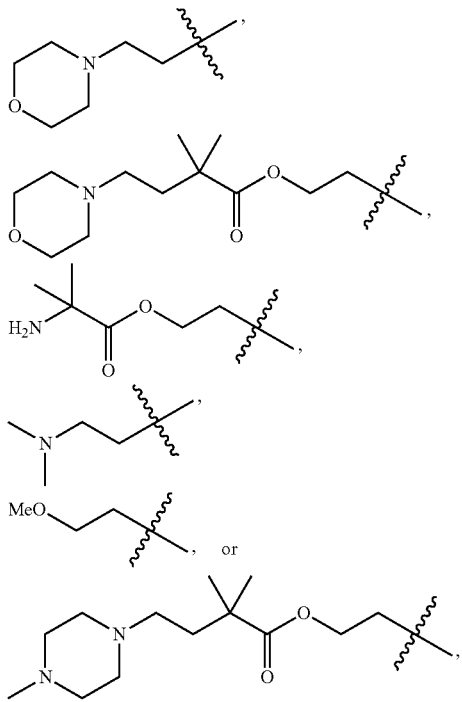
X is —S—, W is O, Y is —O—, and Z is —O—.
In some embodiments, R¹ is
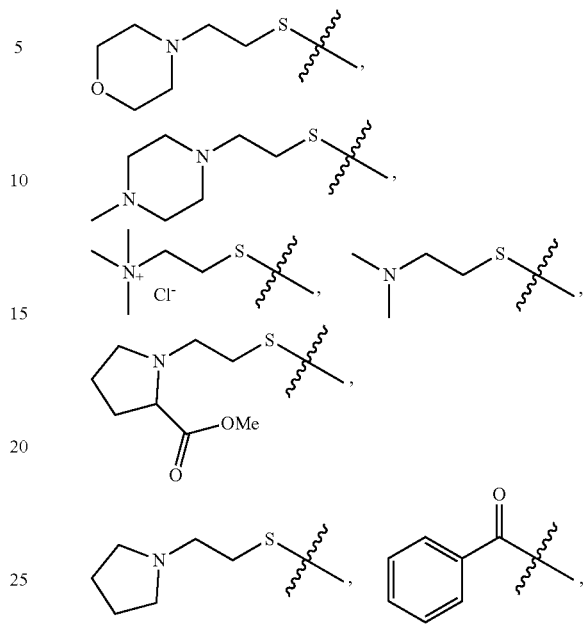
or —S—(C₁-C₁₀ aliphatic).
In some embodiments, R¹ is
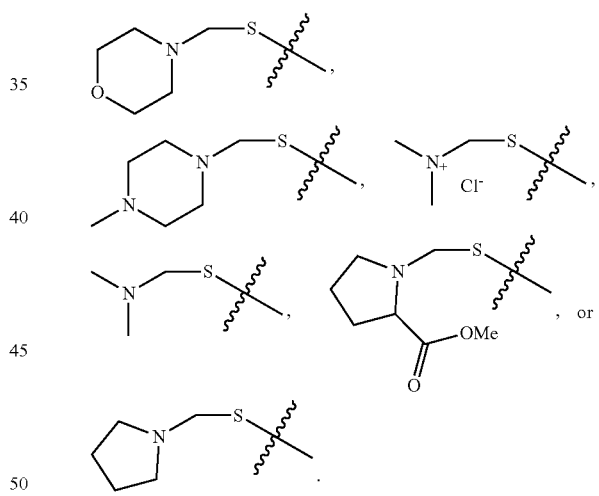
In some embodiments, X is —O— or —S—, and R¹ is
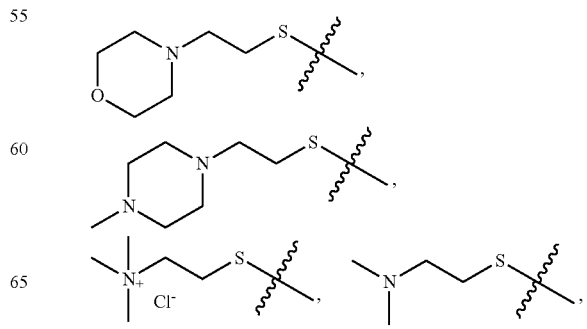

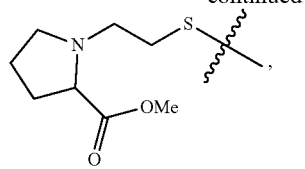,
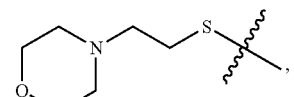 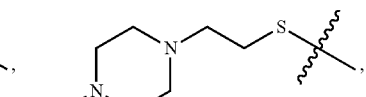
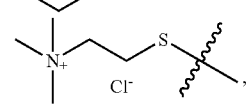 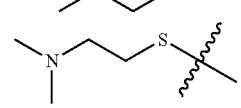 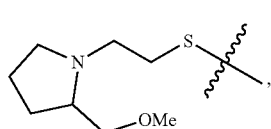 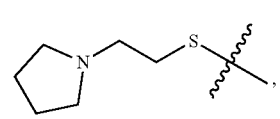
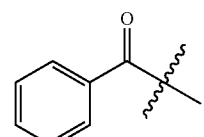 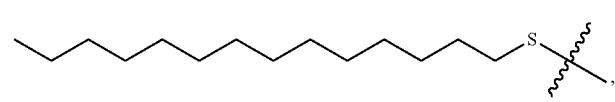,
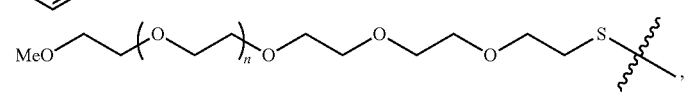,
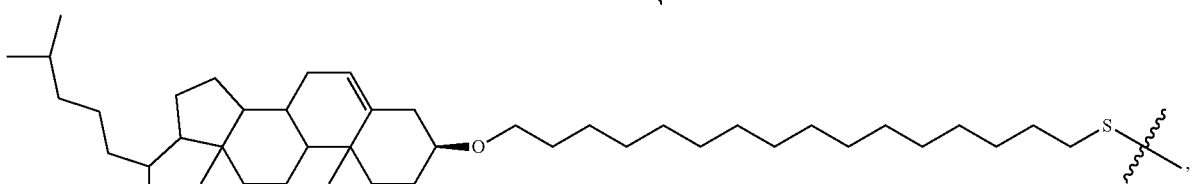,
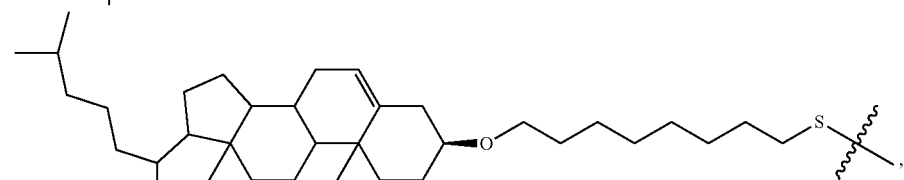,
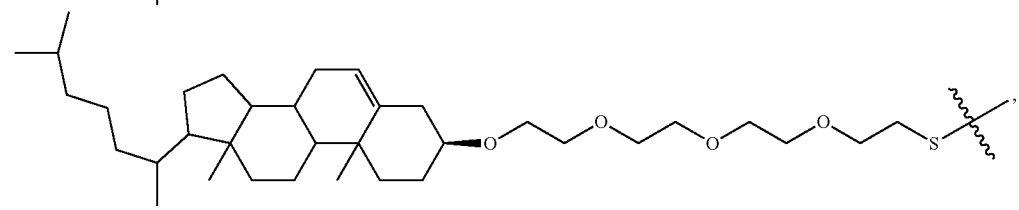,
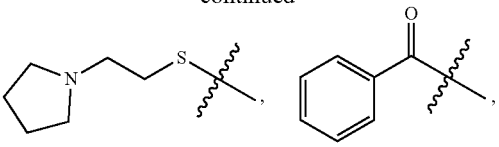
or —S—($C_1$-$C_{10}$ aliphatic).
In some embodiments, X is —O— or —S—, and $R^1$ is
—S—($C_1$-$C_{10}$ aliphatic) or —S—($C_1$-$C_{50}$ aliphatic).
In some embodiments, L is a covalent bond and -L-$R^1$ is $R^1$.
In some embodiments, -L-$R^1$ is not hydrogen.
In some embodiments, —X-L-$R^1$ is $R^1$
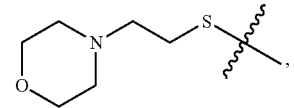 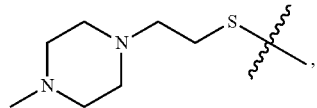 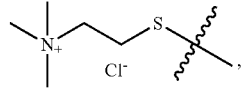,

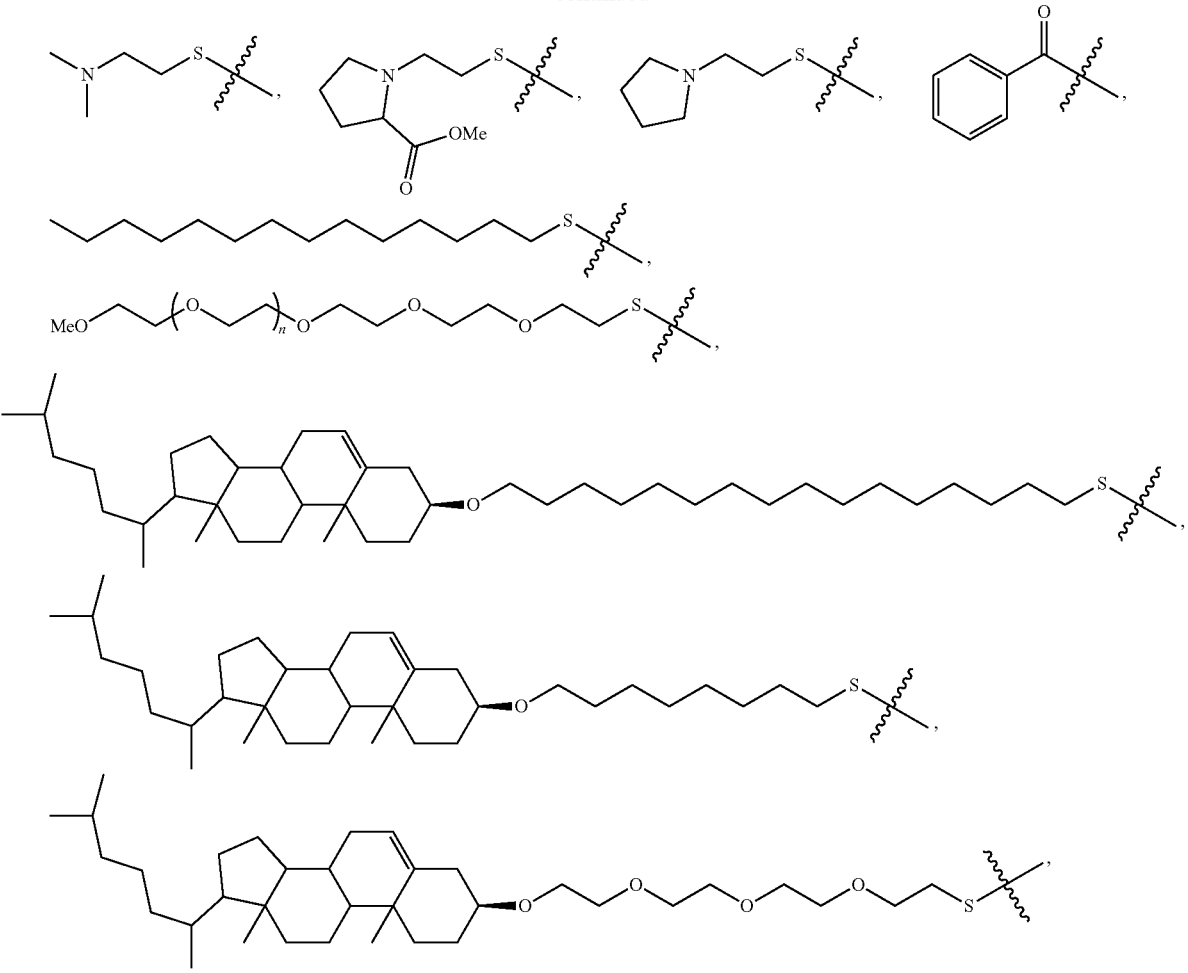
—S—(C₁-C₁₀ aliphatic) or —S—(C₁-C₅₀ aliphatic).
In some embodiments, —X-L-R¹ has the structure of
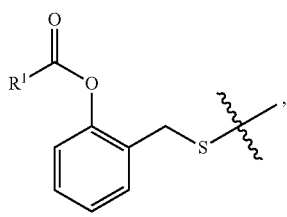
wherein the
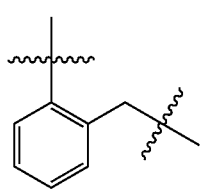 [SMILES: *Cc1ccccc1*]
moiety is optionally substituted. In some embodiments, —X-L-R¹ is
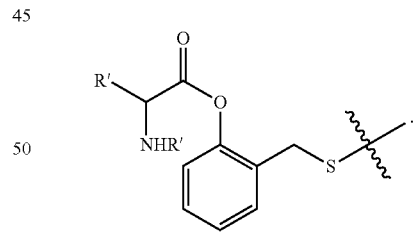
In some embodiments, —X-L-R¹ is
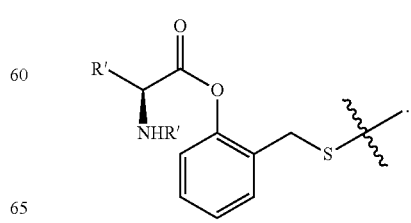

In some embodiments, —X-L-R¹ is

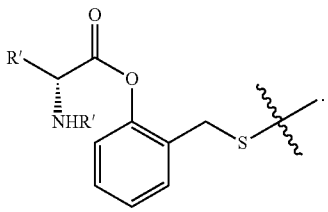

In some embodiments, —X-L-R¹ has the structure of

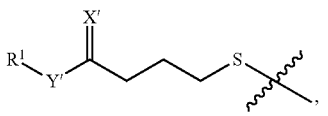

wherein X' is O or S, Y' is —O—, —S— or —NR'—, and the

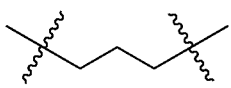

moiety is optionally substituted. In some embodiments, Y' is —O—, —S— or —NH—. In some embodiments,

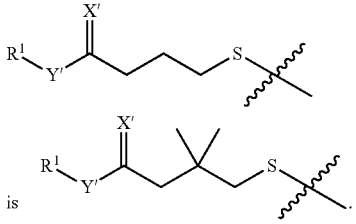

is

In some embodiments,

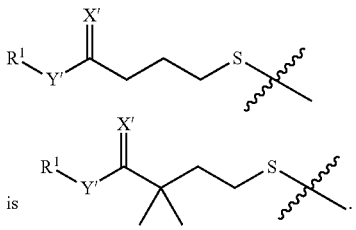

is

In some embodiments,

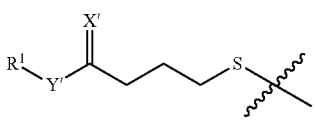

-continued

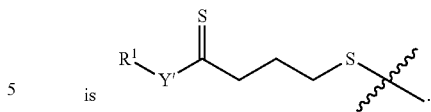

is

In some embodiments, —X-L-R¹ has the structure of

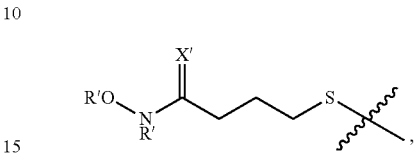

wherein X' is O or S and the

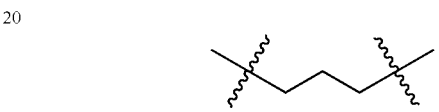

moiety is optionally substituted. In some embodiments,

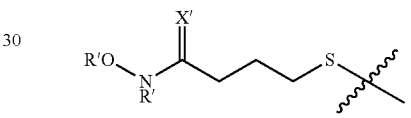

is

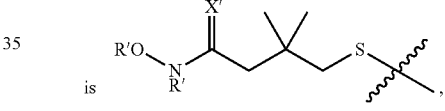

In some embodiments, —X-L-R¹ is

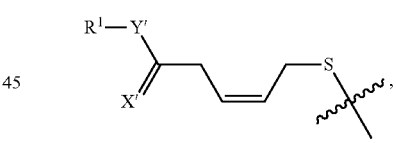

wherein the

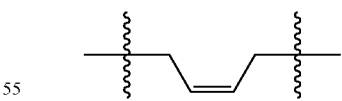

is optionally substituted. In some embodiments, —X-L-R¹ is

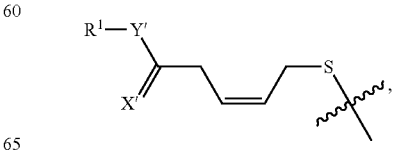

wherein the

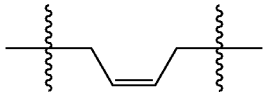 [SMILES: *C/C=C\C*]

is substituted. In some embodiments, —X-L-R¹ is

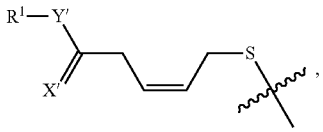

wherein the

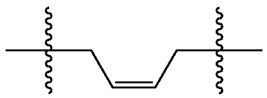 [SMILES: *C/C=C\C*]

is unsubstituted.

In some embodiments, —X-L-R¹ is R¹—C(O)—S-L$^x$-S—, wherein L$^x$ is an optionally substituted group selected from

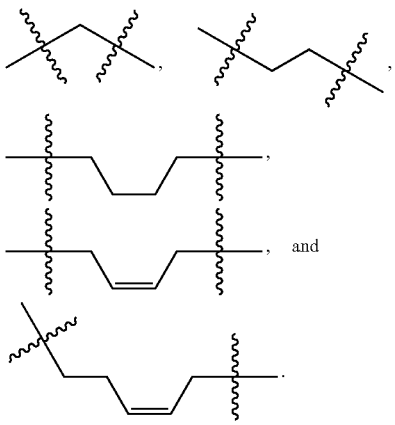

In some embodiments, L$^x$ is

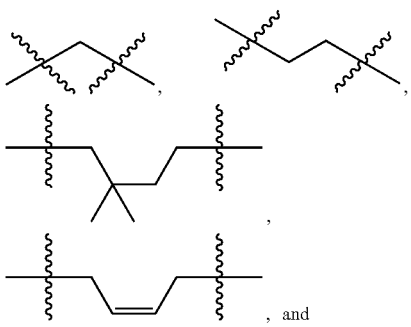

In some embodiments, —X-L-R¹ is (CH$_3$)$_3$C—S—S-L$^x$-S—. In some embodiments, —X-L-R¹ is R¹—C(=X')—Y'—C(R)$_2$—S-L$^x$-S—. In some embodiments, —X-L-R¹ is R—C(=X')—Y'—CH$_2$—S-L$^x$-S—. In some embodiments, —X-L-R¹ is

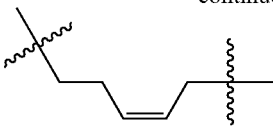

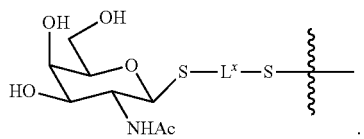

As will be appreciated by a person skilled in the art, many of the —X-L-R¹ groups described herein are cleavable and can be converted to —X⁻ after administration to a subject. In some embodiments, —X-L-R¹ is cleavable. In some embodiments, —X-L-R¹ is —S-L-R¹, and is converted to —S⁻ after administration to a subject. In some embodiments, the conversion is promoted by an enzyme of a subject. As appreciated by a person skilled in the art, methods of determining whether the —S-L-R¹ group is converted to —S⁻ after administration is widely known and practiced in the art, including those used for studying drug metabolism and pharmacokinetics.

In some embodiments, the internucleotidic linkage having the structure of formula I is

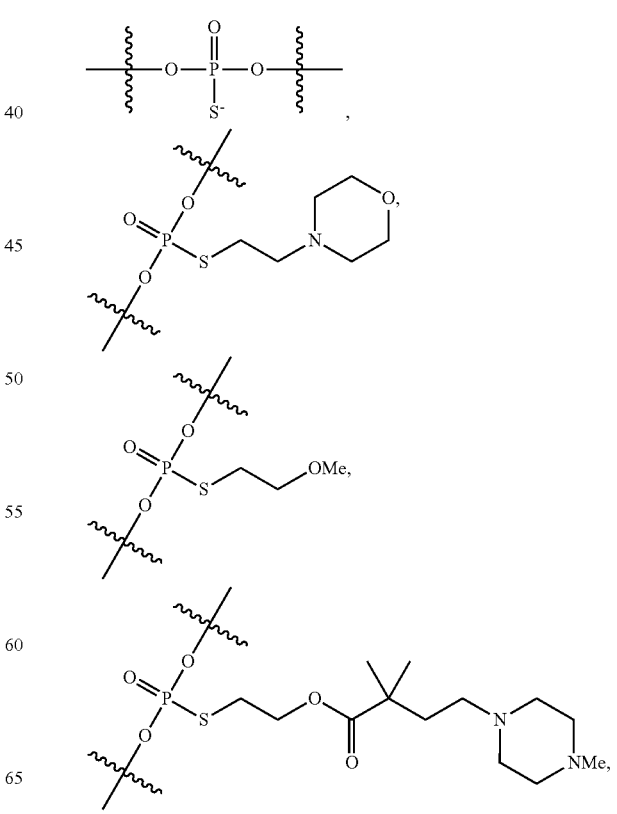

-continued

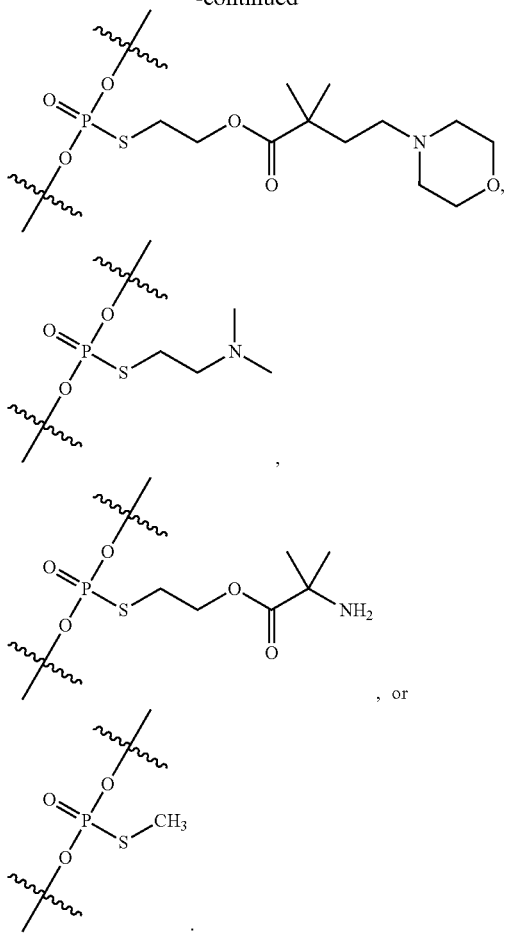

In some embodiments, the internucleotidic linkage of formula I has the structure of formula I-a:

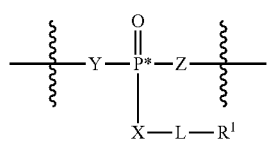

(I-a)

wherein each variable is independently as defined above and described herein.

In some embodiments, the internucleotidic linkage of formula I has the structure of formula I-b:

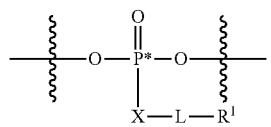

(I-b)

wherein each variable is independently as defined above and described herein.

In some embodiments, the internucleotidic linkage of formula I is an phosphorothioate triester linkage having the structure of formula I-c:

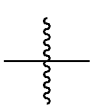

(I-c)

wherein:

P* is an asymmetric phosphorus atom and is either Rp or Sp;

L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

each R' is independently —R, —C(O)R, —CO$_2$R, or —SO$_2$R, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl;

each

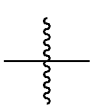

independently represents a connection to a nucleoside; and $R^1$ is not —H when L is a covalent bond.

In some embodiments, the internucleotidic linkage having the structure of formula I is

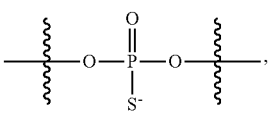 [SMILES: *OP(=O)([S-])O*]

139
-continued
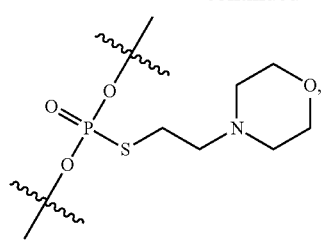
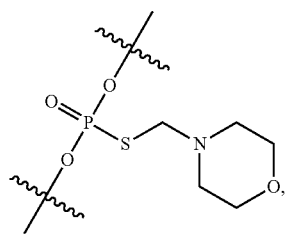
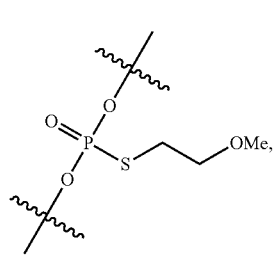 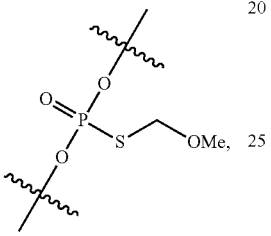
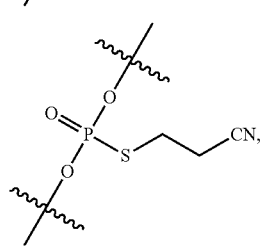
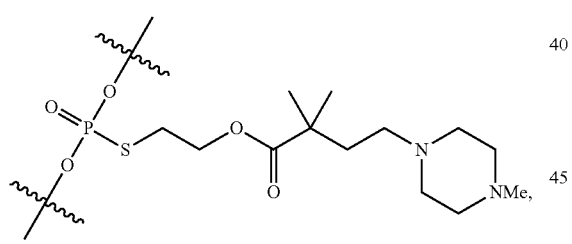
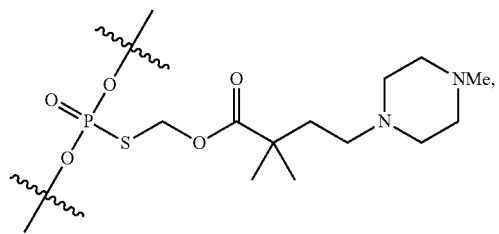
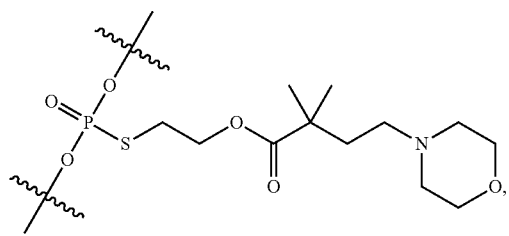
140
-continued
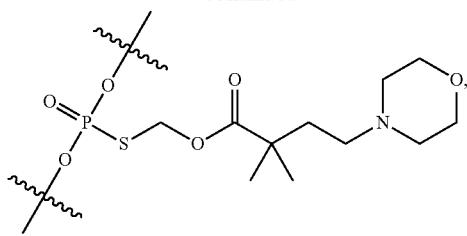
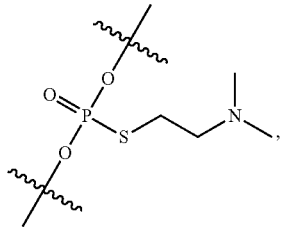
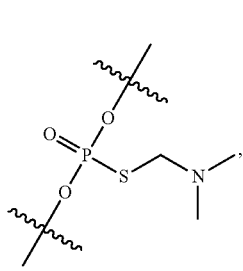
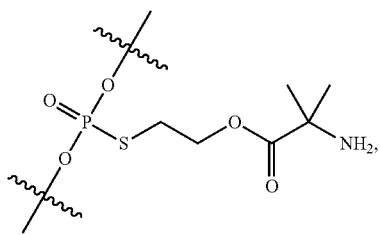
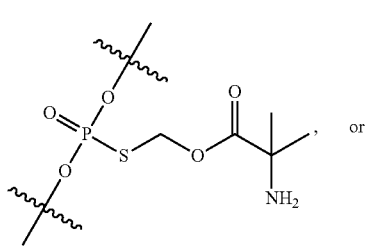, or
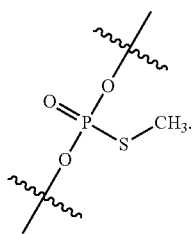
In some embodiments, the internucleotidic linkage having the structure of formula I-c is

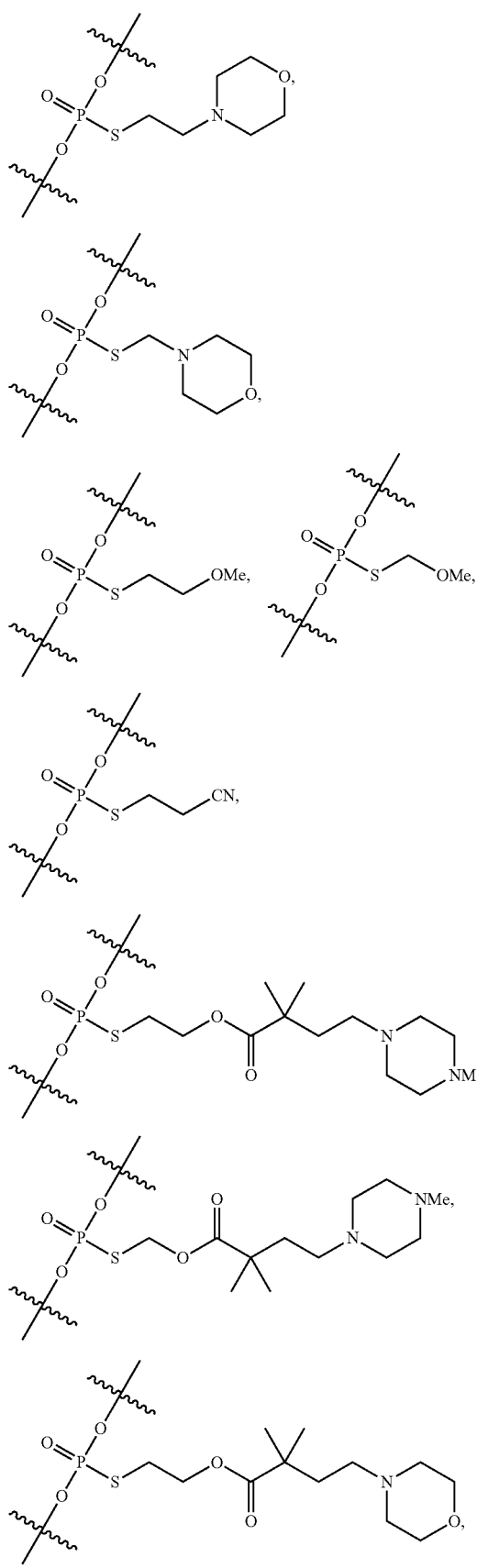
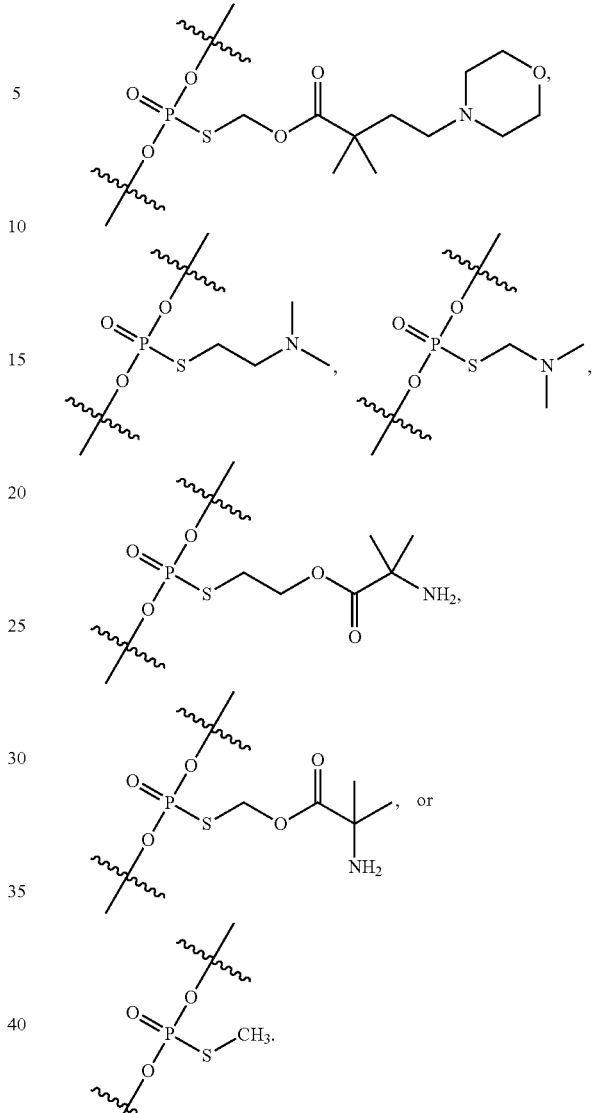

In some embodiments, the present invention provides a chirally controlled oligonucleotide comprising one or more phosphate diester linkages, and one or more modified internucleotide linkages having the formula of I-a, I-b, or I-c.

In some embodiments, the present invention provides a chirally controlled oligonucleotide comprising at least one phosphate diester internucleotidic linkage and at least one phosphorothioate triester linkage having the structure of formula I-c. In some embodiments, the present invention provides a chirally controlled oligonucleotide comprising at least one phosphate diester internucleotidic linkage and at least two phosphorothioate triester linkages having the structure of formula I-c. In some embodiments, the present invention provides a chirally controlled oligonucleotide comprising at least one phosphate diester internucleotidic linkage and at least three phosphorothioate triester linkages having the structure of formula I-c. In some embodiments, the present invention provides a chirally controlled oligonucleotide comprising at least one phosphate diester internucleotidic linkage and at least four phosphorothioate triester linkages having the structure of formula I-c. In some embodiments, the present invention provides a chirally controlled oligonucleotide comprising at least one phosphate diester internucleotidic linkage and at least five phosphorothioate triester linkages having the structure of formula I-c.

In some embodiments, the present invention provides a chirally controlled oligonucleotide comprising a sequence found in GCCTCAGTCTGCTTCGCACC (SEQ ID NO: 9). In some embodiments, the present invention provides a chirally controlled oligonucleotide comprising a sequence found in GCCTCAGTCTGCTTCGCACC (SEQ ID NO: 9), wherein the said sequence has over 50% identity with GCCTCAGTCTGCTTCGCACC (SEQ ID NO: 9). In some embodiments, the present invention provides a chirally controlled oligonucleotide comprising a sequence found in GCCTCAGTCTGCTTCGCACC (SEQ ID NO: 9), wherein the said sequence has over 60% identity with GCCTCAGTCTGCTTCGCACC (SEQ ID NO: 9). In some embodiments, the present invention provides a chirally controlled oligonucleotide comprising a sequence found in GCCTCAGTCTGCTTCGCACC (SEQ ID NO: 9), wherein the said sequence has over 70% identity with GCCTCAGTCTGCTTCGCACC (SEQ ID NO: 9). In some embodiments, the present invention provides a chirally controlled oligonucleotide comprising a sequence found in GCCTCAGTCTGCTTCGCACC (SEQ ID NO: 9), wherein the said sequence has over 80% identity with GCCTCAGTCTGCTTCGCACC (SEQ ID NO: 9). In some embodiments, the present invention provides a chirally controlled oligonucleotide comprising a sequence found in GCCTCAGTCTGCTTCGCACC (SEQ ID NO: 9), wherein the said sequence has over 90% identity with GCCTCAGTCTGCTTCGCACC (SEQ ID NO: 9). In some embodiments, the present invention provides a chirally controlled oligonucleotide comprising a sequence found in GCCTCAGTCTGCTTCGCACC (SEQ ID NO: 9), wherein the said sequence has over 95% identity with GCCTCAGTCTGCTTCGCACC (SEQ ID NO: 9). In some embodiments, the present invention provides a chirally controlled oligonucleotide comprising the sequence of GCCTCAGTCTGCTTCGCACC (SEQ ID NO: 9). In some embodiments, the present invention provides a chirally controlled oligonucleotide having the sequence of GCCTCAGTCTGCTTCGCACC (SEQ ID NO: 9).

In some embodiments, the present invention provides a chirally controlled oligonucleotide comprising a sequence found in GCCTCAGTCTGCTTCGCACC (SEQ ID NO: 9), wherein at least one internucleotidic linkage has a chiral linkage phosphorus. In some embodiments, the present invention provides a chirally controlled oligonucleotide comprising a sequence found in GCCTCAGTCTGCTTCGCACC (SEQ ID NO: 9), wherein at least one internucleotidic linkage has the structure of formula I. In some embodiments, the present invention provides a chirally controlled oligonucleotide comprising a sequence found in GCCTCAGTCTGCTTCGCACC (SEQ ID NO: 9), wherein each internucleotidic linkage has the structure of formula I. In some embodiments, the present invention provides a chirally controlled oligonucleotide comprising a sequence found in GCCTCAGTCTGCTTCGCACC (SEQ ID NO: 9), wherein at least one internucleotidic linkage has the structure of formula I-c. In some embodiments, the present invention provides a chirally controlled oligonucleotide comprising a sequence found in GCCTCAGTCTGCTTCGCACC (SEQ ID NO: 9), wherein each internucleotidic linkage has the structure of formula I-c. In some embodiments, the present invention provides a chirally controlled oligonucleotide comprising a sequence found in GCCTCAGTCTGCTTCGCACC (SEQ ID NO: 9), wherein at least one internucleotidic linkage is

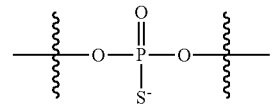

In some embodiments, the present invention provides a chirally controlled oligonucleotide comprising a sequence found in GCCTCAGTCTGCTTCGCACC (SEQ ID NO: 9), wherein each internucleotidic linkage is

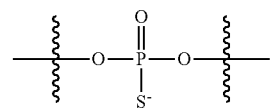

In some embodiments, the present invention provides a chirally controlled oligonucleotide comprising a sequence found in GCCTCAGTCTGCTTCGCACC (SEQ ID NO: 9), wherein at least one internucleotidic linkage is

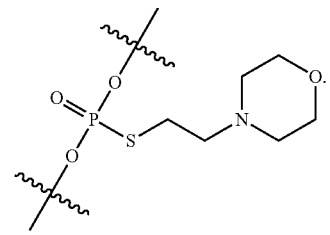 [SMILES: *OP(=O)(O*)SCCN1CCOCC1]

In some embodiments, the present invention provides a chirally controlled oligonucleotide comprising a sequence found in GCCTCAGTCTGCTTCGCACC (SEQ ID NO: 9), wherein each internucleotidic linkage is

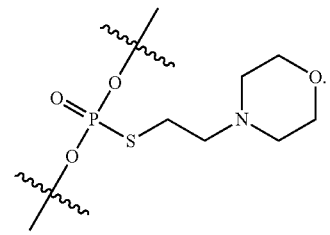 [SMILES: *OP(=O)(O*)SCCN1CCOCC1]

In some embodiments, the present invention provides a chirally controlled oligonucleotide comprising the sequence of GCCTCAGTCTGCTTCGCACC (SEQ ID NO: 9), wherein at least one internucleotidic linkage has a chiral linkage phosphorus. In some embodiments, the present invention provides a chirally controlled oligonucleotide comprising the sequence of GCCTCAGTCTGCTTCGCACC (SEQ ID NO: 9), wherein at least one internucleotidic linkage has the structure of formula I. In some embodiments, the present invention provides a chirally controlled oligonucleotide comprising the sequence of GCCTCAGTCTGCTTCGCACC (SEQ ID NO: 9), wherein each internucleotidic linkage has the structure of formula I. In some embodiments, the present invention provides a chirally controlled oligonucleotide comprising the sequence of GCCTCAGTCTGCTTCGCACC (SEQ ID NO: 9), wherein at least one internucleotidic linkage has the structure of formula I-c. In some embodiments, the present invention provides a chirally controlled oligonucleotide comprising the sequence of GCCTCAGTCTGCTTCGCACC (SEQ ID NO: 9), wherein each internucleotidic linkage has the structure of formula I-c. In some embodiments, the present invention provides a chirally controlled oligonucleotide comprising the sequence of GCCTCAGTCTGCTTCGCACC (SEQ ID NO: 9), wherein at least one internucleotidic linkage is

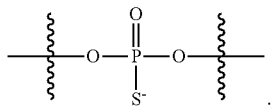 [SMILES: *OP(=O)([S-])O*]

In some embodiments, the present invention provides a chirally controlled oligonucleotide comprising the sequence of GCCTCAGTCTGCTTCGCACC (SEQ ID NO: 9), wherein each internucleotidic linkage is

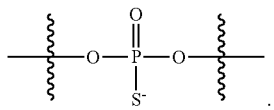 [SMILES: *OP(=O)([S-])O*]

In some embodiments, the present invention provides a chirally controlled oligonucleotide comprising the sequence of GCCTCAGTCTGCTTCGCACC (SEQ ID NO: 9), wherein at least one internucleotidic linkage is

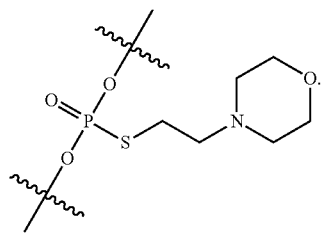 [SMILES: *OP(=O)(O*)SCCN1CCOCC1]

In some embodiments, the present invention provides a chirally controlled oligonucleotide comprising the sequence of GCCTCAGTCTGCTTCGCACC (SEQ ID NO: 9), wherein each internucleotidic linkage is

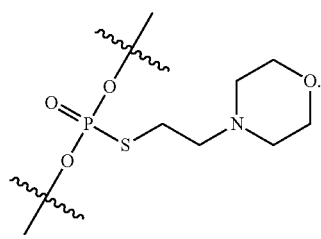 [SMILES: *OP(=O)(O*)SCCN1CCOCC1]

In some embodiments, the present invention provides a chirally controlled oligonucleotide having the sequence of GCCTCAGTCTGCTTCGCACC (SEQ ID NO: 9), wherein at least one internucleotidic linkage has a chiral linkage phosphorus. In some embodiments, the present invention provides a chirally controlled oligonucleotide having the sequence of GCCTCAGTCTGCTTCGCACC (SEQ ID NO: 9), wherein at least one internucleotidic linkage has the structure of formula I. In some embodiments, the present invention provides a chirally controlled oligonucleotide having the sequence of GCCTCAGTCTGCTTCGCACC (SEQ ID NO: 9), wherein each internucleotidic linkage has the structure of formula I. In some embodiments, the present invention provides a chirally controlled oligonucleotide having the sequence of GCCTCAGTCTGCTTCGCACC (SEQ ID NO: 9), wherein at least one internucleotidic linkage has the structure of formula I-c. In some embodiments, the present invention provides a chirally controlled oligonucleotide having the sequence of GCCTCAGTCTGCTTCGCACC (SEQ ID NO: 9), wherein each internucleotidic linkage has the structure of formula I-c. In some embodiments, the present invention provides a chirally controlled oligonucleotide having the sequence of GCCTCAGTCTGCTTCGCACC (SEQ ID NO: 9), wherein at least one internucleotidic linkage is

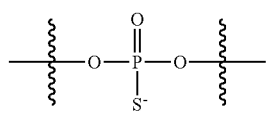

In some embodiments, the present invention provides a chirally controlled oligonucleotide having the sequence of GCCTCAGTCTGCTTCGCACC (SEQ ID NO: 9), wherein each internucleotidic linkage is

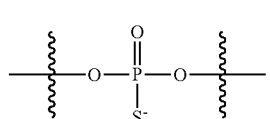

In some embodiments, the present invention provides a chirally controlled oligonucleotide having the sequence of GCCTCAGTCTGCTTCGCACC (SEQ ID NO: 9), wherein at least one internucleotidic linkage is

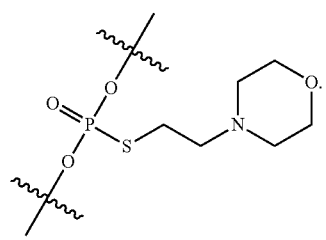 [SMILES: *OP(=O)(O*)SCCN1CCOCC1]

In some embodiments, the present invention provides a chirally controlled oligonucleotide having the sequence of GCCTCAGTCTGCTTCGCACC (SEQ ID NO: 9), wherein each internucleotidic linkage is

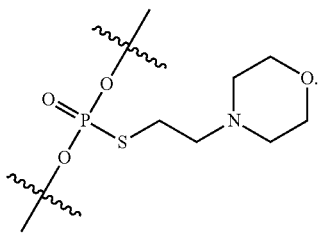 [SMILES: *OP(=O)(O*)SCCN1CCOCC1]

In some embodiments, the present invention provides a chirally controlled oligonucleotide having the sequence of GCCTCAGTCTGCTTCGCACC (SEQ ID NO: 9), wherein at least one linkage phosphorus is Rp. It is understood by a person of ordinary skill in the art that in certain embodiments wherein the chirally controlled oligonucleotide comprises an RNA sequence, each T is independently and optionally replaced with U. In some embodiments, the present invention provides a chirally controlled oligonucleotide having the sequence of GCCTCAGTCTGCTTCGCACC (SEQ ID NO: 9), wherein each linkage phosphorus is Rp. In some embodiments, the present invention provides a chirally controlled oligonucleotide having the sequence of GCCTCAGTCTGCTTCGCACC (SEQ ID NO: 9), wherein at least one linkage phosphorus is Sp. In some embodiments, the present invention provides a chirally controlled oligonucleotide having the sequence of GCCTCAGTCTGCTTCGCACC (SEQ ID NO: 9), wherein each linkage phosphorus is Sp. In some embodiments, the present invention provides a chirally controlled oligonucleotide having the sequence of GCCTCAGTCTGCTTCGCACC (SEQ ID NO: 9), wherein the oligonucleotide is a blockmer. In some embodiments, the present invention provides a chirally controlled oligonucleotide having the sequence of GCCTCAGTCTGCTTCGCACC (SEQ ID NO: 9), wherein the oligonucleotide is a stereoblockmer. In some embodiments, the present invention provides a chirally controlled oligonucleotide having the sequence of GCCTCAGTCTGCTTCGCACC (SEQ ID NO: 9), wherein the oligonucleotide is a P-modification blockmer. In some embodiments, the present invention provides a chirally controlled oligonucleotide having the sequence of GCCTCAGTCTGCTTCGCACC (SEQ ID NO: 9), wherein the oligonucleotide is a linkage blockmer. In some embodiments, the present invention provides a chirally controlled oligonucleotide having the sequence of GCCTCAGTCTGCTTCGCACC (SEQ ID NO: 9), wherein the oligonucleotide is an altmer. In some embodiments, the present invention provides a chirally controlled oligonucleotide having the sequence of GCCTCAGTCTGCTTCGCACC (SEQ ID NO: 9), wherein the oligonucleotide is a stereoaltmer. In some embodiments, the present invention provides a chirally controlled oligonucleotide having the sequence of GCCTCAGTCTGCTTCGCACC (SEQ ID NO: 9), wherein the oligonucleotide is a P-modification altmer. In some embodiments, the present invention provides a chirally controlled oligonucleotide having the sequence of GCCTCAGTCTGCTTCGCACC (SEQ ID NO: 9), wherein the oligonucleotide is a linkage altmer. In some embodiments, the present invention provides a chirally controlled oligonucleotide having the sequence of GCCTCAGTCTGCTTCGCACC (SEQ ID NO: 9), wherein the oligonucleotide is a unimer. In some embodiments, the present invention provides a chirally controlled oligonucleotide having the sequence of GCCTCAGTCTGCTTCGCACC (SEQ ID NO: 9), wherein the oligonucleotide is a stereounimer. In some embodiments, the present invention provides a chirally controlled oligonucleotide having the sequence of GCCTCAGTCTGCTTCGCACC (SEQ ID NO: 9), wherein the oligonucleotide is a P-modification unimer. In some embodiments, the present invention provides a chirally controlled oligonucleotide having the sequence of GCCTCAGTCTGCTTCGCACC (SEQ ID NO: 9), wherein the oligonucleotide is a linkage unimer. In some embodiments, the present invention provides a chirally controlled oligonucleotide having the sequence of GCCTCAGTCTGCTTCGCACC (SEQ ID NO: 9), wherein the oligonucleotide is a gapmer. In some embodiments, the present invention provides a chirally controlled oligonucleotide having the sequence of GCCTCAGTCTGCTTCGCACC (SEQ ID NO: 9), wherein the oligonucleotide is a skipmer.

In some embodiments, the present invention provides a chirally controlled oligonucleotide having the sequence of GCCTCAGTCTGCTTCGCACC (SEQ ID NO: 9), wherein each cytosine is optionally and independently replaced by 5-methylcytosine. In some embodiments, the present invention provides a chirally controlled oligonucleotide having the sequence of GCCTCAGTCTGCTTCGCACC (SEQ ID NO: 9), wherein at least one cytosine is optionally and independently replaced by 5-methylcytosine. In some embodiments, the present invention provides a chirally controlled oligonucleotide having the sequence of GCCTCAGTCTGCTTCGCACC (SEQ ID NO: 9), wherein each cytosine is optionally and independently replaced by 5-methylcytosine.

In some embodiments, a chirally controlled oligonucleotide is designed such that one or more nucleotides comprise a phosphorus modification prone to "autorelease" under certain conditions. That is, under certain conditions, a particular phosphorus modification is designed such that it self-cleaves from the oligonucleotide to provide, e.g., a phosphate diester such as those found in naturally occurring DNA and RNA. In some embodiments, such a phosphorus modification has a structure of —O-L-R$^1$, wherein each of L and R$^1$ is independently as defined above and described herein. In some embodiments, an autorelease group comprises a morpholino group. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a phosphate diester as is found in naturally occurring DNA and RNA.

In some embodiments, a chirally controlled oligonucleotide is designed such that the resulting pharmaceutical properties are improved through one or more particular modifications at phosphorus. It is well documented in the art that certain oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1): 196-208; Bologna et al., (2002), Antisense & Nucleic Acid Drug Development 12:33-41). For instance, Vives et al., (Nucleic Acids Research (1999), 27(20):4071-76) found that tert-butyl SATE pro-oligonucleotides displayed markedly increased cellular penetration compared to the parent oligonucleotide.

In some embodiments, a modification at a linkage phosphorus is characterized by its ability to be transformed to a phosphate diester, such as those present in naturally occurring DNA and RNA, by one or more esterases, nucleases, and/or cytochrome P450 enzymes, including but not limited to, those listed in Table 1, below.

TABLE 1

Example enzymes.

| Family | Gene |
|---|---|
| CYP1 | CYP1A1, CYP1A2, CYP1B1 |
| CYP2 | CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1 |
| CYP3 | CYP3A4, CYP3A5, CYP3A7, CYP3A43 |
| CYP4 | CYP4A11, CYP4A22, CYP4B1, CYP4F2, CYP4F3, CYP4F8, CYP4F11, CYP4F12, CYP4F22, CYP4V2, CYP4X1, CYP4Z1 |
| CYP5 | CYP5A1 |
| CYP7 | CYP7A1, CYP7B1 |
| CYP8 | CYP8A1 (prostacyclin synthase), CYP8B1 (bile acid biosynthesis) |
| CYP11 | CYP11A1, CYP11B1, CYP11B2 |
| CYP17 | CYP17A1 |
| CYP19 | CYP19A1 |
| CYP20 | CYP20A1 |
| CYP21 | CYP21A2 |
| CYP24 | CYP24A1 |
| CYP26 | CYP26A1, CYP26B1, CYP26C1 |
| CYP27 | CYP27A1 (bile acid biosynthesis), CYP27B1 (vitamin D3 1-alpha hydroxylase, activates vitamin D3), CYP27C1 (unknown function) |
| CYP39 | CYP39A1 |
| CYP46 | CYP46A1 |
| CYP51 | CYP51A1 (lanosterol 14-alpha demethylase) |

In some embodiments, a modification at phosphorus results in a P-modification moiety characterized in that it acts as a pro-drug, e.g., the P-modification moiety facilitates delivery of an oligonucleotide to a desired location prior to removal. For instance, in some embodiments, a P-modification moiety results from PEGylation at the linkage phosphorus. One of skill in the relevant arts will appreciate that various PEG chain lengths are useful and that the selection of chain length will be determined in part by the result that is sought to be achieved by PEGylation. For instance, in some embodiments, PEGylation is effected in order to reduce RES uptake and extend in vivo circulation lifetime of an oligonucleotide.

In some embodiments, a PEGylation reagent for use in accordance with the present invention is of a molecular weight of about 300 g/mol to about 100,000 g/mol. In some embodiments, a PEGylation reagent is of a molecular weight of about 300 g/mol to about 10,000 g/mol. In some embodiments, a PEGylation reagent is of a molecular weight of about 300 g/mol to about 5,000 g/mol. In some embodiments, a PEGylation reagent is of a molecular weight of about 500 g/mol. In some embodiments, a PEGylation reagent of a molecular weight of about 1000 g/mol. In some embodiments, a PEGylation reagent is of a molecular weight of about 3000 g/mol. In some embodiments, a PEGylation reagent is of a molecular weight of about 5000 g/mol.

In certain embodiments, a PEGylation reagent is PEG500.
In certain embodiments, a PEGylation reagent is PEG1000.
In certain embodiments, a PEGylation reagent is PEG3000.
In certain embodiments, a PEGylation reagent is PEG5000.

In some embodiments, a P-modification moiety is characterized in that it acts as a PK enhancer, e.g., lipids, PEGylated lipids, etc.

In some embodiments, a P-modification moiety is characterized in that it acts as an agent which promotes cell entry and/or endosomal escape, such as a membrane-disruptive lipid or peptide.

In some embodiments, a P-modification moiety is characterized in that it acts as a targeting agent. In some embodiments, a P-modification moiety is or comprises a targeting agent. The phrase "targeting agent," as used herein, is an entity that is associates with a payload of interest (e.g., with an oligonucleotide or oligonucleotide composition) and also interacts with a target site of interest so that the payload of interest is targeted to the target site of interest when associated with the targeting agent to a materially greater extent than is observed under otherwise comparable conditions when the payload of interest is not associated with the targeting agent. A targeting agent may be, or comprise, any of a variety of chemical moieties, including, for example, small molecule moieties, nucleic acids, polypeptides, carbohydrates, etc. Targeting agents are described further by Adarsh et al., "Organelle Specific Targeted Drug Delivery—A Review," International Journal of Research in Pharmaceutical and Biomedical Sciences, 2011, p. 895.

Exemplary such targeting agents include, but are not limited to, proteins (e.g. Transferrin), oligopeptides (e.g., cyclic and acylic RGD-containing oligopedptides), antibodies (monoclonal and polyclonal antibodies, e.g. IgG, IgA, IgM, IgD, IgE antibodies), sugars/carbohydrates (e.g., monosaccharides and/or oligosaccharides (mannose, mannose-6-phosphate, galactose, and the like)), vitamins (e.g., folate), or other small biomolecules. In some embodiments, a targeting moiety is a steroid molecule (e.g., bile acids including cholic acid, deoxycholic acid, dehydrocholic acid; cortisone; digoxigenin; testosterone; cholesterol; cationic steroids such as cortisone having a trimethylaminomethyl hydrazide group attached via a double bond at the 3-position of the cortisone ring, etc.). In some embodiments, a targeting moiety is a lipophilic molecule (e.g., alicyclic hydrocarbons, saturated and unsaturated fatty acids, waxes, terpenes, and polyalicyclic hydrocarbons such as adamantine and buckminsterfullerenes). In some embodiments, a lipophilic molecule is a terpenoid such as vitamin A, retinoic acid, retinal, or dehydroretinal. In some embodiments, a targeting moiety is a peptide.

In some embodiments, a P-modification moiety is a targeting agent of formula —X-L-R$^1$ wherein each of X, L, and R$^1$ are as defined in Formula I above.

In some embodiments, a P-modification moiety is characterized in that it facilitates cell specific delivery.

In some embodiments, a P-modification moiety is characterized in that it falls into one or more of the above-described categories. For instance, in some embodiments, a P-modification moiety acts as a PK enhancer and a targeting ligand. In some embodiments, a P-modification moiety acts as a pro-drug and an endosomal escape agent. One of skill in the relevant arts would recognize that numerous other such combinations are possible and are contemplated by the present invention.

Nucleobases

In some embodiments, a nucleobase present in a provided oligonucleotide is a natural nucleobase or a modified nucleobase derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Exemplary modified nucleobases are disclosed in Chiu and Rana, *RNA,* 2003, 9, 1034-1048, Limbach et al. *Nucleic Acids Research,* 1994, 22, 2183-2196 and Revankar and Rao, *Comprehensive Natural Products Chemistry,* vol. 7, 313.

Compounds represented by the following general formulae are also contemplated as modified nucleobases:

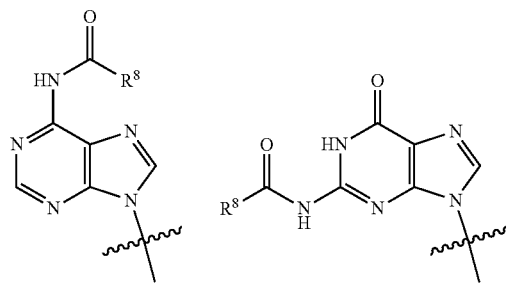

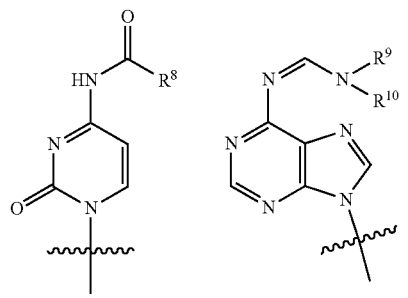

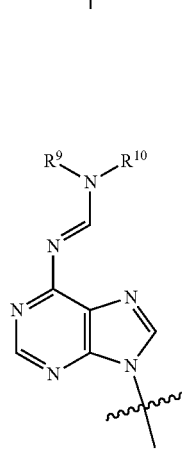

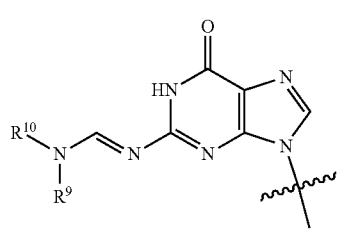

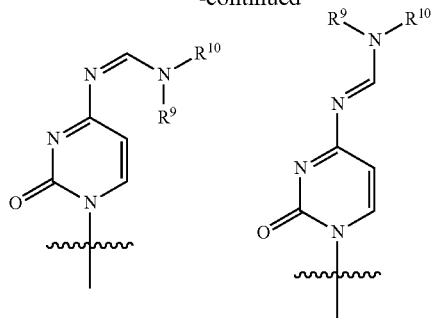

-continued

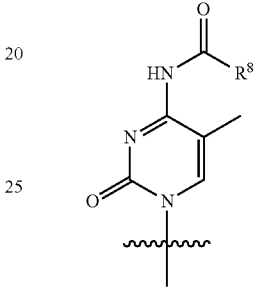

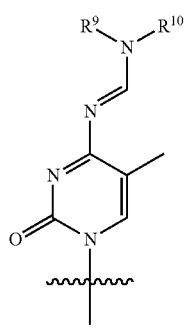

wherein $R^8$ is an optionally substituted, linear or branched group selected from aliphatic, aryl, aralkyl, aryloxylalkyl, carbocyclyl, heterocyclyl or heteroaryl group having 1 to 15 carbon atoms, including, by way of example only, a methyl, isopropyl, phenyl, benzyl, or phenoxymethyl group; and each of $R^9$ and $R^{10}$ is independently an optionally substituted group selected from linear or branched aliphatic, carbocyclyl, aryl, heterocyclyl and heteroaryl.

Modified nucleobases also include expanded-size nucleobases in which one or more aryl rings, such as phenyl rings, have been added. Nucleic base replacements described in the Glen Research catalog (www.glenresearch.com); Krueger A T et al, *Acc. Chem. Res.,* 2007, 40, 141-150; Kool, E T, *Acc. Chem. Res.,* 2002, 35, 936-943; Benner S. A., et al., *Nat. Rev. Genet.,* 2005, 6, 553-543; Romesberg, F. E., et al., *Curr. Opin. Chem. Biol.,* 2003, 7, 723-733; Hirao, I., *Curr. Opin. Chem. Biol.,* 2006, 10, 622-627, are contemplated as useful for the synthesis of the nucleic acids described herein. Some examples of these expanded-size nucleobases are shown below:

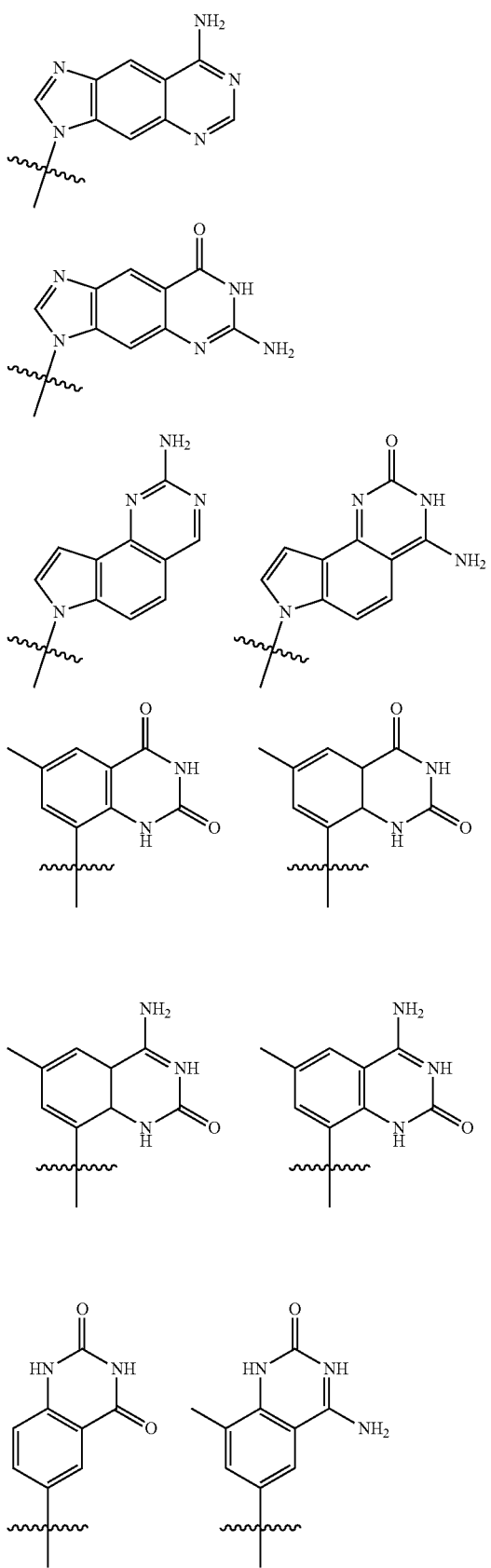

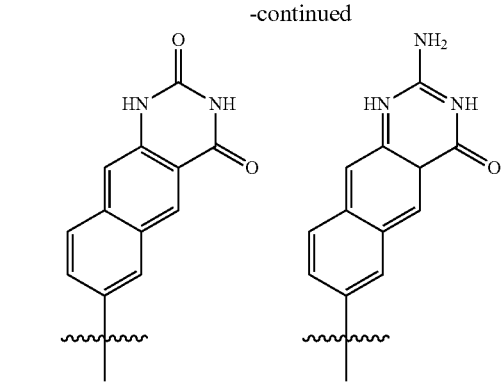

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, E T, *Org. Lett.*, 2002, 4, 4377-4380. Shown below is an example of a porphyrin-derived ring which can be used as a base replacement:

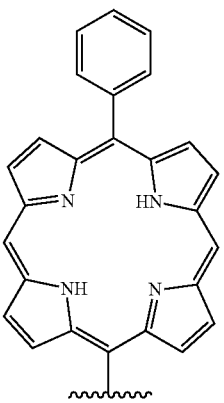 [SMILES: *c1c2nc(cc3ccc([nH]3)c(-c3ccccc3)c3nc(cc4ccc1[nH]4)C=C3)C=C2]

In some embodiments, modified nucleobases are of any one of the following structures, optionally substituted:

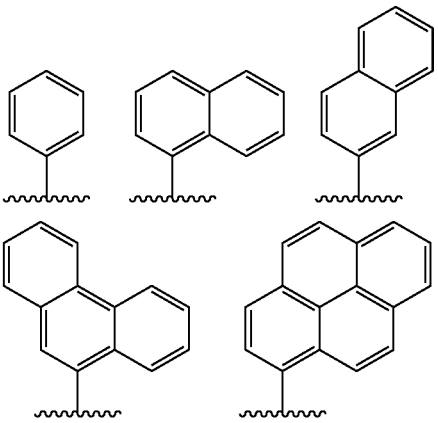

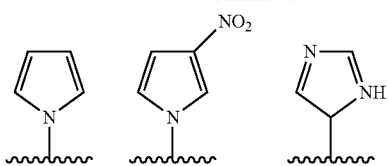

In some embodiments, a modified nucleobase is fluorescent. Exemplary such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

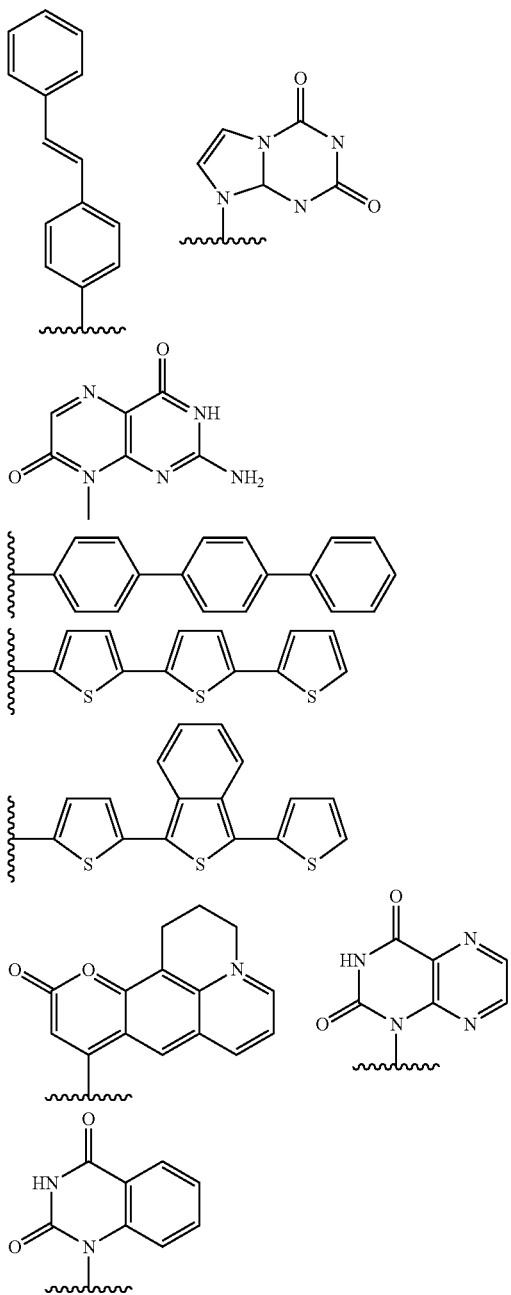

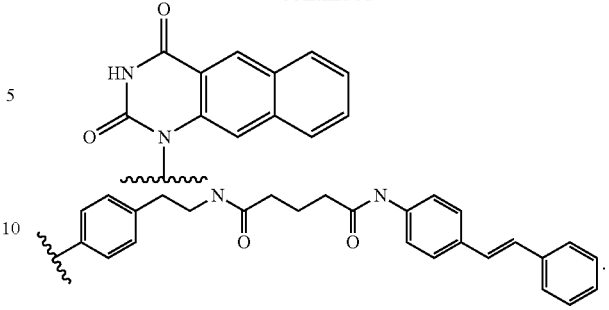

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety. In some embodiments, the substituent on a nucleobase or modified nucleobase is biotin or avidin.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety.

Sugars

The most common naturally occurring nucleotides are comprised of ribose sugars linked to the nucleobases adenosine (A), cytosine (C), guanine (G), and thymine (T) or uracil (U). Also contemplated are modified nucleotides wherein a phosphate group or linkage phosphorus in the nucleotides can be linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with methods of the present invention.

Other modified sugars can also be incorporated within a provided oligonucleotide. In some embodiments, a modified sugar contains one or more substituents at the 2' position including one of the following: —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. Examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'-OH of a ribose is replaced with a substituent including one of the following: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —OCH$_2$CH$_2$OMe.

Modified sugars also include locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, -L- is —O—CH$_2$—, wherein —CH$_2$— is optionally substituted. In some embodiments, -L- is —O—CH$_2$—. In some embodiments, -L- is —O—CH(Et)-. In some embodiments, -L- is between C2 and C4 of a sugar moiety. In some embodiments, a locked nucleic acid has the structure indicated below. A locked nucleic acid of the structure below is indicated, wherein Ba represents a nucleobase or modified nucleobase as described herein, and wherein R$^{2s}$ is —OCH$_2$C4'-.

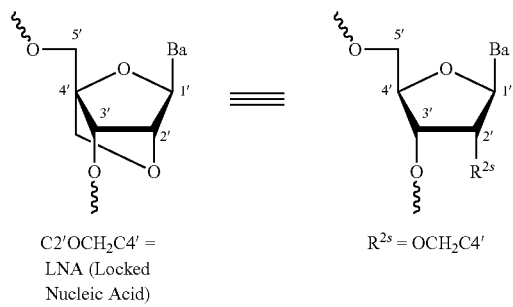

C2'OCH$_2$C4' = LNA (Locked Nucleic Acid)

R$^{2s}$ = OCH$_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xenonucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA) analogues. One example of a GNA analogue is shown below and is described in Zhang, R et al., *J. Am. Chem. Soc.*, 2008, 130, 5846-5847; Zhang L, et al., *J. Am. Chem. Soc.*, 2005, 127, 4174-4175 and Tsai C H et al., *PNAS*, 2007, 14598-14603 (X=O⁻):

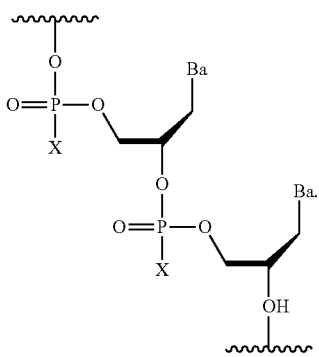

Another example of a GNA derived analogue, flexible nucleic acid (FNA) based on the mixed acetal aminal of formyl glycerol, is described in Joyce G F et al., *PNAS*, 1987, 84, 4398-4402 and Heuberger B D and Switzer C, *J. Am. Chem. Soc.*, 2008, 130, 412-413, and is shown below:

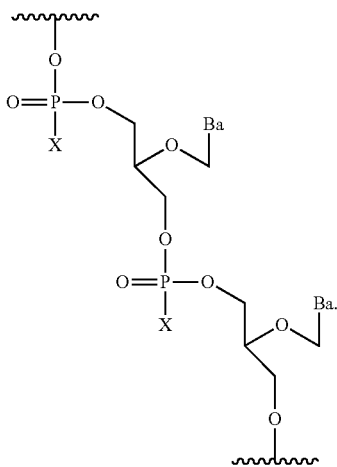

Additional non-limiting examples of modified sugars include hexopyranosyl (6' to 4'), pentopyranosyl (4' to 2'), pentopyranosyl (4' to 3'), or tetrafuranosyl (3' to 2') sugars. In some embodiments, a hexopyranosyl (6' to 4') sugar is of any one in the following formulae:

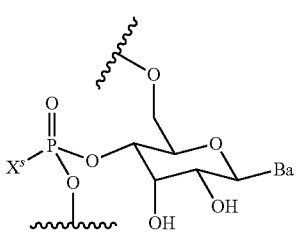

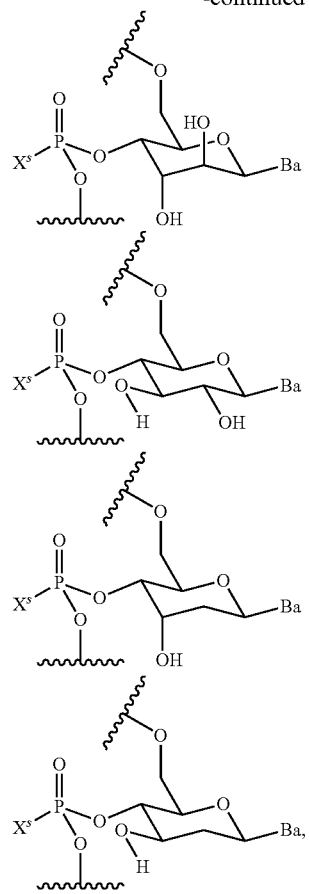

wherein $X^s$ corresponds to the P-modification group "—XLR¹" described herein and Ba is as defined herein.

In some embodiments, a pentopyranosyl (4' to 2') sugar is of any one in the following formulae:

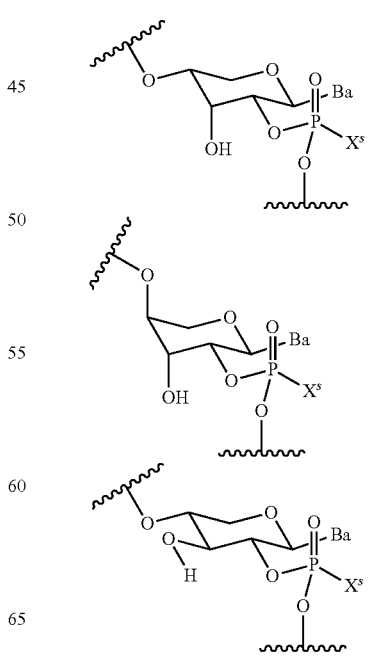

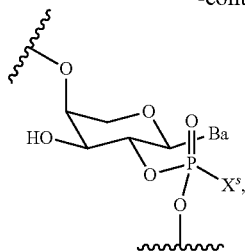

wherein $X^s$ corresponds to the P-modification group "—XLR$^1$" described herein and Ba is as defined herein.

In some embodiments, a pentopyranosyl (4' to 3') sugar is of any one in the following formulae:

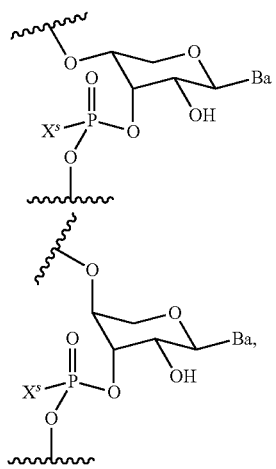

wherein $X^s$ corresponds to the P-modification group "—XLR$^1$" described herein and Ba is as defined herein.

In some embodiments, a tetrafuranosyl (3' to 2') sugar is of either in the following formulae:

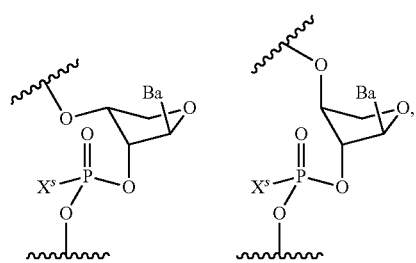

wherein $X^s$ corresponds to the P-modification group "—XLR$^1$" described herein and Ba is as defined herein.

In some embodiments, a modified sugar is of any one in the following formulae:

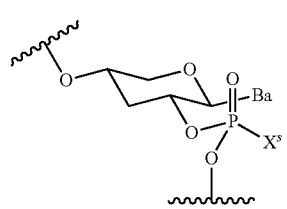

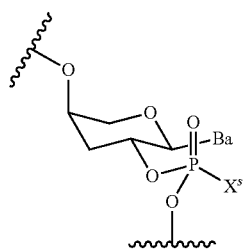

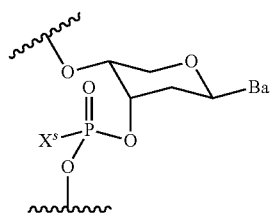

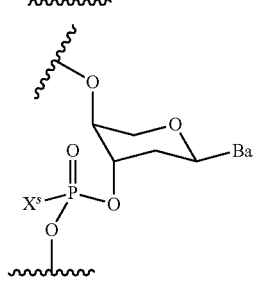

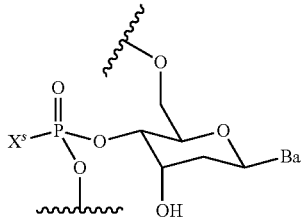

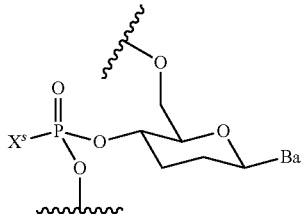

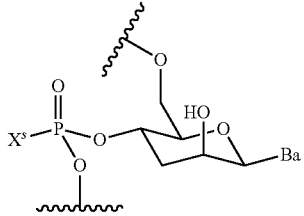

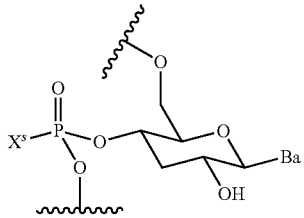

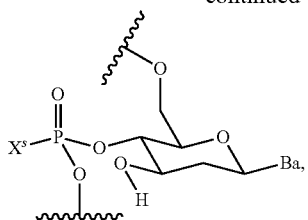

wherein $X^s$ corresponds to the P-modification group "—XLR$^1$" described herein and Ba is as defined herein.

In some embodiments, one or more hydroxyl group in a sugar moiety is optionally and independently replaced with halogen, R'—N(R')$_2$, —OR', or —SR', wherein each R' is independently as defined above and described herein.

In some embodiments, a sugar mimetic is as illustrated below, wherein $X^s$ corresponds to the P-modification group "—XLR$^1$" described herein, Ba is as defined herein, and $X^1$ is selected from —S—, —Se—, —CH$_2$—, —NMe-, —NEt- or —NiPr—.

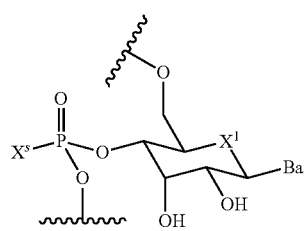
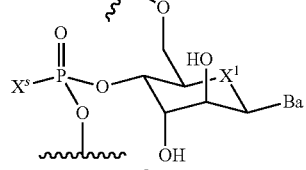
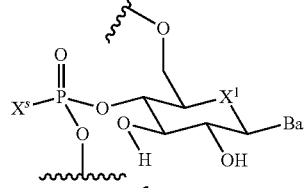
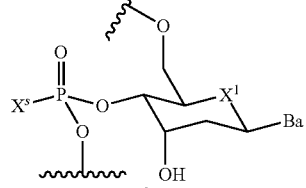
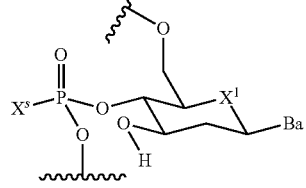
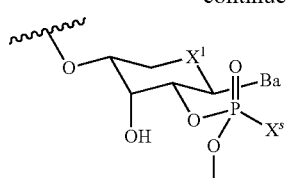
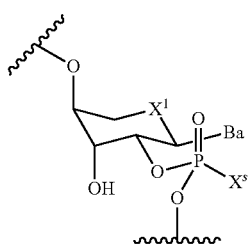
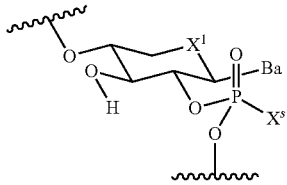
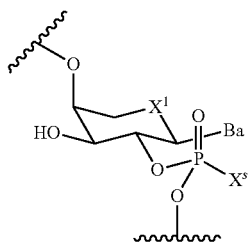
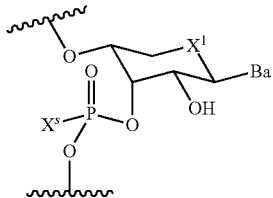
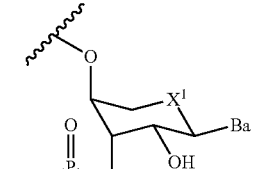
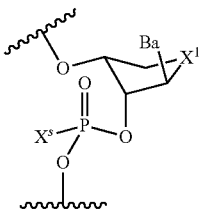
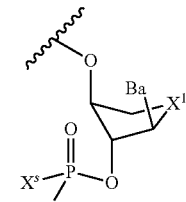
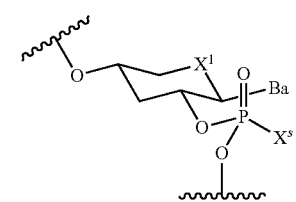

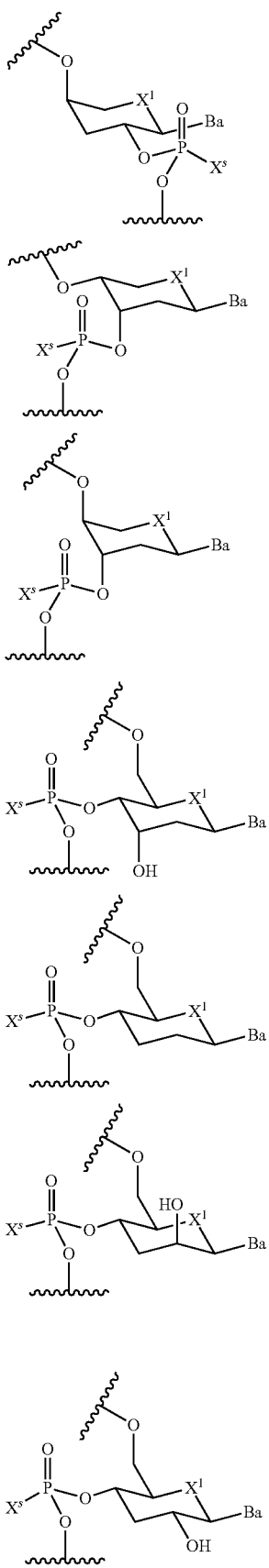

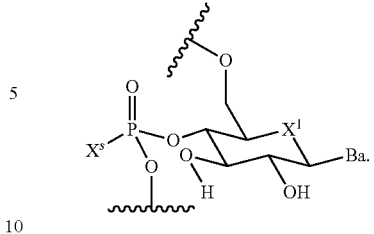

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310). In some embodiments, a modified sugar is any of those described in PCT Publication No. WO2012/030683, incorporated herein by reference, and depicted in the FIGS. 26-30 of the present application.

Oligonucleotides

In some embodiments, the present invention provides oligonucleotides and oligonucleotide compositions that are chirally controlled. For instance, in some embodiments, a provided composition contains predetermined levels of one or more individual oligonucleotide types, wherein an oligonucleotide type is defined by: 1) base sequence; 2) pattern of backbone linkages; 3) pattern of backbone chiral centers; and 4) pattern of backbone P-modifications.

In some embodiments, a provided oligonucleotide is a unimer. In some embodiments, a provided oligonucleotide is a P-modification unimer. In some embodiments, a provided oligonucleotide is a stereounimer. In some embodiments, a provided oligonucleotide is a stereounimer of configuration Rp. In some embodiments, a provided oligonucleotide is a stereounimer of configuration Sp.

In some embodiments, a provided oligonucleotide is an altmer. In some embodiments, a provided oligonucleotide is a P-modification altmer. In some embodiments, a provided oligonucleotide is a stereoaltmer.

In some embodiments, a provided oligonucleotide is a blockmer. In some embodiments, a provided oligonucleotide is a P-modification blockmer. In some embodiments, a provided oligonucleotide is a stereoblockmer.

In some embodiments, a provided oligonucleotide is a gapmer.

In some embodiments, a provided oligonucleotide is a skipmer.

In some embodiments, a provided oligonucleotide is a hemimer. In some embodiments, a hemimer is an oligonucleotide wherein the 5'-end or the 3'-end has a sequence that possesses a structure feature that the rest of the oligonucleotide does not have. In some embodiments, the 5'-end or the 3'-end has or comprises 2 to 20 nucleotides. In some embodiments, a structural feature is a base modification. In some embodiments, a structural feature is a sugar modification. In some embodiments, a structural feature is a P-modification. In some embodiments, a structural feature is stereochemistry of the chiral internucleotidic linkage. In some embodiments, a structural feature is or comprises a base modification, a sugar modification, a P-modification, or stereochemistry of the chiral internucleotidic linkage, or combinations thereof. In some embodiments, a hemimer is an oligonucleotide in which each sugar moiety of the 5'-end sequence shares a common modification. In some embodiments, a hemimer is an oligonucleotide in which each sugar moiety of the 3'-end sequence shares a common modification. In some embodiments, a common sugar modification of the 5' or 3' end sequence is not shared by any other sugar moieties in the oligonucleotide. In some embodiments, an exemplary hemimer is an oligonucleotide comprising a sequence of substituted or unsubstituted 2'-O-alkyl sugar modified nucleosides, bicyclic sugar modified nucleosides, β-D-ribonucleosides or β-D-deoxyribonucleosides (for example 2'-MOE modified nucleosides, and LNA™ or ENA™ bicyclic sugar modified nucleosides) at one terminus and a sequence of nucleosides with a different sugar moiety (such as a substituted or unsubstituted 2'-O-alkyl sugar modified nucleosides, bicyclic sugar modified nucleosides or natural ones) at the other terminus. In some embodiments, a provided oligonucleotide is a combination of one or more of unimer, altmer, blockmer, gapmer, hemimer and skipmer. In some embodiments, a provided oligonucleotide is a combination of one or more of unimer, altmer, blockmer, gapmer, and skipmer. For instance, in some embodiments, a provided oligonucleotide is both an altmer and a gapmer. In some embodiments, a provided nucleotide is both a gapmer and a skipmer. One of skill in the chemical and synthetic arts will recognize that numerous other combinations of patterns are available and are limited only by the commercial availability and/or synthetic accessibility of constituent parts required to synthesize a provided oligonucleotide in accordance with methods of the present invention. In some embodiments, a hemimer structure provides advantageous benefits, as exemplified by FIG. 29. In some embodiments, provided oligonucleotides are 5'-hemimers that comprises modified sugar moieties in a 5'-end sequence. In some embodiments, provided oligonucleotides are 5'-hemimers that comprises modified 2'-sugar moieties in a 5'-end sequence.

In some embodiments, a provided oligonucleotide comprises one or more optionally substituted nucleotides. In some embodiments, a provided oligonucleotide comprises one or more modified nucleotides. In some embodiments, a provided oligonucleotide comprises one or more optionally substituted nucleosides. In some embodiments, a provided oligonucleotide comprises one or more modified nucleosides. In some embodiments, a provided oligonucleotide comprises one or more optionally substituted LNAs.

In some embodiments, a provided oligonucleotide comprises one or more optionally substituted nucleobases. In some embodiments, a provided oligonucleotide comprises one or more optionally substituted natural nucleobases. In some embodiments, a provided oligonucleotide comprises one or more optionally substituted modified nucleobases. In some embodiments, a provided oligonucleotide comprises one or more 5-methylcytidine; 5-hydroxymethylcytidine, 5-formylcytosine, or 5-carboxylcytosine. In some embodiments, a provided oligonucleotide comprises one or more 5-methylcytidine.

In some embodiments, a provided oligonucleotide comprises one or more optionally substituted sugars. In some embodiments, a provided oligonucleotide comprises one or more optionally substituted sugars found in naturally occurring DNA and RNA. In some embodiments, a provided oligonucleotide comprises one or more optionally substituted ribose or deoxyribose. In some embodiments, a provided oligonucleotide comprises one or more optionally substituted ribose or deoxyribose, wherein one or more hydroxyl groups of the ribose or deoxyribose moiety is optionally and independently replaced by halogen, R', —N(R')$_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen, R', —N(R')$_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen. In some embodiments, a provided oligonucleotide comprises one or more optionally substituted deoxyribose, wherein the 2' position of the deoxyribose is optionally and independently substituted with one or more —F. halogen. In some embodiments, a provided oligonucleotide comprises one or more optionally substituted deoxyribose, wherein the 2' position of the deoxyribose is optionally and independently substituted with —OR', wherein each R' is independently as defined above and described herein. In some embodiments, a provided oligonucleotide comprises one or more optionally substituted deoxyribose, wherein the 2' position of the deoxyribose is optionally and independently substituted with —OR', wherein each R' is independently an optionally substituted $C_1$-$C_6$ aliphatic. In some embodiments, a provided oligonucleotide comprises one or more optionally substituted deoxyribose, wherein the 2' position of the deoxyribose is optionally and independently substituted with —OR', wherein each R' is independently an optionally substituted $C_1$-$C_6$ alkyl. In some embodiments, a provided oligonucleotide comprises one or more optionally substituted deoxyribose, wherein the 2' position of the deoxyribose is optionally and independently substituted with —OMe. In some embodiments, a provided oligonucleotide comprises one or more optionally substituted deoxyribose, wherein the 2' position of the deoxyribose is optionally and independently substituted with —O-methoxyethyl.

In some embodiments, a provided oligonucleotide is single-stranded oligonucleotide.

In some embodiments, a provided oligonucleotide is a hybridized oligonucleotide strand. In certain embodiments, a provided oligonucleotide is a partially hybridized oligonucleotide strand. In certain embodiments, a provided oligonucleotide is a completely hybridized oligonucleotide strand. In certain embodiments, a provided oligonucleotide is a double-stranded oligonucleotide. In certain embodiments, a provided oligonucleotide is a triple-stranded oligonucleotide (e.g., a triplex).

In some embodiments, a provided oligonucleotide is chimeric. For example, in some embodiments, a provided oligonucleotide is DNA-RNA chimera, DNA-LNA chimera, etc.

In some embodiments, any one of the structures comprising an oligonucleotide depicted in WO2012/030683 can be modified in accordance with methods of the present invention to provide chirally controlled variants thereof. For example, in some embodiments the chirally controlled variants comprise a stereochemical modification at any one or more of the linkage phosphorus and/or a P-modification at any one or more of the linkage phosphorus. For example, in some embodiments, a particular nucleotide unit of a oligonucleotide of WO2012/030683 is preselected to be stereochemically modified at the linkage phosphorus of that nucleotide unit and/or P-modified at the linkage phosphorus of that nucleotide unit. In some embodiments, a chirally controlled oligonucleotide is of any one of the structures depicted in FIGS. 26-30. In some embodiments, a chirally controlled oligonucleotide is a variant (e.g., modified version) of any one of the structures depicted in FIGS. 26-30. The disclosure of WO2012/030683 is herein incorporated by reference in its entirety.

In some embodiments, a provided oligonucleotide is a therapeutic agent.

In some embodiments, a provided oligonucleotide is an antisense oligonucleotide.

In some embodiments, a provided oligonucleotide is an antigene oligonucleotide.

In some embodiments, a provided oligonucleotide is a decoy oligonucleotide.

In some embodiments, a provided oligonucleotide is part of a DNA vaccine.

In some embodiments, a provided oligonucleotide is an immunomodulatory oligonucleotide, e.g., immunostimulatory oligonucleotide and immunoinhibitory oligonucleotide.

In some embodiments, a provided oligonucleotide is an adjuvant.

In some embodiments, a provided oligonucleotide is an aptamer.

In some embodiments, a provided oligonucleotide is a ribozyme.

In some embodiments, a provided oligonucleotide is a deoxyribozyme (DNAzymes or DNA enzymes).

In some embodiments, a provided oligonucleotide is an siRNA.

In some embodiments, a provided oligonucleotide is a microRNA, or miRNA.

In some embodiments, a provided oligonucleotide is a ncRNA (non-coding RNAs), including a long non-coding RNA (lncRNA) and a small non-coding RNA, such as piwi-interacting RNA (piRNA).

In some embodiments, a provided oligonucleotide is complementary to a structural RNA, e.g., tRNA.

In some embodiments, a provided oligonucleotide is a nucleic acid analog, e.g., GNA, LNA, PNA, TNA and Morpholino.

In some embodiments, a provided oligonucleotide is a P-modified prodrug.

In some embodiments, a provided oligonucleotide is a primer. In some embodiments, a primers is for use in polymerase-based chain reactions (i.e., PCR) to amplify nucleic acids. In some embodiments, a primer is for use in any known variations of PCR, such as reverse transcription PCR (RT-PCR) and real-time PCR.

In some embodiments, a provided oligonucleotide is characterized as having the ability to modulate RNase H activation. For example, in some embodiments, RNase H activation is modulated by the presence of stereocontrolled phosphorothioate nucleic acid analogs, with natural DNA/RNA being more or equally susceptible than the Rp stereoisomer, which in turn is more susceptible than the corresponding Sp stereoisomer.

In some embodiments, a provided oligonucleotide is characterized as having the ability to indirectly or directly increase or decrease activity of a protein or inhibition or promotion of the expression of a protein. In some embodiments, a provided oligonucleotide is characterized in that it is useful in the control of cell proliferation, viral replication, and/or any other cell signaling process.

In some embodiments, a provided oligonucleotide is from about 2 to about 200 nucleotide units in length. In some embodiments, a provided oligonucleotide is from about 2 to about 180 nucleotide units in length. In some embodiments, a provided oligonucleotide is from about 2 to about 160 nucleotide units in length. In some embodiments, a provided oligonucleotide is from about 2 to about 140 nucleotide units in length. In some embodiments, a provided oligonucleotide is from about 2 to about 120 nucleotide units in length. In some embodiments, a provided oligonucleotide is from about 2 to about 100 nucleotide units in length. In some embodiments, a provided oligonucleotide is from about 2 to about 90 nucleotide units in length. In some embodiments, a provided oligonucleotide is from about 2 to about 80 nucleotide units in length. In some embodiments, a provided oligonucleotide is from about 2 to about 70 nucleotide units in length. In some embodiments, a provided oligonucleotide is from about 2 to about 60 nucleotide units in length. In some embodiments, a provided oligonucleotide is from about 2 to about 50 nucleotide units in length. In some embodiments, a provided oligonucleotide is from about 2 to about 40 nucleotide units in length. In some embodiments, a provided oligonucleotide is from about 2 to about 30 nucleotide units in length. In some embodiments, a provided oligonucleotide is from about 2 to about 29 nucleotide units in length. In some embodiments, a provided oligonucleotide is from about 2 to about 28 nucleotide units in length. In some embodiments, a provided oligonucleotide is from about 2 to about 27 nucleotide units in length. In some embodiments, a provided oligonucleotide is from about 2 to about 26 nucleotide units in length. In some embodiments, a provided oligonucleotide is from about 2 to about 25 nucleotide units in length. In some embodiments, a provided oligonucleotide is from about 2 to about 24 nucleotide units in length. In some embodiments, a provided oligonucleotide is from about 2 to about 23 nucleotide units in length. In some embodiments, a provided oligonucleotide is from about 2 to about 22 nucleotide units in length. In some embodiments, a provided oligonucleotide is from about 2 to about 21 nucleotide units in length. In some embodiments, a provided oligonucleotide is from about 2 to about 20 nucleotide units in length.

In some embodiments, a provided oligonucleotide is from about 4 to about 200 nucleotide units in length. In some embodiments, a provided oligonucleotide is from about 4 to about 180 nucleotide units in length. In some embodiments, a provided oligonucleotide is from about 4 to about 160 nucleotide units in length. In some embodiments, a provided oligonucleotide is from about 4 to about 140 nucleotide units in length. In some embodiments, a provided oligonucleotide is from about 4 to about 120 nucleotide units in length. In some embodiments, a provided oligonucleotide is from about 4 to about 100 nucleotide units in length. In some embodiments, a provided oligonucleotide is from about 4 to about 90 nucleotide units in length. In some embodiments, a provided oligonucleotide is from about 4 to about 80 nucleotide units in length. In some embodiments, a provided oligonucleotide is from about 4 to about 70 nucleotide units in length. In some embodiments, a provided oligonucleotide is from about 4 to about 60 nucleotide units in length. In some embodiments, a provided oligonucleotide is from about 4 to about 50 nucleotide units in length. In some embodiments, a provided oligonucleotide is from about 4 to about 40 nucleotide units in length. In some embodiments, a provided oligonucleotide is from about 4 to about 30 nucleotide units in length. In some embodiments, a provided oligonucleotide is from about 4 to about 29 nucleotide units in length. In some embodiments, a provided oligonucleotide is from about 4 to about 28 nucleotide units in length. In some embodiments, a provided oligonucleotide is from about 4 to about 27 nucleotide units in length. In some embodiments, a provided oligonucleotide is from about 4 to about 26 nucleotide units in length. In some embodiments, a provided oligonucleotide is from about 4 to about 25 nucleotide units in length. In some embodiments, a provided oligonucleotide is from about 4 to about 24 nucleotide units in length. In some embodiments, a provided oligonucleotide is from about 4 to about 23 nucleotide units in length. In some embodiments, a provided oligonucleotide is from about 4 to about 22 nucleotide units in length. In some embodiments, a provided oligonucleotide is from about 4 to about 21 nucleotide units in length. In some embodiments, a provided oligonucleotide is from about 4 to about 20 nucleotide units in length.

In some embodiments, a provided oligonucleotide is from about 5 to about 10 nucleotide units in length. In some embodiments, a provided oligonucleotide is from about 10 to about 30 nucleotide units in length. In some embodiments, a provided oligonucleotide is from about 15 to about 25 nucleotide units in length. In some embodiments, a provided oligonucleotide is from about 5, 6, 7, 8, 9, 10, 11, 12, 13, 14, 15, 16, 17, 18, 19, 20, 21, 22, 23, 24, or 25 nucleotide units in length.

In some embodiments, the oligonucleotide is at least 2 nucleotide units in length. In some embodiments, the oligonucleotide is at least 3 nucleotide units in length. In some embodiments, the oligonucleotide is at least 4 nucleotide units in length. In some embodiments, the oligonucleotide is at least 5 nucleotide units in length. In some embodiments, the oligonucleotide is at least 6 nucleotide units in length. In some embodiments, the oligonucleotide is at least 7 nucleotide units in length. In some embodiments, the oligonucle-
otide is at least 8 nucleotide units in length. In some embodiments, the oligonucleotide is at least 9 nucleotide units in length. In some embodiments, the oligonucleotide is at least 10 nucleotide units in length. In some embodiments, the oligonucleotide is at least 11 nucleotide units in length. In some embodiments, the oligonucleotide is at least 12 nucleotide units in length. In some embodiments, the oligonucleotide is at least 13 nucleotide units in length. In some embodiments, the oligonucleotide is at least 14 nucleotide units in length. In some embodiments, the oligonucleotide is at least 15 nucleotide units in length. In some embodiments, the oligonucleotide is at least 16 nucleotide units in length. In some embodiments, the oligonucleotide is at least 17 nucleotide units in length. In some embodiments, the oligonucleotide is at least 18 nucleotide units in length. In some embodiments, the oligonucleotide is at least 19 nucleotide units in length. In some embodiments, the oligonucleotide is at least 20 nucleotide units in length. In some embodiments, the oligonucleotide is at least 21 nucleotide units in length. In some embodiments, the oligonucleotide is at least 22 nucleotide units in length. In some embodiments, the oligonucleotide is at least 23 nucleotide units in length. In some embodiments, the oligonucleotide is at least 24 nucleotide units in length. In some embodiments, the oligonucleotide is at least 25 nucleotide units in length. In some other embodiments, the oligonucleotide is at least 30 nucleotide units in length. In some other embodiments, the oligonucleotide is a duplex of complementary strands of at least 18 nucleotide units in length. In some other embodiments, the oligonucleotide is a duplex of complementary strands of at least 21 nucleotide units in length.

In some embodiments, the 5'-end and/or the 3'-end of a provided oligonucleotide is modified. In some embodiments, the 5'-end and/or the 3'-end of a provided oligonucleotide is modified with a terminal cap moiety. Exemplary such modifications, including terminal cap moieties are extensively described herein and in the art, for example but not limited to those described in US Patent Application Publication US 2009/0023675A1.

In some embodiments, oligonucleotides of an oligonucleotide type characterized by:
1) a common base sequence and length;
2) a common pattern of backbone linkages; and
3) a common pattern of backbone chiral centers;
have the same chemical structure. For example, they have the same base sequence, the same pattern of backbone linkages (i.e., pattern of internucleotidic linkage types, for example, phosphate, phosphorothioate, etc), the same pattern of backbone chiral centers (i.e. pattern of linkage phosphorus stereochemistry (Rp/Sp)), and the same pattern of backbone phosphorus modifications (e.g., pattern of "—XLR$^1$" groups in formula I).

Species of Oligonucleotides

In some embodiments, a provided chirally controlled oligonucleotide comprises the sequence of, or part of the sequence of mipomersen. Mipomersen is based on the following base sequence GCCT/UCAGT/UCT/UGCT/UT/UCGCACC (SEQ ID NO: 64). In some embodiments, one or more of any of the nucleotide or linkages may be modified in accordance with the present invention. In some embodiments, the present invention provides a chirally controlled oligonucleotide having the sequence of G*-C*-C*-U*-C*-dA-dG-dT-dC-dT-dG-dmC-dT-dT-dmC-G*-C̄*-A*-C̄*-C* (SEQ ID NO: 65) [d=2-deoxy, *=2'-O-(2-methoxyethyl)] with 3'→5' phosphorothioate linkages. Exemplary modified mipomersen sequences are described throughout the application, including but not limited to those in Table 2.

In certain embodiments, a provided oligonucleotide is a mipomersen unimer. In certain embodiments, a provided oligonucleotide is mipomersen unimer of configuration Rp.

In certain embodiments, a provided oligonucleotide is a mipomersen unimer of configuration Sp.

Exemplary chirally controlled oligonucleotides comprising the sequence of, or part of the sequence of mipomersen is depicted in Table 2, below.

TABLE 2

Exemplary Mipomersen related sequences.

| Oligo | Stereochemistry/Sequence | Description | SEQ ID NO: |
|---|---|---|---|
| 101 | All-(Rp)-d[GsCsCsTsCsAsGsTsCsTsGsCsTsTsCsGsCsAsCsC] | All-R | 66 |
| 102 | All-(Sp)-d[GsCsCsTsCsAsGsTsCsTsGsCsTsTsCsGsCsAsCsC] | All-S | 67 |
| 103 | (Rp, Rp, Rp, Rp, Rp, Sp, Sp, Sp, Sp, Sp Sp, Sp, Sp, Sp, Rp, Rp, Rp, Rp, Rp)-d[GsCsCsTsCsAsGsTsCsTsGsCsTsTsCsGsCsAsCsC] | 5R-9S-5R | 68 |
| 104 | (Sp, Sp, Sp, Sp, Sp, Rp, Rp, Rp, Rp, Rp Rp, Rp, Rp, Rp, Sp, Sp, Sp, Sp, Sp)-d[GsCsCsTsCsAsGsTsCsTsGsCsTsTsCsGsCsAsCsC] | 5S-9R-5S | 69 |
| 105 | (Sp, Rp, Rp, Rp, Rp, Rp, Rp, Rp, Rp, Rp Rp, Rp, Rp, Rp, Rp, Rp, Rp, Rp, Sp)-d[GsCsCsTsCsAsGsTsCsTsGsCsTsTsCsGsCsAsCsC] | 1S-17R-1S | 70 |
| 106 | (Rp, Sp, Sp, Sp, Sp, Sp, Sp, Sp, Sp, Sp Sp, Sp, Sp, Sp, Sp, Sp, Sp, Sp, Rp)-d[GsCsCsTsCsAsGsTsCsTsGsCsTsTsCsGsCsAsCsC] | 1R-17S-1R | 71 |
| 107 | (Rp, Sp, Rp, Sp, Rp, Sp, Rp, Sp, Rp, Sp Rp, Sp, Rp, Sp, Rp, Sp, Rp, Sp, Rp)-d[GsCsCsTsCsAsGsTsCsTsGsCsTsTsCsGsCsAsCsC] | (R/S)$_9$R | 72 |
| 108 | (Sp, Rp, Sp, Rp, Sp, Rp, Sp, Rp, Sp, Rp Sp, Rp, Sp, Rp, Sp, Rp, Sp, Rp, Sp)-d[GsCsCsTsCsAsGsTsCsTsGsCsTsTsCsGsCsAsCsC] | (S/R)$_9$S | 73 |
| 109 | (Sp, Sp, Sp, Rp, Rp, Rp, Rp, Rp, Rp, Rp Rp, Rp, Rp, Rp, Rp, Rp, Sp, Sp, Sp)d[GsCsCsTsCsAsGsTsCsTsGsCsTsTsCsGsCsAsCsC] | 3S-13R-3S | 74 |
| 110 | (Rp, Rp, Rp, Sp, Sp, Sp, Sp, Sp, Sp, Sp Sp, Sp, Sp, Sp, Sp, Sp, Rp, Rp, Rp)-d[GsCsCsTsCsAsGsTsCsTsGsCsTsTsCsGsCsAsCsC] | 3R-13S-3R | 75 |
| 111 | (Sp, Sp, Sp, Sp, Sp, Sp, Sp, Sp, Sp, Sp Sp, Sp, Sp, Sp, Sp, Sp, Sp, Sp, Rp)-d[GsCsCsTsCsAsGsTsCsTsGsCsTsTsCsGsCsAsCsC] | 18S/R19 | 76 |
| 112 | (Sp, Sp, Sp, Sp, Sp, Sp, Sp, Sp, Rp, Sp Sp, Sp, Sp, Sp, Sp, Sp, Sp, Sp, Sp)-d[GsCsCsTsCsAsGsTsCsTsGsCsTsTsCsGsCsAsCsC] | 18S/R9 | 77 |
| 113 | (Sp, Rp, Sp, Sp, Sp, Sp, Sp, Sp, Sp, Sp Sp, Sp, Sp, Sp, Sp, Sp, Sp, Sp, Sp)-d[GsCsCsTsCsAsGsTsCsTsGsCsTsTsCsGsCsAsCsC] | 18S/R2 | 78 |
| 114 | (Rp, Rp, Sp, Rp, Rp, Sp, Rp, Rp, Sp, Rp Rp, Sp, Rp, Rp, Sp, Rp, Rp, Sp, Rp)-d[GsCsCsTsCsAsGsTsCsTsGsCsTsTsCsGsCsAsCsC] | (RRS)$_6$-R | 79 |
| 115 | (Sp, Rp, Rp, Sp, Rp, Rp, Sp, Rp, Rp, Sp, Rp Rp, Sp, Rp, Rp, Sp, Rp, Rp, Sp)-d[GsCsCsTsCsAsGsTsCsTsGsCsTsTsCsGsCsAsCsC] | S-(RRS)$_6$ | 80 |
| 116 | (Rp, Sp, Rp, Rp, Sp, Rp, Rp, Sp, Rp Rp, Sp, Rp, Rp, Sp, Rp, Rp, Sp, Rp Rp)d[GsCsCsTsCsAsGsTsCsTsGsCsTsTsCsGsCsAsCsC] | RS-(RRS)$_5$-RR | 81 |
| 122 | All-(Rp)-d[Gs1Cs1Cs1Ts1Cs1As1Gs1Ts1Cs1Ts1Gs1Cs1Ts1Ts1Cs1Gs1Cs1As1Cs1C] | All-R | 82 |

TABLE 2-continued

Exemplary Mipomersen related sequences.

| Oligo | Stereochemistry/Sequence | Description | SEQ ID NO: |
|---|---|---|---|
| 123 | (Sp, Rp, Rp, Rp, Rp, Rp, Rp, Rp, Rp, Rp Rp, Rp, Rp, Rp, Rp, Rp, Rp, Rp, Sp)-d[Gs1Cs1Cs1Ts1Cs1As1Gs1Ts1Cs1 Ts1Gs1Cs1Ts1Ts1Cs1Gs1Cs1As1Cs1C] | 1S-17R-1S | 83 |
| 124 | All-(Sp)-d[Gs1Cs1Cs1Ts1Cs1As1Gs1Ts1Cs1Ts1 Gs1Cs1Ts1Ts1Cs1Gs1Cs1As1Cs1C] | All-S | 84 |
| 126 | All-(Rp)-d[Cs2As2Gs2T] | All-R | |
| 127 | All-(Rp)-d[Cs3As3Gs3T] | All-R | |
| 128 | All-(Sp)-d[Cs4As4Gs4T] | All-S | |
| 129 | All-(Sp)-d[Cs5As5Gs5T] | All-S | |
| 130 | All-(Sp)-d[Cs6As6Gs6T] | All-S | |
| 131 | All-(Rp)-d[Gs7Cs7Cs7Ts7Cs7As7Gs7Ts7Cs7Ts7Gs7 Cs7Ts7Ts7Cs7Gs7Cs7As7Cs7C] | All-R | 85 |
| 132 | All-(Sp)-d[Gs7Cs7Cs7Ts7Cs7As7Gs7Ts7Cs7Ts7Gs7 Cs7Ts7Ts7Cs7Gs7Cs7As7Cs7C] | All-S | 86 |
| 133 | (Rp, Rp, Rp, Rp, Rp, Sp, Sp, Sp, Sp, Sp Sp, Sp, Sp, Sp, Rp, Rp, Rp, Rp, Rp)-d[Gs15mCs15mCs1Ts15mCs1As1Gs1Ts15mCs1Ts1 Gs15mCs1Ts1Ts15mCs1Gs15mCs1As15mCs15mC] | 5R-9S-5R | 87 |
| 134 | (Sp, Sp, Sp, Sp, Sp, Rp, Rp, Rp, Rp, Rp Rp, Rp, Rp, Rp, Sp, Sp, Sp, Sp, Sp)-d[Gs15mCs15mCs1Ts15mCs1As1Gs1Ts15mCs1Ts1 Gs15mCs1Ts1Ts15mCs1Gs15mCs1As15mCs15mC] | 5S-9R-5S | 88 |
| 135 | All-(Rp)-d[5mCs1As1Gs1Ts15mCs1Ts1Gs15mCs1Ts1Ts15mCs1 G] | All-R | 89 |
| 136 | All-(Sp)-d[5mCs1As1Gs1Ts15mCs1Ts1Gs15mCs1Ts1Ts15mCs1 G] | All-S | 90 |
| 137 | (Sp, Rp, Rp, Rp, Rp, Rp, Rp, Rp, Rp, Rp, Sp)-d[5mCs1As1Gs1Ts15mCs1Ts1Gs15mCs1Ts1Ts15mCs1 G] | 1S-9R-1S | 91 |
| 138 | (Sp, Sp, Rp, Rp, Rp, Rp, Rp, Rp, Rp, Sp, Sp)-d[5mCs1As1Gs1Ts15mCs1Ts1Gs15mCs1Ts1Ts15mCs1 G] | 2S-7R-2S | 92 |
| 139 | (Rp, Sp, Sp, Sp, Sp, Sp, Sp, Sp, Sp, Sp, Rp)-d[5mCs1As1Gs1Ts15mCs1Ts1Gs15mCs1Ts1Ts15mCs1 G] | 1R-9S-1R | 93 |
| 140 | (Rp, Rp, Sp, Sp, Sp, Sp, Sp, Sp, Sp, Rp, Rp)-d[5mCs1As1Gs1Ts15mCs1Ts1Gs15mCs1Ts1Ts15mCs1 G] | 2R-7S-2R | 94 |
| 141 | (Sp, Sp, Sp, Rp, Rp, Rp, Rp, Rp, Sp, Sp, Sp)-d[5mCs1As1Gs1Ts15mCs1Ts1Gs15mCs1Ts1Ts15mCs1 G] | 3S-5R-3S | 95 |
| 142 | (Rp, Rp, Rp, Sp, Sp, Sp, Sp, Sp, Rp, Rp, Rp)-d[5mCs1As1Gs1Ts15mCs1Ts1Gs15mCs1Ts1Ts15mCs1 G] | 3R-5S-3R | 96 |
| 143 | (Sp, Sp, Rp, Sp, Sp, Rp, Sp, Sp, Rp, Sp, Sp)-d[5mCs1As1Gs1Ts15mCs1Ts1Gs15mCs1Ts1Ts15mCs1 G] | (SSR)$_3$-SS | 97 |
| 144 | (Rp, Rp, Sp, Rp, Rp, Sp, Rp, Rp, Sp, Rp, Rp)-d[5mCs1As1Gs1Ts15mCs1Ts1Gs15mCs1Ts1Ts15mCs1 G] | (RRS)$_3$-RR | 98 |

TABLE 2-continued

Exemplary Mipomersen related sequences.

| Oligo | Stereochemistry/Sequence | Description | SEQ ID NO: |
|---|---|---|---|
| 145 | All-(Rp)-d[5mCs1Ts15mCs1As1Gs1Ts15mCs1Ts1Gs15mCs1Ts1Ts15mCs1Gs15mC] | All-R | 99 |
| 146 | All-(Rp)-d[Gs15mCs1Ts1G] | All-R | |
| 147 | All-(Rp)-d[5mCs1As1Gs1T] | All-R | |
| 148 | All-(Rp)-d[5mCs2As2Gs2Ts25mCs2Ts2Gs25mCs2Ts2Ts25mCs2G] | All-R | 100 |
| 149 | All-(Rp)-d[5mCs4As4Gs4Ts45mCs4Ts4Gs45mCs4Ts4Ts45mCs4G] | All-R | 101 |
| 151 | All-(Sp)-d[Cs1AsGs1T] | All-S | |
| 152 | All-(Sp)-d[Cs1AGs1T] | All-S | |
| 153 | All-(Sp)-d[CAs1GsT] | All-S | |
| 157 | All-(Sp)-d[5mCs1As1Gs1T] | All-S | |
| 158 | (Sp, Sp, Sp, Sp, Sp, Rp, Rp, Rp, Rp, Rp Rp, Rp, Rp, Rp, Sp, Sp, Sp, Sp)-d[GsCsCsTsCsAsGsTsCsTsGsCsTsTsCs1GsCsACsC] | 5S-9R-4S | 102 |
| 159 | (Sp, Sp, Sp, Sp, Sp, Rp, Rp, Rp, Rp, Rp Rp, Rp, Rp, Rp, Sp, Sp, Sp, Sp, Sp)-d[Gs1Cs1Cs1Ts1CsAsGsTsCsTsGsCsTsTsCs1GsCs2As2Cs2C] | 5S-9R-5S | 103 |
| 160 | All-(Rp)-(Gs5mCs5mCsTs5mCs)$_{MOE}$d[AsGsTs5mCsTsGs5mCsTsTs5mCs](Gs5mCsAs5mCs5mC)$_{MOE}$ | All-R | 104 |
| 161 | All-(Sp)-(Gs5mCs5mCsTs5mCs)$_{MOE}$d[AsGsTs5mCsTsGs5mCsTsTs5mCs](Gs5mCsAs5mCs5mC)$_{MOE}$ | All-S | 105 |
| 162 | (Rp, Rp, Rp, Rp, Rp, Sp, Sp, Sp, Sp, Sp Sp, Sp, Sp, Sp, Rp, Rp, Rp, Rp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 5R-9S-5R | 106 |
| 163 | (Sp, Sp, Sp, Sp, Sp, Rp, Rp, Rp, Rp, Rp Rp, Rp, Rp, Rp, Sp, Sp, Sp, Sp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 5S-9R-5S | 107 |
| 164 | (Sp, Rp, Rp, Rp, Rp, Rp, Rp, Rp, Rp, Rp Rp, Rp, Rp, Rp, Rp, Rp, Rp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 1S-17R-1S | 108 |
| 165 | (Rp, Sp, Sp, Sp, Sp, Sp, Sp, Sp, Sp, Sp Sp, Sp, Sp, Sp, Sp, Sp, Sp, Sp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 1R-17S-1R | 109 |
| 166 | (Rp, Sp, Rp, Sp, Rp, Sp, Rp, Sp, Rp, Sp Rp, Sp, Rp, Sp, Rp, Sp, Rp, Sp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | (R/S)$_9$R | 110 |
| 167 | (Sp, Rp, Sp, Rp, Sp, Rp, Sp, Rp, Sp, Rp Sp, Rp, Sp, Rp, Sp, Rp, Sp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | (S/R)$_9$S | 111 |
| 168 | (Sp, Sp, Sp, Rp, Rp, Rp, Rp, Rp, Rp, Rp Rp, Rp, Rp, Rp, Rp, Rp, Sp, Sp, Sp)(Gs5mCs5mCsTs5mCs)$_{MOE}$d[AsGsTs5mCsTsGs5mCsTsTs5mCs](Gs5mCsAs5mCs5mC)$_{MOE}$ | 3S-13R-3S | 112 |

TABLE 2-continued

Exemplary Mipomersen related sequences.

| Oligo | Stereochemistry/Sequence | Description | SEQ ID NO: |
|---|---|---|---|
| 169 | (Rp, Rp, Rp, Sp, Sp, Sp, Sp, Sp, Sp, Sp Sp, Sp, Sp, Sp, Sp, Sp, Rp, Rp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 3R-13S-3R | 113 |
| 170 | (Sp, Sp, Sp, Sp, Sp, Sp, Sp, Sp, Sp Sp, Sp, Sp, Sp, Sp, Sp, Sp, Sp, Sp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 18S/R19 | 114 |
| 171 | (Sp, Sp, Sp, Sp, Sp, Sp, Sp, Rp, Sp Sp, Sp, Sp, Sp, Sp, Sp, Sp, Sp, Sp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 18S/R9 | 115 |
| 172 | (Sp, Rp, Sp, Sp, Sp, Sp, Sp, Sp, Sp Sp, Sp, Sp, Sp, Sp, Sp, Sp, Sp, Sp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 18S/R2 | 116 |
| 173 | (Rp, Rp, Sp, Rp, Rp, Sp, Rp, Rp, Sp, Rp Rp, Sp, Rp, Rp, Sp, Rp, Rp, Sp, Rp)-(Gs5mCs5mCsTs5mCs)MOEd[AsGsTs5mCsTsGs5mCsTsTs5mCs](Gs5mCsAs5mCs5mC)MOE | (RRS)$_6$-R | 117 |
| 174 | (Sp, Rp, Rp, Sp, Rp, Rp, Sp, Rp, Rp, Sp, Rp Rp, Sp, Rp, Rp, Sp, Rp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | S-(RRS)$_6$ | 118 |
| 175 | (Rp, Sp, Rp, Rp, Sp, Rp, Rp, Sp, Rp Rp, Sp, Rp, Rp, Sp, Rp, Rp, Sp, Rp Rp) (Gs5mCs5mCsTs5mCs)$_{MOE}$d[AsGsTs5mCsTsGs5mCsTsTs5mCs](Gs5mCsAs5mCs5mC)$_{MOE}$ | RS-(RRS)$_5$-RR | 119 |
| 176 | (Rp, Sp, Rp, Rp, Sp, Rp, Rp, Sp, Rp Rp, Sp, Rp, Rp, Sp, Rp, Rp, Sp, Rp Rp) (Gs15mCs15mCs1Ts15mCs1)$_{MOE}$d[As1Gs1Ts15mCs1Ts1Gs15mCs1Ts1Ts15mCs1](Gs15mCs1As15mCs15mC)$_{MOE}$ | RS-(RRS)$_5$-RR | 120 |
| 177 | (Rp, Sp, Rp, Rp, Sp, Rp, Rp, Sp, Rp Rp, Sp, Rp, Rp, Sp, Rp, Rp, Sp, Rp Rp) (Gs15mCs15mCs1Ts15mCs1)$_{MOE}$d[AGT5mCTG5mCTT5mC](Gs25mCs2As25mCs25mC)$_{MOE}$ | RS-(RRS)$_5$-RR | 121 |
| 178 | (Sp, Rp, Rp, Sp, Rp, Rp, Sp, Rp, Rp, Sp, Rp Rp, Sp, Rp, Rp, Sp, Rp, Rp, Sp)-(Gs5mCs5mCsTs5mCs)$_{MOE}$d[AsGsTs5mCsTsGs5mCsTsTs5mCs](Gs5mCsAs5mCs5mC)F (F: 2-fluorodeoxyribose) | S-(RRS)$_6$ | 122 |
| 179 | (Rp, Sp, Rp, Rp, Sp, Rp, Rp, Sp, Rp Rp, Sp, Rp, Rp, Sp, Rp, Rp, Sp, Rp Rp) d[Gs8Cs8Cs8Ts8Cs8As8Gs8Ts8Cs8Ts8Gs8Cs8Ts8Ts8Cs8Gs8Cs8As8Cs8C] | RS-(RRS)$_5$-RR | 123 |
| 180 | (Rp, Sp, Rp, Rp, Sp, Rp, Rp, Sp, Rp Rp, Sp, Rp, Rp, Sp, Rp, Rp, Sp, Rp Rp) d[Gs9Cs9Cs9Ts9Cs9As9Gs9Ts9Cs9Ts9Gs9Cs9Ts9Ts9Cs9Gs9Cs9As9Cs9C] | RS-(RRS)$_5$-RR | 124 |
| 181 | (Rp, Sp, Rp, Rp, Sp, Rp, Rp, Sp, Rp Rp, Sp, Rp, Rp, Sp, Rp, Rp, Sp, Rp Rp)d[Gs10Cs10Cs10Ts10Cs10As10Gs10Ts10Cs10Ts10Gs10Cs10Ts10Ts10Cs10Gs10Cs10As10Cs10C] | RS-(RRS)$_5$-RR | 125 |
| 182 | (Rp, Sp, Rp, Rp, Sp, Rp, Rp, Sp, Rp Rp, Sp, Rp, Rp, Sp, Rp, Rp, Sp, Rp Rp)d[Gs11Cs11Cs11Ts11Cs11As11Gs11Ts11Cs11Ts11Gs11Cs11Ts11Ts11Cs11Gs11Cs11As11Cs11C] | RS-(RRS)$_5$-RR | 126 |
| 183 | (Rp, Sp, Rp, Rp, Sp, Rp, Rp, Sp, Rp Rp, Sp, Rp, Rp, Sp, Rp, Rp, Sp, Rp Rp)d[Gs12Cs12Cs12Ts12Cs12As12Gs12Ts12Cs12Ts12Gs12Cs12Ts12Ts12Cs12Gs12Cs12As12Cs12C] | RS-(RRS)$_5$-RR | 127 |

TABLE 2-continued

Exemplary Mipomersen related sequences.

| Oligo | Stereochemistry/Sequence | Description | SEQ ID NO: |
|---|---|---|---|
| 184 | (Rp, Sp, Rp, Rp, Sp, Rp, Rp, Sp, Rp Rp, Sp, Rp, Rp, Sp, Rp, Rp, Sp, Rp Rp)d[Gs13Cs13Cs13Ts13Cs13As13Gs13Ts13Cs13Ts13 Gs13Cs13Ts13Ts13Cs13Gs13Cs13As13Cs13C] | RS-(RRS)5-RR | 128 |
| 185 | (Rp, Sp, Rp, Rp, Sp, Rp, Rp, Sp, Rp Rp, Sp, Rp, Rp, Sp, Rp, Rp, Sp, Rp Rp)d[Gs14Cs14Cs14Ts14Cs14As14Gs14Ts14Cs14Ts14 Gs14Cs14Ts14Ts14Cs14Gs14Cs14As14Cs14C] | RS-(RRS)5-RR | 129 |
| 186 | (Rp, Sp, Rp, Rp, Sp, Rp, Rp, Sp, Rp Rp, Sp, Rp, Rp, Sp, Rp, Rp, Sp, Rp Rp)d[Gs15Cs15Cs15Ts15Cs15As15Gs15Ts15Cs15Ts15 Gs15Cs15Ts15Ts15Cs15Gs15Cs15As15Cs15C] | RS-(RRS)5-RR | 130 |
| 187 | (Rp, Sp, Rp, Rp, Sp, Rp, Rp, Sp, Rp Rp, Sp, Rp, Rp, Sp, Rp, Rp, Sp, Rp Rp)d[GsCsCs1TsCsAs+GsUs2CsUsGsd[CsTs3TsCsGs]C sAs4CsC | RS-(RRS)5-RR | 131 |
| 188 | (Sp, Sp, Sp, Sp, Sp, Rp, Rp, Rp, Rp, Rp Rp, Rp, Rp, Rp, Sp, Sp, Sp, Sp)-d[GsCsCsTsCsAsGsTsCsTsGsCsTsTsCsGsCsACsC] | 5S-9R-4S | 132 |
| 189 | (Sp, Sp, Sp, Sp, Sp, Rp, Rp, Rp, Rp, Rp Rp, Rp, Rp, Rp, Sp, Sp, Sp, Sp)-d[Gs1Cs1Cs1Ts1Cs1As1Gs1Ts1Cs1Ts1Gs1Cs1Ts1Ts1C s1Gs1Cs1ACs1C] | 5S-9R-4S | 133 |
| 190 | (Sp, Sp, Sp, Sp, Sp, Rp, Rp, Rp, Rp, Rp Rp, Rp, Rp, Rp, Sp, sp, sp, Sp)-d[Gs8Cs8Cs8Ts8Cs8As8Gs8Ts8Cs8Ts8Gs8Cs8Ts8Ts8C s8Gs8Cs1ACs8C] | 5S-9R-4S | 134 |
| 191 | (Sp, Sp, Sp, Sp, Sp, Rp, Rp, Rp, Rp, Rp Rp, Rp, Rp, Rp, Sp, sp, sp, Sp)-d[Gs9Cs9Cs9Ts9Cs9As9Gs9Ts9Cs9Ts9Gs9Cs9Ts9Ts9C s9Gs9Cs1ACs9C] | 5S-9R-4S | 135 |
| 192 | (Sp, Sp, Sp, Sp, Sp, Rp, Rp, Rp, Rp, Rp Rp, Rp, Rp, Rp, Sp, Sp, Sp, Sp)-d[Gs10Cs10Cs10Ts10Cs10As10Gs10Ts10Cs10Ts10Gs1 0Cs10Ts10Ts10Cs10Gs10Cs1ACs10C] | 5S-9R-4S | 136 |
| 193 | (Sp, Sp, Sp, Sp, Sp, Rp, Rp, Rp, Rp, Rp Rp, Rp, Rp, Rp, Sp, Sp, Sp, Sp)-d[Gs11Cs11Cs11Ts11Cs11As11Gs11Ts11Cs11Ts11Gs1 1Cs11Ts11Ts11Cs11Gs11Cs1ACs11C] | 5S-9R-4S | 137 |
| 194 | (Sp, Sp, Sp, Sp, Sp, Rp, Rp, Rp, Rp, Rp Rp, Rp, Rp, Rp, Sp, Sp, Sp, Sp)-d[Gs12Cs12Cs12Ts12Cs12As12Gs12Ts12Cs12Ts12Gs1 2Cs12Ts12Ts12Cs12Gs12Cs1ACs12C] | 5S-9R-4S | 138 |
| 195 | (Sp, Sp, Sp, Sp, Sp, Rp, Rp, Rp, Rp, Rp Rp, Rp, Rp, Rp, Sp, Sp, Sp, Sp)-d[Gs13Cs13Cs13Ts13Cs13As13Gs13Ts13Cs13Ts13Gs1 3Cs13Ts13Ts13Cs13Gs13Cs1ACs13C] | 5S-9R-4S | 139 |
| 196 | (Sp, Sp, Sp, Sp, Sp, Rp, Rp, Rp, Rp, Rp Rp, Rp, Rp, Rp, Sp, Sp, Sp, Sp)-d[Gs14Cs14Cs14Ts14Cs14As14Gs14Ts14Cs14Ts14Gs1 4Cs14Ts14Ts14Cs14Gs14Cs1ACs14C] | 5S-9R-4S | 140 |
| 197 | (Sp, Sp, Sp, Sp, Sp, Rp, Rp, Rp, Rp, Rp Rp, Rp, Rp, Rp, Sp, Sp, Sp, Sp)-d[Gs15Cs15Cs15Ts15Cs15As15Gs15Ts15Cs15Ts15Gs1 5Cs15Ts15Ts15Cs15Gs15Cs1ACs15C] | 5S-9R-4S | 141 |
| 198 | (Sp, Sp, Sp, Sp, Sp, Rp, Rp, Rp, Rp, Rp Rp, Rp, Rp, Rp, Sp, Sp, Sp, Sp)-GsCsCsUsCsAsGsUsCsUsGsCsUsUsCsGsCsACsC | 5S-9R-4S | 142 |

TABLE 2-continued

Exemplary Mipomersen related sequences.

| Oligo | Stereochemistry/Sequence | Description | SEQ ID NO: |
|---|---|---|---|
| 199 | (Sp, Sp, Sp, Sp, Sp, Rp, Rp, Rp, Rp, Rp Rp, Rp, Rp, Rp, Sp, Sp, Sp, Sp)-<br>Gs1Cs1Cs1Us1Cs1As1Gs1Us1Cs1Us1Gs1Cs1Us1Us1Cs1Gs1CsACs1C | 5S-9R-4S | 143 |
| 200 | (Sp, Sp, Sp, Sp, Sp, Rp, Rp, Rp, Rp, Rp Rp, Rp, Rp, Rp, Sp, Sp, Sp, Sp)-<br>Gs8Cs8Cs8Us8Cs8As8Gs8Us8Cs8Us8Gs8Cs8Us8Us8Cs8Gs8Cs1ACs8C | 5S-9R-4S | 144 |
| 201 | (Sp, Sp, Sp, Sp, Sp, Rp, Rp, Rp, Rp, Rp Rp, Rp, Rp, Rp, Sp, Sp, Sp, Sp)-<br>Gs9Cs9Cs9Us9Cs9As9Gs9Us9Cs9Us9Gs9Cs9Us9Us9Cs9Gs9Cs1ACs9C | 5S-9R-4S | 145 |
| 202 | (Sp, Sp, Sp, Sp, Sp, Rp, Rp, Rp, Rp, Rp Rp, Rp, Rp, Rp, Sp, Sp, Sp, Sp)-<br>Gs10Cs10Cs10Us10Cs10As10Gs10Us10Cs10Us10Gs10Cs10Us10Us10Cs10Gs10Cs1ACs10C | 5S-9R-4S | 146 |
| 203 | (Sp, Sp, Sp, Sp, Sp, Rp, Rp, Rp, Rp, Rp Rp, Rp, Rp, Rp, Sp, Sp, Sp, Sp)-<br>Gs11Cs11Cs11Us11Cs11As11Gs11Us11Cs11Us11Gs11Cs11Us11Us11Cs11Gs11Cs1ACs11C | 5S-9R-4S | 147 |
| 204 | (Sp, Sp, Sp, Sp, Sp, Rp, Rp, Rp, Rp, Rp Rp, Rp, Rp, Rp, Sp, Sp, Sp, Sp)-<br>Gs12Cs12Cs12Us12Cs12As12Gs12Us12Cs12Us12Gs12Cs12Us12Us12Cs12Gs12Cs1ACs12C | 5S-9R-4S | 148 |
| 205 | (Sp, Sp, Sp, Sp, Sp, Rp, Rp, Rp, Rp, Rp Rp, Rp, Rp, Rp, Sp, Sp, Sp, Sp)-<br>Gs13Cs13Cs13Us13Cs13As13Gs13Us13Cs13Us13Gs13Cs13Us13Us13Cs13Gs13Cs1ACs13C | 5S-9R-4S | 149 |
| 206 | (Sp, Sp, Sp, Sp, Sp, Rp, Rp, Rp, Rp, Rp Rp, Rp, Rp, Rp, Sp, Sp, Sp, Sp)-<br>Gs14Cs14Cs14Us14Cs14As14Gs14Us14Cs14Us14Gs14Cs14Us14Us14Cs14Gs14Cs1ACs14C | 5S-9R-4S | 150 |
| 207 | (Sp, Sp, Sp, Sp, Sp, Rp, Rp, Rp, Rp, Rp Rp, Rp, Rp, Rp, Sp, Sp, Sp, Sp)-<br>Gs15Cs15Cs15Us15Cs15As15Gs15Us15Cs15Us15Gs15Cs15Us15Us15Cs15Gs15Cs1ACs15C | 5S-9R-4S | 151 |

Oligonucleotide Compositions

The present invention provides compositions comprising or consisting of a plurality of provided oligonucleotides (e.g., chirally controlled oligonucleotide compositions). In some embodiments, all such provided oligonucleotides are of the same type, i.e., all have the same base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR[1]" groups in formula I). In many embodiments, however, provided compositions comprise a plurality of oligonucleotides types, typically in pre-determined relative amounts.

In some embodiments, a provided chirally controlled oligonucleotide composition is a chirally pure mipomersen composition. That is to say, in some embodiments, a provided chirally controlled oligonucleotide composition provides mipomersen as a single diastereomer with respect to the configuration of the linkage phosphorus.

In some embodiments, a provided chirally controlled oligonucleotide composition is a chirally uniform mipomersen composition. That is to say, in some embodiments, every linkage phosphorus of mipomersen is in the Rp configuration or every linkage phosphorus of mipomersen is in the Sp configuration.

In some embodiments, a provided chirally controlled oligonucleotide composition comprises a combination of one or more provided oligonucleotide types. One of skill in the chemical and medicinal arts will recognize that the selection and amount of each of the one or more types of provided oligonucleotides in a provided composition will depend on the intended use of that composition. That is to say, one of skill in the relevant arts would design a provided chirally controlled oligonucleotide composition such that the amounts and types of provided oligonucleotides contained therein cause the composition as a whole to have certain desirable characteristics (e.g., biologically desirable, therapeutically desirable, etc.).

In some embodiments, a provided chirally controlled oligonucleotide composition comprises a combination of two or more provided oligonucleotide types. In some embodiments, a provided chirally controlled oligonucleotide composition comprises a combination of three or more provided oligonucleotide types. In some embodiments, a provided chirally controlled oligonucleotide composition comprises a combination of four or more provided oligonucleotide types. In some embodiments, a provided chirally controlled oligonucleotide composition comprises a combination of five or more provided oligonucleotide types. In some embodiments, a provided chirally controlled oligonucleotide composition comprises a combination of six or more provided oligonucleotide types. In some embodiments, a provided chirally controlled oligonucleotide composition comprises a combination of seven or more provided oligonucleotide types. In some embodiments, a provided chirally controlled oligonucleotide composition comprises a combination of eight or more provided oligonucleotide types. In some embodiments, a provided chirally controlled oligonucleotide composition comprises a combination of nine or more provided oligonucleotide types. In some embodiments, a provided chirally controlled oligonucleotide composition comprises a combination of ten or more provided oligonucleotide types. In some embodiments, a provided chirally controlled oligonucleotide composition comprises a combination of fifteen or more provided oligonucleotide types.

In some embodiments, a provided chirally controlled oligonucleotide composition is a combination of an amount of chirally uniform mipomersen of the Rp configuration and an amount of chirally uniform mipomersen of the Sp configuration.

In some embodiments, a provided chirally controlled oligonucleotide composition is a combination of an amount of chirally uniform mipomersen of the Rp configuration, an amount of chirally uniform mipomersen of the Sp configuration, and an amount of one or more chirally pure mipomersen of a desired diastereomeric form.

In some embodiments, a provided oligonucleotide type is selected from those described in PCT/US2013/050407, which is incorporated herein by reference. In some embodiments, a provided chirally controlled oligonucleotide composition comprises oligonucleotides of a oligonucleotide type selected from those described in PCT/US2013/050407.

Methods for Making Chirally Controlled Oligonucleotides and Compositions Thereof The present invention provides methods for making chirally controlled oligonucleotides and chirally controlled compositions comprising one or more specific nucleotide types. As noted above, the phrase "oligonucleotide type," as used herein, defines an oligonucleotide that has a particular base sequence, pattern of backbone linkages, pattern of backbone chiral centers, and pattern of backbone phosphorus modifications (e.g., "—XLR$^1$" groups). Oligonucleotides of a common designated "type" are structurally identical to one another with respect to base sequence, pattern of backbone linkages, pattern of backbone chiral centers, and pattern of backbone phosphorus modifications.

In some embodiments, a provided chirally controlled oligonucleotide in the invention has properties different from those of the corresponding stereorandom oligonucleotide mixture. In some embodiments, a chirally controlled oligonucleotide has lipophilicity different from that of the stereorandom oligonucleotide mixture. In some embodiments, a chirally controlled oligonucleotide has different retention time on HPLC. In some embodiments, a chirally controlled oligonucleotide may have a peak retention time significantly different from that of the corresponding stereorandom oligonucleotide mixture. During oligonucleotide purification using HPLC as generally practiced in the art, certain chirally controlled oligonucleotides will be largely if not totally lost. During oligonucleotide purification using HPLC as generally practiced in the art, certain chirally controlled oligonucleotides will be largely if not totally lost. One of the consequences is that certain diastereomers of a stereorandom oligonucleotide mixture (certain chirally controlled oligonucleotides) are not tested in assays. Another consequence is that from batches to batches, due to the inevitable instrumental and human errors, the supposedly "pure" stereorandom oligonucleotide will have inconsistent compositions in that diastereomers in the composition, and their relative and absolute amounts, are different from batches to batches. The chirally controlled oligonucleotide and chirally controlled oligonucleotide composition provided in this invention overcome such problems, as a chirally controlled oligonucleotide is synthesized in a chirally controlled fashion as a single diastereomer, and a chirally controlled oligonucleotide composition comprise predetermined levels of one or more individual oligonucleotide types.

One of skill in the chemical and synthetic arts will appreciate that synthetic methods of the present invention provide for a degree of control during each step of the synthesis of a provided oligonucleotide such that each nucleotide unit of the oligonucleotide can be designed and/or selected in advance to have a particular stereochemistry at the linkage phosphorus and/or a particular modification at the linkage phosphorus, and/or a particular base, and/or a particular sugar. In some embodiments, a provided oligonucleotide is designed and/or selected in advance to have a particular combination of stereocenters at the linkage phosphorus of the internucleotidic linkage.

In some embodiments, a provided oligonucleotide made using methods of the present invention is designed and/or determined to have a particular combination of linkage phosphorus modifications. In some embodiments, a provided oligonucleotide made using methods of the present invention is designed and/or determined to have a particular combination of bases. In some embodiments, a provided oligonucleotide made using methods of the present invention is designed and/or determined to have a particular combination of sugars. In some embodiments, a provided oligonucleotide made using methods of the present invention is designed and/or determined to have a particular combination of one or more of the above structural characteristics.

Methods of the present invention exhibit a high degree of chiral control. For instance, methods of the present invention facilitate control of the stereochemical configuration of every single linkage phosphorus within a provided oligonucleotide. In some embodiments, methods of the present invention provide an oligonucleotide comprising one or more modified internucleotidic linkages independently having the structure of formula I.

In some embodiments, methods of the present invention provide an oligonucleotide which is a mipomersen unimer. In some embodiments, methods of the present invention provide an oligonucleotide which is a mipomersen unimer of configuration Rp. In some embodiments, methods of the present invention provide an oligonucleotide which is a mipomersen unimer of configuration Sp.

In some embodiments, methods of the present invention provide a chirally controlled oligonucleotide composition, i.e., an oligonucleotide composition that contains predetermined levels of individual oligonucleotide types. In some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises a plurality of oligonucleotide types. Exemplary chirally controlled oligonucleotide compositions made in accordance with the present invention are described herein.

In some embodiments, methods of the present invention provide chirally pure mipomersen compositions with respect to the configuration of the linkage phosphorus. That is to say, in some embodiments, methods of the present invention provide compositions of mipomersen wherein mipomersen exists in the composition in the form of a single diastereomer with respect to the configuration of the linkage phosphorus.

In some embodiments, methods of the present invention provide chirally uniform mipomersen compositions with respect to the configuration of the linkage phosphorus. That is to say, in some embodiments, methods of the present invention provide compositions of mipomersen in which all nucleotide units therein have the same stereochemistry with respect to the configuration of the linkage phosphorus, e.g., all nucleotide units are of the Rp configuration at the linkage phosphorus or all nucleotide units are of the Sp configuration at the linkage phosphorus.

In some embodiments, a provided chirally controlled oligonucleotide is over 50% pure. In some embodiments, a provided chirally controlled oligonucleotide is over about 55% pure. In some embodiments, a provided chirally controlled oligonucleotide is over about 60% pure. In some embodiments, a provided chirally controlled oligonucleotide is over about 65% pure. In some embodiments, a provided chirally controlled oligonucleotide is over about 70% pure. In some embodiments, a provided chirally controlled oligonucleotide is over about 75% pure. In some embodiments, a provided chirally controlled oligonucleotide is over about 80% pure. In some embodiments, a provided chirally controlled oligonucleotide is over about 85% pure. In some embodiments, a provided chirally controlled oligonucleotide is over about 90% pure. In some embodiments, a provided chirally controlled oligonucleotide is over about 91% pure. In some embodiments, a provided chirally controlled oligonucleotide is over about 92% pure. In some embodiments, a provided chirally controlled oligonucleotide is over about 93% pure. In some embodiments, a provided chirally controlled oligonucleotide is over about 94% pure. In some embodiments, a provided chirally controlled oligonucleotide is over about 95% pure. In some embodiments, a provided chirally controlled oligonucleotide is over about 96% pure. In some embodiments, a provided chirally controlled oligonucleotide is over about 97% pure. In some embodiments, a provided chirally controlled oligonucleotide is over about 98% pure. In some embodiments, a provided chirally controlled oligonucleotide is over about 99% pure. In some embodiments, a provided chirally controlled oligonucleotide is over about 99.5% pure. In some embodiments, a provided chirally controlled oligonucleotide is over about 99.6% pure. In some embodiments, a provided chirally controlled oligonucleotide is over about 99.7% pure. In some embodiments, a provided chirally controlled oligonucleotide is over about 99.8% pure. In some embodiments, a provided chirally controlled oligonucleotide is over about 99.9% pure. In some embodiments, a provided chirally controlled oligonucleotide is over at least about 99% pure.

In some embodiments, a chirally controlled oligonucleotide composition is a composition designed to comprise a single oligonucleotide type. In certain embodiments, such compositions are about 50% diastereomerically pure. In some embodiments, such compositions are about 50% diastereomerically pure. In some embodiments, such compositions are about 50% diastereomerically pure. In some embodiments, such compositions are about 55% diastereomerically pure. In some embodiments, such compositions are about 60% diastereomerically pure. In some embodiments, such compositions are about 65% diastereomerically pure. In some embodiments, such compositions are about 70% diastereomerically pure. In some embodiments, such compositions are about 75% diastereomerically pure. In some embodiments, such compositions are about 80% diastereomerically pure. In some embodiments, such compositions are about 85% diastereomerically pure. In some embodiments, such compositions are about 90% diastereomerically pure. In some embodiments, such compositions are about 91% diastereomerically pure. In some embodiments, such compositions are about 92% diastereomerically pure. In some embodiments, such compositions are about 93% diastereomerically pure. In some embodiments, such compositions are about 94% diastereomerically pure. In some embodiments, such compositions are about 95% diastereomerically pure. In some embodiments, such compositions are about 96% diastereomerically pure. In some embodiments, such compositions are about 97% diastereomerically pure. In some embodiments, such compositions are about 98% diastereomerically pure. In some embodiments, such compositions are about 99% diastereomerically pure. In some embodiments, such compositions are about 99.5% diastereomerically pure. In some embodiments, such compositions are about 99.6% diastereomerically pure. In some embodiments, such compositions are about 99.7% diastereomerically pure. In some embodiments, such compositions are about 99.8% diastereomerically pure. In some embodiments, such compositions are about 99.9% diastereomerically pure. In some embodiments, such compositions are at least about 99% diastereomerically pure.

In some embodiments, a chirally controlled oligonucleotide composition is a composition designed to comprise multiple oligonucleotide types. In some embodiments, methods of the present invention allow for the generation of a library of chirally controlled oligonucleotides such that a pre-selected amount of any one or more chirally controlled oligonucleotide types can be mixed with any one or more other chirally controlled oligonucleotide types to create a chirally controlled oligonucleotide composition. In some embodiments, the pre-selected amount of an oligonucleotide type is a composition having any one of the above-described diastereomeric purities.

In some embodiments, the present invention provides methods for making a chirally controlled oligonucleotide comprising steps of:
  (1) coupling;
  (2) capping;
  (3) modifying;
  (4) deblocking; and
  (5) repeating steps (1)-(4) until a desired length is achieved.

When describing the provided methods, the word "cycle" has its ordinary meaning as understood by a person of ordinary skill in the art. In some embodiments, one round of steps (1)-(4) is referred to as a cycle.

In some embodiments, the present invention provides methods for making chirally controlled oligonucleotide compositions, comprising steps of:
  (a) providing an amount of a first chirally controlled oligonucleotide; and
  (b) optionally providing an amount of one or more additional chirally controlled oligonucleotides.

In some embodiments, a first chirally controlled oligonucleotide is an oligonucleotide type, as described herein. In some embodiments, a one or more additional chirally controlled oligonucleotide is a one or more oligonucleotide type, as described herein.

One of skill in the relevant chemical and synthetic arts will recognize the degree of versatility and control over structural variation and stereochemical configuration of a provided oligonucleotide when synthesized using methods of the present invention. For instance, after a first cycle is complete, a subsequent cycle can be performed using a nucleotide unit individually selected for that subsequent cycle which, in some embodiments, comprises a nucleobase and/or a sugar that is different from the first cycle nucleobase and/or sugar. Likewise, the chiral auxiliary used in the coupling step of the subsequent cycle can be different from the chiral auxiliary used in the first cycle, such that the second cycle generates a phosphorus linkage of a different stereochemical configuration. In some embodiments, the stereochemistry of the linkage phosphorus in the newly formed internucleotidic linkage is controlled by using stereochemically pure phosphoramidites. Additionally, the modification reagent used in the modifying step of a subsequent cycle can be different from the modification reagent used in the first or former cycle. The cumulative effect of this iterative assembly approach is such that each component of a provided oligonucleotide can be structurally and configurationally tailored to a high degree. An additional advantage to this approach is that the step of capping minimizes the formation of "n-1" impurities that would otherwise make isolation of a provided oligonucleotide extremely challenging, and especially oligonucleotides of longer lengths.

In some embodiments, an exemplary cycle of the method for making chirally controlled oligonucleotides is illustrated in Scheme I. In Scheme I, ● represents the solid support, and optionally a portion of the growing chirally controlled oligonucleotide attached to the solid support. The chiral auxiliary exemplified has the structure of formula 3-I:

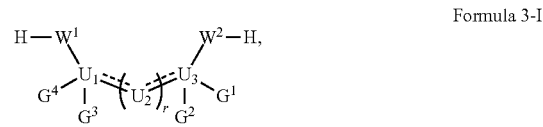

Formula 3-I which is further described below. "Cap" is any chemical moiety introduced to the nitrogen atom by the capping step, and in some embodiments, is an amino protecting group. One of ordinary skill in the art understands that in the first cycle, there may be only one nucleoside attached to the solid support when started, and cycle exit can be performed optionally before deblocking. As understood by a person of skill in the art, $B^{PRO}$ is a protected base used in oligonucleotide synthesis. Each step of the above-depicted cycle of Scheme I is described further below.

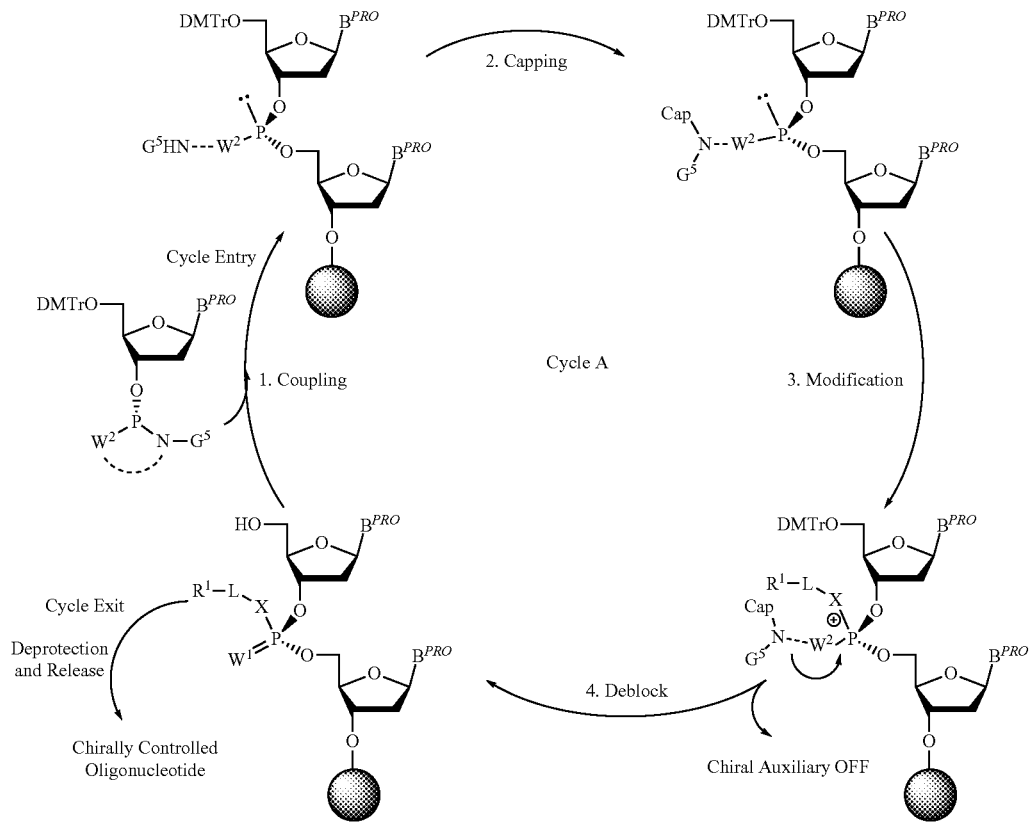

Scheme I. Synthesis of chirally controlled oligonucleotide.

Synthesis on Solid Support

In some embodiments, the synthesis of a provided oligonucleotide is performed on solid phase. In some embodiments, reactive groups present on a solid support are protected. In some embodiments, reactive groups present on a solid support are unprotected. During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. A first nucleoside is bound to a solid support via a linker moiety, i.e. a diradical with covalent bonds between either of a CPG, a polymer or other solid support and a nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. No. 4,725,677 (reissued as Re34,069). In some embodiments, a solid phase is an organic polymer support. In some embodiments, a solid phase is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled polyglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.,* 1983, 105, 661-663; G. R. Gough, M. J. Bruden and P. T. Gilham, *Tetrahedron Lett.,* 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to the attachment of a functional group to the membrane, the use of a linker or spacer group attached to the membrane is also used in some embodiments to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research,* 1991, 19, 1527), TentaGel Support—an aminopolyethyleneglycol derivatized support (see, e.g., Wright, et al., *Tetrahedron Lett.,* 1993, 34, 3373), and Poros-a copolymer of polystyrene/divinylbenzene.

Surface activated polymers have been demonstrated for use in synthesis of natural and modified nucleic acids and proteins on several solid supports mediums. A solid support material can be any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. Other materials can serve as a solid support, depending on the design of the investigator. In consideration of some designs, for example, a coated metal, in particular gold or platinum can be selected (see e.g., US publication No. 20010055761). In one embodiment of oligonucleotide synthesis, for example, a nucleoside is anchored to a solid support which is functionalized with hydroxyl or amino residues. Alternatively, a solid support is derivatized to provide an acid labile trialkoxytrityl group, such as a trimethoxytrityl group (TMT). Without being bound by theory, it is expected that the presence of a trialkoxytrityl protecting group will permit initial detritylation under conditions commonly used on DNA synthesizers. For a faster release of oligonucleotide material in solution with aqueous ammonia, a diglycoate linker is optionally introduced onto the support.

In some embodiments, a provided oligonucleotide alternatively is synthesized from the 5' to 3' direction. In some embodiments, a nucleic acid is attached to a solid support through its 5' end of the growing nucleic acid, thereby presenting its 3' group for reaction, i.e. using 5'-nucleoside phosphoramidites or in enzymatic reaction (e.g. ligation and polymerization using nucleoside 5'-triphosphates). When considering the 5' to 3' synthesis the iterative steps of the present invention remain unchanged (i.e. capping and modification on the chiral phosphorus).

Linking Moiety

A linking moiety or linker is optionally used to connect a solid support to a compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—$CH_2$—$CH_2$—CO—), or an oxalyl linker (—CO—CO—). In some embodiments, the linking moiety and the nucleoside are bonded together through an ester bond. In some embodiments, a linking moiety and a nucleoside are bonded together through an amide bond. In some embodiments, a linking moiety connects a nucleoside to another nucleotide or nucleic acid. Suitable linkers are disclosed in, for example, *Oligonucleotides And Analogues A Practical Approach,* Ekstein, F. Ed., TRL Press, N.Y., 1991, Chapter 1 and Solid-Phase Supports for Oligonucleotide Synthesis, Pon, R. T., *Curr. Prot. Nucleic Acid Chem.,* 2000, 3.1.1-3.1.28.

A linker moiety is used to connect a compound comprising a free nucleophilic moiety to another nucleoside, nucleotide, or nucleic acid. In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attached the oligonucleotide to the solid support (Ravikumar et al., *Org. Process Res. Dev.,* 2008, 12 (3), 399-410). In some embodiments, other universal linkers are used (Pon, R. T., *Curr. Prot. Nucleic Acid Chem.,* 2000, 3.1.1-3.1.28). In some embodiments, various orthogonal linkers (such as disulfide linkers) are used (Pon, R. T., *Curr. Prot. Nucleic Acid Chem.,* 2000, 3.1.1-3.1.28).

General Conditions—Solvents for Synthesis

Syntheses of provided oligonucleotides are generally performed in aprotic organic solvents. In some embodiments, a solvent is a nitrile solvent such as, e.g., acetonitrile. In some embodiments, a solvent is a basic amine solvent such as, e.g., pyridine. In some embodiments, a solvent is an ethereal solvent such as, e.g., tetrahydrofuran. In some embodiments, a solvent is a halogenated hydrocarbon such as, e.g., dichloromethane. In some embodiments, a mixture of solvents is used. In certain embodiments a solvent is a mixture of any one or more of the above-described classes of solvents.

In some embodiments, when an aprotic organic solvent is not basic, a base is present in the reacting step. In some embodiments where a base is present, the base is an amine base such as, e.g., pyridine, quinoline, or N,N-dimethylaniline. Exemplary other amine bases include pyrrolidine, piperidine, N-methyl pyrrolidine, pyridine, quinoline, N,N-dimethylaminopyridine (DMAP), or N,N-dimethylaniline.

In some embodiments, a base is other than an amine base.

In some embodiments, an aprotic organic solvent is anhydrous. In some embodiments, an anhydrous aprotic organic solvent is freshly distilled. In some embodiments, a freshly distilled anhydrous aprotic organic solvent is a basic amine solvent such as, e.g., pyridine. In some embodiments, a freshly distilled anhydrous aprotic organic solvent is an ethereal solvent such as, e.g., tetrahydrofuran. In some embodiments, a freshly distilled anhydrous aprotic organic solvent is a nitrile solvent such as, e.g., acetonitrile.

Activation

An achiral H-phosphonate moiety is treated with the first activating reagent to form the first intermediate. In one embodiment, the first activating reagent is added to the reaction mixture during the condensation step. Use of the first activating reagent is dependent on reaction conditions such as solvents that are used for the reaction. Examples of the first activating reagent are phosgene, trichloromethyl chloroformate, bis(trichloromethyl)carbonate (BTC), oxalyl chloride, Ph$_3$PCl$_2$, (PhO)$_3$PCl$_2$, N,N'-bis(2-oxo-3-oxazolidinyl)phosphinic chloride (BopCl), 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

The example of achiral H-phosphonate moiety is a compound shown in the above Scheme. DBU represents 1,8-diazabicyclo[5.4.0]undec-7-ene. H$^+$DBU may be, for example, ammonium ion, alkylammonium ion, heteroaromatic iminium ion, or heterocyclic iminium ion, any of which is primary, secondary, tertiary or quaternary, or a monovalent metal ion.

Reacting with Chiral Reagent

After the first activation step, the activated achiral H-phosphonate moiety reacts with a chiral reagent, which is represented by formula (Z-I) or (Z-I'), to form a chiral intermediate of formula (Z-Va), (Z-Vb), (Z-Va'), or (Z-Vb').

Stereospecific Condensation Step

A chiral intermediate of Formula Z-Va ((Z-Vb), (Z-Va'), or (Z-Vb')) is treated with the second activating reagent and a nucleoside to form a condensed intermediate. The nucleoside may be on solid support. Examples of the second activating reagent are 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate. A chiral intermediate of Formula Z-Va ((Z-Vb), (Z-Va'), or (Z-Vb')) may be isolated as a monomer. Usually, the chiral intermediate of Z-Va ((Z-Vb), (Z-Va'), or (Z-Vb')) is not isolated and undergoes a reaction in the same pot with a nucleoside or modified nucleoside to provide a chiral phosphite compound, a condensed intermediate. In other embodiments, when the method is performed via solid phase synthesis, the solid support comprising the compound is filtered away from side products, impurities, and/or reagents.

Capping Step

If the final nucleic acid is larger than a dimer, the unreacted —OH moiety is capped with a blocking group and the chiral auxiliary in the compound may also be capped with a blocking group to form a capped condensed intermediate. If the final nucleic acid is a dimer, then the capping step is not necessary.

Modifying Step

The compound is modified by reaction with an electrophile. The capped condensed intermediate may be executed modifying step. In some embodiments, the modifying step is performed using a sulfur electrophile, a selenium electrophile or a boronating agent. Examples of modifying steps are step of oxidation and sulfurization.

In some embodiments of the method, the sulfur electrophile is a compound having one of the following formulas:

$S_8$(Formula Z-B), $Z^{z1}$—S—S—$Z^{z2}$, or $Z^{z1}$—S—$V^z$—$Z^{z2}$;

wherein $Z^{z1}$ and $Z^{z2}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z1}$ and $Z^{z2}$ are taken together to form a 3 to 8 membered alicyclic or heterocyclic ring, which may be substituted or unsubstituted; $V^z$ is $SO_2$, O, or $NR^f$; and $R^f$ is hydrogen, alkyl, alkenyl, alkynyl, or aryl.

In some embodiments of the method, the sulfur electrophile is a compound of following Formulae Z-A, Z-B, Z-C, Z-D, Z-E, or Z-F:

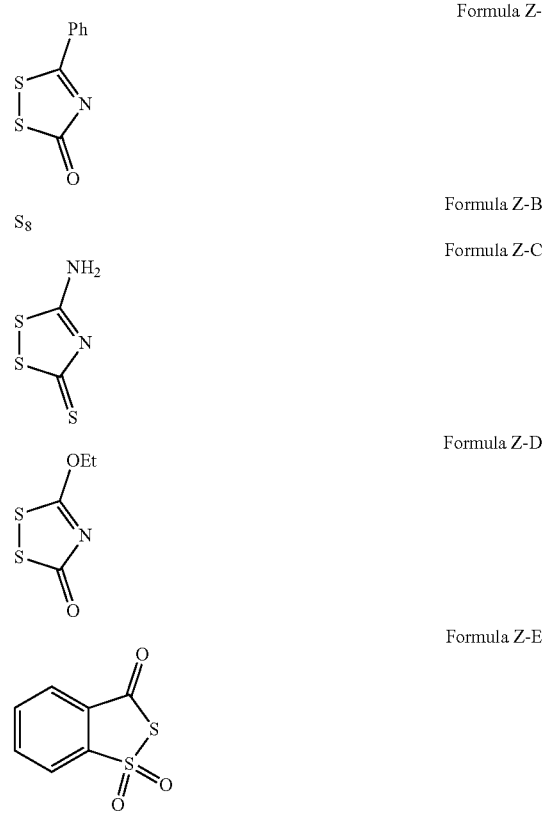

-continued

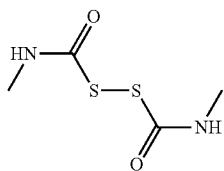
Formula Z-F

In some embodiments, the selenium electrophile is a compound having one of the following formulae:

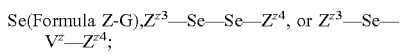

wherein $Z^{z3}$ and $Z^{z4}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z3}$ and $Z^{z4}$ are taken together to form a 3 to 8 membered alicyclic or heterocyclic ring, which may be substituted or unsubstituted; $V^z$ is $SO_2$, S, O, or $NR^f$; and $R^f$ is hydrogen, alkyl, alkenyl, alkynyl, or aryl.

In some embodiments, the selenium electrophile is a compound of Formula Z-G, Z-H, Z-I, Z-J, Z-K, or Z-L.

Se     Formula Z-G

KSeCN     Formula Z-H

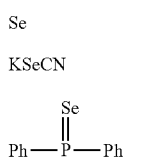
Formula Z-I

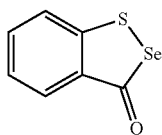
Formula Z-J

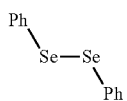
Formula Z-K

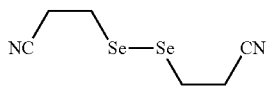
Formula Z-L

In some embodiments, the boronating agent is borane-N,N-diisopropylethylamine ($BH_3$ DIPEA), borane-pyridine ($BH_3$ Py), borane-2-chloropyridine ($BH_3$ CPy), borane-aniline ($BH_3$ An), borane-tetrahydrofuran ($BH_3$ THF), or borane-dimethylsulfide ($BH_3$ $Me_2S$).

In some embodiments of the method, the modifying step is an oxidation step. In some embodiments of the method, the modifying step is an oxidation step using similar conditions as described above in this application. In some embodiments, an oxidation step is as disclosed in, e.g., JP 2010-265304 A and WO2010/064146.

Chain Elongation Cycle and De-Protection Step

The capped condensed intermediate is deblocked to remove the blocking group at the 5'-end of the growing nucleic acid chain to provide a compound. The compound is optionally allowed to re-enter the chain elongation cycle to form a condensed intermediate, a capped condensed intermediate, a modified capped condensed intermediate, and a 5'-deprotected modified capped intermediate. Following at least one round of chain elongation cycle, the 5'-deprotected modified capped intermediate is further deblocked by removal of the chiral auxiliary ligand and other protecting groups for, e.g., nucleobase, modified nucleobase, sugar and modified sugar protecting groups, to provide a nucleic acid. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. In embodiments where a solid support is used, the phosphorus-atom modified nucleic acid is then cleaved from the solid support. In certain embodiments, the nucleic acids is left attached on the solid support for purification purposes and then cleaved from the solid support following purification.

In yet other embodiments, the nucleoside comprising a 5'-OH moiety is an intermediate obtained from another known nucleic acid synthetic method. In yet other embodiments, the nucleoside comprising a 5'-OH moiety is an intermediate obtained from another known nucleic acid synthetic method as described in this application. In yet other embodiments, the nucleoside comprising a 5'-OH moiety is an intermediate obtained from another known nucleic acid synthetic method comprising one or more cycles illustrated in Scheme I. In yet other embodiments, the nucleoside comprising a 5'-OH moiety is an intermediate obtained from another known nucleic acid synthetic method comprising one or more cycles illustrated in Scheme I-b, I-c or I-d.

In some embodiments, the present invention provides oligonucleotide synthesis methods that use stable and commercially available materials as starting materials. In some embodiments, the present invention provides oligonucleotide synthesis methods to produce stereocontrolled phosphorus atom-modified oligonucleotide derivatives using an achiral starting material.

In some embodiments, the method of the present invention does not cause degradations under the de-protection steps. Further the method does not require special capping agents to produce phosphorus atom-modified oligonucleotide derivatives.

Condensing Reagent

Condensing reagents ($C_R$) useful in accordance with methods of the present invention are of any one of the following general formulae:

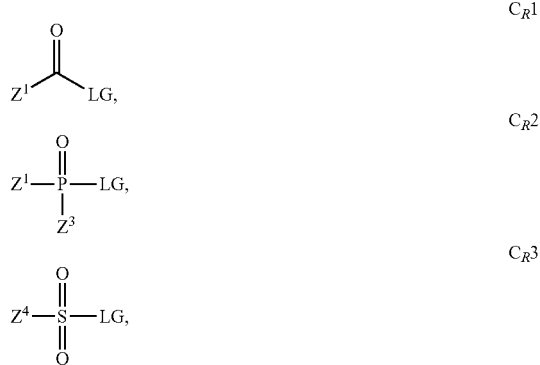

-continued

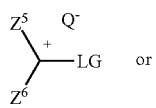

C_R4

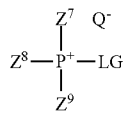

C_R5 wherein $Z^1$, $Z^2$, $Z^3$, $Z^4$, $Z^5$, $Z^6$, $Z^7$, $Z^8$, and $Z^9$ are independently optionally substituted group selected from alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring; $Q^-$ is a counter anion; and LG is a leaving group.

In some embodiments, a counter ion of a condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In some embodiments, a leaving group of a condensing reagent $C_R$ is F, Cl, Br, I, 3-nitro-1,2,4-triazole, imidazole, alkyltriazole, tetrazole, pentafluorobenzene, or 1-hydroxybenzotriazole.

Examples of condensing reagents used in accordance with methods of the present invention include, but are not limited to, pentafluorobenzoyl chloride, carbonyldiimidazole (CDI), 1-mesitylenesulfonyl-3-nitrotriazole (MSNT), 1-ethyl-3-(3'-dimethylaminopropyl)carbodiimide hydrochloride (EDCI-HCl), benzotriazole-1-yloxytris(dimethylamino)phosphonium hexafluorophosphate (PyBOP), N,N'-bis(2-oxo-3-oxazolidinyl)phosphinic chloride (BopCl), 2-(1H-7-azabenzotriazol-1-yl)-1,1,3,3-tetramethyluronium hexafluorophosphate (HATU), and O-benzotriazole-N,N,N',N'-tetramethyluronium hexafluorophosphate (HBTU), DIPCDI; N,N'-bis(2-oxo-3-oxazolidinyl)phosphinic bromide (BopBr), 1,3-dimethyl-2-(3-nitro-1,2,4-triazol-1-yl)-2-pyrrolidin-1-yl-1,3,2-diazaphospholidinium hexafluorophosphate (MNTP), 3-nitro-1,2,4-triazol-1-yl-tris(pyrrolidin-1-yl)phosphonium hexafluorophosphate (PyNTP), bromotripyrrolidinophosphonium hexafluorophosphate (PyBrOP); O-(benzotriazol-1-yl)-N,N,N',N'-tetramethyluronium tetrafluoroborate (TBTU); and tetramethylfluoroformamidinium hexafluorophosphate (TFFH). In certain embodiments, a counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$.

In some embodiments, a condensing reagent is 1-(2,4,6-triisopropylbenzenesulfonyl)-5-(pyridin-2-yl) tetrazolide, pivaloyl chloride, bromotrispyrrolidinophosphonium hexafluorophosphate, N,N'-bis(2-oxo-3-oxazolidinyl) phosphinic chloride (BopCl), or 2-chloro-5,5-dimethyl-2-oxo-1,3,2-dioxaphosphinane. In some embodiment, a condensing reagent is N,N'-bis(2-oxo-3-oxazolidinyl)phosphinic chloride (BopCl). In some embodiments, a condensing reagent is selected from those described in WO/2006/066260).

In some embodiments, a condensing reagent is 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP):

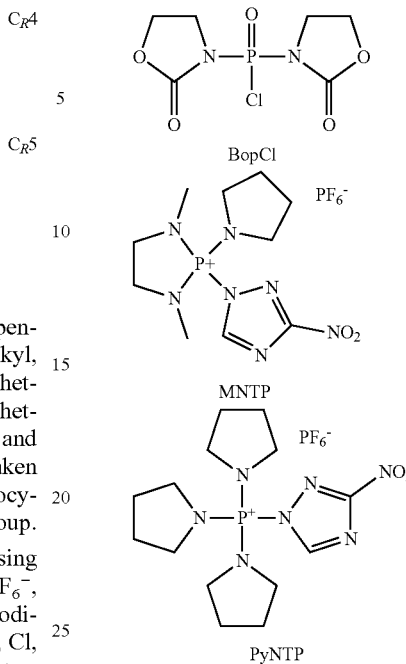

BopCl

MNTP

PyNTP

Selection of Base and Sugar of Nucleoside Coupling Partner

As described herein, nucleoside coupling partners for use in accordance with methods of the present invention can be the same as one another or can be different from one another. In some embodiments, nucleoside coupling partners for use in the synthesis of a provided oligonucleotide are of the same structure and/or stereochemical configuration as one another. In some embodiments, each nucleoside coupling partner for use in the synthesis of a provided oligonucleotide is not of the same structure and/or stereochemical configuration as certain other nucleoside coupling partners of the oligonucleotide. Exemplary nucleobases and sugars for use in accordance with methods of the present invention are described herein. One of skill in the relevant chemical and synthetic arts will recognize that any combination of nucleobases and sugars described herein are contemplated for use in accordance with methods of the present invention.

Coupling Step:

Exemplary coupling procedures and chiral reagents and condensing reagents for use in accordance with the present invention are outlined in, inter alia, Wada I (JP4348077; WO2005/014609; WO2005/092909), Wada II (WO2010/064146), and Wada III (WO2012/039448). Chiral nucleoside coupling partners for use in accordance with the present invention are also referred to herein as "Wada amidites." In some embodiments, a coupling partner has the structure of

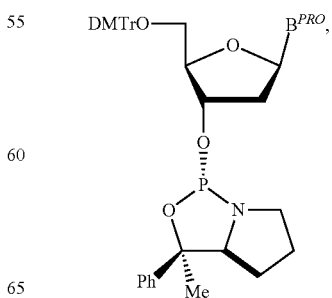

wherein $B^{PRO}$ is a protected nucleobase. In some embodiments, a coupling partner has the structure of
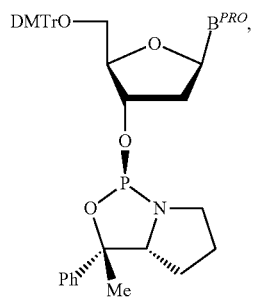
wherein $B^{PRO}$ is a protected nucleobase. Exemplary chiral phosphoramidites as coupling partner are depicted below:
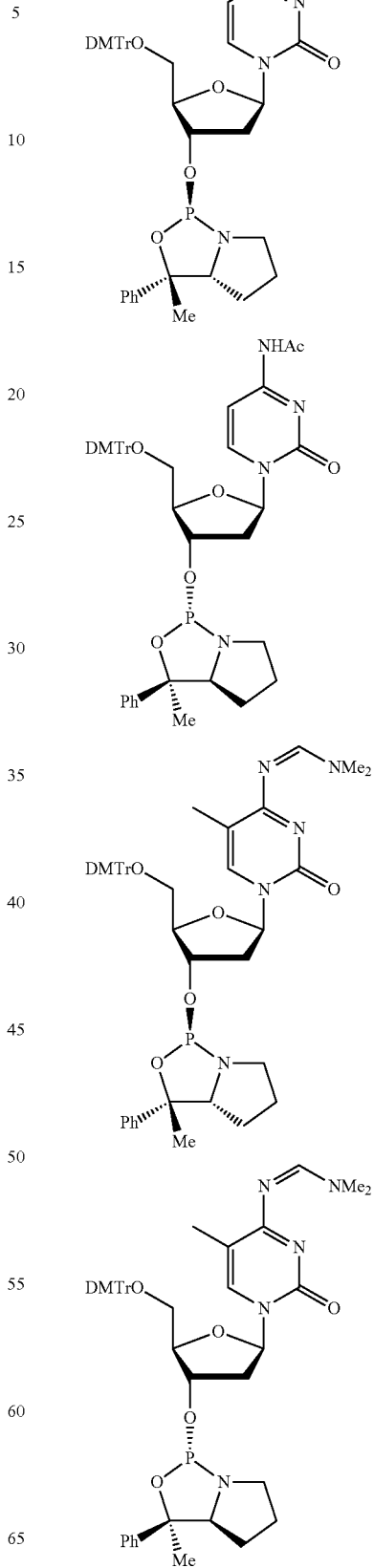

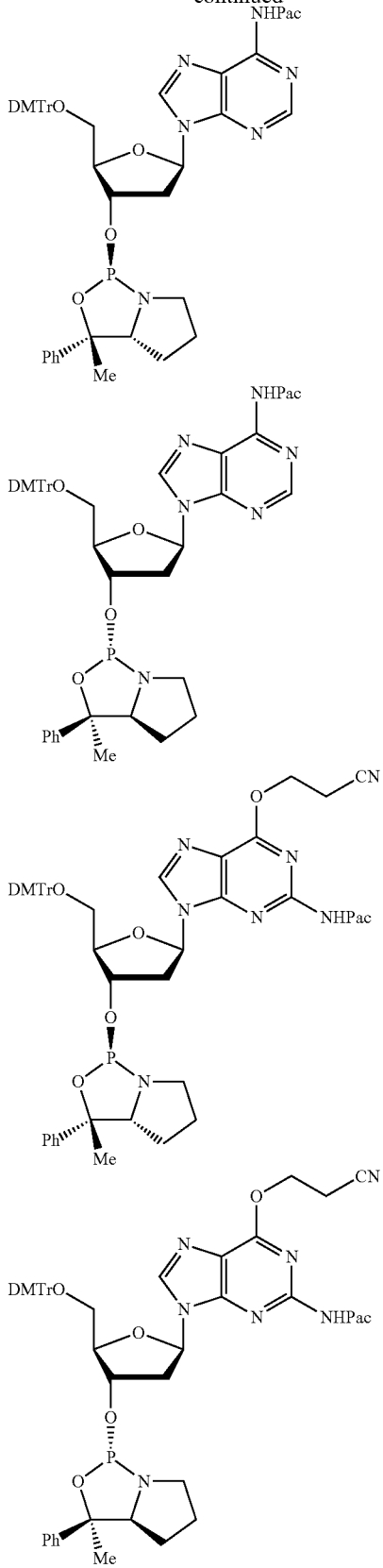

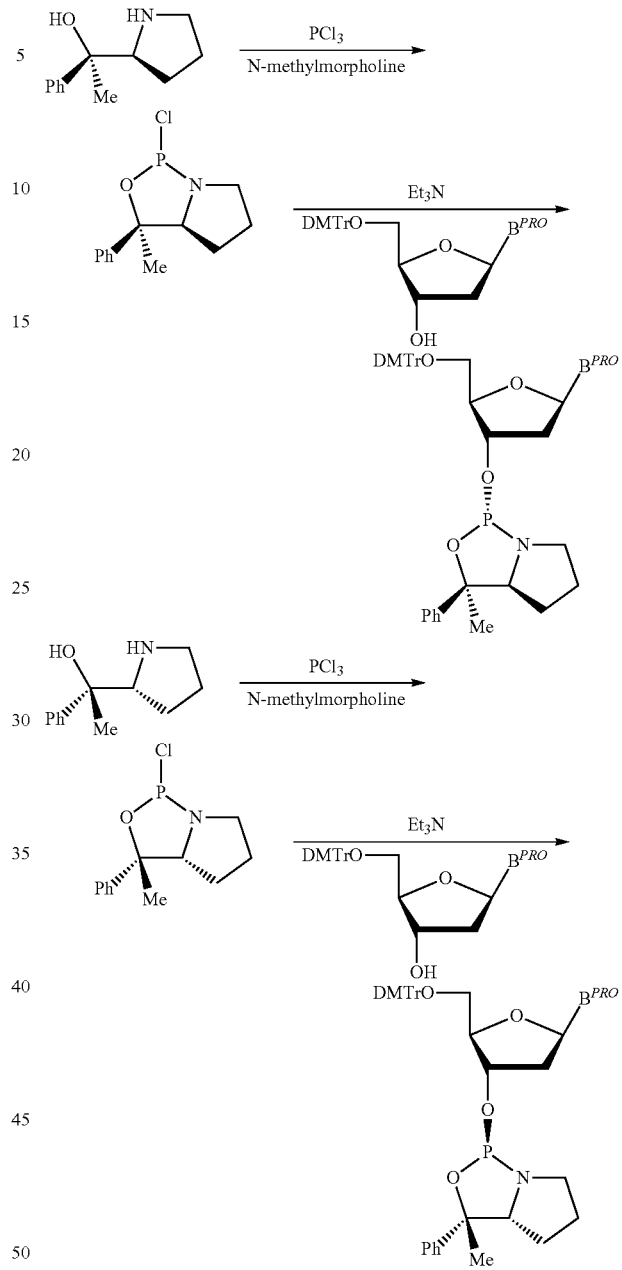

Scheme II, Exemplary synthesis of coupling partner.

One of the methods used for synthesizing the coupling partner is depicted in Scheme II, below.

In some embodiments, the step of coupling comprises reacting a free hydroxyl group of a nucleotide unit of an oligonucleotide with a nucleoside coupling partner under suitable conditions to effect the coupling. In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

Once the appropriate hydroxyl group of the growing oligonucleotide has been deblocked, the support is washed and dried in preparation for delivery of a solution comprising a chiral reagent and a solution comprising an activator. In some embodiments, a chiral reagent and an activator are delivered simultaneously. In some embodiments, co-delivery comprises delivering an amount of a chiral reagent in solution (e.g., a phosphoramidite solution) and an amount of activator in a solution (e.g., a CMPT solution) in a polar aprotic solvent such as a nitrile solvent (e.g., acetonitrile).

In some embodiments, the step of coupling provides a crude product composition in which the chiral phosphite product is present in a diastereomeric excess of >95%. In some embodiments, the chiral phosphite product is present in a diastereomeric excess of >96%. In some embodiments, the chiral phosphite product is present in a diastereomeric excess of >97%. In some embodiments, the chiral phosphite product is present in a diastereomeric excess of >98%. In some embodiments, the chiral phosphite product is present in a diastereomeric excess of >99%.

Capping Step:

Provided methods for making chirally controlled oligonucleotides comprise a step of capping. In some embodiments, a step of capping is a single step. In some embodiments, a step of capping is two steps. In some embodiments, a step of capping is more than two steps.

In some embodiments, a step of capping comprises steps of capping the free amine of the chiral auxiliary and capping any residual unreacted 5' hydroxyl groups. In some embodiments, the free amine of the chiral auxiliary and the unreacted 5' hydroxyl groups are capped with the same capping group. In some embodiments, the free amine of the chiral auxiliary and the unreacted 5' hydroxyl groups are capped with different capping groups. In certain embodiments, capping with different capping groups allows for selective removal of one capping group over the other during synthesis of the oligonucleotide. In some embodiments, the capping of both groups occurs simultaneously. In some embodiments, the capping of both groups occurs iteratively.

In certain embodiments, capping occurs iteratively and comprises a first step of capping the free amine followed by a second step of capping the free 5' hydroxyl group, wherein both the free amine and the 5' hydroxyl group are capped with the same capping group. For instance, in some embodiments, the free amine of the chiral auxiliary is capped using an anhydride (e.g., phenoxyacetic anhydride, i.e., Pac₂O) prior to capping of the 5' hydroxyl group with the same anhydride. In certain embodiments, the capping of the 5' hydroxyl group with the same anhydride occurs under different conditions (e.g., in the presence of one or more additional reagents). In some embodiments, capping of the 5' hydroxyl group occurs in the presence of an amine base in an ethereal solvent (e.g., NMI (N-methylimidazole) in THF). The phrase "capping group" is used interchangeably herein with the phrases "protecting group" and "blocking group".

In some embodiments, an amine capping group is characterized in that it effectively caps the amine such that it prevents rearrangement and/or decomposition of the intermediate phosphite species. In some embodiments, a capping group is selected for its ability to protect the amine of the chiral auxiliary in order to prevent intramolecular cleavage of the internucleotide linkage phosphorus.

In some embodiments, a 5' hydroxyl group capping group is characterized in that it effectively caps the hydroxyl group such that it prevents the occurrence of "shortmers," e.g., "n-m" (m and n are integers and m<n; n is the number of bases in the targeted oligonucleotide) impurities that occur from the reaction of an oligonucleotide chain that fails to react in a first cycle but then reacts in one or more subsequent cycles. The presence of such shortmers, especially "n−1", has a deleterious effect upon the purity of the crude oligonucleotide and makes final purification of the oligonucleotide tedious and generally low-yielding.

In some embodiments, a particular cap is selected based on its tendency to facilitate a particular type of reaction under particular conditions. For instance, in some embodiments, a capping group is selected for its ability to facilitate an E1 elimination reaction, which reaction cleaves the cap and/or auxiliary from the growing oligonucleotide. In some embodiments, a capping group is selected for its ability to facilitate an E2 elimination reaction, which reaction cleaves the cap and/or auxiliary from the growing oligonucleotide. In some embodiments, a capping group is selected for its ability to facilitate a β-elimination reaction, which reaction cleaves the cap and/or auxiliary from the growing oligonucleotide.

Modifying Step:

As used herein, the phrase "modifying step", "modification step" and "P-modification step" are used interchangeably and refer generally to any one or more steps used to install a modified internucleotidic linkage. In some embodiments, the modified internucleotidic linkage having the structure of formula I. A P-modification step of the present invention occurs during assembly of a provided oligonucleotide rather than after assembly of a provided oligonucleotide is complete. Thus, each nucleotide unit of a provided oligonucleotide can be individually modified at the linkage phosphorus during the cycle within which the nucleotide unit is installed.

In some embodiments, a suitable P-modification reagent is a sulfur electrophile, selenium electrophile, oxygen electrophile, boronating reagent, or an azide reagent.

For instance, in some embodiments, a selenium reagent is elemental selenium, a selenium salt, or a substituted diselenide. In some embodiments, an oxygen electrophile is elemental oxygen, peroxide, or a substituted peroxide. In some embodiments, a boronating reagent is a borane-amine (e.g., N,N-diisopropylethylamine (BH₃·DIPEA), borane-pyridine (BH₃·Py), borane-2-chloropyridine (BH₃·CPy), borane-aniline (BH₃·An)), a borane-ether reagent (e.g., borane-tetrahydrofuran (BH₃·THF)), a borane-dialkylsulfide reagent (e.g., BH₃·Me₂S), aniline-cyanoborane, or a triphenylphosphine-carboalkoxyborane. In some embodiments, an azide reagent is comprises an azide group capable of undergoing subsequent reduction to provide an amine group.

In some embodiments, a P-modification reagent is a sulfurization reagent as described herein. In some embodiments, a step of modifying comprises sulfurization of phosphorus to provide a phosphorothioate linkage or phosphorothioate triester linkage. In some embodiments, a step of modifying provides an oligonucleotide having an internucleotidic linkage of formula I.

In some embodiments, the present invention provides sulfurizing reagents, and methods of making, and use of the same.

In some embodiments, such sulfurizing reagents are thiosulfonate reagents. In some embodiments, a thiosulfonate reagent has a structure of formula S-I:

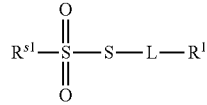

S-I wherein:

$R^{s1}$ is R; and each of R, L and $R^1$ is independently as defined and described above and herein.

In some embodiments, the sulfurizing reagent is a bis(thiosulfonate) reagent. In some embodiments, the bis(thiosulfonate) reagent has the structure of formula S-II.

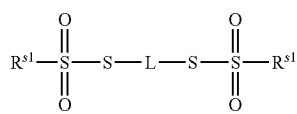

S-II wherein each of $R^{s1}$ and L is independently as defined and described above and herein.

As defined generally above, $R^{s1}$ is R, wherein R is as defined and described above and herein. In some embodiments, $R^{s1}$ is optionally substituted aliphatic, aryl, heterocyclyl or heteroaryl. In some embodiments, $R^{s1}$ is optionally substituted alkyl. In some embodiments, $R^{s1}$ is optionally substituted alkyl. In some embodiments, $R^{s1}$ is methyl. In some embodiments, $R^{s1}$ is cyanomethyl. In some embodiments, $R^{s1}$ is nitromethyl. In some embodiments, $R^{s1}$ is optionally substituted aryl. In some embodiments, $R^{s1}$ is optionally substituted phenyl. In some embodiments, $R^{s1}$ is phenyl. In some embodiments, $R^{s1}$ is p-nitrophenyl. In some embodiments, $R^{s1}$ is p-methylphenyl. In some embodiments, $R^{s1}$ is p-chlorophenyl. In some embodiments, $R^{s1}$ is o-chlorophenyl. In some embodiments, $R^{s1}$ is 2,4,6-trichlorophenyl. In some embodiments, $R^{s1}$ is pentafluorophenyl. In some embodiments, $R^{s1}$ is optionally substituted heterocyclyl. In some embodiments, $R^{s1}$ is optionally substituted heteroaryl.

In some embodiments, $R^{s1}$—S(O)$_2$S— is

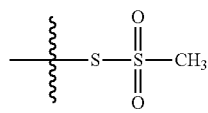 [SMILES: *SS(C)(=O)=O]

(MTS). In some embodiments, $R^{s1}$—S(O)$_2$S— is

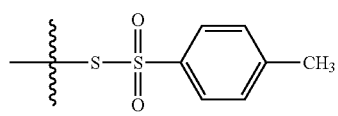

(TTS). In some embodiments, $R^{s1}$—S(O)$_2$S— is

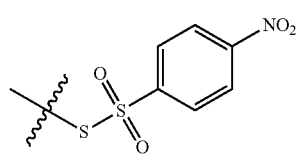 [SMILES: *SS(=O)(=O)c1ccc([N+](=O)[O-])cc1]

(NO$_2$PheTS). In some embodiments, $R^{s1}$—S(O)$_2$S— is

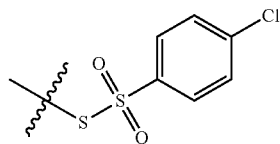 [SMILES: *SS(=O)(=O)c1ccc(Cl)cc1]

(p-ClPheTS). In some embodiments, $R^{s1}$—S(O)$_2$S— is

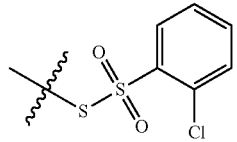 [SMILES: *SS(=O)(=O)c1ccccc1Cl]

(o-ClPheTS). In some embodiments, $R^{s1}$—S(O)$_2$S— is

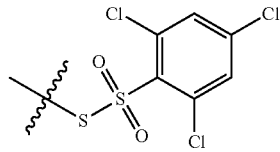 [SMILES: *SS(=O)(=O)c1c(Cl)cc(Cl)cc1Cl]

(2,4,6-TriClPheTS). In some embodiments, $R^{s1}$—S(O)$_2$S— is

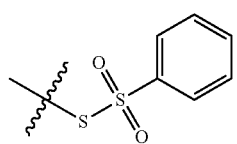 [SMILES: *SS(=O)(=O)c1ccccc1]

(PheTS). In some embodiments, $R^{s1}$—S(O)$_2$S— is

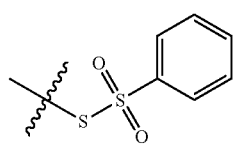 [SMILES: *SS(=O)(=O)c1ccccc1]

(PFPheTS). In some embodiments, $R^{s1}$—S(O)$_2$S— is

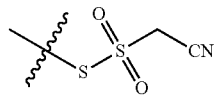 [SMILES: *SS(=O)(=O)CC#N]

(a-CNMTS). In some embodiments, $R^{s1}$—S(O)$_2$S— is

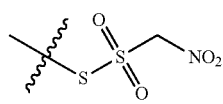 [SMILES: *SS(=O)(=O)C[N+](=O)[O-]]

(a-NO$_2$MTS). In some embodiments, R$^{s1}$—S(O)$_2$S— is

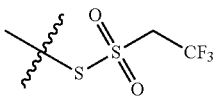 [SMILES: *SS(=O)(=O)CC(F)(F)F]

(a-CF$_3$MTS). In some embodiments, R$^{s1}$—S(O)$_2$S— is

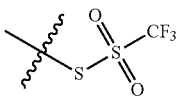

(a-CF$_3$TS). In some embodiments, R$^{s1}$—S(O)$_2$S— is

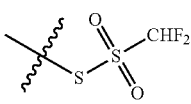

(a-CHF$_2$TS). In some embodiments, R$^{s1}$—S(O)$_2$S— is

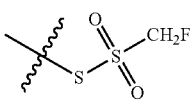

(a-CH$_2$FTS).

In some embodiments, the sulfurizing reagent has the structure of S-I or S-II, wherein L is —S—R$^{L3}$— or —S—C(O)—R$^{L3}$—. In some embodiments, L is —S—R$^{L3}$— or —S—C(O)—R$^{L3}$—, wherein R$^{L3}$ is an optionally substituted C$_1$-C$_6$ alkylene. In some embodiments, L is —S—R$^{L3}$— or —S—C(O)—R$^{L3}$—, wherein R$^{L3}$ is an optionally substituted C$_1$-C$_6$ alkenylene. In some embodiments, L is —S—R$^{L3}$— or —S—C(O)—R$^{L3}$—, wherein R$^{L3}$ is an optionally substituted C$_1$-C$_6$ alkylene wherein one or more methylene units are optionally and independently replaced by an optionally substituted C$_1$-C$_6$ alkenylene, arylene, or heteroarylene. In some embodiments, R$^{L3}$ is an optionally substituted —S—(C$_1$-C$_6$ alkenylene)-, —S—(C$_1$-C$_6$ alkylene)-, —S—(C$_1$-C$_6$ alkylene)-arylene-(C$_1$-C$_6$ alkylene)-, —S—CO-arylene-(C$_1$-C$_6$ alkylene)-, or —S—CO—(C$_1$-C$_6$ alkylene)-arylene-(C$_1$-C$_6$ alkylene)-. In some embodiments, the sulfurizing reagent has the structure of S-I or S-II, wherein L is —S—R$^{L3}$— or —S—C(O)—R$^{L3}$—, and the sulfur atom is connected to R$^1$.

In some embodiments, the sulfurizing reagent has the structure of S-I or S-II, wherein L is alkylene, alkenylene, arylene or heteroarylene.

In some embodiments, the sulfurizing reagent has the structure of S-I or S-II, wherein L is

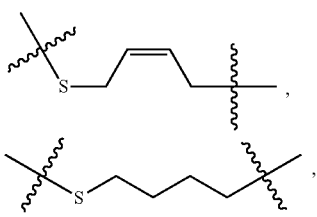

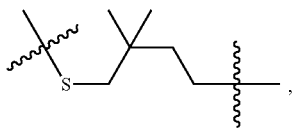

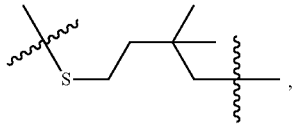

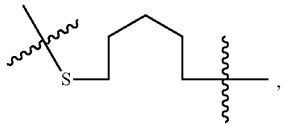

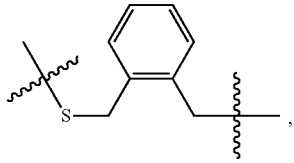

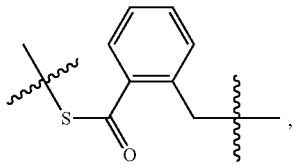

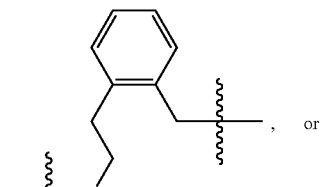

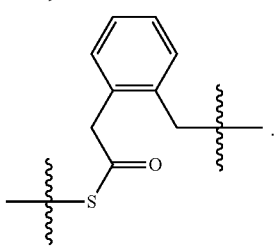

, or

In some embodiments, L is

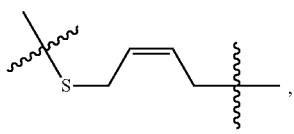

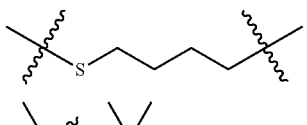

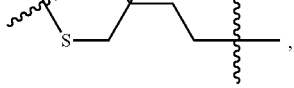

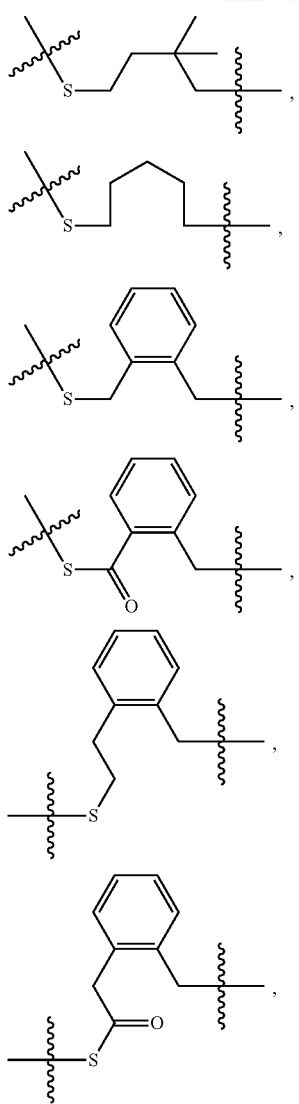
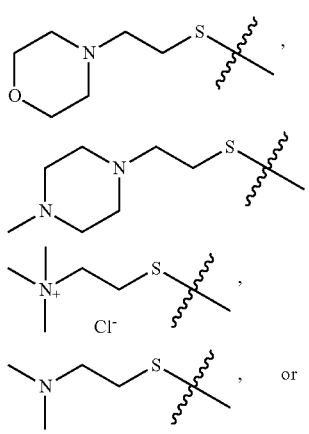
wherein the sulfur atom is connected to $R^1$.
In some embodiments, the sulfurizing reagent has the structure of S-I or S-II, wherein $R^1$ is
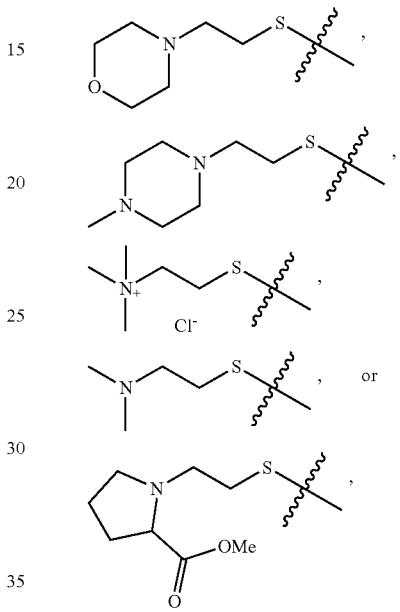
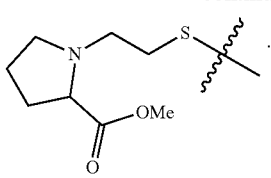
In some embodiments, $R^1$ is
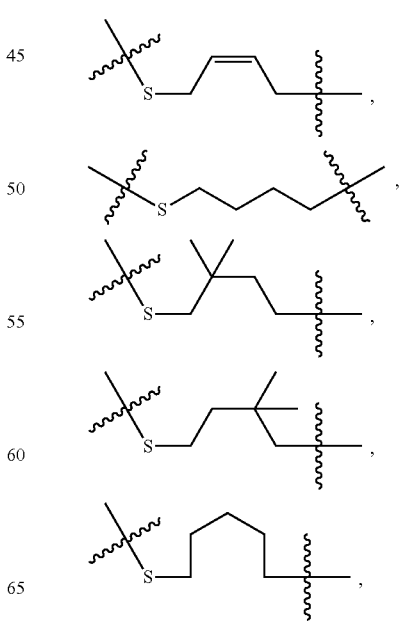
wherein the sulfur atom is connected to L.
In some embodiments, the sulfurizing reagent has the structure of S-I or S-II, wherein L is -continued

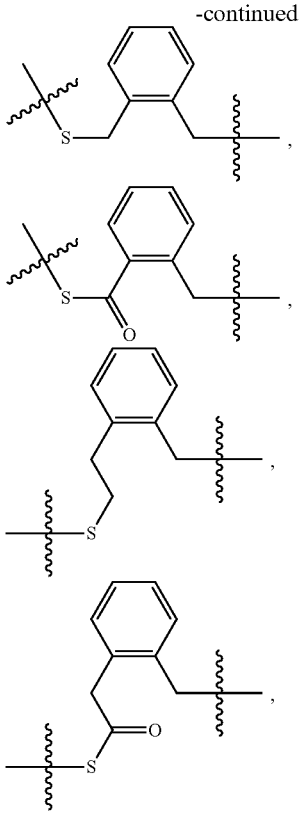

wherein the sulfur atom is connected to $R^1$; and $R^1$ is

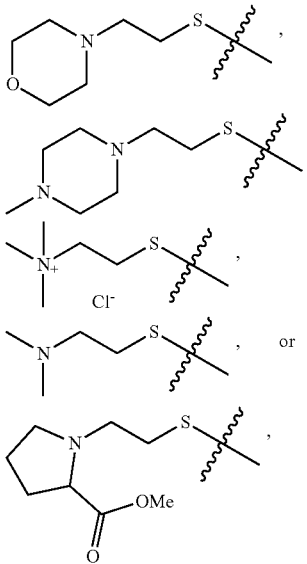

wherein the sulfur atom is connected to L.

In some embodiments, the sulfurizing reagent has the structure of S-I or S-II, wherein $R^1$ is —S—$R^{L2}$, wherein $R^{L2}$ is as defined and described above and herein. In some embodiments, $R^{L2}$ is an optionally substituted group selected from —S—($C_1$-$C_6$ alkylene)-heterocyclyl, —S—($C_1$-$C_6$ alkenylene)-heterocyclyl, —S—($C_1$-$C_6$ alkylene)-N(R')$_2$, —S—($C_1$-$C_6$ alkylene)-N(R')$_3$, wherein each R' is as defined above and described herein.

In some embodiments, -L-$R^1$ is —$R^{L3}$S—S—$R^{L2}$, wherein each variable is independently as defined above and described herein. In some embodiments, -L-$R^1$ is —$R^{L3}$—C(O)—S—S—$R^{L2}$, wherein each variable is independently as defined above and described herein.

Exemplary bis(thiosulfonate) reagents of formula S-II are depicted below:

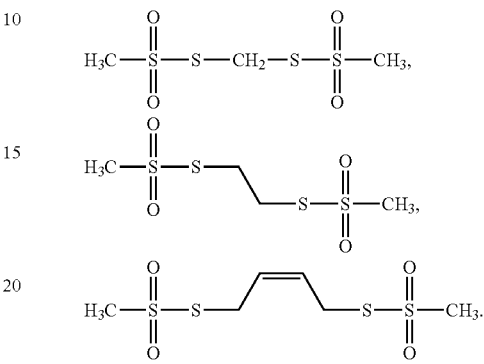

In some embodiments, the sulfurization reagent is a compound having one of the following formulae:

$$S_8, R^{s2}—S—S—R^{s3}, \text{ or } R^{s2}—S—X^s—R^{s3},$$

wherein:
each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or
$R^{s2}$ and $R^{s3}$ are taken together with the atoms to which they are bound to form an optionally substituted heterocyclic or heteroaryl ring;
$X^s$ is —S(O)$_2$—, —O—, or —N(R')—; and
R' is as defined and described above and herein.

In some embodiments, the sulfurization reagent is $S_8$,

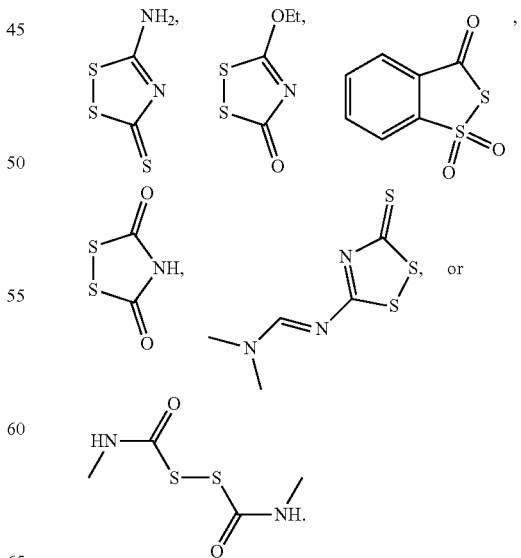

In some embodiments, the sulfurization reagent is S$_8$,
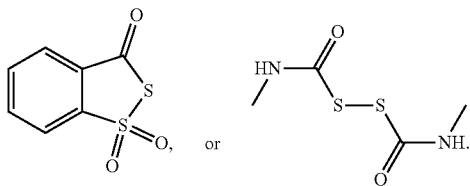
In some embodiments, the sulfurization reagent is
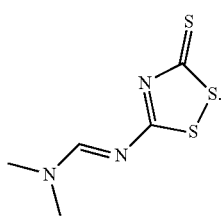
Exemplary sulfuring reagents are depicted in Table 5 below.
TABLE 5
Exemplary sulfurization reagents.
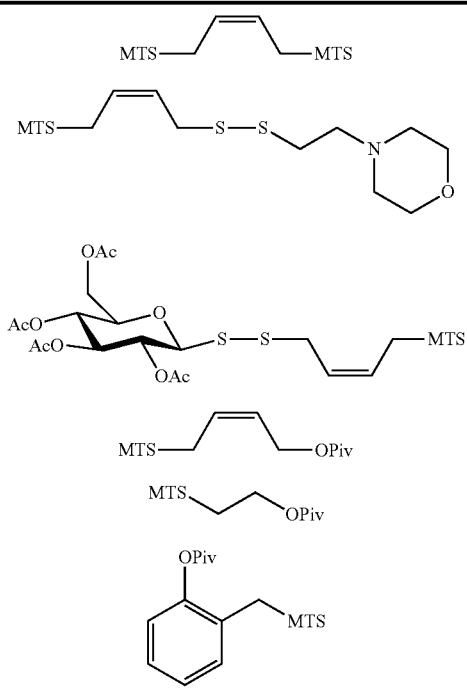
TABLE 5-continued
Exemplary sulfurization reagents.
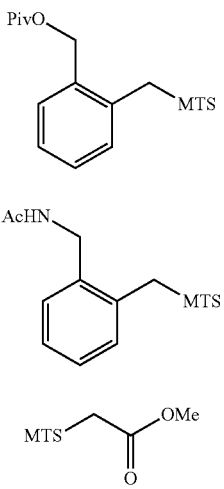
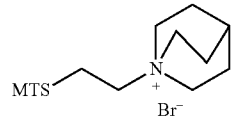
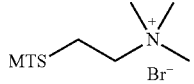
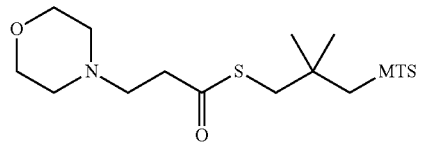
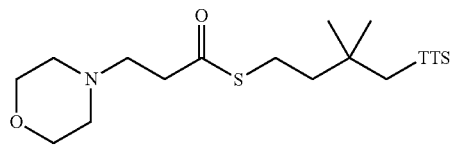
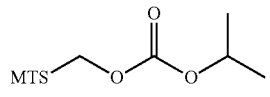
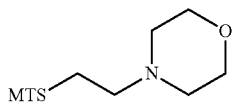
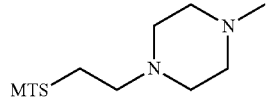

TABLE 5-continued
Exemplary sulfurization reagents.
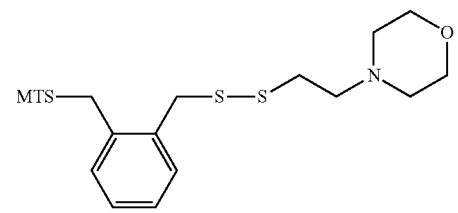
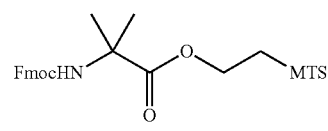
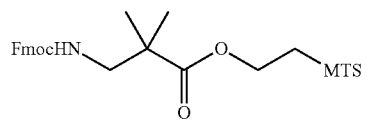
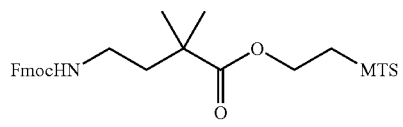
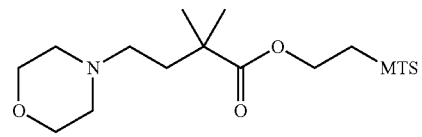
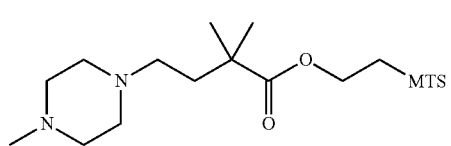
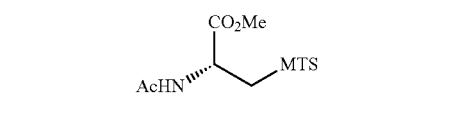
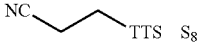
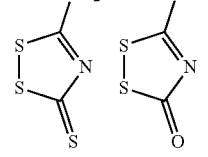
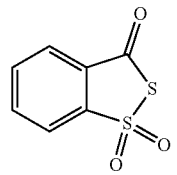 [SMILES: O=C1SS(=O)(=O)c2ccccc21]
TABLE 5-continued
Exemplary sulfurization reagents.
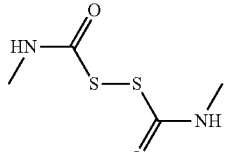
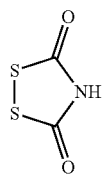
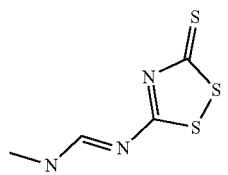
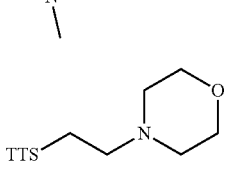
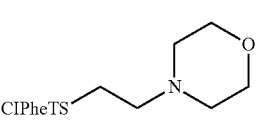
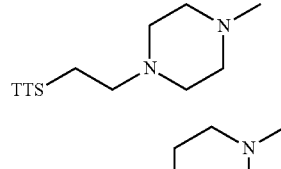
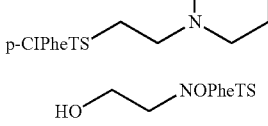
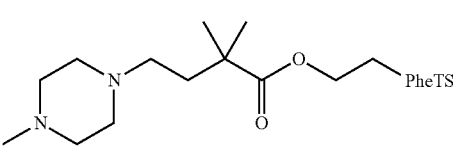
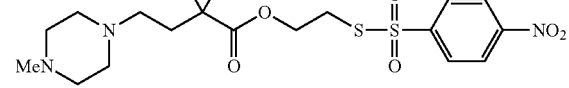
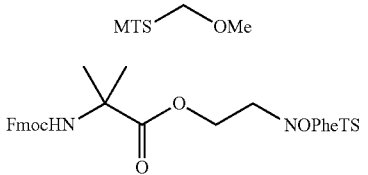

TABLE 5-continued

Exemplary sulfurization reagents.

TTS-CH₂-C(Me)₂-OMe

FmocHN-C(Me)₂-C(=O)-O-CH₂CH₂-NOPheTS

TTS-CH₂-C(Me)₂-N(Me)-

FmocHN-CH₂-C(Me)₂-C(=O)-O-CH₂CH₂-NOPheTS

MTS-CH₂-C(Me)₂-CN

Morpholine-CH₂CH₂-C(Me)₂-C(=O)-O-CH₂CH₂-NOPheTS

In some embodiments, a provided sulfurization reagent is used to modify an H-phosphonate. For instance, in some embodiments, an H-phosphonate oligonucleotide is synthesized using, e.g., a method of Wada I or Wada II, and is modified using a sulfurization reagent of formula S-I or S-II:

$$R^{s1}-\underset{\underset{O}{\|}}{\overset{\overset{O}{\|}}{S}}-S-L-R^1 \quad \text{S-I}$$

$$R^{s1}-\underset{\underset{O}{\|}}{\overset{\overset{O}{\|}}{S}}-S-L-S-\underset{\underset{O}{\|}}{\overset{\overset{O}{\|}}{S}}-R^{s1}, \quad \text{S-II}$$

wherein each of $R^{s1}$, L, and $R^1$ are as described and defined above and herein.

In some embodiments, the present invention provides a process for synthesizing a phosphorothioate triester, comprising steps of:

i) reacting an H-phosphonate of structure:

$$-Y-\underset{\underset{H}{|}}{\overset{\overset{W}{|}}{P^*}}-Z-$$

wherein each of W, Y, and Z are as described and defined above and herein, with a silylating reagent to provide a silyloxyphosphonate; and ii) reacting the silyloxyphosphonate with a sulfurization reagent of structure S-I or S-II:

$$R^{s1}-\underset{\underset{O}{\|}}{\overset{\overset{O}{\|}}{S}}-S-L-R^1 \quad \text{S-I}$$

$$R^{s1}-\underset{\underset{O}{\|}}{\overset{\overset{O}{\|}}{S}}-S-L-S-\underset{\underset{O}{\|}}{\overset{\overset{O}{\|}}{S}}-R^{s1}, \quad \text{S-II}$$

to provide a phosphorothiotriester.

In some embodiments, a selenium electrophile is used instead of a sulfurizing reagent to introduce modification to the internucleotidic linkage. In some embodiments, a selenium electrophile is a compound having one of the following formulae:

$$Se, R^{s2}-Se-Se-R^{s3}, \text{ or } R^{s2}-Se-X-R^{s3},$$

wherein:
each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or
$R^{s2}$ and $R^{s3}$ are taken together with the atoms to which they are bound to form an optionally substituted heterocyclic or heteroaryl ring;
$X^s$ is $-S(O)_2-$, $-O-$, or $-N(R')-$; and
R' is as defined and described above and herein.

In other embodiments, the selenium electrophile is a compound of Se, KSeCN,

Ph-P(=Se)(Ph)-Ph, benzisoselenazolone structure, Ph-Se-Se-Ph, or NC-CH₂CH₂-Se-Se-CH₂CH₂-CN.

In some embodiments, the selenium electrophile is Se or

NC-CH₂CH₂-Se-Se-CH₂CH₂-CN.

In some embodiments, a sulfurization reagent for use in accordance with the present invention is characterized in that the moiety transferred to phosphorus during sulfurization is a substituted sulfur (e.g., —SR) as opposed to a single sulfur atom (e.g., —S⁻ or =S).

In some embodiments, a sulfurization reagent for use in accordance with the present invention is characterized in that the activity of the reagent is tunable by modifying the reagent with a certain electron withdrawing or donating group.

In some embodiments, a sulfurization reagent for use in accordance with the present invention is characterized in that it is crystalline. In some embodiments, a sulfurization reagent for use in accordance with the present invention is characterized in that it has a high degree of crystallinity. In certain embodiments, a sulfurization reagent for use in accordance with the present invention is characterized by ease of purification of the reagent via, e.g., recrystallization. In certain embodiments, a sulfurization reagent for use in accordance with the present invention is characterized in that it is substantially free from sulfur-containing impurities. In some embodiments, sulfurization reagents which are substantially free from sulfur-containing impurities show increased efficiency.

In some embodiments, the provided chirally controlled oligonucleotide comprises one or more phosphate diester linkages. To synthesize such chirally controlled oligonucleotides, one or more modifying steps are optionally replaced with an oxidation step to install the corresponding phosphate diester linkages. In some embodiments, the oxidation step is performed in a fashion similar to ordinary oligonucleotide synthesis. In some embodiments, an oxidation step comprises the use of $I_2$. In some embodiments, an oxidation step comprises the use of $I_2$ and pyridine. In some embodiments, an oxidation step comprises the use of 0.02 M $I_2$ in a THF/pyridine/water (70:20:10-v/v/v) co-solvent system. An exemplary cycle is depicted in Scheme I-c.

In some embodiments, a phosphorothioate precursor is used to synthesize chirally controlled oligonucleotides comprising phosphorothioate linkages. In some embodiments, such a phosphorothioate precursor is

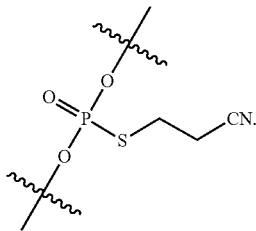

In some embodiments,

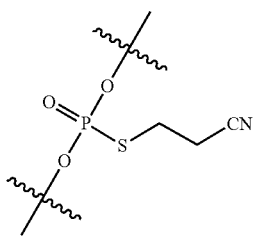

is converted into phosphorothioate diester linkages during standard deprotection/release procedure after cycle exit. Examples are further depicted below.

In some embodiments, the provided chirally controlled oligonucleotide comprises one or more phosphate diester linkages and one or more phosphorothioate diester linkages. In some embodiments, the provided chirally controlled oligonucleotide comprises one or more phosphate diester linkages and one or more phosphorothioate diester linkages, wherein at least one phosphate diester linkage is installed after all the phosphorothioate diester linkages when synthesized from 3' to 5'. To synthesize such chirally controlled oligonucleotides, in some embodiments, one or more modifying steps are optionally replaced with an oxidation step to install the corresponding phosphate diester linkages, and a phosphorothioate precursor is installed for each of the phosphorothioate diester linkages. In some embodiments, a phosphorothioate precursor is converted to a phosphorothioate diester linkage after the desired oligonucleotide length is achieved. In some embodiments, the deprotection/release step during or after cycle exit converts the phosphorothioate precursors into phosphorothioate diester linkages. In some embodiments, a phosphorothioate precursor is characterized in that it has the ability to be removed by a beta-elimination pathway. In some embodiments, a phosphorothioate precursor is

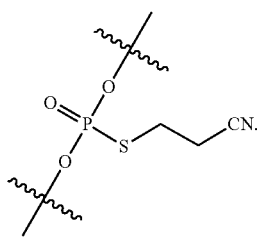

As understood by one of ordinary skill in the art, one of the benefits of using a phosphorothioate precursor, for instance,

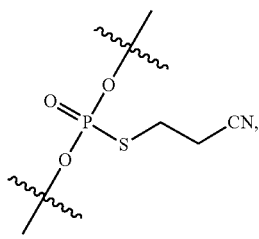

during synthesis is that

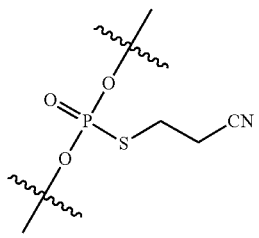

is more stable than phosphorothioate in certain conditions.

In some embodiments, a phosphorothioate precursor is a phosphorus protecting group as described herein, e.g., 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, 4-[N-methyl-N-(2,2,2-trifluoroacetyl)amino]butyl. Examples are further depicted below.

Methods for synthesizing a desired sulfurization reagent are described herein and in the examples section.

As noted above, in some embodiments, sulfurization occurs under conditions which cleave the chiral reagent from the growing oligonucleotide. In some embodiments, sulfurization occurs under conditions which do not cleave the chiral reagent from the growing oligonucleotide.

In some embodiments, a sulfurization reagent is dissolved in a suitable solvent and delivered to the column. In certain embodiments, the solvent is a polar aprotic solvent such as a nitrile solvent. In some embodiments, the solvent is acetonitrile. In some embodiments, a solution of sulfurization reagent is prepared by mixing a sulfurization reagent (e.g., a thiosulfonate derivative as described herein) with BSTFA (N,O-bis-trimethylsilyl-trifluoroacetamide) in a nitrile solvent (e.g., acetonitrile). In some embodiments, BSTFA is not included. For example, the present inventors have found that relatively more reactive sulfurization reagents of general formula $R^{s2}$—S—$S(O)_2$—$R^{s3}$ can often successfully participate in sulfurization reactions in the absence of BSTFA. To give but one example, the inventors have demonstrated that where $R^{s2}$ is p-nitrophenyl and $R^{s3}$ is methyl then no BSTFA is required. In light of this disclosure, those skilled in the art will readily be able to determine other situations and/or sulfurization reagents that do not require BSTFA.

In some embodiments, the sulfurization step is performed at room temperature. In some embodiments, the sulfurization step is performed at lower temperatures such as about 0° C., about 5° C., about 10° C., or about 15° C. In some embodiments, the sulfurization step is performed at elevated temperatures of greater than about 20° C.

In some embodiments, a sulfurization reaction is run for about 1 minute to about 120 minutes. In some embodiments, a sulfurization reaction is run for about 1 minute to about 90 minutes. In some embodiments, a sulfurization reaction is run for about 1 minute to about 60 minutes. In some embodiments, a sulfurization reaction is run for about 1 minute to about 30 minutes. In some embodiments, a sulfurization reaction is run for about 1 minute to about 25 minutes. In some embodiments, a sulfurization reaction is run for about 1 minute to about 20 minutes. In some embodiments, a sulfurization reaction is run for about 1 minute to about 15 minutes. In some embodiments, a sulfurization reaction is run for about 1 minute to about 10 minutes. In some embodiments, a sulfurization reaction is run for about 5 minute to about 60 minutes.

In some embodiments, a sulfurization reaction is run for about 5 minutes. In some embodiments, a sulfurization reaction is run for about 10 minutes. In some embodiments, a sulfurization reaction is run for about 15 minutes. In some embodiments, a sulfurization reaction is run for about 20 minutes. In some embodiments, a sulfurization reaction is run for about 25 minutes. In some embodiments, a sulfurization reaction is run for about 30 minutes. In some embodiments, a sulfurization reaction is run for about 35 minutes. In some embodiments, a sulfurization reaction is run for about 40 minutes. In some embodiments, a sulfurization reaction is run for about 45 minutes. In some embodiments, a sulfurization reaction is run for about 50 minutes. In some embodiments, a sulfurization reaction is run for about 55 minutes. In some embodiments, a sulfurization reaction is run for about 60 minutes.

It was unexpectedly found that certain of the sulfurization modification products made in accordance with methods of the present invention are unexpectedly stable. In some embodiments, it the unexpectedly stable products are phosphorothioate triesters. In some embodiments, the unexpectedly stable products are chirally controlled oligonucleotides comprising one or more internucleotidic linkages having the structure of formula I-c.

One of skill in the relevant arts will recognize that sulfurization methods described herein and sulfurization reagents described herein are also useful in the context of modifying H-phosphonate oligonucleotides such as those described in Wada II (WO2010/064146).

In some embodiments, the sulfurization reaction has a stepwise sulfurization efficiency that is at least about 80%, 85%, 90%, 95%, 96%, 97%, or 98%. In some embodiments, the sulfurization reaction provides a crude dinucleotide product composition that is at least 98% pure. In some embodiments, the sulfurization reaction provides a crude tetranucleotide product composition that is at least 90% pure. In some embodiments, the sulfurization reaction provides a crude dodecanucleotide product composition that is at least 70% pure. In some embodiments, the sulfurization reaction provides a crude icosanucleotide product composition that is at least 50% pure.

Once the step of modifying the linkage phosphorus is complete, the oligonucleotide undergoes another deblock step in preparation for re-entering the cycle. In some embodiments, a chiral auxiliary remains intact after sulfurization and is deblocked during the subsequent deblock step, which necessarily occurs prior to re-entering the cycle. The process of deblocking, coupling, capping, and modifying, are repeated until the growing oligonucleotide reaches a desired length, at which point the oligonucleotide can either be immediately cleaved from the solid support or left attached to the support for purification purposes and later cleaved. In some embodiments, one or more protecting groups are present on one or more of the nucleotide bases, and cleavage of the oligonucleotide from the support and deprotection of the bases occurs in a single step. In some embodiments, one or more protecting groups are present on one or more of the nucleotide bases, and cleavage of the oligonucleotide from the support and deprotection of the bases occurs in more than one steps. In some embodiments, deprotection and cleavage from the support occurs under basic conditions using, e.g., one or more amine bases. In certain embodiments, the one or more amine bases comprise propyl amine. In certain embodiments, the one or more amine bases comprise pyridine.

In some embodiments, cleavage from the support and/or deprotection occurs at elevated temperatures of about 30° C. to about 90° C. In some embodiments, cleavage from the support and/or deprotection occurs at elevated temperatures of about 40° C. to about 80° C. In some embodiments, cleavage from the support and/or deprotection occurs at elevated temperatures of about 50° C. to about 70° C. In some embodiments, cleavage from the support and/or deprotection occurs at elevated temperatures of about 60° C. In some embodiments, cleavage from the support and/or deprotection occurs at ambient temperatures.

Exemplary purification procedures are described herein and/or are known generally in the relevant arts.

Noteworthy is that the removal of the chiral auxiliary from the growing oligonucleotide during each cycle is beneficial for at least the reasons that (1) the auxiliary will not have to be removed in a separate step at the end of the oligonucleotide synthesis when potentially sensitive functional groups are installed on phosphorus; and (2) unstable phosphorus-auxiliary intermediates prone to undergoing side reactions and/or interfering with subsequent chemistry are avoided. Thus, removal of the chiral auxiliary during each cycle makes the overall synthesis more efficient.

While the step of deblocking in the context of the cycle is described above, additional general methods are included below.

Deblocking Step

In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

In some embodiments, acidification is used to remove a blocking group. In some embodiments, the acid is a Brønsted acid or Lewis acid. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring and or other sugar ring. In some embodiments, an acid is selected from $R^{a1}COOH$, $R^{a1}SO_3H$, $R^{a3}SO_3H$,

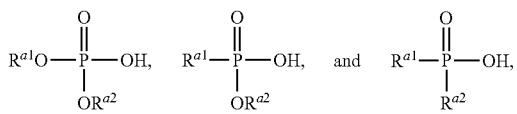

wherein each of $R^{a1}$ and $R^{a2}$ is independently hydrogen or an optionally substituted alkyl or aryl, and $R^{a3}$ is an optionally substituted alkyl or aryl.

In some embodiments, acidification is accomplished by a Lewis acid in an organic solvent. Exemplary such useful Lewis acids are $Zn(X^a)_2$ wherein $X^a$ is Cl, Br, I, or $CF_3SO_3$.

In some embodiments, the step of acidifying comprises adding an amount of a Brønsted or Lewis acid effective to remove a blocking group without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid or trichloroacetic acid in an organic solvent or 80% acetic acid in water. The concentration of any Brønsted or Lewis acid used in this step is selected such that the concentration of the acid does not exceed a concentration that causes cleavage of a nucleobase from a sugar moiety.

In some embodiments, acidification comprises adding 1% trifluoroacetic acid in an organic solvent. In some embodiments, acidification comprises adding about 0.1% to about 8% trifluoroacetic acid in an organic solvent. In some embodiments, acidification comprises adding 3% dichloroacetic acid or trichloroacetic acid in an organic solvent. In some embodiments, acidification comprises adding about 0.1% to about 10% dichloroacetic acid or trichloroacetic acid in an organic solvent. In some embodiments, acidification comprises adding 3% trichloroacetic acid in an organic solvent. In some embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to an acidic solvent. In certain embodiments, the cation scavengers can be triethylsilane or triisopropylsilane. In some embodiments, a blocking group is deblocked by acidification, which comprises adding 1% trifluoroacetic acid in an organic solvent. In some embodiments, a blocking group is deblocked by acidification, which comprises adding 3% dichloroacetic acid in an organic solvent. In some embodiments, a blocking group is deblocked by acidification, which comprises adding 3% trichloroacetic acid in an organic solvent. In some embodiments, a blocking group is deblocked by acidification, which comprises adding 3% trichloroacetic acid in dichloromethane.

In certain embodiments, methods of the present invention are completed on a synthesizer and the step of deblocking the hydroxyl group of the growing oligonucleotide comprises delivering an amount solvent to the synthesizer column, which column contains a solid support to which the oligonucleotide is attached. In some embodiments, the solvent is a halogenated solvent (e.g., dichloromethane). In certain embodiments, the solvent comprises an amount of an acid. In some embodiments, the solvent comprises an amount of an organic acid such as, for instance, trichloroacetic acid. In certain embodiments, the acid is present in an amount of about 1% to about 20% w/v. In certain embodiments, the acid is present in an amount of about 1% to about 10% w/v. In certain embodiments, the acid is present in an amount of about 1% to about 5% w/v. In certain embodiments, the acid is present in an amount of about 1 to about 3% w/v. In certain embodiments, the acid is present in an amount of about 3% w/v. Methods for deblocking a hydroxyl group are described further herein. In some embodiments, the acid is present in 3% w/v is dichloromethane.

In some embodiments, the chiral auxiliary is removed before the deblocking step. In some embodiments, the chiral auxiliary is removed during the deblocking step.

In some embodiments, cycle exit is performed before the deblocking step. In some embodiments, cycle exit is preformed after the deblocking step.

General Conditions for Blocking Group/Protecting Group Removal

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups such as phthalimido, 9-fluorenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin- 4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., *Tetrahedron*, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from nucleic acids. In some embodiments, all blocking groups are removed. In some embodiments, a portion of blocking groups are removed. In some embodiments, reaction conditions can be adjusted to selectively remove certain blocking groups.

In some embodiments, nucleobase blocking groups, if present, are cleavable with an acidic reagent after the assembly of a provided oligonucleotide. In some embodiment, nucleobase blocking groups, if present, are cleavable under neither acidic nor basic conditions, e.g. cleavable with fluoride salts or hydrofluoric acid complexes. In some embodiments, nucleobase blocking groups, if present, are cleavable in the presence of base or a basic solvent after the assembly of a provided oligonucleotide. In certain embodiments, one or more of the nucleobase blocking groups are characterized in that they are cleavable in the presence of base or a basic solvent after the assembly of a provided oligonucleotide but are stable to the particular conditions of one or more earlier deprotection steps occurring during the assembly of the provided oligonucleotide.

In some embodiments, blocking groups for nucleobases are not required. In some embodiments, blocking groups for nucleobases are required. In some embodiments, certain nucleobases require one or more blocking groups while other nucleobases do not require one or more blocking groups.

In some embodiments, the oligonucleotide is cleaved from the solid support after synthesis. In some embodiments, cleavage from the solid support comprises the use of propylamine. In some embodiments, cleavage from the solid support comprises the use of propylamine in pyridine. In some embodiments, cleavage from the solid support comprises the use of 20% propylamine in pyridine. In some embodiments, cleavage from the solid support comprises the use of propylamine in anhydrous pyridine. In some embodiments, cleavage from the solid support comprises the use of 20% propylamine in anhydrous pyridine. In some embodiments, cleavage from the solid support comprises use of a polar aprotic solvent such as acetonitrile, NMP, DMSO, sulfone, and/or lutidine. In some embodiments, cleavage from the solid support comprises use of solvent, e.g., a polar aprotic solvent, and one or more primary amines (e.g., a $C_{1-10}$ amine), and/or one or more of methoxylamine, hydrazine, and pure anhydrous ammonia.

In some embodiments, deprotection of oligonucleotide comprises the use of propylamine. In some embodiments, deprotection of oligonucleotide comprises the use of propylamine in pyridine. In some embodiments, deprotection of oligonucleotide comprises the use of 20% propylamine in pyridine. In some embodiments deprotection of oligonucleotide comprises the use of propylamine in anhydrous pyridine. In some embodiments, deprotection of oligonucleotide comprises the use of 20% propylamine in anhydrous pyridine.

In some embodiments, the oligonucleotide is deprotected during cleavage.

In some embodiments, cleavage of oligonucleotide from solid support, or deprotection of oligonucleotide, is performed at about room temperature. In some embodiments, cleavage of oligonucleotide from solid support, or deprotection of oligonucleotide, is performed at elevated temperature. In some embodiments, cleavage of oligonucleotide from solid support, or deprotection of oligonucleotide, is performed at above about 30° C., 40° C., 50° C., 60° C., 70° C., 80° C. 90° C. or 100° C. In some embodiments, cleavage of oligonucleotide from solid support, or deprotection of oligonucleotide, is performed at about 30° C., 40° C., 50° C., 60° C., 70° C., 80° C. 90° C. or 100° C. In some embodiments, cleavage of oligonucleotide from solid support, or deprotection of oligonucleotide, is performed at about 40-80° C. In some embodiments, cleavage of oligonucleotide from solid support, or deprotection of oligonucleotide, is performed at about 50-70° C. In some embodiments, cleavage of oligonucleotide from solid support, or deprotection of oligonucleotide, is performed at about 60° C.

In some embodiments, cleavage of oligonucleotide from solid support, or deprotection of oligonucleotide, is performed for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed for about 0.1-5 hrs. In some embodiments, cleavage of oligonucleotide from solid support, or deprotection of oligonucleotide, is performed for about 3-10 hrs. In some embodiments, cleavage of oligonucleotide from solid support, or deprotection of oligonucleotide, is performed for about 5-15 hrs. In some embodiments, cleavage of oligonucleotide from solid support, or deprotection of oligonucleotide, is performed for about 10-20 hrs. In some embodiments, cleavage of oligonucleotide from solid support, or deprotection of oligonucleotide, is performed for about 15-25 hrs. In some embodiments, cleavage of oligonucleotide from solid support, or deprotection of oligonucleotide, is performed for about 20-40 hrs. In some embodiments, cleavage of oligonucleotide from solid support, or deprotection of oligonucleotide, is performed for about 2 hrs. In some embodiments, cleavage of oligonucleotide from solid support, or deprotection of oligonucleotide, is performed for about 5 hrs. In some embodiments, cleavage of oligonucleotide from solid support, or deprotection of oligonucleotide, is performed for about 10 hrs. In some embodiments, cleavage of oligonucleotide from solid support, or deprotection of oligonucleotide, is performed for about 15 hrs. In some embodiments, cleavage of oligonucleotide from solid support, or deprotection of oligonucleotide, is performed for about 18 hrs. In some embodiments, cleavage of oligonucleotide from solid support, or deprotection of oligonucleotide, is performed for about 24 hrs.

In some embodiments, cleavage of oligonucleotide from solid support, or deprotection of oligonucleotide, is performed at room temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at room temperature for about 5-48 hrs. In some embodiments, cleavage of oligonucleotide from solid support, or deprotection of oligonucleotide, is performed at room temperature for about 10-24 hrs. In some embodiments, cleavage of oligonucleotide from solid support, or deprotection of oligonucleotide, is performed at room temperature for about 18 hrs. In some embodiments, cleavage of oligonucleotide from solid support, or deprotection of oligonucleotide, is performed at elevated temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at elevated temperature for about 0.5-5 hrs. In some embodiments, cleavage of oligonucleotide from solid support, or deprotection of oligonucleotide, is performed at about 60° C. for about 0.5-5 hrs. In some embodiments, cleavage of oligonucleotide from solid support, or deprotection of oligonucleotide, is performed at about 60° C. for about 2 hrs.

In some embodiments, cleavage of oligonucleotide from solid support, or deprotection of oligonucleotide comprises the use of propylamine and is performed at room temperature or elevated temperature for more than 0.1 hr, 1 hr, 2 hrs, 5 hrs, 10 hrs, 15 hrs, 20 hrs, 24 hrs, 30 hrs, or 40 hrs. Exemplary conditions are 20% propylamine in pyridine at room temperature for about 18 hrs, and 20% propylamine in pyridine at 60° C. for about 18 hrs, In some embodiments, an activator is a "Wada" activator, i.e., the activator is from any one of Wada I, II, or III documents cited above.

Exemplary activating groups are depicted below:

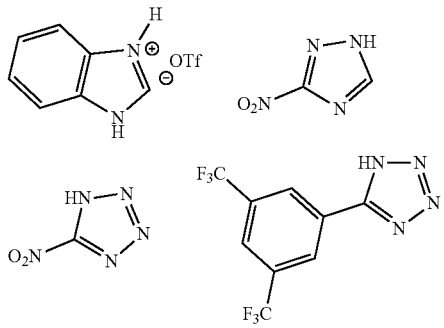

In some embodiments, an activating reagent is selected from

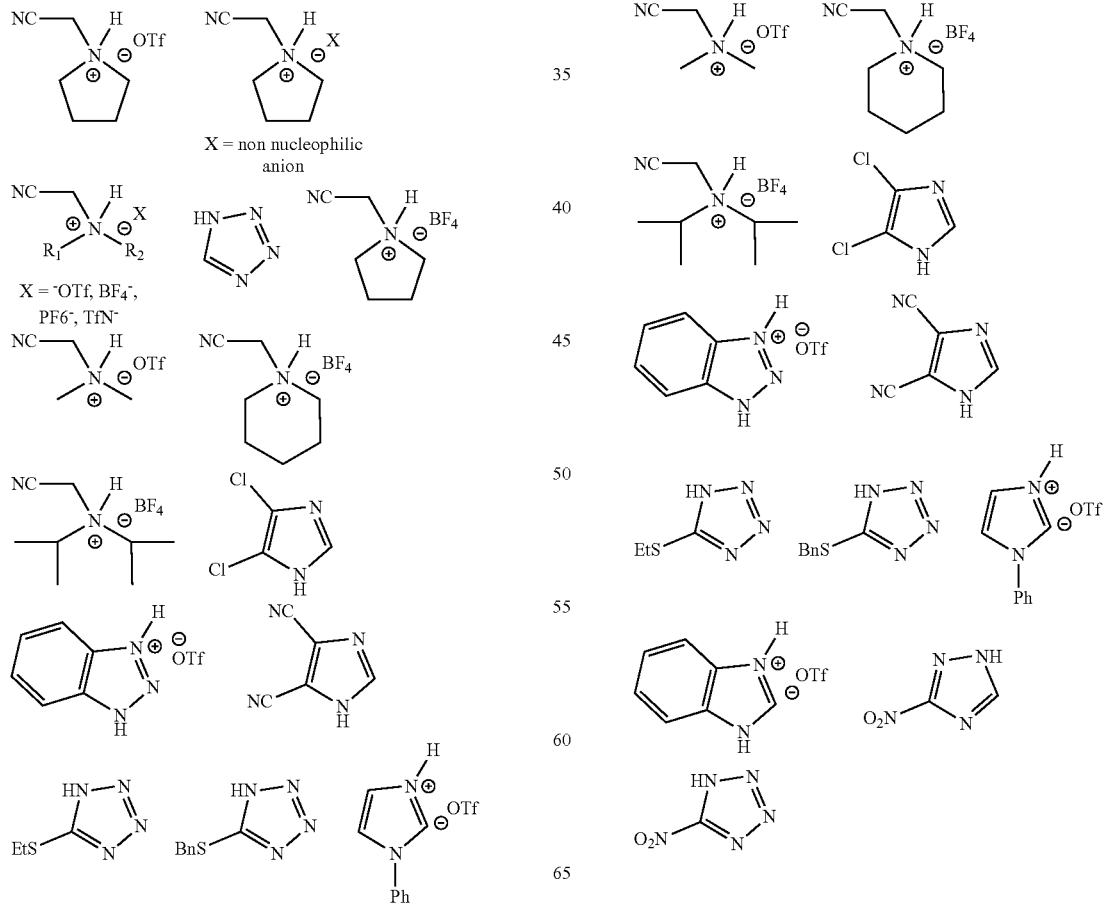

An exemplary cycle is depicted in Scheme I-b.
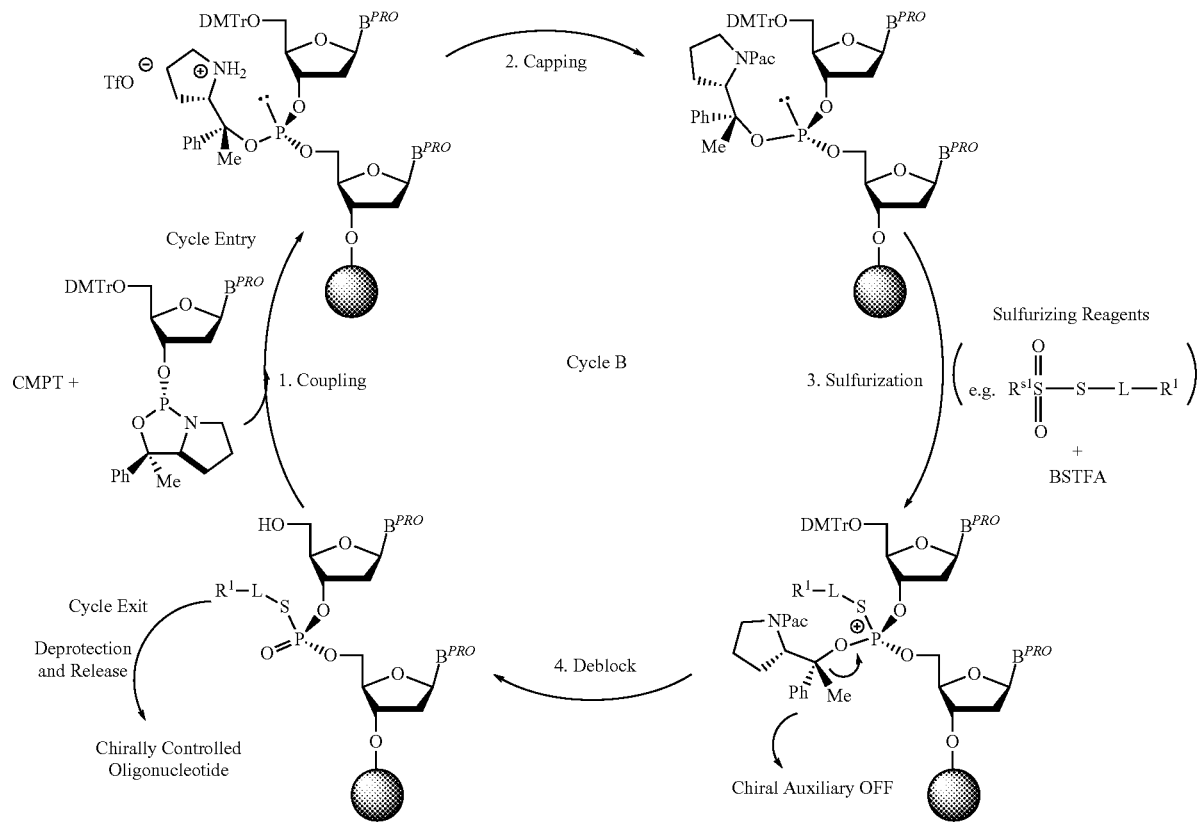
An exemplary cycle is illustrated in Scheme I-c.
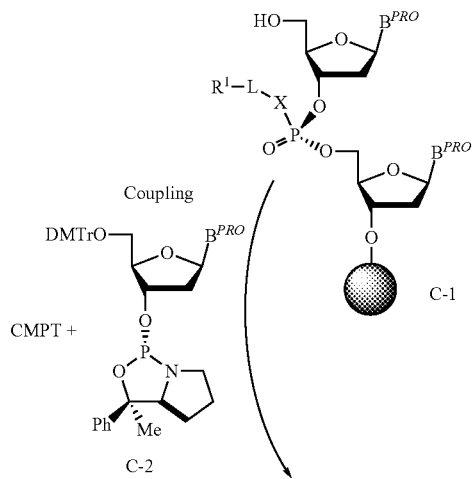

231

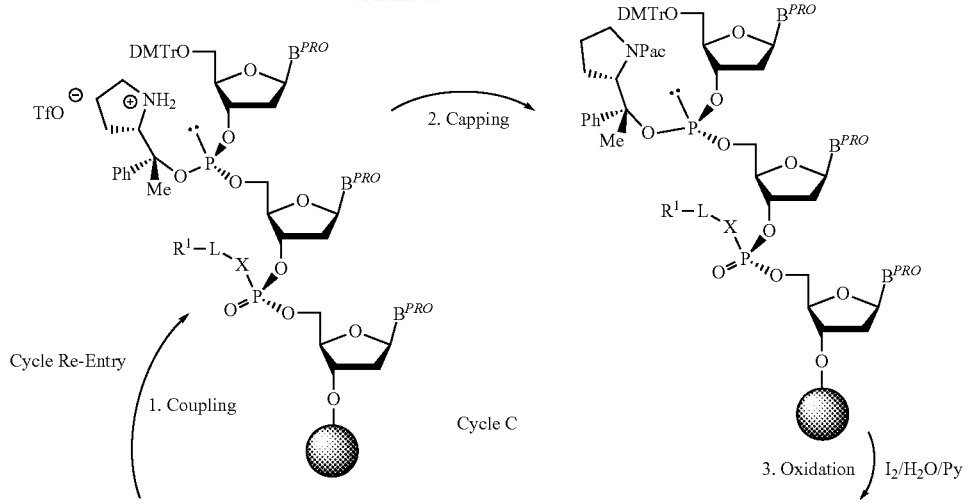

232

-continued

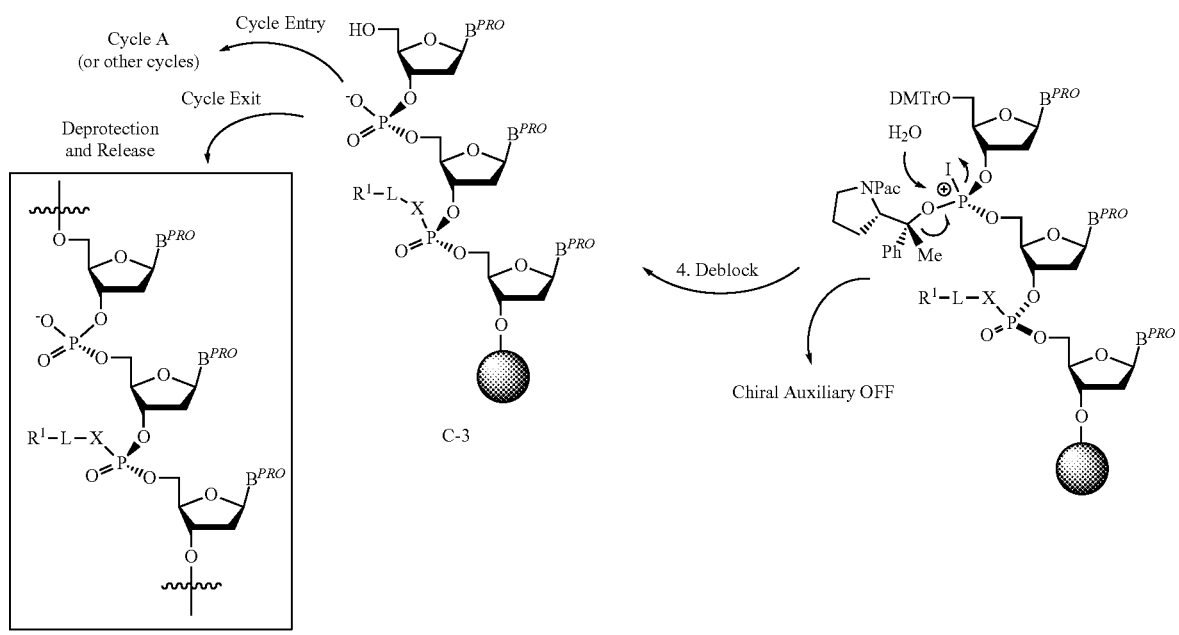

In Scheme I-c, oligonucleotide (or nucleotide, or oligonucleotide with modified internucleotidic linkage) on solid support (C-1) is coupled with phosphoramidite C-2. After coupling and capping, an oxidation step is performed. After deblocking, a phosphate diester linkage is formed. The cycle product C-3 can either re-enter cycle C to install more phosphate diester linkage, or enter other cycles to install other types of internucleotidic linkages, or go to cycle exit.

In some embodiments, non-chirally pure phosphoramidite can be used instead of C-2 in Scheme I-c. In some embodiments, β-cyanoethylphosphoramidites protected with DMTr is used. In some embodiments, the phosphoramidite being used has the structure of

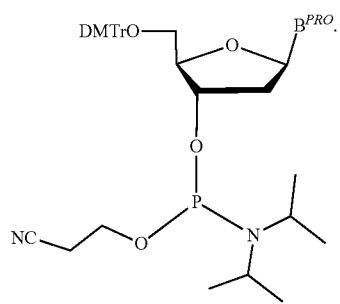

In some embodiments, the use of a phosphorothioate diester precursor increases the stability of oligonucleotide during synthesis. In some embodiments, the use of a phosphorothioate diester precursor improves the efficiency of chirally controlled oligonucleotide synthesis. In some embodiments, the use of a phosphorothioate diester precursor improves the yield of chirally controlled oligonucleotide synthesis. In some embodiments, the use of a phosphorothioate diester precursor improves the product purity of chirally controlled oligonucleotide synthesis.

In some embodiments, the phosphorothioate diester precursor in the above-mentioned methods is

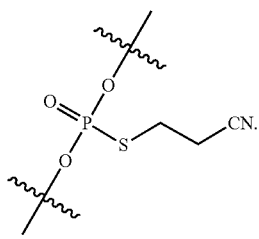

In some embodiments,

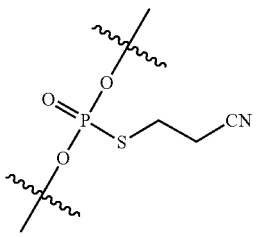

is converted to a phosphorothioate diester linkage during deprotection/release. An exemplary cycle is depicted in Scheme I-d. More examples are depicted below.

Scheme I-d. Phosphorothioate diester precursor in chirally controlled oligonucleotide synthesis.

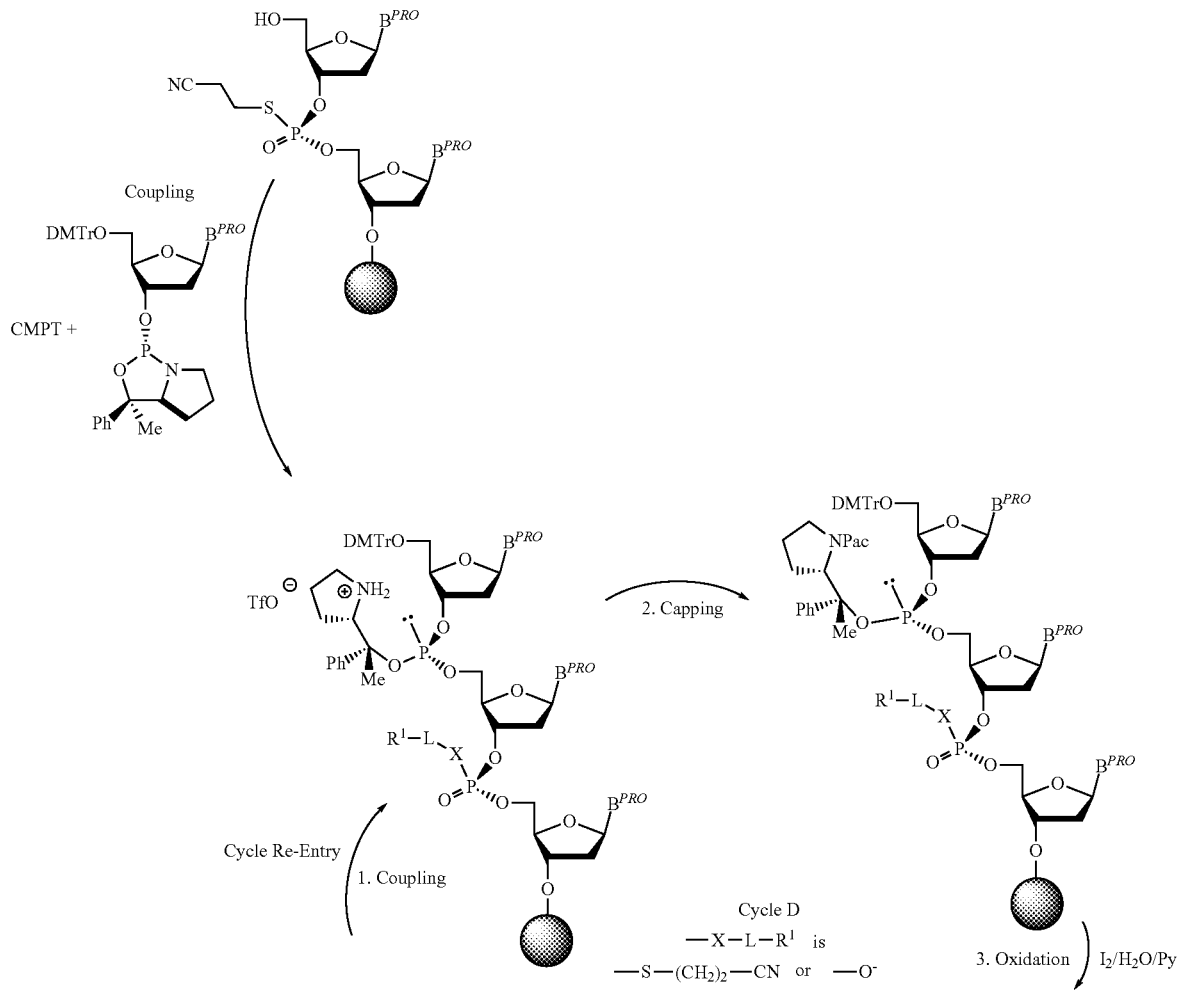

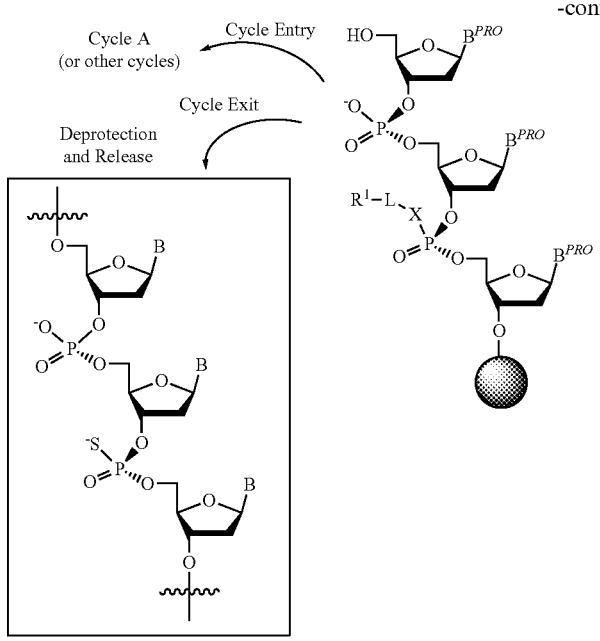
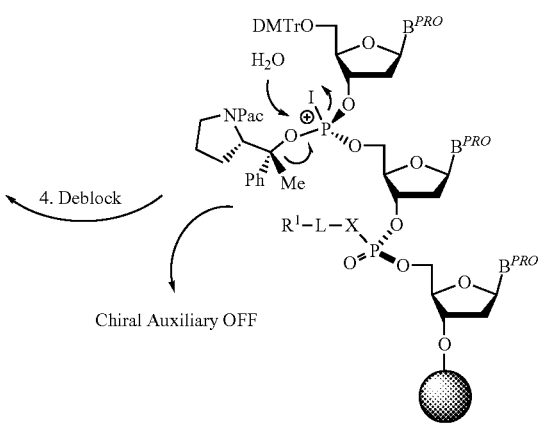

As illustrated in Scheme I-d, both phosphorothioate and phosphate diester linkages can be incorporated into the same chirally controlled oligonucleotide. As understood by a person of ordinary skill in the art, the provided methods do not require that the phosphorothioate diester and the phosphate diester to be consecutive—other internucleotidic linkages can form between them using a cycle as described above. In Scheme I-d, phosphorothioate diester precursors,

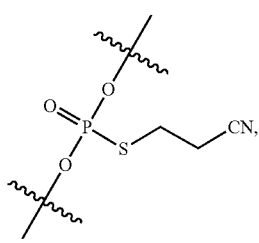

are installed in place of the phosphorothioate diester linkages. In some embodiments, such replacement provided increased synthesis efficiency during certain steps, for instance, the oxidation step. In some embodiments, the use of phosphorothioate diester precursors generally improve the stability of chirally controlled oligonucleotides during synthesis and/or storage. After cycle exit, during deprotection/release, the phosphorothioate diester precursor is converted to phosphorothioate diester linkage. In some embodiments, it is beneficial to use phosphorothioate diester precursor even when no phosphate diester linkage is present in the chirally controlled oligonucleotide, or no oxidation step is required during synthesis.

As in Scheme I-c, in some embodiments, non-chirally pure phosphoramidite can be used for cycles comprising oxidation steps. In some embodiments, β-cyanoethylphosphoramidites protected with DMTr is used. In some embodiments, the phosphoramidite being used has the structure of

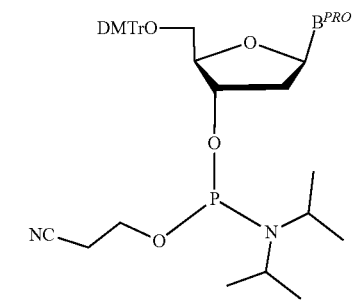

In some embodiments, methods of the present invention provide chirally controlled oligonucleotide compositions that are enriched in a particular oligonucleotide type.

In some embodiments, at least about 10% of a provided crude composition is of a particular oligonucleotide type. In some embodiments, at least about 20% of a provided crude composition is of a particular oligonucleotide type. In some embodiments, at least about 30% of a provided crude composition is of a particular oligonucleotide type. In some embodiments, at least about 40% of a provided crude composition is of a particular oligonucleotide type. In some embodiments, at least about 50% of a provided crude composition is of a particular oligonucleotide type. In some embodiments, at least about 60% of a provided crude composition is of a particular oligonucleotide type. In some embodiments, at least about 70% of a provided crude composition is of a particular oligonucleotide type. In some embodiments, at least about 80% of a provided crude composition is of a particular oligonucleotide type. In some embodiments, at least about 90% of a provided crude composition is of a particular oligonucleotide type. In some embodiments, at least about 95% of a provided crude composition is of a particular oligonucleotide type.

In some embodiments, at least about 1% of a provided composition is of a particular oligonucleotide type. In some embodiments, at least about 2% of a provided composition is of a particular oligonucleotide type. In some embodiments, at least about 3% of a provided composition is of a particular oligonucleotide type. In some embodiments, at least about 4% of a provided composition is of a particular oligonucleotide type. In some embodiments, at least about 5% of a provided composition is of a particular oligonucleotide type. In some embodiments, at least about 10% of a provided composition is of a particular oligonucleotide type. In some embodiments, at least about 20% of a provided composition is of a particular oligonucleotide type. In some embodiments, at least about 30% of a provided composition is of a particular oligonucleotide type. In some embodiments, at least about 40% of a provided composition is of a particular oligonucleotide type. In some embodiments, at least about 50% of a provided composition is of a particular oligonucleotide type. In some embodiments, at least about 60% of a provided composition is of a particular oligonucleotide type. In some embodiments, at least about 70% of a provided composition is of a particular oligonucleotide type. In some embodiments, at least about 80% of a provided composition is of a particular oligonucleotide type. In some embodiments, at least about 90% of a provided composition is of a particular oligonucleotide type. In some embodiments, at least about 95% of a provided composition is of a particular oligonucleotide type.

Biological Applications and Exemplary Use

Among other things, the present invention recognizes that properties and activities of an oligonucleotide can be adjusted by optimizing its pattern of backbone chiral centers through the use of provided chirally controlled oligonucleotide compositions. In some embodiments, the present invention provides chirally controlled oligonucleotide compositions, wherein the oligonucleotides have a common pattern of backbone chiral centers which enhances their stability and/or biological activity. In some embodiments, a pattern of backbone chiral centers provides unexpectedly increased stability. In some embodiments, a pattern of backbone chiral centers, surprisingly, provides greatly increased activity. In some embodiments, a pattern of backbone chiral centers provides both increased stability and activity. In some embodiments, when an oligonucleotide is utilized to cleave a nucleic acid polymer, a pattern of backbone chiral centers of the oligonucleotide, surprisingly by itself, changes the cleavage pattern of a target nucleic acid polymer. In some embodiments, a pattern of backbone chiral centers effectively prevents cleavage at secondary sites. In some embodiments, a pattern of backbone chiral centers creates new cleavage sites. In some embodiments, a pattern of backbone chiral centers minimizes the number of cleavage sites. In some embodiments, a pattern of backbone chiral centers minimizes the number of cleavage sites so that a target nucleic acid polymer is cleaved at only one site within the sequence of the target nucleic acid polymer that is complementary to the oligonucleotide. In some embodiments, a pattern of backbone chiral centers enhances cleavage efficiency at a cleavage site. In some embodiments, a pattern of backbone chiral centers of the oligonucleotide improves cleavage of a target nucleic acid polymer. In some embodiments, a pattern of backbone chiral centers increases selectivity. In some embodiments, a pattern of backbone chiral centers minimizes off-target effect. In some embodiments, a pattern of backbone chiral centers increase selectivity, e.g., cleavage selectivity among target sequences differing by point mutations or single nucleotide polymorphisms (SNPs). In some embodiments, a pattern of backbone chiral centers increase selectivity, e.g., cleavage selectivity among target sequences differing by only one point mutation or single nucleotide polymorphism (SNP).

In some embodiments, the present invention provides a method for controlled cleavage of a nucleic acid polymer, comprising providing a chirally controlled oligonucleotide composition comprising oligonucleotides defined by having:
1) a common base sequence and length, wherein the common base sequence is or comprises a sequence that is complementary to a sequence found in the nucleic acid polymer;
2) a common pattern of backbone linkages;
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers; and wherein the nucleic acid polymer is cleaved in a cleavage pattern that is different than the cleavage pattern when chirally uncontrolled oligonucleotide composition is provided.

As used herein, a cleavage pattern of a nucleic acid polymer is defined by the number of cleavage sites, the locations of the cleavage sites, and the percentage of cleavage at each sites. In some embodiments, a cleavage pattern has multiple cleavage sites, and the percentage of cleavage at each site is different. In some embodiments, a cleavage pattern has multiple cleavage sites, and the percentage of cleavage at each site is the same. In some embodiments, a cleavage pattern has only one cleavage site. In some embodiments, cleavage patterns differ from each other in that they have different numbers of cleavage sites. In some embodiments, cleavage patterns differ from each other in that at least one cleavage location is different. In some embodiments, cleavage patterns differ from each other in that the percentage of cleavage at at least one common cleavage site is different. In some embodiments, cleavage patterns differ from each other in that they have different numbers of cleavage sites, and/or at least one cleavage location is different, and/or the percentage of cleavage at at least one common cleavage site is different.

In some embodiments, the present invention provides a method for controlled cleavage of a nucleic acid polymer, the method comprising steps of:
contacting a nucleic acid polymer whose nucleotide sequence comprises a target sequence with a chirally controlled oligonucleotide composition comprising oligonucleotides of a particular oligonucleotide type characterized by:
1) a common base sequence and length, wherein the common base sequence is or comprises a sequence that is complementary to a target sequence found in the nucleic acid polymer;
2) a common pattern of backbone linkages; and
3) a common pattern of backbone chiral centers;
which composition is chirally controlled in that it is enriched, relative to a substantially racemic preparation of oligonucleotides having the particular base sequence and length, for oligonucleotides of the particular oligonucleotide type.

In some embodiments, the present invention provides a method for controlled cleavage of a nucleic acid polymer, the method comprising steps of:
contacting a nucleic acid polymer whose nucleotide sequence comprises a target sequence with a chirally controlled oligonucleotide composition comprising oligonucleotides of a particular oligonucleotide type characterized by:
1) a common base sequence and length, wherein the common base sequence is or comprises a sequence that is complementary to a target sequence found in the nucleic acid polymer;
2) a common pattern of backbone linkages; and
3) a common pattern of backbone chiral centers;

which composition is chirally controlled in that it is enriched, relative to a substantially racemic preparation of oligonucleotides having the particular base sequence and length, for oligonucleotides of the particular oligonucleotide type, the contacting being performed under conditions so that cleavage of the nucleic acid polymer occurs.

In some embodiments, the present invention provides a method for changing a first cleavage pattern of a nucleic acid polymer resulted from using a first oligonucleotide composition, comprising providing a second chirally controlled oligonucleotide composition comprising oligonucleotides defined by having:
1) a common base sequence and length, wherein the common base sequence is or comprises a sequence that is complementary to a sequence found in the nucleic acid polymer;
2) a common pattern of backbone linkages;
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers; and wherein the nucleic acid polymer is cleaved in a cleavage pattern that is different than the first cleavage pattern.

In some embodiments, the present invention provides a method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising:
contacting the nucleic acid polymer with a chirally controlled oligonucleotide composition of oligonucleotides having the particular base sequence and length, which composition is chirally controlled in that it is enriched, relative to a substantially racemic preparation of oligonucleotides having the particular base sequence and length, for oligonucleotides of a single oligonucleotide type characterized by:
1) the particular base sequence and length;
2) a particular pattern of backbone linkages; and
3) a particular pattern of backbone chiral centers, the contacting being performed under conditions so that cleavage of the nucleic acid polymer occurs.

In some embodiments, a provided chirally controlled oligonucleotide composition reduces the number of cleavage sites within the target sequence. In some embodiments, a provided chirally controlled oligonucleotide composition provides single-site cleavage within the target sequence. In some embodiments, a chirally controlled oligonucleotide composition provides enhanced cleavage rate at a cleavage site within the target sequence. In some embodiments, a chirally controlled oligonucleotide composition provides enhanced efficiency at a cleavage site within the target sequence. In some embodiments, a chirally controlled oligonucleotide composition provides increased turn-over in cleaving a target nucleic acid polymer.

In some embodiments, cleavage occurs with a cleavage pattern differs from a reference cleavage pattern. In some embodiments, a reference cleavage pattern is one observed when a nucleic acid polymer is contacted under comparable conditions with a reference oligonucleotide composition. In some embodiments, a reference oligonucleotide composition is a chirally uncontrolled (e.g., stereorandom) oligonucleotide composition of oligonucleotides that share the common base sequence and length of a chirally controlled oligonucleotide composition. In some embodiments, a reference oligonucleotide composition is a substantially racemic preparation of oligonucleotides that share the common sequence and length.

In some embodiments, a nucleic acid polymer is RNA. In some embodiments, a nucleic acid polymer is an oligonucleotide. In some embodiments, a nucleic acid polymer is an RNA oligonucleotide. In some embodiments, a nucleic acid polymer is a transcript. In some embodiments, oligonucleotides of a provided chirally controlled oligonucleotide composition form duplexes with a nucleic acid polymer to be cleaved.

In some embodiments, a nucleic acid polymer is cleaved by an enzyme. In some embodiments, an enzyme cleaves a duplex formed by a nucleic acid polymer. In some embodiments, an enzyme is RNase H. In some embodiments, an enzyme is Dicer. In some embodiments, an enzyme is an Argonaute protein. In some embodiments, an enzyme is Ago2. In some embodiments, an enzyme is within a protein complex. An exemplary protein complex is RNA-induced silencing complex (RISC).

In some embodiments, a provided chirally controlled oligonucleotide composition comprising oligonucleotides with a common pattern of backbone chiral centers provides unexpectedly high selectivity so that nucleic acid polymers that have only small sequence variations within a target region can be selectively targeted. In some embodiments, a nucleic acid polymer is a transcript from an allele. In some embodiments, transcripts from different alleles can be selectively targeted by provided chirally controlled oligonucleotide compositions.

Figure 21:
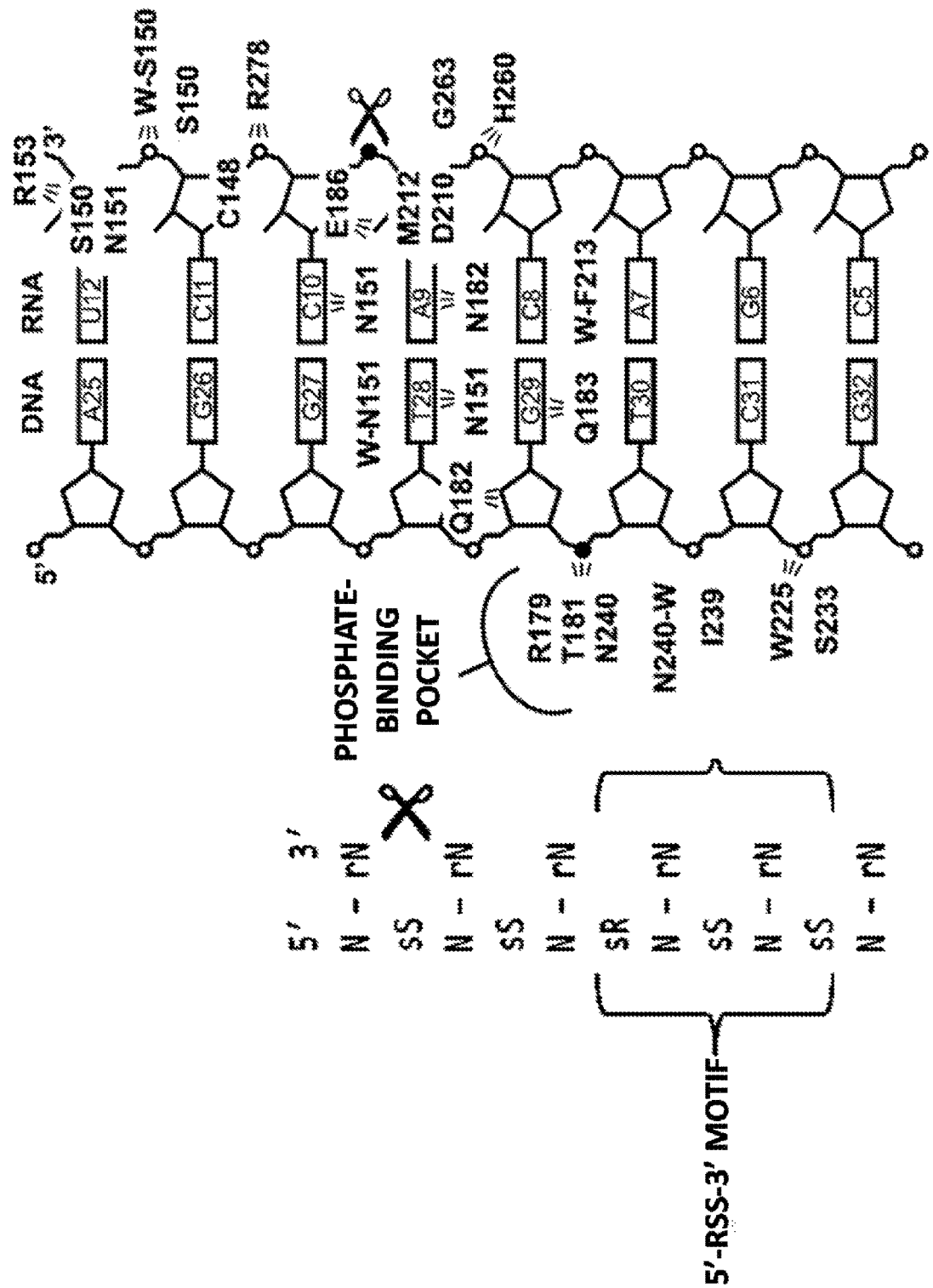
FIG. 21. An exemplary proposed cleavage. Provided chirally controlled oligonucleotide compositions are capable of cleaving targets as depicted.

In some embodiments, provided chirally controlled oligonucleotide compositions and methods thereof enables precise control of cleavage sites within a target sequence. In some embodiments, a cleavage site is around a sequence of RpSpSp backbone chiral centers. In some embodiments, a cleavage site is upstream of and near a sequence of RpSpSp backbone chiral centers. In some embodiments, a cleavage site is within 5 base pairs upstream of a sequence of RpSpSp backbone chiral centers. In some embodiments, a cleavage site is within 4 base pairs upstream of a sequence of RpSpSp backbone chiral centers. In some embodiments, a cleavage site is within 3 base pairs upstream of a sequence of RpSpSp backbone chiral centers. In some embodiments, a cleavage site is within 2 base pairs upstream of a sequence of RpSpSp backbone chiral centers. In some embodiments, a cleavage site is within 1 base pair upstream of a sequence of RpSpSp backbone chiral centers. In some embodiments, a cleavage site is downstream of and near a sequence of RpSpSp backbone chiral centers. In some embodiments, a cleavage site is within 5 base pairs downstream of a sequence of RpSpSp backbone chiral centers. In some embodiments, a cleavage site is within 4 base pairs downstream of a sequence of RpSpSp backbone chiral centers. In some embodiments, a cleavage site is within 3 base pairs downstream of a sequence of RpSpSp backbone chiral centers. In some embodiments, a cleavage site is within 2 base pairs downstream of a sequence of RpSpSp backbone chiral centers. In some embodiments, a cleavage site is within 1 base pair downstream of a sequence of RpSpSp backbone chiral centers. Among other things, the present invention therefore provides control of cleavage sites with in a target sequence. In some embodiments, an exemplary cleavage is depicted in FIG. 21. In some embodiments, cleavage depicted in FIG. 21 is designated as cleavage at a site two base pairs downstream a sequence of RpSpSp backbone chiral centers. As extensively described in the present disclosure, a sequence of RpSpSp backbone chiral centers can be found in a single or repeating units of (Np)m(Rp)n(Sp)t, (Np)t(Rp)n(Sp)m, (Sp)m(Rp)n(Sp)t, (Sp)t(Rp)n(Sp)m, (Rp)n(Sp)m, (Rp)m(Sp)n, (Sp)mRp and/or Rp(Sp)m, each of which is independently as defined above and described herein. In some embodiments, a provided chirally controlled oligonucleotide composition creates a new cleavage site 2 base pairs downstream of RpSpSp backbone chiral centers in a target molecule (e.g., see FIG. 21), wherein said new cleavage site does not exist if a reference (e.g., chirally uncontrolled) oligonucleotide composition is used (cannot be detected). In some embodiments, a provided chirally controlled oligonucleotide composition enhances cleavage at a cleavage site 2 base pairs downstream of RpSpSp backbone chiral centers in a target molecule (e.g., see FIG. 21), wherein cleavage at such a site occurs at a higher percentage than when a reference (e.g., chirally uncontrolled) oligonucleotide composition is used. In some embodiments, cleavage at such a site by a provided chirally controlled oligonucleotide composition is at least 2, 3, 4, 5, 6, 7, 8, 9, 10, 20, 30, 40, 50, 60, 70, 80, 90, 100, 200, 500 or 1000 fold of that by a reference oligonucleotide composition (for example, when measured by percentage of cleavage at a site). In some embodiments, a provided chirally controlled oligonucleotide composition provides accelerated cleavage at a cleavage site 2 base pairs downstream of RpSpSp backbone chiral centers in a target molecule (e.g., see FIG. 21), compared to when a reference (e.g., chirally uncontrolled) oligonucleotide composition is used. In some embodiments, cleavage by a provided chirally controlled oligonucleotide composition is at least 2, 3, 4, 5, 6, 7, 8, 9, 10, 20, 30, 40, 50, 60, 70, 80, 90, 100, 200, 500 or 1000 fold faster than that by a reference oligonucleotide composition. In some embodiments, a cleavage site of a provided chirally controlled oligonucleotide composition 2 base pairs downstream of RpSpSp backbone chiral centers in a target molecule (e.g., see FIG. 21) is a cleavage site when a reference (e.g., chirally uncontrolled) oligonucleotide composition is used. In some embodiments, a cleavage site of a provided chirally controlled oligonucleotide composition 2 base pairs downstream of RpSpSp backbone chiral centers in a target molecule (e.g., see FIG. 21) is within one base pair of a cleavage site when a reference (e.g., chirally uncontrolled) oligonucleotide composition is used. In some embodiments, a cleavage site of a provided chirally controlled oligonucleotide composition 2 base pairs downstream of RpSpSp backbone chiral centers in a target molecule (e.g., see FIG. 21) is within 2 base pairs of a cleavage site when a reference (e.g., chirally uncontrolled) oligonucleotide composition is used. In some embodiments, it is within 3 base pairs. In some embodiments, it is within 4 base pairs. In some embodiments, it is within 5 base pairs. In some embodiments, a cleavage site of a provided chirally controlled oligonucleotide composition 2 base pairs downstream of RpSpSp backbone chiral centers in a target molecule is one of the major cleavage sites when a reference (e.g., chirally uncontrolled) oligonucleotide composition is used. In some embodiments, such a site is the cleavage site with the highest cleavage percentage when a reference (e.g., chirally uncontrolled) oligonucleotide composition is used. In some embodiments, a cleavage site of a provided chirally controlled oligonucleotide composition 2 base pairs downstream of RpSpSp backbone chiral centers in a target molecule is one of the cleavage sites with higher cleavage rate when a reference (e.g., chirally uncontrolled) oligonucleotide composition is used. In some embodiments, such a site is the cleavage site with the highest cleavage rate when a reference (e.g., chirally uncontrolled) oligonucleotide composition is used.

Figure 18:
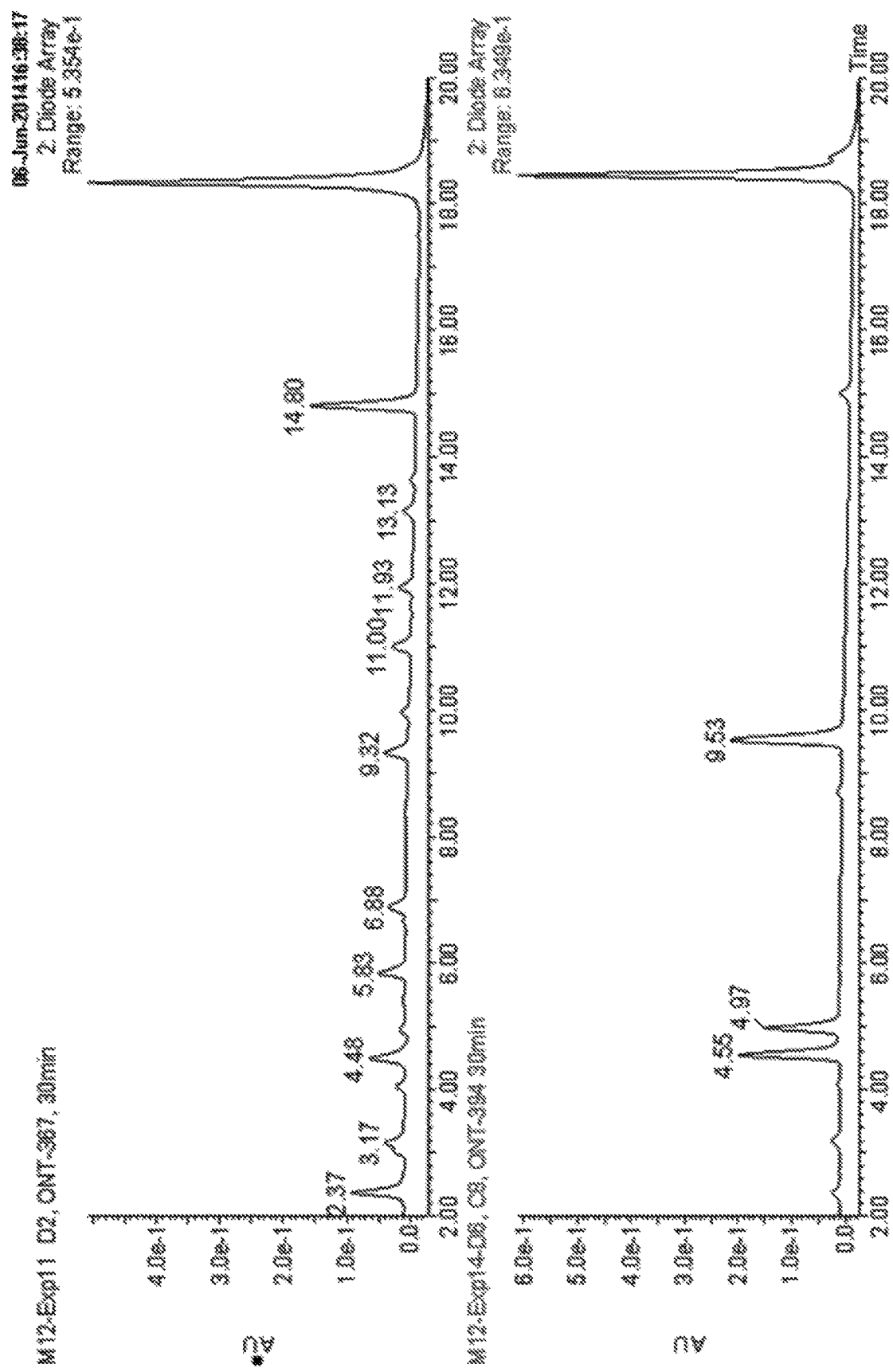
FIG. 18. Exemplary UV chromatograms of RNA cleavage products obtained when RNA (ONT-388) was duplexed with stereorandom DNA, ONT-367 (top) and stereopure DNA with repeat triplet motif-3'-SSR-5', ONT-394 (bottom)). 2.35 min: 7mer; 3.16 min: 8mer and p-6mer; 4.48 min: P-7mer; 5.83 min: P-8mer; 6.88 min: 12mer; 9.32 min: 13mer; 10.13 min: P-11mer; 11.0 min: P-12mer and 14mer; 11.93 min: P-13mer; 13.13 min: P-14mer. ONT-394 (on the bottom) peak assignment: 4.55 min: p-7mer; 4.97 min: 10mer; 9.53 min: 13mer.
Figure 19:
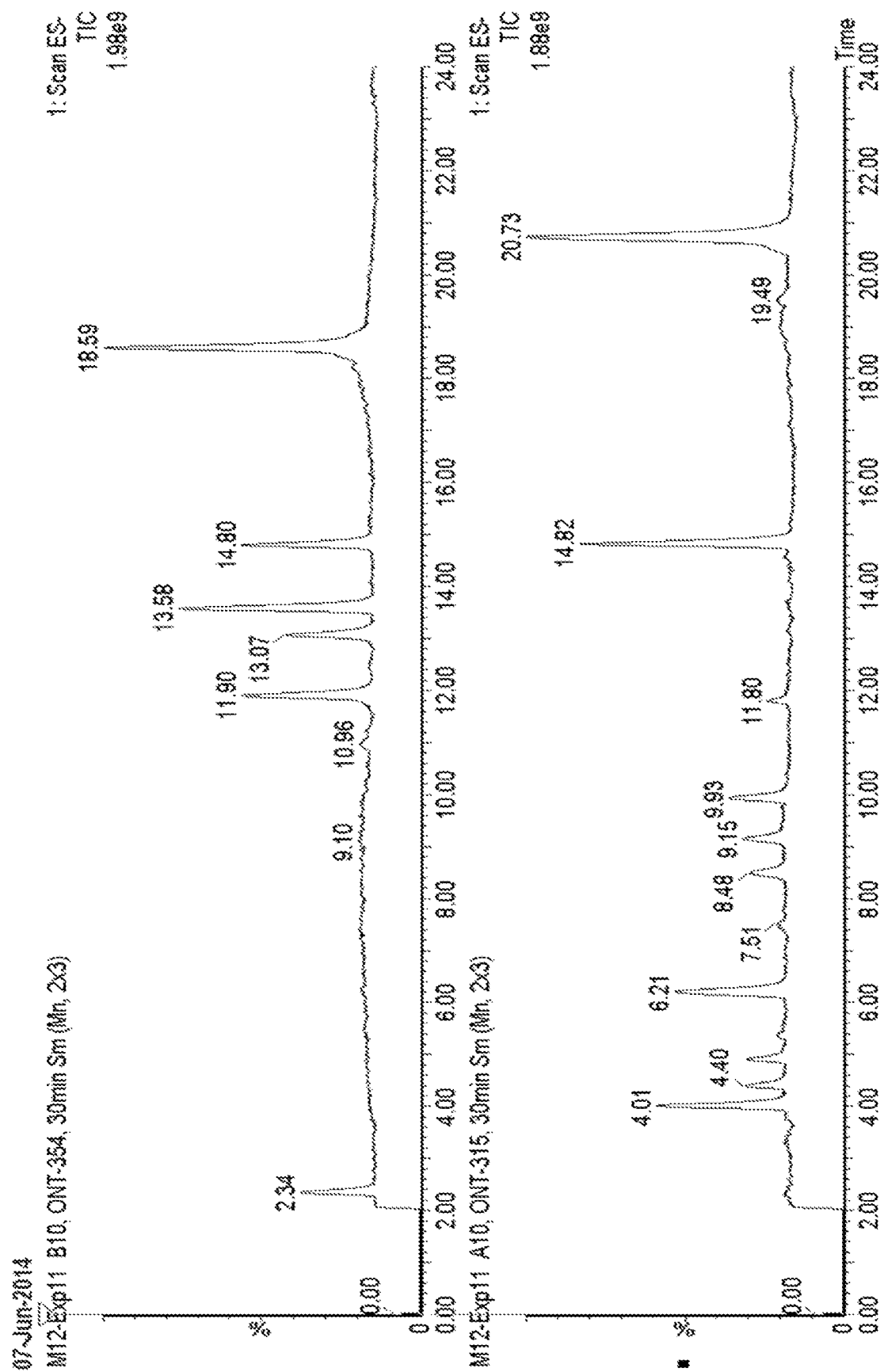
FIG. 19. Electrospray Ionization Spectrum of RNA cleavage products. RNA fragments obtained from the duplex ONT-387, RNA/ONT-354, (7-6-7, DNA-2'-OMe-DNA) on the top and ONT-387, RNA/ONT-315, (5-10-5,2'-MOE Gapmer) at the bottom when these duplexes were incubated with RNase H for 30 min in the presence of 1× RNse H buffer.

In some embodiments, a provided chirally controlled oligonucleotide composition enhances cleavage at one or more sites, e.g., relative to a reference (e.g., chirally uncontrolled/stereorandom) oligonucleotide composition. In some embodiments, a provided chirally controlled oligonucleotide composition selectively enhances cleavage at a single site relative to a reference (e.g., chirally uncontrolled/stereorandom) composition. In some embodiments, a chirally controlled oligonucleotide composition enhances cleavage at a site by providing a higher cleavage rate. In some embodiments, a chirally controlled oligonucleotide composition enhances cleavage at a site by providing a higher percentage of cleavage at said site. Percentage of cleavage at a site can be determined by various methods widely known and practiced in the art. In some embodiments, percentage of cleavage at a site is determined by analysis of cleavage products, for example, as by HPLC-MS as illustrated in FIG. 18, FIG. 19 and FIG. 30; see also exemplary cleavage maps such as FIG. 9, FIG. 10, FIG. 11, FIG. 14, FIG. 22, FIG. 25 and FIG. 26. In some embodiments, enhancement is relative to a reference oligonucleotide composition. In some embodiments, enhancement is relative to another cleavage site. In some embodiments, a provided chirally controlled oligonucleotide composition enhances cleavage at a site that is a preferred cleavage site of a reference oligonucleotide composition. In some embodiments, a preferred cleavage site, or a group of preferred cleavage sites, is a site or sites that have relatively higher percentage of cleavage compared to one or more other cleavage sites. In some embodiments, preferred cleavage sites can indicate preference of an enzyme. For example, for RNase H, when a DNA oligonucleotide is used, resulting cleavage sites may indicate preference of RNase H. In some embodiments, a provided chirally controlled oligonucleotide composition enhances cleavage at a site that is a preferred cleavage site of an enzyme. In some embodiments, a provided chirally controlled oligonucleotide composition enhances cleavage at a site that is not a preferred cleavage site of a reference oligonucleotide composition. In some embodiments, a provided chirally controlled oligonucleotide composition enhances cleavage at a site that is not a cleavage site of a reference oligonucleotide composition, effectively creating a new cleavage site which does not exist when a reference oligonucleotide composition is used. In some embodiments, a provided chirally controlled oligonucleotide composition enhances cleavage at a site within 5 base pairs from a targeted mutation or SNP, thereby increasing selective cleavage of the undesired target oligonucleotide. In some embodiments, a provided chirally controlled oligonucleotide composition enhances cleavage at a site within 4 base pairs from a targeted mutation or SNP, thereby increasing selective cleavage of the undesired target oligonucleotide. In some embodiments, a provided chirally controlled oligonucleotide composition enhances cleavage at a site within 3 base pairs from a targeted mutation or SNP, thereby increasing selective cleavage of the undesired target oligonucleotide. In some embodiments, a provided chirally controlled oligonucleotide composition enhances cleavage at a site within 2 base pairs from a targeted mutation or SNP, thereby increasing selective cleavage of the undesired target oligonucleotide. In some embodiments, a provided chirally controlled oligonucleotide composition enhances cleavage at a site immediately upstream or downstream targeted mutation or SNP, thereby increasing selective cleavage of the undesired target oligonucleotide (e.g., FIG. 22, Panel D, muRNA).

In some embodiments, a provided chirally controlled oligonucleotide composition suppresses cleavage at one or more sites, e.g., relative to a reference (e.g., chirally uncontrolled/stereorandom) oligonucleotide composition. In some embodiments, a provided chirally controlled oligonucleotide composition selectively suppresses cleavage at a single site relative to a reference (e.g., chirally uncontrolled/stereorandom) composition. In some embodiments, a chirally controlled oligonucleotide composition suppresses cleavage at a site by providing a lower cleavage rate. In some embodiments, a chirally controlled oligonucleotide composition suppresses cleavage at a site by providing a lower percentage of cleavage at said site. In some embodiments, suppression is relative to a reference oligonucleotide composition. In some embodiments, suppression is relative to another cleavage site. In some embodiments, a provided chirally controlled oligonucleotide composition suppresses cleavage at a site that is a preferred cleavage site of a reference oligonucleotide composition. In some embodiments, a preferred cleavage site, or a group of preferred cleavage sites, is a site or sites that have relatively higher percentage of cleavage compared to one or more other cleavage sites. In some embodiments, preferred cleavage sites can indicate preference of an enzyme. For example, for RNase H, when a DNA oligonucleotide is used, resulting cleavage sites may indicate preference of RNase H. In some embodiments, a provided chirally controlled oligonucleotide composition suppresses cleavage at a site that is a preferred cleavage site of an enzyme. In some embodiments, a provided chirally controlled oligonucleotide composition suppresses cleavage at a site that is not a preferred cleavage site of a reference oligonucleotide composition. In some embodiments, a provided chirally controlled oligonucleotide composition suppresses all cleavage sites of a reference oligonucleotide composition. In some embodiments, a provided chirally controlled oligonucleotide composition generally enhances cleavage of target oligonucleotides. In some embodiments, a provided chirally controlled oligonucleotide composition generally suppresses cleavage of non-target oligonucleotides. In some embodiments, a provided chirally controlled oligonucleotide composition enhances cleavage of target oligonucleotides and suppresses cleavage of non-target oligonucleotides. Using FIG. 22, Panel D, as an example, a target oligonucleotide for cleavage is muRNA, while a non-target oligonucleotide is wtRNA. In a subject comprising a diseased tissue comprising a mutation or SNP, a target oligonucleotide for cleavage can be transcripts with a mutation or SNP, while a non-target oligonucleotide can be normal transcripts without a mutation or SNP, such as those expressed in healthy tissues.

In some embodiments, besides patterns of backbone chiral centers described herein, provided oligonucleotides optionally comprises modified bases, modified sugars, modified backbone linkages and any combinations thereof. In some embodiments, a provided oligonucleotide is a unimer, altmer, blockmer, gapmer, hemimer and skipmer. In some embodiments, a provided oligonucleotide comprises one or more unimer, altmer, blockmer, gapmer, hemimer or skipmer moieties, or any combinations thereof. In some embodiments, besides patterns of backbone chiral centers herein, a provided oligonucleotide is a hemimer. In some embodiments, besides patterns of backbone chiral centers herein, a provided oligonucleotide is a 5'-hemimer with modified sugar moieties. In some embodiments, a provided oligonucleotide is 5'-hemimer with 2'-modified sugar moieties. Suitable modifications are widely known in the art, e.g., those described in the present application. In some embodiments, a modification is 2'-F. In some embodiments, a modification is 2'-MOE. In some embodiments, a modification is s-cEt.

In some embodiments, the present invention provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
    contacting a sample comprising transcripts of the target nucleic acid sequence with a chirally controlled oligonucleotide composition comprising oligonucleotides of a particular oligonucleotide type characterized by:
      1) a common base sequence and length;
      2) a common pattern of backbone linkages;
      3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

In some embodiments, the present invention provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
    contacting a sample comprising transcripts of the target nucleic acid sequence with a chirally controlled oligonucleotide composition comprising oligonucleotides of a particular oligonucleotide type characterized by:
      1) a common base sequence and length;
      2) a common pattern of backbone linkages;
      3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence, the contacting being performed under conditions determined to permit the composition to suppress transcripts of the particular allele.

In some embodiments, the present invention provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
  contacting a sample comprising transcripts of the target nucleic acid sequence with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
  a) greater than when the composition is absent;
  b) greater than a level of suppression observed for another allele of the same nucleic acid sequence; or
  c) both greater than when the composition is absent, and greater than a level of suppression observed for another allele of the same nucleic acid sequence.

In some embodiments, the present invention provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
  contacting a sample comprising transcripts of the target nucleic acid sequence with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
  a) greater than when the composition is absent;
  b) greater than a level of suppression observed for another allele of the same nucleic acid sequence; or
  c) both greater than when the composition is absent, and greater than a level of suppression observed for another allele of the same nucleic acid sequence,
the contacting being performed under conditions determined to permit the composition to suppress transcripts of the particular allele.

In some embodiments, a transcript is suppressed by cleavage of said transcript. In some embodiments, a specific nucleotide characteristic sequence element is in an intron. In some embodiments, a specific nucleotide characteristic sequence element is in an exon. In some embodiments, a specific nucleotide characteristic sequence element is partially in an exon and partially in an intron. In some embodiments, a specific nucleotide characteristic sequence element comprises a mutation that differentiates an allele from other alleles. In some embodiments, a mutation is a deletion. In some embodiments, a mutation is an insertion. In some embodiments, a mutation is a point mutation. In some embodiments, a specific nucleotide characteristic sequence element comprises at least one single nucleotide polymorphism (SNP) that differentiates an allele from other alleles.

In some embodiments, a target nucleic acid sequence is a target gene.

In some embodiments, the present invention provides a method for allele-specific suppression of a gene whose sequence comprises at least one single nucleotide polymorphism (SNP), comprising providing a chirally controlled oligonucleotide composition comprising oligonucleotides defined by having:
  1) a common base sequence and length, wherein the common base sequence is or comprises a sequence that is completely complementary to a sequence found in a transcript from the first allele but not to the corresponding sequence found in a transcript from the second allele, wherein the sequence found in the transcripts comprises a SNP site;
  2) a common pattern of backbone linkages;
  3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers;
wherein the transcript from the first allele is suppressed at least five folds more than that from the second allele.

In some embodiments, the present invention provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

In some embodiments, the present invention provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
 contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
 which composition is chirally controlled in that it is enriched, relative to a substantially racemic preparation of oligonucleotides having the same base sequence and length, for oligonucleotides of the particular oligonucleotide type;
 wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene,
the contacting being performed under conditions determined to permit the composition to suppress transcripts of the particular allele.

In some embodiments, the present invention provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
 contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
 which composition is chirally controlled in that it is enriched, relative to a substantially racemic preparation of oligonucleotides having the same base sequence and length, for oligonucleotides of the particular oligonucleotide type;
 wherein the common base sequence for the oligonucleotides of the particular oligonucleotide type is or comprises a sequence that is complementary to the characteristic sequence element that defines a particular allele, the composition being characterized in that when it is contacted with a system expressing transcripts of both the target allele and another allele of the same gene, transcripts of the particular allele are suppressed at a level at least 2 fold greater than a level of suppression observed for another allele of the same gene,
the contacting being performed under conditions determined to permit the composition to suppress expression of the particular allele.

In some embodiments, the present invention provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
 contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
 which composition is chirally controlled in that it is enriched, relative to a substantially racemic preparation of oligonucleotides having the same base sequence and length, for oligonucleotides of the particular oligonucleotide type;
 wherein the common base sequence for the oligonucleotides of the particular oligonucleotide type is or comprises a sequence that is complementary to the characteristic sequence element that defines a particular allele, the composition being characterized in that when it is contacted with a system expressing transcripts of the target gene, it shows suppression of expression of transcripts of the particular allele at a level that is:
  a) at least 2 fold in that transcripts from the particular allele are detected in amounts that are 2 fold lower when the composition is present relative to when it is absent;
  b) at least 2 fold greater than a level of suppression observed for another allele of the same gene; or
  c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, the present invention provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
 contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
 which composition is chirally controlled in that it is enriched, relative to a substantially racemic preparation of oligonucleotides having the same base sequence and length, for oligonucleotides of the particular oligonucleotide type;
 wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:

a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene, the contacting being performed under conditions determined to permit the composition to suppress transcripts of the particular allele.

In some embodiments, the present invention provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;

which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:

a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene, the contacting being performed under conditions determined to permit the composition to suppress expression of the particular allele.

In some embodiments, suppression of transcripts of a particular allele is at a level that is greater than when the composition is absent. In some embodiments, suppression of transcripts of a particular allele is at a level that is at least 1.1 fold relative to when the composition is absent, in that transcripts from the particular allele are detected in amounts that are at least 1.1 fold lower when the composition is present relative to when it is absent. In some embodiments, a level is at least 1.2 fold. In some embodiments, a level is at least 1.3 fold. In some embodiments, a level is at least 1.4 fold. In some embodiments, a level is at least 1.5 fold. In some embodiments, a level is at least 1.6 fold. In some embodiments, a level is at least 1.7 fold. In some embodiments, a level is at least 1.8 fold. In some embodiments, a level is at least 1.9 fold. In some embodiments, a level is at least 2 fold. In some embodiments, a level is at least 3 fold. In some embodiments, a level is at least 4 fold. In some embodiments, a level is at least 5 fold. In some embodiments, a level is at least 6 fold. In some embodiments, a level is at least 7 fold. In some embodiments, a level is at least 8 fold. In some embodiments, a level is at least 9 fold. In some embodiments, a level is at least 10 fold. In some embodiments, a level is at least 11 fold. In some embodiments, a level is at least 12 fold. In some embodiments, a level is at least 13 fold. In some embodiments, a level is at least 14 fold. In some embodiments, a level is at least 15 fold. In some embodiments, a level is at least 20 fold. In some embodiments, a level is at least 30 fold. In some embodiments, a level is at least 40 fold. In some embodiments, a level is at least 50 fold. In some embodiments, a level is at least 75 fold. In some embodiments, a level is at least 100 fold. In some embodiments, a level is at least 150 fold. In some embodiments, a level is at least 200 fold. In some embodiments, a level is at least 300 fold. In some embodiments, a level is at least 400 fold. In some embodiments, a level is at least 500 fold. In some embodiments, a level is at least 750 fold. In some embodiments, a level is at least 1000 fold. In some embodiments, a level is at least 5000 fold.

In some embodiments, suppression of transcripts of a particular allele is at a level that is greater than a level of suppression observed for another allele of the same nucleic acid sequence. In some embodiments, suppression of transcripts of a particular allele is at a level that is at least 1.1 fold greater than a level of suppression observed for another allele of the same nucleic acid sequence. In some embodiments, a level is at least 1.2 fold. In some embodiments, a level is at least 1.3 fold. In some embodiments, a level is at least 1.4 fold. In some embodiments, a level is at least 1.5 fold. In some embodiments, a level is at least 1.6 fold. In some embodiments, a level is at least 1.7 fold. In some embodiments, a level is at least 1.8 fold. In some embodiments, a level is at least 1.9 fold. In some embodiments, a level is at least 2 fold. In some embodiments, a level is at least 3 fold. In some embodiments, a level is at least 4 fold. In some embodiments, a level is at least 5 fold. In some embodiments, a level is at least 6 fold. In some embodiments, a level is at least 7 fold. In some embodiments, a level is at least 8 fold. In some embodiments, a level is at least 9 fold. In some embodiments, a level is at least 10 fold. In some embodiments, a level is at least 11 fold. In some embodiments, a level is at least 12 fold. In some embodiments, a level is at least 13 fold. In some embodiments, a level is at least 14 fold. In some embodiments, a level is at least 15 fold. In some embodiments, a level is at least 20 fold. In some embodiments, a level is at least 30 fold. In some embodiments, a level is at least 40 fold. In some embodiments, a level is at least 50 fold. In some embodiments, a level is at least 75 fold. In some embodiments, a level is at least 100 fold. In some embodiments, a level is at least 150 fold. In some embodiments, a level is at least 200 fold. In some embodiments, a level is at least 300 fold. In some embodiments, a level is at least 400 fold. In some embodiments, a level is at least 500 fold. In some embodiments, a level is at least 750 fold. In some embodiments, a level is at least 1000 fold. In some embodiments, a level is at least 5000 fold.

In some embodiments, suppression of transcripts of a particular allele is at a level that is greater than when the composition is absent, and at a level that is greater than a level of suppression observed for another allele of the same nucleic acid sequence. In some embodiments, suppression of transcripts of a particular allele is at a level that is at least 1.1 fold relative to when the composition is absent, and at least 1.1 fold greater than a level of suppression observed for another allele of the same nucleic acid sequence. In some embodiments, each fold is independently as described above.

In some embodiments, a system is a composition comprising a transcript. In some embodiments, a system is a composition comprising transcripts from different alleles. In some embodiments, a system can be in vivo or in vitro, and in either way can comprise one or more cells, tissues, organs or organisms. In some embodiments, a system comprises one or more cells. In some embodiments, a system comprises one or more tissues. In some embodiments, a system comprises one or more organs. In some embodiments, a system comprises one or more organisms. In some embodiments, a system is a subject.

In some embodiments, suppression of a transcript, or suppression of expression of an allele from which a transcript is transcribed, can be measured in in vitro assay. In some embodiments, a sequence from a transcript and comprising a specific nucleotide characteristic sequence element is used in assays instead of the full-length transcript. In some embodiments, an assay is a biochemical assay. In some embodiments, an assay is a biochemical assay wherein a nucleic acid polymer, for example, a transcript or a sequence from a transcript and comprising a specific nucleotide characteristic sequence element, is tested for cleavage by an enzyme in the presence of a chirally controlled oligonucleotide composition.

In some embodiments, a provided chirally controlled oligonucleotide composition is administered to a subject. In some embodiments, a subject is an animal. In some embodiments, a subject is a plant. In some embodiments, a subject is a human.

In some embodiments, for allele-specific suppression of transcripts from a particular allele, transcripts are cleaved at a site near a sequence difference, for example a mutation, within a specific nucleotide characteristic sequence element, which sequence difference differentiates transcripts from a particular allele from transcripts from the other alleles. In some embodiments, transcripts are selectively cleaved at a site near such a sequence difference. In some embodiments, transcripts are cleaved at a higher percentage at a site near such a sequence difference that when a chirally uncontrolled oligonucleotide composition is used. In some embodiments, transcripts are cleaved at the site of a sequence difference. In some embodiments, transcripts are cleaved only at the site of a sequence difference within a specific nucleotide characteristic sequence element. In some embodiments, transcripts are cleaved at a site within 5 base pairs downstream or upstream a sequence difference. In some embodiments, transcripts are cleaved at a site within 4 base pairs downstream or upstream a sequence difference. In some embodiments, transcripts are cleaved at a site within 3 base pairs downstream or upstream a sequence difference. In some embodiments, transcripts are cleaved at a site within 2 base pairs downstream or upstream a sequence difference. In some embodiments, transcripts are cleaved at a site within 1 base pair downstream or upstream a sequence difference. In some embodiments, transcripts are cleaved at a site within 5 base pairs downstream a sequence difference. In some embodiments, transcripts are cleaved at a site within 4 base pairs downstream a sequence difference. In some embodiments, transcripts are cleaved at a site within 3 base pairs downstream a sequence difference. In some embodiments, transcripts are cleaved at a site within 2 base pairs downstream a sequence difference. In some embodiments, transcripts are cleaved at a site within 1 base pair downstream a sequence difference. In some embodiments, transcripts are cleaved at a site within 5 base pairs upstream a sequence difference. In some embodiments, transcripts are cleaved at a site within 4 base pairs upstream a sequence difference. In some embodiments, transcripts are cleaved at a site within 3 base pairs upstream a sequence difference. In some embodiments, transcripts are cleaved at a site within 2 base pairs upstream a sequence difference. In some embodiments, transcripts are cleaved at a site within 1 base pair upstream a sequence difference. Such precise control of cleavage patterns, and the resulting highly selective suppression of transcripts from a particular allele, would not be possible without chirally controlled oligonucleotide compositions and methods thereof provided by Applicant in this disclosure.

In some embodiments, the present invention provides methods for treating a subject, or preventing a disease in a subject, by specifically suppress transcripts from a particular allele, for example, an allele that causes or may cause a disease. In some embodiments, the present invention provides methods for treating a subject suffering from a disease, comprising administering to the subject a pharmaceutical composition comprising a chirally controlled oligonucleotide composition, wherein transcripts from an allele that causes or contributes to the disease is selectively suppressed. In some embodiments, the present invention provides methods for treating a subject suffering from a disease, comprising administering to the subject a pharmaceutical composition comprising a chirally controlled oligonucleotide composition, wherein transcripts from an allele that causes the disease is selectively suppressed. In some embodiments, the present invention provides methods for treating a subject suffering from a disease, comprising administering to the subject a pharmaceutical composition comprising a chirally controlled oligonucleotide composition, wherein transcripts from an allele that contributes to the disease is selectively suppressed. In some embodiments, the present invention provides methods for treating a subject suffering from a disease, comprising administering to the subject a pharmaceutical composition comprising a chirally controlled oligonucleotide composition, wherein transcripts from an allele that is related to the disease is selectively suppressed. In some embodiments, the present invention provides methods for preventing a disease in a subject, by specifically suppress transcripts from a particular allele that may cause a disease. In some embodiments, the present invention provides methods for preventing a disease in a subject, by specifically suppress transcripts from a particular allele that increases risk of a disease in the subject. In some embodiments, a provided method comprises administering to the subject a pharmaceutical composition comprising a chirally controlled oligonucleotide composition. In some embodiments, a pharmaceutical composition further comprises a pharmaceutical carrier.

Diseases that involves disease-causing alleles are widely known in the art, including but not limited to those described in Hohjoh, *Pharmaceuticals* 2013, 6, 522-535; US patent application publication US 2013/0197061; Østergaard et al., *Nucleic Acids Research* 2013, 41(21), 9634-9650; and Jiang et al., *Science* 2013, 342, 111-114. In some embodiments, a disease is Huntington's disease. In some embodiments, a disease is human hypertrophic cardiomyopathy (HCM). In some embodiments, a disease is dilated cardiomyopathy. In some embodiments, a disease-causing allele is an allele of myosin heavy chains (MHC). In some embodiments, an exemplary disease is selected from:

| Disease | Target gene | Target variation |
|---|---|---|
| Familial Alzheimer's disease | Amyloid precursor protein (APP) | K670N-M671L (Swedish mutant) |
| | Amyloid precursor protein (APP) | K670N-M671L (Swedish mutant) |
| | Amyloid precursor protein (APP) | V717F (London mutant) |
| | Amyloid precursor protein (APP) | V717I (London mutant) |
| | Preseniline 1 (PSEN1) | L392V |
| Amyotrophic lateral sclerosis (ALS) | Superoxide dismutase (SOD1) | G93A |
| | Superoxide dismutase (SOD1) | G85R |
| Slow channel congenital myasthenic syndrome (SCCMS) | Acetylcholine receptor (AChR) | aS226F |
| Machado-Joseph disease/spinocerebellar ataxia type 3 (MJD/SCA3) | ATAXIN3/MJD1 | SNPs linked to expanded CAG repeat |
| Spinocerebellar ataxia type 7 (SCA7) | Ataxin-7 (ATXN7) | SNP linked to expanded CAG repeat |
| Parkinson's disease | Leucine-rich repeat kinase 2 (LRRK2) | R1441G, R1441C |
| | Leucine-rich repeat kinase 2 (LRRK2) | G20195S |
| | alpha-synuclein | A30P |
| Huntington disease | Huntington (HTT) | SNPs linked to expanded CAG repeat |
| Hypertrophic cardiomyopathy | MYH7 | R403Q |
| Frontotemporal dementia with parkinsonism linked to chromosome 17 (FTDP-17) | Microtubule-associated protein TAU (MAPT) | V337M |
| Ethlers-Danlos syndrome (vEDS) | Procollagen type III (COL3A1) | G252V |
| Sickle cell anemia | Hemoglobin-beta locus (HBB) | E6V |
| Familial amyloidotic polyneuropathy (FAP) | Transthyretin (TTR) | V30M |
| Fibrodysplasia ossificans progressiva (FOP) | Activin A receptor type I (ACVR1) | R206H, G356D |
| | Activin A receptor type I (ACVR1) | R206H |
| Tumors | Phosphoinositide-3-kinase, catalytic, alpha polypeptide (PIK3CA) | 1633G -> A 3140A -> G |
| Spinocerebellar ataxia type 1 (SCA1) | Ataxin-1 (ATXN1) | flanking region of expanded CAG repeat |
| Familial Alzheimer's disease | Amyloid precursor protein (APP) | K670N-M671L (Swedish mutant) |
| | Amyloid precursor protein (APP) | K670N-M671L (Swedish mutant) |
| | Amyloid precursor protein (APP) | V717F (London mutant) |
| | Amyloid precursor protein (APP) | V717I (London mutant) |
| | Preseniline 1 (PSEN1) | L392V |
| Amyotrophic lateral sclerosis (ALS) | Superoxide dismutase (SOD1) | G93A |
| | Superoxide dismutase (SOD1) | G85R |
| Slow channel congenital myasthenic syndrome (SCCMS) | Acetylcholine receptor (AChR) | aS226F, aT254I, aS269I |
| Frontotemporal dementia with parkinsonism linked to chromosome 17 (FTDP-17) | Microtubule-associated protein TAU (MAPT) | V337M |
| Ehlers-Danlos syndrome (vEDS) | Procollagen type III (COL3A1) | G252V |
| Sickle cell anemia | Hemoglobin-beta locus (HBB) | E6V |
| Familial amyloidotic polyneuropathy (FAP) | Transthyretin (TTR) | V30M |
| Fibrodysplasia ossificans progressiva (FOP) | Activin A receptor type I (ACVR1) | R206H, G356D |
| | Activin A receptor type I (ACVR1) | R206H |
| Tumors | KRAS | G12V, G12D, G13D |
| Tumors | Phosphoinositide-3-kinase, catalytic, alpha polypeptide (PIK3CA) | G1633A, A3140G |
| Spinocerebellar ataxia type 1 (SCA1) | Ataxin-1 (ATXN1) | SNPs linked to expanded CAG repeat |
| Spinocerebellar ataxia type 7 (SCA7) | Ataxin-7 (ATXN7) | SNPs linked to expanded CAG repeat |
| Spinocerebellar Ataxia Type 3 (SCA3)/Machado-Joseph Disease | Ataxin-3 (ATXN3) | SNPs linked to expanded CAG repeat |
| Parkinson's disease | Leucine-rich repeat kinase 2 (LRRK2) | R1441G, R1441C |
| | Leucine-rich repeat kinase 2 (LRRK2) | G20195S |
| | Alpha-synuclein (SNCA) | A30P, A53T, E46K |
| Huntington's disease | Huntingtin (HTT) | SNPs linked to expanded CAG repeat |
| Huntington's disease-like 2 | JPH3 | SNPs linked to expanded CTG repeat |
| Friedreich's ataxia | FXN | SNPs linked to expanded GAA repeat |
| Fragile X mental retardation syndrome/fragile X tremor ataxia syndrome | FMR1 | SNPs linked to expanded CGG repeat |
| Myotonic Dystrophy (DM1) | DMPK | SNPs linked to expanded CTG repeat |

In some embodiments, exemplary targets of, and diseases that can be treated by, provided chirally controlled oligonucleotide compositions and methods, comprises:

-continued

| Disease | Target gene | Target variation |
|---|---|---|
| Myotonic Dystophy (DM2) | ZNF9 | SNPs linked to expanded CTG repeat |
| Spinal-Bulbar Muscular Atrophy | AR | SNPs linked to expanded CAG repeat |
| Hypertrophic cardiomyopathy | MHY7 | R403Q |

In some embodiments, a target Huntingtin site is selected from rs9993542_C, rs362310_C, rs362303_C, rs10488840_G, rs363125_C, rs363072_A, rs7694687_C, rs363064_C, rs363099_C, rs363088_A, rs34315806_C, rs2298967_T, rs362272_G, rs362275_C, rs362306_G, rs3775061_A, rs1006798_A, rs16843804_C, rs3121419_C, rs362271_G, rs362273_A, rs7659144_C, rs3129322_T, rs3121417_G, rs3095074_G, rs362296_C, rs108850_C, rs2024115_A, rs916171_C, rs7685686_A, rs6844859_T, rs4690073_G, rs2285086_A, rs362331_T, rs363092_C, rs3856973_G, rs4690072_T, rs7691627_G, rs2298969_A, rs2857936_C, rs6446723_T, rs762855_A, rs1263309_T, rs2798296_G, rs363096_T, rs10015979_G, rs11731237_T, rs363080_C, rs2798235_G and rs362307_T. In some embodiments, a target Huntingtin site is selected from rs34315806_C, rs362273_A, rs362331_T, rs363099_C, rs7685686_A, rs362306_G, rs363064_C, rs363075_G, rs2276881_G, rs362271_G, rs362303_C, rs362322_A, rs363088_A, rs6844859_T, rs3025838_C, rs363081_G, rs3025849_A, rs3121419_C, rs2298967_T, rs2298969_A, rs16843804_C, rs4690072_T, rs362310_C, rs3856973_G, and rs2285086_A. In some embodiments, a target Huntingtin site is selected from rs362331_T, rs7685686_A, rs6844859_T, rs2298969_A, rs4690072_T, rs2024115_A, rs3856973_G, rs2285086_A, rs363092_C, rs7691627_G, rs10015979_G, rs916171_C, rs6446723_T, rs11731237_T, rs362272_G, rs4690073_G, and rs363096_T. In some embodiments, a target Huntingtin site is selected from rs362267, rs6844859, rs1065746, rs7685686, rs362331, rs362336, rs2024115, rs362275, rs362273, rs362272, rs3025805, rs3025806, rs35892913, rs363125, rs17781557, rs4690072, rs4690074, rs1557210, rs363088, rs362268, rs362308, rs362307, rs362306, rs362305, rs362304, rs362303, rs362302, rs363075 and rs2298969. In some embodiments, a target Huntingtin site is selected from:

Frequency of Heterozygosity for 24 SNP Sites in the Huntingtin mRNA

| Location in mRNA (Position, nt) | Reference Number | Percent Heterozygosity Controls | HD Patients |
|---|---|---|---|
| ORF, exon 20 (2822) | rs363075 | G/A, 10.3% (G/G, 89.7%) | G/A, 12.8% (G/G, 86.2%; A/A, 0.9%) |
| ORF, exon 25 (3335) | rs35892913 | G/A, 10.3% (G/G, 89.7%) | G/A, 13.0% (G/G, 86.1%; A/A, 0.9%) |
| ORF, exon 25 (3389) | rs1065746 | G/C, 0% (G/G, 100%) | G/C, 0.9% (G/G, 99.1%) |
| ORF, exon 25 (3418) | rs17781557 | T/G, 12.9% (T/T, 87.1%) | T/G, 1.9% (T/T, 98.1%) |
| ORF, exon 29 (3946) | rs4690074 | C/T, 37.9% (C/C, 50.9%; T/T, 11.2) | C/T, 35.8% (C/C, 59.6%; T/T, 4.6%) |
| ORF, exon 39 (5304) | rs363125 | C/A, 17.5% (C/C, 79.0%; A/A, 3.5%) | C/A, 11.0% (C/C, 87.2%; A/A, 1.8%) |

Frequency of Heterozygosity for 24 SNP Sites in the Huntingtin mRNA

| Location in mRNA (Position, nt) | Reference Number | Percent Heterozygosity Controls | HD Patients |
|---|---|---|---|
| ORF, exon 44 (6150) | exon 44 | G/A, 0% (G/G, 100%) | G/A, 2.8% (G/G, 97.2%) |
| ORF, exon 48 (6736) | rs362336 | G/A, 38.7% (G/G, 49.6%; A/A, 11.7%) | G/A, 37.4% (G/G, 57.9%; A/A, 4.7%) |
| ORF, exon 50 (7070) | rs362331 | T/C, 45.7% (T/T, 31.0%; C/C, 23.3%) | T/C, 39.4% (T/T, 49.5%; C/C, 11.0%) |
| ORF, exon 57 (7942) | rs362273 | A/G, 40.3% (A/A, 48.2%; G/G, 11.4%) | A/G, 35.2% (A/A, 60.2%; G/G, 4.6%) |
| ORF, exon 61 (8501) | rs362272 | G/A, 37.1% (G/G, 51.7%; A/A, 11.2%) | G/A, 36.1% (G/G, 59.3%; A/A, 4.6%) |
| ORF, exon 65 (9053) | rs3025806 | A/T, 0% (C/C, 100%) | A/T, 0% (C/C, 100%) |
| ORF, exon 65 (9175) | exon 65 | G/A, 2.3% (G/G, 97.7%) | G/A, 0% (G/G, 100%) |
| ORF, exon 67 (9523) | rs362308 | T/C, 0% (T/T, 100%) | T/C, 0% (T/T, 100%) |
| 3'UTR, exon 67 (9633) | rs362307 | C/T, 13.0% (C/C, 87.0%) | C/T, 48.6% (C/C, 49.5%; T/T, 1.9%) |
| 3'UTR, exon 67 (9888) | rs362306 | G/A, 36.0% (G/G, 52.6%; A/A, 11.4%) | G/A, 35.8% (G/G, 59.6%; A/A, 4.6%) |
| 3'UTR, exon 67 (9936) | rs362268 | C/G, 36.8% (C/C, 50.0%; G/G 13.2%) | C/G, 35.8% (C/C, 59.6%; G/G, 4.6%) |
| 3'UTR, exon 67 (9948) | rs362305 | C/G, 20.2% (C/C, 78.1%; G/G 1.8%) | C/G, 11.9% (C/C, 85.3%; G/G, 2.8%) |
| 3'UTR, exon 67 (10060) | rs362304 | C/A, 22.8% (C/C, 73.7%; A/A, 3.5%) | C/A, 11.9% (C/C, 85.3%; AA, 2.8%) |
| 3'UTR, exon 67 (10095) | rs362303 | C/T, 18.4% (C/C, 79.8%; T/T, 1.8%) | C/A, 11.9% (C/C, 85.3%; T/T, 2.8%) |
| 3'UTR, exon 67 (10704) | rs1557210 | C/T, 0% (C/C, 100%) | C/T, 0% (C/C, 100%) |
| 3'UTR, exon 67 (10708) | rs362302 | C/T, 4.3% (C/C, 95.7%) | C/T, 0% (C/C, 100%) |
| 3'UTR, exon 67 (10796) | rs3025805 | G/T, 0% (G/G, 100%) | G/T, 0% (G/G, 100%) |
| 3'UTR, exon 67 (11006) | rs362267 | C/T, 36.2% (C/C, 52.6%; T/T, 11.2%) | C/T, 35.5% (C/C, 59.8%; T/T, 4.7%) |

In some embodiments, a chirally controlled oligonucleotide composition targets two or more sites. In some embodiments, targeted two or more sites are selected from sited listed herein.

It is understood by a person having ordinary skill in the art that provided methods apply to any similar targets containing a mismatch. In some embodiments, a mismatch is between a maternal and paternal gene. Additional exemplary targets for suppression and/or knockdown, including allele-specific suppression and/or knockdown, can be any genetic abnormalities, e.g., mutations, related to any diseases. In some embodiments, a target, or a set of targets, is selected from genetic determinants of diseases, e.g., as disclosed in Xiong, et al., The human splicing code reveals new insights into the genetic determinants of disease. *Science* Vol. 347 no. 6218 DOI: 10.1126/science.1254806. In some embodiments, a mismatch is between a mutant and a wild type.

In some embodiments, provided chirally controlled oligonucleotide compositions and methods are used to selectively suppress oligonucleotides with a mutation in a disease. In some embodiments, a disease is cancer. In some embodiments, provided chirally controlled oligonucleotide compositions and methods are used to selectively suppress transcripts with mutations in cancer. In some embodiments, provided chirally controlled oligonucleotide compositions and methods are used to suppress transcripts of KRAS. Exemplary target KRAS sites comprises G12V=GGU→GUU Position 227 G→U, G12D=GGU→GAU Position 227 G→A and G13D=GGC→GAC Position 230 G→A.

In some embodiments, provided chirally controlled oligonucleotide compositions and methods provide allele-specific suppression of a transcript in an organism. In some embodiments, an organism comprises a target gene for which two or more alleles exist. For example, a subject has a wild type gene in its normal tissues, while the same gene is mutated in diseased tissues such as in a tumor. In some embodiments, the present invention provides chirally controlled oligonucleotide compositions and methods that selectively suppress one allele, for example, one with a mutation or SNP. In some embodiments, the present invention provides treatment with higher efficacy and/or low toxicity, and/or other benefits as described in the application.

In some embodiments, provided chirally controlled oligonucleotide compositions comprises oligonucleotides of one oligonucleotide type. In some embodiments, provided chirally controlled oligonucleotide compositions comprises oligonucleotides of only one oligonucleotide type. In some embodiments, provided chirally controlled oligonucleotide compositions has oligonucleotides of only one oligonucleotide type. In some embodiments, provided chirally controlled oligonucleotide compositions comprises oligonucleotides of two or more oligonucleotide types. In some embodiments, using such compositions, provided methods can target more than one target. In some embodiments, a chirally controlled oligonucleotide composition comprising two or more oligonucleotide types targets two or more targets. In some embodiments, a chirally controlled oligonucleotide composition comprising two or more oligonucleotide types targets two or more mismatches. In some embodiments, a single oligonucleotide type targets two or more targets, e.g., mutations. In some embodiments, a target region of oligonucleotides of one oligonucleotide type comprises two or more "target sites" such as two mutations or SNPs.

In some embodiments, oligonucleotides in a provided chirally controlled oligonucleotide composition optionally comprise modified bases or sugars. In some embodiments, a provided chirally controlled oligonucleotide composition does not have any modified bases or sugars. In some embodiments, a provided chirally controlled oligonucleotide composition does not have any modified bases. In some embodiments, oligonucleotides in a provided chirally controlled oligonucleotide composition comprise modified bases and sugars. In some embodiments, oligonucleotides in a provided chirally controlled oligonucleotide composition comprise a modified base. In some embodiments, oligonucleotides in a provided chirally controlled oligonucleotide composition comprise a modified sugar. Modified bases and sugars for oligonucleotides are widely known in the art, including but not limited in those described in the present disclosure. In some embodiments, a modified base is 5-mC. In some embodiments, a modified sugar is a 2'-modified sugar. Suitable 2'-modification of oligonucleotide sugars are widely known by a person having ordinary skill in the art. In some embodiments, 2'-modifications include but are not limited to 2'-OR$^1$, wherein R$^1$ is not hydrogen. In some embodiments, a 2'-modification is 2'-OR$^1$, wherein R$^1$ is optionally substituted $C_{1-6}$ aliphatic. In some embodiments, a 2'-modification is 2'-MOE. In some embodiments, a modification is 2'-halogen. In some embodiments, a modification is 2'-F. In some embodiments, modified bases or sugars may further enhance activity, stability and/or selectivity of a chirally controlled oligonucleotide composition, whose common pattern of backbone chiral centers provides unexpected activity, stability and/or selectivity.

In some embodiments, a provided chirally controlled oligonucleotide composition does not have any modified sugars. In some embodiments, a provided chirally controlled oligonucleotide composition does not have any 2'-modified sugars. In some embodiments, the present invention surprisingly found that by using chirally controlled oligonucleotide compositions, modified sugars are not needed for stability, activity, and/or control of cleavage patterns. Furthermore, in some embodiments, the present invention surprisingly found that chirally controlled oligonucleotide compositions of oligonucleotides without modified sugars deliver better properties in terms of stability, activity, turn-over and/or control of cleavage patterns. For example, in some embodiments, it is surprising found that chirally controlled oligonucleotide compositions of oligonucleotides having no modified sugars dissociates much faster from cleavage products and provide significantly increased turn-over than compositions of oligonucleotides with modified sugars.

In some embodiments, oligonucleotides of provided chirally controlled oligonucleotide compositions useful for provided methods have structures as extensively described in the present disclosure. In some embodiments, an oligonucleotide has a wing-core-wing structure as described. In some embodiments, the common pattern of backbone chiral centers of a provided chirally controlled oligonucleotide composition comprises (Sp)mRp as described. In some embodiments, the common pattern of backbone chiral centers of a provided chirally controlled oligonucleotide composition comprises (Sp)$_2$Rp. In some embodiments, the common pattern of backbone chiral centers of a provided chirally controlled oligonucleotide composition comprises (Sp)m(Rp)n as described. In some embodiments, the common pattern of backbone chiral centers of a provided chirally controlled oligonucleotide composition comprises (Rp)n(Sp)m as described. In some embodiments, the common pattern of backbone chiral centers of a provided chirally controlled oligonucleotide composition comprises Rp(Sp)m as described. In some embodiments, the common pattern of backbone chiral centers of a provided chirally controlled oligonucleotide composition comprises Rp(Sp)$_2$. In some embodiments, the common pattern of backbone chiral centers of a provided chirally controlled oligonucleotide composition comprises (Sp)m(Rp)n(Sp)t as described. In some embodiments, the common pattern of backbone chiral centers of a provided chirally controlled oligonucleotide composition comprises (Sp)mRp(Sp)t as described. In some embodiments, the common pattern of backbone chiral centers of a provided chirally controlled oligonucleotide composition comprises (Sp)t(Rp)n(Sp)m as described. In some embodiments, the common pattern of backbone chiral centers of a provided chirally controlled oligonucleotide composition comprises (Sp)tRp(Sp)m as described. In some embodiments, the common pattern of backbone chiral centers of a provided chirally controlled oligonucleotide composition comprises SpRpSpSp. In some embodiments, the common pattern of backbone chiral centers of a provided chirally controlled oligonucleotide composition comprises (Sp)$_2$Rp(Sp)$_2$. In some embodiments, the common pattern of backbone chiral centers of a provided chirally controlled oligonucleotide composition comprises (Sp)$_3$Rp(Sp)$_3$. In some embodiments, the common pattern of backbone chiral centers of a provided chirally controlled oligonucleotide composition comprises (Sp)$_4$Rp(Sp)$_4$. In some embodiments, the common pattern of backbone chiral centers of a provided chirally controlled oligonucleotide composition comprises $(Sp)tRp(Sp)_5$. In some embodiments, the common pattern of backbone chiral centers of a provided chirally controlled oligonucleotide composition comprises $SpRp(Sp)_5$. In some embodiments, the common pattern of backbone chiral centers of a provided chirally controlled oligonucleotide composition comprises $(Sp)_2Rp(Sp)_5$. In some embodiments, the common pattern of backbone chiral centers of a provided chirally controlled oligonucleotide composition comprises $(Sp)_3Rp(Sp)_5$. In some embodiments, the common pattern of backbone chiral centers of a provided chirally controlled oligonucleotide composition comprises $(Sp)_4Rp(Sp)_5$. In some embodiments, the common pattern of backbone chiral centers of a provided chirally controlled oligonucleotide composition comprises $(Sp)_5Rp(Sp)_5$. In some embodiments, a common pattern of backbone chiral centers has only one Rp, and each of the other internucleotidic linkages is Sp. In some embodiments, a common base length is greater than 10, 11, 12, 13, 14, 15, 16, 17, 18, 19, 20, 21, 22, 23, 24, 25, 26, 27, 28, 29, 30, 32, 35, 40, 45 or 50 as described in the present disclosure. In some embodiments, a common base length is greater than 10. In some embodiments, a common base length is greater than 11. In some embodiments, a common base length is greater than 12. In some embodiments, a common base length is greater than 13. In some embodiments, a common base length is greater than 14. In some embodiments, a common base length is greater than 15. In some embodiments, a common base length is greater than 16. In some embodiments, a common base length is greater than 17. In some embodiments, a common base length is greater than 18. In some embodiments, a common base length is greater than 19. In some embodiments, a common base length is greater than 20. In some embodiments, a common base length is greater than 21. In some embodiments, a common base length is greater than 22. In some embodiments, a common base length is greater than 23. In some embodiments, a common base length is greater than 24. In some embodiments, a common base length is greater than 25. In some embodiments, a common base length is greater than 26. In some embodiments, a common base length is greater than 27. In some embodiments, a common base length is greater than 28. In some embodiments, a common base length is greater than 29. In some embodiments, a common base length is greater than 30. In some embodiments, a common base length is greater than 31. In some embodiments, a common base length is greater than 32. In some embodiments, a common base length is greater than 33. In some embodiments, a common base length is greater than 34. In some embodiments, a common base length is greater than 35.

In some embodiments, a provided chirally controlled oligonucleotide composition provides higher turn-over. In some embodiments, cleavage products from a nucleic acid polymer dissociate from oligonucleotides of a provided chirally controlled oligonucleotide composition at a faster rate than from oligonucleotides of a reference oligonucleotide composition, for example, a chirally uncontrolled oligonucleotide composition. In some embodiments, a provided chirally controlled oligonucleotide composition can be administered in lower unit dosage, and/or total dosage, and/or fewer doses than chirally uncontrolled oligonucleotide composition.

In some embodiments, a chirally controlled oligonucleotide composition provides fewer cleavage sites in the sequence of a nucleic acid polymer that is complementary to its common base sequence or a sequence within its common base sequence when compared to a reference oligonucleotide composition. In some embodiments, a chirally controlled oligonucleotide composition provides fewer cleavage sites in the sequence of a nucleic acid polymer that is complementary to its common base sequence. In some embodiments, a nucleic acid polymer is selectively cleaved at a single site within the sequence that is complimentary to the common base sequence, or a sequence within the common base sequence, of a chirally controlled oligonucleotide composition. In some embodiments, a chirally controlled oligonucleotide composition provides higher cleavage percentage at a cleavage site within the sequence that is complimentary to the common base sequence, or a sequence within the common base sequence, of the chirally controlled oligonucleotide composition. In some embodiments, a chirally controlled oligonucleotide composition provides higher cleavage percentage at a cleavage site within the sequence that is complimentary to the common base sequence of the chirally controlled oligonucleotide composition. In some embodiments, a site having a higher cleavage percentage is a cleavage site when a reference oligonucleotide composition is used. In some embodiments, a site having a higher cleavage percentage is a cleavage site that is not present when a reference oligonucleotide composition is used.

It is surprisingly found that with reduced number of cleavage sites in the complimentary sequence, cleavage rate can be unexpectedly increased and/or higher cleavage percentage can be achieved. As demonstrated in the examples of this disclosure, provided chirally controlled oligonucleotide compositions that produce fewer cleavage sites, especially those that provide single-site cleavage, within the complementary sequences of target nucleic acid polymers provide much higher cleavage rates and much lower levels of remaining un-cleaved nucleic acid polymers. Such results are in sharp contrast to general teachings in the art in which more cleavage sites have been pursued in order to increase the cleavage rate.

In some embodiments, a chirally controlled oligonucleotide composition increases cleavage rate by 1.5 fold compared to a reference oligonucleotide composition. In some embodiments, cleavage rate is increased by at least 2 fold. In some embodiments, cleavage rate is increased by at least 3 fold. In some embodiments, cleavage rate is increased by at least 4 fold. In some embodiments, cleavage rate is increased by at least 5 fold. In some embodiments, cleavage rate is increased by at least 6 fold. In some embodiments, cleavage rate is increased by at least 7 fold. In some embodiments, cleavage rate is increased by at least 8 fold. In some embodiments, cleavage rate is increased by at least 9 fold. In some embodiments, cleavage rate is increased by at least 10 fold. In some embodiments, cleavage rate is increased by at least 11 fold. In some embodiments, cleavage rate is increased by at least 12 fold. In some embodiments, cleavage rate is increased by at least 13 fold. In some embodiments, cleavage rate is increased by at least 14 fold. In some embodiments, cleavage rate is increased by at least 15 fold. In some embodiments, cleavage rate is increased by at least 20 fold. In some embodiments, cleavage rate is increased by at least 30 fold. In some embodiments, cleavage rate is increased by at least 40 fold. In some embodiments, cleavage rate is increased by at least 50 fold. In some embodiments, cleavage rate is increased by at least 60 fold. In some embodiments, cleavage rate is increased by at least 70 fold. In some embodiments, cleavage rate is increased by at least 80 fold. In some embodiments, cleavage rate is increased by at least 90 fold. In some embodiments, cleavage rate is increased by at least 100 fold. In some embodiments, cleavage rate is increased by at least 200 fold. In some embodiments, cleavage rate is increased by at least 300 fold. In some embodiments, cleavage rate is increased by at least 400 fold. In some embodiments, cleavage rate is increased by at least 500 fold. In some embodiments, cleavage rate is increased by at least more than 500 fold.

In some embodiments, a chirally controlled oligonucleotide composition provides a lower level of remaining, un-cleaved target nucleic acid polymer compared to a reference oligonucleotide composition. In some embodiments, it is 1.5 fold lower. In some embodiments, it is at least 2 fold lower. In some embodiments, it is at least 3 fold lower. In some embodiments, it is at least 4 fold lower. In some embodiments, it is at least 5 fold lower. In some embodiments, it is at least 6 fold lower. In some embodiments, it is at least 7 fold lower. In some embodiments, it is at least 8 fold lower. In some embodiments, it is at least 9 fold lower. In some embodiments, it is at least 10 fold lower. In some embodiments, it is at least 11 fold lower. In some embodiments, it is at least 12 fold lower. In some embodiments, it is at least 13 fold lower. In some embodiments, it is at least 14 fold lower. In some embodiments, it is at least 15 fold lower. In some embodiments, it is at least 20 fold lower. In some embodiments, it is at least 30 fold lower. In some embodiments, it is at least 40 fold lower. In some embodiments, it is at least 50 fold lower. In some embodiments, it is at least 60 fold lower. In some embodiments, it is at least 70 fold lower. In some embodiments, it is at least 80 fold lower. In some embodiments, it is at least 90 fold lower. In some embodiments, it is at least 100 fold lower. In some embodiments, it is at least 200 fold lower. In some embodiments, it is at least 300 fold lower. In some embodiments, it is at least 400 fold lower. In some embodiments, it is at least 500 fold lower. In some embodiments, it is at least 1000 fold lower.

As discussed in detail herein, the present invention provides, among other things, a chirally controlled oligonucleotide composition, meaning that the composition contains a plurality of oligonucleotides of at least one type. Each oligonucleotide molecule of a particular "type" is comprised of preselected (e.g., predetermined) structural elements with respect to: (1) base sequence; (2) pattern of backbone linkages; (3) pattern of backbone chiral centers; and (4) pattern of backbone P-modification moieties. In some embodiments, provided oligonucleotide compositions contain oligonucleotides that are prepared in a single synthesis process. In some embodiments, provided compositions contain oligonucleotides having more than one chiral configuration within a single oligonucleotide molecule (e.g., where different residues along the oligonucleotide have different stereochemistry); in some such embodiments, such oligonucleotides may be obtained in a single synthesis process, without the need for secondary conjugation steps to generate individual oligonucleotide molecules with more than one chiral configuration.

Oligonucleotide compositions as provided herein can be used as agents for modulating a number of cellular processes and machineries, including but not limited to, transcription, translation, immune responses, epigenetics, etc. In addition, oligonucleotide compositions as provided herein can be used as reagents for research and/or diagnostic purposes. One of ordinary skill in the art will readily recognize that the present invention disclosure herein is not limited to particular use but is applicable to any situations where the use of synthetic oligonucleotides is desirable. Among other things, provided compositions are useful in a variety of therapeutic, diagnostic, agricultural, and/or research applications.

In some embodiments, provided oligonucleotide compositions comprise oligonucleotides and/or residues thereof that include one or more structural modifications as described in detail herein. In some embodiments, provided oligonucleotide compositions comprise oligonucleoties that contain one or more nucleic acid analogs. In some embodiments, provided oligonucleotide compositions comprise oligonucleotides that contain one or more artificial nucleic acids or residues, including but not limited to: peptide nucleic acids (PNA), Morpholino and locked nucleic acids (LNA), glycon nucleic acids (GNA), threose nucleic acids (TNA), Xeno nucleic acids (ZNA), and any combination thereof.

In any of the embodiments, the invention is useful for oligonucleotide-based modulation of gene expression, immune response, etc. Accordingly, stereodefined, oligonucleotide compositions of the invention, which contain oligonucleotides of predetermined type (i.e., which are chirally controlled, and optionally chirally pure), can be used in lieu of conventional stereo-random or chirally impure counterparts. In some embodiments, provided compositions show enhanced intended effects and/or reduced unwanted side effects. Certain embodiments of biological and clinical/therapeutic applications of the invention are discussed explicitly below.

Various dosing regimens can be utilized to administer provided chirally controlled oligonucleotide compositions. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week for more than one week. In some embodiments, a dosing regimen comprises administering one dose per week for 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks for more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month for more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for about 30 weeks. In some embodiments, a dosing regimen comprises administering one dose per week for 26 weeks. In some embodiments, a chirally controlled oligonucleotide composition is administered according to a dosing regimen that differs from that utilized for a chirally uncontrolled (e.g., stereorandom) oligonucleotide composition of the same sequence, and/or of a different chirally controlled oligonucleotide composition of the same sequence. In some embodiments, a chirally controlled oligonucleotide composition is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, a chirally controlled oligonucleotide composition is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, a chirally controlled oligonucleotide composition has a longer dosing regimen compared to the corresponding chirally uncontrolled oligonucleotide composition. In some embodiments, a chirally controlled oligonucleotide composition has a shorter time period between at least two doses compared to the corresponding chirally uncontrolled oligonucleotide composition. Without wishing to be limited by theory, Applicant notes that in some embodiments longer dosing regimen, and/or shorter time periods between doses, may be due to the improved safety of a chirally controlled oligonucleotide composition.

A single dose can contain various amounts of a type of chirally controlled oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more (e.g., about 350, 400, 450, 500, 550, 600, 650, 700, 750, 800, 850, 900, 950, 1000 or more) mg of a type of chirally controlled oligonucleotide. In some embodiments, a single dose contains about 1 mg of a type of chirally controlled oligonucleotide. In some embodiments, a single dose contains about 5 mg of a type of chirally controlled oligonucleotide. In some embodiments, a single dose contains about 10 mg of a type of chirally controlled oligonucleotide. In some embodiments, a single dose contains about 15 mg of a type of chirally controlled oligonucleotide. In some embodiments, a single dose contains about 20 mg of a type of chirally controlled oligonucleotide. In some embodiments, a single dose contains about 50 mg of a type of chirally controlled oligonucleotide. In some embodiments, a single dose contains about 100 mg of a type of chirally controlled oligonucleotide. In some embodiments, a single dose contains about 150 mg of a type of chirally controlled oligonucleotide. In some embodiments, a single dose contains about 200 mg of a type of chirally controlled oligonucleotide. In some embodiments, a single dose contains about 250 mg of a type of chirally controlled oligonucleotide. In some embodiments, a single dose contains about 300 mg of a type of chirally controlled oligonucleotide. In some embodiments, a chirally controlled oligonucleotide is administered at a lower amount in a single dose, and/or in total dose, than a chirally uncontrolled oligonucleotide. In some embodiments, a chirally controlled oligonucleotide is administered at a lower amount in a single dose, and/or in total dose, than a chirally uncontrolled oligonucleotide due to improved efficacy. In some embodiments, a chirally controlled oligonucleotide is administered at a higher amount in a single dose, and/or in total dose, than a chirally uncontrolled oligonucleotide. In some embodiments, a chirally controlled oligonucleotide is administered at a higher amount in a single dose, and/or in total dose, than a chirally uncontrolled oligonucleotide due to improved safety.

Biologically Active Oligonucleotides

A provided oligonucleotide composition as used herein may comprise single stranded and/or multiply stranded oligonucleotides. In some embodiments, single-stranded oligonucleotides contain self-complementary portions that may hybridize under relevant conditions so that, as used, even single-stranded oligonucleotides may have at least partially double-stranded character. In some embodiments, an oligonucleotide included in a provided composition is single-stranded, double-stranded, or triple-stranded. In some embodiments, an oligonucleotide included in a provided composition comprises a single-stranded portion and a multiple-stranded portion within the oligonucleotide. In some embodiments, as noted above, individual single-stranded oligonucleotides can have double-stranded regions and single-stranded regions.

In some embodiments, provided compositions include one or more oligonucleotides fully or partially complementary to strand of: structural genes, genes control and/or termination regions, and/or self-replicating systems such as viral or plasmid DNA. In some embodiments, provided compositions include one or more oligonucleotides that are or act as siRNAs or other RNA interference reagents (RNAi agents or iRNA agents), shRNA, antisense oligonucleotides, self-cleaving RNAs, ribozymes, fragment thereof and/or variants thereof (such as Peptidyl transferase 23S rRNA, RNase P, Group I and Group II introns, GIR1 branching ribozymes, Leadzyme, Hairpin ribozymes, Hammerhead ribozymes, HDV ribozymes, Mammalian CPEB3 ribozyme, VS ribozymes, glmS ribozymes, CoTC ribozyme, etc.), microRNAs, microRNA mimics, supermirs, aptamers, antimirs, antagomirs, Ul adaptors, triplex-forming oligonucleotides, RNA activators, long non-coding RNAs, short non-coding RNAs (e.g., piRNAs), immunomodulatory oligonucleotides (such as immunostimulatory oligonucleotides, immunoinhibitory oligonucleotides), GNA, LNA, ENA, PNA, TNA, morpholinos, G-quadruplex (RNA and DNA), antiviral oligonucleotides, and decoy oligonucleotides.

In some embodiments, provided compositions include one or more hybrid (e.g., chimeric) oligonucleotides. In the context of the present disclosure, the term "hybrid" broadly refers to mixed structural components of oligonucleotides. Hybrid oligonucleotides may refer to, for example, (1) an oligonucleotide molecule having mixed classes of nucleotides, e.g., part DNA and part RNA within the single molecule (e.g., DNA-RNA); (2) complementary pairs of nucleic acids of different classes, such that DNA:RNA base pairing occurs either intramolecularly or intermolecularly; or both; (3) an oligonucleotide with two or more kinds of the backbone or internucleotide linkages.

In some embodiments, provided compositions include one or more oligonucleotide that comprises more than one classes of nucleic acid residues within a single molecule. For example, in any of the embodiments described herein, an oligonucleotide may comprise a DNA portion and an RNA portion. In some embodiments, an oligonucleotide may comprise a unmodified portion and modified portion.

Provided oligonucleotide compositions can include oligonucleotides containing any of a variety of modifications, for example as described herein. In some embodiments, particular modifications are selected, for example, in light of intended use. In some embodiments, it is desirable to modify one or both strands of a double-stranded oligonucleotide (or a double-stranded portion of a single-stranded oligonucleoties). In some embodiments, the two strands (or portions) include different modifications. In some embodiments, the two strands include the same modifications. One of skill in the art will appreciate that the degree and type of modifications enabled by methods of the present invention allow for numerous permutations of modifications to be made. Exemplary such modifications are described herein and are not meant to be limiting.

The phrase "antisense strand" as used herein, refers to an oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. The terms "antisense strand" and "guide strand" are used interchangeably herein.

The phrase "sense strand" refers to an oligonucleotide that has the same nucleoside sequence, in whole or in part, as a target sequence such as a messenger RNA or a sequence of DNA. The terms "sense strand" and "passenger strand" are used interchangeably herein.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant. In some embodiments, a target sequence is associated with a disease or disorder.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol.* LIT pp. 123-133; Frier et al., 1986, *Proc. Nat. Acad. Sci. USA* 83:9373-9377; Turner et al., 1987, *I. Ain. Chem. Soc.* 109:3783-3785)

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, e.g., under physiological conditions in the case of in vivo assays or therapeutic treatment, or in the case of in vitro assays, under conditions in which the assays are performed. In some embodiments, non-target sequences differ from corresponding target sequences by at least 5 nucleotides.

When used as therapeutics, a provided oligonucleotide is administered as a pharmaceutical composition. In some embodiments, the pharmaceutical composition comprises a therapeutically effective amount of a provided oligonucleotide comprising, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In another embodiment, the pharmaceutical composition is formulated for intravenous injection, oral administration, buccal administration, inhalation, nasal administration, topical administration, ophthalmic administration or otic administration. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Pharmaceutical Compositions

When used as therapeutics, a provided oligonucleotide or oligonucleotide composition described herein is administered as a pharmaceutical composition. In some embodiments, the pharmaceutical composition comprises a therapeutically effective amount of a provided oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present invention provides a pharmaceutical composition comprising chirally controlled oligonucleotide, or composition thereof, in admixture with a pharmaceutically acceptable excipient. One of skill in the art will recognize that the pharmaceutical compositions include the pharmaceutically acceptable salts of the chirally controlled oligonucleotide, or composition thereof, described above.

A variety of supramolecular nanocarriers can be used to deliver nucleic acids. Exemplary nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, polymer micelles, quantum dots and lipoplexes.

Additional nucleic acid delivery strategies are known in addition to the exemplary delivery strategies described herein.

In therapeutic and/or diagnostic applications, the compounds of the invention can be formulated for a variety of modes of administration, including systemic and topical or localized administration. Techniques and formulations generally may be found in Remington, The Science and Practice of Pharmacy, (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection.

The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g., patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with oligonucleotides of this invention. For example, chemotherapeutic agents or other anti-proliferative agents may be combined with the oligonucleotides of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

The function and advantage of these and other embodiments of the present invention will be more fully understood from the examples described below. The following examples are intended to illustrate the benefits of the present invention, but do not exemplify the full scope of the invention.

In some embodiments, the present invention provides the following exemplary embodiments:

E1. A chirally controlled oligonucleotide composition comprising oligonucleotides defined by having:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

E2. The composition of example E1, wherein one or more bases are modified.

E3. The composition of example E1, wherein none of the bases are modified.

E4. The composition of any one of the preceding examples, wherein the common base sequence has at least 8 bases.

E5. The composition of any one of the preceding examples, wherein the common base sequence has at least 10 bases.

E6. The composition of any one of the preceding examples, wherein the common base sequence has at least 15 bases.

E7. The composition of any one of the preceding examples, wherein at least about 20% of the oligonucleotides in the composition have the common base sequence and length, the common pattern of backbone linkages, and the common pattern of backbone chiral centers.

E8. The composition of any one of the preceding examples, wherein at least about 50% of the oligonucleotides in the composition have the common base sequence and length, the common pattern of backbone linkages, and the common pattern of backbone chiral centers.

E9. The composition of any one of the preceding examples, wherein at least about 80% of the oligonucleotides in the composition have the common base sequence and length, the common pattern of backbone linkages, and the common pattern of backbone chiral centers.

E10. The composition of any one of the preceding examples, wherein at least about 85% of the oligonucleotides in the composition have the common base sequence and length, the common pattern of backbone linkages, and the common pattern of backbone chiral centers.

E11. The composition of any one of the preceding examples, wherein at least about 90% of the oligonucleotides in the composition have the common base sequence and length, the common pattern of backbone linkages, and the common pattern of backbone chiral centers.

E12. The composition of any one of the preceding examples, wherein at least about 95% of the oligonucleotides in the composition have the common base sequence and length, the common pattern of backbone linkages, and the common pattern of backbone chiral centers.

E13. The composition of any one of the preceding examples, wherein at least about 97% of the oligonucleotides in the composition have the common base sequence and length, the common pattern of backbone linkages, and the common pattern of backbone chiral centers.

E14. The composition of any one of the preceding examples, wherein at least about 98% of the oligonucleotides in the composition have the common base sequence and length, the common pattern of backbone linkages, and the common pattern of backbone chiral centers.

E15. The composition of any one of the preceding examples, wherein at least about 99% of the oligonucleotides in the composition have the common base sequence and length, the common pattern of backbone linkages, and the common pattern of backbone chiral centers.

E16. The composition of any one of the preceding examples, wherein the single oligonucleotide comprises one or more chiral, modified phosphate linkages.

E17. The composition of any one of the preceding examples, wherein the single oligonucleotide has a wing-core-wing structure.

E18. The composition of any one of the preceding examples, wherein each wing optionally contains chiral internucleotidic linkages.

E19. The composition of any one of the preceding examples, wherein the chiral internucleotidic linkages within each wing independently have the same stereochemistry.

E20. The composition of any one of the preceding examples, wherein the chiral internucleotidic linkages of both wings are of the same stereochemistry.

E21. The composition of any one of the preceding examples, wherein the chiral internucleotidic linkages within each wing independently have the same stereochemistry, and the stereochemistry of the first wing is different from that of the second wing.

E22. The composition of any one of the preceding examples, wherein the first wing region independently has a length of one or more bases.

E23. The composition of any one of the preceding examples, wherein the first wing region independently has a length of two or more bases.

E24. The composition of any one of the preceding examples, wherein the first wing region independently has a length of three or more bases.

E25. The composition of any one of the preceding examples, wherein the first wing region independently has a length of four or more bases.

E26. The composition of any one of the preceding examples, wherein the first wing region independently has a length of five or more bases.

E27. The composition of any one of the preceding examples, wherein the first wing region independently has a length of less than eight bases.

E28. The composition of any one of the preceding examples, wherein the second wing region independently has a length of one or more bases.
E29. The composition of any one of the preceding examples, wherein the second wing region independently has a length of two or more bases.
E30. The composition of any one of the preceding examples, wherein the second wing region independently has a length of three or more bases.
E31. The composition of any one of the preceding examples, wherein the second wing region independently has a length of four or more bases.
E32. The composition of any one of the preceding examples, wherein the second wing region independently has a length of five or more bases.
E33. The composition of any one of the preceding examples, wherein the second wing region independently has a length of less than eight bases.
E34. The composition of any one of the preceding examples, wherein the core region has a length of five or more bases.
E36. The composition of any one of the preceding examples, wherein the core region has a length of six or more bases.
E37. The composition of any one of the preceding examples, wherein the core region has a length of seven or more bases.
E38. The composition of any one of the preceding examples, wherein the core region has a length of eight or more bases.
E39. The composition of any one of the preceding examples, wherein the core region has a length of nine or more bases.
E40. The composition of any one of the preceding examples, wherein the core region has a length of 10 or more bases.
E41. The composition of any one of the preceding examples, wherein the core region has a length of 15 or more bases.
E42. The composition of any one of the preceding examples, wherein the core region has repeating pattern of internucleotidic linkage stereochemistry.
E43. The composition of any one of the preceding examples, wherein the repeating pattern of internucleotidic linkage stereochemistry is (Sp)m(Rp)n or (Rp)n(Sp)m, wherein each of m and n is independently 1, 2, 3, 4, 5, 6, 7 or 8.
E44. The composition of example E43, wherein m>n.
E45. The composition of example E43 or E44, wherein n is 1.
E46. The composition of any one of the preceding examples, wherein the core region comprises a internucleotidic linkage stereochemistry pattern of (Sp)n(Rp)n or (Rp)n(Sp)m, wherein each of m and n is independently 2, 3, 4, 5, 6, 7 or 8.
E47. The composition of example E46, wherein m>n.
E48. The composition of example E47, wherein n is 1.
E49. The composition of any one of the preceding examples, wherein 50% percent or more of the chiral internucleotidic linkages of the core region have Sp configuration.
E50. The composition of any one of the preceding examples, wherein 60% percent or more of the chiral internucleotidic linkages of the core region have Sp configuration.
E51. The composition of any one of the preceding examples, wherein the core region comprises at least 2 Rp internucleotidic linkages.
E52. The composition of any one of the preceding examples, wherein the core region comprises at least 3 Rp internucleotidic linkages.
E53 The composition of any one of the preceding examples, wherein the core region comprises at least 4 Rp internucleotidic linkages.
E54. The composition of any one of the preceding examples, wherein the core region comprises at least 5 Rp internucleotidic linkages.
E55. The composition of any one of the preceding examples, wherein at least 5 backbone internucleotidic linkages are chiral.
E56. The composition of any one of the preceding examples, wherein each backbone internucleotidic linkage is chiral.
E57. The composition of any one of examples E1-E55 wherein at least one backbone internucleotidic linkage is a phosphate linkage.
E58. The composition of any one of examples E1-E16, wherein the single oligonucleotide comprises a region in which at least one of the first, second, third, fifth, seventh, eighteenth, nineteenth and twentieth internucleotidic linkages is chiral.
E59. The composition of example E58, wherein at least two of the first, second, third, fifth, seventh, eighteenth, nineteenth and twentieth internucleotidic linkages are chiral.
E60. The composition of any one of examples E58-E59, wherein at least three of the first, second, third, fifth, seventh, eighteenth, nineteenth and twentieth internucleotidic linkages are chiral.
E61. The composition of any one of examples E58-E60, wherein at least four of the first, second, third, fifth, seventh, eighteenth, nineteenth and twentieth internucleotidic linkages are chiral.
E62. The composition of any one of examples E58-E61, wherein at least one internucleotidic linkage in the region is achiral.
E63. The composition of any one of examples E58-E62, wherein at least one internucleotidic linkage in the region is a phosphate linkage.
E64. The composition of any one of examples E58-E63, wherein at least 10% of the internucleotidic linkages in the region are phosphate linkages.
E65. The composition of any one of examples E58-E64, wherein the first internucleotidic linkage is an Sp modified internucleotidic linkage.
E66. The composition of any one of examples E58-E64, wherein the first internucleotidic linkage is an Rp modified internucleotidic linkage.
E67. The composition of any one of examples E58-E66, wherein the second internucleotidic linkage is an Sp modified internucleotidic linkage.
E68. The composition of any one of examples E58-E66, wherein the second internucleotidic linkage is an Rp modified internucleotidic linkage.
E69. The composition of any one of examples E58-E68, wherein the third internucleotidic linkage is an Sp modified internucleotidic linkage.
E70. The composition of any one of examples E58-E68, wherein the third internucleotidic linkage is an Rp modified internucleotidic linkage.
E71. The composition of any one of examples E58-E70, wherein the fifth internucleotidic linkage is an Sp modified internucleotidic linkage.
E72. The composition of any one of examples E58-E70, wherein the fifth internucleotidic linkage is an Rp modified internucleotidic linkage.
E73. The composition of any one of examples E58-E72, wherein the seventh internucleotidic linkage is an Sp modified internucleotidic linkage.
E74. The composition of any one of examples E58-E72, wherein the seventh internucleotidic linkage is an Rp modified internucleotidic linkage.
E75. The composition of any one of examples E58-E74, wherein the eighteenth internucleotidic linkage is an Sp modified internucleotidic linkage.

E76. The composition of any one of examples E58-E74, wherein the eighteenth internucleotidic linkage is an Rp modified internucleotidic linkage.
E77. The composition of any one of examples E58-E76, wherein the nineteenth internucleotidic linkage is an Sp modified internucleotidic linkage.
E78. The composition of any one of examples E58-E76, wherein the nineteenth internucleotidic linkage is an Rp modified internucleotidic linkage.
E79. The composition of any one of examples E58-E78, wherein the twentieth internucleotidic linkage is an Sp modified internucleotidic linkage.
E80. The composition of any one of examples E58-E78, wherein the twentieth internucleotidic linkage is an Rp modified internucleotidic linkage.
E81. The composition of any one of examples E58-E80, wherein the region has a length of 21 bases.
E82. The composition of any one of examples E58-E81, wherein the single oligonucleotide has a length of 21 bases.
E83. The composition of any one of examples E58-E82, wherein the chiral internucleotidic linkage is phosphorothioate.
E84. The composition of any one of the preceding examples, wherein the chiral internucleotidic linkage has the structure of formula I.
E85. The composition of any one of the preceding examples, wherein the single oligonucleotide does not have 2'-OR$^1$ on a sugar moiety.
E86. The composition of any one of the preceding examples, wherein each sugar moiety does not have 2'-MOE.
E87. The composition of any one of the preceding examples, wherein the single oligonucleotide is not (Sp, Sp, Rp, Sp, Sp, Rp, Sp, Sp, Rp, Sp, Sp)-d [5mCs1As1Gs1Ts15mCs1Ts1Gs15mCs1Ts1Ts15mCs1G] (SEQ ID NO: 152) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCsTs5mCsAsGsTs5mCsTsGs5mCsTsTs5mCs<u>Gs5mCsAs5mCs5mC</u> (5R-(SSR)3-5R) (SEQ ID NO: 153), wherein in the underlined nucleotide are 2'-O-MOE modified.
E88. The composition of any one of the preceding examples, wherein the single oligonucleotide is not an oligonucleotide selected from:

| ONT-106 | (Rp)-uucuAGAccuG uuuuGcuudTsdT | PCSK9 sense | (SEQ ID NO: 154) |
|---|---|---|---|
| ONT-107 | (Sp)-uucuAGAccuGu uuuGcuudTsdT | PCSK9 sense | (SEQ ID NO: 155) |
| ONT-108 | (Rp)-AAGcAAAAcAGG UCuAGAAdTsdT | PCSK9 antisense | (SEQ ID NO: 156) |
| ONT-109 | (Sp)-AAGcAAAAcAGGU CuAGAAdTsdT | PCSK9 antisense | (SEQ ID NO: 157) |
| ONT-110 | (Rp, Rp)-asAGcAAAA cAGGUCuAGAAdTsdT | PCSK9 anti sense | (SEQ ID NO: 158) |
| ONT-111 | (Sp, Rp)-asGcAAAAc AGGUCuAGAAdTsdT | PCSK9 anti sense | (SEQ ID NO: 159) |
| ONT-112 | (Sp, Sp)-asGcAAAAc AGGUCuAGAAdTsdT | PCSK9 anti sense | (SEQ ID NO: 160) |
| ONT-113 | (Rp, Sp)-asGcAAAAcA GGUCuAGAAdTsdT | PCSK9 anti sense | (SEQ ID NO: 161) | wherein lower case letters represent 2'OMe RNA residues; capital letters represent 2'OH RNA residues; and bolded and "s" indicates a phosphorothioate moiety; and

| PCSK9 (1) | (All (Sp))-ususc susAsGsAscscsusG sususususGscsusu sdTsdT | (SEQ ID NO: 162) |
|---|---|---|
| PCSK9 (2) | (All (Rp))-ususc susAsGsAscscsusG sususususGscsusu sdTsdT | (SEQ ID NO: 163) |
| PCSK9 (3) | (All (Sp))-ususcu AsGsAsccuGsuuuuG scuusdTsdT | (SEQ ID NO: 164) |
| PCSK9 (4) | (All (Rp))-ususcu AsGsAsccuGsuuuuG scuusdTsdT | (SEQ ID NO: 165) |
| PCSK9 (5) | (Rp, Sp, Rp, Sp, Rp, Sp, Rp, Sp, Rp, Sp, Rp, Sp, Rp, Sp, Rp, Sp, Rp, Sp, Rp, Sp)-ususcsusAsGsAscs csusGsusususususGs csususdTsdT | (SEQ ID NO: 166) |
| PCSK9 (6) | (Sp, Rp, Sp, Rp, Sp, Rp, Sp, Rp, Sp, Rp, Sp, Rp, Sp, Rp, Sp, Rp, Sp, Rp, Sp, Rp)-ususcsusAsGsAscs csusGsusususususGs csususdTsdT | (SEQ ID NO: 167) | wherein lower case letters represent 2'-OMe RNA residues; capital letters represent RNA residues; d=2'-deoxy residues; and "s" indicates a phosphorothioate moiety; and

| PCSK9 (7) | (All (Sp))-AsAs GscsAsAsAsAscsA sGsGsUsCsusAsGs AsAsdTsdT | (SEQ ID NO: 168) |
|---|---|---|
| PCSK9 (8) | (All (Sp))-AsAs GscsAsAsAsAscsA sGsGsUsCsusAsGs AsAsdTsdT | (SEQ ID NO: 169) |
| PCSK9 (9) | (All (Rp))-AsA GcAAAAcsAsGsGs UsCsusAsGsAsAs dTsdT | (SEQ ID NO: 170) |
| PCSK9 (10) | (All (Sp))-AsAG cAAAAcsAsGsGsUs CsusAsGsAsAsdTs dT | (SEQ ID NO: 171) |
| PCSK9 (11) | (All (Rp))-AAs GscsAsAsAsAscsA GGUCuAGAAdTsdT | (SEQ ID NO: 172) |
| PCSK9 (12) | (All (Sp))-AAs GscsAsAsAsAscsA GGUCuAGAAdTsdT | (SEQ ID NO: 173) |
| PCSK9 (13) | (All (Rp))-AsA sGscAsAsAsAscsA sGsGsUsCsuAsGs AsAsdTsdT | (SEQ ID NO: 174) |
| PCSK9 (14) | (All (Sp))-AsA sGscAsAsAsAscsA sGsGsUsCsuAsGs AsAsdTsdT | (SEQ ID NO: 175) |

| | | |
|---|---|---|
| PCSK9 (15) | (All (Rp))-AsA GcAAAsAscAsGsG sUsCsusAsGsAsA sdTsdT | (SEQ ID NO: 176) |
| PCSK9 (16) | (All (Sp))-AsA GcAAAsAscAsGsG sUsCsusAsGsAsA sdTsdT | (SEQ ID NO: 177) |
| PCSK9 (17) | (Rp, Sp, Rp, Sp, Rp, Sp, Rp, Sp, Rp, Sp, Rp, Sp, Rp, Sp)- AsAGcAAAsAs cAsGsGsUsCs usAsGsAsAsd TsdT | (SEQ ID NO: 178) |
| PCSK9 (18) | (Sp, Rp, Sp, Rp, Sp, Rp, Sp, Rp, Sp, Rp, Sp, Rp, Sp, Rp)- AsAGcAAAsAs cAsGsGsUsCs usAsGsAsAsd TsdT | (SEQ ID NO: 179) | wherein lower case letters represent 2'-OMe RNA residues; capital letters represent RNA residues; d=2'-deoxy residues; "s" indicates a phosphorothioate moiety; and

| | | |
|---|---|---|
| PCSK9 (19) | (All (Rp))-UfsusC fsusAfsgsAfscsCfs usGfsusUfsusUfsgs CfsusUfsdTsdT | (SEQ ID NO: 180) |
| PCSK9 (20) | (All (Sp))-Ufsus CfsusAfsgsAfscsC fsusGfsusUfsusUf sgsCfsusUfsdTsdT | (SEQ ID NO: 181) |
| PCSK9 (21) | (All (Rp))-UfsuC fsuAfsgAfscCfsuG fsuUfsuUfsgCfsuU fsdTsdT | (SEQ ID NO: 182) |
| PCSK9 (22) | (All (Sp))-UfsuC fsuAfsgAfscCfsuG fsuUfsuUfsgCfsuU fsdTsdT | (SEQ ID NO: 183) |
| PCSK9 (23) | (Rp, Sp, Rp, Sp, Rp, Sp, Rp, Sp, Rp, Sp, Rp, Sp, Rp, Sp, Rp, Sp)- UfsusCfsusAfsgs AfscsCfsusGfsus UfsusUfsgsCfsus UfsdTsdT | (SEQ ID NO: 184) |
| PCSK9 (24) | (Sp, Rp, Sp, Rp, Sp, Rp, Sp, Rp, Sp, Rp, Sp, Rp, Sp, Rp, Sp, Rp,Sp, Rp)- UfsusCfsusAfsgsAfs csCfsusGfsusUfsusU fsgsCfsusUfsdTsdT | (SEQ ID NO: 185) | wherein lower case letters represent 2'-OMe RNA residues; capital letters represent 2'-F RNA residues; d=2'-deoxy residues; and "s" indicates a phosphorothioate moiety; and

| | | |
|---|---|---|
| PCSK9 (25) | (All (Rp))-asAf sgsCfsasAfsasAf scsAfsgsGfsusCfs usAfsgsAfsasdTsdT | (SEQ ID NO: 186) |
| PCSK9 (26) | (All (Sp))-asA fsgsCfsasAfsas AfscsAfsgsGfsus CfsusAfsgsAfsasd TsdT | (SEQ ID NO: 187) |
| PCSK9 (27) | (All (Rp))-asAfg CfaAfaAfcsAfsgs GfsusCfsusAfsgs AfsasdTsdT | (SEQ ID NO: 188) |
| PCSK9 (28) | (All (Sp))-asAfg CfaAfaAfcsAfsgs GfsusCfsusAfsgs AfsasdTsdT | (SEQ ID NO: 189) |
| PCSK9 (29) | (All (Rp))-asAf sgCfsaAfsaAfsc AfsgGfsuCfsuA fsgAfsadTsdT | (SEQ ID NO: 190) |
| PCSK9 (30) | (All (Sp))-as AfsgCfsaAfsa AfscAfsgGfsu CfsuAfsgAfsad TsdT | (SEQ ID NO: 191) |
| PCSK9 (31) | (Rp, Sp, Rp, Sp, Rp, Sp, Rp, Sp, Rp, Sp, Rp, Sp, Rp, Sp)-as AfgCfaAfasAfsc AfsgsGfsusCfsu sAfsgsAfsasd TsdT | (SEQ ID NO: 192) |
| PCSK9 (32) | (Sp, Rp, Sp, Rp, Sp, Rp, Sp, Rp, Sp, Rp)-asAfgCfa AfasAfscAfsgs GfsusCfsusAfsgs AfsasdTsdT | (SEQ ID NO: 193) | wherein lower case letters represent 2'-OMe RNA residues; capital letters represent 2'-F RNA residues; d=2'-deoxy residues; and "s" indicates a phosphorothioate moiety.

E89. The composition of any one of the preceding examples, wherein at least about 50% of the internucleotidic linkages are in the Sp configuration.

E90. The composition of any one of the preceding examples, wherein the core portion comprises at least about 5 nucleotides.

E91. The composition of any one of the preceding examples, wherein the core portion comprises at least about 10 nucleotides.

E92. The composition of any one of the preceding examples, wherein the core portion comprises at least about 15 nucleotides.

E93. The composition of any one of the preceding examples, wherein the core portion comprises at least about 20 nucleotides.

E94. The composition of any one of the preceding examples, wherein the core portion comprises at least about 25 nucleotides.

E95. The composition of any one of the preceding examples, wherein (Sp)m(Rp)n or (Rp)n(Sp)m is SSR.

E96. The composition of any one of examples E1-E95, wherein (Sp)m(Rp)n or (Rp)n(Sp)m is RRS.

E97. The composition of any one of the preceding examples, wherein a repeating pattern is a motif comprising at least about 20% of backbone chiral centers in the Sp conformation.

E98. The composition of any one of the preceding examples, wherein a repeating pattern is a motif comprising at least about 50% of backbone chiral centers in the Sp conformation.

E99. The composition of any one of the preceding examples, wherein a repeating pattern is a motif comprising at least about 66% of backbone chiral centers in the Sp conformation.

E100. The composition of anyone of the preceding examples, wherein a repeating pattern is a motif comprising at least about 75% of backbone chiral centers in the Sp conformation.

E101. The composition of anyone of the preceding examples, wherein a repeating pattern is a motif comprising at least about 80% of backbone chiral centers in the Sp conformation.

E102. A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type.

E103. The composition of example E102, wherein the common base sequence is or comprises a sequence that is complementary to a target sequence, wherein when contacted with a nucleic acid polymer comprising the target sequence, the chirally controlled oligonucleotide composition provides an altered cleavage pattern than a reference cleavage pattern from a reference oligonucleotide composition.

E104. The composition of example E103, wherein the nucleic acid polymer is RNA, and a reference oligonucleotide composition is a substantially racemic preparation of oligonucleotides that share the common sequence and length.

E105. The composition of example E103, wherein the nucleic acid polymer is RNA, and a reference oligonucleotide composition is a chirally uncontrolled oligonucleotide composition of oligonucleotides that share the common sequence and length.

E106. The composition of anyone of examples E103-E105, wherein the altered cleavage pattern has fewer cleavage sites than the reference cleavage pattern.

E107. The composition of anyone of examples E103-E106, wherein the altered cleavage pattern has only one cleavage site within the target sequence, and the reference cleavage pattern has two or more cleavage sites within the target sequence.

E108. The composition of example E102, wherein the common base sequence for the oligonucleotides of the single oligonucleotide type is or comprises a sequence that is complementary to a characteristic sequence element that defines a particular allele of a target gene relative to other alleles of the same target gene that exist in a population, the composition being characterized in that, when it is contacted with a system expressing transcripts of both the target allele and another allele of the same gene, transcripts of the particular allele are suppressed at a level at least 2 fold greater than a level of suppression observed for another allele of the same gene.

E109. The composition of example E102, wherein the common base sequence for the oligonucleotides of the single oligonucleotide type is or comprises a sequence that is complementary to a characteristic sequence element that defines a particular allele of a target gene relative to other alleles of the same target gene that exist in a population, the composition being characterized in that, when it is contacted with a system expressing transcripts of the target gene, it shows suppression of expression of transcripts of the particular allele at a level that is:
a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene.

E110. The composition of anyone of examples E102-E109, wherein oligonucleotides of the particular oligonucleotide type comprise a modified base.

E111. The composition of anyone of examples E102-E110, wherein oligonucleotides of the particular oligonucleotide type comprise a modified sugar.

E112. The composition of example E111, wherein the modified sugar comprises a 2'-modification.

E113. The composition of example E112, wherein the 2'-modification is 2'-OR$^1$.

E114. The composition of example E113, wherein the 2'-modification is 2'-MOE.

E115. The composition of anyone of examples E102-E109, wherein oligonucleotides of the particular oligonucleotide type have no modified base or modified sugar.

E116. The composition of anyone of examples E102-E115, wherein the pattern of backbone chiral centers of the particular oligonucleotide type comprises (Sp)m(Rp)n, wherein m is 2, 3, 4, 5, 6, 7 or 8 and n is 1, 2, 3, 4, 5, 6, 7 or 8.

E117. The composition of anyone of examples E102-E116, wherein the pattern of backbone chiral centers of the particular oligonucleotide type comprises (Sp)mRp, wherein m is 2, 3, 4, 5, 6, 7 or 8.

E118. The composition of anyone of examples E102-E117, wherein the pattern of backbone chiral centers of the particular oligonucleotide type comprises (Sp)$_2$Rp.

E119. The composition of anyone of examples E102-E118, wherein the pattern of backbone chiral centers of the particular oligonucleotide type comprises repeating (Sp)m(Rp)n, wherein m is 2, 3, 4, 5, 6, 7 or 8 and n is 1, 2, 3, 4, 5, 6, 7 or 8.

E120. The composition of anyone of examples E102-E119, wherein the pattern of backbone chiral centers of the particular oligonucleotide type comprises repeating (Sp)mRp, wherein m is 2, 3, 4, 5, 6, 7 or 8.

E121. The composition of anyone of examples E102-E120, wherein the pattern of backbone chiral centers of the particular oligonucleotide type comprises repeating (Sp)$_2$Rp.

E122. The composition of anyone of examples E102-E115, wherein the pattern of backbone chiral centers of the particular oligonucleotide type comprises (Rp)n(Sp)m, wherein m is 2, 3, 4, 5, 6, 7 or 8 and n is 1, 2, 3, 4, 5, 6, 7 or 8.

E123. The composition of anyone of examples E102-E115, wherein the pattern of backbone chiral centers of the particular oligonucleotide type comprises Rp(Sp)m, wherein m is 2, 3, 4, 5, 6, 7 or 8.

E124. The composition of anyone of examples E102-E115, wherein the pattern of backbone chiral centers of the particular oligonucleotide type comprises Rp(Sp)$_2$.

E125. The composition of anyone of examples E102-E115, wherein the pattern of backbone chiral centers of the particular oligonucleotide type comprises repeating (Rp)n(Sp)m, wherein m is 2, 3, 4, 5, 6, 7 or 8 and n is 1, 2, 3, 4, 5, 6, 7 or 8.

E126. The composition of anyone of examples E102-E115, wherein the pattern of backbone chiral centers of the particular oligonucleotide type comprises repeating Rp(Sp)m, wherein m is 2, 3, 4, 5, 6, 7 or 8.

E127. The composition of anyone of examples E102-E115, wherein the pattern of backbone chiral centers of the particular oligonucleotide type comprises repeating Rp(Sp)$_2$.

E128. The composition of anyone of examples E102-E115, wherein the pattern of backbone chiral centers of the particular oligonucleotide type comprises (Np)t(Rp)n(Sp)m, wherein each n and t is independently 1, 2, 3, 4, 5, 6, 7 or 8, m is 2, 3, 4, 5, 6, 7 or 8, and each Np is independent Rp or Sp.

E129. The composition of anyone of examples E102-E115, wherein the pattern of backbone chiral centers of the particular oligonucleotide type comprises (Sp)t(Rp)n(Sp)m, wherein each n and t is independently 1, 2, 3, 4, 5, 6, 7 or 8 and m is 2, 3, 4, 5, 6, 7 or 8.

E130. The composition of example E128 or E129, wherein n is 1.

E131. The composition of anyone of examples E128-E130, wherein t is 2, 3, 4, 5, 6, 7 or 8.

E132. The composition of anyone of examples E128-E131, wherein m is 2, 3, 4, 5, 6, 7 or 8.

E133. The composition of anyone of examples E128-E131, wherein at least one of t and m is greater than 5.

E134. The composition of anyone of examples E102-E115, wherein the pattern of backbone chiral centers of the particular oligonucleotide type comprises SpSpRpSpSp.

E135. The composition of anyone of examples E102-E134, wherein oligonucleotides of the particularly oligonucleotide type has only one Rp, and each of the other internucleotidic linkages is Sp.

E136. The composition of anyone of examples E102-E135, wherein the common base length of the particular oligonucleotide type is greater than 10.

E137. The composition of anyone of examples E102-E136, wherein each chiral internucleotidic linkage in oligonucleotides of the particular oligonucleotide type has a structure of formula I

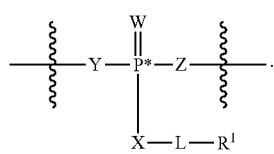

(I)

E138. The composition of example E137, wherein X is S, and Y and Z are O.

E139. The composition of example E137 or E138, wherein -L-R$^1$ is not —H.

E140. The composition of example E137 or E138, wherein a structure of formula I is a phosphorothioate diester linkage.

E141. The composition of anyone of examples E102-E140, wherein oligonucleotides of the particular oligonucleotide type are antisense oligonucleotide, antagomir, microRNA, pre-microRNs, antimir, supermir, ribozyme, U1 adaptor, RNA activator, RNAi agent, decoy oligonucleotide, triplex forming oligonucleotide, aptamer or adjuvant.

E142. A method for controlled cleavage of a nucleic acid polymer, the method comprising steps of:
    contacting a nucleic acid polymer whose nucleotide sequence comprises a target sequence with a chirally controlled oligonucleotide composition comprising oligonucleotides of a particular oligonucleotide type characterized by:
    1) a common base sequence and length, wherein the common base sequence is or comprises a sequence that is complementary to a target sequence found in the nucleic acid polymer;
    2) a common pattern of backbone linkages; and
    3) a common pattern of backbone chiral centers;
which composition is chirally controlled in that it is enriched, relative to a substantially racemic preparation of oligonucleotides having the particular base sequence and length, for oligonucleotides of the particular oligonucleotide type.

E143. The method of example E142, wherein the contacting being performed under conditions so that cleavage of the nucleic acid polymer occurs.

E144. The method of any one of examples E142-E143, wherein the cleavage occurs with a cleavage pattern that differs from a reference cleavage pattern observed when the nucleic acid polymer is contacted under comparable conditions with a reference oligonucleotide composition.

E145. A method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising:
    contacting the nucleic acid polymer with a chirally controlled oligonucleotide composition of oligonucleotides having the particular base sequence and length, which composition is chirally controlled in that it is enriched, relative to a substantially racemic preparation of oligonucleotides having the particular base sequence and length, for oligonucleotides of a single oligonucleotide type characterized by:
    1) the particular base sequence and length;
    2) a particular pattern of backbone linkages; and
    3) a particular pattern of backbone chiral centers.

E146. The method of example E145, wherein the contacting being performed under conditions so that cleavage of the nucleic acid polymer occurs.

E147. The method of any one of examples E144-E146, wherein the reference oligonucleotide composition is a substantially racemic preparation of oligonucleotides that share the common sequence and length.

E148. The method of any one of examples E144-E146, wherein the reference oligonucleotide composition is a chirally uncontrolled oligonucleotide composition of oligonucleotides that share the common sequence and length.

E149. The method of any one of examples E144-E148, wherein the cleavage pattern provided by the chirally controlled oligonucleotide composition differs from a reference cleavage pattern in that it has fewer cleavage sites within the target sequence found in the nucleic acid polymer than the reference cleavage pattern.

E150. The method of example E149, wherein the cleavage pattern provided by the chirally controlled oligonucleotide composition has a single cleavage site within the target sequence found in the nucleic acid polymer than the reference cleavage pattern.

E151. The method of example E150, wherein the single cleavage site is a cleavage site in the reference cleavage pattern.

E152. The method of example E150, wherein the single cleavage site is a cleavage site not in the reference cleavage pattern.

E153. The method of anyone of examples E144-E148, wherein the cleavage pattern provided by the chirally controlled oligonucleotide composition differs from a reference cleavage pattern in that it increases cleavage percentage at a cleavage site.

E154. The method of example E153, wherein the cleavage site with increased cleavage percentage is a cleavage site in the reference cleavage pattern.

E155. The method of example E153, wherein the cleavage site with increased cleavage percentage is a cleavage site not in the reference cleavage pattern.

E156. The method of anyone of examples E142-E155, wherein the chirally controlled oligonucleotide composition provides a higher cleavage rate of the target nucleic acid polymer than a reference oligonucleotide composition.

E157. The method of anyone of examples E142-E156, where the cleavage rate is at least 5 fold higher.

E158. The method of anyone of examples E142-E157, wherein the chirally controlled oligonucleotide composition provides a lower level of remaining un-cleaved target nucleic acid polymer than a reference oligonucleotide composition.

E159. The method of anyone of examples E142-E158, wherein the remaining un-cleaved target nucleic acid polymer is at least 5 fold lower.

E160. The methods of anyone of examples E142-E159, wherein the cleavage products from the nucleic acid polymer dissociate from oligonucleotides of the particular oligonucleotide type in the chirally controlled oligonucleotide composition at a faster rate than from oligonucleotides of the reference oligonucleotide composition.

E161. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
  contacting a sample comprising transcripts of the target nucleic acid sequence with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

E162. A method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

E163. The method of example E161 or E162, the contacting being performed under conditions determined to permit the composition to suppress transcripts of the particular allele.

E164. A method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of both the target allele and another allele of the same gene, transcripts of the particular allele are suppressed at a level at least 2 fold greater than a level of suppression observed for another allele of the same gene.

E165. The method of example E164, wherein the contacting being performed under conditions determined to permit the composition to suppress expression of the particular allele.

E166. The method of anyone of examples E161-E165, wherein transcripts of the particular allele are suppressed at a level at least 5, 10, 20, 50, 100, 200 or 500 fold greater than a level of suppression observed for another allele of the same gene.

E167. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
  contacting a sample comprising transcripts of the target nucleic acid sequence with a chirally controlled oligonucleotide composition comprising oligonucleotides of a particular oligonucleotide type characterized by:
    1) a common base sequence and length;
    2) a common pattern of backbone linkages;
    3) a common pattern of backbone chiral centers;
  which composition is chirally controlled in that it is enriched, relative to a substantially racemic preparation of oligonucleotides having the same base sequence and length, for oligonucleotides of the particular oligonucleotide type;
  wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
    a) greater than when the composition is absent;
    b) greater than a level of suppression observed for another allele of the same nucleic acid sequence; or
    c) both greater than when the composition is absent, and greater than a level of suppression observed for another allele of the same nucleic acid sequence.

E168. A method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
    1) a common base sequence and length;
    2) a common pattern of backbone linkages;
    3) a common pattern of backbone chiral centers;
  which composition is chirally controlled in that it is enriched, relative to a substantially racemic preparation of oligonucleotides having the same base sequence and length, for oligonucleotides of the particular oligonucleotide type;
  wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
    a) at least 2 fold in that transcripts from the particular allele are detected in amounts that are 2 fold lower when the composition is present relative to when it is absent;
    b) at least 2 fold greater than a level of suppression observed for another allele of the same gene; or
    c) both at least 2 fold in that transcripts from the particular allele are detected in amounts that are 2 fold lower when the composition is present relative to when it is absent, and at least 2 fold greater than a level of suppression observed for another allele of the same gene.

E169. The method of example E167 or E168, the contacting being performed under conditions determined to permit the composition to suppress transcripts of the particular allele.

E170. A method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
    1) a common base sequence and length;
    2) a common pattern of backbone linkages;
    3) a common pattern of backbone chiral centers;
  which composition is chirally controlled in that it is enriched, relative to a substantially racemic preparation of oligonucleotides having the same base sequence and length, for oligonucleotides of the particular oligonucleotide type;
  wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
    a) at least 2 fold in that transcripts from the particular allele are detected in amounts that are 2 fold lower when the composition is present relative to when it is absent;
    b) at least 2 fold greater than a level of suppression observed for another allele of the same gene; or
    c) both at least 2 fold in that transcripts from the particular allele are detected in amounts that are 2 fold lower when the composition is present relative to when it is absent, and at least 2 fold greater than a level of suppression observed for another allele of the same gene.

E171. The method of example E170, wherein the contacting being performed under conditions determined to permit the composition to suppress expression of the particular allele.

E172. The method of anyone of examples E167-E171, wherein transcripts of the particular allele are suppressed at a level that is at least 5, 10, 20, 50, 100, 200 or 500 fold in that transcripts from the particular allele are detected in amounts that are 2 fold lower when the composition is present relative to when it is absent.

E173. The method of anyone of examples E167-E172, wherein transcripts of the particular allele are suppressed at a level that is at least 5, 10, 20, 50, 100, 200 or 500 fold greater than a level of suppression observed for another allele of the same gene.

E174. The method of anyone of example E161-E173, wherein the system is an in vitro or in vivo system.

E175. The method of anyone of example E161-E174, wherein the system comprises one or more cells, tissues or organs.

E176. The method of anyone of example E161-E174, wherein the system comprises one or more organisms.
E177. The method of anyone of example E161-E174, wherein the system comprises one or more subjects.
E178. The method of anyone of examples E161-E177, wherein transcripts of the particular allele are cleaved.
E179. The method of anyone of examples E161-E178, wherein the specific nucleotide characteristic sequence element is present within an intron of the target nucleic acid sequence or gene.
E180. The method of anyone of examples E161-E178, wherein the specific nucleotide characteristic sequence element is present within an exon of the target nucleic acid sequence or gene.
E181. The method of anyone of examples E161-E178, wherein the specific nucleotide characteristic sequence element spans an exon and an intron of the target nucleic acid sequence or gene.
E182. The method of anyone of examples E161-E181, wherein the specific nucleotide characteristic sequence element comprises a mutation.
E183. The method of anyone of examples E161-E181, wherein the specific nucleotide characteristic sequence element comprises a SNP.
E184. The method of anyone of example E142-E183, wherein the chirally controlled oligonucleotide composition is administered to a subject.
E185. The method of anyone of example E142-E184, wherein the target nucleic acid polymer or transcripts are oligonucleotides.
E186. The method of anyone of example E142-E185, wherein the target nucleic acid polymer or transcripts are RNA.
E187. The method of anyone of example E142-E186, wherein oligonucleotides of the particular oligonucleotide type in the chirally controlled oligonucleotide composition form duplexes with the nucleic acid polymer or transcripts.
E188. The method of anyone of example E142-E187, wherein the nucleic acid polymer or transcripts are cleaved by an enzyme.
E189. The method of anyone of example E142-E188, wherein the enzyme is RNase H.
E190. The method of anyone of example E142-E188, wherein the enzyme is an Argonaute protein or within the RNA-induced silencing complex (RISC).
E191. The composition of anyone of examples E102-E141, wherein the oligonucleotide type is not (Sp, Sp, Rp, Sp, Sp, Rp, Sp, Sp, Rp, Sp, Sp)-d [5mCs1As1Gs1Ts15mCs1Ts1Gs15mCs1Ts1Ts15mCs1G] (SEQ ID NO: 194) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCsTs5mCsAsGsTs5mCsTsGs5mCsTsTs 5mCsGs5mCsAs5mCs5mC (5R-(SSR)3-5R) (SEQ ID NO: 195), wherein in the underlined nucleotide are 2'-O-MOE modified.
E192. The composition of anyone of examples E102-E141, wherein the oligonucleotide has a wing-core-wing motif, wherein the pattern of backbone chiral centers of the core region comprises (Np)t(Rp)n(Sp)m, wherein each n and t is independently 1, 2, 3, 4, 5, 6, 7 or 8, m is 2, 3, 4, 5, 6, 7 or 8, and each Np is independent Rp or Sp.
E193. The composition of anyone of examples E102-E141, wherein the oligonucleotide has a wing-core-wing motif, wherein the pattern of backbone chiral centers of the core region comprises (Sp)t(Rp)n(Sp)m, wherein each n and t is independently 1, 2, 3, 4, 5, 6, 7 or 8, and m is 2, 3, 4, 5, 6, 7 or 8.
E194. The composition of anyone of examples E192 or E193, wherein n is 1.
E195. The composition of any one of examples E192-E194, wherein m is 2.
E196. The composition of any one of examples E192-E194, wherein m is 3, 4, 5, 6, 7 or 8.
E197. The composition of any one of examples E192-E194, wherein m is 4, 5, 6, 7 or 8.
E198. The composition of any one of examples E192-E194, wherein m is 5, 6, 7, or 8.
E199. The composition of any one of examples E192-E194, wherein m is 6, 7 or 8.
E200. The composition of any one of examples E192-E194, wherein m is 7 or 8.
E201. The composition of any one of examples E192-E194, wherein m is 8.
E202. The composition of any one of examples E192-E201, wherein t is 1.
E203. The composition of any one of examples E192-E201, wherein t is 2, 3, 4, 5, 6, 7 or 8.
E204. The composition of any one of examples E192-E201, wherein t is 3, 4, 5, 6, 7 or 8.
E205. The composition of any one of examples E192-E201, wherein t is 4, 5, 6, 7 or 8.
E206. The composition of any one of examples E192-E201, wherein t is 5, 6, 7 or 8.
E207. The composition of any one of examples E192-E201, wherein t is 6, 7 or 8.
E208. The composition of any one of examples E192-E201, wherein t is 7 or 8.
E209. The composition of any one of examples E192-E201, wherein t is 8.
E210. The composition of any one of examples E192-E209, wherein each wing region independently has a length of two or more bases.
E211. The composition of anyone of examples E192-E210, wherein all internucleotidic linkages are chiral, modified phosphate linkages.
E212. The composition of anyone of examples E192-E211, wherein the core region has a length of 11, 12, 13, 14, 15, 16, 17, 18, 19, 20, 25, or more bases.
E213. The composition of any one of examples E102-E141 and E192-E212, wherein the common base sequence has at least 18 bases.
E214. The composition of any one of examples E102-E141 and E192-E212, wherein the common base sequence has at least 19 bases.
E215. The composition of any one of examples E102-E141 and E192-E212, wherein the common base sequence has at least 19 bases.
E216. The composition of any one of examples E102-E141 and E192-E212, wherein the common base sequence has at least 19 bases.
E217. The composition of any one of examples E102-E141 and E192-E212, wherein the common base sequence has at least 19 bases.
E218. The composition of any one of examples E102-E141 and E192-E212, wherein the common base sequence has at least 19 bases.
E219. The composition of any one of examples E102-E141 and E192-E212, wherein the common base sequence has at least 19 bases.
E220. The composition of any one of examples E102-E141 and E192-E212, wherein the common base sequence has at least 19 bases.
E221. The composition of any one of examples E102-E141 and E192-E220, wherein the oligonucleotide is not an oligonucleotide selected from: (Sp, Sp, Rp, Sp, Sp, Rp, Sp, Sp, Rp, Sp, Sp, Sp)-d[5mCs1As1Gs1Ts15mCs1Ts1Gs15mCs1Ts1Ts15mCs1G] (SEQ ID NO: 196) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCsTs5mCsAsGsTs5mCsTsGs5mCsTs Ts5mCsGs5mCsAs5mCs5mC (5R-(SSR)3-5R) (SEQ ID NO: 197), wherein in the underlined nucleotide are 2'-O-MOE modified.

E222. The composition of any one of examples E102-E141 and E192-E221, wherein the oligonucleotide is not an oligonucleotide selected from:

| | | | |
|---|---|---|---|
| ONT-106 | (Rp)-uucuAGAccuGuuuuGcuudTsdT | PCSK9 sense | (SEQ ID NO: 198) |
| ONT-107 | (Sp)-uucuAGAccuGuuuuGcuudTsdT | PCSK9 sense | (SEQ ID NO: 199) |
| ONT-108 | (Rp)-AAGcAAAAcAGGUCuAGAAdTsdT | PCSK9 antisense | (SEQ ID NO: 200) |
| ONT-109 | (Sp)-AAGcAAAAcAGGUCuAGAAdTsdT | PCSK9 antisense | (SEQ ID NO: 201) |
| ONT-110 | (Rp, Rp)-asAGcAAAAcAGGUCuAGAAdTsdT | PCSK9 antisense | (SEQ ID NO: 202) |
| ONT-111 | (Sp, Rp)-asGcAAAAcAGGUCuAGAAdTsdT | PCSK9 antisense | (SEQ ID NO: 203) |
| ONT-112 | (Sp, Sp)-asGcAAAAcAGGUCuAGAAdTsdT | PCSK9 antisense | (SEQ ID NO: 204) |
| ONT-113 | (Rp, Sp)-asGcAAAAcAGGUCuAGAAdTsdT | PCSK9 antisense | (SEQ ID NO: 205) | wherein lower case letters represent 2'OMe RNA residues; capital letters represent 2'OH RNA residues; and bolded and "s" indicates a phosphorothioate moiety; and

| | | |
|---|---|---|
| PCSK9 (1) | (All (Sp))-ususcsusAsGsAscscsusGsususususGscsusudTsdT | (SEQ ID NO: 206) |
| PCSK9 (2) | (All (Rp))-ususcsusAsGsAscscsusGsususususGscsusudTsdT | (SEQ ID NO: 207) |
| PCSK9 (3) | (All (Sp))-usucuAsGsAsccuGsuuuuGscuusdTsdT | (SEQ ID NO: 208) |
| PCSK9 (4) | (All (Rp))-usucuAsGsAsccuGsuuuuGscuusdTsdT | (SEQ ID NO: 209) |
| PCSK9 (5) | (Rp, Sp, Rp, Sp, Rp, Sp, Rp, Sp, Rp, Sp, Rp, Sp, Rp, Sp, Rp, Sp, Rp, Sp, Rp, Sp)-ususcsusAsGsAscscsusGsususususGscsusudTsdT | (SEQ ID NO: 210) |
| PCSK9 (6) | (Sp, Rp, Sp, Rp, Sp, Rp, Sp, Rp, Sp, Rp, Sp, Rp, Sp, Rp, Sp, Rp, Sp, Rp, Sp, Rp)-ususcsusAsGsAscscsusGsususususGscsusudTsdT | (SEQ ID NO: 211) | wherein lower case letters represent 2'-OMe RNA residues; capital letters represent RNA residues; d=2'-deoxy residues; and "s" indicates a phosphorothioate moiety; and

| | | |
|---|---|---|
| PCSK9 (7) | (All (Rp))-AsAsGscsAsAsAsAscsAsGsGsUsCsusAsGsAsAsdTsdT | (SEQ ID NO: 212) |
| PCSK9 (8) | (All (Sp))-AsAsGscsAsAsAsAscsAsGsGsUsCsusAsGsAsAsdTsdT | (SEQ ID NO: 213) |
| PCSK9 (9) | (All (Rp))-AsAGcAAAAcsAsGsGsUsCsusAsGsAsAsdTsdT | (SEQ ID NO: 214) |
| PCSK9 (10) | (All (Sp))-AsAGcAAAAcsAsGsGsUsCsusAsGsAsAsdTsdT | (SEQ ID NO: 215) |
| PCSK9 (11) | (All (Rp))-AAsGscsAsAsAsAsAsAscAGGUCuAGAAdTsdT | (SEQ ID NO: 216) |
| PCSK9 (12) | (All (Sp))-AAsGscsAsAsAsAsAsAscAGGUCuAGAAdTsdT | (SEQ ID NO: 217) |
| PCSK9 (13) | (All (Rp))-AsAsGscAsAsAsAscAsGsGsUsCsusAsGsAsAsdTsdT | (SEQ ID NO: 218) |
| PCSK9 (14) | (All (Sp))-AsAsGscAsAsAsAscAsGsGsUsCsusAsGsAsAsdTsdT | (SEQ ID NO: 219) |
| PCSK9 (15) | (All (Rp))-AsAGcAAAsAscAsGsGsUsCsusAsGsAsAsdTsdT | (SEQ ID NO: 220) |
| PCSK9 (16) | (All (Sp))-AsAGcAAAsAscAsGsGsUsCsusAsGsAsAsdTsdT | (SEQ ID NO: 221) |
| PCSK9 (17) | (Rp, Sp, Rp, Sp, Rp, Sp, Rp, Sp, Rp, Sp, Rp, Sp, Rp, Sp)-AsAGcAAAsAscAsGsGsUsCsusAsGsAsAsdTsdT | (SEQ ID NO: 222) |
| PCSK9 (18) | (Sp, Rp, Sp, Rp, Sp, Rp, Sp, Rp, Sp, Rp, Sp, Rp, Sp, Rp)-AsAGcAAAsAscAsGsGsUsCsusAsGsAsAsdTsdT | (SEQ ID NO: 223) | wherein lower case letters represent 2'-OMe RNA residues; capital letters represent RNA residues; d=2'-deoxy residues; "s" indicates a phosphorothioate moiety; and

| | | |
|---|---|---|
| PCSK9 (19) | (All (Rp))-UfsusCfsusAfsgsAfscsCfsusGfsusUfsusUfsgsCfsusUfsdTsdT | (SEQ ID NO: 224) |

| | | |
|---|---|---|
| PCSK9 (20) | (All (Sp))-Ufsus CfsusAfsgsAfscsC fsusGfsusUfsusUf sgsCfsusUfsdTsdT | (SEQ ID NO: 225) |
| PCSK9 (21) | (All (Rp))-UfsuC fsuAfsgAfscCfsuG fsuUfsuUfsgCfsuU fsdTsdT | (SEQ ID NO: 226) |
| PCSK9 (22) | (All (Sp))-UfsuCf suAfsgAfscCfsuGfs uUfsuUfsgCfsuUfsd TsdT | (SEQ ID NO: 227) |
| PCSK9 (23) | (Rp, Sp, Rp, Sp, Rp, Sp, Rp, Sp, Rp, Sp, Rp, Sp, Rp, Sp, Rp, Sp, Rp, Sp, Rp, Sp)- UfsusCfsusAfsgsA fscsCfsusGfsusUf susUfsgsCfsusUfs dTsdT | (SEQ ID NO: 228) |
| PCSK9 (24) | (Sp, Rp, Sp, Rp, Sp, Rp, Sp, Rp, Sp, Rp, Sp, Rp, Sp, Rp, Sp, Rp, Sp, Rp, Sp, Rp)- UfsusCfsusAfsgs AfscsCfsusGfsus UfsusUfsgsCfsus UfsdTsdT | (SEQ ID NO: 229) | wherein lower case letters represent 2'-OMe RNA residues; capital letters represent 2'-F RNA residues; d=2'-deoxy residues; and "s" indicates a phosphorothioate moiety; and

| | | |
|---|---|---|
| PCSK9 (25) | (All (Rp))-asAfsgsCfsas AfsasAfscsAfsgsGfsusCfs usAfsgsAfsasdTsdT | (SEQ ID NO: 230) |
| PCSK9 (26) | (All (Sp))-asAfsgsCfsas AfsasAfscsAfsgsGfsusCfs usAfsgsAfsasdTsdT | (SEQ ID NO: 231) |
| PCSK9 (27) | (All (Rp))-asAfgCfaAfaA fcsAfsgsGfsusCfsusAfsgs AfsasdTsdT | (SEQ ID NO: 232) |
| PCSK9 (28) | (All (Sp))-asAfgCfaAfaA fcsAfsgsGfsusCfsusAfsgs AfsasdTsdT | (SEQ ID NO: 233) |
| PCSK9 (29) | (All (Rp))-asAfsgCfsaAf saAfscAfsgGfsuCfsuAfsgA fsadTsdT | (SEQ ID NO: 234) |
| PCSK9 (30) | (All (Sp))-asAfsgCfsaAf saAfscAfsgGfsuCfsuAfsgA fsadTsdT | (SEQ ID NO: 235) |
| PCSK9 (31) | (Rp, Sp, Rp, Sp, Rp, Sp, Rp, Sp, Rp, Sp, Rp, Sp, Rp, Sp)-asAfgCfaAfasAfs cAfsgsGfsusCfsusAfsgsAf sasdTsdT | (SEQ ID NO: 236) |
| PCSK9 (32) | (Sp, Rp, Sp, Rp, Sp, Rp, Sp, Rp, Sp, Rp, Sp, Rp, Sp, Rp)-asAfgCfaAfasAfs cAfsgsGfsusCfsusAfsgsAf sasdTsdT | (SEQ ID NO: 237) |

E223. The composition of any one of examples E1-E141 and E192-E222, wherein the oligonucleotide is not an oligonucleotide selected from: d[$A_R C_S A_R C_S A_R C_S A_R C_S A_R C$] (SEQ ID NO: 54), d[$C_S C_S C_S C_R C_R C_S C_S C_S C_S C$] (SEQ ID NO: 55), d[$C_S C_S C_S C_S C_S C_R C_R C_S C_S C$] (SEQ ID NO: 56) and d[$C_S C_S C_S C_S C_S C_R C_R C_S C_S C$] (SEQ ID NO: 57), wherein R is Rp phosphorothioate linkage, and S is Sp phosphorothioate linkage.

E224. The composition of any one of examples E1-E141 and E192-E223, wherein the oligonucleotide is not an oligonucleotide selected from: GGA$_R$T$_S$G$_R$T$_S$T$_R$$^m$C$_S$TCGA (SEQ ID NO: 58), GGA$_R$T$_R$G$_S$T$_S$T$_R$$^m$C$_R$TCGA (SEQ ID NO: 59), GGA$_S$T$_S$G$_R$T$_R$T$_S$$^m$C$_S$TCGA (SEQ ID NO: 60), wherein R is Rp phosphorothioate linkage, S is Sp phosphorothioate linkage, all other linkages are PO, and each $^m$C is a 5-methyl cytosine modified nucleoside.

E225. The composition of any one of examples E1-E141 and E192-E224, wherein the oligonucleotide is not an oligonucleotide selected from: T$_k$T$_k$$^m$C$_k$AGT$^m$CATGA$^m$CT$_k$T$^m$C$_k$$^m$C$_k$ (SEQ ID NO: 61), wherein each nucleoside followed by a subscript 'k' indicates a (S)-cEt modification, R is Rp phosphorothioate linkage, S is Sp phosphorothioate linkage, each $^m$C is a 5-methyl cytosine modified nucleoside, and all internucleoside linkages are phosphorothioates (PS) with stereochemistry patterns selected from RSSSRSRRRS, RSSSSSSSSS, SRRSRSSSSR, SRSRSSRSSR, RRRSSSRSSS, RRRSSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

E226. The composition of any one of examples E1-E141 and E192-E225, wherein the oligonucleotide is not an oligonucleotide selected from: T$_k$T$_k$$^m$C$_k$AGT$^m$CATGA$^m$CTT$_k$$^m$C$_k$$^m$C$_k$ (SEQ ID NO: 62), wherein each nucleoside followed by a subscript 'k' indicates a (S)-cEt modification, R is Rp phosphorothioate linkage, S is Sp phosphorothioate linkage, each $^m$C is a 5-methyl cytosine modified nucleoside and all internucleoside linkages are phosphorothioates (PS) with stereochemistry patterns selected from: RSSSRSRRRS, RSSSSSSSSS, SRRSRSSSSR, SRSRSSRSSR, RRRSSSRSSS, RRRSSSRSR, RSSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

E227. The composition of any one of examples E1-E141 and E192-E226, wherein the composition comprises a predetermined level of oligonucleotides of one oligonucleotide type characterized by a common base sequence, a common pattern of backbone linkages, a common pattern of backbone chiral centers, and a common pattern of backbone phosphorus modifications.

E228. The composition of any one of claims E1-E141 and E192-E226, wherein the common pattern of backbone chiral centers comprises at least about 20% of backbone chiral centers in the Sp conformation.

E229. The composition of any one of claims E1-E141 and E192-E226, wherein the common pattern of backbone chiral centers comprises at least about 50% of backbone chiral centers in the Sp conformation.

E230. The composition of any one of claims E1-E141 and E192-E226, wherein the common pattern of backbone chiral centers comprises at least about 66% of backbone chiral centers in the Sp conformation.
E231. The composition of anyone of claims E1-E141 and E192-E226, wherein the common pattern of backbone chiral centers comprises at least about 75% of backbone chiral centers in the Sp conformation.
E232. The composition of any one of claims E1-E141 and E192-E226, wherein the common pattern of backbone chiral centers comprises at least about 80% of backbone chiral centers in the Sp conformation.
E233. A pharmaceutical composition, comprising a composition of any one of claims E1-E141 and E191-E232.
E234. The method of anyone of examples E142-E190, wherein the chirally controlled oligonucleotide composition is a composition of any one of examples E1-E101.
E235. The method of anyone of examples E142-E190, wherein the chirally controlled oligonucleotide composition is a composition of any one of examples E102-E141 and E191.
E236. The method of any one of examples E142-E190, wherein the chirally controlled oligonucleotide composition is a composition of any one of examples E102-E141 and E191-E233.

EXEMPLIFICATION

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

Example 1. In Vitro Metabolic Stabilities of Human Chiromersens in Preincubated Rat Whole Liver Homogenates The present Example describes comparisons of in vitro whole rat liver homogenate stability of Mipomersen (stereochemical mixture) with chirally controlled oligonucleotide compositions of Mipomersen ("chiromersens"). The method, among other things, is useful in screening compounds to predict in vivo half lives.

As is known in the art, Mipomersen (previously ISIS 301012, sold under the trade name Kynamro) is a 20mer oligonucleotide whose base sequence is antisense to a portion of the apolipoprotein B gene. Mipomersen inhibits apolipoprotein B gene expression, presumably by targeting mRNA. Mipomersen has the following structure:

(SEQ ID NO: 65)

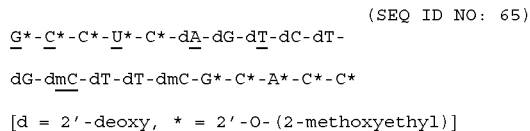

G*-C*-C*-U*-C*-dA-dG-dT-dC-dTdG-dmC-dT-dT-dmC-G*-C*-A*-C*-C*

[d = 2'-deoxy, * = 2'-O-(2-methoxyethyl)]

with 3'→5' phosphorothioate linkages. Thus, Mipomersen has 2'-O-methoxyethyl-modified ribose residues at both ends, and deoxyribose residues in the middle.

Tested chirally pure Mipomersen analogs described in this Example included 3'→5' phosphorothioate linkages. In some embodiments, tested analogs include one or more 2'-O-(2-methoxyethyl)-modified residues; in some embodiments, tested analogs include only 2'-deoxy residues. Particular tested analogs had the structures set forth below in Tables 3 and 4.

Protocol: We used the protocol reported by Geary et al. (Oligonucleotides, Volume 20, Number 6, 2010) with some modifications.

Test system: Six male Sprague-Dawley rats (*Rattus norvegicus*) were supplied by Charles River Laboratories, Inc., (Hollister, Calif.), and were received at SNBL USA.

Tissue Collection: Animals were acclimated to the study room for two days prior to tissue collection. At the time of tissue collection, animals were anesthetized with an intraperitoneal (IP) injection of sodium pentobarbital solution. Liver perfusion was performed using 500 mL of chilled saline/animal, administered via the hepatic portal vein. After perfusion, the livers were dissected and maintained on ice. Livers were minced into small pieces then weighed.

Liver Homogenate Preparation: The minced pieces of liver tissues were transferred to tared 50 mL centrifuge tubes and weighed. Chilled homogenization buffer (100 mM Tris pH 8.0, 1 mM magnesium acetate, with antibiotic-antimycotic agents) was added to each tube, such that the tube(s) contained 5 mL of buffer per gram of tissue. Using a QIAGEN TissueRuptor tissue homogenizer, the liver/buffer mixture was homogenized while maintaining the tube on ice. The protein concentration of the liver homogenate pool was determined using a Pierce BCA protein assay. Liver homogenates were divided into 5 mL aliquots, transferred to appropriately sized labeled cryovials and stored at −60° C.

Incubation Conditions: 5 ml aliquots of frozen liver homogenate (protein concentration=22.48 mg/ml) were thawed and incubated at 37° C. for 24 hrs. Six eppendorf tubes (2 ml) were taken for each oligomer in table 1and 450 ul of homogenate was added in each tube. 50 ul ASO (200 uM) was added to each tube. Immediately after mixing, 125 ul of (5×) stop buffer (2.5% IGEPAL, 0.5M NaCl, 5 mM EDTA, 50 mM Tris, pH=8.0) and 12.5 ul of 20 mg/ml Proteinase K (Ambion, #AM2546) was added to one tube for 0 hour time point. The remaining reaction mixtures were incubated at 37° C. with shaking at 400 rpm on VWR Incubating Microplate shaker. After incubation for a designated period (1, 2, 3, 4, and 5 days), each mixture was treated with 125 ul of (5×) stop buffer (2.5% IGEPAL, 0.5M NaCl, 5 mM EDTA, 50 mM Tris, pH=8.0) and 12.5 ul of 20 mg/ml Proteinase K (Ambion, #AM2546).

Work up and Bioanalysis: ISIS 355868 (5'-GCGTTT<u>GCTCTTCTTCTTGCGTTTTTT</u>-3' (SEQ ID NO: 238)), a 27-mer oligonucleotide (underlined bases are MOE modified) was used as the internal standard for quantitation of chiromersens. 50 ul of internal standard (200 uM) was added to each tube followed by addition of 250 ul of 30% ammonium hydroxide, 800 ul of Phenol:Chloroform:iso-amyl alcohol (25:24:1). After mixing and centrifugation at 600 rpg, the aqueous layer was evaporated on speed vac to 100 ul and loaded on Sep Pak column (C18, 1 g, WAT 036905). All the aqueous washings (2×20 ml) of Sep pak column were tested with quick Ion Exchange method to ensure that no product was found there. 50% ACN (3.5 ml) was used to elute the oligonucleotide and metabolites and the column was further washed with 70% CAN (3.5) ensure that there was nothing left on the column. Five fractions were collected for each sequence. Water wash 1, 2, 3, ACN1 and 2 using Visiprep system (Sigma, part number: 57031-U).

Ion Exchange Method

| | Time | Flow (ml/min) | % A | % B | Curve |
|---|------|---------------|-----|-----|-------|
| | Time | 1.0 | 95 | 5 | |
| 1 | 2 | 1.0 | 95 | 5 | 1 |
| 2 | 3 | 1.0 | 75 | 25 | 6 |
| 3 | 10 | 1.0 | 35 | 65 | 6 |
| 4 | 10.1 | 1.0 | 95 | 5 | 6 |
| 5 | 12.5 | 1.0 | 95 | 5 | 1 |

Buffer A=10 mM Tris HCl, 50% ACN, pH=8.0
Buffer B=A+800 mM NaClO4
Column=DNA pac 100
Column Temperature 60° C.
Wash method was used after each run (Described in M9-Exp21) using the same buffers as above and 50:50 (methanol:water) in buffer line C.

| | Time | Flow (ml/min) | % A | % B | % C | Curve |
|---|------|---------------|-----|-----|-----|-------|
| | Time | 1.0 | 0 | 0 | 100 | |
| 1 | 5.5 | 1.0 | 0 | 0 | 100 | 1 |
| 2 | 5.6 | 1.0 | 100 | 0 | 0 | 6 |
| 3 | 7.5 | 1.0 | 100 | 0 | 0 | 6 |
| 4 | 7.6 | 1.0 | 95 | 5 | 0 | 6 |
| 5 | 12.5 | 1.0 | 95 | 5 | 0 | 1 |

Acetonitrile eluate was concentrated to dryness and dissolved in 100 ul water to be analyzed using RPHPIPC.
Eluant A=10 mM Tributylammonium acetate, pH=7.0
Eluant B=ACN (HPLC grade, B& J)
Column: XTerra MS C18, 3.5 um, 4.6×50 mm, Part number: 186000432
Guard column from Phenomenex, part number: KJ0-4282
Column Temperature=60° C.
HPLC Gradient:

| | Time | Flow (ml/min) | % A | % B | Curve |
|---|------|---------------|-----|-----|-------|
| 1 | | 1.0 | 65 | 35 | |
| 2 | 5.0 | 1.0 | 65 | 35 | 1 |
| 3 | 30.0 | 1.0 | 40 | 60 | 6 |
| 4 | 35.0 | 1.0 | 5 | 90 | 6 |
| 5 | 36.0 | 1.0 | 65 | 35 | 6 |
| 6 | 40.0 | 1.0 | 65 | 35 | 1 |

For Analytical RP HPLC, 10 ul of this stock solution was added to 40 ul water and 40 ul was injected.

TABLE 3

| S.NO. | Sequence | Description |
|-------|----------|-------------|
| ONT-41 | Gs5mCs5mCsTs5mCs AsGsTs5mCsTsGs5m CsTsTs5mCsGs5mCs As5mCs5mC (SEQ ID NO: 239) | Mipomersen |
| ONT-87 | Gs5mCs5mCsTs5mCs AsGsTs5mCsTsGs5m CsTsTs5mC3Gs5mCs As5mCs5mC (SEQ ID NO: 240) | MOE-wing-core-wing design-(human) RNAse H substrate 1 5R-(SSR)₃-5R |

TABLE 3-continued

| S.NO. | Sequence | Description |
|-------|----------|-------------|
| ONT-154 | Gs5mCs5mCsTs5mCs AsGsTs5mCsTsGs5m CsTsTs5mCsGs5mCs As5mCs5mC (SEQ ID NO: 241) | All deoxy, (5S-(SSR)₃-5S) |
| ONT-70 | Gs5mCsGsTsTsTsGs 5mCsTs5mCsTsTs5m CsTsTs5mCsTsTsGs 5mCGsTsTsTsTsT (SEQ ID NO: 242) | ISIS 355868 internal standard for quantitation of Mipomersen |

Discussion: 2' modifications in antisense and siRNAs are predicted to stabilize these molecules and increase their the persistence in plasma and tissues compared with wild-type DNAs and siRNAs.

2'-MOE wing-core-wing design in Mipomersen. The first generation antisense oligonucleotides employed in the first antisense clinical trials had 2'-deoxy ribonucleotide residues and phosphorothioate internucleoside linkages. Subsequently, second generation antisense oligonucleotides were developed, which were typically of what is referred to herein as "5-10-5 2'-MOE wing-core-wing design", in that five (5) residues at each end were 2'-O-methoxyethyl (2'-MOE)-modified residues and ten (10) residues in the middle were 2'-deoxy ribonucleotides; the internucleotide linkages of such oligonucleotides were phosphorothioates. Such "5-10-5 2'-MOE wing-core-wing" oligonucleotides exhibited marked improvement in potency over first generation (PCT/US2005/033837). Similar wing-core-wing motifs like 2-16-2, 3-14-3, 4-12-4, or 5-10-5 were designed to improve the stability of oligonucleotides to nucleases, while at the same time maintaining enough DNA structure for RNase activity.

Chirally pure oligonucleotides. The present invention provides chirally pure oligonucleotides and demonstrates, among other things, that selection of stereochemistry in and of itself can improve oligonucleotide stability (i.e., independent of residue modification such as 2'MOE modification). Indeed, the present invention demonstrates that chirally pure phosphorothioate oligonucleotides can provide same or better stability than corresponding 2'-modified stereorandom phosphorothioate compounds.

In some embodiments, tested chirally pure oligonucleotides are of the general structure X-Y-X with respect to stereochemistry in that they contain wing "X" regions (typically about 1-10 residues long) where all residues have the same stereochemistry flanking a core "Y" region in which stereochemistry varies. In many embodiments, about 20-50% of the nucleotide analogs in tested such oligonucleotides are not substrates for RNase H. The ability to control the stereochemistry of phosphorothioates in DNA enables us to protect the oligomers from degradation by nucleases while maintaining the RNase active sites. One of these designs is ONT-154 where wings of the oligonucleotide have been stabilized by Sp phosphorothioate chemistry with retention of few Rp phosphorothioates which are better substrates for RNase H (Molecular Cell, 2007). The crystal structure of human RNase H complexed with DNA/RNA duplex shows that the Phosphate-binding pocket of the enzyme makes contacts with four contiguous phosphates of DNA. The first three contacts seem stronger than fourth one and they prefer Pro-R/Pro-R/Pro-S oxygen atoms of each of these three phosphates. Combining the stability advantage coming from Sp stereochemistry with RNase H active sites, several sequences can be designed to compete with/or improve upon 2'-modifications. From rat whole liver homogenate stability experiment comparing Mipomersen (ONT-41) with our rational (chiral control) design with and without 2'-modifications (ONT-87 and ONT-54) (Table 1 and FIG. 1) it is evident that through removal of the 2'-modifications and careful chiral control with Rp and Sp phosphorothioates, we can improve the stability of these oligonucleotides which later affect the efficacy in vivo.

TABLE 4

Hu chiromersens studied for rat whole live homogenate stability

| Sequence | Description | Target | Tm (° C.) | SEQ ID NO: |
|---|---|---|---|---|
| ONT-41 | Gs5mCs5mCsTs5mCsAsGs Ts5mCsTsGs5mCsTsTs5m CsGs5mCsAs5mCs5mC | Hu ApoB | 80.7 | 243 |
| ONT-75 | Gs5mCs5mCsTs5mCsAsGs Ts5mCsTsGs5mCsTsTs5m CsGs5mCsAs5mCs5mC | Hu ApoB | 85.0 | 244 |
| ONT-77 | Gs5mCs5mCsTs5mCsAsGs Ts5mCsTsGs5mCsTsTs5m CsGs5mCsAs5mCs5mC | Hu ApoB | 79.9 | 245 |
| ONT-80 | Gs5mCs5mCsTs5mCsAsGs Ts5mCsTsGs5mCsTsTs5m CsGs5mCsAs5mCs5mC | Hu ApoB | 75.8 | 246 |
| ONT-81 | Gs5mCs5mCsTs5mCsAsGs Ts5mCsTsGs5mCsTsTs5m CsGs5mCsAs5mCs5mC | Hu ApoB | 80.7 | 247 |
| ONT-87 | Gs5mCs5mCsTs5mCsAsGs Ts5mCsTsGs5mCsTsTs5m CsGs5mCsAs5mCs5mC | Hu ApoB | 82.4 | 248 |
| ONT-88 | Gs5mCs5mCsTs5mCsAsGs Ts5mCsTsGs5mCsTsTs5m CsGs5mCsAs5mCs5mC | Hu ApoB | 78.9 | 249 |
| ONT-89 | Gs5mCs5mCsTs5mCsAsGs Ts5mCsTsGs5mCsTsTs5m CsGs5mCsAs5mCs5mC | Hu ApoB | 80.9 | 250 |
| ONT-70 | Gs5mCsGsTsTsTsGs5mCs Ts5mCsTsTs5mCsTsTs5m CsTsTsGs5mCGsTsTsTs TsTsT | ISIS 355868 internal standard | | 251 |

TABLE 5

Mouse chiromersens studied for rat whole live homogenate stability

| Sequence | Description | Target | SEQ ID NO: |
|---|---|---|---|
| ONT-83 | GsTs5mCs5mCs5mCsTsGsAsAs GsAsTsGsTs5mCsAsAsTsGs5mC | Mouse ApoB | 252 |
| ONT-82 | GsTs5mCs5mCs5mCsTsGsAsAs GsAsTsGsTs5mCsAsAsTsGs5mC | Mouse ApoB | 253 |
| ONT-84 | GsTs5mCs5mCs5mCsTsGsAsAs GsAsTsGsTs5mCsAsAsTsGs5mC | Mouse ApoB | 254 |
| ONT-85 | GsTs5mCs5mCs5mCsTsGsAsAs GsAsTsGsTs5mCsAsAsTsGs5mC | Mouse ApoB | 255 |
| ONT-86 | GsTs5mCs5mCs5mCsTsGsAsAs GsAsTsGsTs5mCsAsAsTsGs5mC | Mouse ApoB | 256 |

Example 2. Exemplary Chirally Controlled siRNA Molecules

TABLE 1

Summary of Phosphodiester Polar interactions with h-Ago-2 and h-Ago-1

| Phosphate* | Residue | Length/Å | Config |
|---|---|---|---|
| Science 2012 hAgo-2 | | | |
| 2 | Asn551 | 2.7 | Pro(S) |
|   | Gln548 | 2.9 | Pro(S) |
| 3 | Lys566 | 3.1 | Pro(R) |
|   | Arg792 | 3.4 | Pro(R) |
| 4 | Tyr790 | 2.6 | Pro(R) |
|   | Arg792 | 3.0 | Pro(R) |
|   |        | 2.8 | Pro(R) |
|   |        | 3.4 | Pro(S) |
| 5 | Ser798 | 2.7 | Pro(R) |
|   |        | 2.9 | Pro(R) |
|   | Tyr804 | 2.8 | Pro(S) |
| 6 | Lys709 | 3.0 | Pro(S) |
|   | Arg761 | 2.9 | Pro(R) |
|   | His753 | 2.8 | Pro(R) |
| 7 | Arg714 | 2.9 | Pro(R) |
|   |        | 3.0 | Pro(R) |
|   | Arg761 | 3.0 | Pro(S) |

| Phosphate | Residue | Length/Å | Config |
|---|---|---|---|
| Cell 2012 hAgo-2 | | | |
| 2 | Asn551 | 2.7 | Pro(S) |
|   | Gln548 | 3.1 | Pro(S) |
|   | Gln548 | 2.9 | Pro(R) |
| 3 | Lys566 | 2.9 | Pro(R) |
|   | Arg792 | 3.3 | Pro(R) |
| 4 | Tyr790 | 2.8 | Pro(R) |
|   | Arg792 | 2.8 | Pro(R) |
| 5 | Ser798 | 2.6 | Pro(R) |
|   |        | 2.9 | Pro(R) |
|   | Tyr804 | 2.5 | Pro(S) |
| 6 | Lys709 | 3.2 | Pro(S) |
|   | Arg761 | 2.8 | Pro(R) |
|   | His753 | 3.0 | Pro(R) |
| 7 | Arg714 | 2.8 | Pro(R) |
|   |        | 3.1 | Pro(R) |
|   | Arg761 | 2.8 | Pro(S) |
| 8 | Arg761 | 2.4 | Pro(R) |
|   | Ala221 | 3.5 | Pro(R) |
| 9 | Arg351 | 2.2 | Pro(R) |
| 10 | Arg710 | 2.5 | Pro(R) |
| 18 |  | No contacts | |
| 19 | Tyr311 | 3.1 | Pro(R) |
|   | Arg315 | 2.8 | Pro(R) |
| 20 | His271 | 3.1 | Pro(R) |
|   | His319 | 3.4 | Pro(S) |
|   | Tyr311 | 2.2 | Pro(S) |

| Phosphate | Residue | Length/Å | Config |
|---|---|---|---|
| Cell Rep 2013, h-Ago-1[+] | | | |
| 2 | Asn549 | 2.7 | Pro(S) |
|   | Gln546 | 2.9 | Pro(S) |
|   |        | 2.8 | Pro(R) |
| 2 | Lys564 | 2.9 | Pro(R) |
|   | Arg790 | 3.4 | Pro(R) |
|   |        | 3.3 | Pro(R) |
| 4 | Try788 | 2.7 | Pro(R) |
|   | Arg790 | 3.3 | Pro(R) |
| 5 | Ser796 | 2.5 | Pro(R) |
|   |        | 2.8 | Pro(R) |
|   | Tyr802 | 2.6 | Pro(S) |

TABLE 1-continued

Summary of Phosphodiester Polar interactions with h-Ago-2 and h-Ago-1

| | | | |
|---|---|---|---|
| 6 | Lys707 | 2.8 | Pro(S) |
| | Arg759 | 2.7 | Pro(R) |
| | His751 | 3.0 | Pro(R) |
| 7 | Arg712 | 3.1 | Pro(S) |
| | | 3.3 | Pro(S) |
| | Arg373 | 3.4 | Pro(R) |
| | Thr757 | 2.9 | Pro(R) |
| 8 | Arg759 | 2.2 | Pro(S) |
| | His790 | 3.4 | Pro(R) |
| | Ser218 | 2.7 | Pro(R) |
| 9 | Arg349 | 3.5 | Pro(R) |
| | Arg708 | 2.9 | Pro(S) |
| 10 | Arg708 | 3.2 | Pro(R) |
| | | 2.9 | Pro(R) |
| 21 | Tyr309 | 2.6 | Pro(S) |
| | Tyr314 | 2.6 | Pro(S) |
| | His269 | 3.0 | Pro(R) |

*Phosphate No. from 5'-end
†Complexed with h-let-7 22mer

The present invention, despite teachings in the art to the contrary, recognizes that stereochemistry of internucleotidic linkages can be utilized to increase stability and activity of oligonucleotides through chirally controlled oligonucleotide compositions. Such chirally controlled oligonucleotide compositions can provide much better results than chirally uncontrolled oligonucleotide compositions as demonstrated in this disclosure.

There are two reported crystal structures of RNA complexed with human Argonaute-2 protein (hAgo2): The Crystal Structure of Human Argonaute-2, Science, 2012 (PDB-4ei3); and The Structure of Human Argonaute-2 in Complex with miR-20a Cell, 2012 PDB-4f3t). In addition, there is one reported crystal structure of Let-7 RNA complexed with human Argonaute-1 protein (hAgo-1): The Making of a Slicer: Activation of Human Argonaute-1, Cell Rep. 2013 (PDB-4krf).

Based upon the information contained in these publications, it was anticipated that some judgments could be made about advantageous preferences for stereochemistry at the internucleotidic phosphate linkage if the phosphodiester bonds were to be replaced by phosphorothioate diester bonds. These advantages could relate to significantly improved potency, stability and other pharmacological properties. With this in mind, the computer program Pymol was used to locate all polar interactions between the protein and the internucleotidic phosphodiester linkage of the crystallized RNA for all three structures. Polar interactions at a distance of more than 3.5 Å were ignored.

The results of this analysis are summarized in Table 1. A particular phosphorus atom from the phosphodiester backbone on the RNA was assigned a Pro(R) or a Pro(S) configuration based upon the assumption that in the phosphorothioate diester analog the quite similar bond would be made between the polar group on an amino acid residue and the respectful phosphate oxygen atom. The sulfur substitution, instead of non-bridging oxygen would therefore confer a unique stereochemistry (either (Sp) or (Rp) absolute configuration) on the phosphorus atom within that motif.

Of note is the extraordinarily good agreement between the two structures of hAgo-2 in complex with RNA. Also, there is an excellent agreement between the structures of hAgo-1 and hAgo-2 in complex with RNA, indicating that the conformation that the RNA molecule adopts is highly conserved between these two proteins. Any conclusions or rules which are formed based upon the results of this analysis are likely, therefore, to be valid for both protein molecules.

As can be seen, there is usually more than one polar interaction at any one phosphodiester group, with the exception of those between the phosphodiesters at phosphate positions 9 and 10 and hAgo-2 (Cell 2012) which adopt exclusively Pro(Rp) preference through bonding with Arg351 and Arg710 respectively.

However, shorter distances (corresponding to stronger interactions) as well as the number of bonds per oxygen can suggest a predominant interaction for the Pro(Rp) or the Pro(Sp) oxygens: hence resulting in several interactions which are predominantly of one stereochemical type or the other. Within this group are the interactions between the phosphodiesters at phosphate positions 2 (Sp), 3 (Rp), 4 (Rp), 6 (Rp), 8 (Sp), 19 (Rp), 20 (Sp) and 21 (Sp).

Of the remaining interactions, there does not appear to be a preference for one particular stereochemistry to be adopted over the other, so the preferred stereochemistry could be either (Sp) or (Rp).

Within this category are the interactions formed between the phosphodiesters at phosphate positions 5 (Rp or Sp) and 7 (Rp or Sp).

For interactions at the other phosphate backbone, there is no crystal structure information, so stereochemistry at these positions can similarly be either (Rp) or (Sp) until empirical data shows otherwise.

To this end, Table 6 contains several non-limiting exemplary siRNA general constructs which can be conceived to take advantage of this preference for stereochemistry at individual phosphorothioate diester motifs.

TABLE 6

Exemplary general siRNA constructs

| PS* | Chirally Controlled Antisense Strand Construct | | | | | |
|---|---|---|---|---|---|---|
| 2 | (Sp) | (Rp) | (Sp) | (Rp) | (Sp) | (Rp) |
| 3 | (Rp) | (Sp) | (Rp) | (Sp) | (Rp) | (Sp) |
| 4 | (Rp) | (Sp) | PO | PO | (Rp) | (Sp) |
| 5 | (Rp) or (Sp) | (Sp) or (Rp) | PO | PO | PO | PO |
| 6 | (Rp) | (Sp) | PO | PO | (Rp) | (Sp) |
| 7 | (Rp) or (Sp) | (Sp) or (Rp) | PO | PO | PO | PO |
| 8 | (Sp) | (Rp) | PO | PO | (Sp) | (Rp) |
| 9 | (Rp) | (Sp) | PO | PO | (Rp) | (Sp) |
| 10 | (Rp) | (Sp) | PO | PO | (Rp) | (Sp) |
| 11 | (Rp) or (Sp) | (Sp) or (Rp) | PO | PO | PO | PO |
| 12 | (Rp) or (Sp) | (Sp) or (Rp) | PO | PO | PO | PO |
| 13 | (Rp) or (Sp) | (Sp) or (Rp) | PO | PO | PO | PO |
| 14 | (Rp) or (Sp) | (Sp) or (Rp) | PO | PO | PO | PO |
| 15 | (Rp) or (Sp) | (Sp) or (Rp) | PO | PO | PO | PO |
| 16 | (Rp) or (Sp) | (Sp) or (Rp) | PO | PO | PO | PO |
| 17 | (Rp) or (Sp) | (Sp) or (Rp) | PO | PO | PO | PO |
| 18 | (Rp) or (Sp) | (Sp) or (Rp) | PO | PO | PO | PO |
| 19 | (Rp) | (Sp) | PO | PO | (Rp) | (Sp) |
| 20 | (Sp) | (Rp) | (Sp) | (Rp) | (Sp) | (Rp) |
| 21 | (Sp) | (Rp) | (Sp) | (Rp) | (Sp) | (Rp) |

*The number indicates the phosphate position from the 5' end of the antisense strand of the siRNA, (e.g. #2 is located between nucleotides 1 and 2 and #21 is located between nucleotides 20 and 21). (Sp) and (Rp) designates stereochemistry of phosphorus atom on phosphorothioate (PS) diester internucleotidic linkage at the indicated position. PO designates a phosphodiester internucleotidic linkage at the indicated position.

Exemplary siRNAs include but are not limited to siRNAs having a Sp configuration for a chiral phosphorothioate at the 3'end and at the 5'end of the antisense strand of the siRNA duplex, which confers unprecedentedly increased stability in human serum or biological fluids. That same Sp configuration for the chiral phosphorothioate at the 3'end and at the 5'end of the antisense strand of the siRNA duplex confers unprecedentedly increased biological potency caused by increased affinity to the Ago2 protein leading to increased activity within the RISC RNAi silencing complex.

In one embodiment, a single chiral phosphorothioate motif is introduced independently at each position along the antisense or sense strand of the siRNA molecule. For a 21mer, this provides 80 unique sequences, with either an (Sp) or an (Rp) chirally controlled phosphorothioate group. When duplexed independently, 1600 unique combinations of siRNAs are prepared.

siRNA Transfection of Chiral siRNA Molecules

Hep3B, or HeLa cells are reverse transfected at a density of $2.0 \times 10^4$ cells/well in 96-well plates. Transfection of siRNA is carried out with lipofectamine RNAiMax (Life Technologies, cat. No. 13778-150) using the manufacturer's protocol, except with a decreased amount of Lipofectamine RNAiMax of 0.2 ul per well. Twelve, 1:3 siRNA duplex dilutions are created starting at 1 uM. 10 ul of 10× siRNA duplex is then lipoplexed with a prepared mixture of 9.8 ul of serum-free medium and 0.2 ul of Lipofectamine RNAiMax per well. After a 10-15 minute incubation, $2.0 \times 10^4$ cells in 80 ul of EMEM cell growing media (ATCC, 30-2003) is added to bring the final volume to 100 ul per well. Two separate transfection events are performed for each dose.

24 hours after transfection Hep3B or HeLa cells are lysed and mRNA against which the siRNA is targeted is purified using MagMAX™-96 Total RNA Isolation Kit (Life Technologies, AM1830); 15 ul of cDNA is synthesized with High Capacity cDNA Reverse Transcription Kit with RNase Inhibitor (Life Technologies, 4374967). Gene expression is evaluated by Real-Time PCR on a Lightcycler 480 (Roche) using a Probes Master Mix (Roche, 04 707 494 001) according to manufacturer's protocol.

IC50s and Data Analysis

Delta delta Ct method is used to calculate values. Samples are normalized to hGAPDH and calibrated to mock transfected and untreated samples. A stereo-random molecule is used as a control. The data is represented as a mean of 2 biological replicates using Graphpad Prism. A four-parameter linear regression curve is fitted to the data and the bottom and top are constrained to a 0 and 100 constants respectively in order to calculate a relative IC50.

The present Example demonstrates successful inhibition of target gene expression using siRNA agents comprised of chirally controlled oligonucleotides as described herein. Specifically, this Example describes hybridization of individual oligonucleotide strands prepared through chirally controlled synthesis as described herein, so that double-stranded chirally controlled siRNA oligonucleotide compositions are provided. This Example further demonstrates successful transfection of cells with such agents and, moreover, successful inhibition of target gene expression.

In Vitro Metabolic Stabilities of Human PCSK9 siRNA Duplexes Having Stereocontrolled Phosphorothioate Diester Linkages in Human Serum.

10 μM siRNA duplexes were incubated in 90% human serum (50 μL, Sigma, H4522) at 37° C. for 24 hours. A 0 min time point (50 μL) was prepared as well as a PBS control incubation time point (50 μL), where the 10 μM siRNA duplex was incubated in 90% 1×PBS (50 μL at 37° C. for 24 hours. After completion of the incubation, to each time point, were added 10 μL of Stop-Solution (0.5 M NaCl, 50 mM TRIS, 5 mM EDTA, 2.5% IGEPAL), followed by 3.2 μL of Proteinase K (20 mg/mL, Ambion). The samples were incubated at 60° C. for 20 min, and then centrifuged at 2000 rpm for 15 min. The final reaction mixtures were directly analyzed in denaturing IEX HPLC (injection volume 50 μL). The ratio of integrated area at 24 h and 0 min was used to determine the % of degradation for each siRNA.

Figure 1:
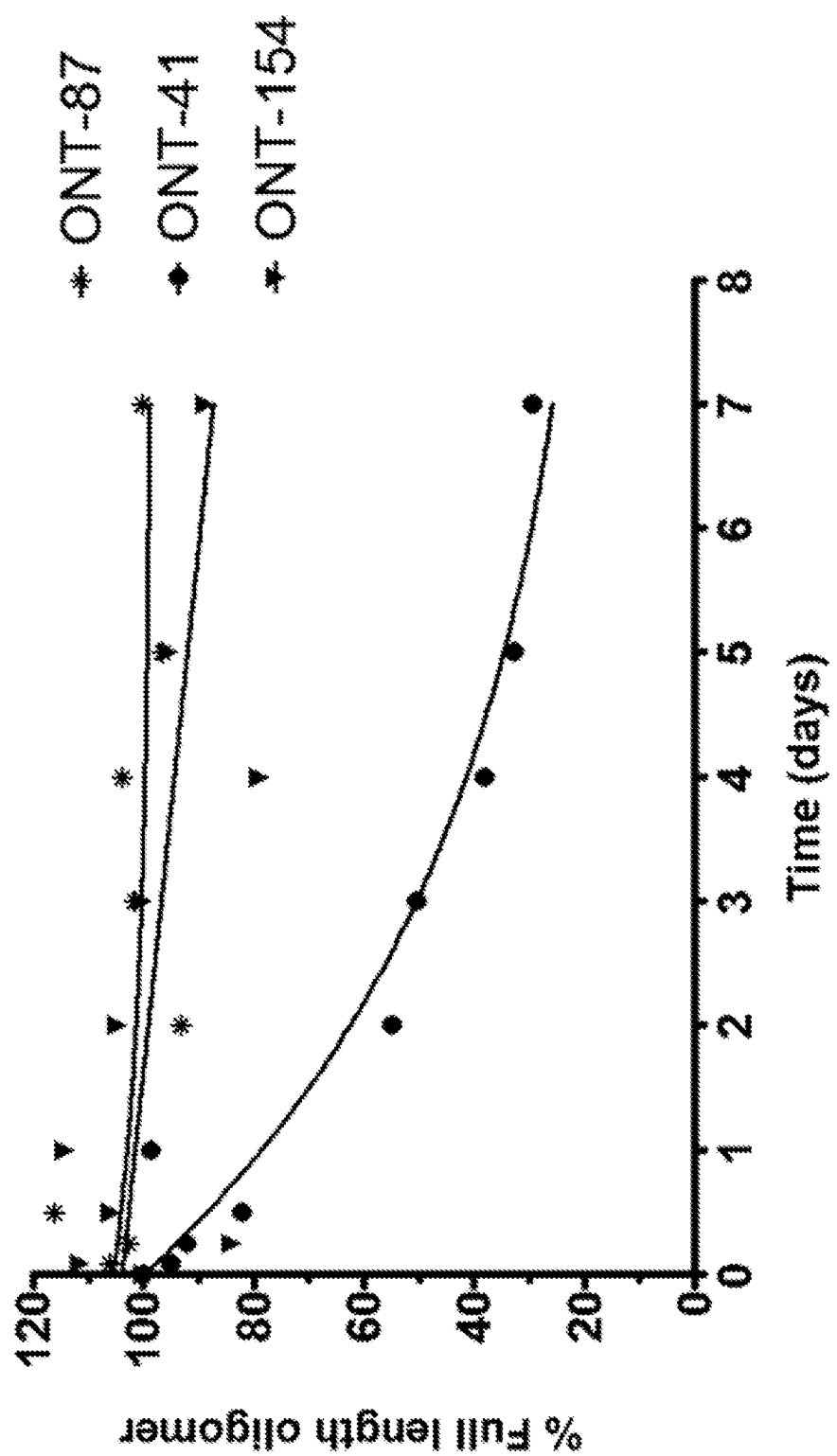
FIG. 1. Reverse phase HPLCs after incubation with rat liver homogenate. Total amounts of oligonucleotides remaining when incubated with rat whole liver homogenate at 37° C. at different days were measured. The in-vitro metabolic stability of ONT-154 was found to be similar to ONT-87 which has 2'-MOE wings while both have much better stability than 2'-MOE gapmer which is stereorandom (ONT-41, Mipomersen). The amount of full length oligomer remaining was measured by reverse phase HPLC where peak area of the peak of interest was normalized with internal standard.
Figure 2:
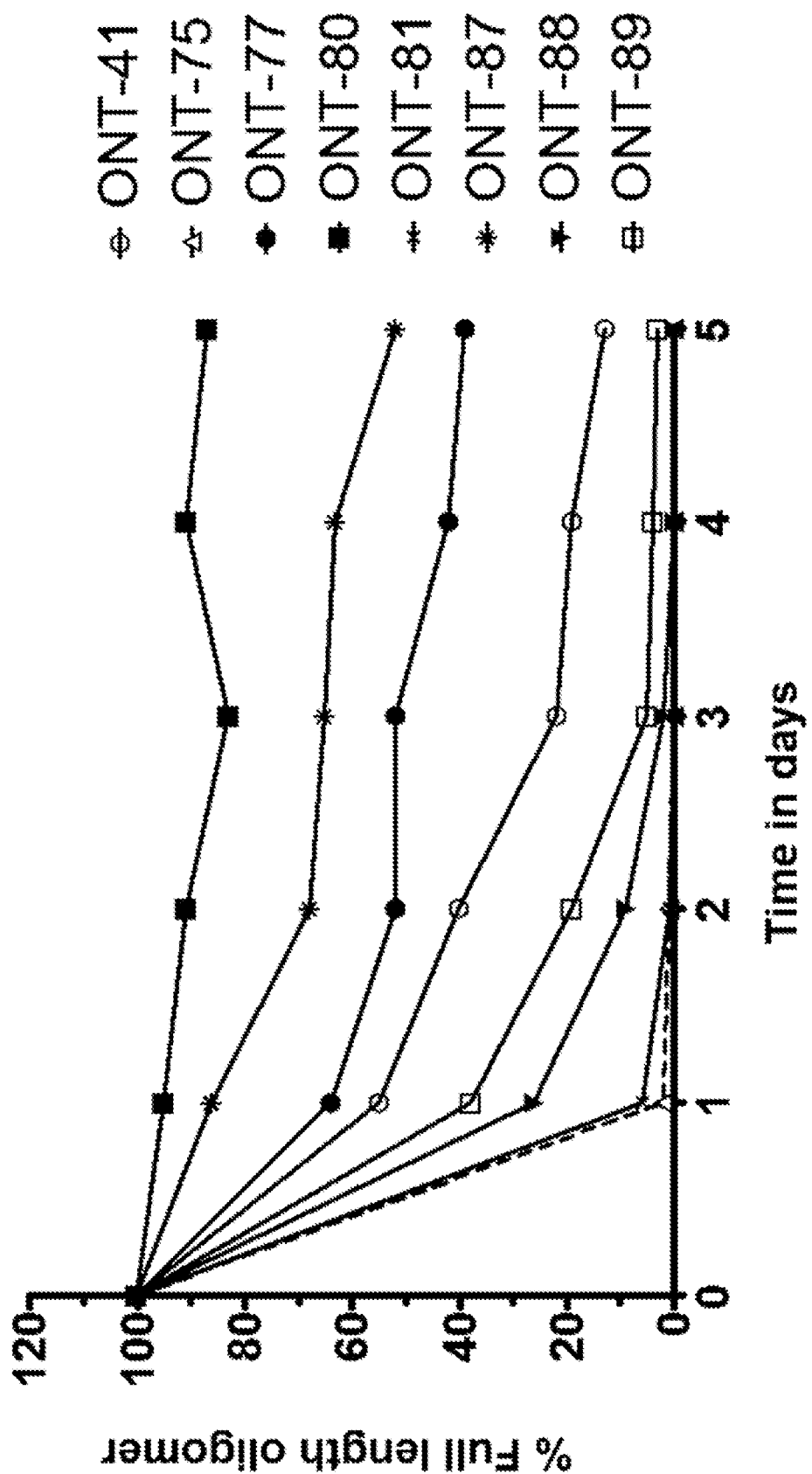
FIG. 2. Degradation of various chirally pure analogues of Mipomersen (ONT-41) in rat whole liver homogenate. Total amounts of oligonucleotide remaining when incubated with rat whole liver homogenate at 37° C. at different days were measured. The in-vitro metabolic stability of chirally pure diastereomers of human ApoB sequence ONT-41 (Mipomersen) was found to increase with increased Sp internucleotidic linkages. The amount of full length oligomer remaining was measured by reverse phase HPLC where peak area of the peak of interest was normalized with internal standard.
Figure 3:
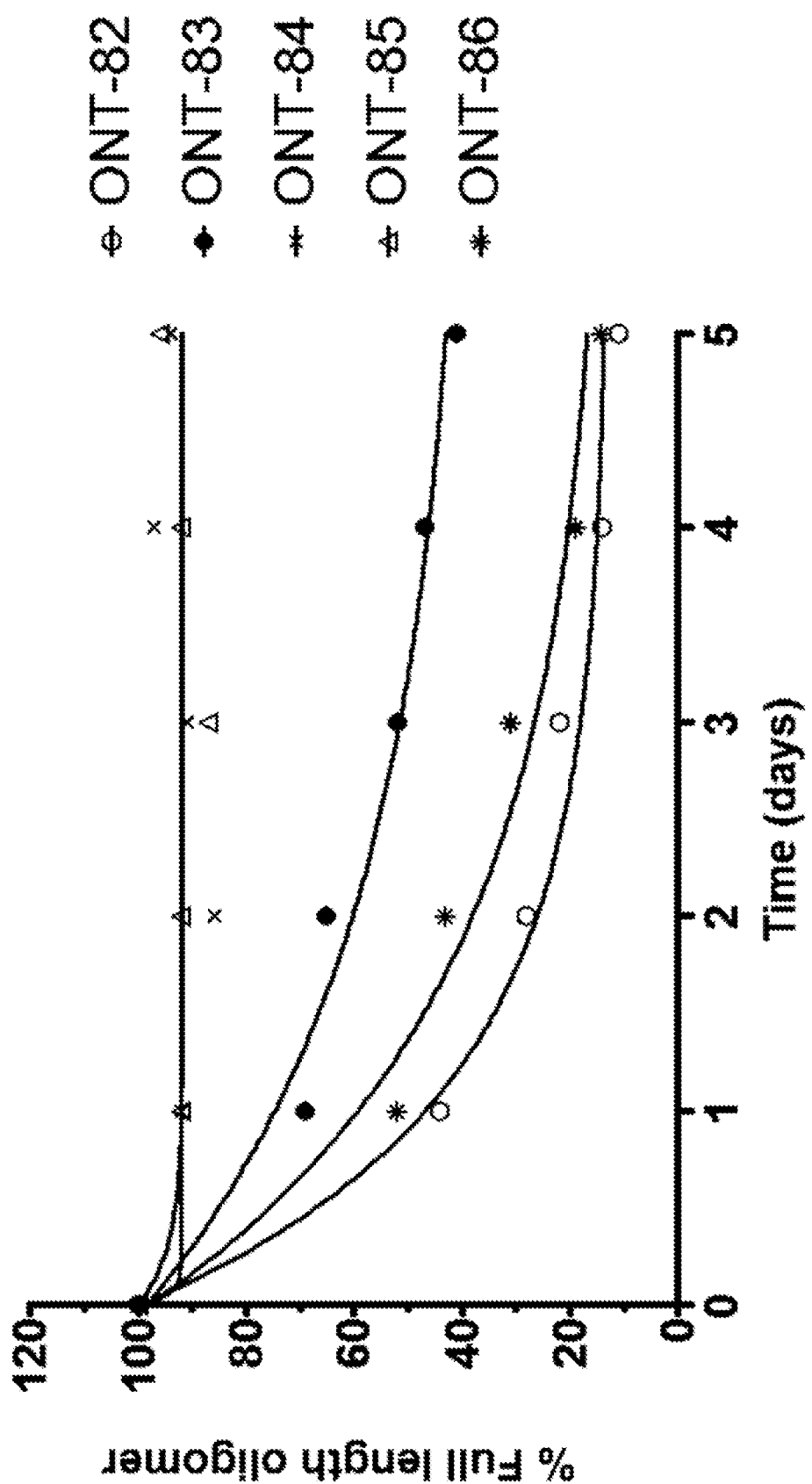
FIG. 3. Degradation of various chirally pure analogues of mouse ApoB sequence (ISIS 147764, ONT-83) in rat whole liver homogenate. Total amounts of oligonucleotide remaining when incubated with rat whole liver homogenate at 37° C. at different days were measured. The in-vitro metabolic stability of chirally pure diastereomers of murine ApoB sequence (ONT-83, 2'-MOE gapmer, stereorandom phosphorothioate) was found to increase with increased Sp internucleotidic linkages. The amount of full length oligomer remaining was measured by reverse phase HPLC where peak area of the peak of interest was normalized with internal standard.
Figure 4:
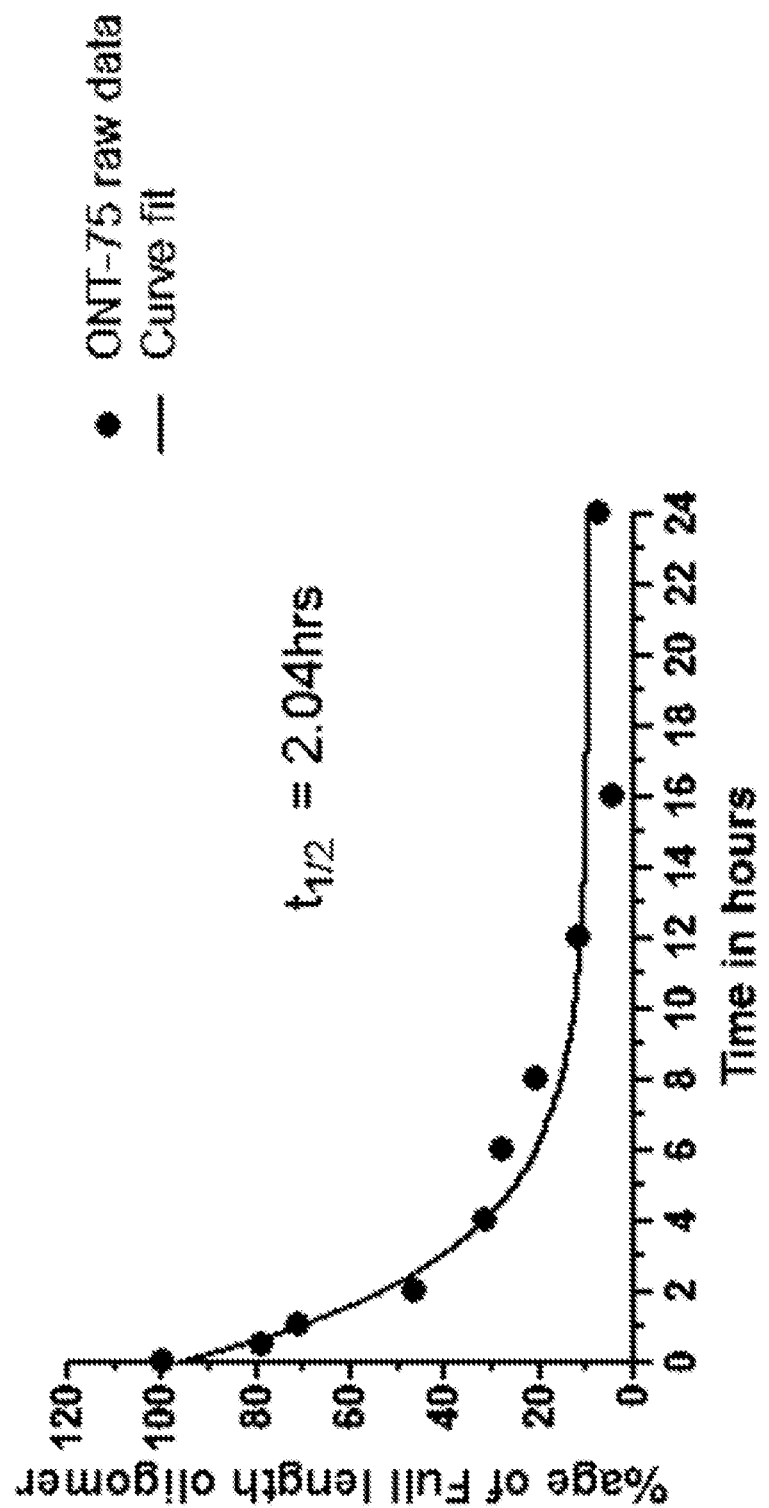
FIG. 4. Degradation of Mipomersen analogue ONT-75 in rat whole liver homogenate over a period of 24 hrs. This figure illustrates stability of ONT-75 in rate whole liver homogenate.
Figure 5:
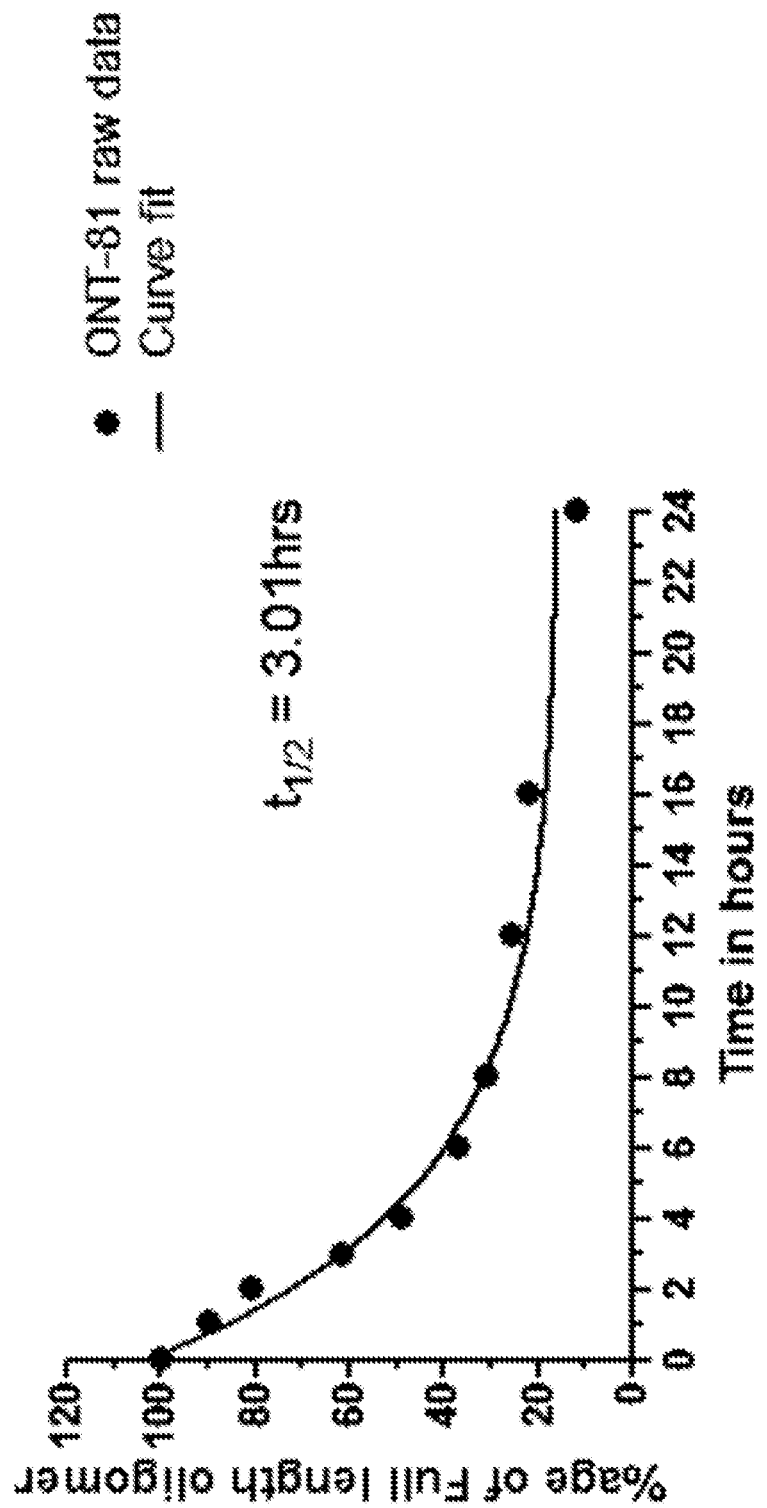
FIG. 5. Degradation of Mipomersen analogue ONT-81 in rat whole liver homogenate over a period of 24 hrs. This figure illustrates stability of ONT-81 in rate whole liver homogenate.

It was observed that the stereochemistry configuration of the single phosphorothioate at position 21 (3'end) of both the antisense strand and the sense strand of the siRNA had a crucial impact on the stability of the duplex upon incubation in Human Serum (FIG. 1). As illustrated in the FIG. 1 and as determined following the integration ratio of the degradation pattern, an (Rp, Rp) siRNA duplex exhibited a significant 55.0% degradation after 24 h. The stereorandom mixture of phosphorothioates in the stereorandom siRNA showed 25.2% degradation after 24 h. The (Sp/Sp) siRNA showed only minor 7.3% degradation after 24 h. This illustrates the drastic impact that phosphorothioate stereochemistry confers to therapeutic siRNAs. Additional exemplary data were presented in FIG. 2, FIG. 3, FIG. 4 and FIG. 5.

It is observed that each of the stereopure constructs show different potency ($IC_{50}$ values) dependent on the position of the phosphorothioate motif along the backbone. It is also observed that different $IC_{50}$ values are obtained dependent upon whether the phosphorothioate motif at any single position is (Sp) or (Rp). The impact of stereochemistry upon stability is likewise clear and differentiating, using either Human Serum described above, or Human Hepatic Cytosol extract or Snake Venom Phosphodiesterase, or isolated endonuclease or isolated exonuclease.

Certain design rules may be formulated based upon data obtained in the above example. These design information can be applied for the introduction of multiple chiral phosphorothioate linkages within the antisense and/or sense strand of the siRNA as exemplified below. The present invention recognizes that an increased amount of chiral phosphorothioate within the antisense and/or sense strand of the siRNA, introduced at the right positions and having the right stereochemistry configuration leads to greatly improved siRNA constructs in terms of potency and metabolic stability in vitro—translating into greatly pharmacologically enhanced therapeutic siRNAs.

Exemplary Chirally Controlled siRNA Oligonucleotides Targeting PCSK9

Proprotein convertase subtilisin/kexin type 9 (PCSK9), is an enzyme involved in cholesterol metabolism. PCSK9 binds to the receptor for low density lipoprotein (LDL), triggering its destruction. Although LDL associated with the receptor is also eliminated when the receptor is destroyed, the net effect of PCSK9 binding in fact increases LDL levels, as the receptor would otherwise cycle back to the cell surface and remove more cholesterol.

Several companies are developing therapeutic agents that target PCSK9. Of particular relevance to the present disclosure, each of Isis Pharmaceuticals, Santaris Pharma, and Alnylam Pharmaceuticals is developing a nucleic acid agent that inhibits PCSK9. The Isis Pharmaceuticals product, an antisense oligonucleotide, has been shown to increase expression of the LDLR and decrease circulating total cholesterol levels in mice (Graham et al "Antisense inhibition of proprotein convertase subtilisin/kexin type 9 reduces serum LDL in hyperlipidemic mice". *J. Lipid Res.* 48 (4): 763-7, April 2007). Initial clinical trials with the Alnylam Pharmaceuticals product, ALN-PCS, reveal that RNA interference offers an effective mechanism for inhibiting PCSK9 (Frank-Kamenetsky et al "Therapeutic RNAi targeting PCSK9 acutely lowers plasma cholesterol in rodents and LDL cholesterol in nonhuman primates". *Proc. Natl. Acad. Sci. U.S.A.* 105 (33): 11915-20, August 2008).

In some embodiments, despite known results to the contrary, the present invention recognizes that phosphorothioate motifs of one stereochemical conformation or another can be rationally designed to take advantage of increased potency, stability and other pharmacological qualities through chirally controlled oligonucleotide compositions. To reinforce this concept, table 3 contains exemplary stereochemically pure constructs based on an siRNA sequence which targets PCSK9 messenger RNA.

In this exemplary embodiment, a single chiral phosphorothioate motif is introduced independently at each position along the antisense or sense strand of the siRNA molecule. For a 21mer, this provides 80 unique sequences, with either an (Sp) or an (Rp) chirally controlled phosphorothioate group. When duplexed independently, 1600 unique combinations of siRNAs are prepared.

In other exemplary embodiments, a single chiral phosphorothioate motif is introduced independently at each position along the antisense or sense strand of the siRNA molecule, while a 3'-(Sp) phosphorothioate linkage is conserved. For a 21mer, this provides another additional 80 unique sequences, with either an (Sp) or an (Rp) chirally controlled phosphorothioate group. When duplexed independently, 1600 unique combinations of siRNAs are prepared.

In other exemplary embodiments, multiple chiral phosphorothioate motifs are introduced independently at several positions along the antisense or sense strand of the siRNA molecule, following the codes described in Table 7, while a 3'-(Sp) phosphorothioate linkage is conserved.

TABLE 7

Example of PCSK-9 Sense and Antisense RNAs

| PCSK9 | siRNA Sense Strands | SEQ ID NO: |
|---|---|---|
| PCSK9 (1) | (Rp)-uucuAGAccuGuuuuGcuudTsdT | 257 |
| PCSK9 (2) | (Sp)-uucuAGAccuGuuuuGcuudTsdT | 258 |
| PCSK9 (3) | (Rp)-uucuAGAccuGuuuuGcuusdTdT | 259 |
| PCSK9 (4) | (Sp)-uucuAGAccuGuuuuGcuusdTdT | 260 |
| PCSK9 (5) | (Rp)-uucuAGAccuGuuuuGcusudTdT | 261 |
| PCSK9 (6) | (Sp)-uucuAGAccuGuuuuGcusudTdT | 262 |
| PCSK9 (7) | (Rp)-uucuAGAccuGuuuuGcsuudTdT | 263 |
| PCSK9 (8) | (Sp)-uucuAGAccuGuuuuGcsuudTdT | 264 |
| PCSK9 (9) | (Rp)-uucuAGAccuGuuuuGscuudTdT | 265 |
| PCSK9 (10) | (Sp)-uucuAGAccuGuuuuGscuudTdT | 266 |
| PCSK9 (11) | (Rp)-uucuAGAccuGuuuusGcuudTdT | 267 |
| PCSK9 (12) | (Sp)-uucuAGAccuGuuuusGcuudTdT | 268 |
| PCSK9 (13) | (Rp)-uucuAGAccuGuuusuGcuudTdT | 269 |
| PCSK9 (14) | (Sp)-uucuAGAccuGuuusuGcuudTdT | 270 |
| PCSK9 (15) | (Rp)-uucuAGAccuGuusuuGcuudTdT | 271 |
| PCSK9 (16) | (Sp)-uucuAGAccuGuusuuGcuudTdT | 272 |
| PCSK9 (17) | (Rp)-uucuAGAccuGusuuuGcuudTdT | 273 |
| PCSK9 (18) | (Sp)-uucuAGAccuGusuuuGcuudTdT | 274 |
| PCSK9 (19) | (Rp)-uucuAGAccuGsuuuuGcuudTdT | 275 |
| PCSK9 (20) | (Sp)-uucuAGAccuGsuuuuGcuudTdT | 276 |
| PCSK9 (21) | (Rp)-uucuAGAccusGuuuuGcuudTdT | 277 |
| PCSK9 (22) | (Sp)-uucuAGAccusGuuuuGcuudTdT | 278 |
| PCSK9 (23) | (Rp)-uucuAGAccsuGuuuuGcuudTdT | 279 |
| PCSK9 (24) | (Sp)-uucuAGAccsuGuuuuGcuudTdT | 280 |
| PCSK9 (25) | (Rp)-uucuAGAcscuGuuuuGcuudTdT | 281 |
| PCSK9 (26) | (Sp)-uucuAGAcscuGuuuuGcuudTdT | 282 |
| PCSK9 (27) | (Rp)-uucuAGAsccuGuuuuGcuudTdT | 283 |
| PCSK9 (28) | (Sp)-uucuAGAsccuGuuuuGcuudTdT | 284 |
| PCSK9 (29) | (Rp)-uucuAGsAccuGuuuuGcuudTdT | 285 |
| PCSK9 (30) | (Sp)-uucuAGsAccuGuuuuGcuudTdT | 286 |
| PCSK9 (31) | (Rp)-uucuAsGAccuGuuuuGcuudTdT | 287 |
| PCSK9 (32) | (Sp)-uucuAsGAccuGuuuuGcuudTdT | 288 |
| PCSK9 (33) | (Rp)-uucusAGAccuGuuuuGcuudTdT | 289 |
| PCSK9 (34) | (Sp)-uucusAGAccuGuuuuGcuudTdT | 290 |
| PCSK9 (35) | (Rp)-uucsuAGAccuGuuuuGcuudTdT | 291 |
| PCSK9 (36) | (Sp)-uucsuAGAccuGuuuuGcuudTdT | 292 |
| PCSK9 (37) | (Rp)-uuscuAGAccuGuuuuGcuudTdT | 293 |
| PCSK9 (38) | (Sp)-uuscuAGAccuGuuuuGcuudTdT | 294 |
| PCSK9 (38) | (Rp)-usucuAGAccuGuuuuGcuudTdT | 295 |
| PCSK9 (40) | (Sp)-usucuAGAccuGuuuuGcuudTdT | 296 |

NOTE:
lower case letters represent 2'-OMe RNA residues; capital letters represent RNA residues; d = 2'-deoxy residues; and "s" indicates a phosphorothioate moiety.

Synthesis examples for Human PCSK9 siRNA Antisense Strands having several chiral phosphorothioate internucleotide linkages and full chiral phosphorothioate internucleotide linkages.

| | Human PCSK9 siRNA Antisense Strands | SEQ ID NO: |
|---|---|---|
| PCSK9 (41) | (Rp)-AAGcAAAAcAGGUCuAGAAdTsdT | 297 |
| PCSK9 (42) | (Sp)-AAGcAAAAcAGGUCuAGAAdTsdT | 298 |
| PCSK9 (43) | (Rp)-AAGcAAAAcAGGUCuAGAAsdTdT | 299 |

-continued

| | Human PCSK9 siRNA Antisense Strands | SEQ ID NO: |
|---|---|---|
| PCSK9 (44) | (Sp)-AAGcAAAAcAGGUCuAGAAsdTdT | 300 |
| PCSK9 (45) | (Rp)-AAGcAAAAcAGGUCuAGAsAdTdT | 301 |
| PCSK9 (46) | (Sp)-AAGcAAAAcAGGUCuAGAsAdTdT | 302 |
| PCSK9 (47) | (Rp)-AAGcAAAAcAGGUCuAGsAAdTdT | 303 |
| PCSK9 (48) | (Sp)-AAGcAAAAcAGGUCuAGsAAdTdT | 304 |
| PCSK9 (49) | (Rp)-AAGcAAAAcAGGUCuAsGAAdTdT | 305 |
| PCSK9 (50) | (Sp)-AAGcAAAAcAGGUCuAsGAAdTdT | 306 |
| PCSK9 (51) | (Rp)-AAGcAAAAcAGGUCusAGAAdTdT | 307 |
| PCSK9 (52) | (Sp)-AAGcAAAAcAGGUCusAGAAdTdT | 308 |
| PCSK9 (53) | (Rp)-AAGcAAAAcAGGUCsuAGAAdTdT | 309 |
| PCSK9 (54) | (Sp)-AAGcAAAAcAGGUCsuAGAAdTdT | 310 |
| PCSK9 (55) | (Rp)-AAGcAAAAcAGGUsCuAGAAdTdT | 311 |
| PCSK9 (56) | (Sp)-AAGcAAAAcAGGUsCuAGAAdTdT | 312 |
| PCSK9 (57) | (Rp)-AAGcAAAAcAGGsUCuAGAAdTdT | 313 |
| PCSK9 (58) | (Sp)-AAGcAAAAcAGGsUCuAGAAdTdT | 314 |
| PCSK9 (59) | (Rp)-AAGcAAAAcAGsGUCuAGAAdTdT | 315 |
| PCSK9 (60) | (Sp)-AAGcAAAAcAGsGUCuAGAAdTdT | 316 |
| PCSK9 (61) | (Rp)-AAGcAAAAcAsGGUCuAGAAdTdT | 317 |
| PCSK9 (62) | (Sp)-AAGcAAAAcAsGGUCuAGAAdTdT | 318 |
| PCSK9 (63) | (Rp)-AAGcAAAAcsAGGUCuAGAAdTdT | 319 |
| PCSK9 (64) | (Sp)-AAGcAAAAcsAGGUCuAGAAdTdT | 320 |
| PCSK9 (65) | (Rp)-AAGcAAAAscAGGUCuAGAAdTdT | 321 |
| PCSK9 (66) | (Sp)-AAGcAAAAscAGGUCuAGAAdTdT | 322 |
| PCSK9 (67) | (Rp)-AAGcAAAsAcAGGUCuAGAAdTdT | 323 |
| PCSK9 (68) | (Sp)-AAGcAAAsAcAGGUCuAGAAdTdT | 324 |
| PCSK9 (69) | (Rp)-AAGcAAsAAcAGGUCuAGAAdTdT | 325 |
| PCSK9 (70) | (Sp)-AAGcAAsAAcAGGUCuAGAAdTdT | 326 |
| PCSK9 (71) | (Rp)-AAGcAsAAAcAGGUCuAGAAdTdT | 327 |
| PCSK9 (72) | (Sp)-AAGcAsAAAcAGGUCuAGAAdTdT | 328 |
| PCSK9 (73) | (Rp)-AAGcsAAAAcAGGUCuAGAAdTdT | 329 |
| PCSK9 (74) | (Sp)-AAGcsAAAAcAGGUCuAGAAdTdT | 330 |
| PCSK9 (75) | (Rp)-AAGscAAAAcAGGUCuAGAAdTdT | 331 |
| PCSK9 (76) | (Sp)-AAGscAAAAcAGGUCuAGAAdTdT | 332 |
| PCSK9 (77) | (Rp)-AAsGcAAAAcAGGUCuAGAAdTdT | 333 |
| PCSK9 (78) | (Sp)-AAsGcAAAAcAGGUCuAGAAdTdT | 334 |
| PCSK9 (77) | (Rp)-AsAGcAAAAcAGGUCuAGAAdTdT | 335 |
| PCSK9 (78) | (Sp)-AsAGcAAAAcAGGUCuAGAAdTdT | 336 |
| PCSK9 (79) | (Rp, Sp)-AAGcAAAAcAGGUCuAGAAsdTsdT | 337 |

| | Human PCSK9 siRNA Antisense Strands | SEQ ID NO: |
|---|---|---|
| PCSK9 (80) | (Sp, Sp)-AAGcAAAAcAGGUCuAGAAsdTsdT | 338 |
| PCSK9 (81) | (Rp, Sp)-AAGcAAAAcAGGUCuAGAsAdTsdT | 339 |
| PCSK9 (82) | (Sp, Sp)-AAGcAAAAcAGGUCuAGAsAdTsdT | 340 |
| PCSK9 (83) | (Rp, Sp)-AAGcAAAAcAGGUCuAGsAAdTsdT | 341 |
| PCSK9 (84) | (Sp, Sp)-AAGcAAAAcAGGUCuAGsAAdTsdT | 342 |
| PCSK9 (85) | (Rp, Sp)-AAGcAAAAcAGGUCuAsGAAdTsdT | 343 |
| PCSK9 (86) | (Sp, Sp)-AAGcAAAAcAGGUCuAsGAAdTsdT | 344 |
| PCSK9 (87) | (Rp, Sp)-AAGcAAAAcAGGUCusAGAAdTsdT | 345 |
| PCSK9 (88) | (Sp, Sp)-AAGcAAAAcAGGUCusAGAAdTsdT | 346 |
| PCSK9 (89) | (Rp, Sp)-AAGcAAAAcAGGUCsuAGAAdTsdT | 347 |
| PCSK9 (90) | (Sp, Sp)-AAGcAAAAcAGGUCsuAGAAdTsdT | 348 |
| PCSK9 (91) | (Rp, Sp)-AAGcAAAAcAGGUsCuAGAAdTsdT | 349 |
| PCSK9 (92) | (Sp, Sp)-AAGcAAAAcAGGUsCuAGAAdTsdT | 350 |
| PCSK9 (93) | (Rp, Sp)-AAGcAAAAcAGGsUCuAGAAdTsdT | 351 |
| PCSK9 (94) | (Sp, Sp)-AAGcAAAAcAGGsUCuAGAAdTsdT | 352 |
| PCSK9 (95) | (Rp, Sp)-AAGcAAAAcAGsGUCuAGAAdTsdT | 353 |
| PCSK9 (96) | (Sp, Sp)-AAGcAAAAcAGsGUCuAGAAdTsdT | 354 |
| PCSK9 (97) | (Rp, Sp)-AAGcAAAAcAsGGUCuAGAAdTsdT | 355 |
| PCSK9 (98) | (Sp, Sp)-AAGcAAAAcAsGGUCuAGAAdTsdT | 356 |
| PCSK9 (99) | (Rp, Sp)-AAGcAAAAcsAGGUCuAGAAdTsdT | 357 |
| PCSK9 (100) | (Sp, Sp)-AAGcAAAAcsAGGUCuAGAAdTsdT | 358 |
| PCSK9 (101) | (Rp, Sp)-AAGcAAAAscAGGUCuAGAAdTsdT | 359 |
| PCSK9 (102) | (Sp, Sp)-AAGcAAAAscAGGUCuAGAAdTsdT | 360 |
| PCSK9 (103) | (Rp, Sp)-AAGcAAAsAcAGGUCuAGAAdTsdT | 361 |
| PCSK9 (104) | (Sp, Sp)-AAGcAAAsAcAGGUCuAGAAdTsdT | 362 |
| PCSK9 (105) | (Rp, Sp)-AAGcAAsAAcAGGUCuAGAAdTsdT | 363 |
| PCSK9 (106) | (Sp, Sp)-AAGcAAsAAcAGGUCuAGAAdTsdT | 364 |
| PCSK9 (107) | (Rp, Sp)-AAGcAsAAAcAGGUCuAGAAdTsdT | 365 |
| PCSK9 (108) | (Sp, Sp)-AAGcAsAAAcAGGUCuAGAAdTsdT | 366 |
| PCSK9 (109) | (Rp, Sp)-AAGcsAAAAcAGGUCuAGAAdTsdT | 367 |
| PCSK9 (110) | (Sp, Sp)-AAGcsAAAAcAGGUCuAGAAdTsdT | 368 |
| PCSK9 (111) | (Rp, Sp)-AAGscAAAAcAGGUCuAGAAdTsdT | 369 |
| PCSK9 (112) | (Sp, Sp)-AAGscAAAAcAGGUCuAGAAdTsdT | 370 |
| PCSK9 (113) | (Rp, Sp)-AAsGcAAAAcAGGUCuAGAAdTsdT | 371 |
| PCSK9 (114) | (Sp, Sp)-AAsGcAAAAcAGGUCuAGAAdTsdT | 372 |
| PCSK9 (115) | (Rp, Sp)-AsAGcAAAAcAGGUCuAGAAdTsdT | 373 |
| PCSK9 (116) | (Sp, Sp)-AsAGcAAAAcAGGUCuAGAAdTsdT | 374 |
| PCSK9 (117) | (Rp, Sp, Sp, Sp, Rp, Sp, Sp, Sp, Rp, Rp)-AsAsGscAsAAsAscsAGGUCuAGAsAsdTsdT | 375 |

-continued

| Human PCSK9 siRNA Antisense Strands | | SEQ ID NO: |
|---|---|---|
| PCSK9 (118) | (Sp, Rp, Rp, Rp, Sp, Rp, Rp, Rp, Sp, Sp)-<br>AsAsGscAsAAsAscsAGGUCuAGAsAsdTsdT | 376 |

NOTE:
lower case letters represent 2'-OMe RNA residues; capital letters represent RNA
residues; d = 2'-deoxy residues; and "s" indicates a phosphorothioate moiety.

Example 3. Stereopure FOXO-1 Antisense Analogs

Rational Design—Chirally Controlled Antisense Oligonucleotide Compositions

The unprecedented nuclease stability determined in vivo and in a whole rat liver homogenate model of the Sp-chiral phosphorothioate internucleotide linkage is applied in the novel design of new types of RNaseH substrate gapmers, whereby the external flanks are composed of unmodified DNA and the internal gap core is modified with 2' chemical modifications (2'OMe, 2'MOE, 2'LNA, 2'F, etc). Eventually this design is extended to fully unmodified DNA therapeutic oligonucleotides wherein careful chiral control of the phosphorothioate backbone confers the desired pharmacological properties of the RNaseH therapeutic oligonucleotide.

The application of the triplet-phosphate repeating motif designed after studying the crystal structure of human RNaseH has been employed as well. The crystal structure of RNaseH has been previously published (Structure of Human RNase H1 Complexed with an RNA/DNA Hybrid: Insight into HIV Reverse Transcription, Nowotny et al., Molecular Cell, Volume 28, Issue 2, 264-276, 2007, pdb file: 2qkb). Among other things, the present invention recognizes the importance of internucleotidic linkage stereochemistry of oligonucleotides, for example, in settings herein. Upon performing in silico analysis upon this structure using the program Pymol, Applicant found that the phosphate-binding pocket of Human RNase H1 makes polar contacts with three contiguous phosphates of the complexed DNA, and interacts preferentially with the Pro-R/Pro-R/Pro-S (or with the Pro-S/Pro-S/Pro-R) respective oxygen atoms of each of these three phosphates. Based on this observation we designed two chiral architectures with repeating (RRS) and (SSR) triplet phosphorothioates motifs as designed RNase H substrates. Applicant also designed other internucleotidic linkage stereochemical patterns. As demonstrated by exemplary results provide herein, provided chirally controlled oligonucleotide compositions of oligonucleotide types that comprises certain backbone internucleotidic linkage patterns (patterns backbone chiral centers) provides significantly increased activity and/or kinetics. Among others, a sequence of 5'-RSS-3' backbone chiral centers is particularly useful and delivers unexpected results as described in the present disclosure.

The combination of increased Sp chiral backbone (for enzymatic stability and other pharmacologically advantageous properties) and (RRS) or (SSR) repeating triplet chiral backbone motifs (for enhancing the property as RNase H substrate) are also utilized in the novel designs; "S" represents Sp-phosphorothioate linkage and "R" represents Rp-phosphorothioate linkage.

Another alternative design is based on the increased amount of Sp chiral phosphorothioate backbone in extended repeating motifs such as: (SSSR)n, SR(SSSR)n, SSR(SSSR) n, SSR(SSSR)n; (SSSSR)n, SR(SSSSR)n, SSR(SSSSR)n, SSR(SSSSR)n, SSSR(SSSSR)n; (SSSSSR)n; SR(SSSSSR) n, SSR(SSSSSR)n, SSR(SSSSSR)n, SSSR(SSSSSR)n, SSSSR(SSSSSR)n; etc., where n=0-50, depending on the number of respective internucleotide linkages; "S" represents Sp-phosphorothioate linkage and "R" represents Rp-phosphorothioate linkage. In some embodiments, n is 0. In some embodiments, R is 1-50. In some embodiments, R is 1. In some embodiments, a common pattern of backbone chiral centers of a provided chirally controlled oligonucleotide composition comprises a motif described herein. In some embodiments, a motif is in the core region. In some embodiments, n is 0. In some embodiments, R is 1-50. In some embodiments, R is 1. In some embodiments, n is 2. In some embodiments, n is 3. In some embodiments, n is 4. In some embodiments, n is 5.

Another alternative design is based on the "invert" architecture design of the stereo backbone ("stereo invert-mers"). These result from positioning the stereochemistry of the chiral phosphorothioate in a inverting manner, exposing some Sp-rich motifs at the 5' and 3' end extremities of the oligonucleotide as well as the middle portion of the oligonucleotide and having the repeating stereochemistry motifs positioned in a invert image manner on both sides, such as:

SS(SSR)n(SSS)(RSS)nSS;

SS(SSR)n(SRS)(RSS)nSS;

SS(SSR)n(SSR)(RSS)nSS;

SS(SSR)n(RSS)(RSS)nSS;

SS(RSS)n(SSS)(SSR)nSS;

SS(RSS)n(SRS)(SSR)nSS;

SS(RSS)n(SSR)(SSR)nSS;

SS(RSS)n(RSS)(SSR)nSS; etc., where n=0-50, depending on the number of respective internucleotide linkages; "S" represents Sp-phosphorothioate linkage and "R" represents Rp-phosphorothioate linkage. In some embodiments, a common pattern of backbone chiral centers of a provided chirally controlled oligonucleotide composition comprises a motif described herein. In some embodiments, a motif is in the core region. In some embodiments, n is 0. In some embodiments, n is 1. In some embodiments, n is 1-50. In some embodiments, n is 2. In some embodiments, n is 3. In some embodiments, n is 4. In some embodiments, n is 5.

Initial Screen

Synthesis: Summary for Oligonucleotide Synthesis on a DNA/RNA Synthesizer MerMade-12 (2'-Deoxy and 2'-OMe Cycle)

| step | reaction | reagent | delivery volume (mL) | wait time (sec) |
|---|---|---|---|---|
| 1 | detritylation | 3% TCA in DCM | 4 × 1 | N.A. |
| 2 | coupling | 0.15M phosphoramidite in ACN + 0.45M ETT in ACN | 2 × 0.5 mL | 60 + 60 (DNA), 300 + 300 (2'-OMe RNA) |

| step | reaction | reagent | delivery volume (mL) | wait time (sec) |
|---|---|---|---|---|
| 3 | capping | 5% Pac₂O in THF/2,6-lutidine + 16% NMI in THF | 1 | 60 |
| 4 | oxidation | 0.02 Iodine in water/pyridine | 1 | 240 |

Stereorandom PS Oligonucleotides Having DNA-2'-OMe-DNA (7-6-7) Design:

```
ONT-141    d(CsCsCsTsCsTsGs)gsaststsgsasd(GsCsAsTsCsCsA)    (SEQ ID NO: 377)
ONT-142    d(AsAsGsCsTsTsTs)gsgststsgsgsd(GsCsAsAsCsAsC)    (SEQ ID NO: 378)
ONT-143    d(AsGsTsCsAsCsTs)tsgsgsgsasgsd(CsTsTsCsTsCsC)    (SEQ ID NO: 379)
ONT-144    d(CsAsCsTsGsGs)gsasgscststsd(CsTsCsCsTsGsG)      (SEQ ID NO: 380)
ONT-145    d(AsTsAsGsCsCsAs)tststsgscsasgsd(CsTsGsCsTsCsA)  (SEQ ID NO: 381)
ONT-146    d(TsGsGsAsTsTsGs)asgscsaststscsd(CsAsCsCsAsAsG)  (SEQ ID NO: 382)
ONT-147    d(CsCsAsTsAsGsCs)csaststsgscsd(AsGsCsTsGsCsT)    (SEQ ID NO: 383)
ONT-148    d(GsTsCsAsCsTsTs)gsgsgsasgscsd(TsTsCsTsCsT)      (SEQ ID NO: 384)
ONT-149    d(CsCsAsGsGsGsCs)ascstscsaststsd(CsTsGsCsAsTsG)  (SEQ ID NO: 385)
ONT-150    d(GsCsCsAsTsCsCs)asasgstscsasd(CsTsTsGsGsGsA)    (SEQ ID NO: 386)
ONT-151    d(GsAsAsGsCsTsTs)tsgsgststsgsd(GsGsCsAsAsCsA)    (SEQ ID NO: 387)
ONT-152    d(CsTsGsGsAsTsTs)gsasgscsaststsd(CsCsAsCsCsAsA)  (SEQ ID NO: 388)
ONT-183    d(CsAsAsGsTsCsAs)cststsgsgsgsd(AsGsCsTsTsCsT)    (SEQ ID NO: 389)
ONT-184    d(AsTsGsCsAsTs)cscsasasgststsd(CsAsCsTsTsGsG)    (SEQ ID NO: 390)
ONT-185    d(AsTsGsAsGsAsTs)gscscstsgsgsd(CsTsGsCsCsAsT)    (SEQ ID NO: 391)
ONT-186    d(TsGsGsGsAsGs)cststscststscsd(CsTsGsGsTsGsG)    (SEQ ID NO: 392)
ONT-187    d(TsGsGsGsAsGsCs)tstscstscscscsd(TsGsGsTsGsGsA)  (SEQ ID NO: 393)
ONT-188    d(TsTsAsTsGsAsGs)astsgscscststsd(GsGsCsTsGsCsC)  (SEQ ID NO: 394)
ONT-189    d(GsTsTsAsTsGsAs)gsaststsgscscsd(TsGsGsCsTsGsC)  (SEQ ID NO: 395)
ONT-190    d(CsCsAsAsGsTsCs)ascststsgsgsgsd(GsAsGsCsTsTsC)  (SEQ ID NO: 396)
ONT-191    d(AsGsCsTsTsTsGs)gststsgsgsgsd(CsAsAsCsAsCsA)    (SEQ ID NO: 397)
ONT-192    d(TsAsTsGsAsGsAs)tsgscscstsgsgsd(GsCsTsGsCsCsA)  (SEQ ID NO: 398)
ONT-193    d(TsGsTsTsAsTsGs)asgsaststsgscsd(CsTsGsCsGsCsTsG)(SEQ ID NO: 399)
ONT-194    d(AsTsCsCsAsAsGs)tscsascststsd(GsGsGsAsGsCsT)    (SEQ ID NO: 400)
ONT-195    d(GsGsGsAsAsGsCs)tststsgsgststsd(TsGsGsGsCsAsA)  (SEQ ID NO: 401)
ONT-196    d(CsTsCsCsAsTsCs)csaststsgsasgsd(GsTsCsAsTsTsC)  (SEQ ID NO: 402)
ONT-197    d(AsAsGsTsCsAsCs)tstsgsgsgsasd(GsCsTsTsCsTsC)    (SEQ ID NO: 403)
ONT-198    d(CsCsAsTsCsAs)asgstscsascsd(TsTsGsGsGsAsG)      (SEQ ID NO: 404)
ONT-199    d(TsCsCsAsAsGsTs)csascststsgsd(GsGsAsGsCsTsT)    (SEQ ID NO: 405)
ONT-200    d(CsCsTsCsTsGsGs)aststsgsasgsd(CsAsTsCsCsAsC)    (SEQ ID NO: 406)
ONT-201    d(AsCsTsGsGsGs)asgscststscsd(TsCsCsTsGsGsT)      (SEQ ID NO: 407)
ONT-202    d(CsTsTsGsGsGsAs)gscststscststsd(CsCsTsGsGsTsG)  (SEQ ID NO: 408)
ONT-203    d(CsAsTsGsCsAs)tscscsasasgsd(TsCsAsCsTsTsG)      (SEQ ID NO: 409)
ONT-204    d(TsGsCsCsAsTsCs)csasasgststscsd(AsCsTsTsGsGsG)  (SEQ ID NO: 410)
```

-continued

```
ONT-205    d(TsCsCsAsTsCsCs)astsgsasgsgsd(TsCsAsTsTsCsC)    (SEQ ID NO: 411)

ONT-206    d(AsGsGsGsCsAsCs)tscsastscstsd(GsCsAsTsGsGsG)     (SEQ ID NO: 412)

ONT-207    d(CsCsAsGsTsTsCs)cststscsastsd(TsCsTsGsCsAsC)     (SEQ ID NO: 413)

ONT-208    d(CsAsTsAsGsCsCs)aststsgscsasd(GsCsTsGsCsTsC)     (SEQ ID NO: 414)

ONT-209    d(TsCsTsGsGsAsTs)tsgsasgscsasd(TsCsCsAsCsCsA)     (SEQ ID NO: 415)

ONT-210    d(GsGsAsTsTsGsAs)gscsastscscsd(AsCsCsAsAsGsA)     (SEQ ID NO: 416)
```

Biology In Vitro Data in HepG2 Cells for the Initial DNA-2'-OMe-DNA (7-6-7) Design: (d Upper Case)=DNA; Lower Case=2'-OMe; s=Phosphorothioate.

| FOXO1 | | |
|---|---|---|
| | Levels at 20 nM (%) | SD |
| ONT-141 | 89 | 6 |
| ONT-142 | 45 | 1 |
| ONT-143 | 98 | 2 |
| ONT-144 | 89 | 1 |
| ONT-145 | 46 | 5 |
| ONT-146 | 99 | 1 |
| ONT-147 | 66 | 6 |
| ONT-148 | 101 | 2 |
| ONT-149 | 95 | 6 |
| ONT-150 | 58 | 4 |
| ONT-151 | 41 | 5 |
| ONT-152 | 84 | 5 |
| ONT-183 | 95 | 2 |
| ONT-184 | 58 | 4 |
| ONT-185 | 42 | 2 |
| ONT-186 | 96 | 4 |
| ONT-187 | 92 | 3 |
| ONT-188 | 47 | 5 |
| ONT-189 | 63 | 5 |
| ONT-190 | 83 | 2 |
| ONT-191 | 58 | 4 |
| ONT-192 | 46 | 2 |
| ONT-193 | 58 | 2 |
| ONT-194 | 76 | 1 |
| ONT-195 | 66 | 0 |
| ONT-196 | 77 | 2 |
| ONT-197 | 90 | 6 |
| ONT-198 | 42 | 4 |
| ONT-199 | 68 | 1 |
| ONT-200 | 89 | 6 |
| ONT-201 | 91 | 2 |
| ONT-202 | 94 | 2 |
| ONT-203 | 86 | 1 |
| ONT-204 | 58 | 2 |
| ONT-205 | 75 | 3 |
| ONT-206 | 94 | 5 |
| ONT-207 | 96 | 0 |
| ONT-208 | 54 | 0 |
| ONT-209 | 87 | 4 |
| ONT-210 | 92 | 4 |

| FOXO1 | | |
|---|---|---|
| | Levels at 200 nM (%) | SD |
| ONT-141 | 37 | 4 |
| ONT-142 | 45 | 4 |
| ONT-143 | 46 | 2 |
| ONT-144 | 42 | 5 |
| ONT-145 | 53 | 4 |
| ONT-146 | 31 | 2 |
| ONT-147 | 28 | 8 |
| ONT-148 | 45 | 4 |
| ONT-149 | 29 | 5 |
| ONT-150 | 32 | 6 |
| ONT-151 | 38 | 4 |
| ONT-152 | 30 | 5 |
| ONT-183 | 60 | 5 |
| ONT-184 | 34 | 2 |
| ONT-185 | 50 | 2 |
| ONT-186 | 86 | 3 |
| ONT-187 | 76 | 6 |
| ONT-188 | 50 | 5 |
| ONT-189 | 38 | 2 |
| ONT-190 | 51 | 1 |
| ONT-191 | 43 | 5 |
| ONT-192 | 54 | 7 |
| ONT-193 | 41 | 6 |
| ONT-194 | 50 | 1 |
| ONT-195 | 43 | 6 |
| ONT-196 | 33 | 7 |
| ONT-197 | 57 | 4 |
| ONT-198 | 40 | 5 |
| ONT-199 | 50 | 5 |
| ONT-200 | 28 | 9 |
| ONT-201 | 46 | 6 |
| ONT-202 | 57 | 9 |
| ONT-203 | 27 | 7 |
| ONT-204 | 36 | 6 |
| ONT-205 | 29 | 5 |
| ONT-206 | 81 | 0 |
| ONT-207 | 37 | 4 |
| ONT-208 | 43 | 3 |
| ONT-209 | 35 | 4 |
| ONT-210 | 40 | 4 |

Stereorandom PS Oligonucleotides Having 2'-OMe-DNA-2'OMe (3-14-3) Design: (d Upper Case)=DNA; Lower Case=2'-OMe; s=Phosphorothioate.

```
ONT-129    cscscsd(TsCsTsGsGsAsTsTsGsAsGsCsAsTs)cscsa    (SEQ ID NO: 417)

ONT-130    asasgsd(CsTsTsTsGsGsTsTsGsGsGsCsAsAs)csasc    (SEQ ID NO: 418)

ONT-131    asgstsd(CsAsCsTsTsGsGsGsAsGsCsTsTsCs)tscsc    (SEQ ID NO: 419)

ONT-132    csascsd(TsTsGsGsAsGsCsTsTsCsTsCsCs)tsgsg     (SEQ ID NO: 420)

ONT-133    astsasd(GsCsAsTsTsGsCsAsGsCsTsGsCs)tscsa     (SEQ ID NO: 421)

ONT-134    tsgsgsd(AsTsTsGsAsGsCsAsTsCsCsAsCsCs)asasg   (SEQ ID NO: 422)
```

-continued

| | | |
|---|---|---|
| ONT-135 | cscsasd(TsAsGsCsCsAsTsTsGsCsAsGsCsTs)gscst | (SEQ ID NO: 423) |
| ONT-136 | gstscsd(AsCsTsGsGsAsGsCsTsTsCsTs)cscst | (SEQ ID NO: 424) |
| ONT-137 | cscsasd(GsGsGsCsAsTsCsAsTsCsTsGsCs)astsg | (SEQ ID NO: 425) |
| ONT-138 | gscscsd(AsTsCsCsAsAsGsTsCsAsCsTsTsGs)gsgsa | (SEQ ID NO: 426) |
| ONT-139 | gsasasd(GsCsTsTsTsGsGsTsTsGsGsGsCsAs)ascsa | (SEQ ID NO: 427) |
| ONT-140 | cstsgsd(GsAsTsGsAsGsCsAsTsCsCsAsCs)csasa | (SEQ ID NO: 428) |
| ONT-155 | csasasd(GsTsCsAsCsTsTsGsGsGsAsGsCsTs)tscst | (SEQ ID NO: 429) |
| ONT-156 | astsgsd(CsCsAsTsCsCsAsAsGsTsCsAsCsTs)tsgsg | (SEQ ID NO: 430) |
| ONT-157 | astsgsd(AsGsAsTsGsCsCsTsGsGsGsCsTsGsCs)csast | (SEQ ID NO: 431) |
| ONT-158 | tstsgsd(GsGsAsGsCsTsTsCsTsCsCsTsGsGs)tsgsg | (SEQ ID NO: 432) |
| ONT-159 | tsgsgsd(GsAsGsCsTsTsCsTsCsCsTsGsGsTs)gsgsa | (SEQ ID NO: 433) |
| ONT-160 | tstsasd(TsGsAsGsAsTsGsCsCsTsGsGsCsTs)gscsc | (SEQ ID NO: 434) |
| ONT-161 | gststsd(AsTsGsAsGsAsTsGsCsCsTsGsGsCs)tsgsc | (SEQ ID NO: 435) |
| ONT-162 | cscsasd(AsGsTsCsAsCsTsTsGsGsGsAsGsCs)tstsc | (SEQ ID NO: 436) |
| ONT-163 | asgscsd(TsTsTsGsGsTsTsGsGsGsCsAsAsCs)ascsa | (SEQ ID NO: 437) |
| ONT-164 | tsastsd(GsAsGsAsTsGsCsCsTsGsGsCsTsGs)cscsa | (SEQ ID NO: 438) |
| ONT-165 | tsgstsd(TsAsTsGsAsGsAsTsGsCsCsTsGsGs)cstsg | (SEQ ID NO: 439) |
| ONT-166 | astscsd(CsAsAsGsTsCsAsCsTsTsGsGsGsAs)gscst | (SEQ ID NO: 440) |
| ONT-167 | gsgsgsd(AsAsGsCsTsTsGsGsTsGsGsGsGs)csasa | (SEQ ID NO: 441) |
| ONT-168 | cstscsd(CsAsTsCsCsAsTsGsAsGsGsTsCsAs)tstsc | (SEQ ID NO: 442) |
| ONT-169 | asasgsd(TsCsAsCsTsGsGsGsAsGsCsTsTs)cstsc | (SEQ ID NO: 443) |
| ONT-170 | cscsasd(TsCsCsAsAsGsTsCsAsCsTsTsGsGs)gsasg | (SEQ ID NO: 444) |
| ONT-171 | tscscsd(AsAsGsTsCsAsCsTsTsGsGsGsAsGs)cstst | (SEQ ID NO: 445) |
| ONT-172 | cscstsd(CsTsGsGsAsTsGsAsGsCsAsTsCs)csasc | (SEQ ID NO: 446) |
| ONT-173 | ascstsd(TsGsGsGsAsGsCsTsTsCsTsCsCsTs)gsgst | (SEQ ID NO: 447) |
| ONT-174 | cststsd(GsGsGsAsGsCsTsTsCsTsCsCsTsGs)gstsg | (SEQ ID NO: 448) |
| ONT-175 | csastsd(GsCsCsAsTsCsCsAsAsGsTsCsAsCs)tstsg | (SEQ ID NO: 449) |
| ONT-176 | tsgscsd(CsAsTsCsCsAsAsGsTsCsAsCsTsTs)gsgsg | (SEQ ID NO: 450) |
| ONT-177 | tscscsd(AsTsCsCsAsTsGsAsGsGsTsCsAsTs)tscsc | (SEQ ID NO: 451) |
| ONT-178 | asgsgsd(GsCsAsCsTsCsAsTsCsTsGsCsAsTs)gsgsg | (SEQ ID NO: 452) |
| ONT-179 | cscsasd(GsTsTsCsCsTsTsCsAsTsTsCsTsGs)csasc | (SEQ ID NO: 453) |
| ONT-180 | csastsd(AsGsCsCsAsTsTsGsCsAsGsCsTsGs)cstsc | (SEQ ID NO: 454) |
| ONT-181 | tscstsd(GsGsAsTsTsGsAsGsCsAsTsCsCsAs)cscsa | (SEQ ID NO: 455) |
| ONT-182 | gsgsasd(TsTsGsAsGsCsAsTsCsCsAsCsCsAs)asgsa | (SEQ ID NO: 456) |

Biology In Vitro Data in HepG2 Cells for the 2'-OMe-DNA-2'-OMe (3-14-3) Design:

| | FOXO1 | |
|---|---|---|
| | Levels at 20 nM (%) | SD |
| ONT-129 | 82 | 5 |
| ONT-130 | 49 | 4 |
| ONT-131 | 92 | 3 |
| ONT-132 | 91 | 2 |
| ONT-133 | 58 | 3 |
| ONT-134 | 73 | 2 |
| ONT-135 | 65 | 5 |
| ONT-136 | 92 | 2 |
| ONT-137 | 94 | 2 |
| ONT-138 | 78 | 1 |
| ONT-139 | 61 | 1 |
| ONT-140 | 82 | 4 |
| ONT-155 | 95 | 2 |
| ONT-156 | 74 | 1 |
| ONT-157 | 56 | 2 |
| ONT-158 | 93 | 1 |
| ONT-159 | 94 | 1 |
| ONT-160 | 71 | 1 |
| ONT-161 | 67 | 1 |
| ONT-162 | 89 | 1 |
| ONT-163 | 55 | 7 |
| ONT-164 | 68 | 4 |
| ONT-165 | 70 | 1 |
| ONT-166 | 89 | 4 |
| ONT-167 | 81 | 0 |
| ONT-168 | 81 | 0 |
| ONT-169 | 94 | 0 |
| ONT-170 | 88 | 1 |
| ONT-171 | 92 | 4 |
| ONT-172 | 86 | 2 |
| ONT-173 | 90 | 1 |
| ONT-174 | 93 | 2 |
| ONT-175 | 84 | 1 |
| ONT-176 | 80 | 2 |
| ONT-177 | 83 | 2 |
| ONT-178 | 95 | 2 |
| ONT-179 | 93 | 8 |
| ONT-180 | 68 | 7 |
| ONT-181 | 85 | 5 |
| ONT-182 | 80 | 5 |

| | FOXO1 | |
|---|---|---|
| | Levels at 200 nM (%) | SD |
| ONT-129 | 27 | 1 |
| ONT-130 | 46 | 4 |
| ONT-131 | 53 | 9 |
| ONT-132 | 53 | 2 |
| ONT-133 | 48 | 6 |
| ONT-134 | 35 | 9 |
| ONT-135 | 45 | 15 |
| ONT-136 | 40 | 7 |
| ONT-137 | 50 | 4 |
| ONT-138 | 80 | 3 |
| ONT-139 | 40 | 3 |
| ONT-140 | 33 | 13 |
| ONT-155 | 52 | 2 |
| ONT-156 | 35 | 4 |
| ONT-157 | 39 | 2 |
| ONT-158 | 87 | 6 |
| ONT-159 | 89 | 5 |
| ONT-160 | 33 | 10 |
| ONT-161 | 40 | 11 |
| ONT-162 | 60 | 7 |
| ONT-163 | 42 | 8 |
| ONT-164 | 34 | 10 |
| ONT-165 | 38 | 1 |
| ONT-166 | 62 | 9 |
| ONT-167 | 64 | 1 |
| ONT-168 | 38 | 2 |
| ONT-169 | 67 | 3 |
| ONT-170 | 74 | 8 |
| ONT-171 | 65 | 5 |
| ONT-172 | 33 | 18 |
| ONT-173 | 72 | 15 |
| ONT-174 | 65 | 15 |
| ONT-175 | 38 | 21 |
| ONT-176 | 48 | 8 |
| ONT-177 | 28 | 5 |
| ONT-178 | 97 | 11 |
| ONT-179 | 47 | 6 |
| ONT-180 | 56 | 12 |
| ONT-181 | 45 | 26 |
| ONT-182 | 33 | 17 |

Hit Selection:

```
ONT-151   d(GsAsAsGsCsTsTs)tsgsgststsgsd(GsGsCsAsAsCsA)   (SEQ ID NO: 457)

ONT-198   d(CsCsAsTsCsCsAs)asgstscsascsd(TsTsGsGsGsAsG)   (SEQ ID NO: 458)

ONT-185   d(AsTsGsAsGsAsTs)gscscstsgsgsd(CsTsGsCsCsAsT)   (SEQ ID NO: 459)

ONT-142   d(AsAsGsCsTsTsTs)gsgststsgsgsd(GsCsAsAsCsAsC)   (SEQ ID NO: 460)

ONT-145   d(AsTsAsGsCsCsAs)tstsgscsasgsd(CsTsGsCsTsCsA)   (SEQ ID NO: 461)

ONT-192   d(TsAsTsGsAsGsAs)tsgscscstsgsd(GsCsTsGsCsCsA)   (SEQ ID NO: 462)

ONT-188   d(TsTsAsTsGsAsGs)astsgscscstsd(GsGsCsTsGsCsC)   (SEQ ID NO: 463)
```

Secondary Screen. Chemistry and Stereochemistry Screen Summary for Oligonucleotide Synthesis on a DNA/RNA Synthesizer MerMade-12 (Stereodefined Phosphorothioate 2'-Deoxy and 2'-OMe Cycle)

| step | reaction | reagent | delivery vol (mL) | wait time (sec) |
|---|---|---|---|---|
| 1 | detritylation | 3% TCA in DCM | 4 × 1 | N. A. |
| 2 | coupling | 0.15M chiral phosphoramidite in ACN + 2M CMPT in ACN | 2 × 0.5 | 2 × 450 (2'-OMe RNA)<br>2 × 300 (DNA) |

| step | reaction | reagent | delivery vol (mL) | wait time (sec) |
|---|---|---|---|---|
| 3 | capping 1 | 5% Pac$_2$O in THF/2,6-lutidine | 1 | 60 |
| 4 | capping 2 | 5% Pac$_2$O in THF/2,6-lutidine + 16% NMI in THF | 1 | 60 |
| 5 | sulfurization | 0.3M S-(2-cyanoethyl) methylthiosulfonate 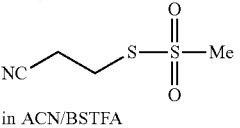 in ACN/BSTFA | 1 | 600 |

Examples Applied on the FOXO1 Hit Sequences:
Examples include but are not limited to:

(SEQ ID NO: 464)
(Sp, Sp, Sp, Sp, Sp, Sp, Sp, Rp, Sp, Sp, Rp, Sp, Sp, Rp, Sp, Sp, Sp, Sp, Sp)d[CsCsAsTsCsCsAsAsGsTsCsAsCsTsTsGsGsGsAsG]

(SEQ ID NO: 465)
(Sp, Sp, Sp, Sp, Sp, Rp, Sp, Sp, Rp, Sp, Sp, Rp, Sp, Sp, Rp, Sp, Sp, Sp, Sp)d[CsCsAsTsCsCsAsAsGsTsCsAsCsTsTsGsGsGsAsG]

(SEQ ID NO: 466)
(Sp, Sp, Sp, Rp, Sp, Sp, Rp, Sp, Sp, Rp, Sp, Sp, Rp, Sp, Sp, Rp, Sp, Sp, Sp)d[GsAsAsGsCsTsTsTsGsGsTsTsGsGsGsCsAsAsCsA]

(SEQ ID NO: 467)
(Sp, Sp, Rp, Sp, Sp, Rp, Sp, Sp, Rp, Sp, Sp, Rp, Sp, Sp, Rp, Sp, Sp, Rp, Sp)d[CsCsAsTsCsCsAsAsGsTsCsAsCsTsTsGsGsGsAsG]

(SEQ ID NO: 468)
(Sp, Sp, Sp, Sp, Sp, Rp, Rp, Sp, Rp, Rp, Sp, Rp, Rp, Sp, Sp, Sp, Sp, Sp, Sp)d[CsCsAsTsCsCsAsAsGsTsCsAsCsTsTsGsGsGsAsG]

(SEQ ID NO: 469)
(Sp, Sp, Sp, Sp, Rp, Rp, Sp, Rp, Rp, Sp, Rp, Rp, Sp, Rp, Rp, Sp, Sp, Sp, Sp)d[GsAsAsGsCsTsTsTsGsGsTsTsGsGsGsCsAsAsCsA]

(SEQ ID NO: 470)
(Sp, Sp, Sp, Sp, Sp, Sp, Sp, Rp, Sp, Sp, Rp, Sp, Sp, Rp, Sp, Sp, Sp, Sp, Sp)d[AsTsGsAsGsAsTsGsCsCsTsGsGsCsTsGsCsCsAsT]

(SEQ ID NO: 471)
(Sp, Sp, Sp, Sp, Sp, Rp, Sp, Sp, Rp, Sp, Sp, Rp, Sp, Sp, Rp, Sp, Sp, Sp, Sp)d[AsTsGsAsGsAsTsGsCsCsTsGsGsCsTsGsCsCsAsT]

(SEQ ID NO: 472)
(Sp, Sp, Sp, Rp, Sp, Sp, Rp, Sp, Sp, Rp, Sp, Sp, Rp, Sp, Sp, Rp, Sp, Sp, Sp)d[AsTsGsAsGsAsTsGsCsCsTsGsGsCsTsGsCsCsAsT]

(SEQ ID NO: 473)
(Sp, Sp, Rp, Sp, Sp, Rp, Sp, Sp, Rp, Sp, Sp, Rp, Sp, Sp, Rp, Sp, Sp, Rp, Sp)d[AsTsGsAsGsAsTsGsCsCsTsGsGsCsTsGsCsCsAsT]

(SEQ ID NO: 474)
(Sp, Sp, Sp, Sp, Sp, Rp, Rp, Sp, Rp, Rp, Sp, Rp, Rp, Sp, Sp, Sp, Sp, Sp, Sp)d[GsAsAsGsCsTsTsTsGsGsTsTsGsGsGsCsAsAsCsA]

(SEQ ID NO: 475)
(Sp, Sp, Rp, Sp, Sp, Rp, Sp, Sp, Rp, Sp, Rp, Sp, Sp, Rp, Sp, Sp, Rp, Sp, Sp)d[CsCsAsTsCsCsAs](AsGsTsCsAsCs)$_{OMe}$d[TsTsGsGsGsAsG]

(SEQ ID NO: 476)
(Sp, Sp, Rp, Sp, Sp, Rp, Sp, Sp, Rp, Sp, Rp, Sp, Sp, Rp, Sp, Sp, Rp, Sp, Sp)d[AsTsGsAsGsAsTs](GsCsCsTsGsGs)$_{OMe}$d[CsTsGsCsCsAsT]

(SEQ ID NO: 477)
(Sp, Sp, Rp, Sp, Sp, Rp, Sp, Sp, Rp, Sp, Rp, Sp, Sp, Rp, Sp, Sp, Rp, Sp, Sp)d[CsCsAsTsCsCsAs](AsGsTsCsAsCs)$_{LNA}$d[TsTsGsGsGsAsG]

(SEQ ID NO: 478)
(Sp, Sp, Rp, Sp, Sp, Rp, Sp, Sp, Rp, Sp, Rp, Sp, Sp, Rp, Sp, Sp, Rp, Sp, Sp)d[AsTsGsAsGsAsTs](GsCsCsTsGsGs)$_{LNA}$d[CsTsGsCsCsAsT]

-continued (SEQ ID NO: 479)
(Sp, Sp, Rp, Sp, Sp, Rp, Sp, Sp, Rp, Sp, Rp, Sp, Sp, Rp, Sp, Sp, Rp, Sp, Sp)d[CsCsAsTsCsCsAs](AsGsTsCsAsCs)<sub>MOE</sub>d[TsTsGsGsGsAsG]

(SEQ ID NO: 480)
(Sp, Sp, Rp, Sp, Sp, Rp, Sp, Sp, Rp, Sp, Rp, Sp, Sp, Rp, Sp, Rp, Sp, Sp)d[AsTsGsAsGsAsTs](GsCsCsTsGsGs)<sub>MOE</sub>d[CsTsGsCsCsAsT]

(SEQ ID NO: 481)
(Sp, Sp, Sp, Sp, Sp, Rp, Sp, Sp, Rp, Sp, Sp, Rp, Sp, Sp, Rp, Sp, Rp, Sp, Sp)(CsCsAs)<sub>OMe</sub>d[TsCsCsAsAsGsTsCsAsCsTsTsGsGs](GsAsG)ome (SEQ ID NO: 482)
(Sp, Sp, Sp, Sp, Sp, Rp, Sp, Sp, Rp, Sp, Sp, Rp, Sp, Sp, Rp, Sp, Rp, Sp, Sp)(AsTsGs)<sub>MOE</sub>d[AsGsAsTsGsCsCsTsGsGsCsTsGsCs](CsAsT)MOE (SEQ ID NO: 483)
(Sp, Sp, Sp, Sp, Sp, Rp, Sp, Sp, Rp, Sp, Sp, Rp, Sp, Sp, Rp, Sp, Sp, Sp, Sp)(CsCsAs)<sub>LNA</sub>d[TsCsCsAsAsGsTsCsAsCsTsTsGsGs](GsAsG)LNA (SEQ ID NO: 484)
(Sp, Sp, Sp, Sp, Sp, Rp, Sp, Sp, Rp, Sp, Sp, Rp, Sp, Sp, Rp, Sp, Sp, Sp, Sp)(AsTsGs)<sub>OMe</sub>d[AsGsAsTsGsCsCsTsGsGsCsTsGsCs](CsAsT)ome (SEQ ID NO: 485)
(Sp, Sp, Sp, Rp, Sp, Sp, Sp, Rp, Sp, Sp, Sp, Rp, Sp, Sp, Sp, Sp, Rp, Sp, Sp)d[CsCsAsTsCsCsAsAsGsTsCsAsCsTsTsGsGsGsAsG]

(SEQ ID NO: 486)
(Sp, Sp, Sp, Rp, Sp, Sp, Sp, Rp, Sp, Sp, Sp, Rp, Sp, Sp, Sp, Sp, Rp, Sp, Sp)d[AsTsGsAsGsAsTsGsCsCsTsGsGsCsTsGsCsCsAsT]

(SEQ ID NO: 487)
(Sp, Sp, Rp, Sp, Sp, Sp, Rp, Sp, Sp, Rp, Sp, Sp, Sp, Rp, Sp, Sp, Sp, Sp)d[GsAsAsGsCsTsTsTsGsGsGsTsGsGsGsCsAsAsCsA]

(SEQ ID NO: 488)
(Sp, Rp, Sp, Sp, Sp, Rp, Sp, Sp, Sp, Rp, Sp, Sp, Sp, Rp, Sp, Sp, Sp, Rp, Sp)d[AsTsGsAsGsAsTsGsCsCsTsGsGsCsTsGsCsCsAsT]

(SEQ ID NO: 489)
(Sp, Sp, Sp, Sp, Rp, Sp, Sp, Sp, Rp, Sp, Sp, Sp, Sp, Rp, Sp, Sp, Sp, Sp)d[CsCsAsTsCsCsAsAsGsTsCsAsCsTsTsGsGsGsAsG]

(SEQ ID NO: 490)
(Sp, Sp, Sp, Rp, Sp, Sp, Sp, Sp, Rp, Sp, Sp, Sp, Sp, Rp, Sp, Sp, Sp, Sp)d[AsTsGsAsGsAsTsGsCsCsTsGsGsCsTsGsCsCsAsT]

(SEQ ID NO: 491)
(Sp, Sp, Rp, Sp, Sp, Sp, Sp, Rp, Sp, Sp, Sp, Sp, Rp, Sp, Sp, Sp, Sp, Rp, Sp)d[GsAsAsGsCsTsTsTsGsGsGsTsGsGsGsCsAsAsCsA]

(SEQ ID NO: 492)
(Sp, Rp, Sp, Sp, Sp, Sp, Rp, Sp, Sp, Sp, Sp, Rp, Sp, Sp, Sp, Sp, Rp, Sp)d[AsTsGsAsGsAsTsGsCsCsTsGsGsCsTsGsCsCsAsT]

(SEQ ID NO: 493)
(Sp, Sp, Sp, Sp, Sp, Rp, Sp, Sp, Sp, Sp, Rp, Sp, Sp, Sp, Sp, Sp, Rp, Sp)d[CsCsAsTsCsCsAsAsGsTsCsAsCsTsTsGsGsGsAsG]

(SEQ ID NO: 494)
(Sp, Sp, Rp, Sp, Sp, Sp, Sp, Rp, Sp, Sp, Sp, Sp, Rp, Sp, Sp, Sp, Sp)d[CsCsAsTsCsCsAsAsGsTsCsAsCsTsTsGsGsGsAsG]

(SEQ ID NO: 495)
(Sp, Rp, Sp, Sp, Sp, Sp, Rp, Sp, Sp, Sp, Sp, Sp, Rp, Sp, Sp, Sp, Sp)d[AsTsGsAsGsAsTsGsCsCsTsGsGsCsTsGsCsCsAsT]

(SEQ ID NO: 496)
(Sp, Sp, Sp, Sp, Rp, Sp, Sp, Rp, Sp, Sp, Sp, Rp, Sp, Sp, Rp, Sp, Sp, Sp)d[CsCsAsTsCsCsAsAsGsTsCsAsCsTsTsGsGsGsAsG]

(SEQ ID NO: 497)
(Sp, Sp, Sp, Sp, Rp, Sp, Sp, Rp, Sp, Sp, Rp, Rp, Sp, Sp, Rp, Sp, Sp, Sp)d[CsCsAsTsCsCsAsAsGsTsCsAsCsTsTsGsGsGsAsG]

(SEQ ID NO: 498)
(Sp, Sp, Sp, Sp, Rp, Sp, Sp, Rp, Sp, Rp, Sp, Rp, Sp, Sp, Rp, Sp, Sp, Sp)d[CsCsAsTsCsCsAsAsGsTsCsAsCsTsTsGsGsGsAsG]

```
                                                              (SEQ ID NO: 499)
(Sp, Sp, Rp, Sp, Sp, Rp, Sp, Sp, Sp, Rp, Sp, Sp, Sp, Rp, Sp, Sp, Rp, Sp,
Sp)d[CsCsAsTsCsCsAsAsGsTsCsAsCsTsTsGsGsGsAsG]

(SEQ ID NO: 500)
(Sp, Sp, Rp, Sp, Sp, Rp, Sp, Sp, Sp, Sp, Sp, Sp, Sp, Rp, Sp, Sp, Rp, Sp,
Sp)d[CsCsAsTsCsCsAsAsGsTsCsAsCsTsTsGsGsGsAsG]

(SEQ ID NO: 501)
(Sp, Sp, Sp, Sp, Rp, Sp, Sp, Rp, Sp, Sp, Sp, Rp, Sp, Sp, Rp, Sp, Sp, Sp,
Sp)d[CsCsAsTsCsCsAsAsGsTsCsAsCsTsTsGsGsGsAsG]

(SEQ ID NO: 502)
(Sp, Sp, Sp, Sp, Rp, Sp, Sp, Rp, Sp, Rp, Sp, Rp, Sp, Sp, Rp, Sp, Sp, Sp,
Sp) (CsCs) OMe d[AsTsCsCsAsAs](GsTsCs) OMe d[AsCsTsTsGsGsGs](AsG)ome (SEQ ID NO: 503)
(Sp, Sp, Sp, Sp, Rp, Sp, Sp, Rp, Sp, Rp, Sp, Rp, Sp, Sp, Rp, Sp, Sp, Sp, Sp)
(CsCs) LNA d[AsTsCsCsAsAsGsTsCsAsCsTsTsGsGsGs](AsG)LNA (SEQ ID NO: 504)
(Sp, Sp, Rp, Sp, Sp, Rp, Sp, Sp, Sp, Rp, Sp, Sp, Sp, Rp, Sp, Sp, Rp, Sp, Sp)
(CsCs) MOE d[AsTsCsCsAsAsGsTsCsAsCsTsTsGsGsGs](AsG) MOE E (SEQ ID NO: 505)
(Sp, Sp, Rp, Sp, Sp, Rp, Sp, Sp, Sp, Sp, Sp, Sp, Sp, Rp, Sp, Sp, Rp, Sp, Sp)
(CsCs) OMe d[AsTsCsCsAsAsGsTsCsAsCsTsTsGsGsGs](AsG) OMe
```

Example 4. Suppression of Nucleic Acid Polymer

Among other things, the present invention provides chirally controlled oligonucleotide compositions and methods thereof that deliver unexpected results when, e.g., used for suppressing nucleic acid polymers through, in some cases, cleavage of such nucleic acid polymers. Examples include but are not limited to those presented herein.

RNase H Assay

Cleavage rate of nucleic acid polymers by nucleases, for example, RNA by RNase H, is important with respect to the use of oligonucleotides in therapeutic technologies such as antisense technology. Using our assay, we investigated the cleavage rates and analyzed the metabolites for chirally controlled oligonucleotide compositions of particular oligonucleotide types (P-diastereomers) when oligonucleotides of the particular oligonucleotide types are bound to complementary RNA. Results below also illustrate the importance of cleavage patterns recognized by the present invention.

RNase H used herein is a ubiquitously expressed endonuclease that hydrolyses the RNA strand of a RNA/DNA hybrid. It plays an important role in the mode of action of antisense oligonucleotides. In some embodiments, RNase H cleavage rate is significantly reduced when the RNA substrate is structured (Lima, W. F., Venkatraman, M., Crooke, S. T. The Influence of Antisense Oligonucleotide-induced RNA Structure on *Escherichia coli* RNase H1 Activity *The Journal Of Biological Chemistry* 272, No. 29, 18191-18199, (1997)). Furthermore, the 2'-MOE gapmer designs (5-10-5) offer higher affinities for RNA targets leading to minimal turnover of the antisense strand. Presence of 2'-MOE modifications in the wings also reduce the number of RNase H cleavage sites.

To study the RNA cleavage rate, the present invention provides a simple assay to quantify the length of RNA remaining after incubation with RNase H. The provided method, among other things, provides the relative rates of RNase H cleavage for stereorandom 2'-modified gapmers, stereorandom DNA oligonucleotide compositions and chirally pure P-diastereomers (chirally controlled oligonucleotide compositions of a corresponding oligonucleotide type) for various oligomers for different targets. Changing the stereochemistry at 2'-modified regions and the DNA core provides information with respect to how stereochemistry in these regions affects the interaction of RNase H to its substrates. RNase H reaction mixtures at different time points were analyzed by LCMS to determine the cleavage pattern. The present invention, among other things, provides nucleic acid polymer, for example RNA, cleavage rates and cleavage patterns (maps) that are critical to design stereochemical nucleic acid architectures for optimal activity, e.g., antisense activity.

Equipment:
Alliance HPLC, 2489-TUV, 2695E-Equipped with autosampler
Cary100 (Agilent Technologies)
Methods:
DNA/RNA Duplex Preparation: Oligonucleotide concentrations were determined by measuring the absorbance in water at 260 nm. DNA/RNA duplexes were prepared by mixing equimolar solutions oligonucleotides with each strand concentration of 10 uM. The mixtures were heated at 90° C. for 2 minutes in water bath and were cooled down slowly over several hours.

Human RNase H Protein Expression and Purification: Human RNase HC clone was obtained from Prof Wei Yang's laboratory at NIH Bethesda. The protocol for obtaining this human RNase HC (residues 136-286) has been described (Nowotny, M. et al. Structure of Human RNase H1 Complexed with an RNA/DNA Hybrid: Insight into HIV Reverse Transcription. *Molecular Cell* 28, 264-276, (2007). The protein expression was carried out by following reported protocol with the exception that the resulting protein had an N-terminal His6 tag (SEQ ID NO: 621). BL21(DE3) *E. coli* cells in LB medium were used for protein expression. Cells were grown at 37° C. till OD600 reached around 0.7. The cultures were then cooled and 0.4 mM IPTG was added to induce protein expression overnight at 16° C. *E. coli* extract was prepared by sonication in buffer A (40 mM $NaH_2PO_4$ (pH 7.0), 1 M NaCl, 5% glycerol, 2.8 mM β-mercaptoethanol and 10 mM imidazole) with the addition of protease inhibitors (Sigma-Aldrich). The extract was purified by Ni affinity column using buffer A plus 60 mM imidazole. The protein was eluted with a linear gradient of 60 to 300 mM imidazole. The protein peak was collected and was further purified on a Mono S column (GE Healthcare) with a 100 mM-500 mM gradient of NaCl in buffer B. Fractions containing RNase HC were concentrated to 0.3 mg/ml in the storage buffer (20 mM HEPES (pH 7.0), 100 mM NaCl, 5% glycerol, 0.5 mM EDTA, 2 mM DTT) and stored at −20° C. 0.3 mg/ml enzyme concentration corresponds to 17.4 uM based on its reported extinction coefficient (32095 cm$^{-1}$M$^{-1}$) and MW (18963.3 Da units).

RNase H assay: In a 96-well plate, to 25 μL DNA/RNA duplex (10 μM) was added 5 μL of 10× RNase H buffer followed by 15 μL water. The mixture was incubated at 37° C. for a few minutes and then 5 μL of 0.1 μM stock solution of enzyme was added to give total volume of 50 μL with final substrate/enzyme concentration 5 μM/0.01 μM (500:1) and was further incubated at 37° C. Various ratios of the DNA/RNA duplex: RNase H protein were studied using these conditions to find an optimal ratio to study the kinetics. The reactions were quenched at different time points using 10 μL of 500 mM EDTA disodium solution in water. For zero min time point, EDTA was added to the reaction mixture before the addition of enzyme. Controls were run to ensure that EDTA was able to successfully inhibit the enzyme activity completely. After all the reactions were quenched 10 μL of each reaction mixture was injected on to analytical HPLC column (XBridge C18, 3.5 um, 4.6×150 mm, Waters Part #186003034). Kcat/Km can be measured by a number of methods, such as FRET (Fluorescence Resonance Energy Transfer) dependent RNase H assay using dual labeled RNA and monitored by SpectraMax.

Solid Phase Extraction Protocol for sample preparation for LCMS: 96 well plate (Waters part #186002321) was used to clean the RNase H reaction mixture before running LCMS. 500 μL of acetonitrile followed by water was used to equilibrate the plate under mild vacuum with the help of manifold (Millipore part #MSV MHTS00). Precaution was taken not to let the plate dry. About 50-100 μL of RNase H reaction mixture was loaded in each well followed by water washings (2 mL) under mild vacuum. 2×500 μL of 70% ACN/Water was used to recover the sample. The recovered samples were transferred to 2 mL centrifuge tubes and were concentrated to dryness in speed vac. Each dry sample was reconstituted in 100 μL water and 10 μL was injected on Acquity UPLC@OST C18 1.7 um, 2.1×50 mm (part #186003949) for LCMS analysis.

For mass spectrometry analysis, the reaction mixtures after quenching were cleaned using $C_{18}$ 96 well plate (Waters). The oligomers were eluted in 70% Acetonitrile/Water. The Acetonitrile was evaporated using speedvac and the resulting residue was reconstituted in water for injection.
Eluent A=50 mM Triethyl ammonium acetate
Eluent B=Acetonitrile
Column Temperature=60° C.
UV was recorded at 254 nm and 280 nm
RP-HPLC Gradient Method

| | Time (min) | Flow (ml/min) | % A | % B | Curve |
|---|---|---|---|---|---|
| 1 | 0.0 | 1.00 | 95.0 | 5.0 | |
| 2 | 2.00 | 1.00 | 95.0 | 5.0 | 1 |
| 3 | 22.00 | 1.00 | 80.0 | 20.0 | 6 |
| 4 | 25.00 | 1.00 | 5.0 | 95.0 | 6 |
| 5 | 25.5 | 1.00 | 95.0 | 5.0 | 1 |
| 6 | 30 | 1.00 | 95.0 | 5.0 | 1 |

Figure 6:
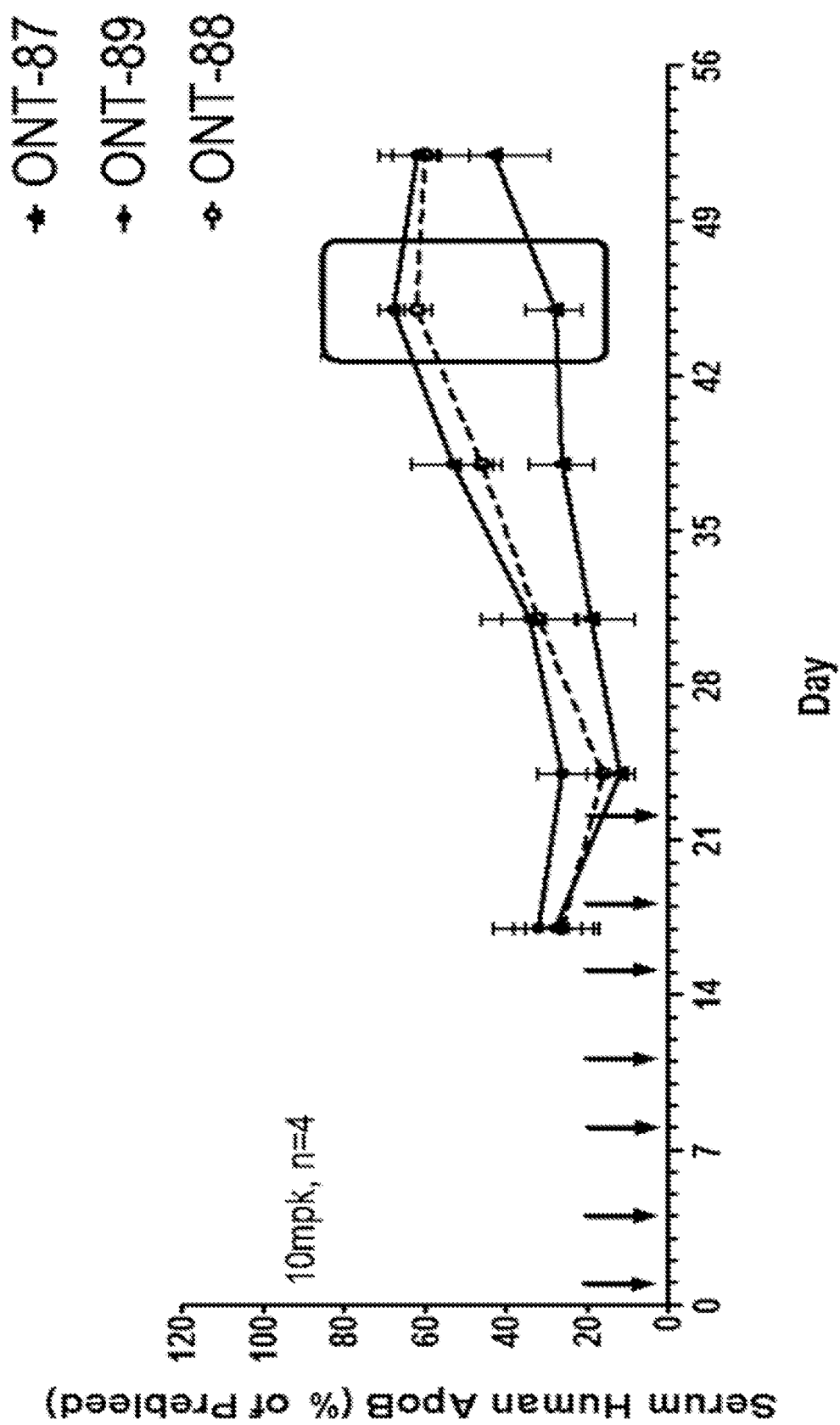
FIG. 6. Durations of knockdown for ONT-87, ONT-88, and ONT-89. Stereoisomers can exhibit substantially different durations of knockdown. ONT-87 results in substantially more durable suppression than other stereoisomers. Increased duration of action of ONT-87 in multiple in vivo studies were observed. ONT-88 showed similar efficacy and recovery profile as ONT-41 (Mipomersen) in certain in-vivo studies. Hu ApoB transgenic mice, n=4, were dosed with 10 mpk IP bolus, 2×/week for three weeks. The mice were randomized to study groups, and dosed intraperitoneally (IP) at 10 mg/kg on Days 1, 4, 8, 11, 15, 18, and 22, based on individual mouse body weight measured prior to dosing on each dosing day. Blood was collected on days 0, 17, 24, 31, 38, 45 and 52 by submandibular (cheek) bleed and at sacrifice on Day 52 by cardiac puncture and then processed to serum. ApoB was measured by ELISA. Highlighted: 72% vs. 35% knock-down maintained at 3 weeks postdose.
Figure 8:
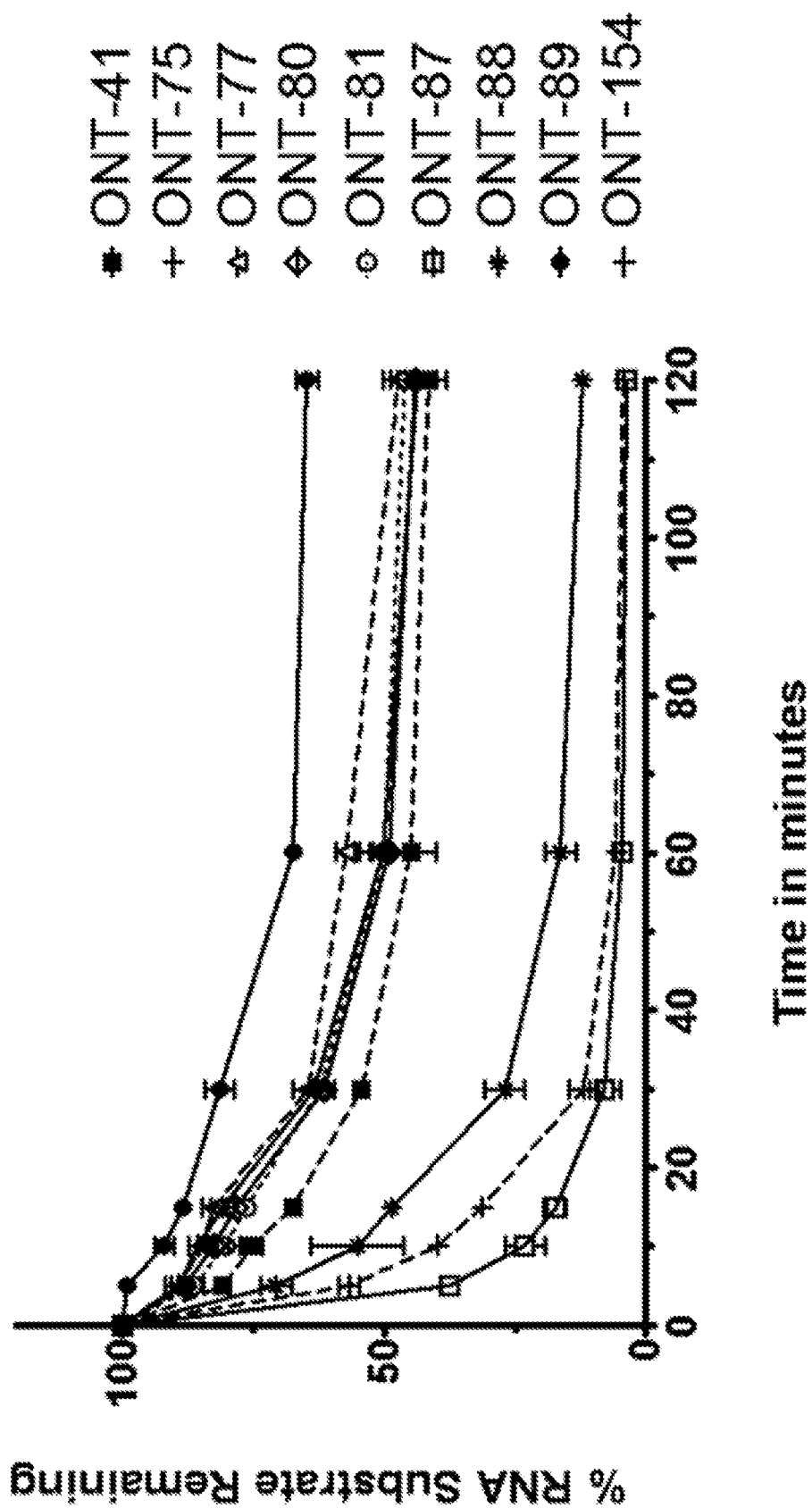
FIG. 8. Effect of stereochemistry on RNase H activity. Oligonucleotides were hybridized with RNA and then incubated with RNase H at 37° C. in the presence of 1× RNase H buffer. From top to bottom at 120 min: ONT-89, ONT-77, ONT-81, ONT-80, ONT-75, ONT-41, ONT-88, ONT-154, ONT-87, with ONT-77/154 very close to each other.
Figure 9:
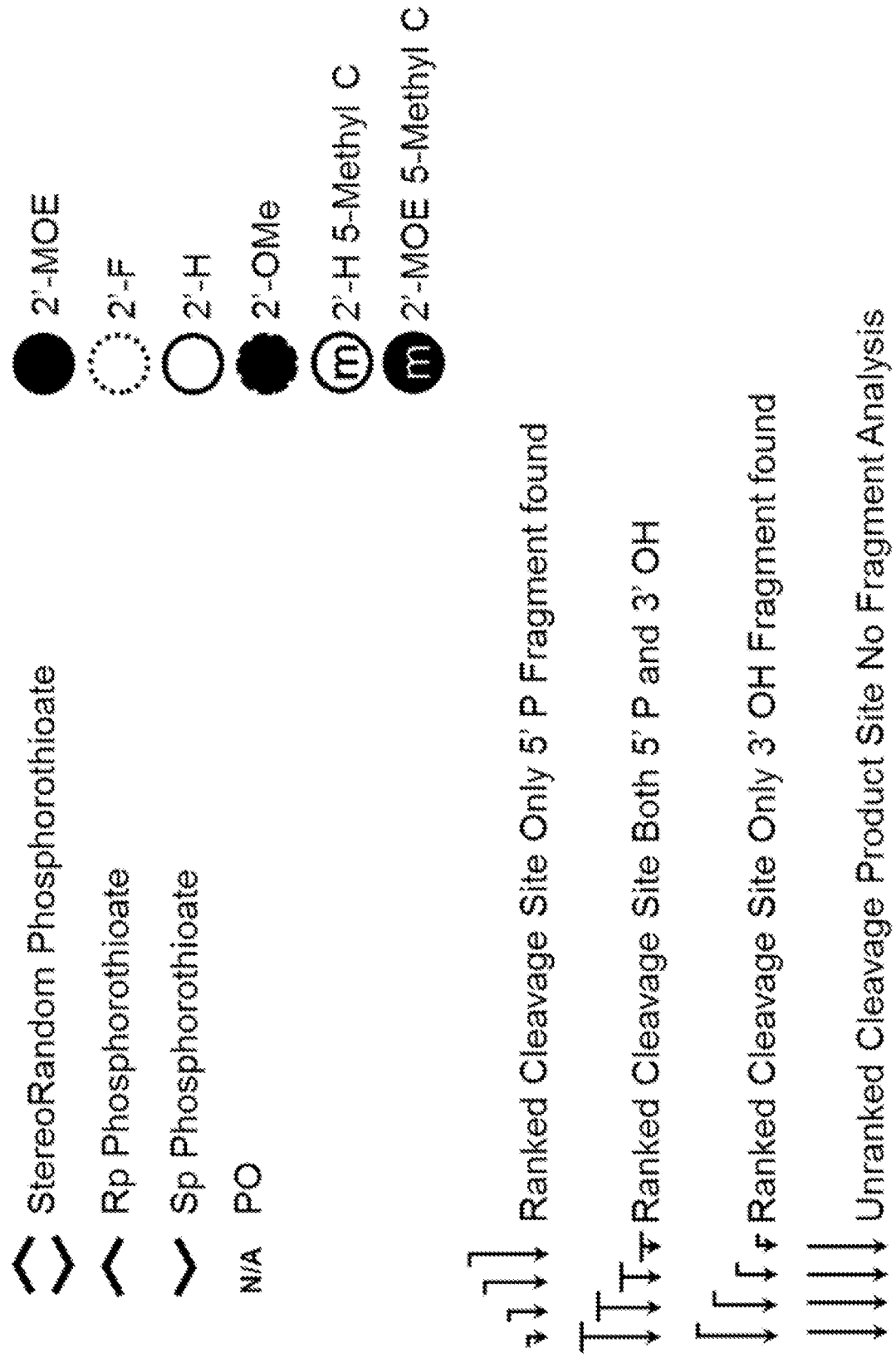
FIG. 9. Analysis of human RNase H1 cleavage of a 20-mer RNA when hybridized with different preparations of stereoisomers of phosphorothioate oligonucleotides targeting the same region of human ApoB mRNA. Specific sites of cleavage are strongly influenced by the distinct stereochemistries. Arrows represent position of cleavage (cleavage sites). Products were analyzed by UPLC/MS. The length of the arrow signifies the amount of products present in the reaction mixture which was determined from the ratio of UV peak area to theoretical extinction coefficient of that fragment (the larger the arrow, the more the detected cleavage products). (A). Legend for cleavage maps. (B) and (C): cleavage maps of oligonucleotides. ONT-41 (SEQ ID NO: 239), ONT-75 (SEQ ID NO: 244), ONT-77 (SEQ ID NO: 245), ONT-80 (SEQ ID NO: 246), ONT-81 (SEQ ID NO: 247), ONT-87 (SEQ ID NO: 248), ONT-88 (SEQ ID NO: 249), ONT-89 (SEQ ID NO: 250), and ONT-154 (SEQ ID NO: 241).
Figure 9:
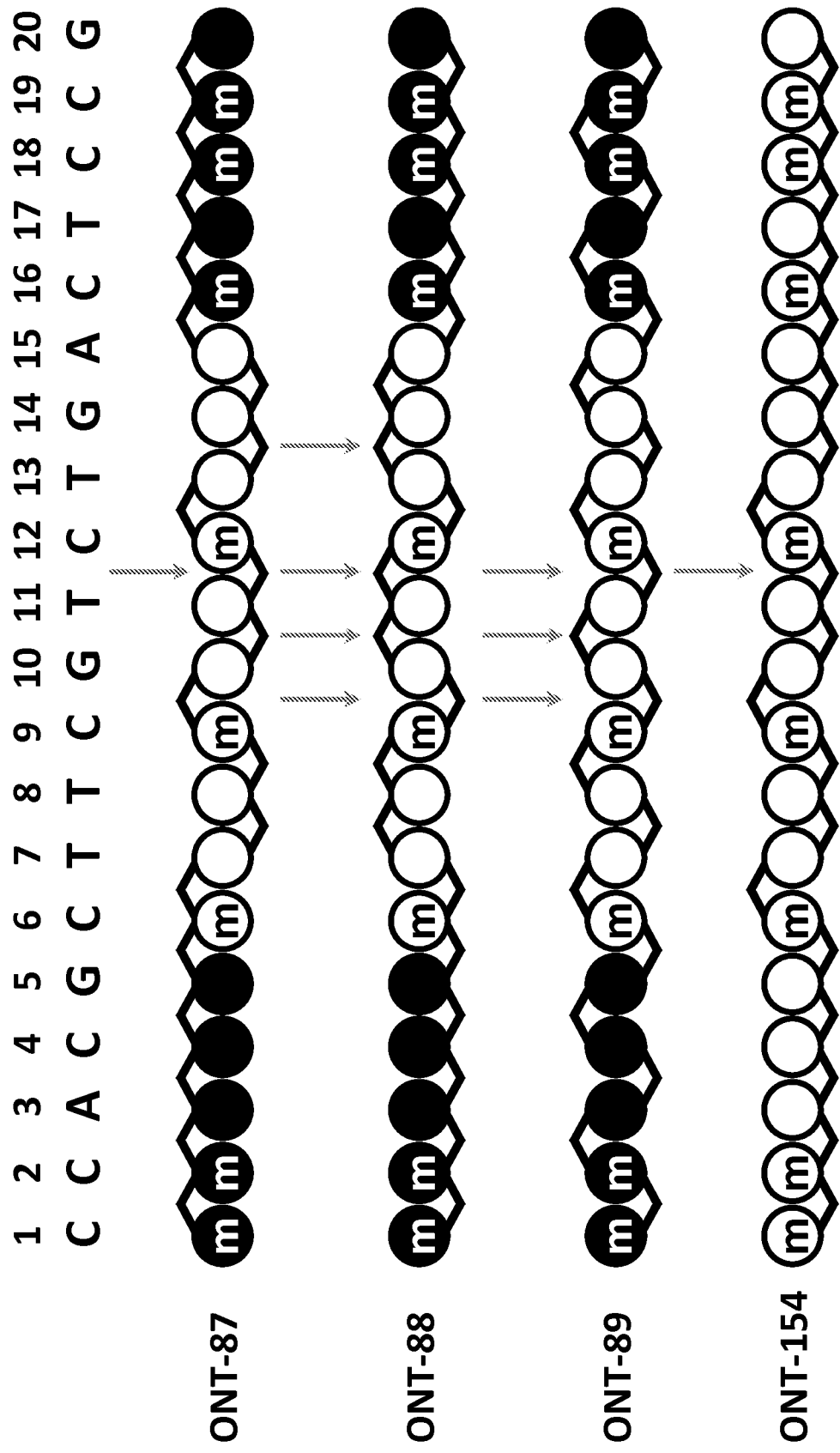
Figure 10:
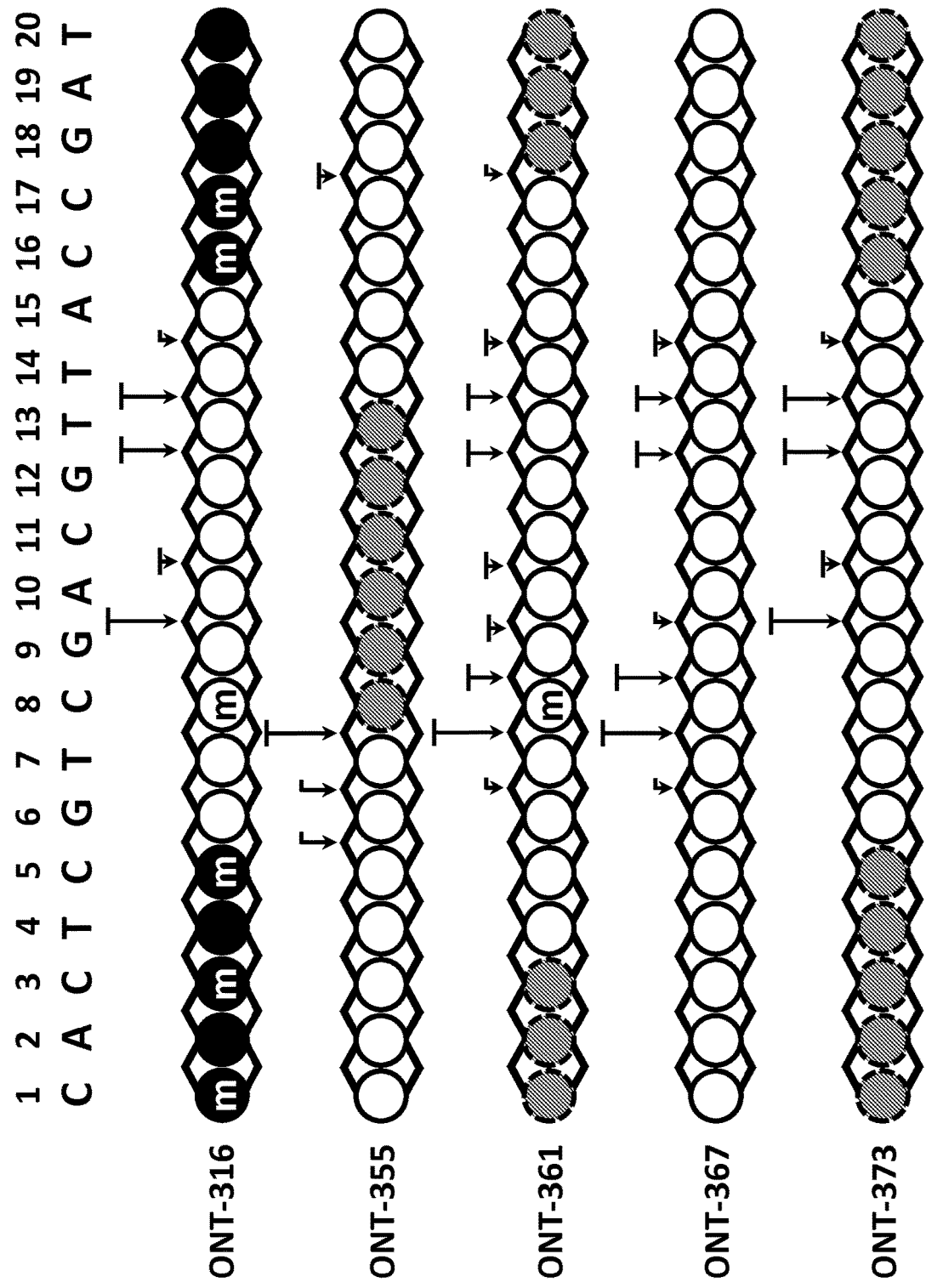
FIG. 10. Cleavage maps of different oligonucleotide compositions ((A)-(C)). These three sequences target different regions in FOXO1 mRNA. Each sequence was studied with five different chemistries. Cleavage maps are derived from reaction mixtures obtained after 30 minutes of incubation of respective duplexes with RNase H1C in the presence of 1×PBS buffer at 37° C. Arrows indicate sites of cleavage. (⊤) indicates that both fragments, 5'-phosphate specie as well as 5'-OH 3'-OH specie were identified in reaction mixtures. (⌈) indicates that only 5'-phosphate specie was detected and (⌉) indicates that 5'-OH 3'-OH component was detected in mass spectrometry analysis. The length of the arrow signifies the amount of products present in the reaction mixture which was determined from the ratio of UV peak area to theoretical extinction coefficient of that fragment (the larger the arrow, the more the detectable cleavage products). Only in the cases where 5'-OH 3'-OH was not detected in the reaction mixture, 5'-phosphate specie peak was used for quantification. Cleavage rates were determined by measuring amount of full length RNA remaining in the reaction mixtures by reverse phase HPLC. Reactions were quenched at fixed time points by 30 mM Na$_2$EDTA. ONT-316 (SEQ ID NO: 516), ONT-355 (SEQ ID NO: 517), ONT-361 (SEQ ID NO: 518), ONT-367 (SEQ ID NO: 519), ONT-373 (SEQ ID NO: 520), ONT-302 (SEQ ID NO: 522), ONT-352 (SEQ ID NO: 523), ONT-358 (SEQ ID NO: 524), ONT-364 (SEQ ID NO: 525), ONT-370 (SEQ ID NO: 526), ONT-315 (SEQ ID NO: 528), ONT-354 (SEQ ID NO: 529), ONT-360 (SEQ ID NO: 530), ONT-366 (SEQ ID NO: 531), and ONT-372 (SEQ ID NO: 532).
Figure 10:
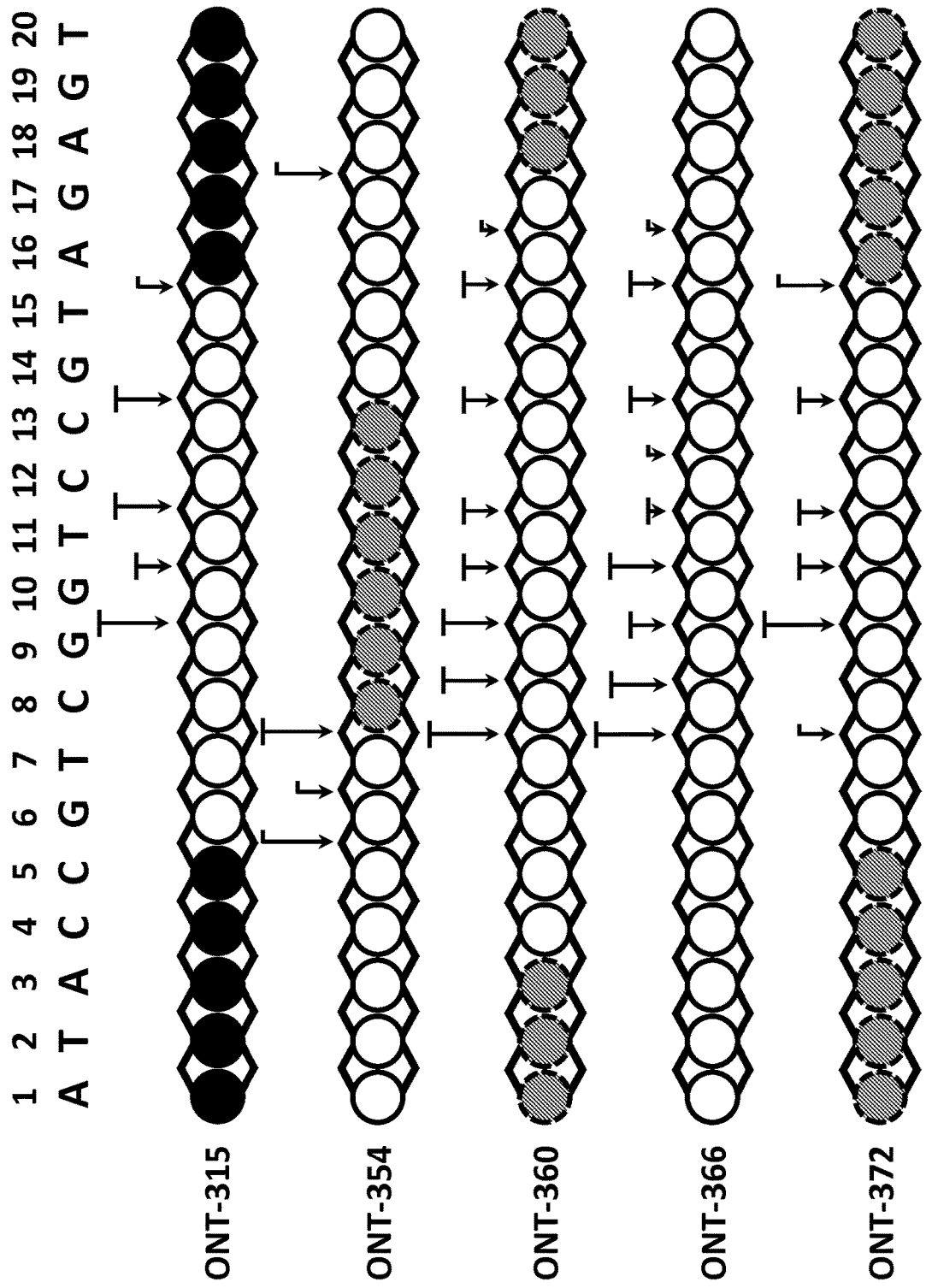

On HPLC chromatograms, peak areas corresponding to full length RNA oligomer (ONT-28) were integrated, normalized using the DNA peak and were plotted against time (FIG. 8). ONT-87 demonstrated superior cleavage for complementary RNA when in duplex form, in comparison to the other product candidates and Mipomersen. Since all the diastereomers in this panel have 2′-MOE modified wings that do not activate RNase H enzyme, without the intention to be limited by theory, Applicant notes that activity is likely dictated by the stereochemistry in the DNA core. Heteroduplexes with ONT-77 to ONT-81 including Mipomersen in the antisense strand show very similar RNA cleavage rates. ONT-89 with alternating Sp/Rp stereochemistry showed the least activity in the tested time frame under the tested conditions. Among the tested oligonucleotides with MOE modifications, ONT-87 and ONT-88 units in the antisense strand exhibited increased in activity in comparison to the rest of the heteroduplexes. Particularly, ONT-87 provided surprisingly high cleavage rate and unexpected low level of remaining target RNA. Additional exemplary data were illustrated in FIG. 6 and FIG. 24.

In Vitro Oligonucleotide Transfection Assay: Transfection assays are widely known and practiced by persons having ordinary skill in the art. An exemplary protocol is described herein. Hep3B cells are reverse transfected with Lipofectamine 2000 (Life Technologies, Cat. No. 11668-019) at 18×10$^3$ cells/well density in 96-well plates using the manufacturer's protocol. For dose response curves eight 1/3 serial dilutions are used starting from 60-100 nM. 25 μL of 6× oligonucleotide concentration is mixed with a prepared mixture of 0.4 μL Lipofectamine 2000 with 25 μL of serum-free medium Opti-MEM medium (Gibco, Cat. No. 31985-062) per well. After a 20 min minute incubation, 100 μL of 180×10$^3$ cells/ml suspended in 10% FBS in DMEM cell culture media (Gibco, Cat. No. 11965-092) is added to bring the final volume to 150 μL per well. 24-48 hours post transfection Hep3B cells are lysed by adding 75 μL of Lysis Mixture with 0.5 mg/ml Proteinase K using QuantiGene Sample Processing Kit for Cultured Cells (Affymetrix, Cat. No. QS0103). The Target mRNA and GAPDH mRNA expression levels in cell lysates are measured using Affymetrix QuantiGene 2.0 Assay Kit (Cat. No. QS0011) according to the manufacturer's protocol. The Target mRNA expression is normalized to GAPDH mRNA expression from the same sample; and relative Target/GAPDH levels are compared to transfections using Lipofectamine 2000 only (no oligonucleotide) control. Dose response curves are generated by GraphPad Prism 6 using nonlinear regression log (inhibitor) vs. response curve fit with variable slope (4 parameters). For exemplary results, see FIG. 24, FIG. 27 and FIG. 29.

Example 5. Provided Compositions and Methods Provide Control of Cleavage Patterns The present invention surprisingly found that internucleotidic linkage stereochemistry pattern has unexpected impact on cleavage patterns of nucleic acid polymers. By changing common patterns of backbone chiral centers of chirally controlled oligonucleotide compositions, numbers of cleavage sites, cleavage percentage at a cleavage site, and/or locations of cleavage sits can be surprisingly altered, both independently and in combination. As described in the example herein, provided compositions and methods can provide control over cleavage patterns of nucleic acid polymers.

Using similar assay conditions, various chirally controlled oligonucleotide compositions of different oligonucleotide types were tested. Exemplary cleavage patterns of the target RNA sequence is presented in FIG. 9. Certain pattern of backbone chiral centers, such as that in ONT-87 and ONT-154, surprisingly produces only one cleavage site in the target sequence. Moreover, it is surprisingly found that oligonucleotides providing single cleavage site, such as ONT-87 and ONT-154, provide unexpectedly high cleavage rate and low level of remaining target nucleic acid polymer. See also FIG. 8, FIG. 10 and FIG. 11.

Example 6. Exemplary Cleavage of FOXO1 mRNA

Figure 11:
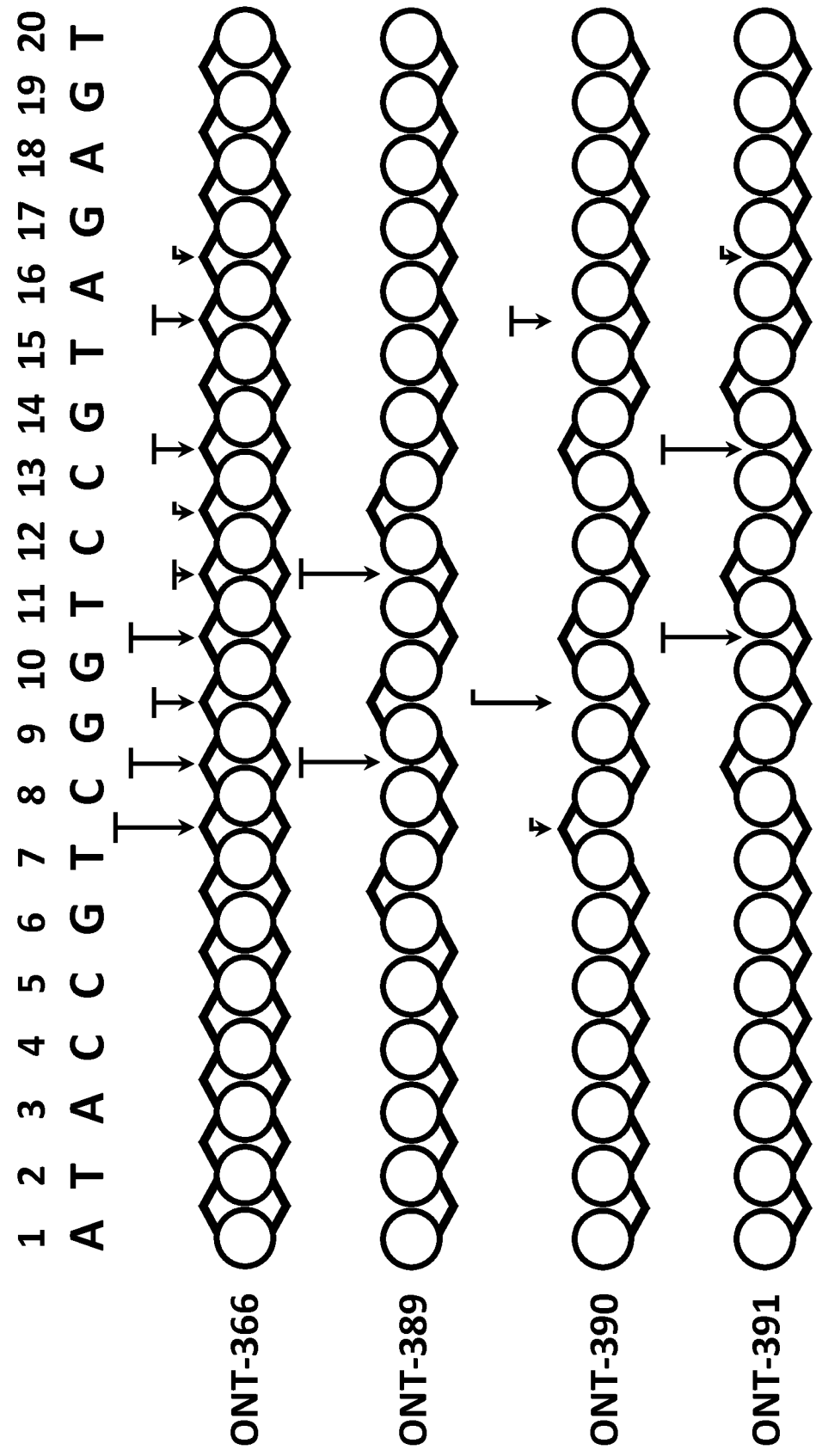
FIG. 11. Cleavage maps of oligonucleotide compositions having different common base sequences and lengths ((A)-(B)). The maps show a comparison of stereorandom DNA compositions (top panel) with three distinct and stereochemically pure oligonucleotide compositions. Data compare results of chirally controlled oligonucleotide compositions with two stereorandom phosphorothioate oligonucleotide compositions (ONT-366 and ONT-367) targeting different regions in FOXO1 mRNA. Each panel shows a comparison of stereorandom DNA (top panel) with three distinct and stereochemically pure oligonucleotide preparations. Cleavage maps were derived from reaction mixtures obtained after 30 minutes of incubation of respective duplexes with RNase H1C in the presence of 1×PBS buffer at 37° C. Arrows indicate sites of cleavage. (⊤) indicates that both fragments, 5'-phosphate specie as well as 5'-OH 3'-OH specie were identified in reaction mixtures. (⌈) indicates that only 5'-phosphate specie was detected and (⌉) indicates that 5'-OH 3'-OH component was detected in mass spectrometry analysis. The length of the arrow signifies the amount of metabolite present in the reaction mixture which was determined from the ratio of UV peak area to theoretical extinction coefficient of that fragment (the larger the arrow, the more the detectable cleavage products). Only in the cases where 5'-OH 3'-OH was not detected in the reaction mixture, 5'-phosphate specie peak was used for quantification. ONT-366 (SEQ ID NO: 531), ONT-389 (SEQ ID NO: 565), ONT-390 (SEQ ID NO: 566), ONT-391 (SEQ ID NO: 567), ONT-367 (SEQ ID NO: 519), ONT-392 (SEQ ID NO: 568), ONT-393 (SEQ ID NO: 569), and ONT-394 (SEQ ID NO: 570).
Figure 11:
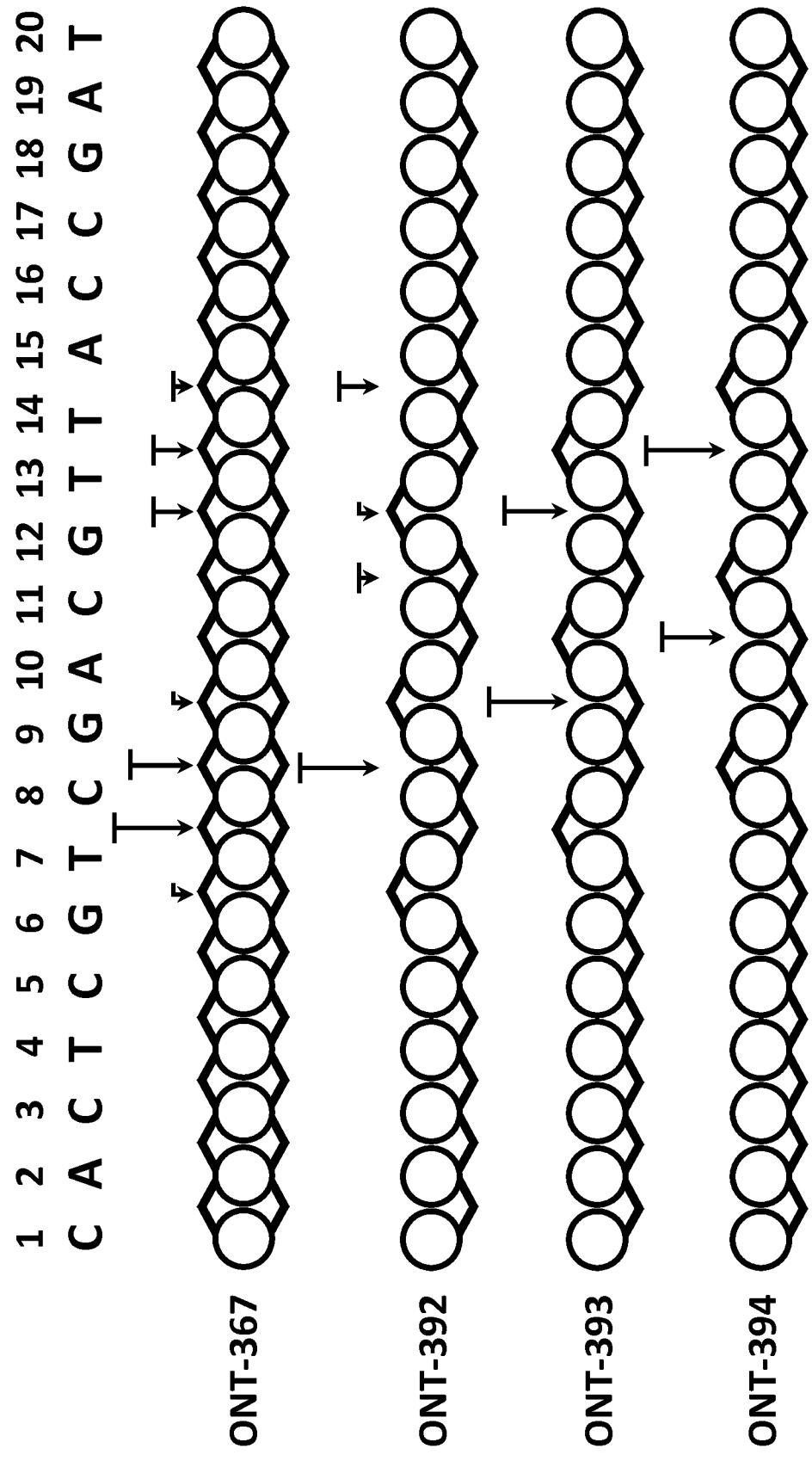
Figure 12:
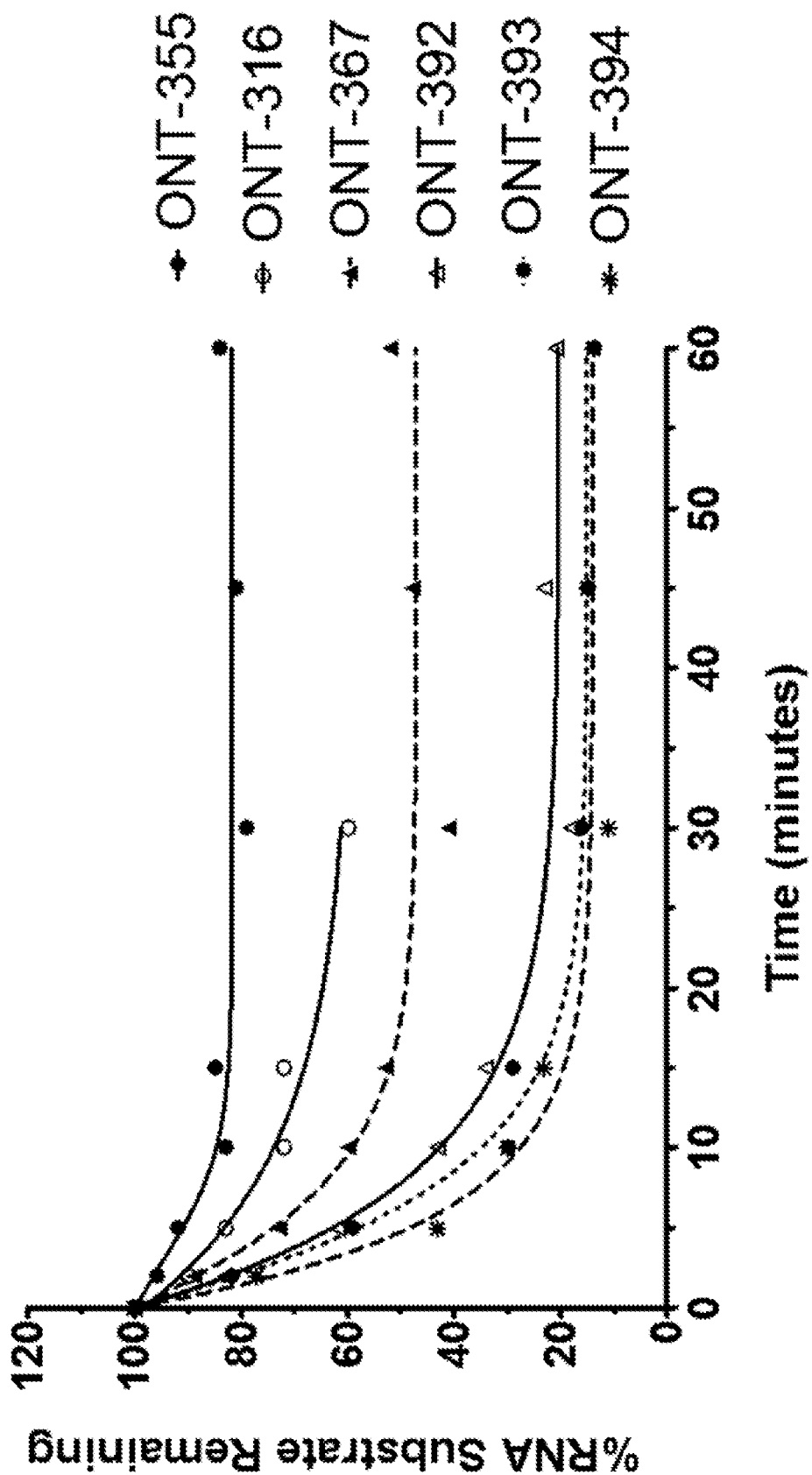
FIG. 12. Effect of stereochemistry on RNase H activity. In two independent experiments, antisense oligonucleotides targeting an identical region of FOXO1 mRNA were hybridized with RNA and then incubated with RNase H at 37° C. in the presence of 1× RNase H buffer. Disappearance of full length RNA was measured from its peak area at 254 nm using RP-HPLC. (A): from top to bottom at 60 min: ONT-355, ONT-316, ONT-367, ONT-392, ONT-393 and ONT-394 (ONT-393 and ONT-394 about the same at 60 min; ONT-393 had higher % RNA substrate remaining at 5 min). (B): from top to bottom at 60 min: ONT-315, ONT-354, ONT-366, ONT-391, ONT-389 and ONT-390. Cleavage rates were determined by measuring amount of full length RNA remaining in the reaction mixtures by reverse phase HPLC. Reactions were quenched at fixed time points by 30 mM $Na_2EDTA$.
Figure 12:
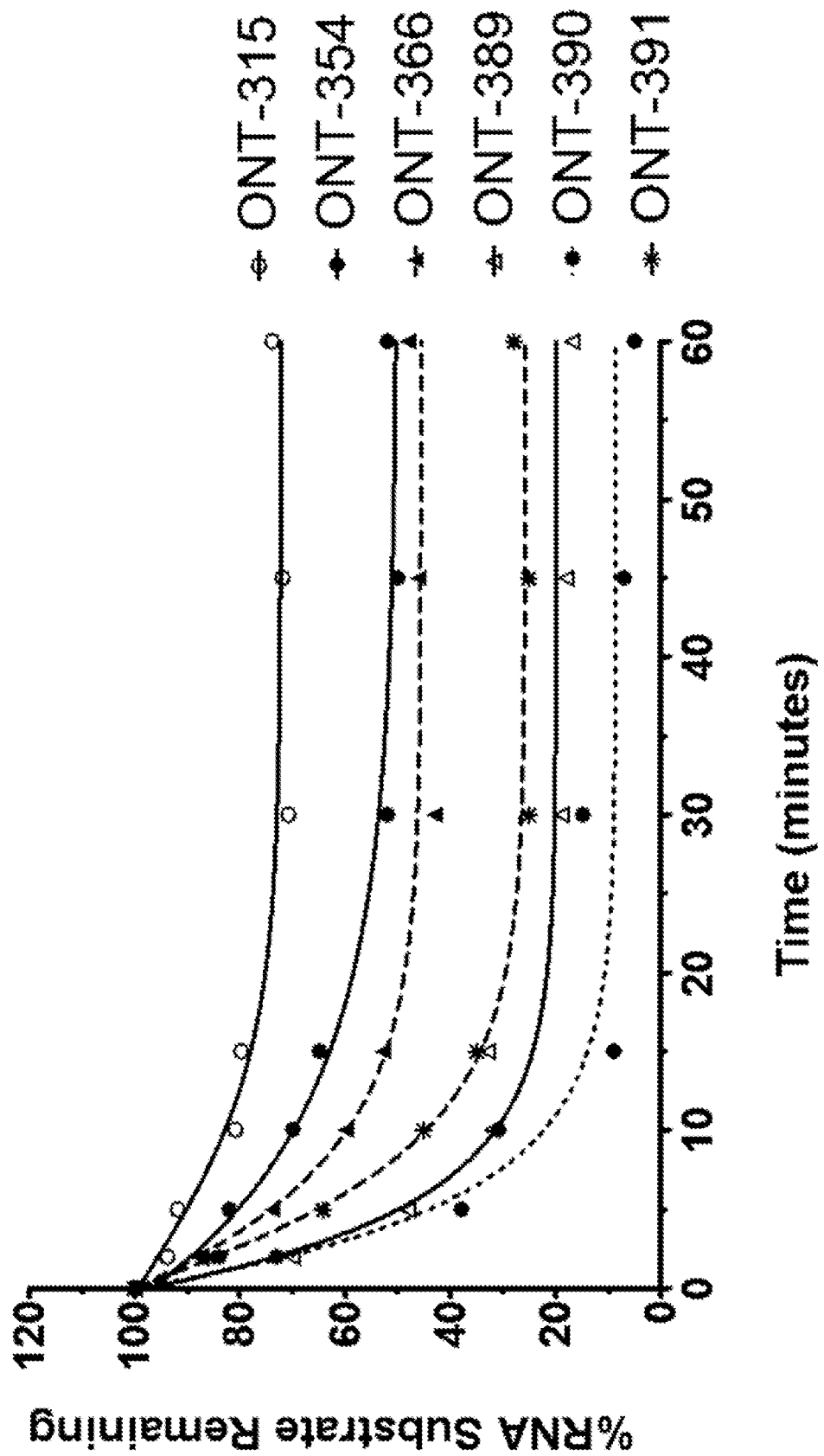

Oligonucleotide compositions targeting different regions of FOXO1 mRNA were tested in cleavage assays as described above. In each case, chirally controlled oligonucleotide compositions were shown to be capable of providing altered cleavage patterns relative to reference cleavage patterns from chirally uncontrolled oligonucleotide compositions sharing the same common base sequence and length. For exemplary results, see FIG. 10 and FIG. 11. As shown in FIG. 12, exemplary chirally controlled oligonucleotide compositions provide both significantly faster cleavage rates and unexpectedly low levels of remaining substrates when compared to reference chirally uncontrolled oligonucleotide compositions. In some embodiments, as shown in FIG. 11, the cleavage sites are associated with RpSpSp backbone chiral center sequence. In some embodiments, cleavage sites are two base pairs upstream of RpSpSp.

Exemplary oligonucleotide compositions are listed below.

ciation may be inhibited and oligonucleotides may not be able to dissociate and find other target strands to form duplexes and cause the target strands to be cleaved. The Tm of ONT-316 (5-10-5 2'-MOE Gapmer) to complementary RNA is 76° C. After a cut or a few cuts in the RNA sequence complementary to the oligonucleotides, the 2'-MOE fragments may remain bound to RNA and thus cannot cause the other target molecules to be cleaved. Thermal melting temperatures of DNA strands generally are much lower when duplexed to RNA, for example, ONT-367 (63° C.) and ONT-392 60° C.). Additionally, thermal stability in DNA sequences is often relatively uniformly distributed compared to 2'-MOE modified oligonucleotides. In some embodiments, oligonucleotides in provided chirally controlled oligonucleotide compositions do not contain 2'-modifications such as 2'-MOE. In some embodiments, oligonucleotides in provided chirally controlled oligonucleotide compositions, which do not contain 2'-modifications such as 2'-MOE, more easily dissociate from nucleic acid polymer cleavage fragments, and have higher turn-over than oligonucleotides having 2'-modifications such as 2'-MOE. In some embodiments, the present invention provides an all DNA designs, in which oligonucleotides do not have 2'-modifications. In some embodiments, chirally controlled oligonucleotide compositions wherein oligonucleotides having no 2'-modification provides higher turn-over of a nuclease such as RNase H. In some embodiments, after cleavage RNase H dissociates more easily from duplex formed by RNA and

| Oligo | Sequence | Description | Tm (° C.) | SEQ ID NO: |
|---|---|---|---|---|
| ONT-366 | dTsdGsdAsdGsdAsdTsdGsdCsdCsdTsdGsdGsdCsdTsdGsdCsdCsdAsdTsdA | All DNA | 66.5 | 506 |
| ONT-389 | dTsdGsdAsdGsdAsdTsdGsdCsdCsdTsdGsdGsdCsdTsdGsdCsdCsdAsdTsdA | $S_7RSSRSSRS_5$ | 64.3 | 507 |
| ONT-390 | dTsdGsdAsdGsdAsdTsdGsdCsdCsdTsdGsdGsdCsdTsdGsdCsdCsdAsdTsdA | $S_6RSSRSSRS_6$ | 64.6 | 508 |
| ONT-391 | dTsdGsdAsdGsdAsdTsdGsdCsdCsdTsdGsdGsdCsdTsdGsdCsdCsdAsdTsdA | $S_5RSSRSSRS_7$ | 64.3 | 509 |
| ONT-387 | rUrArUrGrGrCrArGrCrCrArGrGrCrArUrCrUrCrA | complementary RNA |  | 510 |
| ONT-367 | dTsdAsdGsdCsdCsdAsdTsdTsdGsdCsdAsdGsdCsdTsdGsdCsdTsdCsdAsdC | All DNA | 62.9 | 511 |
| ONT-392 | dTsdAsdGsdCsdCsdAsdTsdTsdGsdCsdAsdGsdCsdTsdGsdCsdTsdCsdAsdC | $S_7RSSRSSRS_5$ | 59.5 | 512 |
| ONT-393 | dTsdAsdGsdCsdCsdAsdTsdTsdGsdCsdAsdGsdCsdTsdGsdCsdTsdCsdAsdC | $S_6RSSRSSRS_6$ | 60 | 513 |
| ONT-394 | dTsdAsdGsdCsdCsdAsdTsdTsdGsdCsdAsdGsdCsdTsdGsdCsdTsdCsdAsdC | $S_5RSSRSSRS_7$ | 59.5 | 514 |
| ONT-388 | rGrUrGrArGrCrArGrCrUrGrCrArArUrGrGrCrUrA | complementary RNA |  | 515 |

Figure 13:
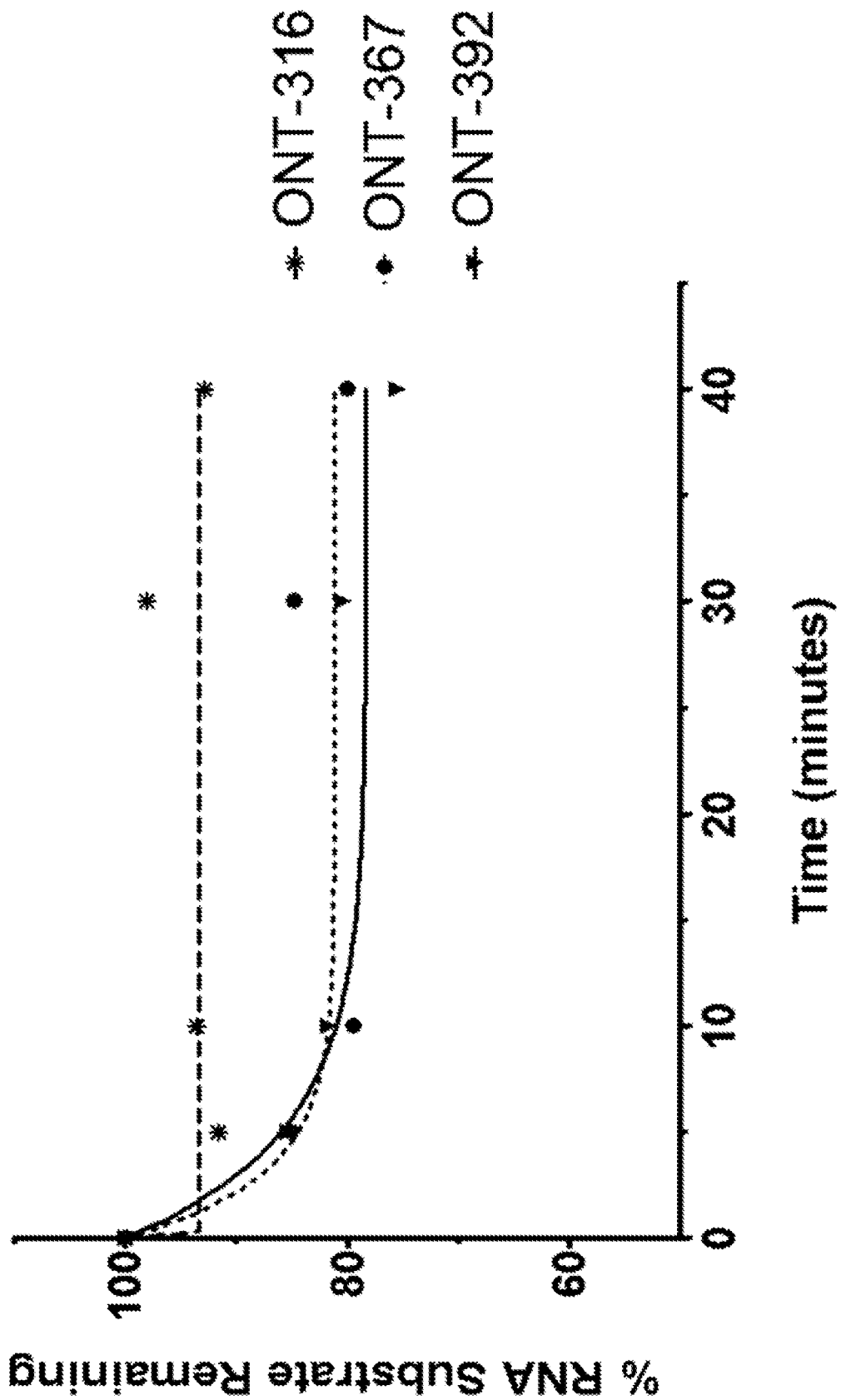
FIG. 13. Turnover of antisense oligonucleotides. The duplexes were made with each DNA strand concentration equal to 6 μM and RNA being 100 μM. These duplexes were incubated with 0.02 μM RNase H enzyme and disappearance of full length RNA was measured from its peak area at 254 nm using RP-HPLC. Cleavage rates were determined by measuring amount of full length RNA remaining in the reaction mixtures by reverse phase HPLC. Reactions were quenched at fixed time points by 30 mM $Na_2EDTA$. From top to bottom at 40 min: ONT-316, ONT-367 and ONT-392.

Example 7. Exemplary Chirally Controlled Oligonucleotide Compositions Provide Higher Turn-Over In cases where the Tm of cleaved nucleic acid polymer fragments, for example RNA fragments, to oligonucleotides is greater than a physiological temperature, product dissociation may be inhibited and oligonucleotides of provided chirally controlled oligonucleotide compositions. Using similar protocols as described above, turn-over of two exemplary chirally controlled oligonucleotide compositions of oligonucleotide type ONT-367 and ONT-392 indeed showed higher turn-over rate than reference chirally uncontrolled oligonucleotide compositions (see FIG. 13).

Example 8. Exemplary Cleavage of FOXO1 mRNA

Figure 14:
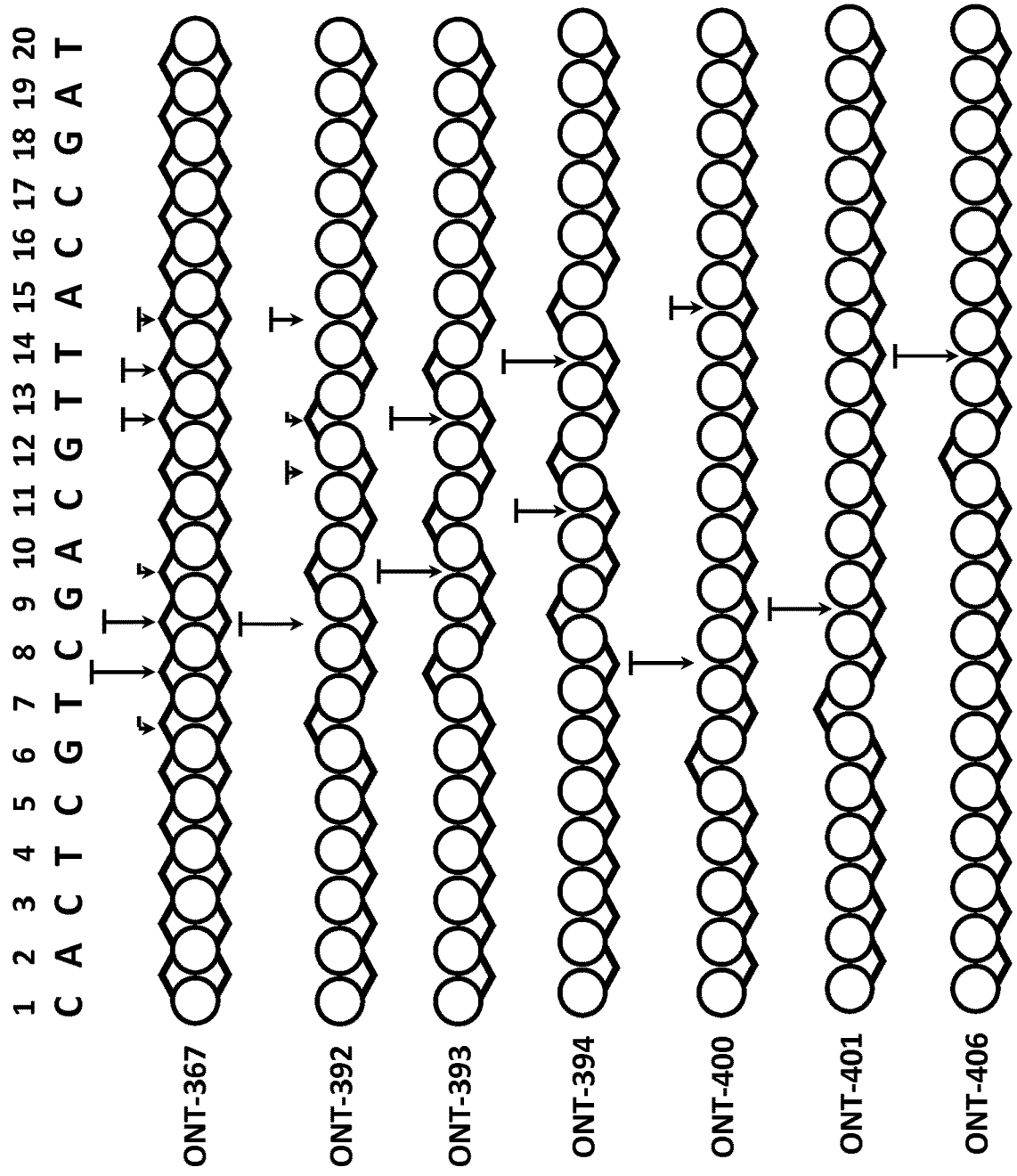
FIG. 14. Cleavage map comparing a stereorandom phosphorothioate oligonucleotide with six distinct and stereochemically pure oligonucleotide preparations targeting the same FOXO1 mRNA region. ONT-367 (SEQ ID NO: 519), ONT-392 (SEQ ID NO: 568), ONT-393 (SEQ ID NO: 569), ONT-394 (SEQ ID NO: 570), ONT-400 (SEQ ID NO: 575), ONT-401 (SEQ ID NO: 576), and ONT-406 (SEQ ID NO: 581).

As exemplified in FIG. 14, chirally controlled oligonucleotide compositions and methods thereof in the present disclosure can provide controlled cleavage of nucleic acid polymers. In some embodiments, chirally controlled oligonucleotide compositions of the present invention produces altered cleavage pattern in terms of number of cleavage sites, location of cleavage sites, and/or relative cleavage percentage of cleavage sites. In some embodiments, as exemplified by ONT-401 and ONT-406, chirally controlled oligonucleotide compositions provide single site cleavage.

In some embodiments, only one component from RNA cleavage was detected. Without the intention to be limited by theory, Applicant notes that such observation could be due to the processive nature of RNase H enzyme which could make multiple cuts on the same duplex resulting in much shorter 5'-OH 3'-OH fragments.

Figure 15:
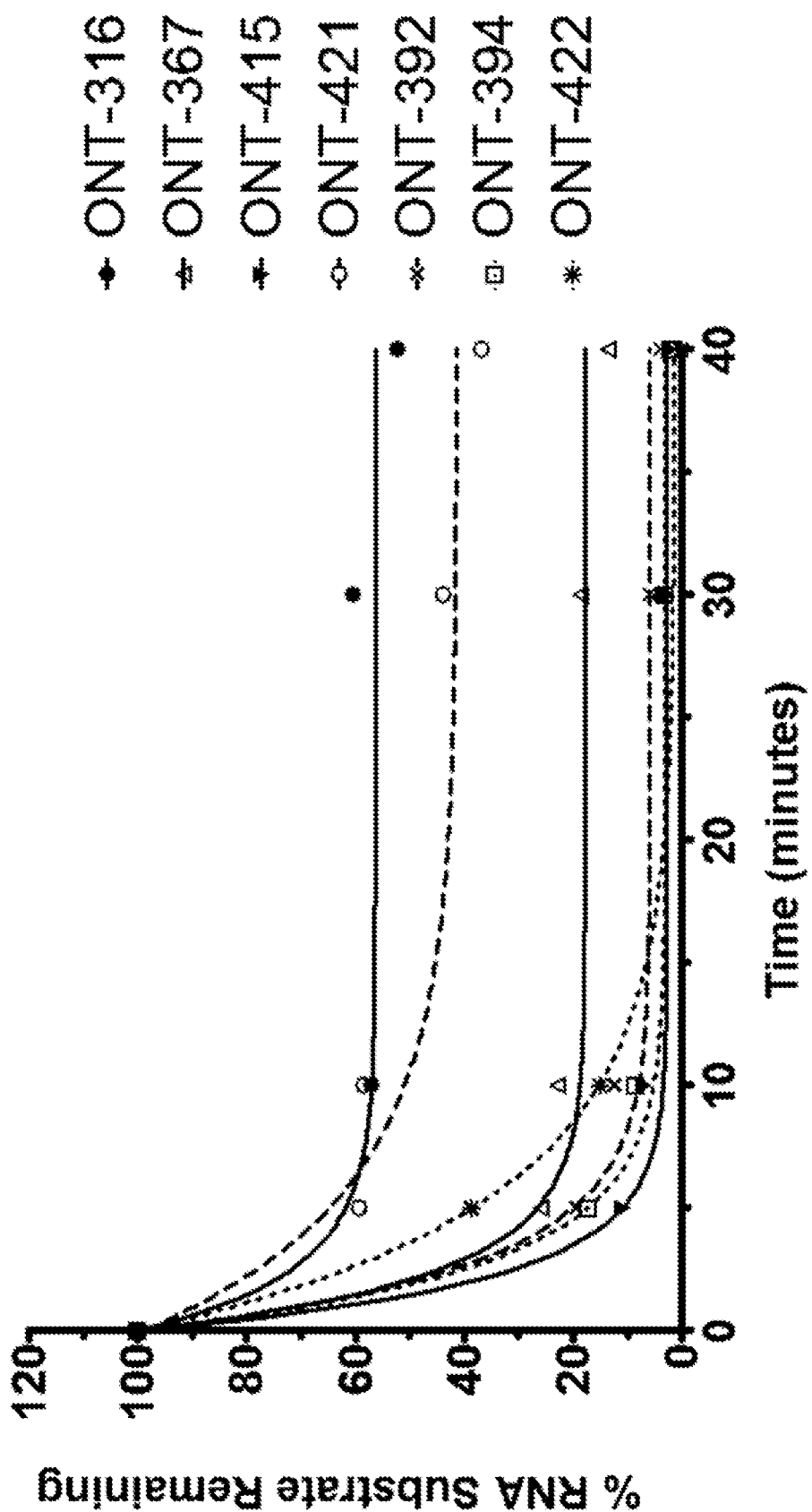
FIG. 15. Effect of stereochemistry on RNase H activity. Antisense oligonucleotides were hybridized with RNA and then incubated with RNase H at 37° C. in the presence of 1× RNase H buffer. Dependence of stereochemistry upon RNase H activity was observed. Also evident in comparing ONT-367 (stereorandom DNA) and ONT-316 (5-10-5 2'-MOE Gapmer) is the strong dependence of compositional chemistry upon RNase H activity. From top to bottom at 40 min: ONT-316, ONT-421, ONT-367, ONT-392, ONT-394, ONT-415, and ONT-422 (ONT-394/415/422 have similar levels at 40 min; at 5 min, ONT-422>ONT-394>ONT-415 in % RNA remaining in DNA/RNA duplex).
Figure 16:
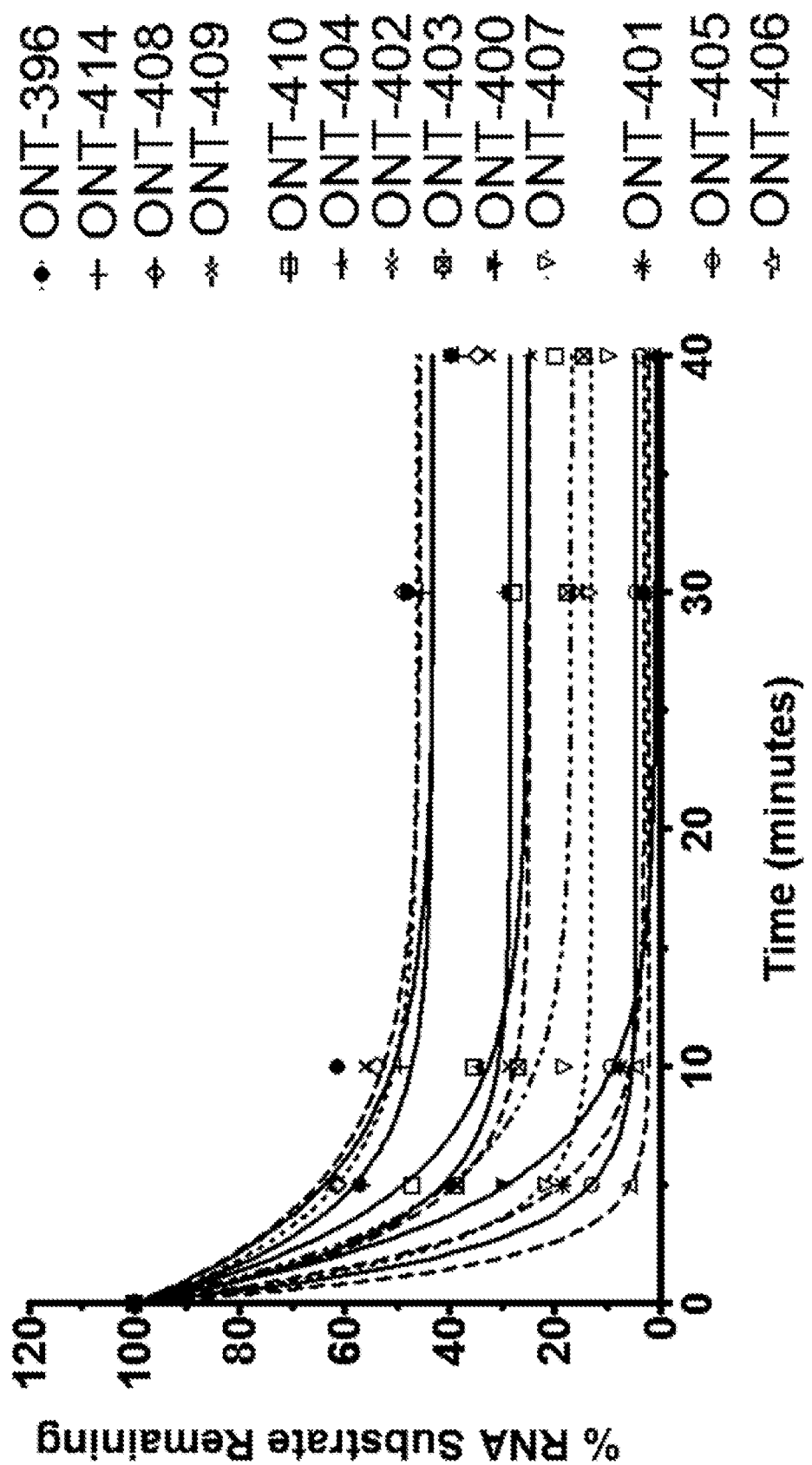
FIG. 16. Effect of stereochemistry on RNase H activity. Antisense oligonucleotides targeting an identical region of FOXO1 mRNA were hybridized with RNA and then incubated with RNase H at 37° C. in the presence of 1× RNase H buffer. Dependence of stereochemistry upon RNase H activity was observed. Form top to bottom at 40 min: ONT-396, ONT-409, ONT-414, ONT-408 (ONT-396/409/414/408 have similar levels at 40 min), ONT-404, ONT-410, ONT-402 (ONT-404/410/408 have similar levels at 40 min), ONT-403, ONT-407, ONT-405, ONT-401, ONT-406 and ONT-400 (ONT-401/405/406/400 have similar levels at 40 min).
Figure 17:
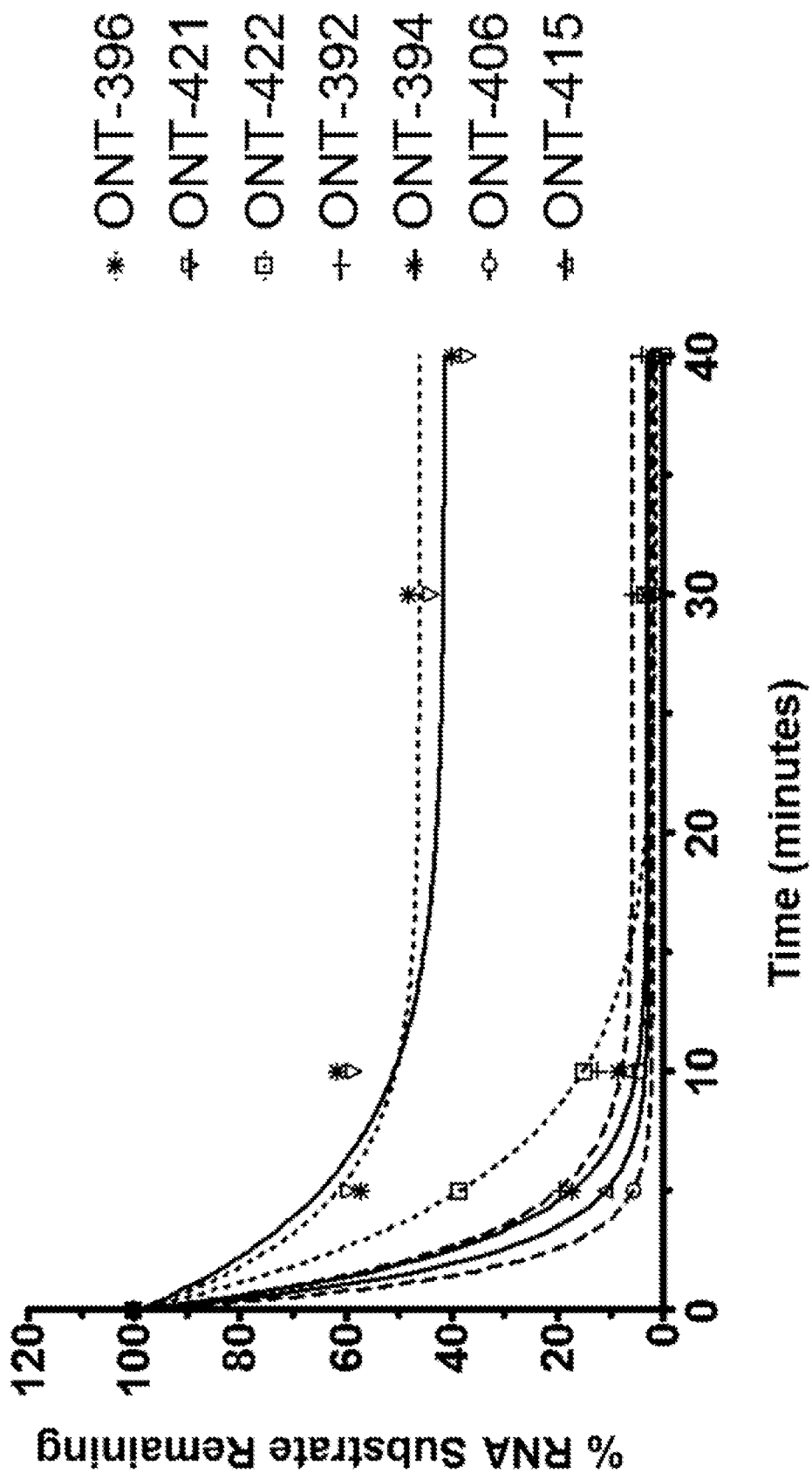
FIG. 17. Effect of stereochemistry on RNase H activity. Antisense oligonucleotides targeting an identical region of FOXO1 mRNA were hybridized with RNA and then incubated with RNase H at 37° C. in the presence of 1× RNase H buffer. Dependence of stereochemistry upon RNase H activity was observed. ONT-406 was observed to elicit cleavage of duplexed RNA at a rate in slight excess of that of the phosphodiester oligonucleotide ONT-415. From top to bottom at 40 min: ONT-396, ONT-421, ONT-392, ONT-394, ONT-415 ONT-406, and ONT-422 (ONT-394/415/406 have similar levels at 40 min; at 5 min, ONT-394>ONT-415>ONT-406 in % RNA remaining in DNA/RNA duplex).
Figure 20:
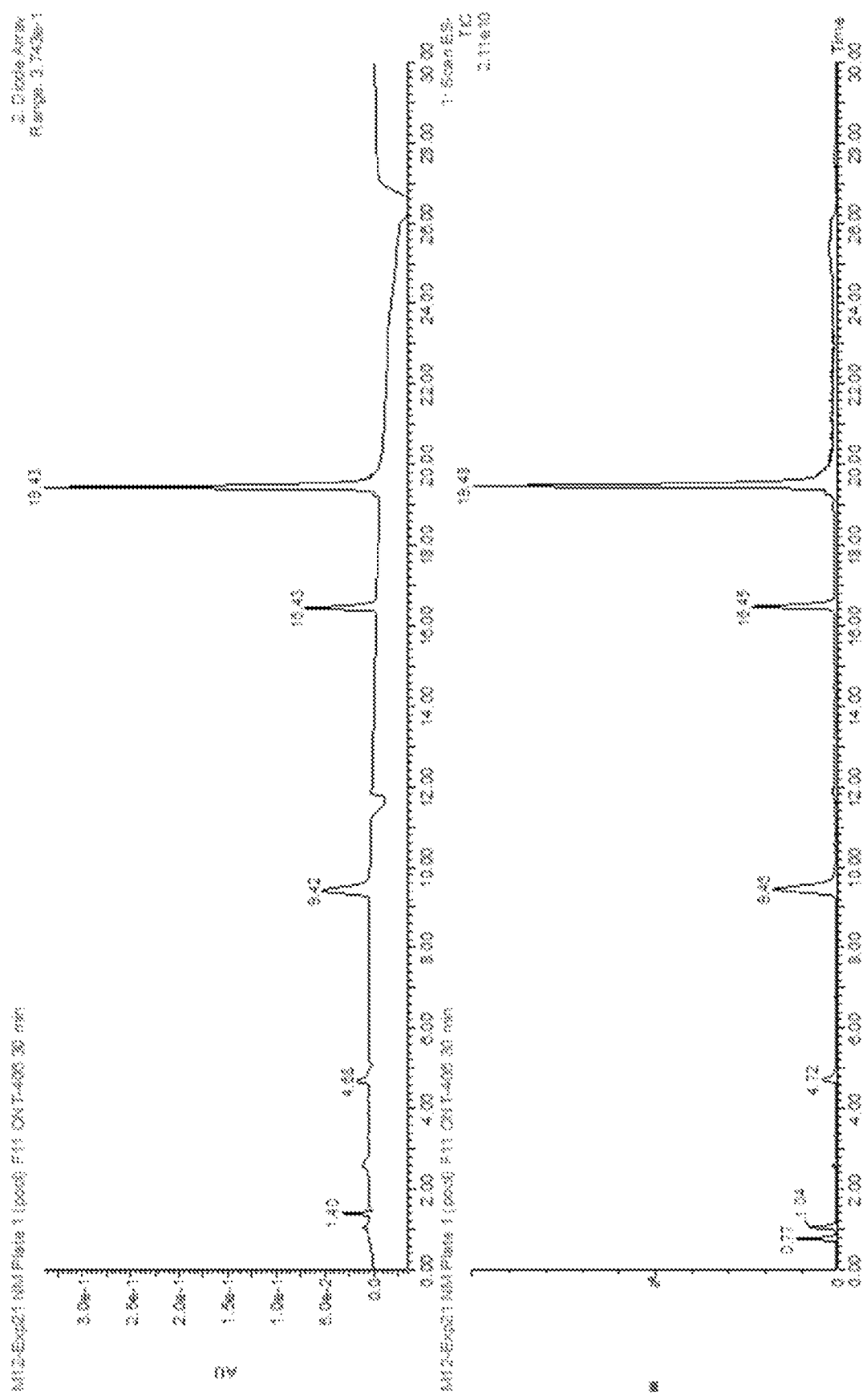
FIG. 20. UV Chromatogram and TIC of ONT-406 and ONT-388 duplex after 30 minutes of incubation with RNase H.

Additional chirally controlled oligonucleotide compositions were further tested. As described above, provided chirally controlled oligonucleotide compositions provides unexpected results, for example, in terms of cleavage rate and % RNA remaining in DNA/RNA duplex. See FIGS. 15-17. Example analytical data were presented in FIGS. 18-20. Without the intention to be limited by theory, Applicant notes that in some embodiments, cleavage may happen as depicted in FIG. 21. In FIG. 17, it is noted ONT-406 was observed to elicit cleavage of duplexed RNA at a rate in slight excess of that of the natural DNA oligonucleotide ONT-415 having the same base sequence and length. Applicant notes that chirally controlled oligonucleotide compositions of ONT-406, and other chirally controlled oligonucleotide compositions provided in this disclosure, have other preferred properties that an ONT-415 composition does not have, for example, better stability profiles in vitro and/or in vivo. Additional exemplary data were presented in FIG. 25. Also, as will be appreciated by those skilled in the art, exemplary data illustrated in FIG. 26 and FIG. 27 confirm that provided exemplary chirally controlled oligonucleotide compositions, especially when so designed to control the cleavage patterns through patterns of backbone chiral centers, produced much better results than reference oligonucleotide compositions, e.g., a stereorandom oligonucleotide composition. As exemplified in FIG. 26, controlled patterns of backbone chiral centers, among other things, can selectively increase and/or decrease cleavage at existing cleavage site when a DNA oligonucleotide is used, or creates entirely new cleavage sites that do not exist when a DNA oligonucleotide is used (see FIG. 25, ONT-415). In some embodiments, cleavage sites from a DNA oligonucleotide indicate endogenous cleavage preference of RNase H. As confirmed by FIG. 27, provided chirally controlled oligonucleotide compositions are capable of modulating target cleavage rate. In some embodiments, approximately 75% of the variance in cellular activity is accounted for by differences in cleavage rate which can be controlled through patterns of backbone chiral centers. As provided in this Application, further structural features such as base modifications and their patterns, sugar modification and their patterns, internucleotidic linkage modifications and their patterns, and/or any combinations thereof, can be combined with patterns of backbone chiral centers to provide desired oligonucleotide properties.

Example 9. Exemplary Allele-Specific Suppression of mHTT

In some embodiments, the present invention provides chirally controlled oligonucleotide compositions and methods thereof for allele-specific suppression of transcripts from one particular allele with selectivity over the others. In some embodiments, the present invention provides allele-specific suppression of mHTT.

Figure 22:
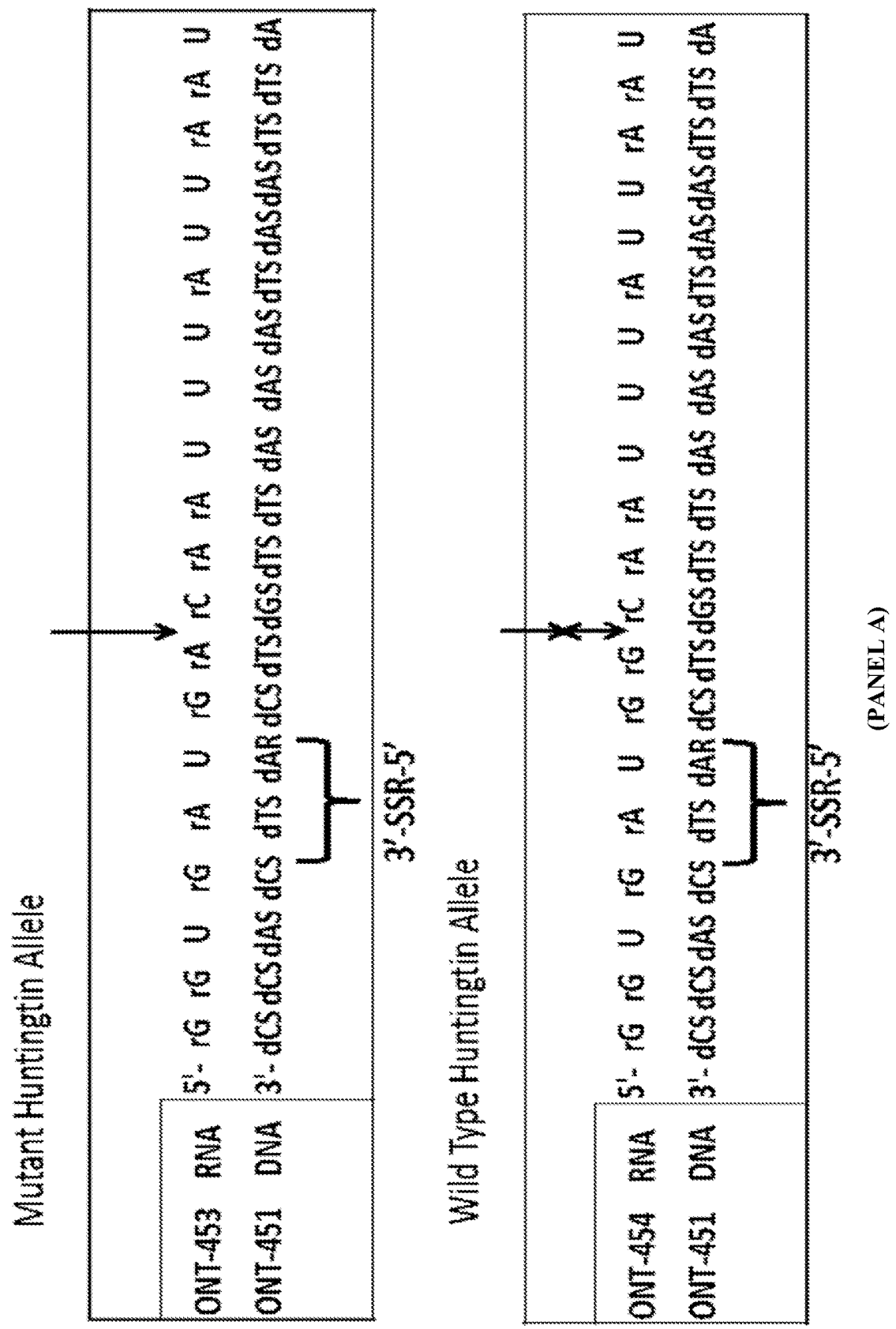
FIG. 22. Exemplary allele specific cleavage targeting mutant Huntingtin mRNA. (A) and (B): exemplary oligonucleotides. (C)-(E): cleavage maps. (F)-(H): RNA cleavage. Stereorandom and chirally controlled oligonucleotide compositions were prepared to target single nucleotide polymorphisms for allele selective suppression of mutant Huntingtin. ONT-450 (stereorandom) targeting ONT-453 (muHTT) and ONT-454 (wtHTT) showed marginal differentiation in RNA cleavage and their cleavage maps. Chirally controlled ONT-451 with selective placement of 3'-SSR-5' motif in RNase H recognition site targeting ONT-453 (muHTT) and ONT-454 (wtHTT) showed large differentiation in RNA cleavage rate. From the cleavage map, it is notable that 3'-SSR-5' motif is placed to direct the cleavage between positions 8 and 9 which is after the mismatch if read from 5'-end of RNA. ONT-452 with selective placement of 3'-SSR-5' motif in RNase H recognition site targeting ONT-453 (muHTT) and ONT-454 (wtHTT) showed moderate differentiation in RNA cleavage rate. 3'-SSR-5' motif was placed to direct the cleavage at positions 7 and 8 which is before the mismatch if read from 5'-end of RNA. Exemplary data illustrate significance of position in placement of 3'-SSR-5' motif to achieve enhanced discrimination for allele specific cleavage. All cleavage maps are derived from the reaction mixtures obtained after 5 minutes of incubation of respective duplexes with RNase H1C in the presence of 1×PBS buffer at 37° C. Arrows indicate sites of cleavage. (┬) indicates that both fragments, 5'-phosphate specie as well as 5'-OH 3'-OH specie were identified in reaction mixtures. (┌) indicates that only 5'-phosphate specie was detected and (┐) indicates that 5'-OH 3'-OH component was detected in mass spectrometry analysis. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate specie peak was used for quantification. ONT-450 (SEQ ID NO: 555), ONT-451 (SEQ ID NO: 593), ONT-452 (SEQ ID NO: 594), ONT-453 (SEQ ID NO: 563), ONT-454 (SEQ ID NO: 564).
Figure 22:
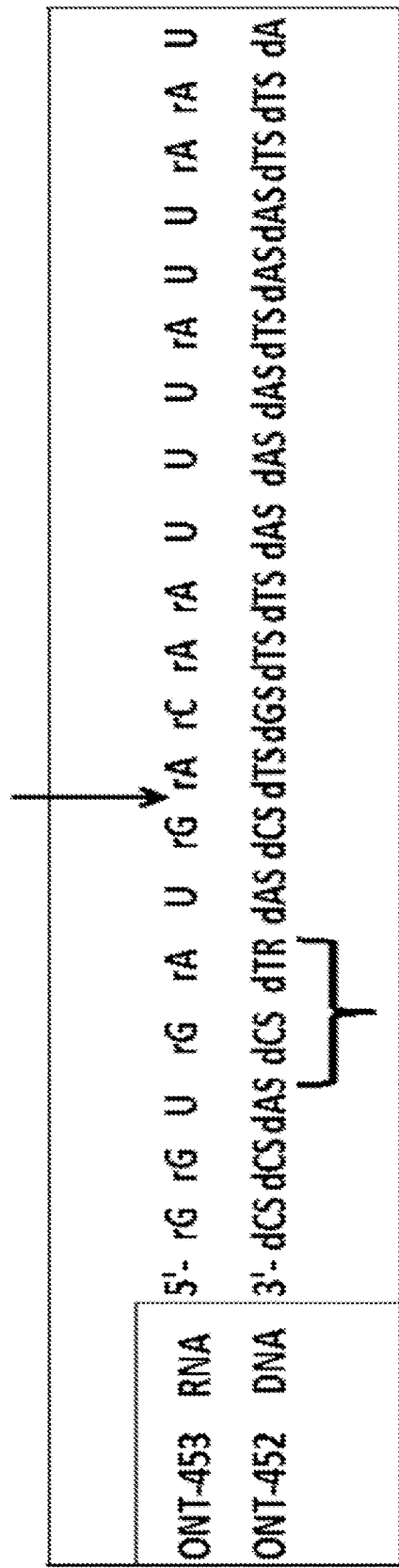
Figure 22:
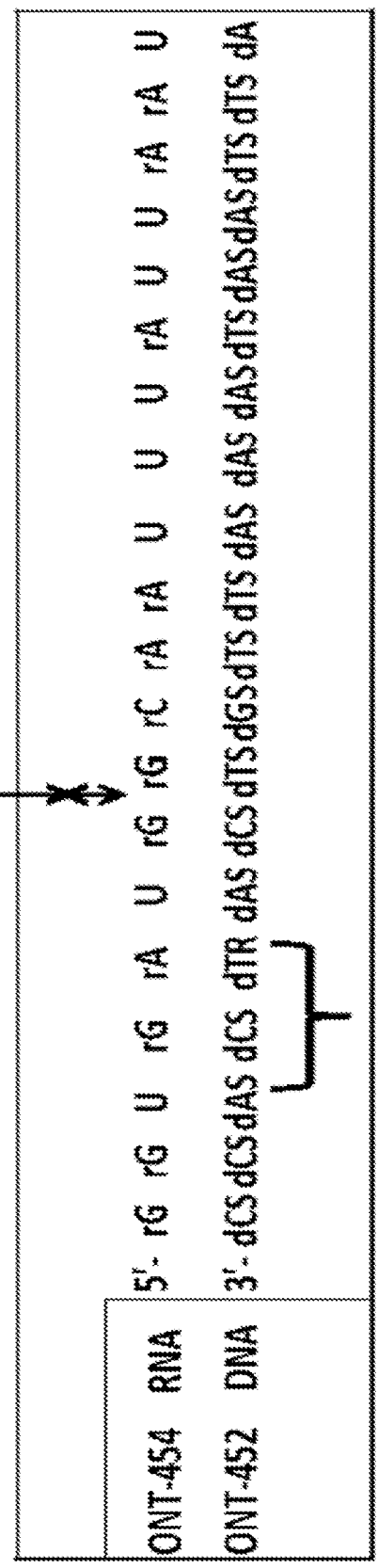
Figure 22:
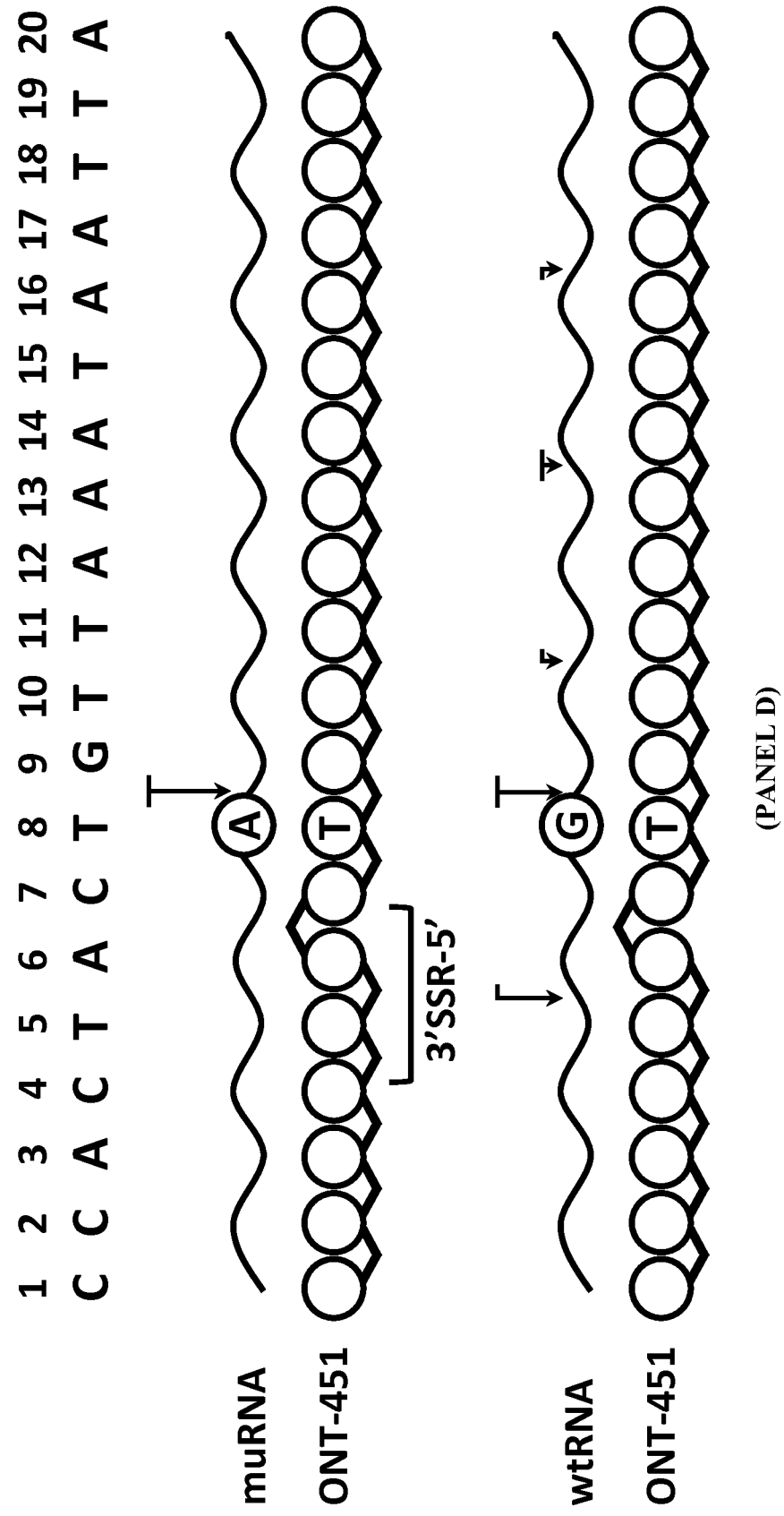
Figure 22:
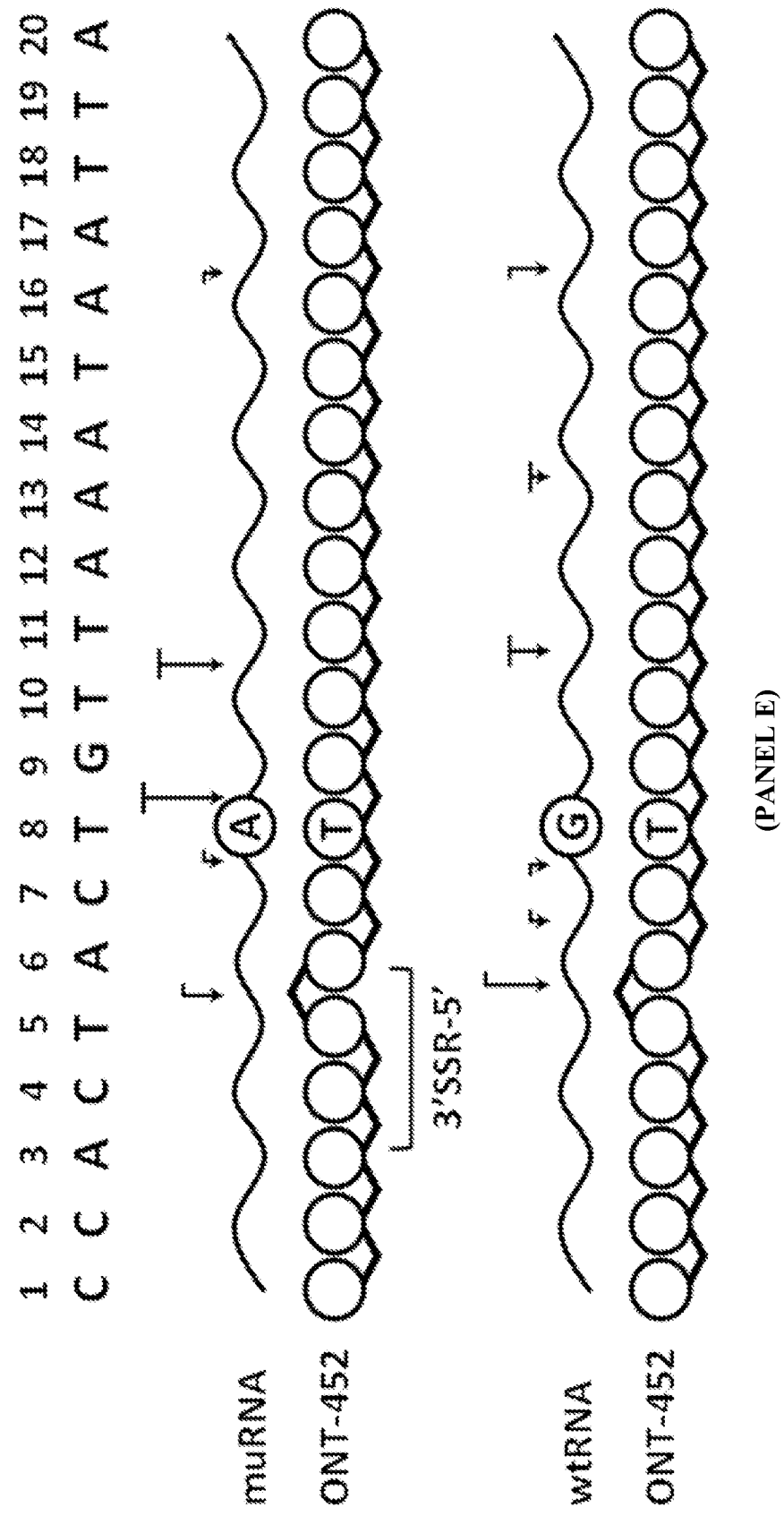
Figure 22:
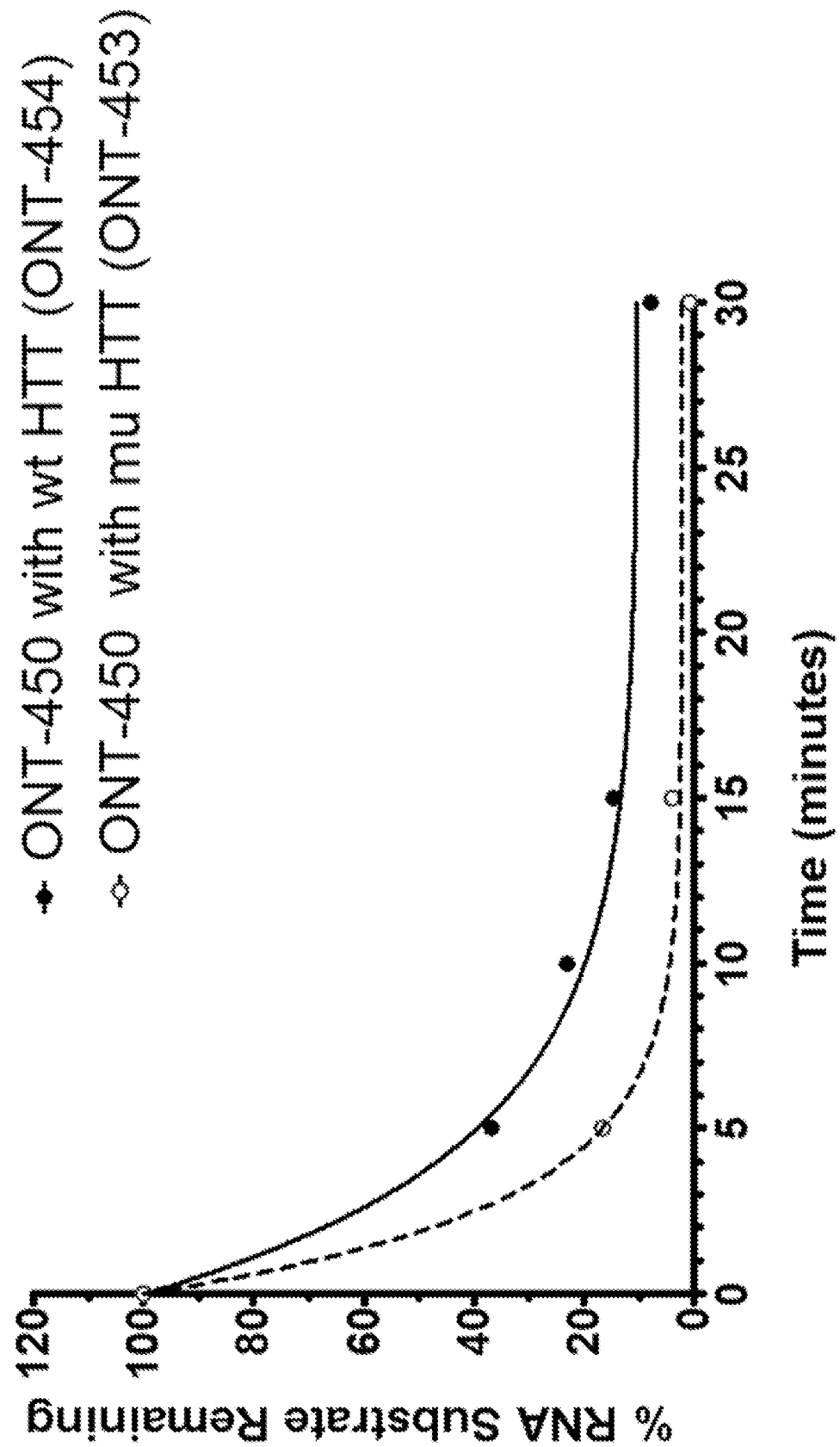
Figure 22:
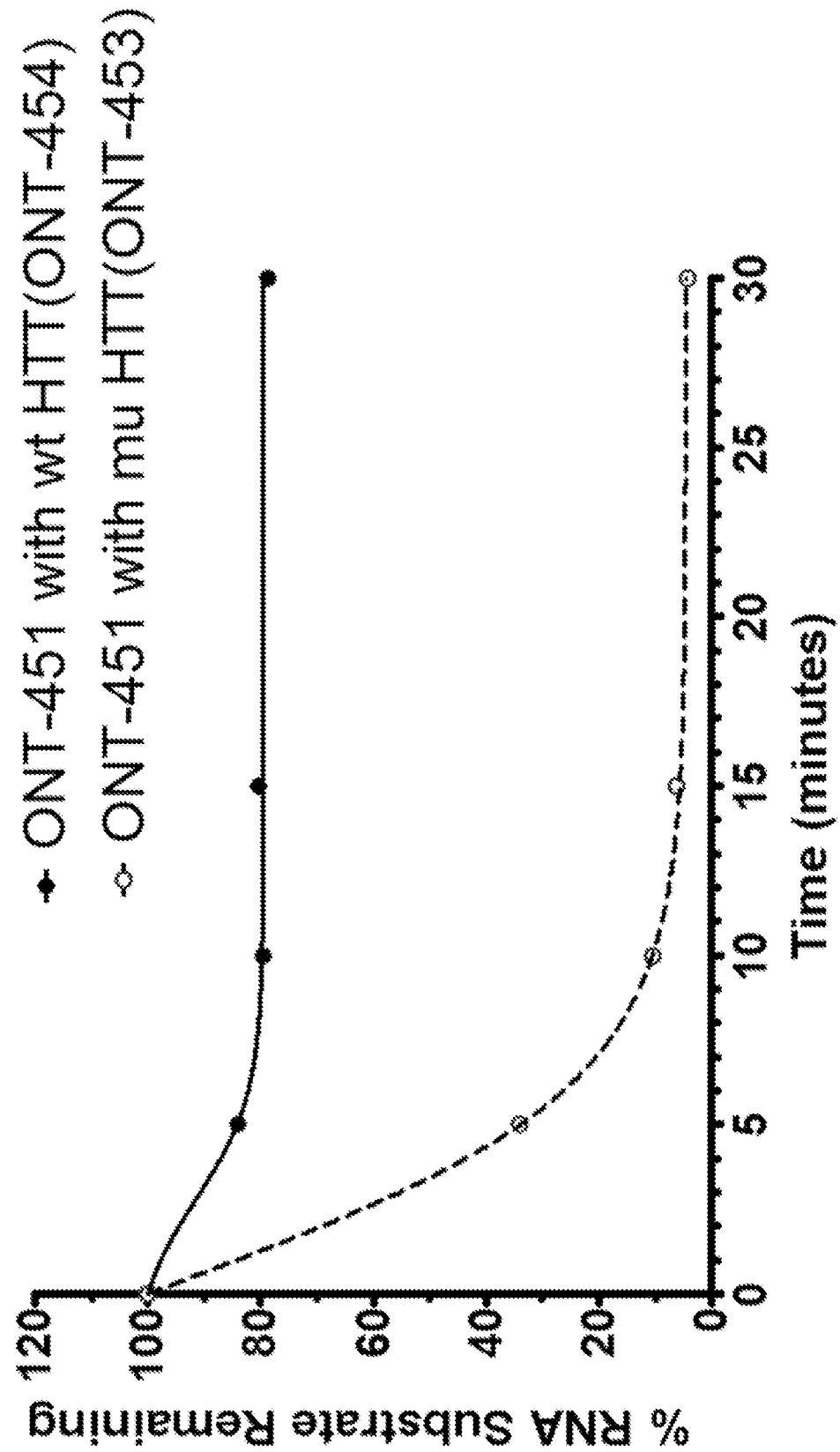
Figure 22:
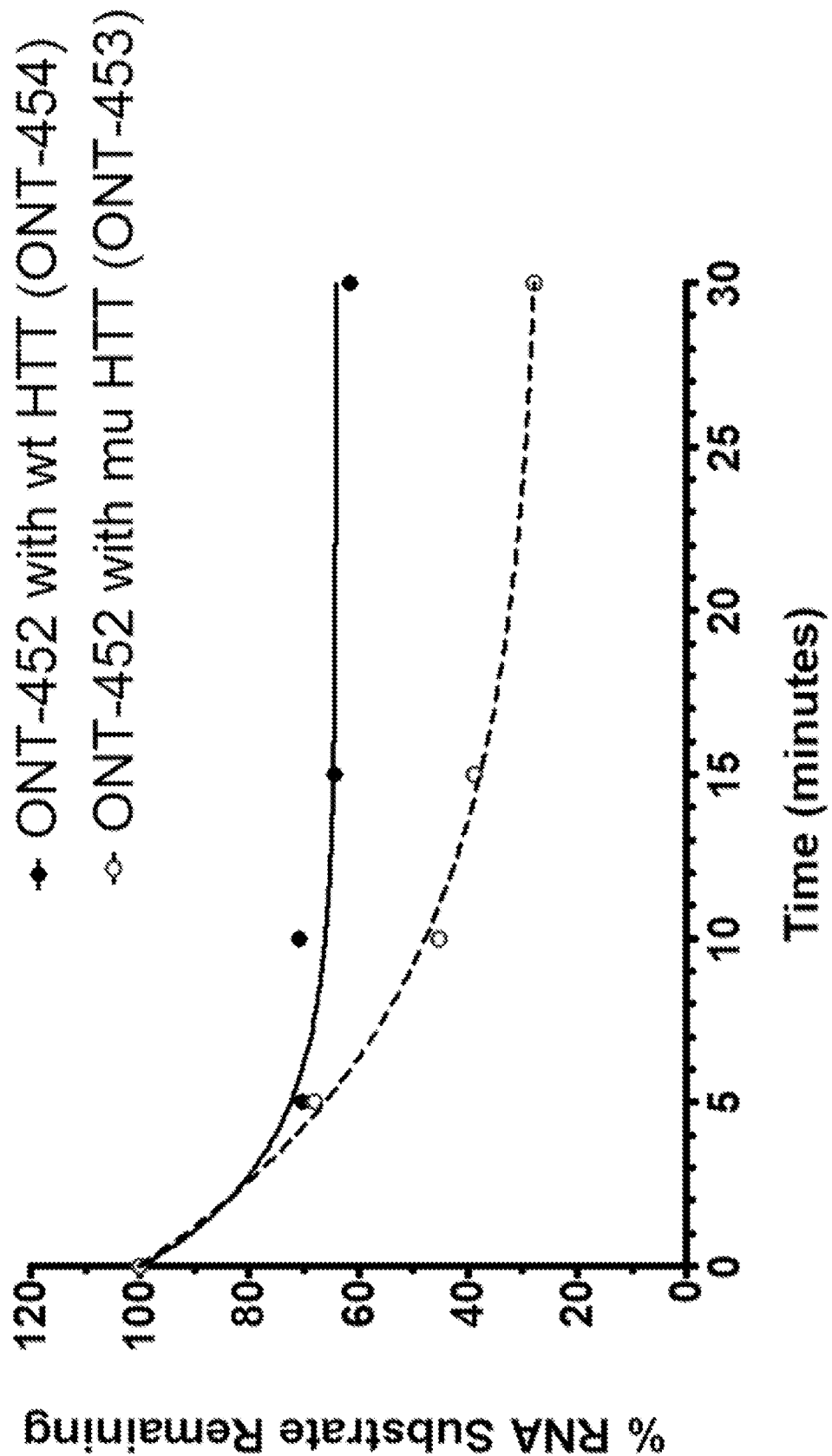

FIG. 22 illustrates exemplary chirally controlled oligonucleotide compositions that specifically suppress transcripts from one allele but not the others. Oligonucleotides 451 and 452 were tested with transcripts from both exemplified alleles using biochemical assays described above. Allele-specific suppression is also tested in cells and animal models using similar procedures as described in Hohjoh, *Pharmaceuticals* 2013, 6, 522-535; US patent application publication US 2013/0197061; and Østergaard et al., *Nucleic Acids Research*, 2013, 41(21), 9634-9650. In all cases, transcripts from the target allele are selectively suppressed over those from the other alleles. As will be appreciated by those skilled in the art, exemplary data illustrated in FIG. 22 confirm that provided exemplary chirally controlled oligonucleotide compositions, especially when so designed to control the cleavage patterns through stereochemistry, produced much better results than reference oligonucleotide compositions, in this case, a stereorandom oligonucleotide composition. As confirmed by FIG. 22, patterns of backbone chiral centers can dramatically change cleavage patterns (FIG. 22 C-E), and stereochemistry patterns can be employed to position cleavage site at the mismatch site (FIG. 22 C-E), and/or can dramatically improve selectivity between the mutant and wild type (FIG. 22 G-H). In some embodiments, chirally controlled oligonucleotide compositions are incubated with wtRNA and muRNA of a target and both the duplexes are incubated with RNase H.

Huntingtin Allele Tm

| | |
|---|---|
| Mutant Huntingtin Allele ONT-453/ONT-451 | 38.8° C. |
| Wild Type Huntingtin Allele ONT-454/ONT-451 | 37.3° C. |
| Mutant Huntingtin Allele ONT-453/ONT-452 | 38.8° C. |
| Wild Type Huntingtin Allele ONT-454/ONT-452 | 36.5° C. |
| Mutant Huntingtin Allele ONT-453/ONT-450 | 40.3° C. |
| Wild Type Huntingtin Allele ONT-454/ONT-450 | 38.8° C. |

Example 10. Exemplary Allele-Specific Suppression of FOXO1

In some embodiments, the present invention provides allele-specific suppression of FOXO1.

Figure 23:
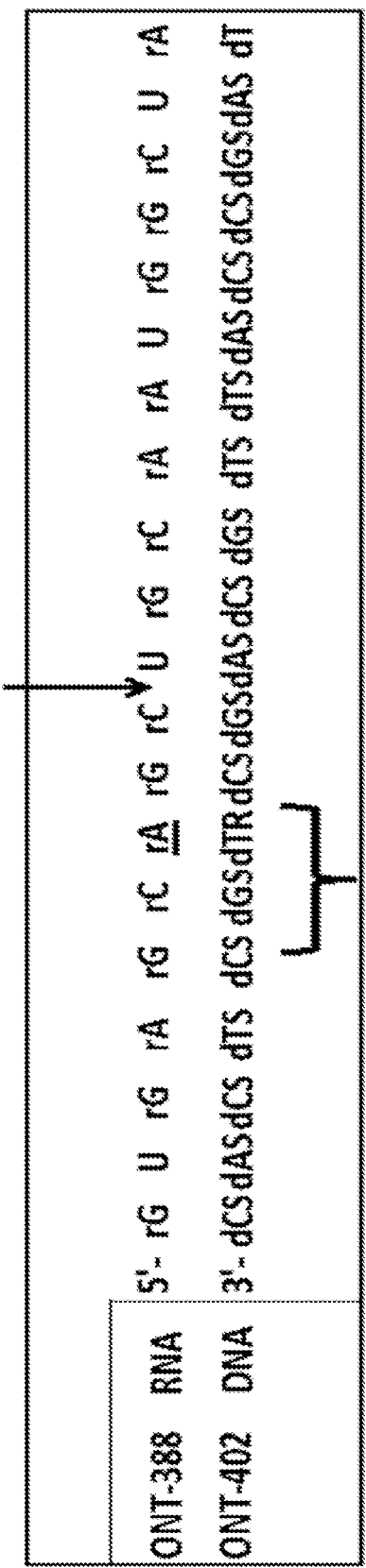
FIG. 23. (A)-(C): exemplary allele specific cleavage targeting FOXO1 mRNA. ONT-388 (SEQ ID NO: 559), ONT-442 (SEQ ID NO: 561), ONT-443 (SEQ ID NO: 562)
Figure 23:
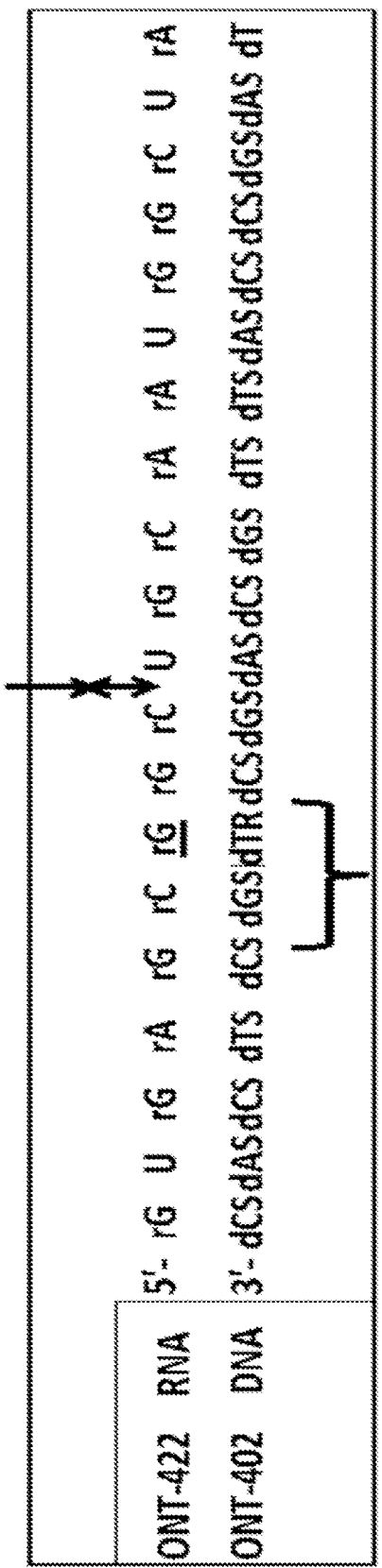

FIG. 23 illustrates exemplary chirally controlled oligonucleotide compositions that specifically suppress transcripts from one allele but not the others. Oligonucleotides ONT-400, ONT-402 and ONT-406 were tested with transcripts from both exemplified alleles using biochemical assays described above. Allele-specific suppression is also tested in cells and animal models using similar procedures as described in Hohjoh, *Pharmaceuticals* 2013, 6, 522-535; US patent application publication US 2013/0197061; Østergaard et al., *Nucleic Acids Research* 2013, 41(21), 9634-9650; and Jiang et al., *Science* 2013, 342, 111-114. Transcripts from the target allele are selectively suppressed over those from the other alleles. In some cases, two RNAs with mismatch ONT-442 (A/G, position 7th) and ONT-443 (A/G, position $13^{th}$) from ONT-388 are synthesized and are duplexed with ONT-396 to ONT-414. RNase H assay are performed to obtain cleavage rates and cleavage maps.

Example 11. Certain Exemplary Oligonucleotides and Oligonucleotide Compositions Stereorandom oligonucleotides with different 2' substitution chemistries targeting three distinct regions of FOXO1 mRNA with the thermal melting temperatures when duplexed with complementary RNA. The concentration of each strand was 1 uM in 1×PBS buffer.

| Oligo | Sequence | Description | Tm (° C.) | SEQ ID NO: |
|---|---|---|---|---|
| ONT-316 | TeosAeosGeos5mCeos5mCeosdAsdTsdTsdGs5mdCsdAsdGs5mdCsdTsdGs5mCeosTeos5mCeosAeos5mCeo | 5-10-5 (2'-MOE Gapmer) | 76.7 | 516 |
| ONT-355 | dTsdAsdGsdCsdCsdAsdTstsgscsasgscsdTsdGsdCsdTsdCsdAsdC | 7-6-7 (DNA-2'-OMe-DNA) Gapmer | 71.2 | 517 |
| ONT-361 | tsasgsdCsdCsdAsdTsdTsdGsdCsdAsdGsdCsdTsdGsdCsdTscsascs | 3-14-3 (2'-OMe-DNA-2'-OMe) Gapmer | 65.8 | 518 |
| ONT-367 | dTsdAsdGsdCsdCsdAsdTsdTsdGsdCsdAsdGsdCsdTsdGsdCsdTsdCsdAsdC | All DNA | 62.9 | 519 |
| ONT-373 | tsasgscscsdAsdTsdTsdGsdCsdAsdGsdCsdTsdGscstscsasc | 5-10-5 (2'-OMe Gapmer) | 71.8 | 520 |
| ONT-388 | rGrUrGrArGrCrArGrCrUrGrCrArArUrGrGrCrUrA | Complementary RNA | | 521 |
| ONT-302 | Teos5mCeos5mCeosAeosGeosdTsdTs5mdCs5mdCsdTsdTs5mdCsdAsdTsdTs5mCeosTeosGeos5mCeosAeo | 5-10-5 (2'-MOE Gapmer) | 72.5 | 522 |
| ONT-352 | dTsdCsdCsdAsdGsdTsdTscscststscsasdTsdTsdCsdTsdGsdCsdA | 7-6-7 (DNA-2'-OMe-DNA) Gapmer | 65.4 | 523 |
| ONT-358 | tscscsdAsdGsdTsdTsdCsdCsdTsdTsdCsdAsdTsdTsdCsdTsgscsas | 3-14-3 (2'-OMe-DNA-2'-OMe) Gapmer | 62.6 | 524 |
| ONT-364 | dTsdCsdCsdAsdGsdTsdTsdCsdCsdTsdTsdCsdAsdTsdTsdCsdTsdGsdCsdA | All DNA | 58.4 | 525 |
| ONT-370 | tscscsasgsdTsdTsdCsdCsdTsdTsdCsdAsdTsdTscstsgscsa | 5-10-5 (2'-OMe Gapmer) | 68 | 526 |
| ONT-386 | rUrGrCrArGrArArUrGrArArGrGrArArCrUrGrGrA | Complementary RNA | | 527 |
| ONT-315 | TeosGeosAeosGeosAeosdTsdGs5mdCs5mdCsdTsdGsdGs5mdCsdTsdGs5mCeos5mCeosAeosTeosAeo | 5-10-5 (2'-MOE Gapmer) | 77.5 | 528 |
| ONT-354 | dTsdGsdAsdGsdAsdTsdGscscstsgsgscsdTsdGsdCsdCsdAsdTsdA | 7-6-7 (DNA-2'-OMe-DNA) Gapmer | 75.5 | 529 |
| ONT-360 | tsgsasdGsdAsdTsdGsdCsdCsdTsdGsdGsdCsdTsdGsdCsdCsastsas | 3-14-3 (2'-OMe-DNA-2'-OMe) Gapmer | 69 | 530 |
| ONT-366 | dTsdGsdAsdGsdAsdTsdGsdCsdCsdTsdGsdGsdCsdTsdGsdCsdCsdAsdTsdA | All DNA | 66.5 | 531 |
| ONT-372 | tsgsasgsasdTsdGsdCsdCsdTsdGsdGsdCsdTsdGscscsastsa | 5-10-5 (2'-OMe Gapmer) | 74.4 | 532 |
| ONT-387 | rUrArUrGrCrArGrCrCrArGrGrCrArGrCrArUrCrUrCrA | Complementary RNA | | 533 |

Additional exemplary stereorandom oligonucleotide compositions are listed below.

| Oligo | Sequence (5' to 3') | SEQ ID NO: |
|---|---|---|
| ONT-41 | (Gs5mCs5mCsTs5mCs)$_{MOE}$d[AsGsTs5mCsTsGs5mCsTsTs5mCs](Gs5mCsAs5mCs5mC)$_{MOE}$ | 534 |
| ONT-70 | (Gs5mCs)$_{MOE}$d[GsTsTsTsGs5mCsTs5mCsTsTs5mCsTs](5mCsTsTsGs5mCGs)$_{MOE}$d[TsTsTsTs](TsT)$_{MOE}$ | 535 |
| ONT-83 | (GsTs5mCs5mCs5mCs)$_{MOE}$d(TsGsAsAsGsAsTsGsTs5mCs](AsAsTsGs5mC)$_{MOE}$ | 536 |

-continued

| Oligo | Sequence (5' to 3') | SEQ ID NO: |
|---|---|---|
| ONT-302 | (Ts5mCs5mCsAsGs)$_{MOE}$d[TsTs5mCs5mCsTsTs5mCsAsTsTs](5mCsTsGs5mCsA)$_{MOE}$ | 537 |
| ONT-315 | (TsGsAsGsAs)$_{MOE}$d[TsGs5mCs5mCsTsGsGs5mCsTsGs](5mCs5mCsAsTsA)$_{MOE}$ | 538 |
| ONT-316 | (TsAsGs5mCs5mCs)$_{MOE}$d[AsTsTsGs5mCsAsGs5mCsTsGs5m](CsTs5mCsAs5mC)$_{MOE}$ | 539 |
| ONT-352 | [TsCsCsAsGsTsTs](cscstststscsas)$_{OMe}$d[TsTsCsTsGsCsA] | 540 |
| ONT-354 | [TsGsAsGsAsTsGs](CsCsTsGsGsCs)$_{OMe}$d[TsGsCsCsAsTsA] | 541 |
| ONT-355 | [TsAsGsCsCsAsTs](TsGsCsAsGsCs)$_{OMe}$d[TsGsCsTsCsAsC] | 542 |
| ONT-358 | (TsCsCs)$_{OMe}$d[AsGsTsTsCsCsTsTsCsAsTsTsCsTs](GsCsA)$_{OMe}$ | 543 |
| ONT-360 | (TsGsAs)$_{OMe}$d[GsAsTsGsCsCsTsGsGsCsTsGsCsCs](AsTsA)$_{OMe}$ | 544 |
| ONT-361 | (TsAsGs)$_{OMe}$d[CsCsAsTsGsCsAsGsCsTsGsCsTs](CsAsC)$_{OMe}$ | 545 |
| ONT-364 | [TsCsCsAsGsTsTsCsCsTsTsCsAsTsTsCsTsGsCsA] | 546 |
| ONT-366 | [TsGsAsGsAsTsGsCsCsTsGsGsCsTsGsCsCsAsTsA] | 547 |
| ONT-367 | [TsAsGsCsCsAsTsTsGsCsAsGsCsTsGsCsTsCsAsC] | 548 |
| ONT-370 | (TsCsCsAsGs)$_{OMe}$d[TsTsCsCsTsTsCsAsTsTs](CsTsGsCsA)$_{OMe}$ | 549 |
| ONT-372 | (TsGsAsGsAs)$_{OMe}$d[TsGsCsCsTsGsGsCsTsGs](CsCsAsTsA)$_{OMe}$ | 550 |
| ONT-373 | (TsAsGsCsCs)$_{OMe}$d[AsTsTsGsCsAsGsCsTsGs](CsTsCsAsC)$_{OMe}$ | 551 |
| ONT-440 | (UsAsGsCsCs)$_F$d[AsTsTsGsCsAsGsCsTsGsCsTsCsAsC] | 552 |
| ONT-441 | (UsAsGsCsCs)$_F$d[AsTsTsGsCsAsGsCsTsGsC] | 553 |
| ONT-460 | (TsAsGsCsCs)$_{OMe}$d[AsTsTsGsCsAsGsCsTsGsCsTsCsAsC] | 554 |
| ONT-450 | [AsTsTsAsAsTsAsAsAsTsTsGsTsCsAsTsCsAsCsC] | 555 |

Exemplary RNA and DNA oligonucleotides are listed below.

| Oligo | Sequence (5' to 3') | SEQ ID NO: |
|---|---|---|
| ONT-28 | rGrGrUrGrCrGrArArGrCrArGrArCrUrGrArGrGrC | 556 |
| ONT-386 | rUrGrCrArGrArArUrGrArArGrGrArArCrUrGrGrA | 557 |
| ONT-387 | rUrArUrGrGrCrArGrCrCrArGrGrCrArUrCrUrCrA | 558 |
| ONT-388 | rGrUrGrArGrCrArGrCrUrGrCrArArUrGrGrCrUrA | 559 |
| ONT-415 | d[TAGCCATTGCAGCTGCTCAC] | 560 |
| ONT-442 | rUrGrArGrCrGrGrCrUrGrCrArArUrGrGrCrUrA | 561 |
| ONT-443 | rGrUrGrArGrCrArGrCrUrGrCrGrArUrGrGrCrUrA | 562 |
| ONT-453 | rGrGrUrGrArUrGrArCrArArUrUrUrArUrUrArArU | 563 |
| ONT-454 | rGrGrUrGrArUrGrrCrArArUrUrUrArUrUrArArU | 564 |

Exemplary chirally pure oligonucleotides are presented below. In some embodiments, the present invention provides corresponding chirally controlled oligonucleotide compositions of each of the following exemplary oligonucleotides.

| Oligo | Stereochemistry/Sequence (5' to 3') | Description | SEQ ID NO: |
|---|---|---|---|
| ONT-389 | (Sp, Sp, Sp, Sp, Sp, Sp, Sp, Rp, Sp, Sp, Rp, Sp, Sp, Rp, Sp, Sp, Sp, Sp, Sp)-d[TsGsAsGsAsTsGsCsCsTsGsGsCsTsGsCsCsAsTsA] | 7S-(RSS)₃-3S | 565 |
| ONT-390 | (Sp, Sp, Sp, Sp, Sp, Sp, Rp, Sp, Sp, Rp, Sp, Sp, Rp, Sp, Sp, Sp, Sp, Sp, Sp)-d[TsGsAsGsAsTsGsCsCsTsGsGsCsTsGsCsCsAsTsA] | 6S-(RSS)₃-4S | 566 |
| ONT-391 | (Sp, Sp, Sp, Sp, Sp, Rp, Sp, Sp, Rp, Sp, Sp, Rp, Sp, Sp, Sp, Sp, Sp, Sp, Sp)-d[TsGsAsGsAsTsGsCsCsTsGsGsCsTsGsCsCsAsTsA] | 5S-(RSS)₃-5S | 567 |
| ONT-392 | (Sp, Sp, Sp, Sp, Sp, Sp, Sp, Rp, Sp, Sp, Rp, Sp, Sp, Rp, Sp, Sp, Sp, Sp, Sp)-d[TsAsCsCsAsTsTsGsCsAsGsCsTsGsCsTsCsAsC] | 7S-(RSS)₃-3S | 568 |
| ONT-393 | (Sp, Sp, Sp, Sp, Sp, Sp, Rp, Sp, Sp, Rp, Sp, Sp, Rp, Sp, Sp, Sp, Sp, Sp, Sp)-d[TsAsCsCsAsTsTsGsCsAsGsCsTsGsCsTsCsAsC] | 6S-(RSS)₃-4S | 569 |
| ONT-394 | (Sp, Sp, Sp, Sp, Sp, Rp, Sp, Sp, Rp, Sp, Sp, Rp, Sp, Sp, Sp, Sp, Sp, Sp, Sp)-d[TsAsCsCsAsTsTsGsCsAsGsCsTsGsCsTsCsAsC] | 5S-(RSS)₃-5S | 570 |
| ONT-396 | (Sp, Sp, Sp, Sp, Sp, Sp, Sp, Sp, Sp, Sp, Sp, Sp, Sp, Sp, Sp, Sp, Sp, Sp, Rp)-d[TsAsCsCsAsTsTsGsCsAsGsCsTsGsCsTsCsAsC] | 18S-1R | 571 |
| ONT-397 | (Sp, Sp, Sp, Sp, Sp, Sp, Sp, Sp, Sp, Sp, Sp, Sp, Sp, Sp, Sp, Sp, Sp, Rp, Sp)-d[TsAsCsCsAsTsTsGsCsAsGsCsTsGsCsTsCsAsC] | 17S-RS | 572 |
| ONT-398 | (Sp, Sp, Sp, Sp, Sp, Sp, Sp, Sp, Sp, Sp, Sp, Sp, Sp, Sp, Sp, Sp, Rp, Sp, Sp)-d[TsAsCsCsAsTsTsGsCsAsGsCsTsGsCsTsCsAsC] | 16S-(RSS) | 573 |
| ONT-399 | (Sp, Sp, Sp, Sp, Sp, Sp, Sp, Sp, Sp, Sp, Sp, Sp, Sp, Sp, Sp, Rp, Sp, Sp, Sp)-d[TsAsCsCsAsTsTsGsCsAsGsCsTsGsCsTsCsAsC] | 15S-(RSS)-1S | 574 |
| ONT-400 | (Sp, Sp, Sp, Sp, Sp, Sp, Sp, Sp, Sp, Sp, Sp, Sp, Sp, Sp, Rp, Sp, Sp, Sp, Sp)-d[TsAsCsCsAsTsTsGsCsAsGsCsTsGsCsTsCsAsC] | 14S-(RSS)-2S | 575 |
| ONT-401 | (Sp, Sp, Sp, Sp, Sp, Sp, Sp, Sp, Sp, Sp, Sp, Sp, Sp, Sp, Rp, Sp, Sp, Sp, Sp, Sp)-d[TsAsCsCsAsTsTsGsCsAsGsCsTsGsCsTsCsAsC] | 13S-(RSS)-3S | 576 |
| ONT-402 | (Sp, Sp, Sp, Sp, Sp, Sp, Sp, Sp, Sp, Sp, Sp, Sp, Rp, Sp, Sp, Sp, Sp, Sp, Sp)-d[TsAsCsCsAsTsTsGsCsAsGsCsTsGsCsTsCsAsC] | 12S-(RSS)-4S | 577 |
| ONT-403 | (Sp, Sp, Sp, Sp, Sp, Sp, Sp, Sp, Sp, Sp, Sp, Rp, Sp, Sp, Sp, Sp, Sp, Sp, Sp)-d[TsAsCsCsAsTsTsGsCsAsGsCsTsGsCsTsCsAsC] | 11S-(RSS)-5S | 578 |
| ONT-404 | (Sp, Sp, Sp, Sp, Sp, Sp, Sp, Sp, Sp, Sp, Rp, Sp, Sp, Sp, Sp, Sp, Sp, Sp, Sp)-d[TsAsCsCsAsTsTsGsCsAsGsCsTsGsCsTsCsAsC] | 10S-(RSS)-6S | 579 |
| ONT-405 | (Sp, Sp, Sp, Sp, Sp, Sp, Sp, Sp, Sp, Rp, Sp, Sp, Sp, Sp, Sp, Sp, Sp, Sp, Sp)-d[TsAsCsCsAsTsTsGsCsAsGsCsTsGsCsTsCsAsC] | 9S-(RSS)-7S | 580 |
| ONT-406 | (Sp, Sp, Sp, Sp, Sp, Sp, Sp, Sp, Rp, Sp, Sp, Sp, Sp, Sp, Sp, Sp, Sp, Sp, Sp)-d[TsAsCsCsAsTsTsGsCsAsGsCsTsGsCsTsCsAsC] | 8S-(RSS)-8S | 581 |
| ONT-407 | (Sp, Sp, Sp, Sp, Sp, Sp, Sp, Rp, Sp, Sp, Sp, Sp, Sp, Sp, Sp, Sp, Sp, Sp, Sp)-d[TsAsCsCsAsTsTsGsCsAsGsCsTsGsCsTsCsAsC] | 7S-(RSS)-9S | 582 |
| ONT-408 | (Sp, Sp, Sp, Sp, Sp, Sp, Rp, Sp, Sp, Sp, Sp, Sp, Sp, Sp, Sp, Sp, Sp, Sp, Sp)-d[TsAsCsCsAsTsTsGsCsAsGsCsTsGsCsTsCsAsC] | 6S-(RSS)-10S | 583 |

-continued

| Oligo | Stereochemistry/Sequence (5' to 3') | Description | SEQ ID NO: |
|---|---|---|---|
| ONT-409 | (Sp, Sp, Sp, Sp, Sp, Rp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 5S-(RSS)-11S | 584 |
| ONT-410 | (Sp, Sp, Sp, Sp, Rp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 4S-(RSS)-12S | 585 |
| ONT-411 | (Sp, Sp, Sp, Rp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 3S-(RSS)-13S | 586 |
| ONT-412 | (Sp, Sp, Rp, Sp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 2S-(RSS)-14S | 587 |
| ONT-413 | (Sp, Rp, Sp, Sp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | S-(RSS)-15S | 588 |
| ONT-414 | (Rp, Sp, Sp, Sp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | (RSS)-16S | 589 |
| ONT-421 | All-(Sp)-d[TsAsGsCsCsAsTsTsGsCsAsGsCsTsGsCsTsCsAsC] | All S | 590 |
| ONT-422 | (Sp, Sp, Sp, Sp, Sp, Sp, Sp, Sp, Rp, Sp, Sp, Sp, Sp, Sp, Rp, Sp, Sp, Sp, Sp)-C6-amino-d[TsAsGsCsCsAsTsTsGsCsAsGsCsTsGsCsTsCsAsC] | 8S-(RSS)-3S-(RSS)-2S | 591 |
| ONT-455 | All-(Rp)-d[TsAsGsCsCsAsTsTsGsCsAsGsCsTsGsCsTsCsAsC] | All R | 592 |
| ONT-451 | (Sp, Sp, Sp, Sp, Sp, Sp, Sp, Sp, Sp, Sp, Sp, Sp, Rp, Sp, Sp, Sp, Sp, Sp, Sp)-d[AsTsTsAsAsTsAsAsAsAsTsGsTsCsAsTsCsAsCsC] | 13S-(RSS)-3S | 593 |
| ONT-452 | (Sp, Sp, Sp, Sp, Sp, Sp, Sp, Sp, Sp, Sp, Sp, Sp, Sp, Sp, Rp, Sp, Sp, Sp, Sp)-d[AsTsTsAsAsTsAsAsAsAsTsGsTsCsAsTsCsAsCsC] | 14S-(RSS)-2S | 594 |
| ONT-75 | All-(Rp)-(Gs5mCs5mCsTs5mCs)$_{MOE}$d[AsGsTs5mCsTsGs5mCsTsTs5mCs](Gs5mCsAs5mCs5mC)$_{MOE}$ | All R | 595 |
| ONT-76 | (Sp, Rp, Rp, Sp, Rp, Sp, Sp, Sp, Sp, Sp, Sp, Sp, Sp, Sp, Sp, Sp, Rp, Sp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | SRRSR-11S-RSR | 596 |
| ONT-77 | (Rp, Rp, Rp, Rp, Rp, Sp, Sp, Sp, Sp, Sp, Sp, Sp, Sp, Sp, Sp, Rp, Rp, Rp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 5R-10S-4R | 597 |
| ONT-80 | All-(Sp)-(Gs5mCs5mCsTs5mCs)$_{MOE}$d[AsGsTs5mCsTsGs5mCsTsTs5mCs](Gs5mCsAs5mCs5mC)$_{MOE}$ | All S | 598 |
| ONT-81 | (Sp, Sp, Sp, Sp, Sp, Rp, Rp, Rp, Rp, Rp, Rp, Rp, Rp, Rp, Rp, Sp, Sp, Sp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 5S-10R-4S | 599 |
| ONT-82 | All-(Rp)-(GsTs5mCs5mCs5mCs)$_{MOE}$d[TsGsAsAsGsAsTsGsTs5mCs](AsAsTsGs5mC)$_{MOE}$ | All R | 600 |
| ONT-84 | All-(Sp)-(GsTs5mCs5mCs5mCs)$_{MOE}$d[TsGsAsAsGsAsTsGsTs5mCs[(AsAsTsGs5mC)$_{MOE}$ | All S | 601 |
| ONT-85 | (Rp, Rp, Rp, Rp, Rp, Sp, Sp, Sp, Sp, Sp, Sp, Sp, Sp, Sp, Sp, Rp, Rp, Rp, Rp)-(GsTs5mCs5mCs5mCs)$_{MOE}$d[TsGsAsAsGsAsTsGsTs5mCs](AsAsTsGs5mC)$_{MOE}$ | 5R-10S-4R | 602 |

| Oligo | Stereochemistry/Sequence (5' to 3') | Description | SEQ ID NO: |
|---|---|---|---|
| ONT-86 | (Sp, Sp, Sp, Sp, Sp, Rp, Rp, Rp, Rp, Rp, Rp, Rp, Rp, Rp, Rp, Sp, Sp, Sp, Sp)-(GsTs5mCs5mCs5mCs)$_{MOE}$d[TsGsAsAsGsAsTsGsTs5mCs](AsAsTsGs5mC)$_{MOE}$ | 5S-10R-4S | 603 |
| ONT-87 | (Rp, Rp, Rp, Rp, Rp, Sp, Sp, Rp, Sp, Sp, Rp, Sp, Sp, Rp, Rp, Rp, Rp, Rp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 5R-2S-(RSS)$_2$-6R | 604 |
| ONT-88 | (Sp, Sp, Sp, Sp, Sp, Rp, Rp, Sp, Rp, Rp, Sp, Rp, Rp, Sp, Sp, Sp, Sp, Sp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 5S-(RRS)$_3$-5S | 605 |
| ONT-89 | (Sp, Rp, Sp, Rp, Sp, Rp, Sp, Rp, Sp, Rp, Sp, Rp, Sp, Rp, Sp, Rp, Sp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | (SR)$_9$S | 606 |
| ONT-154 | (Sp, Sp, Sp, Sp, Sp, Sp, Sp, Rp, Sp, Sp, Rp, Sp, Sp, Rp, Sp, Sp, Sp, Sp, Sp)-d[Gs5mCs5mCsTs5mCsAsGsTs5mCsTsGs5mCsTsTs5mCsGs5mCsAs5mCs5mC | 7S-(RSS)$_3$-3S | 607 |
| ONT-75 | All-(Rp)-(Gs5mCs5mCsTs5mCs)$_{MOE}$d[AsGsTs5mCsTsGs5mCsTsTs5mCs](Gs5mCsAs5mCs5mC)$_{MOE}$ | All-R | 608 |
| ONT-80 | All-(Sp)-(Gs5mCs5mCsTs5mCs)$_{MOE}$d[AsGsTs5mCsTsGs5mCsTsTs5mCs](Gs5mCsAs5mCs5mC)$_{MOE}$ | All-S | 609 |

Additional exemplary oligonucleotides targeting FOXO1 with Tm are presented below. In some embodiments, the present invention provides corresponding chirally controlled oligonucleotide compositions of each of the following exemplary oligonucleotides.

| Oligo | Sequence | Tm (° C.) | SEQ ID NO: |
|---|---|---|---|
| ONT-439 | [UsAsGs]$_F$d[CsCsAsTsTsGsCsAsGsCsTsGsCsTs][CsAsC]F | 68.3 | 610 |
| ONT-440 | [UsAsGsCsCs]$_F$d[AsTsTsGsCsAsGsCsTsGsCsTsCsAsC] | 70.0 | 611 |
| ONT-441 | [UsAsGsCsCs]$_F$d[AsTsTsGsCsAsGsCsTsGsC] | 65.5 | 612 |
| ONT-455 | All-(Rp)-d[TsAsGsCsCsAsTsTsGsCsAsGsCsTsGsCsTsCsAsC] | 66.8 | 613 |
| ONT-316 | [TsAsGs5mCs5mCs]$_{MOE}$d[AsTsTsGs5mCsAsGs5mCsTsGs][5mCsTs5mCsAs5mC]$_{MOE}$ | 76.9 | 614 |
| ONT-367 | d[TsAsGsCsCsAsTsTsGsCsAsGsCsTsGsCsTsCsAsC] | 62.8 | 615 |
| ONT-415 | d[TAGCCATTGCAGCTGCTCAC] | 72.6 | 616 |
| ONT-416 | [TsAsGsCsCsAsTsTsGsCsAsGsCs]$_{MOE}$d[TsGsCsTsCSAsC] | 78.4 | 617 |
| ONT-421 | All-(Sp)-d[TsAsGsCsCsAsTsTsGsCsAsGsCsTsGsCsTsCsAsC] | 59.2 | 618 |
| ONT-394 | (Sp, Sp, Sp, Sp, Sp, Rp, Sp, Sp, Rp, Sp, Sp, Rp, Sp, Sp, Sp, Sp, Sp, Sp, Sp)-d[TsAsGsCsCsAsTsTsGsCsAsGsCsTsGsCsTsCsAsC] | 60.0 | 619 |
| ONT-406 | (Sp, Sp, Sp, Sp, Sp, Sp, Sp, Sp, Rp, Sp, Sp, Sp, Sp, Sp, Sp, Sp, Sp, Sp, Sp)-d[TsAsGsCsCsAsTsTsGsCsAsGsCsTsGsCsTsCsAsC] | 58.5 | 620 |

Example 12. Exemplary Additional Controlled Cleavage by Provided Chirally Controlled Oligonucleotide Compositions As will be appreciated by those skilled in the art, exemplary data illustrated in FIG. 26 confirm that provided chirally controlled oligonucleotide compositions and methods thereof provided unexpected results compared to reference compositions, such as stereorandom oligonucleotide compositions. Among other things, chirally controlled oligonucleotide compositions can produce controlled cleavage patterns, including but not limited to controlling of positions of cleavage sites, numbers of cleavage sites, and relative cleavage percentage of cleavage sites. See also exemplary data presented in FIG. 27.

Example 13. Stability of Chirally Controlled Oligonucleotide Compositions

Figure 7:
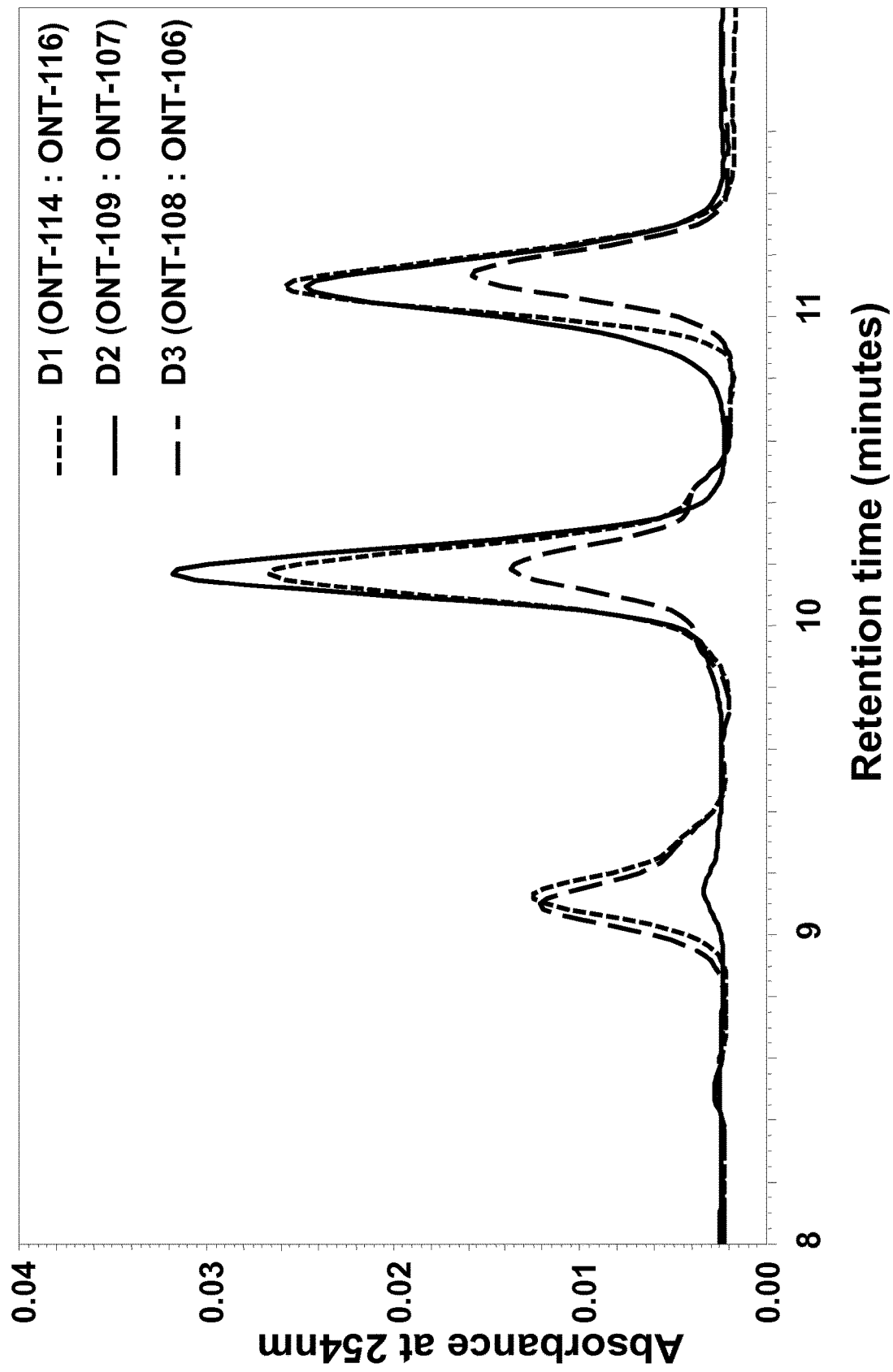
FIG. 7. HPLC profiles exhibiting the difference in metabolic stability determined in Human Serum for siRNA duplexes having several Rp, Sp or stereorandom phosphorothioate linkages.

As will be appreciated by those skilled in the art, exemplary data illustrated in FIG. 26 confirm that stability of provided chirally controlled oligonucleotide compositions can be adjusted by varying patterns of backbone chiral centers. For exemplary data, see FIG. 7 and FIG. 28. An exemplary protocol for performing serum stability experiment is described below.

Protocol: P-stereochemically pure PS DNA (ONT-396-ONT-414 (single Rp walk from 3'end to 5'end)), stereorandom PS DNA (ONT-367), all-Sp PS DNA (ONT-421) and all-Rp PS DNA (ONT-455) were incubated in Rat serum (Sigma, R9759) (0 h and 48 h) and analyzed by IEX-HPLC.

Incubation Method: 5 µL of 250 µM of each DNA solutions and 45 µL of Rat serum were mixed and incubated at 37° C. for each time points (0 h and 48 h). At each time points, reaction was stopped by adding 25 µL of 150 mM EDTA solution, 30 µL of Lysis buffer (epricentre, MTC096H) and 3 µL of Proteinase K solution (20 mg/mL). The mixture was incubated at 60° C. for 20 min then 20 µL of the mixture was injected to IEX-HPLC and analyzed.

Incubation Control Sample: Mixture of 5 µL of 250 µM of each DNA solutions and 103 µL of 1×PBS buffer were prepared and 20 µL of the mixture was analyzed by IEX-HPLC as controls in order to check the absolute quantification.

Exemplary Analytical Method:
IEx-HPLC
A: 10 mM TrisHCl, 50% ACN (pH 8.0)
B: 10 mM TrisHCl, 800 mM NaCl, 50% ACN (pH 8.0)
C: Water-ACN (1:1, v/v)
Temp: 60° C.
Column: DIONEX DNAPac PA-100, 250×4 mm
Gradient:

|   | Time  | Flow | % A  | % B  | % C | % D | Curve |
|---|-------|------|------|------|-----|-----|-------|
| 1 | 0.00  | 1.00 | 95.0 | 5.0  | 0.0 | 0.0 | 6     |
| 2 | 1.00  | 1.00 | 95.0 | 5.0  | 0.0 | 0.0 | 1     |
| 3 | 2.00  | 1.00 | 75.0 | 25.0 | 0.0 | 0.0 | 6     |
| 4 | 10.00 | 1.00 | 5.0  | 95.0 | 0.0 | 0.0 | 6     |
| 5 | 10.10 | 1.00 | 95.0 | 5.0  | 0.0 | 0.0 | 6     |
| 6 | 12.50 | 1.00 | 95.0 | 5.0  | 0.0 | 0.0 | 1     |

Washing:

|   | Time  | Flow | % A  | % B   | % C   | % D | Curve |
|---|-------|------|------|-------|-------|-----|-------|
| 1 | 0.01  | 1.00 | 0.0  | 0.0   | 100.0 | 0.0 | 6     |
| 2 | 5.50  | 1.00 | 0.0  | 0.0   | 100.0 | 0.0 | 1     |
| 3 | 5.60  | 1.00 | 0.0  | 100.0 | 0.0   | 0.0 | 6     |
| 4 | 7.50  | 1.00 | 0.0  | 100.0 | 0.0   | 0.0 | 1     |
| 5 | 7.60  | 1.00 | 95.0 | 5.0   | 0.0   | 0.0 | 6     |
| 6 | 12.50 | 1.00 | 95.0 | 5.0   | 0.0   | 0.0 | 1     |

Column Temperature: 60° C.

Washing was performed every after the sample run.

Percentage of remained PS DNA was calculated by the analysis of the ratio from the 0 h to 48 h using the area of integration of HPLC chromatogram.

Example 14. Exemplary Analytical Results (FIG. 19)

Peak assignments for FIG. 19 (Top panel, M12-Exp11 B10, ONT-354, 30 min)

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 2.34  | 1100.6 | 733.7   |         |        |        |
| 11.91 |        | 1390.6  | 1042.6  |        |        |
| 13.07 |        | 1500.08 | 1125.5  |        | 750.73 |
|       |        | 1805.29 | 1354.19 |        |        |
| 13.58 |        | 1603.39 | 1202.2  | 961.35 | 801.15 |
| 14.80 |        |         | 1589.9  | 1271.4 | 1059.5 |
| 18.59 |        |         | 1653.3  | 1323.3 | 1101.6 |

| Retention time (minutes) | Observed MW | 5'-p-RNA fragment | 3'-OH and 5'-OH, RNA | DNA |
|---|---|---|---|---|
| 2.34  | 2203.2  |       | 7mer         |           |
| 11.91 | 4176    | 13mer |              |           |
| 13.07 | 4505.7  | 14mer |              |           |
|       | 5418.87 |       | 17mer        |           |
| 13.58 | 4812.8  | 15mer |              |           |
| 14.80 | 6362.5  |       | 20mer, ONT-387 |         |
| 18.59 | 6615.4  |       |              | ONT-354   |

Peak assignments for FIG. 19 (Bottom panel, M12-Exp11 A10, ONT-315, 30 min)

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 4.01  | 1425.33 | 950.15  |         |         |        |
| 4.4   | 1100.83 | 733.69  |         |         |        |
| 4.94  | 1578.34 | 1051.54 |         |         |        |
| 6.21  | 1741.91 | 1161.89 | 870.37  |         |        |
|       | 1445.42 | 963.31  | 722.97  |         |        |
| 8.48  | 1610    | 1073.3  |         |         |        |
| 9.15  |         | 1391.2  | 1043.1  |         |        |
| 9.93  | 1763.4  | 1174.7  |         |         |        |
| 11.8  |         | 1602.3  | 1201.7  |         |        |
| 14.82 |         |         |         |         |        |
| 20.73 |         |         | 1809.94 | 1447.82 | 1205.9 |

| Retention time (minutes) | Observed MW | 5'-p-RNA fragment | 3'-OH and 5'-OH, RNA | DNA |
|---|---|---|---|---|
| 4.01 | 2853.45 | | 9mer | |
| 4.4 | 2203.66 | 7mer | | |
| 4.94 | 3158.47 | | 10mer | |
| 6.21 | 3487.52 | | 11mer | |
| | 2892.84 | 9mer | | |
| 8.48 | 3220.94 | 10mer | | |
| 9.15 | 4177 | | 13mer | |
| 9.93 | 3528.88 | 11mer | | |
| 11.8 | 4810 | | 15mer | |
| 14.82 | | | 20mer, ONT-387 | |
| 20.73 | 7244.3 | | | ONT-315 |

Example 15. Exemplary Analytical Results (FIG. 30)

Peak assignments for FIG. 30 (Top panel, M12-Exp11 D2, ONT-367, 30 min)

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 2.36 | 1120.28 | 746.25 | | | |
| 3.15 | 1292.41 | 861.32 | | | |
| 4.04 | | 975.92 | | | |
| 4.49 | 1140.6 | 759.78 | | | |
| 5.83 | 1305.21 | 869.65 | 652.31 | | |
| 6.88 | 1923.23 | 1281.69 | 961.28 | | |
| 9.32 | | 1390.76 | 1043.29 | 833.72 | |
| 9.96 | 1783.85 | 1187.98 | 891.6 | 712.94 | |
| 11.01 | 1936.14 | 1289.93 | | | |
| | | 1501.52 | 1125.4 | 899.89 | |
| 11.93 | | 1405.25 | 1053.78 | 842.84 | |
| 13.15 | | 1514.72 | 1135.72 | | |
| 14.81 | | | 1609.95 | 1287.53 | 1072.58 |
| 18.33 | | | 1587.9 | 1270.2 | 1058.3 |

| Retention time (minutes) | Observed MW | 5'-p-RNA fragment | 3'-OH and 5'-OH, RNA | DNA |
|---|---|---|---|---|
| 2.36 | 2242.56 | | 7mer | |
| 3.15 | 2586.82 | | 8mer | |
| 4.04 | 1953.84 | 6mer | | |
| 4.49 | 2283.2 | 7mer | | |
| 5.83 | 2612.42 | 8mer | | |
| 6.88 | 3849.14 | | 12mer | |
| 9.32 | 4175.28 | | 13mer | |
| 9.96 | 3569.7 | 11mer | | |
| 11.01 | 3874.28 | 12mer | | |
| | 4507.56 | | 14mer | |
| 11.93 | 4218.75 | 13mer | | |
| 13.15 | 4547.16 | 14mer | | |
| 14.81 | 6441.8 | | 20mer, ONT-388 | |
| 18.33 | 6355.6 | | | ONT-367 |

Peak assignments for FIG. 30 (Bottom panel, M12-Exp21 NM Plate1 (pool) F11 ONT-406 30 min

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 4.72 | 1140.6 | 759.78 | | | |
| 9.46 | | 1390.76 | 1043.29 | 833.72 | |
| 16.45 | | | 1609.95 | 1287.53 | 1072.58 |
| 19.48 | | | 1588.1 | 1270.4 | 1058.4 |

| Retention time (minutes) | Observed MW | 5'-p-RNA fragment | 3'-OH and 5'-OH, RNA | DNA |
|---|---|---|---|---|
| 4.72 | 2203.2 | 2283.2 | 7mer | |
| 9.46 | 4176 | 4175.28 | | 13mer |
| 16.45 | 6362.5 | 6441.8 | | 20mer, ONT-388 |
| 19.48 | 6615.4 | 6355.9 | | |

EQUIVALENTS

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A method for cleaving a nucleic acid polymer, comprising contacting the nucleic acid polymer with a composition, wherein the composition is a chirally controlled oligonucleotide composition comprising oligonucleotides of a particular oligonucleotide type defined by having:
   1) a common base sequence and length;
   2) a common pattern of backbone linkages; and
   3) a common pattern of backbone chiral centers,
which composition is chirally controlled in that it is enriched, relative to a substantially racemic preparation of oligonucleotides having the same base sequence and length, for oligonucleotides of the particular oligonucleotide type, wherein:
   the common base sequence has at least 17 bases;
   at least 50% of chiral internucleotidic linkages in each oligonucleotide of the particular oligonucleotide type are Sp; and
   the common pattern of backbone chiral centers comprises from 5' to 3' Rp(Sp)$_2$.

2. The method of claim 1, wherein each chiral, modified phosphate linkage of the oligonucleotides of the particular oligonucleotide type independently has the structure of formula I:

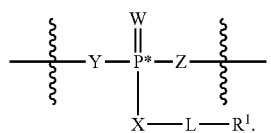

(I)

wherein:
P* is an asymmetric phosphorus atom and is either Rp or Sp;
W is O, S or Se;
each of X, Y and Z is independently —O—, —S—, —N(-L-R$^1$)—, or L;
L is a covalent bond or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
R$^1$ is halogen, R, or an optionally substituted C$_1$-C$_{50}$ aliphatic wherein one or more methylene units are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
   two R' on the same nitrogen are taken together with their intervening atoms to form an optionally substituted heterocyclic or heteroaryl ring, or
   two R' on the same carbon are taken together with their intervening atoms to form an optionally substituted aryl, carbocyclic, heterocyclic, or heteroaryl ring;
-Cy- is an optionally substituted bivalent ring selected from phenylene, carbocyclylene, arylene, heteroarylene, or heterocyclylene;
each R is independently hydrogen, or an optionally substituted group selected from C$_1$-C$_6$ aliphatic, phenyl, carbocyclyl, aryl, heteroaryl, or heterocyclyl; and
each

independently represents a connection to a nucleoside.

3. The method of claim 2, wherein W is O, X is —S—, and Y and Z are —O—.

4. The method of claim 2, wherein X is —S— and -L-R$^1$ is not hydrogen.

5. The method of claim 1, wherein the pattern of backbone chiral centers comprises (Sp)$_2$Rp(Sp)$_2$.

6. The method of claim 5, wherein the common base sequence has at least 20 nucleobases.

7. The method of claim 6, wherein at least 60% of chiral internucleotidic linkages in each oligonucleotide of the particular type are Sp.

8. The method of claim 5, wherein each of the Sp and Rp in the (Sp)$_2$Rp(Sp)$_2$ is independently the configuration of a phosphorothioate diester linkage.

9. The method of claim 8, wherein each chiral phosphate linkage of the oligonucleotides of the particular oligonucleotide type is a phosphorothioate diester linkage.

10. The method of claim 5, wherein the oligonucleotides of the particular oligonucleotide type each comprise one or more phosphate diester linkages.

11. The method of claim 5, wherein the nucleobases of the oligonucleotides of the particular oligonucleotide type are independently selected from adenine, thymine, cytosine, guanine, uracil and 5-methylcytosine.

12. The method of claim 5, wherein the oligonucleotides of the particular oligonucleotide type each comprise a modified sugar.

13. The method of claim 12, wherein the modification of the modified sugar is 2'-OR$^1$, wherein R$^1$ is optionally substituted C$_{1-6}$ aliphatic.

14. The method of claim 12, wherein the modification of the modified sugar is 2'-OMe.

15. The method of claim 12, wherein the modification of the modified sugar is 2'-OCH$_2$CH$_2$OMe.

16. The method of claim 12, wherein the oligonucleotides of the particular oligonucleotide type each comprise a locked nucleic acid sugar.

17. The method of claim 12, wherein the modified sugar comprises a bivalent substituent -L-, wherein -L- is —O—CH$_2$— between C$_2$ and C$_4$ of the sugar, wherein the —CH$_2$— is optionally substituted.

18. The method of claim 12, wherein the modified sugar comprises a bivalent substituent -L-, wherein -L- is —O—CH(Et)- between C$_2$ and C$_4$ of the sugar.

19. A method for inhibiting expression or reducing activity of a protein, comprising contacting a nucleic acid polymer encoding the protein with a composition, wherein the composition is a chirally controlled oligonucleotide composition comprising oligonucleotides of a particular oligonucleotide type defined by having:
1) a common base sequence and length;
2) a common pattern of backbone linkages; and
3) a common pattern of backbone chiral centers, which composition is chirally controlled in that it is enriched, relative to a substantially racemic preparation of oligonucleotides having the same base sequence and length, for oligonucleotides of the particular oligonucleotide type, wherein:

the common base sequence has at least 17 bases;
at least 50% of chiral internucleotidic linkages in each oligonucleotide of the particular oligonucleotide type are Sp; and
the common pattern of backbone chiral centers comprises from 5' to 3' Rp(Sp)$_2$; wherein the common base sequence is complementary to that of a nucleic acid encoding the protein.

20. The method of claim 19, wherein at least 60% of chiral internucleotidic linkages in each oligonucleotide of the particular type are Sp.

21. The method of claim 20, wherein the pattern of backbone chiral centers comprises (Sp)$_2$Rp(Sp)$_2$.

22. The method of claim 21, wherein each of the Sp and Rp in the (Sp)$_2$Rp(Sp)$_2$ is independently the configuration of a phosphorothioate diester linkage.

23. The method of claim 1, wherein each of the Sp and Rp in the Rp(Sp)$_2$ is independently the configuration of a phosphorothioate diester linkage.

24. The method of claim 19, wherein each of the Sp and Rp in the Rp(Sp)$_2$ is independently the configuration of a phosphorothioate diester linkage.

25. The method of claim 19, wherein each chiral, modified phosphate linkage of the oligonucleotides of the particular oligonucleotide type independently has the structure of formula I:

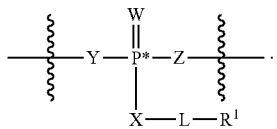

(I)

wherein:
P* is an asymmetric phosphorus atom and is either Rp or Sp;
W is O, S or Se;
each of X, Y and Z is independently —O—, —S—, —N(-L-R$^1$)—, or L;

L is a covalent bond or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

R$^1$ is halogen, R, or an optionally substituted C$_1$-C$_{50}$ aliphatic wherein one or more methylene units are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

each R' is independently —R, —C(O)R, —CO$_2$R, or —SO$_2$R, or:
two R' on the same nitrogen are taken together with their intervening atoms to form an optionally substituted heterocyclic or heteroaryl ring, or
two R' on the same carbon are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, or heterocyclylene;

each R is independently hydrogen, or an optionally substituted group selected from C$_1$-C$_6$ aliphatic, phenyl, carbocyclyl, aryl, heteroaryl, or heterocyclyl; and each

independently represents a connection to a nucleoside.

26. The method of claim 25, wherein W is O, X is —S—, and Y and Z are —O—.

27. The method of claim 21, wherein the oligonucleotides of the particular oligonucleotide type each comprise a modified sugar, wherein the modification of the modified sugar is 2'—OR$^1$, wherein R$^1$ is optionally substituted C$_{1-6}$ aliphatic.

* * * * *

SEQUENCE LISTING

<160> NUMBER OF SEQ ID NOS: 621

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gcctcagtct gcttcgcacc                                               20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gcctcagtct gcttcgcacc                                               20

<210> SEQ ID NO 3
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aatcgatcga tcg                                                      13

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gcctcagtct gcttcgcacc                                               20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gcctcagtct gcttcgcacc                                               20

<210> SEQ ID NO 6
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 6
gcctcagtct gcttcgcacc                                                    20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gcctcagtct gcttcgcacc                                                    20

<210> SEQ ID NO 8
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gugagcagcu gca                                                           13

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gcctcagtct gcttcgcacc                                                    20

<210> SEQ ID NO 10
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
cagtctgctt cg                                                            12

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gcctcagtct gcttcgcacc                                                    20

<210> SEQ ID NO 12
```

```
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
cagtctgctt cg                                                          12

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gcctcagtct gcttcgcacc                                                  20

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
uucuagaccu guuuugcuut t                                                21

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
uucuagaccu guuuugcuut t                                                21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
aagcaaaaca ggucuagaat t                                                21
```

```
<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17
aagcaaaaca ggucuagaat t                                             21

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18
aagcaaaaca ggucuagaat t                                             21

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
agcaaaacag gucuagaatt                                               20

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 20
agcaaaacag gucuagaatt                                               20

<210> SEQ ID NO 21
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 21
agcaaaacag gucuagaatt                                                  20

<210> SEQ ID NO 22
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
uucuagaccu guuuugcuut t                                                21

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 23
uucuagaccu guuuugcuut t                                                21

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 24
uucuagaccu guuuugcuut t                                                21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 25
uucuagaccu guuuugcuut t                                          21

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 26
uucuagaccu guuuugcuut t                                          21

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 27
uucuagaccu guuuugcuut t                                          21

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
aagcaaaaca ggucuagaat t                                          21

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 29
aagcaaaaca ggucuagaat t                                          21

<210> SEQ ID NO 30
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
aagcaaaaca ggucuagaat t                                              21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 31
aagcaaaaca ggucuagaat t                                              21

<210> SEQ ID NO 32
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 32
aagcaaaaca ggucuagaat t                                              21

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 33
aagcaaaaca ggucuagaat t                                              21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<220> FEATURE:
<221> NAME/KEY: source
<223> OTHER INFORMATION: /note="Description of Combined DNA/RNA
      Molecule: Synthetic oligonucleotide"

<400> SEQUENCE: 34
aagcaaaaca ggucuagaat t                                              21

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 35
aagcaaaaca ggucuagaat t                                              21

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 36
aagcaaaaca ggucuagaat t                                              21

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 37
aagcaaaaca ggucuagaat t                                              21

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 38
```

```
aagcaaaaca ggucuagaat t                                              21

<210> SEQ ID NO 39
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 39
aagcaaaaca ggucuagaat t                                              21

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 40
uucuagaccu guuuugcuut t                                              21

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 41
uucuagaccu guuuugcuut t                                              21

<210> SEQ ID NO 42
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 42
uucuagaccu guuuugcuut t                                              21

<210> SEQ ID NO 43
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 43
uucuagaccu guuuugcuut t                                              21

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 44
uucuagaccu guuuugcuut t                                              21

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
uucuagaccu guuuugcuut t                                              21

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 46
aagcaaaaca ggucuagaat t                                              21

<210> SEQ ID NO 47
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

```
        Molecule: Synthetic oligonucleotide"

<400> SEQUENCE: 47
aagcaaaaca ggucuagaat t                                              21

<210> SEQ ID NO 48
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 48
aagcaaaaca ggucuagaat t                                              21

<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 49
aagcaaaaca ggucuagaat t                                              21

<210> SEQ ID NO 50
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 50
aagcaaaaca ggucuagaat t                                              21

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 51
aagcaaaaca ggucuagaat t                                              21
```

```
<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 52
aagcaaaaca ggucuagaat t                                              21

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 53
aagcaaaaca ggucuagaat t                                              21

<210> SEQ ID NO 54
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
acacacacac                                                           10

<210> SEQ ID NO 55
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
cccccccccc                                                           10

<210> SEQ ID NO 56
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
cccccccccc                                                           10

<210> SEQ ID NO 57
```

```
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
cccccccccc                                                           10

<210> SEQ ID NO 58
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
ggatgttctc ga                                                        12

<210> SEQ ID NO 59
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
ggatgttctc ga                                                        12

<210> SEQ ID NO 60
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ggatgttctc ga                                                        12

<210> SEQ ID NO 61
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
ttcagtcatg acttcc                                                    16

<210> SEQ ID NO 62
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
```
ttcagtcatg acttcc                                                16

<210> SEQ ID NO 63
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
gcctcagtct gcttcgcacc                                            20

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (4)..(4)
<223> OTHER INFORMATION: /replace="u"
<220> FEATURE:
<221> NAME/KEY: Variation
<222> LOCATION: (8)..(8)
<223> OTHER INFORMATION: /replace="u"
<220> FEATURE:
<221> NAME/KEY: Variation
<222> LOCATION: (10)..(10)
<223> OTHER INFORMATION: /replace="u"
<220> FEATURE:
<221> NAME/KEY: Variation
<222> LOCATION: (13)..(14)
<223> OTHER INFORMATION: /replace="u"
<220> FEATURE:
<221> NAME/KEY: misc_feature
<222> LOCATION: (1)..(20)
<223> OTHER INFORMATION: /note="Variant nucleotides given in the
      sequence have no preference with respect to those in the
      annotations for variant positions"

<400> SEQUENCE: 64
gcctcagtct gcttcgcacc                                            20

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 65
gccucagtct gcttcgcacc                                            20

<210> SEQ ID NO 66
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
gcctcagtct gcttcgcacc                                             20

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gcctcagtct gcttcgcacc                                             20

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
gcctcagtct gcttcgcacc                                             20

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gcctcagtct gcttcgcacc                                             20

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gcctcagtct gcttcgcacc                                             20

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
gcctcagtct gcttcgcacc                                             20
```

-continued

```
<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gcctcagtct gcttcgcacc                                              20

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
gcctcagtct gcttcgcacc                                              20

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
gcctcagtct gcttcgcacc                                              20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
gcctcagtct gcttcgcacc                                              20

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
gcctcagtct gcttcgcacc                                              20

<210> SEQ ID NO 77
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

```
<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
gcctcagtct gcttcgcacc                                               20

<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
gcctcagtct gcttcgcacc                                               20

<210> SEQ ID NO 80
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
gcctcagtct gcttcgcacc                                               20

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
gcctcagtct gcttcgcacc                                               20

<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gcctcagtct gcttcgcacc                                               20

<210> SEQ ID NO 83
<211> LENGTH: 20
```

Synthetic oligonucleotide"

<400> SEQUENCE: 77
gcctcagtct gcttcgcacc                                               20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
gcctcagtct gcttcgcacc                                                20

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
gcctcagtct gcttcgcacc                                                20

<210> SEQ ID NO 85
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
gcctcagtct gcttcgcacc                                                20

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
gcctcagtct gcttcgcacc                                                20

<210> SEQ ID NO 87
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gcctcagtct gcttcgcacc                                                20

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
```

```
gcctcagtct gcttcgcacc                                              20

<210> SEQ ID NO 89
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
cagtctgctt cg                                                      12

<210> SEQ ID NO 90
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
cagtctgctt cg                                                      12

<210> SEQ ID NO 91
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
cagtctgctt cg                                                      12

<210> SEQ ID NO 92
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
cagtctgctt cg                                                      12

<210> SEQ ID NO 93
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
cagtctgctt cg                                                      12

<210> SEQ ID NO 94
<211> LENGTH: 12
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 94
cagtctgctt cg                                                           12

<210> SEQ ID NO 95
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
cagtctgctt cg                                                           12

<210> SEQ ID NO 96
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
cagtctgctt cg                                                           12

<210> SEQ ID NO 97
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
cagtctgctt cg                                                           12

<210> SEQ ID NO 98
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
cagtctgctt cg                                                           12

<210> SEQ ID NO 99
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
ctcagtctgc ttcgc                                                        15

<210> SEQ ID NO 100
```

-continued

```
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
cagtctgctt cg                                                           12

<210> SEQ ID NO 101
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
cagtctgctt cg                                                           12

<210> SEQ ID NO 102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
gcctcagtct gcttcgcacc                                                   20

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
gcctcagtct gcttcgcacc                                                   20

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
gcctcagtct gcttcgcacc                                                   20

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
```
gcctcagtct gcttcgcacc 20

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
gcctcagtct gcttcgcacc 20

<210> SEQ ID NO 107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
gcctcagtct gcttcgcacc 20

<210> SEQ ID NO 108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gcctcagtct gcttcgcacc 20

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gcctcagtct gcttcgcacc 20

<210> SEQ ID NO 110
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gcctcagtct gcttcgcacc 20

<210> SEQ ID NO 111
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 111
gcctcagtct gcttcgcacc                                              20

<210> SEQ ID NO 112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gcctcagtct gcttcgcacc                                              20

<210> SEQ ID NO 113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
gcctcagtct gcttcgcacc                                              20

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gcctcagtct gcttcgcacc                                              20

<210> SEQ ID NO 115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
gcctcagtct gcttcgcacc                                              20

<210> SEQ ID NO 116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
gcctcagtct gcttcgcacc                                              20
```

```
<210> SEQ ID NO 117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
gcctcagtct gcttcgcacc                                                   20

<210> SEQ ID NO 118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
gcctcagtct gcttcgcacc                                                   20

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
gcctcagtct gcttcgcacc                                                   20

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gcctcagtct gcttcgcacc                                                   20

<210> SEQ ID NO 121
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
gcctcagtct gcttcgcacc                                                   20

<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 122
gcctcagtct gcttcgcacc                                                20

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gcctcagtct gcttcgcacc                                                20

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
gcctcagtct gcttcgcacc                                                20

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
gcctcagtct gcttcgcacc                                                20

<210> SEQ ID NO 126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gcctcagtct gcttcgcacc                                                20

<210> SEQ ID NO 127
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gcctcagtct gcttcgcacc                                                20

<210> SEQ ID NO 128
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 128
gcctcagtct gcttcgcacc                                                  20

<210> SEQ ID NO 129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gcctcagtct gcttcgcacc                                                  20

<210> SEQ ID NO 130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gcctcagtct gcttcgcacc                                                  20

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 131
gcctcagucu gcttcgcacc                                                  20

<210> SEQ ID NO 132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gcctcagtct gcttcgcacc                                                  20

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 133
gcctcagtct gcttcgcacc                                                20

<210> SEQ ID NO 134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gcctcagtct gcttcgcacc                                                20

<210> SEQ ID NO 135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
gcctcagtct gcttcgcacc                                                20

<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
gcctcagtct gcttcgcacc                                                20

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
gcctcagtct gcttcgcacc                                                20

<210> SEQ ID NO 138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gcctcagtct gcttcgcacc                                                20

<210> SEQ ID NO 139
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 139
gcctcagtct gcttcgcacc                                                    20

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gcctcagtct gcttcgcacc                                                    20

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gcctcagtct gcttcgcacc                                                    20

<210> SEQ ID NO 142
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
gccucagucu gcuucgcacc                                                    20

<210> SEQ ID NO 143
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gccucagucu gcuucgcacc                                                    20

<210> SEQ ID NO 144
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
gccucagucu gcuucgcacc                                                    20
```

```
<210> SEQ ID NO 145
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
gccucagucu gcuucgcacc                                                 20

<210> SEQ ID NO 146
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
gccucagucu gcuucgcacc                                                 20

<210> SEQ ID NO 147
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
gccucagucu gcuucgcacc                                                 20

<210> SEQ ID NO 148
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gccucagucu gcuucgcacc                                                 20

<210> SEQ ID NO 149
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
gccucagucu gcuucgcacc                                                 20

<210> SEQ ID NO 150
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 150
gccucagucu gcuucgcacc                                              20

<210> SEQ ID NO 151
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
gccucagucu gcuucgcacc                                              20

<210> SEQ ID NO 152
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
cagtctgctt cg                                                      12

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
gcctcagtct gcttcgcacc                                              20

<210> SEQ ID NO 154
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 154
uucuagaccu guuuugcuut t                                            21

<210> SEQ ID NO 155
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 155
uucuagaccu guuuugcuut t                                               21

<210> SEQ ID NO 156
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 156
aagcaaaaca ggucuagaat t                                               21

<210> SEQ ID NO 157
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 157
aagcaaaaca ggucuagaat t                                               21

<210> SEQ ID NO 158
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 158
aagcaaaaca ggucuagaat t                                               21

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 159
agcaaaacag gucuagaatt                                                 20

<210> SEQ ID NO 160
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 160
agcaaaacag gucuagaatt                                                    20

<210> SEQ ID NO 161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 161
agcaaaacag gucuagaatt                                                    20

<210> SEQ ID NO 162
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 162
uucuagaccu guuuugcuut t                                                  21

<210> SEQ ID NO 163
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 163
uucuagaccu guuuugcuut t                                                  21

<210> SEQ ID NO 164
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 164
uucuagaccu guuuugcuut t                                              21

<210> SEQ ID NO 165
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 165
uucuagaccu guuuugcuut t                                              21

<210> SEQ ID NO 166
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 166
uucuagaccu guuuugcuut t                                              21

<210> SEQ ID NO 167
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 167
uucuagaccu guuuugcuut t                                              21

<210> SEQ ID NO 168
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 168
aagcaaaaca ggucuagaat t                                              21
```

```
<210> SEQ ID NO 169
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 169
aagcaaaaca ggucuagaat t                                             21

<210> SEQ ID NO 170
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 170
aagcaaaaca ggucuagaat t                                             21

<210> SEQ ID NO 171
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 171
aagcaaaaca ggucuagaat t                                             21

<210> SEQ ID NO 172
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 172
aagcaaaaca ggucuagaat t                                             21

<210> SEQ ID NO 173
<211> LENGTH: 21
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 173
aagcaaaaca ggucuagaat t                                        21

<210> SEQ ID NO 174
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 174
aagcaaaaca ggucuagaat t                                        21

<210> SEQ ID NO 175
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 175
aagcaaaaca ggucuagaat t                                        21

<210> SEQ ID NO 176
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 176
aagcaaaaca ggucuagaat t                                        21

<210> SEQ ID NO 177
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 177
aagcaaaaca ggucuagaat t                                          21

<210> SEQ ID NO 178
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 178
aagcaaaaca ggucuagaat t                                          21

<210> SEQ ID NO 179
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 179
aagcaaaaca ggucuagaat t                                          21

<210> SEQ ID NO 180
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 180
uucuagaccu guuuugcuut t                                          21

<210> SEQ ID NO 181
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 181
uucuagaccu guuuugcuut t                                          21

<210> SEQ ID NO 182
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 182
uucuagaccu guuuugcuut t                                              21

<210> SEQ ID NO 183
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 183
uucuagaccu guuuugcuut t                                              21

<210> SEQ ID NO 184
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 184
uucuagaccu guuuugcuut t                                              21

<210> SEQ ID NO 185
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 185
uucuagaccu guuuugcuut t                                              21

<210> SEQ ID NO 186
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 186
aagcaaaaca ggucuagaat t                                             21

<210> SEQ ID NO 187
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 187
aagcaaaaca ggucuagaat t                                             21

<210> SEQ ID NO 188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 188
aagcaaaaca ggucuagaat t                                             21

<210> SEQ ID NO 189
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 189
aagcaaaaca ggucuagaat t                                             21

<210> SEQ ID NO 190
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 190
```
aagcaaaaca ggucuagaat t                                         21

<210> SEQ ID NO 191
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 191
aagcaaaaca ggucuagaat t                                         21

<210> SEQ ID NO 192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 192
aagcaaaaca ggucuagaat t                                         21

<210> SEQ ID NO 193
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 193
aagcaaaaca ggucuagaat t                                         21

<210> SEQ ID NO 194
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
cagtctgctt cg                                                   12

<210> SEQ ID NO 195
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 195
gcctcagtct gcttcgcacc                                                    20

<210> SEQ ID NO 196
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
cagtctgctt cg                                                            12

<210> SEQ ID NO 197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
gcctcagtct gcttcgcacc                                                    20

<210> SEQ ID NO 198
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 198
uucuagaccu guuuugcuut t                                                  21

<210> SEQ ID NO 199
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 199
uucuagaccu guuuugcuut t                                                  21

<210> SEQ ID NO 200
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 200
aagcaaaaca ggucuagaat t                                              21

<210> SEQ ID NO 201
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 201
aagcaaaaca ggucuagaat t                                              21

<210> SEQ ID NO 202
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 202
aagcaaaaca ggucuagaat t                                              21

<210> SEQ ID NO 203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 203
agcaaaacag gucuagaatt                                                20

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 204
agcaaaacag gucuagaatt                                                20

<210> SEQ ID NO 205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 205
agcaaaacag gucuagaatt                                               20

<210> SEQ ID NO 206
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 206
uucuagaccu guuuugcuut t                                             21

<210> SEQ ID NO 207
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 207
uucuagaccu guuuugcuut t                                             21

<210> SEQ ID NO 208
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 208
uucuagaccu guuuugcuut t                                             21

<210> SEQ ID NO 209
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 209
uucuagaccu guuuugcuut t                                              21

<210> SEQ ID NO 210
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 210
uucuagaccu guuuugcuut t                                              21

<210> SEQ ID NO 211
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 211
uucuagaccu guuuugcuut t                                              21

<210> SEQ ID NO 212
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 212
aagcaaaaca ggucuagaat t                                              21

<210> SEQ ID NO 213
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 213
aagcaaaaca ggucuagaat t                                              21

<210> SEQ ID NO 214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 214
aagcaaaaca ggucuagaat t                                              21

<210> SEQ ID NO 215
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 215
aagcaaaaca ggucuagaat t                                              21

<210> SEQ ID NO 216
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 216
aagcaaaaca ggucuagaat t                                              21

<210> SEQ ID NO 217
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 217
aagcaaaaca ggucuagaat t                                              21

<210> SEQ ID NO 218
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 218
aagcaaaaca ggucuagaat t                                            21

<210> SEQ ID NO 219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 219
aagcaaaaca ggucuagaat t                                            21

<210> SEQ ID NO 220
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 220
aagcaaaaca ggucuagaat t                                            21

<210> SEQ ID NO 221
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 221
aagcaaaaca ggucuagaat t                                            21

<210> SEQ ID NO 222
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 222
aagcaaaaca ggucuagaat t                                              21

<210> SEQ ID NO 223
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 223
aagcaaaaca ggucuagaat t                                              21

<210> SEQ ID NO 224
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 224
uucuagaccu guuuugcuut t                                              21

<210> SEQ ID NO 225
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 225
uucuagaccu guuuugcuut t                                              21

<210> SEQ ID NO 226
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 226
```
uucuagaccu guuuugcuut t                                    21

<210> SEQ ID NO 227
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 227
uucuagaccu guuuugcuut t                                    21

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 228
uucuagaccu guuuugcuut t                                    21

<210> SEQ ID NO 229
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 229
uucuagaccu guuuugcuut t                                    21

<210> SEQ ID NO 230
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 230
aagcaaaaca ggucuagaat t                                    21

<210> SEQ ID NO 231
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 231
aagcaaaaca ggucuagaat t                                         21

<210> SEQ ID NO 232
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 232
aagcaaaaca ggucuagaat t                                         21

<210> SEQ ID NO 233
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 233
aagcaaaaca ggucuagaat t                                         21

<210> SEQ ID NO 234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 234
aagcaaaaca ggucuagaat t                                         21

<210> SEQ ID NO 235
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 235
aagcaaaaca ggucuagaat t                                              21

<210> SEQ ID NO 236
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 236
aagcaaaaca ggucuagaat t                                              21

<210> SEQ ID NO 237
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 237
aagcaaaaca ggucuagaat t                                              21

<210> SEQ ID NO 238
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gcgtttgctc ttcttcttgc gtttttt                                        27

<210> SEQ ID NO 239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gcctcagtct gcttcgcacc                                                20

<210> SEQ ID NO 240
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 240
gcctcagtct gcttcgcacc                                               20

<210> SEQ ID NO 241
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gcctcagtct gcttcgcacc                                               20

<210> SEQ ID NO 242
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gcgtttgctc ttcttcttgc gtttttt                                       27

<210> SEQ ID NO 243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
gcctcagtct gcttcgcacc                                               20

<210> SEQ ID NO 244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gcctcagtct gcttcgcacc                                               20

<210> SEQ ID NO 245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
gcctcagtct gcttcgcacc                                               20

<210> SEQ ID NO 246
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gcctcagtct gcttcgcacc                                              20

<210> SEQ ID NO 247
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
gcctcagtct gcttcgcacc                                              20

<210> SEQ ID NO 248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
gcctcagtct gcttcgcacc                                              20

<210> SEQ ID NO 249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
gcctcagtct gcttcgcacc                                              20

<210> SEQ ID NO 250
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
gcctcagtct gcttcgcacc                                              20

<210> SEQ ID NO 251
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
gcgtttgctc ttcttcttgc gtttttt                                      27

```
<210> SEQ ID NO 252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
gtccctgaag atgtcaatgc                                              20

<210> SEQ ID NO 253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
gtccctgaag atgtcaatgc                                              20

<210> SEQ ID NO 254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
gtccctgaag atgtcaatgc                                              20

<210> SEQ ID NO 255
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gtccctgaag atgtcaatgc                                              20

<210> SEQ ID NO 256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gtccctgaag atgtcaatgc                                              20

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 257
uucuagaccu guuuugcuut t                                            21

<210> SEQ ID NO 258
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 258
uucuagaccu guuuugcuut t                                            21

<210> SEQ ID NO 259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 259
uucuagaccu guuuugcuut t                                            21

<210> SEQ ID NO 260
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 260
uucuagaccu guuuugcuut t                                            21

<210> SEQ ID NO 261
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 261
```
uucuagaccu guuuugcuut t                                                      21

<210> SEQ ID NO 262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 262
uucuagaccu guuuugcuut t                                                      21

<210> SEQ ID NO 263
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 263
uucuagaccu guuuugcuut t                                                      21

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 264
uucuagaccu guuuugcuut t                                                      21

<210> SEQ ID NO 265
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 265
uucuagaccu guuuugcuut t                                                      21

<210> SEQ ID NO 266
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 266
uucuagaccu guuuugcuut t                                              21

<210> SEQ ID NO 267
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 267
uucuagaccu guuuugcuut t                                              21

<210> SEQ ID NO 268
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 268
uucuagaccu guuuugcuut t                                              21

<210> SEQ ID NO 269
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 269
uucuagaccu guuuugcuut t                                              21

<210> SEQ ID NO 270
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 270
uucuagaccu guuuugcuut t                                              21

<210> SEQ ID NO 271
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271
uucuagaccu guuuugcuut t                                              21

<210> SEQ ID NO 272
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
uucuagaccu guuuugcuut t                                              21

<210> SEQ ID NO 273
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 273
uucuagaccu guuuugcuut t                                              21

<210> SEQ ID NO 274
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 274
uucuagaccu guuuugcuut t                                              21
```

-continued

<210> SEQ ID NO 275
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 275
uucuagaccu guuuugcuut t                                           21

<210> SEQ ID NO 276
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 276
uucuagaccu guuuugcuut t                                           21

<210> SEQ ID NO 277
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 277
uucuagaccu guuuugcuut t                                           21

<210> SEQ ID NO 278
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 278
uucuagaccu guuuugcuut t                                           21

<210> SEQ ID NO 279
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 279
uucuagaccu guuuugcuut t                                              21

<210> SEQ ID NO 280
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 280
uucuagaccu guuuugcuut t                                              21

<210> SEQ ID NO 281
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 281
uucuagaccu guuuugcuut t                                              21

<210> SEQ ID NO 282
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 282
uucuagaccu guuuugcuut t                                              21

<210> SEQ ID NO 283
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 283
uucuagaccu guuuugcuut t                                          21

<210> SEQ ID NO 284
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 284
uucuagaccu guuuugcuut t                                          21

<210> SEQ ID NO 285
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 285
uucuagaccu guuuugcuut t                                          21

<210> SEQ ID NO 286
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 286
uucuagaccu guuuugcuut t                                          21

<210> SEQ ID NO 287
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 287
uucuagaccu guuuugcuut t                                          21

<210> SEQ ID NO 288
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 288
uucuagaccu guuuugcuut t                                             21

<210> SEQ ID NO 289
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 289
uucuagaccu guuuugcuut t                                             21

<210> SEQ ID NO 290
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 290
uucuagaccu guuuugcuut t                                             21

<210> SEQ ID NO 291
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 291
uucuagaccu guuuugcuut t                                             21

<210> SEQ ID NO 292
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 292
uucuagaccu guuuugcuut t                                              21

<210> SEQ ID NO 293
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 293
uucuagaccu guuuugcuut t                                              21

<210> SEQ ID NO 294
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 294
uucuagaccu guuuugcuut t                                              21

<210> SEQ ID NO 295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 295
uucuagaccu guuuugcuut t                                              21

<210> SEQ ID NO 296
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 296
uucuagaccu guuuugcuut t                                              21

<210> SEQ ID NO 297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 297
aagcaaaaca ggucuagaat t                                              21

<210> SEQ ID NO 298
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 298
aagcaaaaca ggucuagaat t                                              21

<210> SEQ ID NO 299
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 299
aagcaaaaca ggucuagaat t                                              21

<210> SEQ ID NO 300
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 300
aagcaaaaca ggucuagaat t                                              21

<210> SEQ ID NO 301
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 301
aagcaaaaca ggucuagaat t                                              21

<210> SEQ ID NO 302
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 302
aagcaaaaca ggucuagaat t                                              21

<210> SEQ ID NO 303
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 303
aagcaaaaca ggucuagaat t                                              21

<210> SEQ ID NO 304
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 304
aagcaaaaca ggucuagaat t                                              21

<210> SEQ ID NO 305
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 305
aagcaaaaca ggucuagaat t                                              21

<210> SEQ ID NO 306
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 306
aagcaaaaca ggucuagaat t                                              21

<210> SEQ ID NO 307
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 307
aagcaaaaca ggucuagaat t                                              21

<210> SEQ ID NO 308
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 308
aagcaaaaca ggucuagaat t                                              21

<210> SEQ ID NO 309
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 309
aagcaaaaca ggucuagaat t                                              21

<210> SEQ ID NO 310

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 310
aagcaaaaca ggucuagaat t                                              21

<210> SEQ ID NO 311
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 311
aagcaaaaca ggucuagaat t                                              21

<210> SEQ ID NO 312
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 312
aagcaaaaca ggucuagaat t                                              21

<210> SEQ ID NO 313
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 313
aagcaaaaca ggucuagaat t                                              21

<210> SEQ ID NO 314
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 314
aagcaaaaca ggucuagaat t                                              21

<210> SEQ ID NO 315
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 315
aagcaaaaca ggucuagaat t                                              21

<210> SEQ ID NO 316
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 316
aagcaaaaca ggucuagaat t                                              21

<210> SEQ ID NO 317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 317
aagcaaaaca ggucuagaat t                                              21

<210> SEQ ID NO 318
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 318
```
aagcaaaaca ggucuagaat t                                    21

<210> SEQ ID NO 319
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 319
aagcaaaaca ggucuagaat t                                    21

<210> SEQ ID NO 320
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 320
aagcaaaaca ggucuagaat t                                    21

<210> SEQ ID NO 321
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 321
aagcaaaaca ggucuagaat t                                    21

<210> SEQ ID NO 322
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 322
aagcaaaaca ggucuagaat t                                    21

<210> SEQ ID NO 323
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 323
aagcaaaaca ggucuagaat t                                              21

<210> SEQ ID NO 324
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 324
aagcaaaaca ggucuagaat t                                              21

<210> SEQ ID NO 325
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 325
aagcaaaaca ggucuagaat t                                              21

<210> SEQ ID NO 326
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 326
aagcaaaaca ggucuagaat t                                              21

<210> SEQ ID NO 327
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 327
aagcaaaaca ggucuagaat t                                     21

<210> SEQ ID NO 328
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 328
aagcaaaaca ggucuagaat t                                     21

<210> SEQ ID NO 329
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 329
aagcaaaaca ggucuagaat t                                     21

<210> SEQ ID NO 330
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 330
aagcaaaaca ggucuagaat t                                     21

<210> SEQ ID NO 331
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 331
aagcaaaaca ggucuagaat t                                     21

-continued

<210> SEQ ID NO 332
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 332
aagcaaaaca ggucuagaat t                                              21

<210> SEQ ID NO 333
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 333
aagcaaaaca ggucuagaat t                                              21

<210> SEQ ID NO 334
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 334
aagcaaaaca ggucuagaat t                                              21

<210> SEQ ID NO 335
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 335
aagcaaaaca ggucuagaat t                                              21

<210> SEQ ID NO 336
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 336
aagcaaaaca ggucuagaat t                                               21

<210> SEQ ID NO 337
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 337
aagcaaaaca ggucuagaat t                                               21

<210> SEQ ID NO 338
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 338
aagcaaaaca ggucuagaat t                                               21

<210> SEQ ID NO 339
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 339
aagcaaaaca ggucuagaat t                                               21

<210> SEQ ID NO 340
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 340
aagcaaaaca ggucuagaat t							21

<210> SEQ ID NO 341
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 341
aagcaaaaca ggucuagaat t							21

<210> SEQ ID NO 342
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 342
aagcaaaaca ggucuagaat t							21

<210> SEQ ID NO 343
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 343
aagcaaaaca ggucuagaat t							21

<210> SEQ ID NO 344
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 344
aagcaaaaca ggucuagaat t							21

<210> SEQ ID NO 345
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 345
aagcaaaaca ggucuagaat t                                              21

<210> SEQ ID NO 346
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 346
aagcaaaaca ggucuagaat t                                              21

<210> SEQ ID NO 347
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 347
aagcaaaaca ggucuagaat t                                              21

<210> SEQ ID NO 348
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 348
aagcaaaaca ggucuagaat t                                              21

<210> SEQ ID NO 349
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 349
aagcaaaaca ggucuagaat t                                              21

<210> SEQ ID NO 350
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 350
aagcaaaaca ggucuagaat t                                              21

<210> SEQ ID NO 351
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 351
aagcaaaaca ggucuagaat t                                              21

<210> SEQ ID NO 352
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 352
aagcaaaaca ggucuagaat t                                              21

<210> SEQ ID NO 353
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 353
aagcaaaaca ggucuagaat t                                              21
```

```
<210> SEQ ID NO 354
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 354
aagcaaaaca ggucuagaat t                                              21

<210> SEQ ID NO 355
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 355
aagcaaaaca ggucuagaat t                                              21

<210> SEQ ID NO 356
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 356
aagcaaaaca ggucuagaat t                                              21

<210> SEQ ID NO 357
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 357
aagcaaaaca ggucuagaat t                                              21

<210> SEQ ID NO 358
<211> LENGTH: 21
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 358
aagcaaaaca ggucuagaat t                                          21

<210> SEQ ID NO 359
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 359
aagcaaaaca ggucuagaat t                                          21

<210> SEQ ID NO 360
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 360
aagcaaaaca ggucuagaat t                                          21

<210> SEQ ID NO 361
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 361
aagcaaaaca ggucuagaat t                                          21

<210> SEQ ID NO 362
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

```
<400> SEQUENCE: 362
aagcaaaaca ggucuagaat t                                              21

<210> SEQ ID NO 363
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 363
aagcaaaaca ggucuagaat t                                              21

<210> SEQ ID NO 364
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 364
aagcaaaaca ggucuagaat t                                              21

<210> SEQ ID NO 365
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 365
aagcaaaaca ggucuagaat t                                              21

<210> SEQ ID NO 366
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 366
aagcaaaaca ggucuagaat t                                              21

<210> SEQ ID NO 367
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 367
aagcaaaaca ggucuagaat t                                          21

<210> SEQ ID NO 368
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 368
aagcaaaaca ggucuagaat t                                          21

<210> SEQ ID NO 369
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 369
aagcaaaaca ggucuagaat t                                          21

<210> SEQ ID NO 370
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 370
aagcaaaaca ggucuagaat t                                          21

<210> SEQ ID NO 371
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 371
aagcaaaaca ggucuagaat t                                              21

<210> SEQ ID NO 372
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 372
aagcaaaaca ggucuagaat t                                              21

<210> SEQ ID NO 373
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 373
aagcaaaaca ggucuagaat t                                              21

<210> SEQ ID NO 374
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 374
aagcaaaaca ggucuagaat t                                              21

<210> SEQ ID NO 375
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 375
aagcaaaaca ggucuagaat t                                              21
```

```
<210> SEQ ID NO 376
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 376
aagcaaaaca ggucuagaat t                                             21

<210> SEQ ID NO 377
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
ccctctggat tgagcatcca                                               20

<210> SEQ ID NO 378
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
aagctttggt tgggcaacac                                               20

<210> SEQ ID NO 379
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
agtcacttgg gagcttctcc                                               20

<210> SEQ ID NO 380
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
cacttgggag cttctcctgg                                               20

<210> SEQ ID NO 381
<211> LENGTH: 20
<212> TYPE: DNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
atagccattg cagctgctca                                              20

<210> SEQ ID NO 382
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
tggattgagc atccaccaag                                              20

<210> SEQ ID NO 383
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
ccatagccat tgcagctgct                                              20

<210> SEQ ID NO 384
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
gtcacttggg agcttctcct                                              20

<210> SEQ ID NO 385
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
ccagggcact catctgcatg                                              20

<210> SEQ ID NO 386
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
gccatccaag tcacttggga                                              20
```

<210> SEQ ID NO 387
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
gaagctttgg ttgggcaaca                                               20

<210> SEQ ID NO 388
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
ctggattgag catccaccaa                                               20

<210> SEQ ID NO 389
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
caagtcactt gggagcttct                                               20

<210> SEQ ID NO 390
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
atgccatcca agtcacttgg                                               20

<210> SEQ ID NO 391
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
atgagatgcc tggctgccat                                               20

<210> SEQ ID NO 392
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

```
      Synthetic oligonucleotide"

<400> SEQUENCE: 392
ttgggagctt ctcctggtgg                                              20

<210> SEQ ID NO 393
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
tgggagcttc tcctggtgga                                              20

<210> SEQ ID NO 394
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
ttatgagatg cctggctgcc                                              20

<210> SEQ ID NO 395
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
gttatgagat gcctggctgc                                              20

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
ccaagtcact tgggagcttc                                              20

<210> SEQ ID NO 397
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
agctttggtt gggcaacaca                                              20

<210> SEQ ID NO 398
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
tatgagatgc ctggctgcca                                              20

<210> SEQ ID NO 399
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
tgttatgaga tgcctggctg                                              20

<210> SEQ ID NO 400
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
atccaagtca cttgggagct                                              20

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
gggaagcttt ggttgggcaa                                              20

<210> SEQ ID NO 402
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
ctccatccat gaggtcattc                                              20

<210> SEQ ID NO 403
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
```
aagtcacttg ggagcttctc                                          20

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
ccatccaagt cacttgggag                                          20

<210> SEQ ID NO 405
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
tccaagtcac ttgggagctt                                          20

<210> SEQ ID NO 406
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
cctctggatt gagcatccac                                          20

<210> SEQ ID NO 407
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
acttgggagc ttctcctggt                                          20

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
cttgggagct tctcctggtg                                          20

<210> SEQ ID NO 409
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 409
catgccatcc aagtcacttg                                                    20

<210> SEQ ID NO 410
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
tgccatccaa gtcacttggg                                                    20

<210> SEQ ID NO 411
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
tccatccatg aggtcattcc                                                    20

<210> SEQ ID NO 412
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
agggcactca tctgcatggg                                                    20

<210> SEQ ID NO 413
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
ccagttcctt cattctgcac                                                    20

<210> SEQ ID NO 414
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
catagccatt gcagctgctc                                                    20

<210> SEQ ID NO 415
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
tctggattga gcatccacca                                                    20

<210> SEQ ID NO 416
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
ggattgagca tccaccaaga                                                    20

<210> SEQ ID NO 417
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
ccctctggat tgagcatcca                                                    20

<210> SEQ ID NO 418
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
aagctttggt tgggcaacac                                                    20

<210> SEQ ID NO 419
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
agtcacttgg gagcttctcc                                                    20

<210> SEQ ID NO 420
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
```

```
cacttgggag cttctcctgg                                              20

<210> SEQ ID NO 421
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
atagccattg cagctgctca                                              20

<210> SEQ ID NO 422
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
tggattgagc atccaccaag                                              20

<210> SEQ ID NO 423
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
ccatagccat tgcagctgct                                              20

<210> SEQ ID NO 424
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
gtcacttggg agcttctcct                                              20

<210> SEQ ID NO 425
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
ccagggcact catctgcatg                                              20

<210> SEQ ID NO 426
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 426
gccatccaag tcacttggga                                            20

<210> SEQ ID NO 427
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
gaagctttgg ttgggcaaca                                            20

<210> SEQ ID NO 428
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
ctggattgag catccaccaa                                            20

<210> SEQ ID NO 429
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
caagtcactt gggagcttct                                            20

<210> SEQ ID NO 430
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
atgccatcca agtcacttgg                                            20

<210> SEQ ID NO 431
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
atgagatgcc tggctgccat                                            20
```

```
<210> SEQ ID NO 432
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
ttgggagctt ctcctggtgg                                                   20

<210> SEQ ID NO 433
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
tgggagcttc tcctggtgga                                                   20

<210> SEQ ID NO 434
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
ttatgagatg cctggctgcc                                                   20

<210> SEQ ID NO 435
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
gttatgagat gcctggctgc                                                   20

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
ccaagtcact tgggagcttc                                                   20

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 437
agctttggtt gggcaacaca                                              20

<210> SEQ ID NO 438
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
tatgagatgc ctggctgcca                                              20

<210> SEQ ID NO 439
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
tgttatgaga tgcctggctg                                              20

<210> SEQ ID NO 440
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
atccaagtca cttgggagct                                              20

<210> SEQ ID NO 441
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
gggaagcttt ggttgggcaa                                              20

<210> SEQ ID NO 442
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
ctccatccat gaggtcattc                                              20

<210> SEQ ID NO 443
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 443
aagtcacttg ggagcttctc                                                      20

<210> SEQ ID NO 444
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
ccatccaagt cacttgggag                                                      20

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
tccaagtcac ttgggagctt                                                      20

<210> SEQ ID NO 446
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
cctctggatt gagcatccac                                                      20

<210> SEQ ID NO 447
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
acttgggagc ttctcctggt                                                      20

<210> SEQ ID NO 448
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
cttgggagct tctcctggtg                                                      20
```

```
<210> SEQ ID NO 449
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
catgccatcc aagtcacttg                                                    20

<210> SEQ ID NO 450
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
tgccatccaa gtcacttggg                                                    20

<210> SEQ ID NO 451
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
tccatccatg aggtcattcc                                                    20

<210> SEQ ID NO 452
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
agggcactca tctgcatggg                                                    20

<210> SEQ ID NO 453
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
ccagttcctt cattctgcac                                                    20

<210> SEQ ID NO 454
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 454
catagccatt gcagctgctc                                               20

<210> SEQ ID NO 455
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
tctggattga gcatccacca                                               20

<210> SEQ ID NO 456
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
ggattgagca tccaccaaga                                               20

<210> SEQ ID NO 457
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
gaagctttgg ttgggcaaca                                               20

<210> SEQ ID NO 458
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
ccatccaagt cacttgggag                                               20

<210> SEQ ID NO 459
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
atgagatgcc tggctgccat                                               20

<210> SEQ ID NO 460
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
aagctttggt tgggcaacac                                                     20

<210> SEQ ID NO 461
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
atagccattg cagctgctca                                                     20

<210> SEQ ID NO 462
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
tatgagatgc ctggctgcca                                                     20

<210> SEQ ID NO 463
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
ttatgagatg cctggctgcc                                                     20

<210> SEQ ID NO 464
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
ccatccaagt cacttgggag                                                     20

<210> SEQ ID NO 465
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
ccatccaagt cacttgggag                                                     20
```

-continued

<210> SEQ ID NO 466
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
gaagctttgg ttgggcaaca                                              20

<210> SEQ ID NO 467
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
ccatccaagt cacttgggag                                              20

<210> SEQ ID NO 468
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
ccatccaagt cacttgggag                                              20

<210> SEQ ID NO 469
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
gaagctttgg ttgggcaaca                                              20

<210> SEQ ID NO 470
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
atgagatgcc tggctgccat                                              20

<210> SEQ ID NO 471
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

```
Synthetic oligonucleotide"

<400> SEQUENCE: 471
atgagatgcc tggctgccat                                           20

<210> SEQ ID NO 472
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
atgagatgcc tggctgccat                                           20

<210> SEQ ID NO 473
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
atgagatgcc tggctgccat                                           20

<210> SEQ ID NO 474
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
gaagctttgg ttgggcaaca                                           20

<210> SEQ ID NO 475
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
ccatccaagt cacttgggag                                           20

<210> SEQ ID NO 476
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
atgagatgcc tggctgccat                                           20

<210> SEQ ID NO 477
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
ccatccaagt cacttgggag                                              20

<210> SEQ ID NO 478
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
atgagatgcc tggctgccat                                              20

<210> SEQ ID NO 479
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
ccatccaagt cacttgggag                                              20

<210> SEQ ID NO 480
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
atgagatgcc tggctgccat                                              20

<210> SEQ ID NO 481
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
ccatccaagt cacttgggag                                              20

<210> SEQ ID NO 482
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
```
atgagatgcc tggctgccat                                                20

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
ccatccaagt cacttgggag                                                20

<210> SEQ ID NO 484
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
atgagatgcc tggctgccat                                                20

<210> SEQ ID NO 485
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
ccatccaagt cacttgggag                                                20

<210> SEQ ID NO 486
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
atgagatgcc tggctgccat                                                20

<210> SEQ ID NO 487
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
gaagctttgg ttgggcaaca                                                20

<210> SEQ ID NO 488
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 488
atgagatgcc tggctgccat                                              20

<210> SEQ ID NO 489
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
ccatccaagt cacttgggag                                              20

<210> SEQ ID NO 490
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
atgagatgcc tggctgccat                                              20

<210> SEQ ID NO 491
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
gaagctttgg ttgggcaaca                                              20

<210> SEQ ID NO 492
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
atgagatgcc tggctgccat                                              20

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
ccatccaagt cacttgggag                                              20

<210> SEQ ID NO 494
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
ccatccaagt cacttgggag                                                 20

<210> SEQ ID NO 495
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
atgagatgcc tggctgccat                                                 20

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
ccatccaagt cacttgggag                                                 20

<210> SEQ ID NO 497
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
ccatccaagt cacttgggag                                                 20

<210> SEQ ID NO 498
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
ccatccaagt cacttgggag                                                 20

<210> SEQ ID NO 499
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
```
ccatccaagt cacttgggag                                               20

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
ccatccaagt cacttgggag                                               20

<210> SEQ ID NO 501
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
ccatccaagt cacttgggag                                               20

<210> SEQ ID NO 502
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
ccatccaagt cacttgggag                                               20

<210> SEQ ID NO 503
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
ccatccaagt cacttgggag                                               20

<210> SEQ ID NO 504
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
ccatccaagt cacttgggag                                               20

<210> SEQ ID NO 505
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 505
ccatccaagt cacttgggag                                                    20

<210> SEQ ID NO 506
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
tgagatgcct ggctgccata                                                    20

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
tgagatgcct ggctgccata                                                    20

<210> SEQ ID NO 508
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
tgagatgcct ggctgccata                                                    20

<210> SEQ ID NO 509
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
tgagatgcct ggctgccata                                                    20

<210> SEQ ID NO 510
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
uauggcagcc aggcaucuca                                                    20
```

```
<210> SEQ ID NO 511
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
tagccattgc agctgctcac                                                    20

<210> SEQ ID NO 512
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
tagccattgc agctgctcac                                                    20

<210> SEQ ID NO 513
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
tagccattgc agctgctcac                                                    20

<210> SEQ ID NO 514
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
tagccattgc agctgctcac                                                    20

<210> SEQ ID NO 515
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
gugagcagcu gcaauggcua                                                    20

<210> SEQ ID NO 516
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 516
tagccattgc agctgctcac                                          20

<210> SEQ ID NO 517
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
tagccattgc agctgctcac                                          20

<210> SEQ ID NO 518
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
tagccattgc agctgctcac                                          20

<210> SEQ ID NO 519
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
tagccattgc agctgctcac                                          20

<210> SEQ ID NO 520
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
tagccattgc agctgctcac                                          20

<210> SEQ ID NO 521
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
gugagcagcu gcaauggcua                                          20

<210> SEQ ID NO 522
<211> LENGTH: 20
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"

<400> SEQUENCE: 522
tccagttcct tcattctgca                                                 20

<210> SEQ ID NO 523
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
tccagttcct tcattctgca                                                 20

<210> SEQ ID NO 524
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
tccagttcct tcattctgca                                                 20

<210> SEQ ID NO 525
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
tccagttcct tcattctgca                                                 20

<210> SEQ ID NO 526
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
tccagttcct tcattctgca                                                 20

<210> SEQ ID NO 527
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
ugcagaauga aggaacugga                                                 20
```

```
<210> SEQ ID NO 528
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
tgagatgcct ggctgccata                                               20

<210> SEQ ID NO 529
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
tgagatgcct ggctgccata                                               20

<210> SEQ ID NO 530
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
tgagatgcct ggctgccata                                               20

<210> SEQ ID NO 531
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
tgagatgcct ggctgccata                                               20

<210> SEQ ID NO 532
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
tgagatgcct ggctgccata                                               20

<210> SEQ ID NO 533
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 533
uauggcagcc aggcaucuca                                                 20

<210> SEQ ID NO 534
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
gcctcagtct gcttcgcacc                                                 20

<210> SEQ ID NO 535
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
gcgtttgctc ttcttcttgc gtttttt                                         27

<210> SEQ ID NO 536
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
gtccctgaag atgtcaatgc                                                 20

<210> SEQ ID NO 537
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
tccagttcct tcattctgca                                                 20

<210> SEQ ID NO 538
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
tgagatgcct ggctgccata                                                 20

<210> SEQ ID NO 539
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
tagccattgc agctgctcac                                                   20

<210> SEQ ID NO 540
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
tccagttcct tcattctgca                                                   20

<210> SEQ ID NO 541
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
tgagatgcct ggctgccata                                                   20

<210> SEQ ID NO 542
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
tagccattgc agctgctcac                                                   20

<210> SEQ ID NO 543
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
tccagttcct tcattctgca                                                   20

<210> SEQ ID NO 544
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
tgagatgcct ggctgccata                                                   20
```

<210> SEQ ID NO 545
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
tagccattgc agctgctcac                                            20

<210> SEQ ID NO 546
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
tccagttcct tcattctgca                                            20

<210> SEQ ID NO 547
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
tgagatgcct ggctgccata                                            20

<210> SEQ ID NO 548
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
tagccattgc agctgctcac                                            20

<210> SEQ ID NO 549
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
tccagttcct tcattctgca                                            20

<210> SEQ ID NO 550
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 550
tgagatgcct ggctgccata                                                    20

<210> SEQ ID NO 551
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
tagccattgc agctgctcac                                                    20

<210> SEQ ID NO 552
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 552
uagccattgc agctgctcac                                                    20

<210> SEQ ID NO 553
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 553
uagccattgc agctgc                                                        16

<210> SEQ ID NO 554
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
tagccattgc agctgctcac                                                    20

<210> SEQ ID NO 555
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
attaataaat tgtcatcacc                                              20

<210> SEQ ID NO 556
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
ggugcgaagc agacugaggc                                              20

<210> SEQ ID NO 557
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
ugcagaauga aggaacugga                                              20

<210> SEQ ID NO 558
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
uauggcagcc aggcaucuca                                              20

<210> SEQ ID NO 559
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
gugagcagcu gcaauggcua                                              20

<210> SEQ ID NO 560
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
tagccattgc agctgctcac                                              20

<210> SEQ ID NO 561
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
gugagcggcu gcaauggcua                                                       20

<210> SEQ ID NO 562
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
gugagcagcu gcgauggcua                                                       20

<210> SEQ ID NO 563
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
ggugaugaca auuuauuaau                                                       20

<210> SEQ ID NO 564
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
ggugauggca auuuauuaau                                                       20

<210> SEQ ID NO 565
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
tgagatgcct ggctgccata                                                       20

<210> SEQ ID NO 566
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
tgagatgcct ggctgccata                                                       20
```

-continued

```
<210> SEQ ID NO 567
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
tgagatgcct ggctgccata                                              20

<210> SEQ ID NO 568
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
tagccattgc agctgctcac                                              20

<210> SEQ ID NO 569
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
tagccattgc agctgctcac                                              20

<210> SEQ ID NO 570
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
tagccattgc agctgctcac                                              20

<210> SEQ ID NO 571
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
tagccattgc agctgctcac                                              20

<210> SEQ ID NO 572
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 572
tagccattgc agctgctcac                                      20

<210> SEQ ID NO 573
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
tagccattgc agctgctcac                                      20

<210> SEQ ID NO 574
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
tagccattgc agctgctcac                                      20

<210> SEQ ID NO 575
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
tagccattgc agctgctcac                                      20

<210> SEQ ID NO 576
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
tagccattgc agctgctcac                                      20

<210> SEQ ID NO 577
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
tagccattgc agctgctcac                                      20

<210> SEQ ID NO 578
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
tagccattgc agctgctcac                                            20

<210> SEQ ID NO 579
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
tagccattgc agctgctcac                                            20

<210> SEQ ID NO 580
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
tagccattgc agctgctcac                                            20

<210> SEQ ID NO 581
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
tagccattgc agctgctcac                                            20

<210> SEQ ID NO 582
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
tagccattgc agctgctcac                                            20

<210> SEQ ID NO 583
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
```
tagccattgc agctgctcac                                                20

<210> SEQ ID NO 584
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
tagccattgc agctgctcac                                                20

<210> SEQ ID NO 585
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
tagccattgc agctgctcac                                                20

<210> SEQ ID NO 586
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
tagccattgc agctgctcac                                                20

<210> SEQ ID NO 587
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
tagccattgc agctgctcac                                                20

<210> SEQ ID NO 588
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
tagccattgc agctgctcac                                                20

<210> SEQ ID NO 589
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 589
tagccattgc agctgctcac                                                    20

<210> SEQ ID NO 590
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
tagccattgc agctgctcac                                                    20

<210> SEQ ID NO 591
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
tagccattgc agctgctcac                                                    20

<210> SEQ ID NO 592
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
tagccattgc agctgctcac                                                    20

<210> SEQ ID NO 593
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
attaataaat tgtcatcacc                                                    20

<210> SEQ ID NO 594
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
attaataaat tgtcatcacc                                                    20

<210> SEQ ID NO 595
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
gcctcagtct gcttcgcacc                                                   20

<210> SEQ ID NO 596
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
gcctcagtct gcttcgcacc                                                   20

<210> SEQ ID NO 597
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
gcctcagtct gcttcgcacc                                                   20

<210> SEQ ID NO 598
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
gcctcagtct gcttcgcacc                                                   20

<210> SEQ ID NO 599
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
gcctcagtct gcttcgcacc                                                   20

<210> SEQ ID NO 600
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
```

-continued gtccctgaag atgtcaatgc                                          20

<210> SEQ ID NO 601
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
gtccctgaag atgtcaatgc                                          20

<210> SEQ ID NO 602
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
gtccctgaag atgtcaatgc                                          20

<210> SEQ ID NO 603
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
gtccctgaag atgtcaatgc                                          20

<210> SEQ ID NO 604
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
gcctcagtct gcttcgcacc                                          20

<210> SEQ ID NO 605
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
gcctcagtct gcttcgcacc                                          20

<210> SEQ ID NO 606
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 606
gcctcagtct gcttcgcacc                                                20

<210> SEQ ID NO 607
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
gcctcagtct gcttcgcacc                                                20

<210> SEQ ID NO 608
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
gcctcagtct gcttcgcacc                                                20

<210> SEQ ID NO 609
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
gcctcagtct gcttcgcacc                                                20

<210> SEQ ID NO 610
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 610
uagccattgc agctgctcac                                                20

<210> SEQ ID NO 611
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

-continued

<223> OTHER INFORMATION: /note="Description of Combined DNA/RNA
      Molecule: Synthetic oligonucleotide"

<400> SEQUENCE: 611
uagccattgc agctgctcac                                                   20

<210> SEQ ID NO 612
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 612
uagccattgc agctgc                                                       16

<210> SEQ ID NO 613
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
tagccattgc agctgctcac                                                   20

<210> SEQ ID NO 614
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
tagccattgc agctgctcac                                                   20

<210> SEQ ID NO 615
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
tagccattgc agctgctcac                                                   20

<210> SEQ ID NO 616
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616

```
tagccattgc agctgctcac                                                    20

<210> SEQ ID NO 617
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
tagccattgc agctgctcac                                                    20

<210> SEQ ID NO 618
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
tagccattgc agctgctcac                                                    20

<210> SEQ ID NO 619
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
tagccattgc agctgctcac                                                    20

<210> SEQ ID NO 620
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
tagccattgc agctgctcac                                                    20

<210> SEQ ID NO 621
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 621

His His His His His His
1               5
```